United States Patent
Cao et al.

(10) Patent No.: US 8,076,353 B2
(45) Date of Patent: *Dec. 13, 2011

(54) INHIBITION OF VEGF TRANSLATION

(75) Inventors: Liangxian Cao, Parlin, NJ (US); Thomas W. Davis, South Orange, NJ (US); Charles M. Romfo, Easton, PA (US); Christopher R. Trotta, Somerset, NJ (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 1077 days.

This patent is subject to a terminal disclaimer.

(21) Appl. No.: 11/765,871

(22) Filed: Jun. 20, 2007

(65) Prior Publication Data

US 2008/0064683 A1 Mar. 13, 2008
US 2009/0209521 A9 Aug. 20, 2009

Related U.S. Application Data

(63) Continuation-in-part of application No. 11/079,420, filed on Mar. 15, 2005, now Pat. No. 7,601,840, and a continuation-in-part of application No. 11/107,783, filed on Apr. 18, 2005, now Pat. No. 7,767,689, which is a continuation-in-part of application No. 11/079,420, filed on Mar. 15, 2005, now Pat. No. 7,601,840, said application No. 11/765,871 is a continuation-in-part of application No. 11/735,069, filed on Apr. 13, 2007, which is a continuation-in-part of application No. 11/107,783, and a continuation-in-part of application No. 11/079,420.

(60) Provisional application No. 60/814,868, filed on Jun. 20, 2006, provisional application No. 60/552,725, filed on Mar. 15, 2004.

(51) Int. Cl.
*A61K 31/437* (2006.01)
(52) U.S. Cl. ...................................................... 514/292
(58) Field of Classification Search .................. 514/292
See application file for complete search history.

(56) References Cited

U.S. PATENT DOCUMENTS

| | | |
|---|---|---|
| 3,492,304 A | 1/1970 | Shavel et al. |
| 4,014,890 A | 3/1977 | Welch, Jr. et al. |
| 4,720,484 A | 1/1988 | Vincent et al. |

(Continued)

FOREIGN PATENT DOCUMENTS

CA 2099060 A1 12/1993

(Continued)

OTHER PUBLICATIONS

Calabresi P and Chabner BA, "Section IX Chemotherapy of Neoplastic Diseases—Introduction," Goodman & Gilman's The Pharmacological Basis of Therapeutics 10th ed., 2001, Hardman JG, Limbird LE, and Gilman AG, Eds, McGraw-Hill, New York 2001, 1381-1388 (pp. 1381, 1383-1385, and 1388 provided).*

(Continued)

*Primary Examiner* — San-Ming Hui
*Assistant Examiner* — Paul Zarek
(74) *Attorney, Agent, or Firm* — Jones Day

(57) ABSTRACT

In accordance with the present invention, methods for inhibiting the translation of VEGF and methods for decreasing VEGF level by inhibiting VEGF translation are provided. In another aspect of the invention, compounds that inhibit the 5'-UTR-dependent translation of VEGF and methods for identifying such compounds are provided.

39 Claims, 3 Drawing Sheets

U.S. PATENT DOCUMENTS

| | | | |
|---|---|---|---|
| 4,754,038 A | 6/1988 | Abou-Gharbia | |
| 5,039,801 A | 8/1991 | Brossi et al. | |
| 5,120,543 A | 6/1992 | Hagin et al. | |
| 5,206,377 A | 4/1993 | McAfee | |
| 5,314,908 A * | 5/1994 | McAfee | 514/415 |
| 5,382,569 A | 1/1995 | Cody et al. | |
| 5,403,851 A | 4/1995 | D'Orlando et al. | |
| 5,580,878 A | 12/1996 | D'Orlando et al. | |
| 5,622,960 A | 4/1997 | Pommier et al. | |
| 5,633,388 A | 5/1997 | Diana et al. | |
| 5,760,051 A * | 6/1998 | Audia et al. | 514/292 |
| 6,043,252 A | 3/2000 | Bombrun | |
| 6,048,868 A | 4/2000 | Fourtillan et al. | |
| 6,069,150 A * | 5/2000 | Spinelli et al. | 514/312 |
| 6,235,718 B1 | 5/2001 | Balasubramanium et al. | |
| 6,306,870 B1 | 10/2001 | Bombrun | |
| 6,331,543 B1 | 12/2001 | Garvey et al. | |
| 6,350,757 B1 | 2/2002 | Goldstein et al. | |
| 6,376,529 B1 | 4/2002 | Tang et al. | |
| 6,552,017 B1 | 4/2003 | Robichaud et al. | |
| 6,635,638 B2 | 10/2003 | Sui et al. | |
| 6,706,750 B1 | 3/2004 | Bentley et al. | |
| 6,890,933 B1 | 5/2005 | Feng et al. | |
| 7,601,840 B2 | 10/2009 | Moon et al. | |
| 7,767,689 B2 * | 8/2010 | Moon et al. | 514/292 |
| 2002/0016298 A1 | 2/2002 | Hay et al. | |
| 2002/0091125 A1 | 7/2002 | Hay et al. | |
| 2002/0128206 A1 | 9/2002 | Hay et al. | |
| 2002/0173503 A1 | 11/2002 | Robichaud et al. | |
| 2003/0023087 A1 | 1/2003 | Garvey et al. | |
| 2003/0040527 A1 | 2/2003 | Yeh et al. | |
| 2003/0130171 A1 | 7/2003 | Schoenhard | |
| 2003/0220377 A1 | 11/2003 | Chesworth | |
| 2004/0023947 A1 | 2/2004 | Martin et al. | |
| 2004/0058877 A1 | 3/2004 | Hay et al. | |
| 2004/0116458 A1 | 6/2004 | Sawyer et al. | |
| 2004/0127482 A1 | 7/2004 | Robichaud et al. | |
| 2004/0157834 A1 | 8/2004 | Hay et al. | |
| 2004/0186094 A1 | 9/2004 | Robichaud et al. | |
| 2004/0209864 A1 | 10/2004 | Robichaud et al. | |
| 2004/0214223 A1 | 10/2004 | Cao et al. | |
| 2004/0214848 A1 | 10/2004 | Schoenhard | |
| 2004/0229864 A1 | 11/2004 | Bourrain et al. | |
| 2005/0004156 A1 | 1/2005 | Feng et al. | |
| 2005/0054568 A1 | 3/2005 | Ling et al. | |
| 2005/0054634 A1 | 3/2005 | Busch et al. | |
| 2005/0143371 A1 | 6/2005 | Meyers et al. | |
| 2005/0267018 A1 | 12/2005 | Blatt et al. | |
| 2005/0272759 A1 | 12/2005 | Moon et al. | |
| 2005/0282849 A1 | 12/2005 | Moon et al. | |
| 2007/0254878 A1 | 11/2007 | Cao et al. | |
| 2008/0103213 A1 | 5/2008 | Kurzrock et al. | |
| 2008/0293766 A1 | 11/2008 | Diamond et al. | |
| 2009/0017021 A1 | 1/2009 | Davis et al. | |
| 2010/0125065 A1 | 5/2010 | Moon et al. | |
| 2010/0158858 A1 | 6/2010 | Cao et al. | |
| 2010/0179132 A1 | 7/2010 | Moon et al. | |

FOREIGN PATENT DOCUMENTS

| | | |
|---|---|---|
| EP | 0008249 B1 | 8/1981 |
| EP | 0357122 A2 | 3/1990 |
| EP | 0406734 A2 | 1/1991 |
| EP | 0468789 A2 | 1/1992 |
| EP | 0491943 A1 | 7/1992 |
| EP | 0549916 A2 | 7/1993 |
| EP | 0549916 A3 | 8/1993 |
| EP | 0719837 A2 | 12/1995 |
| EP | 0300541 B1 | 3/1996 |
| EP | 1512397 A1 | 3/2005 |
| EP | 1383765 B1 | 12/2006 |
| FR | 2432025 B1 | 2/1980 |
| FR | 2662940 A1 | 12/1991 |
| JP | 3-287586 A | 12/1991 |
| JP | 4-275221 | 9/1992 |
| WO | 94/10175 A1 | 5/1994 |
| WO | 94/11378 A1 | 5/1994 |
| WO | 9410175 A1 | 5/1994 |
| WO | 96/26207 A1 | 8/1996 |
| WO | 9632003 A2 | 10/1996 |
| WO | 9737658 A1 | 10/1997 |
| WO | 97/43287 A1 | 11/1997 |
| WO | 9906390 A1 | 2/1999 |
| WO | 0039314 A1 | 7/2000 |
| WO | 01/21589 A2 | 3/2001 |
| WO | 0121584 A1 | 3/2001 |
| WO | 0147887 A1 | 7/2001 |
| WO | 01/87038 A2 | 11/2001 |
| WO | 01/87038 A3 | 11/2001 |
| WO | 02/051805 A1 | 7/2002 |
| WO | 02/088123 A1 | 11/2002 |
| WO | 03033496 A1 | 4/2003 |
| WO | 03051841 A2 | 6/2003 |
| WO | 03087815 A2 | 10/2003 |
| WO | 03099821 A1 | 12/2003 |
| WO | 03103656 A1 | 12/2003 |
| WO | 2004/035047 A1 | 4/2004 |
| WO | 2004069831 A1 | 8/2004 |
| WO | 2004096766 A1 | 11/2004 |
| WO | 2004110999 A1 | 12/2004 |
| WO | 2004113336 A1 | 12/2004 |
| WO | 2005000246 A2 | 1/2005 |
| WO | 2005005386 A1 | 1/2005 |
| WO | 2005007672 A2 | 1/2005 |
| WO | 2005/014543 A1 | 2/2005 |
| WO | 2005009370 A2 | 2/2005 |
| WO | 2005070930 A2 | 3/2005 |
| WO | 2005037791 A1 | 4/2005 |
| WO | 2005089764 A1 | 9/2005 |
| WO | 2005097162 A2 | 10/2005 |
| WO | 2005113003 A2 | 12/2005 |
| WO | 2006015035 A1 | 2/2006 |
| WO | 2006058088 A2 | 6/2006 |
| WO | 2006/113703 A2 | 10/2006 |
| WO | WO 2008/127714 | 10/2008 |
| WO | WO 2008/127715 | 10/2008 |
| WO | WO 2010/138644 | 12/2010 |
| WO | WO 2010/138652 | 12/2010 |
| WO | WO 2010/138659 | 12/2010 |
| WO | WO 2010/138685 | 12/2010 |
| WO | WO 2010/138695 | 12/2010 |
| WO | WO 2010/138706 | 12/2010 |
| WO | WO 2010/138758 | 12/2010 |

OTHER PUBLICATIONS

Kuldo JM, Ogawara KI, Werner N, Asgeirsdóttir SA, Kamps JA, Kok RJ, and Molema G, "Molecular pathways of endothelial cell activation for (targeted) pharmacological intervention of chronic inflammatory diseases," Current Vascular Pharmacology, Jan. 2005, 3(1), 11-39.*

Roodink I and Leenders WP, "Targeted therapies of cancer: angiogenesis inhibition seems not enough," Cancer Letters, Dec. 2010, 299(1), 1-10.*

Abou-Gharbia et al., "Antipsychotic Activity of Substituted Gamma-Carbolines," J. Med. Chem., 30:1818-1823 (1987).

Akiri et al., "Regulation of Vascular Endothelial Growth Factor (VEGF) Expression is Mediated by Internal Initiation of Translation and Alternative Initiation of Transcription," Oncogene, 17:227-236 (1998).

Asano et al., "Wide Spectrum of Antitumor Activity of a Neutralizing Monoclonal Antibody to Human Vascular Endothelial Growth Factor," Jpn. J. Cancer Res., 90:93-100 (1999).

Bergsland et al., "A Randomized Phase II Trial Comparing rhuMAb VEGF (Recombinant Human Monoclonal Antibody to Vascular Endothelial Cell Growth Factor) Plus 5-Flurouracil/Leucovorin (FU/LV) to FU/LV Alone in Patients with Metastatic Colorectal Cancer," American Society of Clinical Oncology 36th Annual Meeting, May 2000, New Orleans, LA, USA, Abstract No. 939.

Borgström et al., "Neutralizing Anti-Vascular Endothelial Growth Factor Antibody Completely Inhibits Angiogenesis and Growth of Human Prostate Carcinoma Micro Tumors In Vivo," Prostate, 35:1-10 (1998).

Bornes et al., "Control of the Vascular Endothelial Growth Factor Internal Ribosome Entry Side (IRES) Activity and Translation Initiation by Alternatively Spliced Coding Sequences," J. Biol. Chem., 279(18):18717-18726 (2004).

Boyer, "Small Molecule Inhibitors of KDR (VEGFR-2) Kinase: An Overview of Structure Activity Relationships," Current Topics in Medicinal Chemistry, 2:973-1000 (2002).

Brekken et al., "Selective Inhibition of Vascular Endothelial Growth Factor (VEGF) Receptor 2 (KDF/Flk-1) Activity by a Monoclonal Anti-VEGF Antibody Blocks Tumor Growth in Mice," Cancer Res., 60:5117-5124 (2000).

Cao et al., "Synthesis and in vitro Cytotoxic Evaluation of 1,3-Bisubstituted and 1,3,9-Trisubstituted Beta-Carboline Derivatives," European Journal of Medicinal Chemistry, 40:249-257 (2005).

Carmeliet, "Angiogenesis in Health and Disease," Nature Medicine, 9(6):653-660 (2003).

Carmeliet et al., "Abnormal Blood Vessel Development and Lethality in Embryos Lacking a Single VEGF Allele," Nature, 380:435-439 (1996).

Carmeliet et al., "Angiogenesis in Cancer and Other Diseases," Nature, 407:249-257 (2000).

Chomczynski et al., "Single-Step Method of RNA Isolation by Acid Guanidinium Thiocyanate-Phenol-Chloroform Extraction," Anal. Biochem., 162:156-159 (1987).

Claffey et al., "Identification of a Human VPF/VEGF 3' Untranslated Region Mediating Hypoxia-Induced mRNA Stability," Molecular Biology of the Cell, 9:469-481 (1998).

Clark et al., "Ophthalmic Drug Discovery," Nat. Rev. Drug Discovery, 2:448-459 (2003).

Connolly et al., "Human Vascular Permeability Factor," J. Biol. Chem., 264(33):20017-20024 (1989).

DeJong et al., "RNA and RNA-Protein Complexes as Targets for Therapeutic Intervention," Current Topics in Medicinal Chemistry, 2(3):289-302 (2002).

Daugan et al., "The Discovery of Tadalafil: A Novel and Highly Selective PDE5 Inhibitor. 2: 2,3,6,7,12,12a-Hexahydropyrazino[1',2':1,6]pyrido[3,4-b]Indole-1,4-Dione Analogues," J. Med. Chem., 46(21):4533-4542 (2003).

Daugan et al., "The Discovery of Tadalafil: A Novel and Highly Selective PDE5 Inhibitor. 1: 5,6,11,11a-Tetrahydro-1H-imidazo[1',5':1,6]Pyrido[3,4-b]Indole-1,3(2H)-dione Analogues," J. Med. Chem., 46:4525-4532 (2003).

DeVore et al., "A Randomized Phase II Trial Comparing rhuMAb VEGF (Recombinant Humanized Monoclonal Antibody to Vascular Endothelial Cell Growth Factor) Plus Carboplatin/Paclitaxel (CP) to CP Alone in Patients with Stage IIIB/IV NSCLC," American Society of Clinical Oncology 36th Annual Meeting, May 2000, New Orleans, LA, USA, Abstract No. 1896.

Dirix et al., "Elevated Levels of the Angiogenic Cytokines Basic Fibroblast Growth Factor and Vascular Endothelial Growth Factor in Sera of Cancer Patients," Br. J. Cancer, 76(2):238-243 (1997).

Dreyfuss et al., "Messenger-RNA-Binding Proteins and the Messages They Carry," Nature Reviews Molecular Cell Biology, 3:195-205 (2002).

Ellis et al., "Down-Regulation of Vascular Endothelial Growth Factor in Human Colon Carcinoma Cell Lines by Antisense Transfection Decreases Endothelial Cell Proliferation," Surgery, 120(5):871-878 (1996).

Eyetech Study Group (Martin et al.), "Preclinical and Phase 1A Clinical Evaluation of an Anti-VEGF Pegylated Aptamer (EYE001) for the Treatment of Exudative Age•RelatedMacular Degeneration," Retina, The Journal of Retinal and Vitreous Diseases, 22(2):143-52 (2002).

Ferrara et al., "The Biology of Vascular Endothelial Growth Factor," Endocr. Rev., 18(1):4-25 (1997).

Ferrara et al., "Vascular Endothelial Growth Factor is Essential for Corpus Luteum Angiogenesis," Nat. Med., 4(3):336-340 (1998).

Ferrara et al., "Clinical Applications of Angiogenic Growth Factors and Their Inhibitors," Nat. Med., 5(12):1359-64 (1999).

Ferrara, "Role of Vascular Endothelial Growth Factor in Physiologic and Pathologic Angiogenesis: Therapeutic Implications," Semin. Oncol., 29(6 Suppl 16):10-14 (2002).

Filleur et al., "SiRNA-Mediated Inhibition of Vascular Endothelial Growth Factor Severely Limits Tumor Resistance to Antiangiogenic Thrombospondin-1 and Slows Tumor Vascularization and Growth," Cancer Res., 63:3919-22 (2003).

Folkman, "Tumor Angiogenesis: Therapeutic Implications," N. Engl. J. Med., 285(21):1182-6 (1971).

Fong et al., "SU5416 Is a Potent and Selective Inhibitor of the Vascular Endothelial Growth Factor Receptor (Flk-1/KDR) That Inhibits Tyrosine Kinase Catalysis, Tumor Vascularization, and Growth of Multiple Tumor Types," Cancer Res., 59:99-106 (1999).

Fong et al., "Role of the Flt-1 Receptor Tyrosine Kinase in Regulating the Assembly of Vascular Endothelium," Nature, 376:66-70 (1995).

Fuhrmann-Benzakein et al., "Elevated Levels of Angiogenic Cytokines in the Plasma of Cancer Patients," Int. J. Cancer, 85:40-45 (2000).

Funatsu et al., "Angiotensin II and Vascular Endothelial Growth Factor in the Vitreous Fluid of Patients with Diabetic Macular Edema and Other Retinal Disorders," Am. J. Ophthalmol., 133(4):537-43 (2002).

Gasparini et al., "Prognostic Significance of Vascular Endothelial Growth Factor Protein in Node-Negative Breast Carcinoma," J. Natl. Cancer Inst., 89(2):139-147 (1997).

Ge et al., "Regulation of Promoter Activity of the APP Gene by Cytokines and Growth Factors," Ann. N. Y. Acad. Sci., 973:463-467 (2002).

Geng et al., "Inhibition of Vascular Endothelial Growth Factor Receptor Signaling Leads to Reversal of Tumor Resistance to Radiotherapy," Cancer Res., 61:2413-2419 (2001).

Giles et al., "Phase II Study of SU5416-a Small-Molecule, Vascular Endothelial Growth Factor Tyrosine-Kinase Receptor Inhibitor-in Patients with Refractory Myeloproliferative Diseases," Cancer, 97(8):1920-8 (2003).

Goldberg et al., "A 40-bp RNA Element that Mediates Stabilization of Vascular Endothelial Growth Factor mRNA by HuR," J. Biol. Chem., 277(16):13635-40 (2002).

Gordon et al., "Phase I Safety and Pharmacokinetic Study of Recombinant Human Anti-Vascular Endothelial Growth Factor in Patients with Advanced Cancer," J. Clin. Oncol., 19(3):843-850 (2001).

Hanahan et al., "Patterns and Emerging Mechanisms of the Angiogenic Switch During Tumorigenesis," Cell, 86:353-364 (1996).

Henry et al., "Aromatic Isocyanates as Reagents for the Identification of Some Heterocyclic Compounds," J. Am. Chem. Soc., pp. 2297-3000 (1949).

Hicklin et al., "Monoclonal Antibody Strategies to Block Angiogenesis," Drug Discovery Today, 6(10):517-528 (2001).

Holash et al., "Vessel Cooption, Regression, and Growth in Tumors Mediated by Angiopoietins and VEGF," Science, 284:1994-1998 (1999).

Honda et al., "Experimental Subretinal Neovascularization is Inhibited by Adenovirus•MediatedSoluble VEGF/flt•1 Receptor Gene Transfection: A Role of VEGF and Possible Treatment for SRN in Age•RelatedMacular Degeneration," Gene Ther., 7:978-85 (2000).

Huez et al., "Two Independent Internal Ribosome Entry Sites Are Involved in Translation Initiation of Vascular Endothelial Growth Factor mRNA," Mol. Cell. Biol., 18(11):6178-6190 (1998).

Ichihara et al., "Enhancer for Carcinostatic Effect," Derwent AN-1992-376264 (Sep. 30, 1992).

Ikeda et al., "Hypoxia-Induced Transcriptional Activation and Increased mRNA Stability of Vascular Endothelial Growth Factor in C6 Glioma Cells," J. Biol. Chem. 270(34):19761-19766 (1995).

Ishida et al., "Antitumor Agents 201. Cytotoxicity of Harmine and beta-Carboline Analogs," Bioorganic & Medicinal Chemistry Letters, 9:3319-3324 (1999).

Kedersha et al., "Stress Granules: Sites of mRNA Triage that Regulate mRNA Stability and Translatability," Biochemical Society Transactions, 30(6):963-969 (2002).

Kerbel et al., "Clinical Translation of Angiogenesis Inhibitors," Nat. Rev. Cancer, 2:727-39 (2002).

Kim et al., "Inhibition of Vascular Endothelial Growth Factor•InducedAngiogenesis Suppresses Tumor Growth in vivo," Nature, 362:841-844 (1993).

Kozak, "Influences of mRNA Secondary Structure on Initiation by Eukaryotic Ribosomes," PNAS, 83:2850-2854 (1986).
Kraggerud et al., "Regulation of Protein Synthesis in Human Cells Exposed to Extreme Hypoxia," Anticancer Res., 15:683-686 (1995).
Krzystolik et al., "Prevention of Experimental Choroidal Neovascularization with Intravitreal Anti•VascularEndothelial Growth Factor Antibody Fragment," Arch. Ophthalmol., 120:338-346 (2002).
Lai et al., "Evidence that Tristetraprolin Binds to AU-Rich Elements and Promotes the Deadenylation and Destabilization of Tumor Necrosis Factor Alpha mRNA," Molecular and Cellular Biology, 19(6):4311-4323 (1999).
Laird et al., "SU6668 is a Potent Antiangiogenic and Antitumor Agent that Induces Regression of Established Tumors," Cancer Res., 60:4152-60 (2000).
Leclerc et al., "Folypoly-γ-glutamate Synthetase Gene mRNA Splice Variants and Protein Expression in Primary Human Leukemia Cells, Cell Lines, and Normal Human Tissues," Clin. Cancer Res., 7:942-951 (2001).
Leung et al., "Vascular Endothelial Growth Factor is a Secreted Angiogenic Mitogen," Science, 246:1306-1309 (1989).
Levy et al., "Post-Transcriptional Regulation of Vascular Endothelial Growth Factor by Hypoxia," J. Biol. Chem. 271(5):2746-2753 (1996).
Lin et al., "Inhibition of Tumor Growth by Targeting Tumor Endothelium Using a Soluble Vascular Endothelial Growth Factor Receptor," Cell Growth Differ., 9:49-58 (1998).
Lip et al., "Age-Related Macular Degeneration is Associated with Increased Vascular Endothelial Growth Factor, Hemorheology and Endothelial Dysfunction," Ophthalmology, 108(4):705-10 (2001).
Liu et al., "Hypoxia Regulates Vascular Endothelial Growth Factor Gene Expression in Endothelial Cells Identification of a 5'Enhancer," Circ. Res., 77(3):638-643 (1995).
Matter, "Tumor Angiogenesis as a Therapeutic Target," Drug Discovery Today, 6(19):1005-1024 (2001).
Maxwell et al., "The Tumour Suppressor Protein VHL Targets Hypoxia•InducibleFactors for Oxygen•Dependent Proteolysis," Nature, 399:271-275 (1999).
Millauer et al., "Glioblastoma Growth Inhibited in vivo by a Dominant•NegativeFlk•1Mutant," Nature, 367:576-579 (1994).
Miller et al., "The Vascular Endothelial Growth Factor mRNA Contains an Internal Ribosome Entry Site," FEBS Letters, 434:417-420 (1998).
Moulder et al., "Epidermal Growth Factor Receptor (HER1) Tyrosine Kinase Inhibitor ZD1839 (Iressa) Inhibits HER2/neu (erbB2)•OverexpressingBreast Cancer Cells in vitro and in vivo," Cancer Res., 61:8887-95 (2001).
Nicolaus, "Symbiotic Approach to Drug Design," Decision Making in Drug Research (F. Gross, ed., Raven Press, New York, NY), pp. 173-186 (1983).
Ohno-Matsui et al., "Inducible Expression of Vascular Endothelial Growth Factor in Adult Mice Causes Severe Proliferative Retinopathy and Retinal Detachment," Am. J. Pathol., 160(2):711-719 (2002).
Ortega et al., "Signal Relays in the VEGF System," Front. Biosci., 4:d141-152 (1999).
Ozaki et al., "Blockage of Vascular Endothelial Cell Growth Factor Receptor Signaling is Sufficient to Completely Prevent Retinal Neovascularization," Am. J. Pathol., 156(2):697-707 (2000).
Parry et al., "Bioactivity of Anti-Angiogenic Ribozymes Targeting Flt-1 and KDR mRNA," Nucleic Acids Res., 27(13):2569-2577 (1999).
Plouet et al., "Isolation and Characterization of a Newly Identified Endothelial Cell Mitogen Produced by AtT-20 Cells," EMBO J., 8(12):3801-3806 (1989).
Rak et al., "Oncogenes and Tumor Angiogenesis: Differential Modes of Vascular Endothelial Growth Factor Up•Regulationin ras•TransformedEpithelial Cells and Fibroblasts," Cancer Res., 60:490-498 (2000).
Reich et al., "Small Interfering RNA (siRNA) Targeting VEGF Effectively Inhibits Ocular Neovascularization in a Mouse Model," Mol. Vis., 9:210-216 (2003).

Rofstad et al., "Vascular Endothelial Growth Factor, Interleukin 8, Platelet•DerivedEndothelial Cell Growth Factor, and Basic Fibroblast Growth Factor Promote Angiogenesis and Metastasis in Human Melanoma Xenografts," Cancer Res., 60:4932-4938 (2000).
Ryan et al, "Toxicologic Pathology of Unique Biotechnology Agents and Biotherapies," Toxicol. Pathol., 27(1):78-86 (1999).
Saishin et al., "VEGF•TRAPR1R2Suppresses Choroidal Neovascularization and VEGF•InducedBreakdown of the Blood•RetinalBarrier," J. Cell Physiol., 195:241-248 (2003).
Sato et al., "Properties of Two VEGF Receptors, Flt•1and KDR, in Signal Transduction," Annals of New York Academy of Sciences, 902:201-207 (2000).
Schwesinger et al., "Intrachoroidal Neovascularization in Transgenic Mice Overexpressing Vascular Endothelial Growth Factor in the Retinal Pigment Epithelium," Am. J. Pathol., 158(3):1161-1172 (2001).
Semenza, "Regulation of Mammalian O2 Homeostasis by Hypoxia•InducibleFactor 1," Annu. Rev. Cell. Dev. Biol., 15:551-578 (1999).
Shalaby et al., "Failure of Blood•IslandFormation and Vasculogenesis in Flk•1•DeficientMice," Nature, 376:62-66 (1995).
Shanmugasundaram et al., "Synthesis and Biological Activity of Pyrazino[3,2,1-j,k]carbazoles," Indian Journal of Chemistry, 37b:1133-1136 (1998).
Shanmugasundaram et al., "Synthesis of 3-Phenylisoxazolo[3,4-a]carbazoles," Zeitschrift für Naturforschung, 54b:1202-1204 (1999).
Shen et al., "Preclinical Evaluation of a Phosphorothioate Oligonucleotide in the Retina of Rhesus Monkey," Lab Invest., 82(2):167-82 (2002).
Stein et al., "Translation of Vascular Endothelial Growth Factor mRNA by Internal Ribosome Entry: Implications for Translation Under Hypoxia," Mol. Cell. Biol. 18(6):3112-3119 (1998).
Stoecklin et al., "A Constitutive Decay Element Promotes Tumor Necrosis Factor Alpha mRNA Degradation via an AU-Rich Element-Independent Pathway," Molecular and Cellular Biology, 23(10):3506-3515 (2003).
Sugimoto et al., "Neutralization of Circulating Vascular Endothelial Growth Factor (VEGF) by Anti-VEGF Antibodies and Soluble VEGF Receptor 1 (sFlt-1) Induces Proteinuria," J. Biol. Chem., 278(15):12605-8 (2003).
Sun et al., "4-(2-Pyridyl)piperazine-1-carboxamides: Potent Vanilloid Receptor 1 Antagonists," Bioorganic & Medicinal Chem. Lett., 13:3611-3616 (2003).
Tischer et al., "The Human Gene for Vascular Endothelial Growth Factor," J. Biol. Chem., 266(18):11947-11954 (1991).
Trotta et al., "BCR/ABL Activates mdm2 mRNA Translation via the La Antigen," Cancer Cell, 3:145-160 (2003).
Verheul et al., "Platelet and Coagulation Activation with Vascular Endothelial Growth Factor Generation in Soft Tissue Sarcomas," Clin. Cancer Res., 6:166-171 (2000).
Wedge et al., "ZD4190: An Orally Active Inhibitor of Vascular Endothelial Growth Factor Signaling with Broad•Spectrum Antitumor Efficacy," Cancer Res., 60:970-975 (2000).
Witmer et al., "Vascular Endothelial Growth Factors and Angiogenesis in Eye Disease," Prog. Retin Eye Res., 22:1-29 (2003).
Yoshida et al., "Oxidation of Cycloalkan[b]indoles with Iodine Pentoxide (I2O5)," Chem. Pharm. Bull., 35(12):4700-4704 (1987).
Yuan et al., "Time-Dependent Vascular Regression and Permeability Changes in Established Human Tumor Xenografts Induced by an Anti-Vascular Endothelial Growth Factor/Vascular Permeability Factor Antibody," Proc. Natl. Acad. Sci. USA, 93:14765-14770 (1996).
Zhu et al., "Inhibition of Tumor Growth and Metastasis by Targeting Tumor•AssociatedAngiogenesis with Antagonists to the Receptors of Vascular Endothelial Growth Factor," Invest. New Drugs, 17:195-212 (1999).
International Search Report issued in PCT/US2006/14547 on Feb. 26, 2007.
International Search Report issued in PCT/US2005/042484 on Oct. 4, 2006.
International Search Report mailed Oct. 24, 2005, issued in International Application No. PCT/US05/008452.

International Search Report mailed Mar. 8, 2005, issued in International Application No. PCT/US05/008481.
International Search Report mailed Jun. 16, 2006, issued in International Application No. PCT/US05/042483.
International Search Report mailed Jun. 16, 2006, issued in International Application No. PCT/US05/042482.
Unpublished U.S. Appl. No. 10/592,761, filed Sep. 14, 2006.
Unpublished U.S. Appl. No. 11/735,069, filed Apr. 13, 2007.
Unpublished U.S. Appl. No. 11/720,057, filed May 23, 2007.
Unpublished U.S. Appl. No. 11/720,055, filed May 23, 2007.
Unpublished U.S. Appl. No. 11/720,061, filed May 23, 2007.
Babs Copyright 2006 Beilstein MDL on STN, AN 5523540, Abstract of Massiot, G., "Synthesis of Indole Alkaloids and Related Molecules Along Non Biogenetic Routes", Bull. Soc. Chem. Belg., 99(9): 717-728 (1990).
Babs Copyright 2006 Beilstein MDL on STN, AN 5669242, Abstract of Piper et al., "Pictet-Spengler reaction of biogenic amines with carbohydrates. Synthesis of novel C-nucleosides", Can. J. Chem., 61: 2721-2728 (1983).
Babs Copyright 2006 Beilstein MDL on STN, AN 5702218, Abstract of Pogosyan et al., "Synthesis and Biological Activity of 3-R-1,2,3,4-Tetrahydro-4β-Carboline Derivatives", Pharm. Chem. J. (Engl. Transl.), 21(6): 414-417 (1987).
Babs Copyright 2006 Beilstein MDL on STN, AN 5776298, Abstract of Moehrle et al., "Fused Dihydro-1,2,4-triazines", Arch. Pharm. (Weinheim Ger.), 320(3): 198-202 (1987).
Babs Copyright 2006 Beilstein MDL on STN, AN 6010011, Abstract of Waldmann et al., "Asymmetrische Pictet-Spengler-Reaktionen mit N,N-Phthaloyl-Aminosaeuren als chiralen Hilfsgruppen", Angew. Chem. (1995), 107(21), 2608-2610.
Babs Copyright 2006 Beilstein MDL on STN, AN 6236596, Abstract of Lu et al., "Stereoselective Synthesis of Phosphorothioate and Alkylphosphinate Analogs Using a L-Tryptophan Derived Chiral Auxiliary", Tetrahedron, 56(26): 4355-4366 (2000).
Beilstein Copyright 2006 Beilstein MDL on STN, Beilstein Records (BRN): 9976380.
Beilstein Copyright 2006 Beilstein MDL on STN, Beilstein Records (BRN): 9975229.
Beilstein Copyright 2006 Beilstein MDL on STN, Beilstein Records (BRN): 9974267.
Beilstein Copyright 2006 Beilstein MDL on STN, Beilstein Records (BRN): 9973640.
Beilstein Copyright 2006 Beilstein MDL on STN, Beilstein Records (BRN): 9817157.
Beilstein Copyright 2006 Beilstein MDL on STN, Beilstein Records (BRN): 9802212.
Beilstein Copyright 2006 Beilstein MDL on STN, Beilstein Records (BRN): 9793124.
Beilstein Copyright 2006 Beilstein MDL on STN, Beilstein Records (BRN): 9792788.
Beilstein Copyright 2006 Beilstein MDL on STN, Beilstein Records (BRN): 9790084.
Beilstein Copyright 2006 Beilstein MDL on STN, Beilstein Records (BRN): 9784177.
Beilstein Copyright 2006 Beilstein MDL on STN, Beilstein Records (BRN): 9781935.
Beilstein Copyright 2006 Beilstein MDL on STN, Beilstein Records (BRN): 9778052.
Beilstein Copyright 2006 Beilstein MDL on STN, Beilstein Records (BRN): 9715971.
Beilstein Copyright 2006 Beilstein MDL on STN, Beilstein Records (BRN): 9713454.
Beilstein Copyright 2006 Beilstein MDL on STN, Beilstein Records (BRN): 9666272.
Beilstein Copyright 2006 Beilstein MDL on STN, Beilstein Records (BRN): 9664783.
Beilstein Copyright 2006 Beilstein MDL on STN, Beilstein Records (BRN): 9664782.
Beilstein Copyright 2006 Beilstein MDL on STN, Beilstein Records (BRN): 9662877.
Beilstein Copyright 2006 Beilstein MDL on STN, Beilstein Records (BRN): 9662875.
Beilstein Copyright 2006 Beilstein MDL on STN, Beilstein Records (BRN): 9656936.
Beilstein Copyright 2006 Beilstein MDL on STN, Beilstein Records (BRN): 9530614.
Beilstein Copyright 2006 Beilstein MDL on STN, Beilstein Records (BRN): 9529248.
Beilstein Copyright 2006 Beilstein MDL on STN, Beilstein Records (BRN): 9526693.
Beilstein Copyright 2006 Beilstein MDL on STN, Beilstein Records (BRN): 9525620.
Beilstein Copyright 2006 Beilstein MDL on STN, Beilstein Records (BRN): 9525619.
Beilstein Copyright 2006 Beilstein MDL on STN, Beilstein Records (BRN): 9525032.
Beilstein Copyright 2006 Beilstein MDL on STN, Beilstein Records (BRN): 9523521.
Beilstein Copyright 2006 Beilstein MDL on STN, Beilstein Records (BRN): 9520875.
Beilstein Copyright 2006 Beilstein MDL on STN, Beilstein Records (BRN): 9520142.
Beilstein Copyright 2006 Beilstein MDL on STN, Beilstein Records (BRN): 9517212.
Beilstein Copyright 2006 Beilstein MDL on STN, Beilstein Records (BRN): 9504026.
Beilstein Copyright 2006 Beilstein MDL on STN, Beilstein Records (BRN): 9446639.
Beilstein Copyright 2006 Beilstein MDL on STN, Beilstein Records (BRN): 9374742.
Beilstein Copyright 2006 Beilstein MDL on STN, Beilstein Records (BRN): 9371916.
Beilstein Copyright 2006 Beilstein MDL on STN, Beilstein Records (BRN): 9370648.
Beilstein Copyright 2006 Beilstein MDL on STN, Beilstein Records (BRN): 9370647.
Beilstein Copyright 2006 Beilstein MDL on STN, Beilstein Records (BRN): 9370056.
Beilstein Copyright 2006 Beilstein MDL on STN, Beilstein Records (BRN): 9370055.
Beilstein Copyright 2006 Beilstein MDL on STN, Beilstein Records (BRN): 9367542.
Beilstein Copyright 2006 Beilstein MDL on STN, Beilstein Records (BRN): 9364536.
Beilstein Copyright 2006 Beilstein MDL on STN, Beilstein Records (BRN): 9364535.
Beilstein Copyright 2006 Beilstein MDL on STN, Beilstein Records (BRN): 9363589.
Beilstein Copyright 2006 Beilstein MDL on STN, Beilstein Records (BRN): 9362270.
Beilstein Copyright 2006 Beilstein MDL on STN, Beilstein Records (BRN): 9361560.
HCAPLUS Copyright 2006 ACS on STN, AN 1961:112225, Abstract of Vejdelek et al., "Synthetic experiments in the group of hypotensive alkaloids. XXI. Chemistry of 1,2,3,4-tetrahydronorharman-1-carboxylic acid and derivatives", Journal of Medicinal & Pharmaceutical Chemistry, 3: 427-40 (1961).
HCAPLUS Copyright 2006 ACS on STN, AN 1961:99570, Abstract of Mndzhoyan et al., "Syntheses based on harmine and tetrahydroharmine. III. Cyanoethylation of harmine and tetrahydroharmine", Izvest. Akad. Nauk Armyan. S.S.R., Khim. Nauki, 13(No. 14): 297-304 (1960).
HCAPLUS Copyright 2006 ACS on STN, AN 1962:45986, Abstract of Agbalyan, S. G., "Decyanoethylation in 1,2,3,4-tetrahydro-β-carbolines", Izvest. Akad. Nauk Armyan. S.S.R., Khim. Nauki, 14: 277-82 (1961).
HCAPLUS Copyright 2006 ACS on STN, AN 1963:27125, Abstract of Agbalyan, S. G., "Cyanoethylation of harmine and tetrahydroharmine", Izvestiya Akademii Nauk Armyanskoi SSR, Khimicheskie Nauki, 14: 611-16 (1961).
HCAPLUS Copyright 2006 ACS on STN, AN 1963:415546, Walls et al., "Synthesis of 1,2,3,4,6,7-hexahydroindolo [2,3-a]-1,3-trimethylenequinolizine and its intermediates", Bol. Inst. Quim. Univ. Nal. Auton. Mex., 14: 32-47 (1962).

HCAPLUS Copyright 2006 ACS on STN, AN 1964:30874, Abstract of Henecka et al., "Synthesis in the β-carboline series", Med. Chem., Abhandl. Med.-Chem. Forschungsstaetten Farbenfabriken Bayer A.-G., 7: 277-86 (1963).

HCAPLUS Copyright 2006 ACS on STN, AN 1967:115626, Abstract of Elliott et al., "New synthetic approaches to the benz [h] indolo [2,3-a] quinolizine ring system", Journal of Heterocyclic Chemistry, 4(1): 127-9 (1967).

HCAPLUS Copyright 2006 ACS on STN, AN 1967:65442, Abstract of Szantay et al., "Synthesis of substituted octahydroindolo [2,3-a]-quinolizines. The formation of a new type of ring system", Journal of Organic Chemistry, 32(2): 423-7 (1967).

HCAPLUS Copyright 2006 ACS on STN, AN 1969:11546, Abstract of Von Strandtmann et al., "Azecino [2,1-α] tetrahydroisoquinolines and related compounds. I. Reaction of 3,4-dihydroisoquinolines with nonenolizable β-diketones", Journal of Organic Chemistry, 33(11): 4010-15 (1968).

HCAPLUS Copyright 2006 ACS on STN, AN 1971:53396, Abstract of Mukerdzhi et al., "Indole derivatives. LX. Synthesis of β-lactams of the indole series", Khimiya Geterotsiklicheskikh Soedinenii, (12): 1626-30 (1970).

HCAPLUS Copyright 2006 ACS on STN, AN 1971:551703, Abstract of Novak et al., "Synthesis of an analog of Quantril containing the indoloquinolizidine ring", Acta Chimica Academiae Scientiarum Hungaricae, 70(1-2): 91-6 (1971).

HCAPLUS Copyright 2006 ACS on STN, AN 1973:438449, Abstract of Velichkova, St., "MAO [monoamine oxidase] -inhibiting effect of some simplified structural analogs of reserpine", Trudove na Nauchnoizsledovatelskiya Khimikofarmatsevtichen Institut, 8: 321-6 (1972).

HCAPLUS Copyright 2006 ACS on STN, AN 1975:479451, Abstract of Bikova et al., "Synthesis and pharmacological study of new pyridine-N-(acetylamido)-β-carboline derivatives", Trudove na Nauchnoizsledovatelskiya Khimikofarmatsevtichen Institut, 9: 141-53 (1974).

HCAPLUS Copyright 2006 ACS on STN, AN 1978:540332, Abstract of Rehse et al., "Neuropsychotropic activity of reserpine analogs, 1,2,3,4-tetreahydro-β-carbolines", Archiv der Pharmazie (Weinheim, Germany), 311(3): 228-35 (1978).

HCAPLUS Copyright 2006 ACS on STN, AN 1981:30596, Abstract of Bikova et al., "Synthesis and pharmacological testing of β-carbolines with basic substitutes", Trudove na Nauchnoizsledovatelskiya Khimikofarmatsevtichen Institut, 10: 65-84 (1978).

HCAPLUS Copyright 2006 ACS on STN, AN 1983:16659, Abstract of Kumar et al., "Agents acting on CNS. Part XXIX. Synthesis of seco analogs of centbutindole, a potent neuroleptic", European Journal of Medicinal Chemistry, 17(4): 312-16 (1982).

HCAPLUS Copyright 2006 ACS on STN, AN 1983:53150, Abstract of Massiot et al., "α, α'-Bis(phenylthio) carbonyls in organic synthesis", Bulletin de la Societe Chimique de France, (7-8, Pt. 2): 241-8 (1982).

HCAPLUS Copyright 2006 ACS on STN, AN 1985:184894, Abstract of Flecker et al., "Reactions with indole derivatives. LI. Seco-aldehydes from didrovaltratum", Tetrahedron, 40(23): 4843-52 (1984).

HCAPLUS Copyright 2006 ACS on STN, AN 1985:406574, Abstract of Mandal et al., "Synthesis of 3-acetyl-1,4,6,7,12,12b-hexahydroindolo [2,3-a] quinolizine", Heterocycles, 23(4): 931-4 (1985).

HCAPLUS Copyright 2006 ACS on STN, AN 1985:6903, Abstract of Massiot et al., "Synthesis of (-)-ajmalicine from (-)-tryptophan", Journal of the Chemical Society, Chemical Communications, (11): 715-16 (1984).

HCAPLUS Copyright 2006 ACS on STN, AN 1987:138281, Abstract of Bobowski et al., "1, 1-Disubstituted-2,3,4,9-tetrahydro-1H-pyrido [3,4-b] indolecarboxylic acid esters and ketones. The base catalyzed transformation of 1-(2', 3', 4', 9'-tetrahydrospiro [cyclohexane-1, 1'- [1H] pyrido [3,4-b] indol]-2-yl) alkanones into 2-(4,9-dihydro-3H-pyrido[3,4-b]indol-1-yl)-1-alkylcyclohexanols", Journal of Heterocyclic Chemistry, 22(6): 1679-88 (1985).

HCAPLUS Copyright 2006 ACS on STN, AN 1987:509062, Abstract of Blasko et al., "Octahydroindolo [2,3-a] quinolizines and 3,4-dihydro-β-carbolines as new inhibitors of human platelet aggregation", Arzneimittel-Forschung, 37 (6): 667-9 (1987).

HCAPLUS Copyright 2006 ACS on STN, AN 1987:568626, Misztal et al., "Synthesis and pharmacological properties of some 2-substituted 1-(3-pyridyl)-1,2,3,4-tetrahydro-β-carbolines", Polish Journal of Pharmacology and Pharmacy, 39(1): 97-103 (1987).

HCAPLUS Copyright 2006 ACS on STN, AN 1987:590347, Abstract of Pogosyan et al., "Synthesis and biological activity of 3-substituted-1,2,3,4-tetrahydro-β-carboline derivatives", Khimiko-Farmatsevticheskii Zhurnal, 21(6): 678-81 (1987).

HCAPLUS Copyright 2006 ACS on STN, AN 1988:131668, Abstract of Moehrle et al., "Tetracyclic imidazoles", Monatshefte fuer Chemie, 118(4): 477-83 (1987).

HCAPLUS Copyright 2006 ACS on STN, AN 1988:21850, Abstract of Moehrle et al., "Methylhydrazone function as a neighboring group in amine dehydrogenations", Archiv der Pharmazie (Weinheim, Germany), 320(3): 258-63 (1987).

HCAPLUS Copyright 2006 ACS on STN, AN 1988:400244, Abstract of Hulinska et al., "1-Methyl-, 1-phenyl-, and 1-[2-(2-dimethylaminoethoxy)phenyl]-2,3,4,9-tetrahydro-1H-pyrido[3,4-b] indole and their 2-substituted derivatives. Synthesis and pharmacological screening", Collection of Czechoslovak Chemical Communications, 53(2): 373-80 (1988).

HCAPLUS Copyright 2006 ACS on STN, AN 1989:107998, Abstract of Misztal et al., "Synthesis and pharmacological properties of some 2-(3-aminopropionyl)-and 2-(3-aminopropyl)-1-(3-pyridyl)-1,2,3,4-tetrahydro-β-carbolines", Polish Journal of Pharmacology and Pharmacy, 40(4): 413-22 (1988).

HCAPLUS Copyright 2006 ACS on STN, AN 1989:477876, Abstract of Grigg et al., "A dehydration route to azomethine ylides and isoindoles", Journal of the Chemical Society, Perkin Transactions 1: Organic and Bio-Organic Chemistry (1972-1999), (1): 198-200 (1989).

HCAPLUS Copyright 2006 ACS on STN, AN 1989:595214, Abstract of Wasserman et al.,; "The chemistry of vicinal tricarbonyl compounds. Applications in the synthesis of vincamine-related alkaloids", Tetrahedron Letters, 30(7): 873-6 (1989).

HCAPLUS Copyright 2006 ACS on STN, AN 1990:440504, Abstract of Fujii et al., "Synthesis of 1-(pentafluorophenyl)-β-carboline", Journal of Fluorine Chemistry, 46(3): 479-89 (1990).

HCAPLUS Copyright 2006 ACS on STN, AN 1990:552798, Abstract of Rosenmund et al., "Stereoselective synthesis of rac-yohimb-15-enone", Liebigs Annalen der Chemie, (9): 857-62 (1990).

HCAPLUS Copyright 2006 ACS on STN, AN 1991:492679, Abstract of Huizenga et al., "Models of folate cofactors. 22. Lewis acid catalyzed cyclization of carbon-fragment transfer products of folate cofactor models. Synthesis of enantiomerically pure tetracyclic (ABCE) ring system of Aspidosperma alkaloids", Tetrahedron, 47(24): 4155-64 (1991).

HCAPLUS Copyright 2006 ACS on STN, AN 1991:558999, Abstract of Zhang et al., "Stereoselective synthesis of enantiomerically pure 3-acetyl-1,4,6,7,12,12b-hexahydroindolo-2, 3-quinolizine", Huaxue Tongbao, (6): 31-3 (1991).

HCAPLUS Copyright 2006 ACS on STN, AN 1991:583240, Abstract of Misztal et al., "Structure and spectral properties of β-carbolines. Part 4. Synthesis of the new ring system: 9,10,15,15b-tetrahydroindolo [1', 2': 4,3] pyrazino [2,1-a] carbolin-7 (6H)-one", Journal of the Chemical Society, Perkin Transactions 1: Organic and Bio-Organic Chemistry (1972-1999), (8): 1871-4 (1991).

HCAPLUS Copyright 2006 ACS on STN, AN 1991:62055, Abstract of Misztal et al., "Structure and spectral properties of β-carbolines. Part 3. Synthesis and stereochemistry of 1,2,3,4,6,7,9,10,15b,15c-decahydropyrido [1", 2": 1', 2'] pyrazino [4', 3': 1,2] pyrido [3, 4-b] indoles", Journal of the Chemical Society, Perkin Transactions 1: Organic and Bio-Organic Chemistry (1972-1999), (8): 2311-15 (1990).

HCAPLUS Copyright 2006 ACS on STN, AN 1992:448375, Abstract of Kawate et al., "New evidence for the presence of a spiroindolenium species in the Pictet-Spengler reaction", Heterocycles, 33(2): 801-11 (1992).

HCAPLUS Copyright 2006 ACS on STN, AN 1992:470107, Abstract of Qais et al., "Asymmetric syntheses of 1-alkyltetrahydro-β-carbolines and a 9-thio analog", Chemical & Pharmaceutical Bulletin, 39(12): 3338-40 (1991).
HCAPLUS Copyright 2006 ACS on STN, AN 1992:634323, Abstract of Wasserman et al., "Oxidation of Ylide Precursors to Vicinal Tricarbonyls. Applications in Vincamine Alkaloid Synthesis", Tetrahedron, 48(34): 7071-7082 (1992).
HCAPLUS Copyright 2006 ACS on STN, AN 1992:83990, Abstract of McNulty et al., "Diastereoselective Pictet-Spengler reactions of L-(Boc) prolinal: a biomimetic synthesis of eudistomins H and I, and woodinine", Tetrahedron Letters, 32(37): 4875-8 (1991).
HCAPLUS Copyright 2006 ACS on STN, AN 1993:409022, Abstract of Peng et al., "Synthesis of enantiomerically pure indoloquinolizine derivatives", Liebigs Annalen der Chemie, (2): 141-6 (1993).
HCAPLUS Copyright 2006 ACS on STN, AN 1993:603331, Abstract of Kawate et al., "Alkylation of 3,4-dihydro-β-carboline", Chemical & Pharmaceutical Bulletin, 41(2): 287-91 (1993).
HCAPLUS Copyright 2006 ACS on STN, AN 1994:135090, Abstract of Waldmann, et al., "Asymmetric Pictet-Spengler reactions employing amino acid esters as mediators of selectivity", Tetrahedron Letters, 34(37): 5867-70 (1993).
HCAPLUS Copyright 2006 ACS on STN, AN 1994:298503, Abstract of Lehmann et al., "Indoles. X. Synthesis, structure and D2-affinity of the β-carboline analog of flutroline", Archiv der Pharmazie (Weinheim, Germany), 326(12): 947-51 (1993).
HCAPLUS Copyright 2006 ACS on STN, AN 1994:557928, Abstract of McNulty et al., "Diastereoselective Pictet-Spengler reactions of L- (Boc) phenylalaninal and L- (Boc) prolinal: biomimetic syntheses of eudistomin T and (-) -woodinine", Journal of Chemical Society, Perkin Transactions 1: Organic and Bio-Organic Chemistry (1972-1999), (10): 1329-37 (1994).
HCAPLUS Copyright 2006 ACS on STN, AN 1995:202652, Abstract of Lehnert et al., "DNA topoisomerase II inhibition by substituted 1,2,3,4-tetrahydro-β-carboline derivatives", Bioorganic & Medicinal Chemistry Letters, 4(20): 2411-16 (1994).
HCAPLUS Copyright 2006 ACS on STN, AN 1995:347689, Abstract of Zhao et al., "Proton NMR and stereochemistry of synthetic indole alkaloids", Bopuxue Zazhi, 12(1): 71-8 (1995).
HCAPLUS Copyright 2006 ACS on STN, AN 1995:764144, Abstract of Loegers et al., "Mannich Biscyclizations. Total Synthesis of (-)-Ajmalicine", Journal of the American Chemical Society, 117(36): 9139-50 (1995).
HCAPLUS Copyright 2006 ACS on STN, AN 1995:957191, Abstract of Waldmann et al., "Asymmetric Pictet-Spengler reactions employing N, N-phthaloyl amino acids as chiral auxiliary groups", Angewandte Chemie, International Edition in English, 34(21): 2402-3 (1995).
HCAPLUS Copyright 2006 ACS on STN, AN 1996:268475, Abstract of Uematsu et al., "Asymmetric Transfer Hydrogenation of Imines", Journal of the American Chemical Society, 118(20): 4916-17 (1996).
Beilstein Copyright 2006 Beilstein MDL on STN, Beilstein Records (BRN): 9359112.
Beilstein Copyright 2006 Beilstein MDL on STN, Beilstein Records (BRN): 9345640.
Beilstein Copyright 2006 Beilstein MDL on STN, Beilstein Records (BRN): 9344461.
Beilstein Copyright 2006 Beilstein MDL on STN, Beilstein Records (BRN): 9342433.
Beilstein Copyright 2006 Beilstein MDL on STN, Beilstein Records (BRN): 9230699.
Beilstein Copyright 2006 Beilstein MDL on STN, Beilstein Records (BRN): 9162855.
Beilstein Copyright 2006 Beilstein MDL on STN, Beilstein Records (BRN): 9147336.
Beilstein Copyright 2006 Beilstein MDL on STN, Beilstein Records (BRN): 9145027.
Beilstein Copyright 2006 Beilstein MDL on STN, Beilstein Records (BRN): 9102751.
Beilstein Copyright 2006 Beilstein MDL on STN, Beilstein Records (BRN): 9101976.
Beilstein Copyright 2006 Beilstein MDL on STN, Beilstein Records (BRN): 9100379.
Beilstein Copyright 2006 Beilstein MDL on STN, Beilstein Records (BRN): 9100313.
Beilstein Copyright 2006 Beilstein MDL on STN, Beilstein Records (BRN): 9099224.
Beilstein Copyright 2006 Beilstein MDL on STN, Beilstein Records (BRN): 9097021.
Beilstein Copyright 2006 Beilstein MDL on STN, Beilstein Records (BRN): 9096422.
Beilstein Copyright 2006 Beilstein MDL on STN, Beilstein Records (BRN): 9093081.
Beilstein Copyright 2006 Beilstein MDL on STN, Beilstein Records (BRN): 8871444.
Beilstein Copyright 2006 Beilstein MDL on STN, Beilstein Records (BRN): 8870325.
Beilstein Copyright 2006 Beilstein MDL on STN, Beilstein Records (BRN): 8866741.
Beilstein Copyright 2006 Beilstein MDL on STN, Beilstein Records (BRN): 8817881.
Beilstein Copyright 2006 Beilstein MDL on STN, Beilstein Records (BRN): 8816950.
Beilstein Copyright 2006 Beilstein MDL on STN, Beilstein Records (BRN): 8816625.
Beilstein Copyright 2006 Beilstein MDL on STN, Beilstein Records (BRN): 8816426.
Beilstein Copyright 2006 Beilstein MDL on STN, Beilstein Records (BRN): 8816097.
Beilstein Copyright 2006 Beilstein MDL on STN, Beilstein Records (BRN): 8816032.
Beilstein Copyright 2006 Beilstein MDL on STN, Beilstein Records (BRN): 8816007.
Beilstein Copyright 2006 Beilstein MDL on STN, Beilstein Records (BRN): 8815946.
Beilstein Copyright 2006 Beilstein MDL on STN, Beilstein Records (BRN): 8815858.
Beilstein Copyright 2006 Beilstein MDL on STN, Beilstein Records (BRN): 8815758.
Beilstein Copyright 2006 Beilstein MDL on STN, Beilstein Records (BRN): 8815143.
Beilstein Copyright 2006 Beilstein MDL on STN, Beilstein Records (BRN): 8813808.
Beilstein Copyright 2006 Beilstein MDL on STN, Beilstein Records (BRN): 8813211.
Beilstein Copyright 2006 Beilstein MDL on STN, Beilstein Records (BRN): 8813188.
Beilstein Copyright 2006 Beilstein MDL on STN, Beilstein Records (BRN): 8813024.
Beilstein Copyright 2006 Beilstein MDL on STN, Beilstein Records (BRN): 8813017.
Beilstein Copyright 2006 Beilstein MDL on STN, Beilstein Records (BRN): 8812495.
Beilstein Copyright 2006 Beilstein MDL on STN, Beilstein Records (BRN): 8812493.
Beilstein Copyright 2006 Beilstein MDL on STN, Beilstein Records (BRN): 8811818.
Beilstein Copyright 2006 Beilstein MDL on STN, Beilstein Records (BRN): 8811580.
Beilstein Copyright 2006 Beilstein MDL on STN, Beilstein Records (BRN): 8811014.
Beilstein Copyright 2006 Beilstein MDL on STN, Beilstein Records (BRN): 8808882.
Beilstein Copyright 2006 Beilstein MDL on STN, Beilstein Records (BRN): 8808569.
Beilstein Copyright 2006 Beilstein MDL on STN, Beilstein Records (BRN): 8807751.
Beilstein Copyright 2006 Beilstein MDL on STN, Beilstein Records (BRN): 8806692.
Beilstein Copyright 2006 Beilstein MDL on STN, Beilstein Records (BRN): 8800981.
Beilstein Copyright 2006 Beilstein MDL on STN, Beilstein Records (BRN): 8665535.

Beilstein Copyright 2006 Beilstein MDL on STN, Beilstein Records (BRN): 8665534.
Beilstein Copyright 2006 Beilstein MDL on STN, Beilstein Records (BRN): 8644848.
Beilstein Copyright 2006 Beilstein MDL on STN, Beilstein Records (BRN): 8626861.
Beilstein Copyright 2006 Beilstein MDL on STN, Beilstein Records (BRN): 8462875.
HCAPLUS Copyright 2006 ACS on STN, Accession No. 2000:772630, Abstract of WO 2000/064897 A1, Macef et al. (Nov. 2, 2000).
HCAPLUS Copyright 2006 ACS on STN, Accession No. 2001:12443, Abstract of WO 2001/000610 A1, Aventis Pharma Deutschland GmbH (Jan. 4, 2001).
HCAPLUS Copyright 2006 ACS on STN, Accession No. 2001:338479, Abstract of WO 2001/032604 A1, University College London (May 10, 2001).
HCAPLUS Copyright 2006 ACS on STN, Accession No. 2001:62384, Abstract of EP 1 070 716 A1, Adir et Compagnie (Jan. 24, 2001).
HCAPLUS Copyright 2006 ACS on STN, Accession No. 2001:851157, Abstract of WO 2001/087882, Ortho-McNeil Pharmaceutical, Inc. (Nov. 22, 2001).
HCAPLUS Copyright 2006 ACS on STN, Accession No. 2002:275987, Abstract of WO 2002/028858 A2, Lilly Icos LLC (Apr. 11, 2002).
HCAPLUS Copyright 2006 ACS on STN, Accession No. 2002:408517, Abstract of WO 2002/041884, Pain Therapeutics, Inc. (May 30, 2002).
HCAPLUS Copyright 2006 ACS on STN, Accession No. 2002:615404, Abstract of WO 2002/062339 A1, Smithkline Beecham Corporation (Aug. 15, 2002).
HCAPLUS Copyright 2006 ACS on STN, Accession No. 2002:637677, Abstract of WO 2002/064591, Lilly Icos LLC, USA (Aug. 22, 2002).
HCAPLUS Copyright 2006 ACS on STN, Accession No. 2002:946116, Abstract of WO 2002/098428 A1, Lilly Icos LLC (Dec. 12, 2002).
HCAPLUS Copyright 2006 ACS on STN, Accession No. 2003:356232, Abstract of WO 2003/037310 A2, Pain Therapeutics, Inc. (May 8, 2003).
HCAPLUS Copyright 2006 ACS on STN, Accession No. 2003:356260, Abstract of WO 2003/037340 A1, Pain Therapeutics, Inc. (May 8, 2003).
HCAPLUS Copyright 2006 ACS on STN, Accession No. 2003:5960, Abstract of WO 2003/000691 A1, Lilly Icos Llc (Jan. 3, 2003).
HCAPLUS Copyright 2006 ACS on STN, Accession No. 2003:76556, Abstract of WO 2003/007888 A2, Adipogenix, Inc. (Jan. 30, 2003).
HCAPLUS Copyright 2006 ACS on STN, Accession No. 2004:1154677, Abstract of WO 2004/113300 A1, Ono Pharmaceutical Co., Ltd. (Dec. 29, 2004).
HCAPLUS Copyright 2006 ACS on STN, Accession No. 2004:41506, Abstract of WO 2004/005328 A2, Sigma-Tau Industrie Farmaceutiche Riunite S.p.A. (Jan. 15, 2004).
HCAPLUS Copyright 2006 ACS on STN, Accession No. 2004:965248, Abstract of WO 2004/096802, Oscient Pharmaceuticals et al. (Nov. 11, 2004).
HCAPLUS Copyright 2006 ACS on STN, Accession No. 2005:1106860, Abstract of WO 2005/095403, Intermune, Inc. (Oct. 13, 2005).
HCAPLUS Copyright 2006 ACS on STN, Accession No. 2005:371064, Abstract of WO 2005/037214, Intermune, Inc. et al. (Apr. 28, 2005).
HCAPLUS Copyright 2006 ACS on STN, Accession No. 2005:696910, Abstract of WO 2005/070930 A2, Chiron Corporation (Aug. 4, 2005).
HCAPLUS Copyright 2006 ACS on STN, Accession No. 2005:902862, Abstract of WO 2005/077912 A1, Mitsubishi Pharma Corporation (Aug. 25, 2005).
Jiang et al., "Potassium Superoxide as an Alternative Reagent for Winterfeldt Oxidation of β-Carbolines", Organic Letters, 5(1): 43-46 (2003).
List of Compounds from Registry Copyright 2006 ACS on STN.
Marpat Copyright 2006 ACS on STN, Accession No. 109:129416, Abstract of EP 0 272 056 A1, Harbor Branch Oceanographic Institution, Inc. (Jun. 22, 1988).
Marpat Copyright 2006 ACS on STN, Accession No. 116:235610, Abstract of EP 0 466 548 A1, Adir et Cie. (Jan. 15, 1992).
Marpat Copyright 2006 ACS on STN, Accession No. 116:256054, Abstract of WO 1992/000295 A1, Rorer International (Holdings), Inc. (Jan. 9, 1992).
Marpat Copyright 2006 ACS on STN, Accession No. 117:212969, Abstract of WO 1992/006108 A1, Polifarma S.p.A. (Apr. 16, 1992).
Marpat Copyright 2006 ACS on STN, Accession No. 117:234001, Abstract of JP 04173786 A2, Kawaken Fine Chemicals Co., Ltd. (Jun. 22, 1992).
Marpat Copyright 2006 ACS on STN, Accession No. 121:179566, Abstract of WO 1994/010175 A1, United States Dept. of Health and Human Services et al. (May 11, 1994).
Marpat Copyright 2006 ACS on STN, Accession No. 121:301326, Abstract of DE 42 43 496 A1, Boehringer Ingelheim KG (Mar. 10, 1994).
Marpat Copyright 2006 ACS on STN, Accession No. 122:106542, Abstract of WO 1994/014843 A1, Warner-Lambert Co. (Jul. 7, 1994).
Marpat Copyright 2006 ACS on STN, Accession No. 124:117997, Abstract of EP 0 675 112 A1, Bristol-Myers Squibb Co. (Oct. 4, 1995).
Marpat Copyright 2006 ACS on STN, Accession No. 124:203106, Abstract of WO 1995/030687, Boehringer Ingelheim KG et al. (Nov. 16, 1995).
Marpat Copyright 2006 ACS on STN, Accession No. 124:233150, Abstract of DE 44 45 939 A1, Boehringer Ingelheim KG (Nov. 9, 1995).
Marpat Copyright 2006 ACS on STN, Accession No. 124:290283, Abstract of CA 2143588, Bhide et al. (Sep. 25, 1995).
Marpat Copyright 2006 ACS on STN, Accession No. 124:344109, Abstract of EP 0 696 593 A2, Bristol-Myers Squibb Company (Feb. 14, 1996).
Marpat Copyright 2006 ACS on STN, Accession No. 125:33473, Abstract of WO 1996/003377 A1, Sankyo Co., Ltd. (Feb. 8, 1996).
Marpat Copyright 2006 ACS on STN, Accession No. 125:33651, Abstract of CA 2157998, Lilly Industries Ltd. (Mar. 13, 1996).
Marpat Copyright 2006 ACS on STN, Accession No. 129:260346, Abstract of WO 1998/040385 A1, Novo Nordisk A/S (Sep. 17, 1998).
Marpat Copyright 2006 ACS on STN, Accession No. 132:35702, Abstract of WO 1999/064420 A1, Societe De Conseils De Recherches Et D'applications Scientifiques S. A. (Dec. 16, 1999).
Marpat Copyright 2006 ACS on STN, Accession No. 132:88209, Abstract of WO 2000/002878 A1, University of Bristol (Jan. 20, 2000).
Marpat Copyright 2006 ACS on STN, Accession No. 133:247280, Abstract of WO 2000/056304, Harbor Branch Oceanographic Institution, Inc. et al. (Sep. 28, 2000).
Marpat Copyright 2006 ACS on STN, Accession No. 134:252660, Abstract of EP 1 086 947 A1, Pfizer Products Inc. (Mar. 28, 2001).
Marpat Copyright 2006 ACS on STN, Accession No. 134:56654, Abstract of WO 2000/077001 A1, Du Pont Pharmaceuticals Company (Dec. 21, 2000).
Marpat Copyright 2006 ACS on STN, Accession No. 134:56655, Abstract of WO 2000/077002 A1, Du Pont Pharmaceuticals Company (Dec. 21, 2000).
Marpat Copyright 2006 ACS on STN, Accession No. 134:56657, Abstract of WO 2000/077010 A2, Du Pont Pharmaceuticals Company (Dec. 21, 2000).
Marpat Copyright 2006 ACS on STN, Accession No. 135:371735, Abstract of WO 2001/087038, Ortho-McNeil Pharmaceutical, Inc. (Nov. 22, 2001).
Marpat Copyright 2006 ACS on STN, Accession No. 137:140432, Abstract of WO 2002/059129 A2, Bristol-Myers Squibb Company (Aug. 1, 2002).
Marpat Copyright 2006 ACS on STN, Accession No. 137:353008, Abstract of WO 2002/088123 A1, Lilly Icos LLC (Nov. 7, 2002).
Marpat Copyright 2006 ACS on STN, Accession No. 137:78864, Abstract of WO 2002/051842 A1, F. Hoffmann-La Roche A.-G. (Jul. 4, 2002).

Registry Copyright 2006 ACS on STN, Registry No. 335120-76-8.
Registry Copyright 2006 ACS on STN, Registry No. 335120-78-0.
Registry Copyright 2006 ACS on STN, Registry No. 335120-82-6.
Registry Copyright 2006 ACS on STN, Registry No. 335120-84-8.
Registry Copyright 2006 ACS on STN, Registry No. 335120-87-1.
Registry Copyright 2006 ACS on STN, Registry No. 335120-89-3.
Registry Copyright 2006 ACS on STN, Registry No. 335120-91-7.
Registry Copyright 2006 ACS on STN, Registry No. 335120-93-9.
Registry Copyright 2006 ACS on STN, Registry No. 335120-95-1.
Registry Copyright 2006 ACS on STN, Registry No. 335120-97-3.
Registry Copyright 2006 ACS on STN, Registry No. 335120-99-5.
Registry Copyright 2006 ACS on STN, Registry No. 335121-01-2.
Registry Copyright 2006 ACS on STN, Registry No. 335121-03-4.
Registry Copyright 2006 ACS on STN, Registry No. 335121-05-6.
Registry Copyright 2006 ACS on STN, Registry No. 335121-07-8.
Registry Copyright 2006 ACS on STN, Registry No. 335121-11-4.
Registry Copyright 2006 ACS on STN, Registry No. 335121-13-6.
Registry Copyright 2006 ACS on STN, Registry No. 335121-23-8.
Registry Copyright 2006 ACS on STN, Registry No. 335121-25-0.
Registry Copyright 2006 ACS on STN, Registry No. 335121-27-2.
Registry Copyright 2006 ACS on STN, Registry No. 335121-31-8.
Registry Copyright 2006 ACS on STN, Registry No. 335121-33-0.
Registry Copyright 2006 ACS on STN, Registry No. 335121-35-2.
Registry Copyright 2006 ACS on STN, Registry No. 335121-39-6.
Registry Copyright 2006 ACS on STN, Registry No. 335121-41-0.
Registry Copyright 2006 ACS on STN, Registry No. 335121-43-2.
Registry Copyright 2006 ACS on STN, Registry No. 335121-45-4.
Registry Copyright 2006 ACS on STN, Registry No. 335121-49-8.
Registry Copyright 2006 ACS on STN, Registry No. 336120-14-0.
Registry Copyright 2006 ACS on STN, Registry No. 336120-15-1.
Registry Copyright 2006 ACS on STN, Registry No. 336120-16-2.
Registry Copyright 2006 ACS on STN, Registry No. 336120-17-3.
Registry Copyright 2006 ACS on STN, Registry No. 336120-19-5.
Registry Copyright 2006 ACS on STN, Registry No. 336120-20-8.
Registry Copyright 2006 ACS on STN, Registry No. 336120-21-9.
Registry Copyright 2006 ACS on STN, Registry No. 336120-22-0.
Registry Copyright 2006 ACS on STN, Registry No. 336120-23-1.
Registry Copyright 2006 ACS on STN, Registry No. 336120-24-2.
Registry Copyright 2006 ACS on STN, Registry No. 336120-25-3.
Registry Copyright 2006 ACS on STN, Registry No. 336120-26-4.
Registry Copyright 2006 ACS on STN, Registry No. 336120-27-5.
Registry Copyright 2006 ACS on STN, Registry No. 336120-28-6.
Registry Copyright 2006 ACS on STN, Registry No. 336120-29-7.
Registry Copyright 2006 ACS on STN, Registry No. 336120-30-0.
Registry Copyright 2006 ACS on STN, Registry No. 336120-31-1.
Registry Copyright 2006 ACS on STN, Registry No. 336120-33-3.
Registry Copyright 2006 ACS on STN, Registry No. 337317-89-2.
Registry Copyright 2006 ACS on STN, Registry No. 337317-92-7.
Registry Copyright 2006 ACS on STN, Registry No. 337317-95-0.
Beilstein Copyright 2006 Beilstein MDL on STN, Beilstein Records (BRN): 7148211.
Beilstein Copyright 2006 Beilstein MDL on STN, Beilstein Records (BRN): 7145754.
Beilstein Copyright 2006 Beilstein MDL on STN, Beilstein Records (BRN): 7071896.
Beilstein Copyright 2006 Beilstein MDL on STN, Beilstein Records (BRN): 7071895.
Beilstein Copyright 2006 Beilstein MDL on STN, Beilstein Records (BRN): 7071528.
Beilstein Copyright 2006 Beilstein MDL on STN, Beilstein Records (BRN): 7066532.
Beilstein Copyright 2006 Beilstein MDL on STN, Beilstein Records (BRN): 7066215.
Beilstein Copyright 2006 Beilstein MDL on STN, Beilstein Records (BRN): 7065599.
Beilstein Copyright 2006 Beilstein MDL on STN, Beilstein Records (BRN): 7062671.
Beilstein Copyright 2006 Beilstein MDL on STN, Beilstein Records (BRN): 7061800.
Beilstein Copyright 2006 Beilstein MDL on STN, Beilstein Records (BRN): 6885612.
Beilstein Copyright 2006 Beilstein MDL on STN, Beilstein Records (BRN): 6490207.
Beilstein Copyright 2006 Beilstein MDL on STN, Beilstein Records (BRN): 5915066.
Beilstein Copyright 2006 Beilstein MDL on STN, Beilstein Records (BRN): 5914990.
Beilstein Copyright 2006 Beilstein MDL on STN, Beilstein Records (BRN): 5897211.
Beilstein Copyright 2006 Beilstein MDL on STN, Beilstein Records (BRN): 5891878.
Beilstein Copyright 2006 Beilstein MDL on STN, Beilstein Records (BRN): 5679522.
Beilstein Copyright 2006 Beilstein MDL on STN, Beilstein Records (BRN): 5176764.
Beilstein Copyright 2006 Beilstein MDL on STN, Beilstein Records (BRN): 5140134.
Beilstein Copyright 2006 Beilstein MDL on STN, Beilstein Records (BRN): 5134348.
Beilstein Copyright 2006 Beilstein MDL on STN, Beilstein Records (BRN): 4895148.
Beilstein Copyright 2006 Beilstein MDL on STN, Beilstein Records (BRN): 4762626.
Beilstein Copyright 2006 Beilstein MDL on STN, Beilstein Records (BRN): 4635034.
Beilstein Copyright 2006 Beilstein MDL on STN, Beilstein Records (BRN): 4620668.
Beilstein Copyright 2006 Beilstein MDL on STN, Beilstein Records (BRN): 4617494.
Beilstein Copyright 2006 Beilstein MDL on STN, Beilstein Records (BRN): 4604797.
Beilstein Copyright 2006 Beilstein MDL on STN, Beilstein Records (BRN): 4213069.
Beilstein Copyright 2006 Beilstein MDL on STN, Beilstein Records (BRN): 1206456.
Beilstein Copyright 2006 Beilstein MDL on STN, Beilstein Records (BRN): 1206372.
Beilstein Copyright 2006 Beilstein MDL on STN, Beilstein Records (BRN): 942566.
Beilstein Copyright 2006 Beilstein MDL on STN, Beilstein Records (BRN): 850369.
Beilstein Copyright 2006 Beilstein MDL on STN, Beilstein Records (BRN): 845560.
Beilstein Copyright 2006 Beilstein MDL on STN, Beilstein Records (BRN): 843324.
Beilstein Copyright 2006 Beilstein MDL on STN, Beilstein Records (BRN): 592929.
Beilstein Copyright 2006 Beilstein MDL on STN, Beilstein Records (BRN): 382858.
Beilstein Copyright 2006 Beilstein MDL on STN, Beilstein Records (BRN): 382697.
Beilstein Copyright 2006 Beilstein MDL on STN, Beilstein Records (BRN): 382603.
Beilstein Copyright 2006 Beilstein MDL on STN, Beilstein Records (BRN): 382449.
Beilstein Copyright 2006 Beilstein MDL on STN, Beilstein Records (BRN): 360771.
Beilstein Copyright 2006 Beilstein MDL on STN, Beilstein Records (BRN): 356831.
Beilstein Copyright 2006 Beilstein MDL on STN, Beilstein Records (BRN): 326903.
Beilstein Copyright 2006 Beilstein MDL on STN, Beilstein Records (BRN): 309045.
Beilstein Copyright 2006 Beilstein MDL on STN, Beilstein Records (BRN): 297782.
Beilstein Copyright 2006 Beilstein MDL on STN, Beilstein Records (BRN): 264050.
Beilstein Copyright 2006 Beilstein MDL on STN, Beilstein Records (BRN): 263250.
Beilstein Copyright 2006 Beilstein MDL on STN, Beilstein Records (BRN): 9977461.
Beilstein Copyright 2006 Beilstein MDL on STN, Beilstein Records (BRN): 9977460.
Beilstein Copyright 2006 Beilstein MDL on STN, Beilstein Records (BRN): 930285.

Beilstein Copyright 2006 Beilstein MDL on STN, Beilstein Records (BRN): 927125.
Beilstein Copyright 2006 Beilstein MDL on STN, Beilstein Records (BRN): 900708.
Marpat Copyright 2006 ACS on STN, Accession No. 138:11447, Abstract of WO 2002/098875 A1, Lilly Icos LLC (Dec. 12, 2002).
Marpat Copyright 2006 ACS on STN, Accession No. 138:338490, Abstract of WO 2003/033496 A1, Transtech Pharma, Inc. (Apr. 24, 2003).
Marpat Copyright 2006 ACS on STN, Accession No. 139:395821, Abstract of WO 2003/095427 A1, Taisho Pharmaceutical Co., Ltd. (Nov. 20, 2003).
Marpat Copyright 2006 ACS on STN, Accession No. 141:379919, Abstract of WO 2004/092123, Microbia, Inc. (Oct. 28, 2004).
Marpat Copyright 2006 ACS on STN, Accession No. 142:162053, Abstract of FR 2857581 A1, Institut Europeen Biologie Cellulaire (Jan. 21, 2005).
Marpat Copyright 2006 ACS on STN, Accession No. 142:411220, Abstract of CN 1472209, Fuda University (Feb. 4, 2004).
Marpat Copyright 2006 ACS on STN, Accession No. 94:139825, Abstract of JP 55104282 A2, Synthelabo S. A. (Aug. 9, 1980).
Mohan et al., "Pictet-Spengler reaction of solid support: synthesis of 1,2,3,4-tetrahydro-β-carboline libraries", Tetrahedron Letters, 37(23): 3963-3966 (1996).
Neipp et al., "Synthesis of Bridged Azabicyclic Structures via Ring-Closing Olefin Metathesis," J. Org. Chem., 68:8867-8878 (2003).
Registry Copyright 2006 ACS on STN, Registry No. 97405-15-7.
Registry Copyright 2006 ACS on STN, Registry No. 865678-67-7.
Registry Copyright 2006 ACS on STN, Registry No. 289656-58-2.
Registry Copyright 2006 ACS on STN, Registry No. 289656-60-6.
Registry Copyright 2006 ACS on STN, Registry No. 334490-33-4.
Registry Copyright 2006 ACS on STN, Registry No. 334490-34-5.
Registry Copyright 2006 ACS on STN, Registry No. 334490-35-6.
Registry Copyright 2006 ACS on STN, Registry No. 335094-02-5.
Registry Copyright 2006 ACS on STN, Registry No. 335094-03-6.
Registry Copyright 2006 ACS on STN, Registry No. 335094-04-7.
Registry Copyright 2006 ACS on STN, Registry No. 335094-06-9.
Registry Copyright 2006 ACS on STN, Registry No. 335094-07-0.
Registry Copyright 2006 ACS on STN, Registry No. 335094-08-1.
Registry Copyright 2006 ACS on STN, Registry No. 335094-09-2.
Registry Copyright 2006 ACS on STN, Registry No. 335094-11-6.
Registry Copyright 2006 ACS on STN, Registry No. 335094-12-7.
Registry Copyright 2006 ACS on STN, Registry No. 335094-13-8.
Registry Copyright 2006 ACS on STN, Registry No. 335094-14-9.
Registry Copyright 2006 ACS on STN, Registry No. 335094-15-0.
Registry Copyright 2006 ACS on STN, Registry No. 335094-17-2.
Registry Copyright 2006 ACS on STN, Registry No. 335094-20-7.
Registry Copyright 2006 ACS on STN, Registry No. 335094-21-8.
Registry Copyright 2006 ACS on STN, Registry No. 335094-22-9.
Registry Copyright 2006 ACS on STN, Registry No. 335094-23-0.
Registry Copyright 2006 ACS on STN, Registry No. 335094-24-1.
Registry Copyright 2006 ACS on STN, Registry No. 335094-25-2.
Registry Copyright 2006 ACS on STN, Registry No. 335094-26-3.
Registry Copyright 2006 ACS on STN, Registry No. 335094-27-4.
Registry Copyright 2006 ACS on STN, Registry No. 335094-29-6.
Registry Copyright 2006 ACS on STN, Registry No. 335094-31-0.
Registry Copyright 2006 ACS on STN, Registry No. 335120-54-2.
Registry Copyright 2006 ACS on STN, Registry No. 335120-56-4.
Registry Copyright 2006 ACS on STN, Registry No. 335120-58-6.
Registry Copyright 2006 ACS on STN, Registry No. 335120-60-0.
Registry Copyright 2006 ACS on STN, Registry No. 335120-62-2.
Registry Copyright 2006 ACS on STN, Registry No. 335120-64-4.
Registry Copyright 2006 ACS on STN, Registry No. 335120-66-6.
Registry Copyright 2006 ACS on STN, Registry No. 335120-68-8.
Registry Copyright 2006 ACS on STN, Registry No. 335120-72-4.
Registry Copyright 2006 ACS on STN, Registry No. 335120-74-6.
Beilstein Copyright 2006 Beilstein MDL on STN, Beilstein Records (BRN): 8455070.
Beilstein Copyright 2006 Beilstein MDL on STN, Beilstein Records (BRN): 8454267.
Beilstein Copyright 2006 Beilstein MDL on STN, Beilstein Records (BRN): 8454265.
Beilstein Copyright 2006 Beilstein MDL on STN, Beilstein Records (BRN): 8454264.
Beilstein Copyright 2006 Beilstein MDL on STN, Beilstein Records (BRN): 8453888.
Beilstein Copyright 2006 Beilstein MDL on STN, Beilstein Records (BRN): 8453887.
Beilstein Copyright 2006 Beilstein MDL on STN, Beilstein Records (BRN): 8453886.
Beilstein Copyright 2006 Beilstein MDL on STN, Beilstein Records (BRN): 8453110.
Beilstein Copyright 2006 Beilstein MDL on STN, Beilstein Records (BRN): 8450993.
Beilstein Copyright 2006 Beilstein MDL on STN, Beilstein Records (BRN): 8448477.
Beilstein Copyright 2006 Beilstein MDL on STN, Beilstein Records (BRN): 8448341.
Beilstein Copyright 2006 Beilstein MDL on STN, Beilstein Records (BRN): 8445916.
Beilstein Copyright 2006 Beilstein MDL on STN, Beilstein Records (BRN): 8442395.
Beilstein Copyright 2006 Beilstein MDL on STN, Beilstein Records (BRN): 8439487.
Beilstein Copyright 2006 Beilstein MDL on STN, Beilstein Records (BRN): 8437234.
Beilstein Copyright 2006 Beilstein MDL on STN, Beilstein Records (BRN): 8434528.
Beilstein Copyright 2006 Beilstein MDL on STN, Beilstein Records (BRN): 8432032.
Beilstein Copyright 2006 Beilstein MDL on STN, Beilstein Records (BRN): 8372543.
Beilstein Copyright 2006 Beilstein MDL on STN, Beilstein Records (BRN): 8372542.
Beilstein Copyright 2006 Beilstein MDL on STN, Beilstein Records (BRN): 8360332.
Beilstein Copyright 2006 Beilstein MDL on STN, Beilstein Records (BRN): 8355677.
Beilstein Copyright 2006 Beilstein MDL on STN, Beilstein Records (BRN): 8228273.
Beilstein Copyright 2006 Beilstein MDL on STN, Beilstein Records (BRN): 8222993.
Beilstein Copyright 2006 Beilstein MDL on STN, Beilstein Records (BRN): 8081712.
Beilstein Copyright 2006 Beilstein MDL on STN, Beilstein Records (BRN): 8079036.
Beilstein Copyright 2006 Beilstein MDL on STN, Beilstein Records (BRN): 8075760.
Beilstein Copyright 2006 Beilstein MDL on STN, Beilstein Records (BRN): 8021716.
Beilstein Copyright 2006 Beilstein MDL on STN, Beilstein Records (BRN): 8019500.
Beilstein Copyright 2006 Beilstein MDL on STN, Beilstein Records (BRN): 8016588.
Beilstein Copyright 2006 Beilstein MDL on STN, Beilstein Records (BRN): 8011654.
Beilstein Copyright 2006 Beilstein MDL on STN, Beilstein Records (BRN): 7866702.
Beilstein Copyright 2006 Beilstein MDL on STN, Beilstein Records (BRN): 7866701.
Beilstein Copyright 2006 Beilstein MDL on STN, Beilstein Records (BRN): 7755570.
Beilstein Copyright 2006 Beilstein MDL on STN, Beilstein Records (BRN): 7742795.
Beilstein Copyright 2006 Beilstein MDL on STN, Beilstein Records (BRN): 7742792.
Beilstein Copyright 2006 Beilstein MDL on STN, Beilstein Records (BRN): 7742791.
Beilstein Copyright 2006 Beilstein MDL on STN, Beilstein Records (BRN): 7679040.
Beilstein Copyright 2006 Beilstein MDL on STN, Beilstein Records (BRN): 7676206.
Beilstein Copyright 2006 Beilstein MDL on STN, Beilstein Records (BRN): 7675004.

Beilstein Copyright 2006 Beilstein MDL on STN, Beilstein Records (BRN): 7674764.
Beilstein Copyright 2006 Beilstein MDL on STN, Beilstein Records (BRN): 7671562.
Beilstein Copyright 2006 Beilstein MDL on STN, Beilstein Records (BRN): 7662538.
Beilstein Copyright 2006 Beilstein MDL on STN, Beilstein Records (BRN): 7659004.
Beilstein Copyright 2006 Beilstein MDL on STN, Beilstein Records (BRN): 7652157.
Beilstein Copyright 2006 Beilstein MDL on STN, Beilstein Records (BRN): 7470167.
Beilstein Copyright 2006 Beilstein MDL on STN, Beilstein Records (BRN): 7470143.
Beilstein Copyright 2006 Beilstein MDL on STN, Beilstein Records (BRN): 7470039.
Beilstein Copyright 2006 Beilstein MDL on STN, Beilstein Records (BRN): 7469940.
Beilstein Copyright 2006 Beilstein MDL on STN, Beilstein Records (BRN): 7402634.
Beilstein Copyright 2006 Beilstein MDL on STN, Beilstein Records (BRN): 7398947.
Beilstein Copyright 2006 Beilstein MDL on STN, Beilstein Records (BRN): 720845.
Beilstein Copyright 2006 Beilstein MDL on STN, Beilstein Records (BRN): 697548.
Beilstein Copyright 2006 Beilstein MDL on STN, Beilstein Records (BRN): 264804.
Beilstein Copyright 2006 Beilstein MDL on STN, Beilstein Records (BRN): 315587.
Beilstein Copyright 2006 Beilstein MDL on STN, Beilstein Records (BRN): 368153.
Beilstein Copyright 2006 Beilstein MDL on STN, Beilstein Records (BRN): 678238.
Beilstein Copyright 2006 Beilstein MDL on STN, Beilstein Records (BRN): 689657.
Beilstein Copyright 2006 Beilstein MDL on STN, Beilstein Records (BRN): 694521.
Beilstein Copyright 2006 Beilstein MDL on STN, Beilstein Records (BRN): 723806.
Beilstein Copyright 2006 Beilstein MDL on STN, Beilstein Records (BRN): 730528.
Beilstein Copyright 2006 Beilstein MDL on STN, Beilstein Records (BRN): 941361.
Birman et al., "A novel route to the geissoschizine skeleton: the influence of ligands on the diastereoselectivity of the Heck cyclization", Tetrahedron Letters, 39(40): 7219-7222 (1998).
CAPLUS Copyright 2006 ACS on STN, Accession No. 1964:404361, Abstract of Antonaccio et al., "Recent progress in Aspidosperma alkaloids", Anais da Associacao Brasileira de Quimica, 21: 31-7 (1962).
CAPLUS Copyright 2006 ACS on STN, Accession No. 1964:52704, Abstract of Taborsky et al., "Synthesis and preliminary pharmacology of some 9H-pyrido [3,4-b] indoles (β-carbolines) and tryptamines related to serotonin and melatonin", Journal of Medicinal Chemistry, 7(2): 135-41 (1964).
CAPLUS Copyright 2006 ACS on STN, Accession No. 1981:84336, Abstract of Afza et al., "Some new derivatives of tetrahydroharmine", Pakistan Journal of Scientific and Industrial Research, 22(6): 290-2 (1979).
CAPLUS Copyright 2006 ACS on STN, Accession No. 1988:5744, Abstract of O'Malley et al., "Tremorgenic mycotoxins. Synthesis of 6-demethoxyfumitremorgin B", Tetrahedron Letters, 28(11): 1131-4 (1987).
CAPLUS Copyright 2006 ACS on STN, Accession No. 1991:471974, Abstract of Jean et al., "Heteroyohimbine-type indole alkaloids: synthesis of a key intermediate of (+) -ajmalicine from carbohydrates and tryptamine", Discovery and Innovation, 2(3): 42-50 (1990).
CAPLUS Copyright 2006 ACS on STN, Accession No. 1994:481198, Abstract of Herraiz et al., "Separation and characterization of 1,2,3,4-tetrahydro-β-carboline-3-carboxylic acids by HPLC and GC-MS. Identification in wine samples", American Journal of Enology and Viticulture, 45(1): 92-101 (1994).
CAPLUS Copyright 2006 ACS on STN, Accession No. 1995:957085, Abstract of Peters et al., "Endogenous alkaloids in man. Part 24. 2-Trifluoroacetyl-1-methyl-1,2,3,4-tetrahydro-β-carboline, a gas chromatographically useful derivative of the mammalian alkaloid eleagnine", Zeitschrift fuer Naturforschung, B: Chemical Sciences, 50(10): 1564-5 (1995).
CAPLUS Copyright 2006 ACS on STN, Accession No. 1996:127543, Abstract of Pellegrini et al., "Total synthesis of (+)-elacomine and (-) -isoelacomine, two hitherto unnamed oxindole alkaloids from Elaeagnus commutata", Helvetica Chimica Acta, 79(1): 151-68 (1996).
CAPLUS Copyright 2006 ACS on STN, Accession No. 1997:311459, Abstract of Herraiz, T., "Analysis of tetrahydro-β-carbolines and their precursors by electron ionization mass spectrometry. Identification in foodstuffs by gas chromatography/mass spectrometry", Rapid Communications in Mass Spectrometry, 11(7): 762-768 (1997).
CAPLUS Copyright 2006 ACS on STN, Accession No. 1997:303146, Abstract of Tietze et al., "Efficient biomimetic synthesis of indole alkaloids of the vallesiachotamine group by domino Knoevenagel hetero Diels-Alder hydrogenation sequence", Liebigs Annalen/Recueil, (5): 881-886 (1997).
CAPLUS Copyright 2006 ACS on STN, Accession No. 1998:229659, Abstract of Madrigal et al., "Sterereocontrolled Synthesis of 3,6-Dimethyl-2,3,6,7,12,12a-hexahydropyrazino[1,2-b]β-carboline-1,4-diones", Journal of Organic Chemistry, 63(8): 2724-2727 (1998).
CAPLUS Copyright 2006 ACS on STN, Accession No. 1999:726418, Abstract of Itoh et al., "A novel synthesis of chiral 1-allyl-1,2,3,4-tetrahydro-β-carboline employing allyltributyltin and chiral acyl chlorides", Synlett, (11): 1799-1801 (1999).
CAPLUS Copyright 2006 ACS on STN, Accession No. 2003:829870, Abstract of Itoh et al., "Proline-Catalyzed Asymmetric Addition Reaction of 9-Tosyl-3,4-dihydro-β-carboline with Ketones", Organic Letters, 5(23): 4301-4304 (2003).
CAPLUS Copyright 2006 ACS on STN, Accession No. 2003:689601, Abstract of Santos et al., "A novel asymmetric reduction of dihydro-β-carboline derivatives using calix[6]arene/chiral amine as a host complex", Tetrahedron: Asymmetry, 14(17): 2515-2519 (2003).
CAPLUS Copyright 2006 ACS on STN, Accession No. 2003:545316, Abstract of Takayama et al., "First Asymmetric Total Synthesis of Us-7 and -8, Novel D-seco Corynanthe-Type Oxindole Alkaloids from Uncaria attenuata: Structure Revision of Us-7 and Determination of Absolute Stereochemistry", Organic Letters, 5(16): 2967-2970 (2003).
CAPLUS Copyright 2006 ACS on STN, Accession No. 2004:164526, Abstract of Itoh et al., "Syntheses of 1,2,3,4,6,7,12,12b-octahydroindolo [2,3-a]quinolizine and harmicine using a chiral 1-allyl-1,2,3,4-tetrahydro-β-carboline as the starting material", Heterocycles, 63(3): 655-661 (2004).
CAPLUS Copyright 2006 ACS on STN, Accession No. 2004:752104, Abstract of Toscano et al., "Alkaloids and Diterpenes From Croton moritibensis", Pharmaceutical Biology (Lisse, Netherlands), 42(1): 62-67 (2004).
CAPLUS Copyright 2006 ACS on STN, Accession No. 2005:208078, Abstract of Milen et al., "Studies on stereoselective approaches to β-carboline derivatives", Central European Journal of Chemistry, 3(1): 118-136 (2005).
CAPLUS Copyright 2006 ACS on STN, Accession No. 1960:103442, Abstract of Kanaok, Yuichi, "Applications of the Robinson dehydrogenation reaction. IV. Oxidation of some tetrahydro-β-carboline derivs", Chemical & Pharmaceutical Bulletin, 7: 597-601 (1959).
CAPLUS Copyright 2006 ACS on STN, Accession No. 1980:586630, Abstract of Campos et al., "Selenium dioxide oxidations in the β-carboline area", Heterocycles, 14(7): 975-84 (1980).
CAPLUS Copyright 2006 ACS on STN, Accession No. 1981:567018 Beck et al., "Analysis of 1-methyl-1,2,3,4-tetrahydro-β-carboline in alcoholic beverages", Food and Cosmetics Toxicology, 19(2): 173-7 (1981).

CAPLUS Copyright 2006 ACS on STN, Accession No. 1982:523372, Abstract of Allen et al., "Analysis of 1-methyl-1,2,3,4-tetrahydro-β-carboline by GC/MS using deuterium-labeled internal standards", Analytical Chemistry Symposia Series, 11(Stable Isot.): 611-16 (1982).

CAPLUS Copyright 2006 ACS on STN, Accession No. 1982:598438, Abstract of Cain et al., "Dichlorodicyanoquinone oxidations in the indole area. Synthesis of crenatine", Journal of Organic Chemistry, 47(25): 4933-6 (1982).

CAPLUS Copyright 2006 ACS on STN, Accession No. 1983:160991, Abstract of Cain et al., "Selenium dioxide oxidations in the indole area. Synthesis of β-carboline alkaloids", Journal of the American Chemical Society, 105(4): 907-13 (1983).

CAPLUS Copyright 2006 ACS on STN, Accession No. 1983:198514, Abstract of Siddiqui et al., "Studies in harmine series of alkaloids. Part 1. Derivatives of tetrahydroharmine", Pakistan Journal of Scientific and Industrial Research, 25(5): 147-52 (1982).

CAPLUS Copyright 2006 ACS on STN, Accession No. 1996:494549, Abstract of Nakamura et al., "Enantioselective Allylzincation of Cyclic Aldimines in the Presence of Anionic Bis-oxazoline Ligand", Journal of the American Chemical Society, 118(35): 8489-8490 (1996).

CAPLUS Copyright 2006 ACS on STN, Accession No. 2005:240075, Abstract of Roszkowski et al., "Enantioselective synthesis of 1-substituted tetrahydro-β-carboline derivatives via asymmetric transfer hydrogenation", Journal of Molecular Catalysis A: Chemical, 232(1-2): 143-149 (2005).

CAPLUS Copyright 2006 ACS on STN, Accession No. 1930:788, Abstract of Tatsui, G., "Synthesis of carboline derivatives. II", Yakugaku Zasshi, 49: 749-58 (1929).

CAPLUS Copyright 2006 ACS on STN, Accession No. 1930:789, Abstract of Zelinskii et al., "Decomposition of cholesterylene and of cholesteryl ether with aluminum chloride", Ber. 62b: 2199-2202 (1929).

CAPLUS Copyright 2006 ACS on STN, Accession No. 1964:16683, deStevens et al., "Heterocycles. XIV. 2-and3-Azaoctahydroindolo [2,3-a]quinolizines", Journal of Organic Chemistry, 28(11): 3210-12 (1963).

CAPLUS Copyright 2006 ACS on STN, Accession No. 1964:404362 Abdusalamov et al., "Some derivatives of tetrahydroharman", Uzbekskii Khimicheskii Zhurnal, 8(1): 48-50 (1964).

CAPLUS Copyright 2006 ACS on STN, Accession No. 1965:23665, Abstract of Lefer et al., "Potentiation of the cardiovascular effects of norepinephrine by a tetrahydro-β-carboline", Archives Internationales de Pharmacodynamie et de Therapie, 151(3-4): 383-93 (1964).

CAPLUS Copyright 2006 ACS on STN, Accession No. 1965:446445, Abstract of Trojanek et al., "Absolute configuration of vincamine and some other alkaloids of the eburnamine type", Chemistry & Industry (London, United Kingdom), (28): 1261 (1965).

CAPLUS Copyright 2006 ACS on STN, Accession No. 1966:499526, Abstract of Potier et al., "Alkaloids of *Cinchona ledgeriana* leaves. II. Structure of cinschophyllamine and isocinchophyllamine", Bulletin de la Societe Chimique de France, (7): 2309-15 (1966).

CAPLUS Copyright 2006 ACS on STN, Accession No. 1967:473734, Abstract of Abdusalamov et al., "Some tetrahydroharman derivatives", Nauchnye Trudy-Tashkentskii Gosudarstvennyi Universitet im. V. I. Lenina, 286: 76-9 (1966).

CAPLUS Copyright 2006 ACS on STN, Accession No. 1968:95725 McIsaac et al., "Chromatography of β-carbolines", Journal of Chromatography, 31(2): 446-54 (1967).

CAPLUS Copyright 2006 ACS on STN, Accession No. 1979:152436, Abstract of Oikawa et al., "Synthesis of oxidized diketopiperazine alkaloids by the selective oxidation of C-3 side chains of indoles", Tennen Yuki Kagobutsu Toronkai Koen Yoshishu, 21st, 22-7 (1978).

CAPLUS Copyright 2006 ACS on STN, Accession No. 1988:56414, Abstract of Bailey et al., "Synthesis of 3-(2-indolyl)propenoate derivatives of tryptamine, valuable intermediates for the preparation of indole alkaloids", Tetrahedron Letters, 28(25): 2879-82 (1987).

CAPLUS Copyright 2006 ACS on STN, Accession No. 1989:173526, Abstract of Somei et al., "The chemistry of indoles. XLV. A convenient synthetic method of 2-substituted indoles and its application for the synthesis of natural alkaloid, borrerine", Heterocycles, 27(7): 1585-7 (1988).

CAPLUS Copyright 2006 ACS on STN, Accession No. 1998:710496, Abstract of Ottoni et al., "Efficient and simple methods for the introduction of the sulfonyl, acyl, and alkyl protecting groups on the nitrogen of indole and its derivatives", Tetrahedron, 54(46): 13915-13928 (1998).

CAPLUS Copyright 2006 ACS on STN, Accession No. 1999:655036, Abstract of Zhao et al., "Synthesis of 6-amino-acid-substituted 4,6,7,12-tetrahydro-4-oxoindolo [2,3-α]quinolizines", Journal fuer Praktische Chemie (Weinheim, Germany), 341(7): 691-694 (1999).

CAPLUS Copyright 2006 ACS on STN, Accession No. 2000:659238, Abstract of Bringmann et al., "Endogenous alkaloids in man Part 36, chemical modification of the mitochondrial complex I inhibitor 1-trichloromethyl-1,2,3,4-tetrahydro-β-carboline: synthesis and evaluation of N-alkanoyl derivatives", Zeitschrift fuer Naturforschung, C: Journal of Biosciences, 55(7/8): 620-630 (2000).

CAPLUS Copyright 2006 ACS on STN, Accession No. 2001:615283, Abstract of Itoh et al., "Preparation of both enantiomers of 1-allyl-1,2,3,4-tetrahydro-β-carboline using allyltin reagents and a chiral auxiliary derived from L-proline", Tetrahedron, 57(34): 7277-7289 (2001).

CAPLUS Copyright 2006 ACS on STN, Accession No. 2002:928751, Abstract of Itoh et al., "Concise syntheses of harmicine and a pyrrolidino-isoquinoline derivative using chiral 1-allyl adducts of β-carboline and isoquinoline as starting materials", Heterocycles, 58: 115-118 (2002).

CAPLUS Copyright 2006 ACS on STN, Accession No. 2003:190790, Abstract of Fekete et al., "Comparative study on separation of diastereomers by HPLC", Chromatographia, 57(3/4): 147-153 (2003).

CAPLUS Copyright 2006 ACS on STN, Accession No. 2004:1128008, Abstract of Ohba et al., "Synthesis of Na-demthyl-20-deethylsuaveoline, the structure proposed for sellowiine", Heterocycles, 63(12): 2845-2850 (2004).

CAPLUS Copyright 2006 ACS on STN, Accession No. 2005:226859, Abstract of Danieli et al., "Combinatorial Solid-Phase Synthesis of 6-Hydroxy-1,2,3,4-tetrahydro-β-carbolines from L-5-Hydroxytroptophan", Journal of Combinatorial Chemistry, 7(3): 458-462 (2005).

CAPLUS Copyright 2006 ACS on STN, Accession No. 2005:443867, Abstract of Kinderman et al., "Catalytic N-Sulfonyliminium Ion-Mediated Cyclizations to a α-Vinyl-Substituted Isoquinolines and β-Carbolines and Applications in Metathesis", Journal of Organic Chemistry, 70(14): 5519-5527 (2005).

CAPLUS Copyright 2006 ACS on STN, Accession No. 2005:502638, Abstract of Nagata et al., "Cross-metathesis of 1-allylated β-carboline and isoquinoline derivatives", Heterocycles, 65(6):1283-1287.

CAPLUS Copyright 2006 ACS on STN, Accession No. 2005:640103, Abstract of Takasu et al., "Synthesis and evaluation of β-carbolinium cations as new antimalarial agents based on pi-delocalized lipophilic cation (DLC) hypothesis", Chemical & Pharmaceutical Bulletin, 53(6): 653-661 (2005).

Chemcats Copyright 2006 ACS on STN, Accession No. 2006:455990.

Chemcats Copyright 2006 ACS on STN, Accession No. 1999: 170837.

Chemcats Copyright 2006 ACS on STN, Accession No. 2004: 1704901.

Chemcats Copyright 2006 ACS on STN, Accession No. 2004: 2860460.

Chemcats Copyright 2006 ACS on STN, Accession No. 2004: 3826780.

Chemcats Copyright 2006 ACS on STN, Accession No. 2005: 1150844.

Chemcats Copyright 2006 ACS on STN, Accession No. 2005: 1418898.

Chemcats Copyright 2006 ACS on STN, Accession No. 2005: 1937218.
Chemcats Copyright 2006 ACS on STN, Accession No. 2005: 2670194.
Chemcats Copyright 2006 ACS on STN, Accession No. 2005: 3598258.
Chemcats Copyright 2006 ACS on STN, Accession No. 2005: 464357.
Chemcats Copyright 2006 ACS on STN, Accession No. 2005: 691695.
Song et al., "β-Carbolines as Specific Inhibitors of Cyclin-Dependent Kinases," Bioorg. Med. Chem. Lett., 12:1129-1132 (2002).
Cleaveland et al., "Identification of a novel inhibitor (NSC 665564) of dihydroorotate dehydrogenase with a potency equivalent to brequinar", Biochemical and Biophysical Research Communications, 223(3): 654-659 (1996).
Freter et al., "Reactions of 1-aryl-1,2,3,4-tetrahydro-β-carbolines in acid solution", Justus Liebigs Annalen der Chemie, 684: 159-87 (1965).
HCA Copyright 2006 ACS on STN, Accession No. 114:42770, Abstract of EP 0 380 155 A1, Duphar International Research B. V. (Aug. 1, 1990).
HCA Copyright 2006 ACS on STN, Accession No. 116:207832, Abstract of EP 0 468 789 A2, Merck Frosst Canada Inc. (Jan. 29, 1992).
HCA Copyright 2006 ACS on STN, Accession No. 127:149080, Abstract of WO 1997/023458 A1, Warner-Lambert Company et al. (Jul. 3, 1997).
HCA Copyright 2006 ACS on STN, Accession No. 136:325823, Abstract of WO 2002/030421, Curis, Inc. (Apr. 18, 2002).
HCA Copyright 2006 ACS on STN, Accession No. 136:64122, Abstract of WO 2001/098344 A2, Biogen, Inc. (Dec. 27, 2001).
HCAPLUS Copyright 2006 ACS on STN, Accession No. 1995:188469, Abstract of Waldmann et al., "Asymmetric steering of the Pictet-Spengler reaction by means of amino acid esters as chiral auxiliary groups", Tetrahedron, 50(41): 11865-84 (1994).
HCAPLUS Copyright 2006 ACS on STN, Accession No. 1995:470885, Abstract of Soe et al., "Asymmetric Pictet-Spengler reaction with a chiral N-(β-3-indolyl) ethyl-1-methylbenzylamine", Tetrahedron Letters, 36(11): 1857-60 (1995).
HCAPLUS Copyright 2006 ACS on STN, Accession No. 1995:741637, Abstract of Kawashima et al., "Synthesis and pharmacological evaluation of 1,2,3,4-tetrahydro-β-carboline derivatives", Chemical & Pharmaceutical Bulletin, 43(5): 783-7 (1995).
HCAPLUS Copyright 2006 ACS on STN, Accession No. 1996:94639, Abstract of Soe et al., "Asymmetric Pictet-Spengler reaction using α-methylbenzylamine as a chiral auxiliary group", Heterocycles, 42(1): 347-58 (1996).
HCAPLUS Copyright 2006 ACS on STN, Accession No. 1999:241413, Abstract of Kawate et al., "Chiral auxiliary approach to the asymmetric Pictet-Spengler reaction of tryptamines", Heterocycles, 50(2): 1033-1039 (1999).
HCAPLUS Copyright 2006 ACS on STN, Accession No. 2002:862393, Abstract of Jiang et al., "Synthesis of optically pure pyrroloquinolones via Pictet-Spengler and Winterfeldt reactions", Tetrahedron Letters, 43(49): 8941-8945 (2002).
HCAPLUS Copyright 2006 ACS on STN, Accession No. 2003:67259, Abstract of Tsuji et al., "An efficient synthetic approach to optically active β-carboline derivatives via Pictet-Spengler reaction promoted by trimethylchlorosilane", Tetrahedron: Asymmetry, 14(2): 177-180 (2003).
HCAPLUS Copyright 2006 ACS on STN, Accession No. 1990:198356, Abstract of CZ 261296 B1, Protiva, et. al. (Jan. 12, 1989).
HCAPLUS Copyright 2006 ACS on STN, Accession No. 1990:77229, Abstract of CZ 262100 B1, Protiva, et. al. (Feb. 10, 1989).
HCAPLUS Copyright 2006 ACS on STN, Accession No. 1999:131592, Abstract of Venkov et al., "Synthesis of 2-acyltetrahydro-β-carbolines by an intramolecular α-amidoalkylation reaction", Synthetic Communications, 29(3): 487-494 (1999).

HCAPLUS Copyright 2006 ACS on STN, AN 1928:29116, Abstract of Tatsui, G., "Synthesis of carboline derivatives", Yakugaku Zasshi, 48: 453-9 (1928).
HCAPLUS Copyright 2006 ACS on STN, AN 1952:57257, Abstract of Groves et al., "Constitution of yohimbine and related alkaloids. VI. The synthesis of 1,2,3,4,6,7,12,12b-octahydro-2-ketoindolo-[2,3-a]-pyridocoline and 1,2,3,4-tetrahydro [2, 3-a] pyridocoline", Journal of the Chemical Society, 650-61 (1952).
HCAPLUS Copyright 2006 ACS on STN, AN 1958:98075, Abstract of Prasad et al., "Constitution of yohimbine and related alkaloids. XII. Unsuccessful synthetic approaches to yohimbine and alstoniline", Journal of the Chemical Society, 2045-51 (1958).
HCAPLUS Copyright 2006 ACS on STN, AN 1959:122350, Abstract of Bartlett et al., "The alkaloids of Tabernanthe iboga. VIII", Journal of the American Chemical Society, 81: 1932-5 (1959).
HCAPLUS Copyright 2006 ACS on STN, AN 1959:122351, Abstract of Kline, G. Bruce, "Indole alkaloids. A study of the Dieckmann condensation of 1-carbethoxymethyl-2-(2-carbethoxyethyl)-1,2,3,4-tetrahydro-β-carboline. A synthesis of 20-carbethoxy-15(16)-yohimben-17-one", Journal of the American Chemical Society, 81, 2251-5 (1959).
Davis, T. et. al., Abstract 3870 Post-transcriptional control as a novel approach to anti-angiogenesis: development of a small molecule that reduces the production of tumor vascular endothelial growth factor A (VEGF), Abstract presented at 96th annual meeting of American Association for Cancer Research, Apr. 16-20, 2005.
Davis, T. et. al. Post-transcriptional control as a novel approach to anti-angiogenesis: development of a small molecule that reduces the production of tumor vascular endothelial growth factor A (VEGF), Poster presented at 96th annual meeting of American Association for Cancer Research, Apr. 16-20, 2005.
Ullner, P. et. al., Abstract 3857 Post-transcriptional inhibition of vascular endothelial growth factor (VEGF) expression arrests tumor growth at a prevascular stage, Abstract presented at American Association for Cancer Research, Apr. 16-20, 2005.
Hirawat, S., et. al. PTC299: A Novel Post-transcriptional VEGF Expression Inhibitor, Poster presented at 5th International Colorectal Cancer Congress, Oct. 2006.
Hirawat, S., et. al. Phase 1 Single-dose Safety, PK, and Food-effect Study of PTC299, a Novel VEGF Expression Inhibitor for Treatment of Solid Tumors, Poster presented at EORTC in 2006.
Davis, T. et. al., Preclinical Development of PTC299: An Orally Bioavailable Small Molecule Drug That Selectively Inhibits VEGF Protein Production, Tumor Growth, and Microvessel Density, Poster submitted at EORTC in 2006.
Cao, L. et. al., PTC299 Inhibits VEGF Expression Through Its 5' UTR, Poster submitted at EORTC in 2006.
Hirawat, S., et. al., A Phase 1 Multiple-Dose Safety, Pharmacokinetic, and Pharmacodynamic Study of PTC299, a Novel VEGF Expression Inhibitor for Treatment of Solid Tumors, Abstract submitted Nov. 28, 2006 for 2007 meeting of American Association for Cancer Research, Tracking No. 07-AB-4295-AACR.
Hirawat, S., Phase 1 single-dose safety, PK, and food-effect study of PTC299, a novel VEGF expression inhibitor for treatment of solid tumors, Abstract submitted for 19th Meeting of the European Association for Cancer Research on Jun. 12, 2006.
Hirawat, S. et. al., Phase 1 Multiple Dose Safety, Pharmacokinetic, Pharmacodynamic Study of PTC299, a Novel VEGF Expression Inhibitor for the Treatment of Solid Tumors, Poster presented at American Association for Cancer Research, Apr. 14-18, 2007.
Hirawat, S. et. al., Phase 1 studies assessing the safety, PK, and VEGF-modulating effects of PTC299, a novel VEGF expression inhibitor, submitted to American Society of Clinical Oncology on Jan. 9, 2007, Tracking No. 07-AB-33792-ASCO.
PTC299 Phase 1 Study in Healthy Volunteers (Study 002) Power Point Presentation presented at American Association for Cancer Research meeting 2007.
Davis, T., et. al., Discovery and preclinical efficacy of PTC299, an antiangiogenic candidate in clinical development for the treatment of cancer, presented at 10th International Symposium on Anti-Angiogenic Agents in 2008.
Miao, H. et. al., Preclinical and Phase 1 Study Results of PTC 299, an Oral Inhibitor of VEGF Expression, Poster presented Feb. 7-9, 2008.

International Search Report issued on Aug. 4, 2008, in corresponding International Application No. PCT/US2008/004809.

Hirawat et al., "51 Poster Phase 1 single-dose safety, PK, and food-effect study of PTC299, a novel VEGF expression inhibitor for treatment of solid tumors," European Journal of Cancer. Supplement, Pergamon (Oxford, Great Britain), vol. 4, No. 12, pp. 19-20 (Nov. 1, 2006).

Hirawat et al., "Phase 1 studies assessing the safety, PK, and VEGF-modulating effects of PTC299, a novel VEGF expression inhibitor," Journal of Clinical Oncology, ASCO Annual Meeting Proceedings, Part I, vol. 25, No. 18S (Jun. 20, 2007) (URL: http://www.asco.org/ASCO/Abstracts+%26+Virtual+Meeting/Abstracts?&vmview=abst_detail_view&confID=47&abstractID=33792>) (abstract 3562).

HCA Copyright 2006 ACS on STN, Accession No. 134:311102, Abstract of WO 2001/026644, Curis, Inc. (Apr. 19, 2001).

Registry Copyright 2006 ACS on STN, Registry No. 335120-70-2.

Marpat Accession No. 114:37805, Abstract of US 5120543, Hagin, et.al. (Jun. 9, 1992).

Registry Copyright 2006 ACS on STN, Registry No. 337318-01-1.
Registry Copyright 2006 ACS on STN, Registry No. 337318-07-7.
Registry Copyright 2006 ACS on STN, Registry No. 337318-10-2.
Registry Copyright 2006 ACS on STN, Registry No. 337318-13-5.
Registry Copyright 2006 ACS on STN, Registry No. 337318-16-8.
Registry Copyright 2006 ACS on STN, Registry No. 337318-22-6.
Registry Copyright 2006 ACS on STN, Registry No. 337318-25-9.
Registry Copyright 2006 ACS on STN, Registry No. 337318-28-2.
Registry Copyright 2006 ACS on STN, Registry No. 337318-31-7.
Registry Copyright 2006 ACS on STN, Registry No. 337318-34-0.
Registry Copyright 2006 ACS on STN, Registry No. 337318-37-3.
Registry Copyright 2006 ACS on STN, Registry No. 337318-43-1.
Registry Copyright 2006 ACS on STN, Registry No. 337318-46-4.
Registry Copyright 2006 ACS on STN, Registry No. 337318-49-7.
Registry Copyright 2006 ACS on STN, Registry No. 337318-55-5.
Registry Copyright 2006 ACS on STN, Registry No. 337318-58-8.
Registry Copyright 2006 ACS on STN, Registry No. 337318-64-6.
Registry Copyright 2006 ACS on STN, Registry No. 337318-67-9.
Registry Copyright 2006 ACS on STN, Registry No. 337318-70-4.
Registry Copyright 2006 ACS on STN, Registry No. 337318-85-1.
Registry Copyright 2006 ACS on STN, Registry No. 337318-88-4.
Registry Copyright 2006 ACS on STN, Registry No. 337318-91-9.
Registry Copyright 2006 ACS on STN, Registry No. 337318-94-2.
Registry Copyright 2006 ACS on STN, Registry No. 337318-97-5.
Registry Copyright 2006 ACS on STN, Registry No. 337319-03-6.
Registry Copyright 2006 ACS on STN, Registry No. 337319-09-2.
Registry Copyright 2006 ACS on STN, Registry No. 337319-12-7.
Registry Copyright 2006 ACS on STN, Registry No. 337319-21-8.
Registry Copyright 2006 ACS on STN, Registry No. 337319-24-1.
Registry Copyright 2006 ACS on STN, Registry No. 337319-30-9.
Registry Copyright 2006 ACS on STN, Registry No. 337319-33-2.
Registry Copyright 2006 ACS on STN, Registry No. 337319-36-5.
Registry Copyright 2006 ACS on STN, Registry No. 337319-42-3.
Registry Copyright 2006 ACS on STN, Registry No. 337319-48-9.
Registry Copyright 2006 ACS on STN, Registry No. 337331-00-7.
Registry Copyright 2006 ACS on STN, Registry No. 337332-12-4.
Registry Copyright 2006 ACS on STN, Registry No. 337333-42-3.
Registry Copyright 2006 ACS on STN, Registry No. 337334-25-5.
Registry Copyright 2006 ACS on STN, Registry No. 337338-22-4.
Registry Copyright 2006 ACS on STN, Registry No. 337338-52-0.
Registry Copyright 2006 ACS on STN, Registry No. 400867-22-3.

Taylor et al., "Highly enantioselective catalytic acyl-Pictet-Spengler reactions", Journal of the American Chemical Society, 126(34): 10558-10559 (2004).

WPINDEX Copyright 2006 The Thomson Corp on STN, Accession No. 1995-275237, Abstract of WO 1995/019978 A1, (Icos-N) !Icos Corp, et. al. (Jul. 27, 1995).

WPINDEX Copyright 2006 The Thomson Corp on STN, Accession No. 1997-528820, Abstract of EP 0 803 505 A1, (Adir) Adir & Cie, et. al. (Oct. 29, 1997).

WPINDEX Copyright 2006 The Thomson Corp on STN, AN 1990-068877, Abstract of EP 357122 A, (Duin) Duphar Int Res BV, (Sep. 28, 1993).

Yamanaka et al., "A development of Pictet-Spengler reaction in aprotic media using chloroflormates; a short synthesis of borrerine", Heterocycles, 22(2): 371-4 (1984).

Zhang et al., "Concise Enantioselective Syntheses of Quinolactacins A2 and B through Alternative Winterfeldt Oxidation", Journal of Organic Chemistry, 68(11): 4523-4526 (2003).

Trotta C. et. al., PTC299 Inhibits Expression of VEGF Through the 5' Untranslated Region of its mRNA, Poster presented at 10th International Symposium on Anti-Angiogenic Agents, Feb. 2008.

International Search Report issued on Jul. 25, 2008, in corresponding International Application No. PCT/US2008/004810.

HCAPLUS Copyright 2006 ACS on STN, AN 1965:480584, Abstract of Freter et al., "Reactions of 1-aryl-1,2,3,4-tetrahydro-β-carbolines in acid solution", Justus Liebigs Annalen der Chemie, 684: 159-87 (1965).

HCAPLUS Copyright 2006 ACS on STN, AN 1996:512657, Abstract of Legseir et al., "Synthesis of optically active tetrahydro-β-carbolines by the Pictet-Spengler reaction", Journal de la Societe Algerienne de Chimie, 6(1): 17-27 (1996).

HCAPLUS Copyright 2006 ACS on STN, AN 1997:55320, Abstract of Schmidt et al., "Asymmetric control in the Pictet-Spengler reaction by means of N-protected amino acids as chiral auxiliary groups", Chemistry—A European Journal, 2(12): 1566-1571 (1996) Published in: Angew. Chem., Int. Ed. Engl., 35 (23/24).

HCAPLUS Copyright 2006 ACS on STN, AN 1998:355721, Abstract of Bienayme, H., ""Reagent Explosion": an efficient method to increase library size and diversity", Tetrahedron Letters, 39(24): 4255-4258 (1998).

HCAPLUS Copyright 2006 ACS on STN, AN 1999:767765, Abstract of Zhao et al., "Easy generation of an enantiopure general indol alkaloid building block by kinetic resolution", Tetrahedron: Asymmetry, 10(20): 3899-3905 (1999).

HCAPLUS Copyright 2006 ACS on STN, AN 1999:799056, Abstract of Boumendjel et al., "Synthesis of ajmalicine derivatives using Wittig-Horner and Knoevenagel reactions", Tetrahedron Letters, 40(51): 9033-9036 (1999).

HCAPLUS Copyright 2006 ACS on STN, AN 2000:337953, Abstract of You et al., "Application of DDQ in the synthesis of β-carboline alkaloid", Hecheng Huaxue, 8(1): 83-86 (2000). Only English STN Abstract Provided.

HCAPLUS Copyright 2006 ACS on STN, AN 2002:637676, Abstract of WO 2002/064590, Lilly Icos LLC (Aug. 22, 2002).

HCAPLUS Copyright 2006 ACS on STN, AN 2002:659480, Abstract of Bonnefont-Rousselot et al., "Melatonin related compounds inhibit lipid peroxidation during copper or free radical-induced LDL oxidation", Journal of Pineal Research, 33(2): 109-117 (2002).

HCAPLUS Copyright 2006 ACS on STN, AN 2002:861062, Abstract of Joule, J.A., "Product Class 13: indole and its derivatives", Science of Synthesis, 10: 361-652 (2001).

HCAPLUS Copyright 2006 ACS on STN, AN 2003:431047, Abstract of Cheve et al., "Antioxidant activity of pinoline analogues in the LDL oxidation model", Medicinal Chemistry Research, 11(7): 361-379 (2002).

HCAPLUS Copyright 2006 ACS on STN, AN 2004:611809, Abstract of Donova et al., "N-Acyliminium reagents of 3,4-dihydro-β-carboline and acyl chlorides in the reaction of intermolecular α-amidoalkylation toward heteroarormatics", Synthetic Communications, 34(15): 2813-2821 (2004).

HCAPLUS Copyright 2006 ACS on STN, AN 2005:580707, Abstract of Zhuang et al., "Enantioselective Friedel-Crafts type addition of indoles to nitro-olefins using a chiral hydrogen-bonding catalyst—a synthesis of optically active tetrahydro-β-carbolines", Organic & Biomolecular Chemistry, 3(14): 2566-2571 (2005).

HCAPLUS Copyright 2006 ACS on STN, AN 2005:643328, Abstract of Mekhloufi et al., "Antioxidant activity of melatonin and a pinoline derivative on linoleate model system", Journal of Pineal Research, 39(1): 27-33 (2005).

HCAPLUS Copyright 2006 ACS on STN, AN 2005:886847, Abstract of Tailleux et al., "Increased Susceptibility of Low-Density Lipoprotein to Ex Vivo Oxidation in Mice Transgenic for Human Apolipoprotein B Treated with 1 Melatonin-Related Compound Is Not Associated with Atherosclerosis Progression", Journal of Cardiovascular Pharmacology, 46(3): 241-249 (2005).
HCAPLUS Copyright 2006 ACS on STN, AN 1980:22200, Abstract of Kluge et al., "Phosphate reagents for the synthesis of enol ethers and one-carbon homologation to aldehydes", Journal of Organic Chemistry, 44(26): 4847-52 (1979).
HCAPLUS Copyright 2006 ACS on STN, AN 1982:143144, Abstract of Cloudsdale et al., "Synthetic studies in the ajmaline series", Journal of Organic Chemistry, 47(6): 919-28 (1982).
HCAPLUS Copyright 2006 ACS on STN, Accession No. 1965:498671, Abstract of NL 6413518, Omnium Chimique, Societe Anon. (May 24, 1965).
HCAPLUS Copyright 2006 ACS on STN, Accession No. 1966:420748, Abstract of NL 6512087, Imperial Chemical Industries Ltd. (Mar. 17, 1966).
HCAPLUS Copyright 2006 ACS on STN, Accession No. 1972:501562, Abstract of DE 20 61 359 A, Badische Anilin- & Soda-Fabrik AG (Jun. 22, 1972).
HCAPLUS Copyright 2006 ACS on STN, Accession No. 1972:526602, Abstract of DE 20 62 828 A, Boehringer, C. H. (Jun. 22, 1972).
HCAPLUS Copyright 2006 ACS on STN, Accession No. 1977:423246, Abstract of DE 26 37 503 A1, Endo Laboratories Inc. (Mar. 3, 1977).
HCAPLUS Copyright 2006 ACS on STN, Accession No. 1977:468520, Abstract of JP 52031097 A1, Oki et al. (Mar. 9, 1977).
HCAPLUS Copyright 2006 ACS on STN, Accession No. 1980:471821, Abstract of EP 0 008 249, Synthelabo S. A. (Feb. 20, 1980).
HCAPLUS Copyright 2006 ACS on STN, Accession No. 1981:121318, Abstract of JP 55145687 A2, Synthelabo S. A. (Nov. 13, 1980).
HCAPLUS Copyright 2006 ACS on STN, Accession No. 1981:139775, Abstract of EP 0 017 727 A1, Ciba-Geigy A.-G. (Oct. 29, 1980).
HCAPLUS Copyright 2006 ACS on STN, Accession No. 1981:175153, Abstract of EP 0 018 857 A1, Synthelabo S. A. (Nov. 12, 1980).
HCAPLUS Copyright 2006 ACS on STN, Accession No. 1981:497842, Abstract of FR 2456743 A1, Synthelabo S. A. (Dec. 12, 1980).
HCAPLUS Copyright 2006 ACS on STN, Accession No. 1982:35284, Abstract of FR 2460301 A2, Synthelabo S. A. (Jan. 23, 1981).
HCAPLUS Copyright 2006 ACS on STN, Accession No. 1982:550721, Abstract of FR 2486801 A1, Synthelabo S. A. (Jan. 22, 1982).
HCAPLUS Copyright 2006 ACS on STN, Accession No. 1984:490905, Abstract of EP 0 101 574 A1, BASF A.-G. (Feb. 29, 1984).
HCAPLUS Copyright 2006 ACS on STN, Accession No. 1985:24611, Abstract of DE 33 02 126 A1, Boehringer Ingelheim K.-G. (Jul. 26, 1984).
HCAPLUS Copyright 2006 ACS on STN, Accession No. 1986:207248, Abstract of JP 60246385 A2, Sankyo Co., Ltd. (Dec. 6, 1985).
HCAPLUS Copyright 2006 ACS on STN, Accession No. 1988:630991, Abstract of EP 0 273 321 A1, Kawaken Fine Chemicals Co., Ltd. (Jul. 6, 1988).
HCAPLUS Copyright 2006 ACS on STN, Accession No. 1989:205701, Abstract of DE 37 05 220 A1, Boehringer Ingelheim K.-G. (Sep. 1, 1988).
HCAPLUS Copyright 2006 ACS on STN, Accession No. 1989:407060, Abstract of WO 1989/000159 A1, Richter, Gedeon, Vegyeszeti Gyar Rt. (Jan. 12, 1989).
HCAPLUS Copyright 2006 ACS on STN, Accession No. 1989:477986, Abstract of EP 0 300 541 A1, Duphar International Research B. V. (Jan. 25, 1989).
HCAPLUS Copyright 2006 ACS on STN, Accession No. 1989:554290, Abstract of HU 46032 A2, Gyogynoveny Kutato Intezet (Sep. 28, 1988).
HCAPLUS Copyright 2006 ACS on STN, Accession No. 1990:235665, Abstract of JP 01319482 A2, Kawaken Fine Chemicals Co., Ltd. (Dec. 25, 1989).
HCAPLUS Copyright 2006 ACS on STN, Accession No. 1990:441332, Abstract of EP 0 346 847 A2, Hoffmann-La Roche, F., und Co. A.-G. (Dec. 20, 1989).
HCAPLUS Copyright 2006 ACS on STN, Accession No. 1992:235613, Abstract of JP 03287586, Taisho Pharmaceutical Co., Ltd. (Dec. 18, 1991).
HCAPLUS Copyright 2006 ACS on STN, Accession No. 1993:175782, Abstract of JP 04275221 A2, Taisho Pharmaceutical Co., Ltd. (Sep. 30, 1992).
HCAPLUS Copyright 2006 ACS on STN, Accession No. 1994:54535, Abstract of HU 63164 A2, Richter, Gedeon, Vegyeszeti Gyar Rt. (Jul. 28, 1993).
HCAPLUS Copyright 2006 ACS on STN, Accession No. 1995:861292, Abstract of JP 07179467, Nippon Shoji Kk (Jul. 18, 1995).
HCAPLUS Copyright 2006 ACS on STN, Accession No. 1996:311402, Abstract of DE 44 36 190 A1, Bringmann et al. (Apr. 11, 1996).
HCAPLUS Copyright 2006 ACS on STN, Accession No. 1996:425286, Abstract of WO 1996/008490 A1, Cemaf et al. (Mar. 21, 1996).
HCAPLUS Copyright 2006 ACS on STN, Accession No. 1997:244196, Abstract of EP 0 758 021 A2, Polifarma S.P.A. (Feb. 12, 1997).
HCAPLUS Copyright 2006 ACS on STN, Accession No. 1997:618080, Abstract of WO 1997/032860 A1, James Black Foundation Ltd. et al. (Sep. 12, 1997).
HCAPLUS Copyright 2006 ACS on STN, Accession No. 1997:752957, Abstract of WO 1997/043287 A1, Icos Corporation et al. (Nov. 20, 1997).
HCAPLUS Copyright 2006 ACS on STN, Accession No. 2000:191086, Abstract of WO 2000/015639 A1, Icos Corp. (Mar. 23, 2000).
HCAPLUS Copyright 2006 ACS on STN, Accession No. 2000:755247, Abstract of EP 1 046 627 A2, Solvay (Societe Anonyme) (Oct. 25, 2000).
U.S. Appl. No. 13/040,614, Moon et al.
Advisory Action mailed Oct. 7, 2009 from the United States Patent and Trademark Office for U.S. Appl. No. 11/107,783, filed Apr. 18, 2005.
Amendment filed Jan. 29, 2010 for U.S. Appl. No. 11/107,783, filed Apr. 18, 2005.
Amendment filed May 1, 2009 for U.S. Appl. No. 11/079,420, filed Mar. 15, 2005.
Amendment filed Oct. 21, 2009 for U.S. Appl. No. 11/107,783, filed Apr. 18, 2005.
Amendment filed Oct. 8, 2009 for U.S. Appl. No. 11/107,783, filed Apr. 18, 2005.
CAPLUS printout for CAS Reg. No. 15866-90-7, 2009.
CAPLUS printout for CAS Reg. No. 252916-29-3, 2009.
CAPLUS printout for CAS Reg. No. 259188-38-0, 2009.
CAPLUS printout for CAS Reg. No. 341031-54-7, 2009.
CAPLUS printout for CAS Reg. No. 365253-37-8, 2009.
CAPLUS printout for CAS Reg. No. 443913-73-3, 2009.
CAPLUS printout for CAS Reg. No. 862124-26-3, 2009.
Dorwald F.A., 2005, "Side Reactions in Organic Synthesis", Wiley: VCH, Weinheim p. IX of Preface.
Final Office Action mailed May 14, 2009 from the United States Patent and Trademark Office for U.S. Appl. No. 11/107,783, filed Apr. 18, 2005.
Folkman, 1996, "Fighting Cancer by Attacking Its Blood Supply," Scientific American 275(3):150-154.
International Search Report for International Application No. PCT/US10/36287, filed May 27, 2010.
International Search Report for International Application No. PCT/US10/36300, filed May 27, 2010.
International Search Report for International Application No. PCT/US10/36345, filed May 27, 2010.
International Search Report for International Application No. PCT/US10/36364, filed May 27, 2010.

International Search Report for International Application No. PCT/US10/36387, filed May 27, 2010.
International Search Report for International Application No. PCT/US10/36467, filed May 27, 2010.
Nexavar® Product Insert (2005).
Non-Final Office Action mailed Jan. 2, 2008 from the United States Patent and Trademark Office for U.S. Appl. No. 11/079,420, filed Mar. 15, 2005.
Non-Final Office Action mailed Jul. 6, 2010 from the United States Patent and Trademark Office for U.S. Appl. No. 11/735,069, filed Apr. 13, 2007.
Non-Final Office Action mailed Mar. 11, 2008 from the United States Patent and Trademark Office for U.S. Appl. No. 11/107,783, filed Apr. 18, 2005.
Non-Final Office Action mailed Oct. 9, 2008 from the United States Patent and Trademark Office for U.S. Appl. No. 11/107,783, filed Apr. 18, 2005.
Non-Final Office Action mailed Sep. 29, 2008 from the United States Patent and Trademark Office for U.S. Appl. No. 11/079,420, filed Mar. 15, 2005.
Notice of Allowance mailed Apr. 8, 2009 from the United States Patent and Trademark Office for U.S. Appl. No. 11/079,420, filed Mar. 15, 2005.
Notice of Allowance mailed Oct. 30, 2009 from the United States Patent and Trademark Office for U.S. Appl. No. 11/107,783, filed Apr. 18, 2005.
Preliminary Amendment filed Aug. 18, 2005 for U.S. Appl. No. 11/107,783, filed Apr. 18, 2005.
Preliminary Amendment filed Aug. 3, 2007 for U.S. Appl. No. 11/735,069, filed Apr. 13, 2007.
Preliminary Amendment filed Dec. 30, 2009 for U.S. Appl. No. 12/506,485, filed Jul. 21, 2009.
Registry Copyright 2006 ACS on STN, Registry No. 337317-98-3.
Response filed Apr. 26, 2010 to Restriction Requirement mailed Mar. 26, 2010 from the United States Patent and Trademark Office for U.S. Appl. No. 11/735,069, filed Apr. 13, 2007.
Response filed Dec. 29, 2008 to Non-Final Office Action mailed Sep. 29, 2008 from the United States Patent and Trademark Office for U.S. Appl. No. 11/079,420, filed Mar. 15, 2005.
Response filed Feb. 19, 2009 to Non-Final Office Action mailed Oct. 9, 2008 from the United States Patent and Trademark Office for U.S. Appl. No. 11/107,783, filed Apr. 18, 2005.
Response filed Jul. 1, 2008 to Non-Final Office Action mailed Jan. 2, 2008 from the United States Patent and Trademark Office for U.S. Appl. No. 11/079,420, filed Mar. 15, 2005.
Response filed Jul. 11, 2008 to Non-Final Office Action mailed Mar. 11, 2008 from the United States Patent and Trademark Office for U.S. Appl. No. 11/107,783, filed Apr. 18, 2005.
Response filed Sep. 28, 2009 to Final Office Action mailed May 14, 2009 from the United States Patent and Trademark Office for U.S. Appl. No. 11/107,783, filed Apr. 18, 2005.
Restriction Requirement mailed Mar. 26, 2010 from the United States Patent and Trademark Office for U.S. Appl. No. 11/735,069, filed Apr. 13, 2007.
Ruoslahti et al., 2010, "Targeting of drugs and nanoparticles to tumors," J. Cell Biol. 188(6):759-768.
Supplemental Response filed Sep. 25, 2008 to Non-Final Office Action mailed Jan. 2, 2008 from the United States Patent and Trademark Office for U.S. Appl. No. 11/079,420, filed Mar. 15, 2005.
Sutent® Product Insert (2006).

Written Opinion of the International Search Authority for International Application No. PCT/US2006/01547, filed Apr. 17, 2006.
Written Opinion of the International Searching Authority for International Application No. PCT/US10/36287, filed May 27, 2010.
Written Opinion of the International Searching Authority for International Application No. PCT/US10/36300, filed May 27, 2010.
Written Opinion of the International Searching Authority for International Application No. PCT/US10/36345, filed May 27, 2010.
Written Opinion of the International Searching Authority for International Application No. PCT/US10/36364, filed May 27, 2010.
Written Opinion of the International Searching Authority for International Application No. PCT/US10/36387, filed May 27, 2010.
Written Opinion of the International Searching Authority for International Application No. PCT/US10/36467, filed May 27, 2010.
Written Opinion of the International Searching Authority for International Application No. PCT/US2005/008481, filed Mar. 15, 2005.
Written Opinion of the International Searching Authority for International Application No. PCT/US2008/004809, filed Apr. 12, 2008.
Written Opinion of the International Searching Authority for International Application No. PCT/US2008/004810, filed Apr. 12, 2008.
American Macular Degeneration Foundation (AMDF)—Wet Type AMD, http://www.macular.org/wet.html (last visited May 19, 2011).
Boulton et al., 1998, "VEGF localisation in diabetic retinopathy," Br. J. Ophthalmol. 82:561-568.
D'Amato et al., 1995, "Angiogenesis Inhibition in Age-Related Macular Degeneration," Ophthalmology 102(9):1261-1262.
Final Office Action mailed Mar. 16, 2011 from the United States Patent and Trademark Office for U.S. Appl. No. 11/735,069, filed Apr. 13, 2007.
Honda et al., 2000, "Experimental subretinal neovascularization is inhibited by adenovirus-mediated soluble VEGF/flt-1 receptor gene transfection: a role of VEGF and possible treatment for SRN in age-related macular degeneration," Gene Therapy 7:978-985.
Inoue et al., 1998, "Vascular Endothelial Growth Factor (VEGF) Expression in Human Coronary Atherosclerotic Lesions: Possible Pathophysiological Significance of VEGF in Progression of Atherosclerosis," Circulation 98:2108-2116.
Kvanta et al., 1996, "Subfoveal Fibrovascular Membranes in Age-Related Macular Degeneration Express Vascular Endothelial Growth Factor," Ophthalmol. Vis. Sci. 37:1929-1934.
Ray et al., Mar. 2004, "Association of the VEGF Gene With Proliferative Diabetic Retinopathy But Not Proteinuria in Diabetes," Diabetes 53:861-864.
Stompor et al., 2002, "Selected Growth Factors in Peritoneal Dialysis: Their Relationship to Markers of Inflammation, Dialysis Adequacy, Residual Renal Function, and Peritoneal Membrane Transport," Perit. Dial. Int. 22:670-676.
Taichmann et al., 1997, "Human neutrophils secrete vascular endothelial growth factor," J. Leukoc. Biol. 62:397-400.
Xia et al., Jul. 2003, "Transgenic delivery of VEGF to mouse skin leads to an inflammatory condition resembling human psoriasis," Blood 102:161-168.
Response filed Jan. 5, 2011 to Non-Final Office Action mailed Jun. 6, 2010 from the United States Patent and Trademark Office for U.S. Appl. No. 11/735,069, filed Apr. 13, 2007.

* cited by examiner

INHIBITION OF VEGF TRANSLATION

CROSS REFERENCE TO RELATED APPLICATION

This application claims the benefit of U.S. Provisional Application 60/814,868, filed Jun. 20, 2006; this application is also a continuation-in-part of U.S. application Ser. No. 11/079,420, filed Mar. 15, 2005 now U.S. Pat. No. 7,601 840, which claims the benefit of U.S. Provisional Application No. 60/552,725, filed Mar. 15, 2004; this application is also a continuation-in-part of U.S. application Ser. No. 11/107,783, filed Apr. 18, 2005 now U.S. Pat No. 7,767,689, which is a continuation-in-part of U.S. application Ser. No. 11/079,420, filed Mar. 15, 2005 now U.S. Pat. No. 7,601,840, which claims the benefit of U.S. Provisional Application No. 60/552,725, filed Mar. 15, 2004; this application is also a continuation-in-part of U.S. application Ser. No. 11/735,069, filed Apr. 13, 2007, which is a continuation-in-part of U.S. application Ser. No. 11/107,783, filed Apr. 18, 2005 now U.S. Pat. No. 7,767,689, and of U.S. application Ser. No. 11/079, 420, filed Mar. 15, 2005 now U.S. Pat. No. 7,601 840, which claims the benefit of U.S. Provisional Application No. 60/552,725, filed Mar. 15, 2004; the entire contents of which applications are incorporated herein by reference.

FIELD OF THE INVENTION

In accordance with the present invention, methods for inhibiting the translation of VEGF and methods for decreasing VEGF level by inhibiting VEGF translation are provided. In another aspect of the invention, compounds that inhibit the 5'-UTR-dependent translation of VEGF and methods for identifying such compounds are provided.

BACKGROUND OF THE INVENTION

Aberrant angiogenesis plays a critical role in the pathogenesis of numerous diseases, including malignant, ischemic, inflammatory and immune disorders. Numerous cytokines and growth factors that stimulate angiogenesis, such as VEGF, FGF-2, PDGF, IGF-1, TGF, TNF-$\alpha$, G-CSF have been identified, among which, Vascular Endothelial Growth Factor (VEGF) plays a central role in angiogenesis. VEGF, also known as VEGF-A, was initially identified for its ability to induce vascular permeability and to promote vascular endothelial cell proliferation. VEGF is encoded by a single gene that gives rise to four isoforms by alternative splicing. All four isoforms share the same long and GC rich 5'-UTR, as well as a 3'-UTR that includes multiple RNA stability determinants.

VEGF expression is regulated by a number of factors and agents including cytokines, growth factors, steroid hormones and chemicals, and mutations that modulate the activity of oncogenes such as ras or the tumor suppressor gene VHL. The stability and translation efficiency of the VEGF transcript are influenced by sequences in the 5'- and 3'-UTRs. The 5'-UTR contains an internal ribosomal entry site (IRES) and mediates cap-independent translation initiation while the 3'-UTR harbors multiple AU-rich (AUR) stability determinants that have been reported to regulate turnover of VEGF mRNA.

Translation initiation of the VEGF transcript is uniquely regulated. Under hypoxic conditions, translation of most cellular transcripts mediated by cap-dependent translation initiation process is greatly impaired. Initiation of translation of the VEGF mRNA, however, is mediated via the IRES within the VEGF 5'-UTR under hypoxic conditions. Thus, this form of post-transcriptional regulation permits cells to produce large amounts of VEGF protein to support, for example, tumor growth or aberrant neovascularization in ocular diseases under hypoxic conditions. The stability of VEGF mRNA is also enhanced as a consequence of the binding of factors to elements in the 3'-UTR.

Inhibition of VEGF production may reduce angiogenesis and permit treatment of various disease states that are associated with aberrant angiogenesis. As such, there is a need to develop and characterize mechanisms by which VEGF production may be inhibited, including inhibition of VEGF translation.

Small molecules may inhibit VEGF production. Consequently, there is a need to develop, characterize, and optimize small molecules that inhibit translation of the VEGF gene. These molecules may be useful as anti-angiogenesis drugs, including as drugs for treatment of cancer and other pathologies where aberrant vascularization occurs.

All documents referred to herein are incorporated by reference into the present application as though fully set forth herein.

SUMMARY OF THE INVENTION

The present invention includes and provides a method of inhibiting translation of VEGF in a subject in need thereof comprising administering an effective amount of a VEGF translation-inhibiting compound to the subject, wherein translation of VEGF is inhibited.

The present invention also includes and provides a method of inhibiting translation of VEGF in a human with an elevated VEGF level comprising administering an effective amount of a VEGF translation-inhibiting compound to the human, wherein translation of VEGF is inhibited.

The present invention further includes and provides a method of decreasing VEGF level in a subject in need thereof comprising inhibiting translation of VEGF in the subject by administration of a VEGF translation-inhibiting compound; and measuring a decrease in VEGF level in the subject.

The present invention also includes and provides a method of decreasing VEGF level in a human with an elevated VEGF level comprising inhibiting translation of VEGF in the human by administration of a VEGF translation-inhibiting compound; and measuring a decrease in VEGF level in the human.

The present invention includes and provides a method of identifying a compound as a VEGF translation-inhibiting compound comprising contacting a test compound with one or more cells having an elevated VEGF level; measuring a decrease in VEGF translation; and identifying the test compound as a VEGF translation-inhibiting compound by the decrease in VEGF translation.

These and other aspects of the invention will be more clearly understood with reference to the drawings, detailed description, and embodiments.

DETAILED DESCRIPTION OF THE INVENTION

Figure 1:
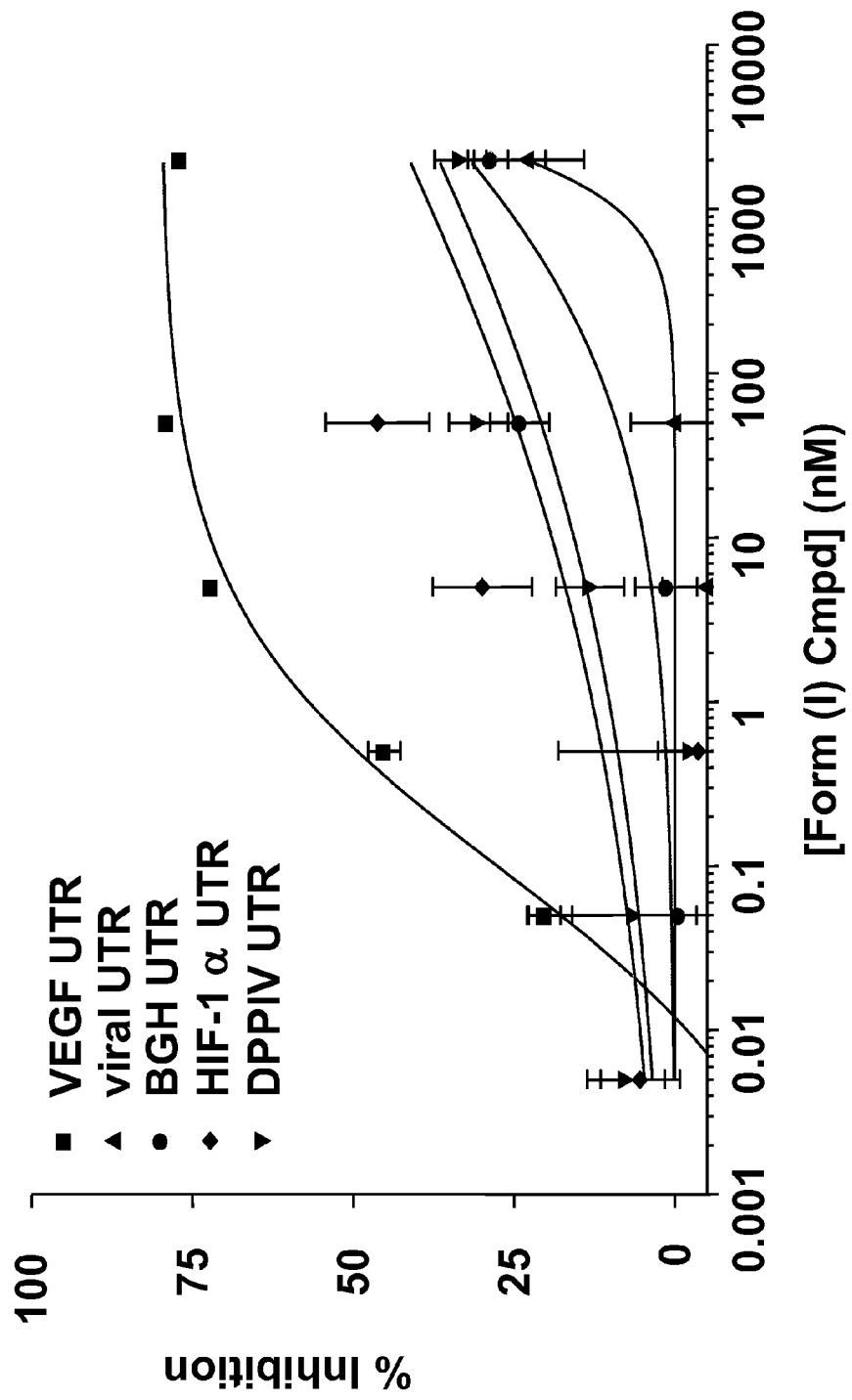
FIG. 1 illustrates inhibition of firefly luciferase reporter gene expression in a VEGF UTR-dependent manner by a compound of Formula I in low nanomolar range.

Aberrant up-regulation of VEGF, a key factor for angiogenesis, is an important contributor to the pathogenesis of disease states such as cancer, diabetic retinopathy, rheumatoid arthritis, psoriasis, atherosclerosis, chronic inflammation, other chronic inflammation-related diseases and disorders, obesity, and exudative macular degeneration. In accordance with the present invention, compounds that inhibit VEGF translation, referred to as VEGF translation-inhibiting compounds or translation-inhibiting compounds, have been identified and methods for their use provided. The VEGF translation-inhibiting compounds of the present invention preferably have nanomolar to sub-nanomolar activity for the inhibition of VEGF translation.

A VEGF translation-inhibiting compound, such as for example a compound for use in the methods of the present invention, may be obtained in any manner. In one embodiment, the VEGF translation-inhibiting compound is obtained by purchase. In another embodiment, the VEGF translation-inhibiting compound is obtained by synthesis. In further embodiments, the compound is obtained by gift or loan.

In various embodiments, compounds that inhibit VEGF translation may be useful in the inhibition of angiogenesis, and/or in the treatment of diabetic retinopathy, rheumatoid arthritis, psoriasis, atherosclerosis, chronic inflammation, a chronic inflammation related disease or disorder, obesity, exudative macular degeneration, or sepsis. In other embodiments, compounds that inhibit VEGF translation may be useful in the treatment of cancer, including for example, in the treatment of a solid tumor cancer, Wilms tumor, neuroblastoma, malignant melanoma, cervical cancer, lung cancer, colon cancer, or any combination of such cancers.

Compounds that inhibit VEGF translation may include one or more chiral centers, and as such may exist as racemic mixtures (R/S) or as enantiomerically pure compositions. The compounds may exist as (R) or (S) isomers (when one chiral center is present) in enantiomerically pure compositions. In an embodiment, VEGF translation inhibition compounds are the (S) isomers and may exist as enantiomerically pure compositions comprising only the (S) isomer. As one of skill in the art will recognize, when more than one chiral center is present, the inhibitory compounds may exist as (R,R), (R,S), (S,R), (S,S), etc. isomers. In an embodiment, compounds are (S,S) or (S,R) isomers.

As used herein, "enantiomerically pure" refers to compositions consisting substantially of a single isomer, preferably consisting of greater than or equal to 90%, 92%, 95%, 98%, 99%, or equal to 100% of a single isomer.

As used herein, a "racemic mixture" is any mixture of isometric forms that are not "enantiomerically pure," including, without limitation, about 50/50, about 60/40, and about 70/30 mixtures.

In an embodiment, a VEGF translation-inhibiting compound includes any compound that inhibits translation of VEGF. In another embodiment, exemplary VEGF translation-inhibiting compounds are carboline derivatives. In another embodiment, exemplary VEGF translation-inhibiting compounds are provided in U.S. Patent Application Publications 2005/0272759 and 2005/0282849, which publications are herein incorporated by reference in their entireties.

For example, preferred compounds of the present invention useful in the inhibition of VEGF translation include those compounds of Formula I:

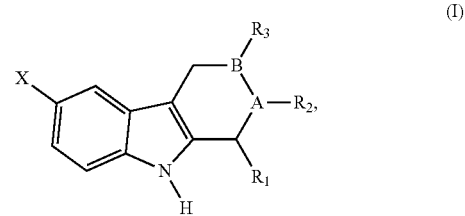

wherein
X is hydrogen; a $C_1$ to $C_6$ alkyl, optionally substituted with one or more halogens; a hydroxyl group; a halogen; a $C_1$ to $C_5$ alkoxy, optionally substituted with a $C_6$ to $C_{10}$ aryl group;
A is C or N;
B is C or N, with the proviso that at least one of A or B is N, and that when A is N, B is C;
$R_1$ is a hydroxyl group; a $C_1$ to $C_8$ alkyl group, optionally substituted with an alkylthio group, a 5 to 10 membered heteroaryl, a $C_6$ to $C_{10}$ aryl group optionally substituted with at least one independently selected $R_o$ group; a $C_2$ to $C_8$ alkenyl group; a $C_2$ to $C_8$ alkynyl group; a 3 to 12 membered heterocycle group, wherein the heterocycle group is optionally substituted with at least one independently selected halogen, oxo, amino, alkylamino, acetamino, thio, or alkylthio group; a 5 to 12 membered heteroaryl group, wherein the heteroaryl group is optionally substituted with at least one independently selected halogen, oxo, amino, alkyl amino, acetamino, thio, or alkylthio group; or a $C_6$ to $C_{10}$ aryl group, optionally substituted with at least one independently selected $R_o$ group;
$R_o$ is a halogen; a cyano; a nitro; a sulfonyl, wherein the sulfonyl is optionally substituted with a $C_1$ to $C_6$ alkyl or a 3 to 10 membered heterocycle; an amino group, wherein the amino group is optionally substituted with a $C_1$ to $C_6$ alkyl, —C(O)—$R_b$, —C(O)O—$R_b$, a sulfonyl, an alkylsulfonyl, a 3 to 10 membered heterocycle group optionally substituted with a —C(O)O—$R_n$; —C(O)—NH—$R_b$; a 5 to 6 membered heterocycle; a 5 to 6 membered heteroaryl; a $C_1$ to $C_6$ alkyl group, wherein the alkyl group is optionally substituted with at least one independently selected hydroxyl, halogen, amino, or 3 to 12 membered heterocycle group, wherein the amino group and heterocycle group are optionally substituted with at least one independently selected $C_1$ to $C_4$ alkyl group, which $C_1$ to $C_4$ alkyl group is optionally substituted with at least one independently selected $C_1$ to $C_4$ alkoxy group, amino group, alkylamino group, or 5 to 10 membered heterocycle group; a —C(O)—$R_n$ group; or an —O$R_a$ group;
$R_a$ is hydrogen; $C_2$ to $C_8$ alkylene; a —C(O)O—$R_b$ group; a —C(O)—NH—$R_b$; a $C_1$ to $C_8$ alkyl, wherein the alkyl group is optionally substituted with at least one independently selected hydroxyl, halogen, $C_1$ to $C_4$ alkoxy, amino, alkylamino, acetamide, —C(O)—$R_b$, —C(O)O—$R_b$, $C_6$ to $C_{10}$ aryl, 3 to 12 membered heterocycle, or 5 to 12 heteroaryl group, further wherein the alkylamino is optionally substituted with a hydroxyl, a $C_1$ to $C_4$ alkoxy, or a 5 to 12 membered heteroaryl optionally substituted with a $C_1$ to $C_4$ alkyl, further wherein the acetamide is optionally substituted with a $C_1$ to $C_4$ alkoxy, sulfonyl, or alkylsulfonyl, further wherein and the heterocycle group is optionally substituted with a $C_1$ to $C_4$ alkyl optionally substituted with a hydroxyl group, —C(O)—$R_n$, —C(O)O—$R_n$, or an oxo group;

$R_b$ is hydroxyl; an amino; an alkylamino, wherein the alkylamino is optionally substituted with a hydroxyl, an amino, an alkylamino, a $C_1$ to $C_4$ alkoxy, a 3 to 12 membered heterocycle optionally substituted with at least one independently selected $C_1$ to $C_6$ alkyl, oxo, —C(O)O—$R_n$, or a 5 to 12 membered heteroaryl optionally substituted with a $C_1$ to $C_4$ alkyl; a $C_1$ to $C_4$ alkoxy; a $C_2$ to $C_8$ alkenyl; a $C_2$ to $C_8$ alkynyl; a $C_6$ to $C_{10}$ aryl, wherein the aryl is optionally substituted with at least one independently selected halogen or $C_1$ to $C_4$ alkoxy; a 5 to 12 membered heteroaryl; 3 to 12 membered heterocycle group, wherein the heterocycle is optionally substituted with at least one independently selected acetamide, —C(O)O—$R_n$, 5 to 6 membered heterocycle, or $C_1$ to $C_6$ alkyl optionally substituted with a hydroxyl, $C_1$ to $C_4$ alkoxy, amino group, or alkylamino group; or a $C_1$ to $C_8$ alkyl, wherein the alkyl is optionally substituted with at least one independently selected $C_1$ to $C_4$ alkoxy, $C_6$ to $C_{10}$ aryl, amino, or 3 to 12 membered heterocycle group, wherein the amino and heterocycle groups are optionally substituted with at least one independently selected $C_1$ to $C_6$ alkyl, oxo, or —C(O)O—$R_n$ group;

$R_2$ is a hydrogen; a hydroxyl; a 5 to 10 membered heteroaryl group; a $C_1$ to $C_8$ alkyl group, wherein the alkyl group is optionally substituted with a hydroxyl, a $C_1$ to $C_4$ alkoxy, a 3 to 10 membered heterocycle, a 5 to 10 membered heteroaryl, or $C_6$ to $C_{10}$ aryl group; a —C(O)—$R_c$ group; a —C(O)O—$R_d$ group; a —C(O)—N($R_d R_d$) group; a —C(S)—N($R_d R_d$) group; a —C(S)—O—$R_e$ group; a —S(O$_2$)—$R_e$, group; a —C(N$R_e$)—S—$R_e$ group; or a —C(S)—S—$R_f$ group;

$R_c$ is hydrogen; an amino, wherein the amino is optionally substituted with at least one independently selected $C_1$ to $C_6$ alkyl or $C_6$ to $C_{10}$ aryl group; a $C_6$ to $C_{10}$ aryl, wherein the aryl is optionally substituted with at least one independently selected halogen, haloalkyl, hydroxyl, $C_1$ to $C_4$ alkoxy, or $C_1$ to $C_6$ alkyl group; —C(O)—$R_n$; a 5 to 6 membered heterocycle, wherein the heterocycle is optionally substituted with a —C(O)—$R_n$ group; a 5 to 6 membered heteroaryl; a thiazoleamino group; a $C_1$ to $C_8$ alkyl group, wherein the alkyl group is optionally substituted with at least one independently selected halogen, a $C_1$ to $C_4$ alkoxy, a phenyloxy, a $C_6$ to $C_{10}$ aryl, —C(O)—$R_n$, —O—C(O)—$R_n$, hydroxyl, or amino group, optionally substituted with a —C(O)O—$R_n$ group;

$R_d$ is independently hydrogen; a $C_2$ to $C_8$ alkenyl group; a $C_2$ to $C_8$ alkynyl group; a $C_6$ to $C_{10}$ aryl group, wherein the aryl is optionally substituted with at least one independently selected halogen, nitro, $C_1$ to $C_6$ alkyl, —C(O)O—$R_e$, or —O$R_e$; or a $C_1$ to $C_8$ alkyl group, wherein the alkyl group is optionally substituted with at least one independently selected halogen, $C_1$ to $C_4$ alkyl, $C_1$ to $C_4$ alkoxy, phenyloxy, $C_6$ to $C_{10}$ aryl, 5 to 6 membered heteroaryl, —C(O)—$R_n$, —O—C(O)—$R_n$, or hydroxyl group, wherein the $C_6$ to $C_{10}$ aryl group is optionally substituted with at least one independently selected halogen or haloalkyl group;

$R_e$ is a hydrogen; a $C_1$ to $C_6$ alkyl group, wherein the alkyl group is optionally substituted with at least one independently selected halogen or alkoxy group; or a $C_6$ to $C_{10}$ aryl group, wherein the aryl group is optionally substituted with at least one independently selected halogen or alkoxy group;

$R_f$ is a $C_1$ to $C_6$ alkyl group, optionally substituted with at least one independently selected halogen, hydroxyl, $C_1$ to $C_4$ alkoxy, cyano, $C_6$ to $C_{10}$ aryl, or —C(O)—$R_n$ group, wherein the alkoxy group may be optionally substituted with at least one $C_1$ to $C_4$ alkoxy group and the aryl group may be optionally substituted with at least one independently selected halogen, hydroxyl, $C_1$ to $C_4$ alkoxy, cyano, or $C_1$ to $C_6$ alkyl group;

$R_n$ is a hydroxyl, $C_1$ to $C_4$ alkoxy, amino, or $C_1$ to $C_6$ alkyl group;

$R_3$ is hydrogen or —C(O)—$R_g$;

$R_g$ is a hydroxyl group; an amino group, wherein the amino is optionally substituted with a $C_6$ to $C_{10}$ cycloalkyl group or a 5 to 10 membered heteroaryl group; or a 5 to 10 membered heterocycle group, wherein the heterocycle group is optionally substituted with a —C(O)—$R_n$ group; and n is 0, 1, 2, or 3.

As will be evident to one of skill in the art, the compounds of Formula I comprise at least one stereocenter (e.g., at the $R_1$ substituent), and may exist as a racemic mixture or as an enantiomerically pure composition. In an embodiment, the compounds of Formula I are the (S) isomer, in an enantiomerically pure composition.

As used herein, the term "alkyl" generally refers to saturated hydrocarbyl radicals of straight, branched or cyclic configuration including methyl, ethyl, n-propyl, isopropyl, n-butyl, isobutyl, sec-butyl, tert-butyl, n-pentyl, n-hexyl, cyclohexyl, n-heptyl, octyl, n-octyl, and the like. In some embodiments, alkyl substituents may include $C_1$ to $C_8$, $C_1$ to $C_6$, or $C_1$ to $C_4$ alkyl groups. The alkyl group may be optionally substituted with one or more halogen or alkoxy groups. For instance, the alkyl group may be a haloalkyl, dihaloalkyl, or trihaloalkyl.

As used herein, "alkenyl" generally refers to linear, branched or cyclic alkene radicals having one or more carbon-carbon double bonds, such as $C_2$ to $C_8$ and $C_2$ to $C_6$ alkenyl groups, including 3-propenyl.

As used herein, "alkynyl" generally refers to linear, branched or cyclic alkyne radicals having one or more carbon-carbon triple bonds, such as $C_2$ to $C_8$ and $C_2$ to $C_6$ alkynyl groups, including hex-3-yne.

As used herein, "aryl" refers to a carbocyclic aromatic zing structure. Included in the scope of aryl groups are aromatic rings having from five to twenty carbon atoms. Aryl ring structures include compounds having one or more ring structures, such as mono-, bi-, or tricyclic compounds. Examples of aryl groups that include phenyl, tolyl, anthracenyl, fluorenyl, indenyl, azulenyl, phenanthrenyl (i.e., phenanthrene), and napthyl (i.e., napthalene) ring structures. In certain embodiments, the aryl group may be optionally substituted.

As used herein, "heteroaryl" refers to cyclic aromatic ring structures in which one or more atoms in the ring, the heteroatom(s), is an element other than carbon. Heteroatoms are typically O, S or N atoms. Included within the scope of heteroaryl, and independently selectable, are O, N, and S heteroaryl ring structures. The ring structure may include compounds having one or more ring structures, such as mono-, bi-, or tricyclic compounds. In some embodiments, the heteroaryl groups may be selected from heteroaryl groups that contain one or more heteroatoms, two or more heteroatoms, three or more heteroatoms, or four or more heteroatoms. Heteroaryl ring structures may be selected from those that contain five or more atoms, six or more atoms, or eight or more atoms. Examples of heteroaryl ring structures include: acridine, benzimidazole, benzoxazole, benzodioxole, benzofuran, dihydro-chromen-4-only, 1,3-diazine, 1,2-diazine, 1,2-diazole, 1,4-diazanaphthalene, furan, furazan, imidazole, indole, isoxazole, isoquinoline, isothiazole, isoindolyl, oxazole, purine, pyridazine, pyrazole, pyridine, pyrazine, pyrimidine, pyrrole, quinoline, quinoxaline, thiazole, thiophene, 1,3,5-triazine, 1,2,4-triazine, 1,2,3-triazine, tetrazole and quinazoline. In certain embodiments, the heteroaryl may be optionally substituted.

As used herein, "heterocycle" refers to cyclic ring structures in which one or more atoms in the ring, the heteroatom(s), is an element other than carbon. Heteroatoms are typically O, S or N atoms. Included within the scope of heterocycle, and independently selectable, are O, N, and S heterocycle ring structures. The ring structure may include compounds having one or more ring structures, such as mono-, bi-, or tricyclic compounds. In some embodiments, the heterocycle groups may be selected from heterocycle groups that contain one or more heteroatoms, two or more heteroatoms, three or more heteroatoms, or four or more heteroatoms. Example of heterocycle groups include morpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl or tetrahydrothiopyranyl and the like. In certain embodiments, the heterocycle may optionally be substituted.

As used herein, "alkanoyl" generally refers to a group with the structure —C(O)—R. In certain embodiments, R may be a hydrogen, an alkyl, an 4-morpholinyl group, or a thiazoleamino group.

As used herein, "alkoxy" generally refers to a group with the structure —O—R. In certain embodiments, R may be an alkyl group, such as a $C_1$ to $C_5$ alkyl group.

For the purposes of this invention, halo substituents may be independently selected from the halogens such as fluorine, chlorine, bromine, iodine, and astatine.

In certain embodiments, X may be hydrogen, methoxy, hydroxyl, benzoxy, or a halogen, including bromide or chloride. In other embodiments, X may be a $C_1$ to $C_4$ alkyl or a haloalkyl.

$R_1$ may be a $C_6$ to $C_8$ aryl group, optionally substituted with at least one $R_0$ group. $R_0$ may be methoxy, benzoxy, a $C_1$ to $C_6$ alkyl, a 5 to 6 membered heteroaryl (such as furyl or imidazole), cyano, nitro, tri-fluoro methyl, or a halogen, and in another embodiment, methoxy, benzoxy, iso-butyl or a halogen, and in another embodiment, methoxy, iso-butyl, bromide or chloride. Alternatively, $R_1$ may be a 5 to 10 membered heteroaryl or 3 to 12 membered heterocycle, such as a pyridinyl group, a thiophene group, a furyl group, a tetrahydro furyl group, and a thiazole group dihydro-chromen-4-onyl group, a 1H-isoindolyl group, or a benzodioxole group.

$R_2$ may be a —$CH_2$-furyl group, a pyrimidyl group, or a —C(O)O—$R_d$ group. $R_d$ may be a $C_1$ to $C_6$ alkyl, optionally substituted with at least one halogen; or a $C_5$ to $C_6$ aryl, optionally substituted with at least one methyl, methoxy, or halogen.

In an embodiment, a class of VEGF translation-inhibiting compounds within Formula I includes those compounds of Formula (I-a) as shown below.

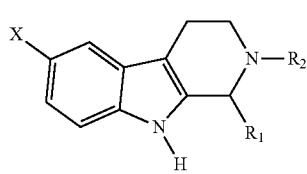

(I-a)

wherein X, $R_1$ and $R_2$ are defined as described with regard to Formula I and the embodiments described herein.

In an embodiment, another class of VEGF translation-inhibiting compounds within Formula I, includes those compounds of Formula (I-b) as shown below.

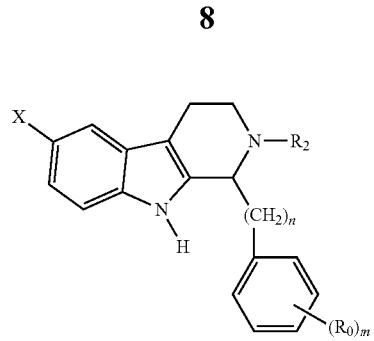

(I-b)

wherein:
X is a halogen;
$R_2$ is as described above with regard to Formula I;
$R_0$ is as described above with regard to Formula I;
m is 0, 1, 2, or 3; and
n is 0, 1, 2, or 3.

In other embodiments, classes of translation-inhibiting compounds within Formula I include the following.

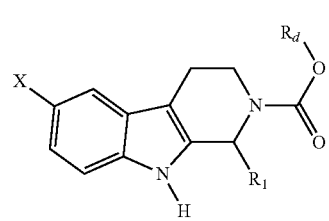

(I-c)

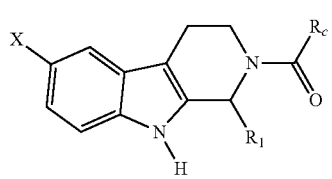

(I-d)

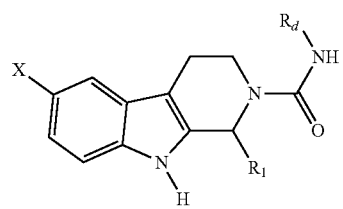

(I-e)

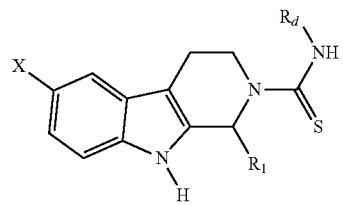

(I-f)

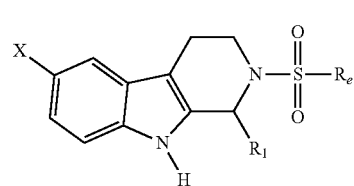

(I-g)

-continued

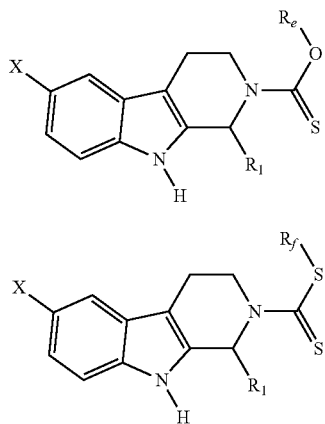

(I-h)

(I-i)

It is understood that substituents X and $R_1$, $R_c$, $R_d$, and $R_e$ of the compounds of Formulas (I-c) to (I-i) are defined as in Formula I.

In other embodiments, translation-inhibiting compounds of the present invention include those of Formulas (I-i) through (I-l), as shown below. In the embodiments of Formulas (I-j) through (I-l), substituents X, $R_1$, $R_2$, $R_3$, etc. are defined as in Formula I, as well as Formulas (I-a) to (I-i).

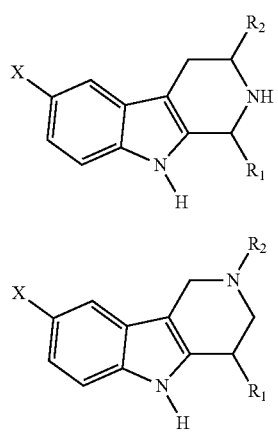

(I-j)

(I-k)

Also included within the scope of the invention are pharmaceutically acceptable salts, hydrates, solvates, clathrates, polymorphs, racemates and stereoisomers of the VEGF translation-inhibiting compounds described herein.

In another aspect of the invention, translation-inhibiting compounds of the present invention include those of Formula (I-l) as shown below.

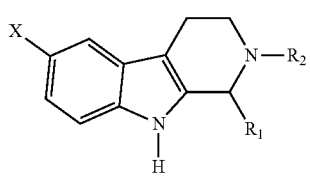

(I-l)

wherein,

X is hydrogen; a hydroxyl group; a halogen; a $C_1$-$C_4$ alkyl; a $C_1$ to $C_5$ alkoxy, optionally substituted with a $C_6$ to $C_8$ aryl group;

$R_1$ is a hydroxyl group; a $C_1$ to $C_8$ alkyl group, optionally substituted with a $C_6$ to $C_8$ aryl group, wherein the $C_6$ to $C_8$ aryl group is optionally substituted with at least one $R_0$ group; a heterocycle group; a heteroaryl group; and a $C_6$ to $C_8$ aryl group, optionally substituted with at least one $R_0$ group;

$R_0$ is a halogen; a $C_1$ to $C_6$ alkyl, optionally substituted with one or more halogen groups; a cyano group; a nitro group; an amino group; an aminoalkyl group; an acetamide group; an imidazole group; or $OR_a$;

$R_a$ is hydrogen; a $C_1$ to $C_6$ alkyl, optionally substituted with a heterocycle group or a $C_6$ to $C_8$ aryl group; or a —C(O)O—$R_b$;

$R_b$ is $C_1$ to $C_4$ alkyl group;

$R_2$ is a hydrogen; a hydroxyl; a heteroaryl group; a $C_1$ to $C_8$ alkyl group, optionally substituted with an alkoxy, hydroxyl, heteroaryl, or $C_6$ to $C_8$ aryl group; a —C(O)—$R_c$ group; a —C(O)O—$R_d$ group; a —C(O)NH—$R_d$ group; a —C(S)NH—$R_d$ group; a —S(O$_2$)—$R_e$ group; or (1S)-isopropyl-carbamic acid tert-butyl ester;

$R_c$ is hydrogen; a 4-morpholinyl group; a thiazoleamino group; a piperazinyl group, optionally substituted with a —C(O)CH$_3$ group; a $C_1$ to $C_6$ alkyl group, optionally substituted with a halogen, an alkoxy, or hydroxyl group;

$R_d$ is hydrogen; a benzyl group; a $C_1$ to $C_8$ alkyl group, optionally substituted with a halogen or an alkoxy group; a $C_6$ to $C_8$ aryl group, optionally substituted with at least one halogen, $C_1$ to $C_5$ alkyl, —C(O)O$R_e$, or $OR_e$;

$R_e$ is a hydrogen; a $C_1$ to $C_6$ alkyl group, optionally substituted with at least one halogen or alkoxy group; or a $C_6$ to $C_8$ aryl group; and n is 0, 1, 2, or 3.

In another embodiment, compounds of Formulas (II), (III) and (IV) are provided, which can be useful for inhibiting VEGF translation:

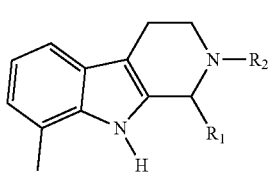

(II)

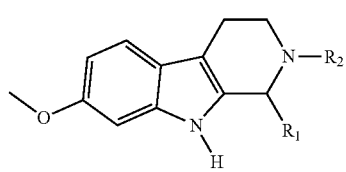

(III)

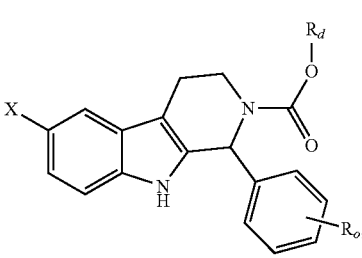

(IV)

wherein X, $R_1$, $R_2$, $R_o$ and $R_d$ are defined as described above with regard with Formula I.

For the purposes of this invention, where one or more functionalities encompassing X, $R_1$, $R_2$, $R_0$, $R_a$, $R_b$, $R_c$, $R_d$, and $R_e$, are incorporated into a molecule of Formulas (I), (II), and (III), including Formulas (I-a) to (I-k), each of the functionalities appearing at any location within the disclosed may be independently selected, and as appropriate, independently substituted. Further, where a more generic substituent is set forth for any position in the molecules of the present invention, it is understood that the generic substituent may be replaced with more specific substituents, and the resulting molecules are within the scope of the molecules of the present invention.

In another embodiment, VEGF translation-inhibiting compounds include the following compounds of Table A.

TABLE A

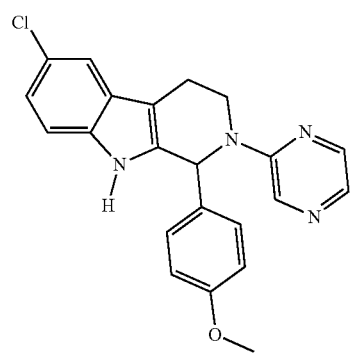

1

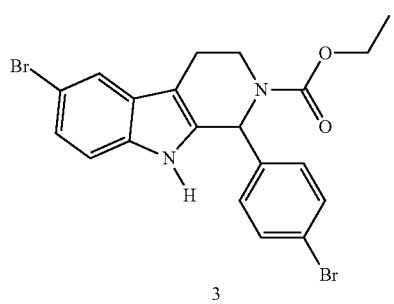

2

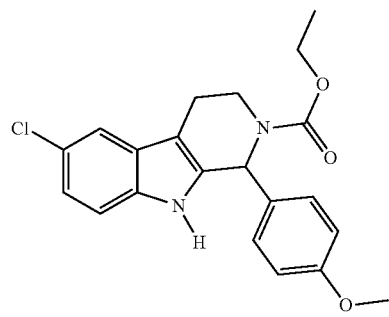

3

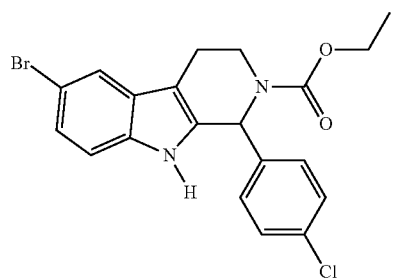

4

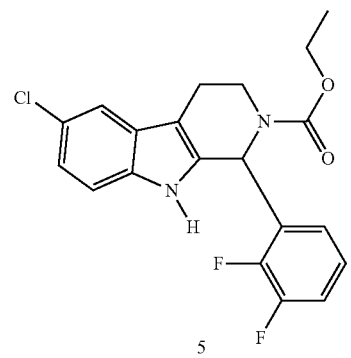

5

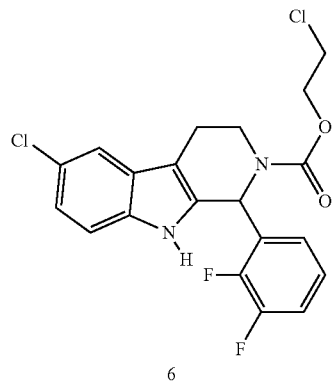

6

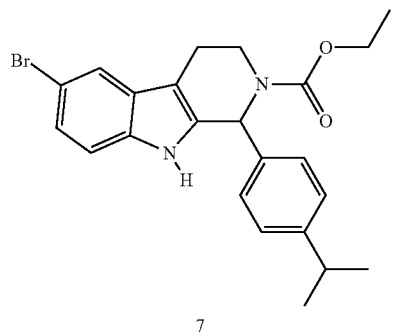

7

TABLE A-continued
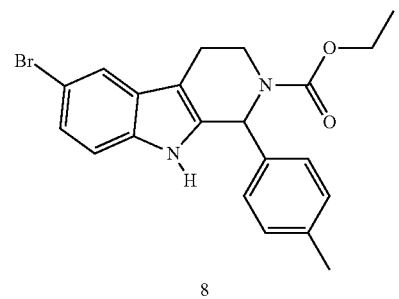
8
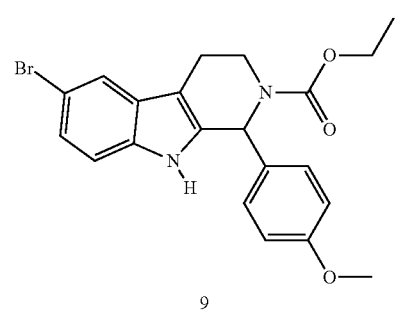
9
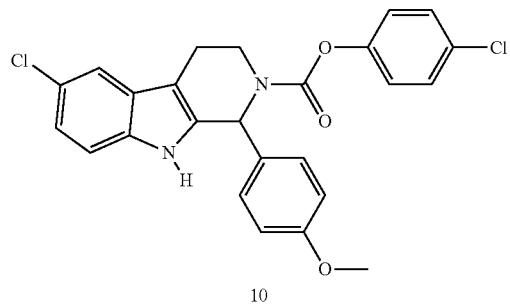
10
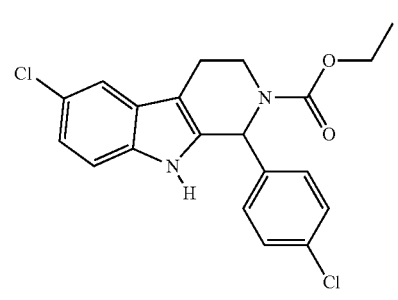
11

12
TABLE A-continued
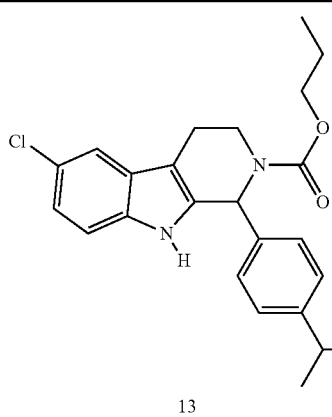
13
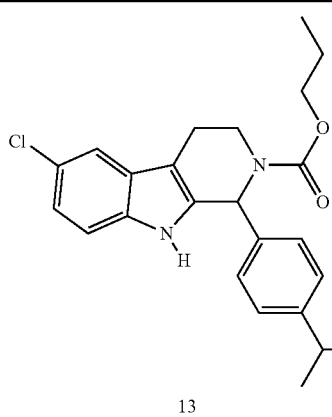
14
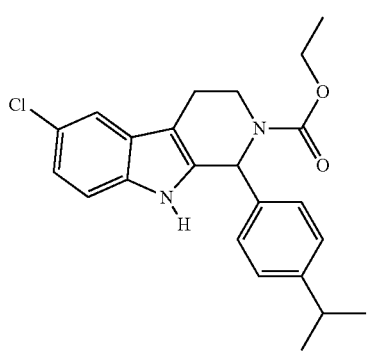
15
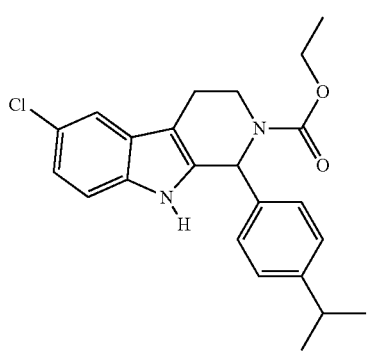
16

TABLE A-continued
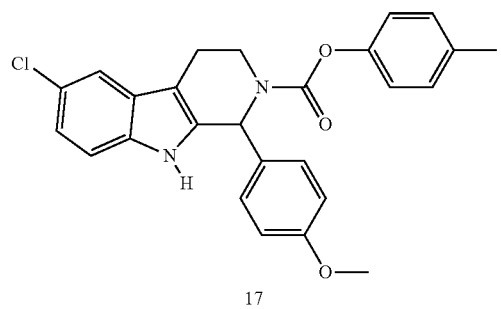
17
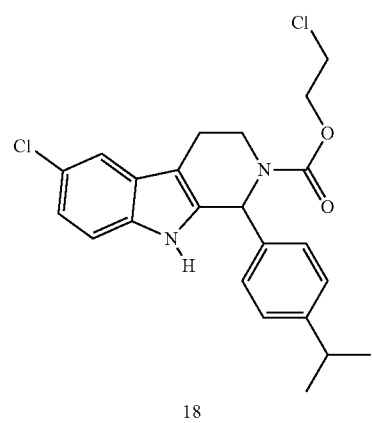
18
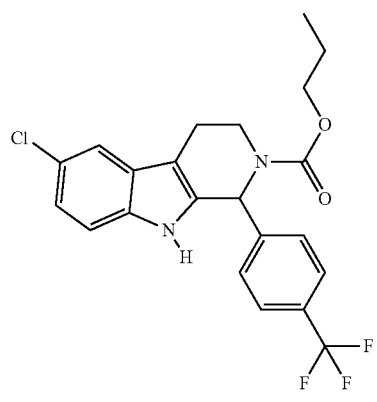
19
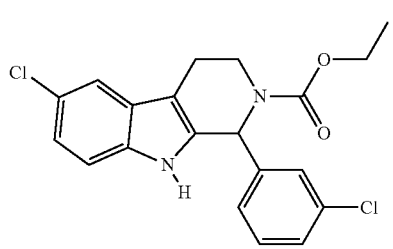
20
TABLE A-continued
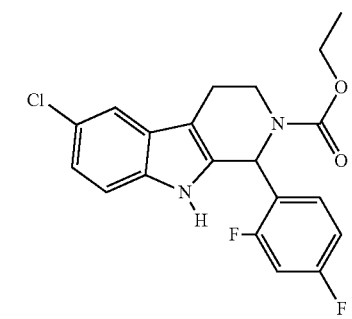
21
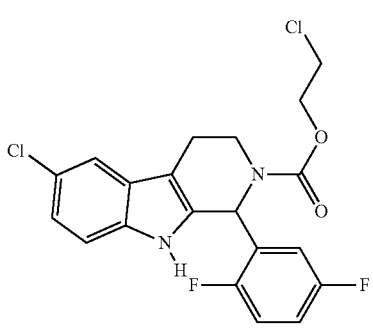
22
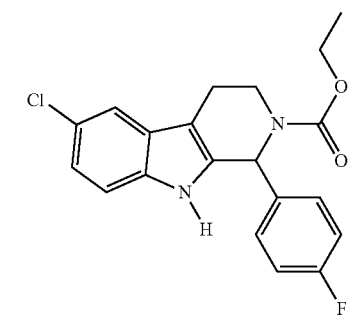
23
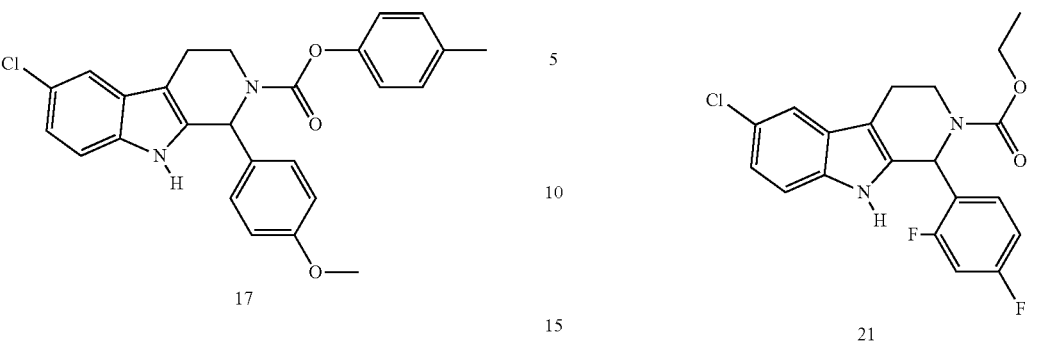
24

TABLE A-continued
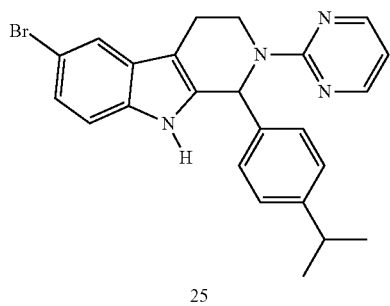
25
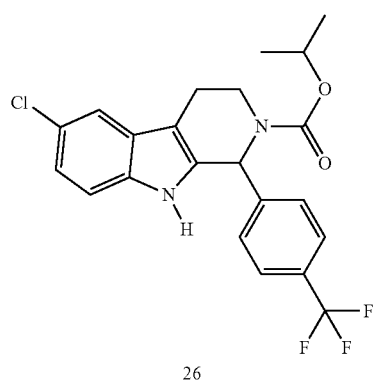
26
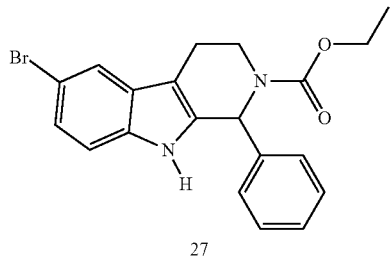
27
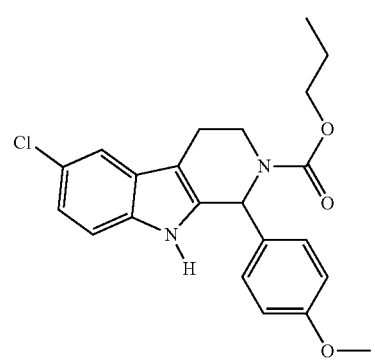
28
TABLE A-continued
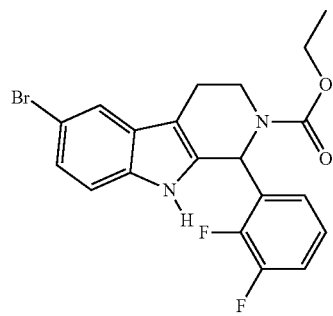
29
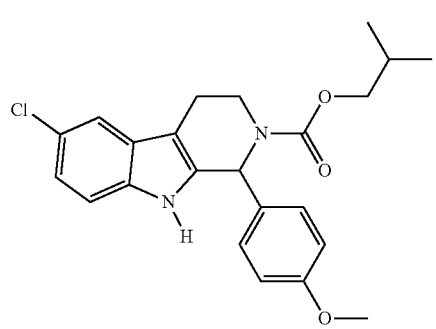
30
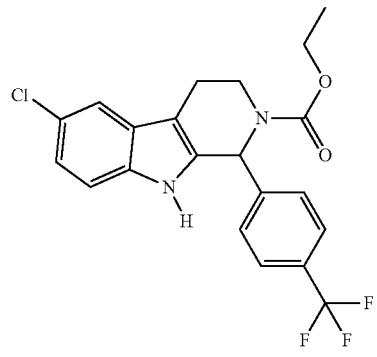
31
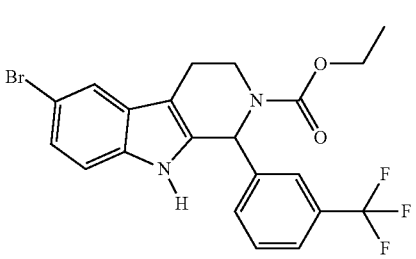
32

TABLE A-continued
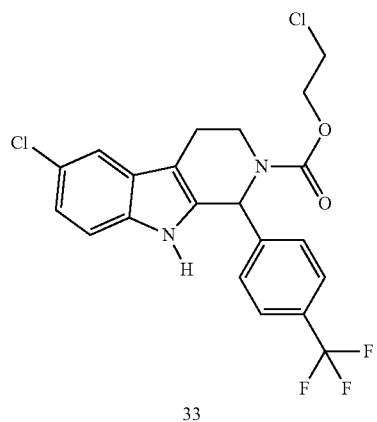
33
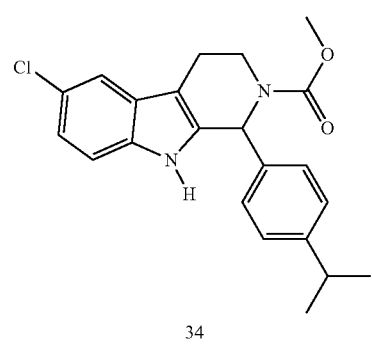
34
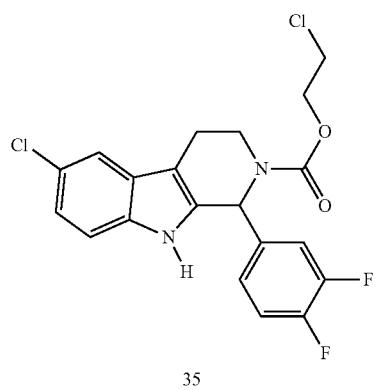
35
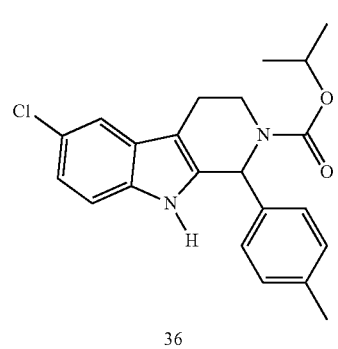
36
TABLE A-continued
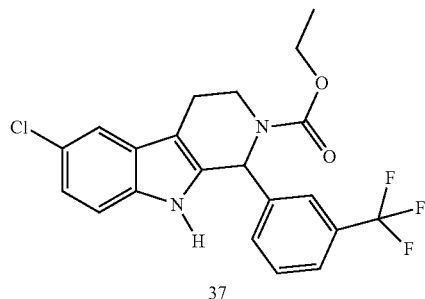
37
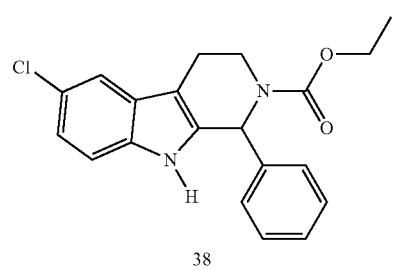
38
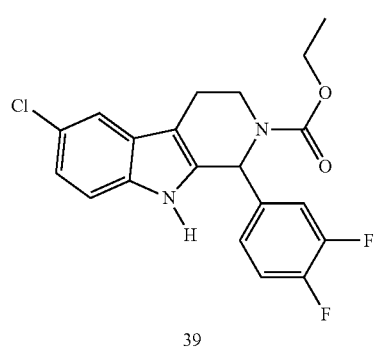
39
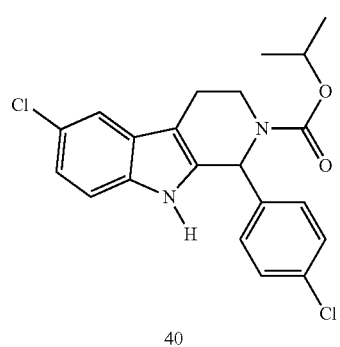
40
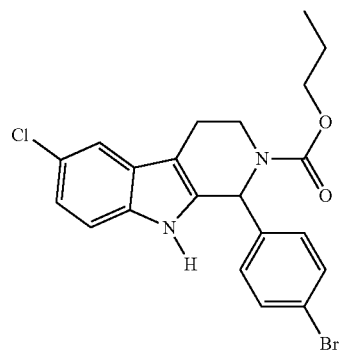
41

TABLE A-continued
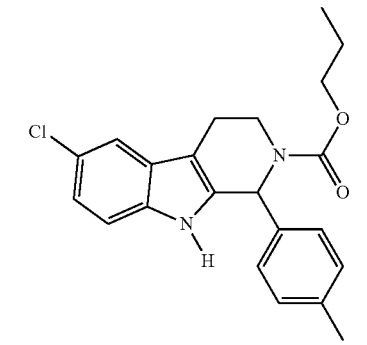
42
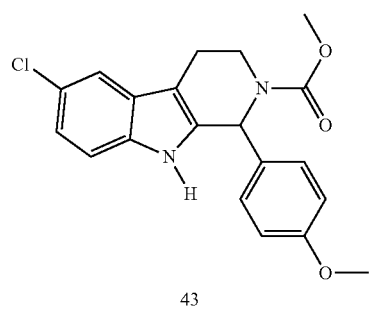
43
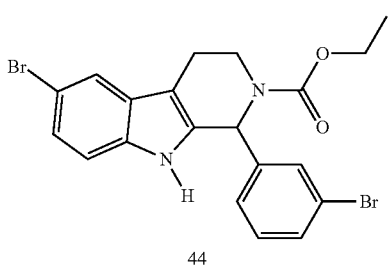
44
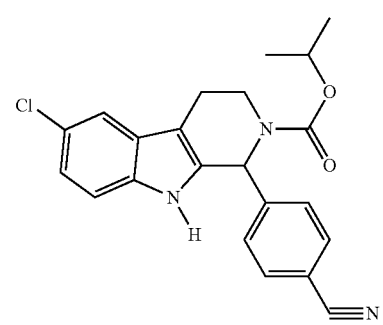
45
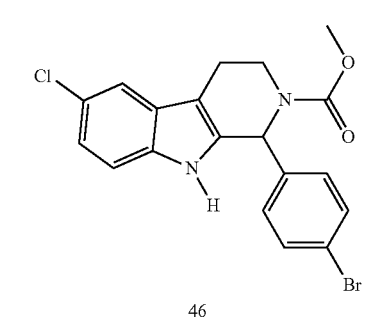
46
TABLE A-continued
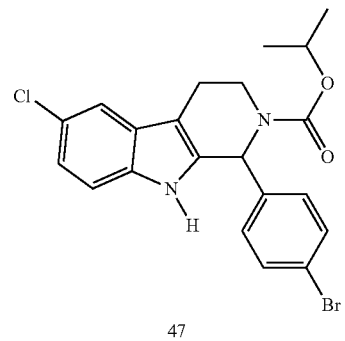
47
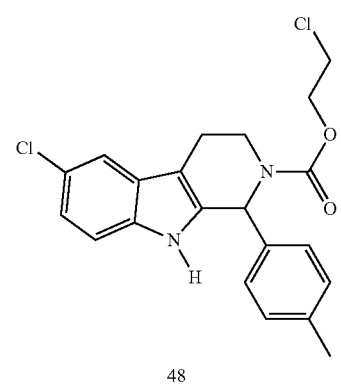
48
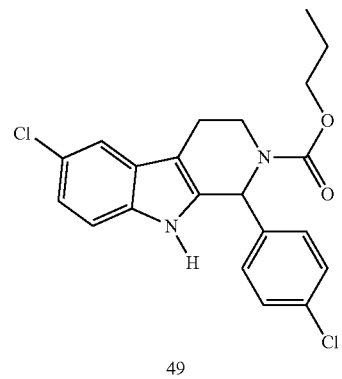
49
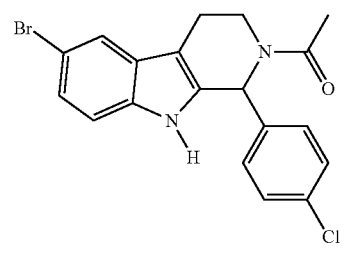
50

TABLE A-continued
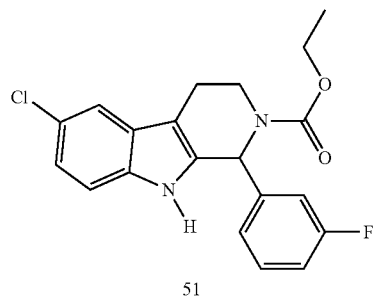
51
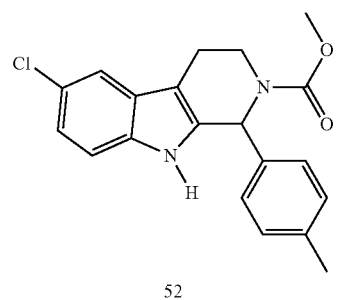
52
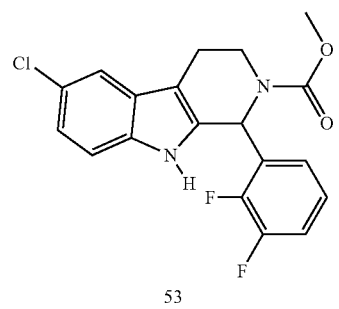
53
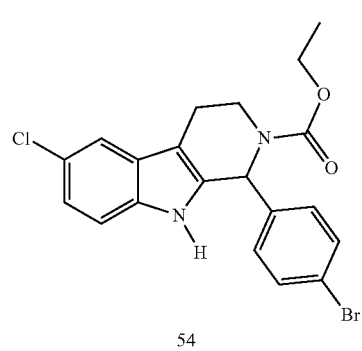
54
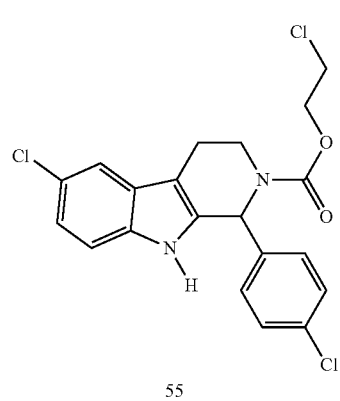
55
TABLE A-continued
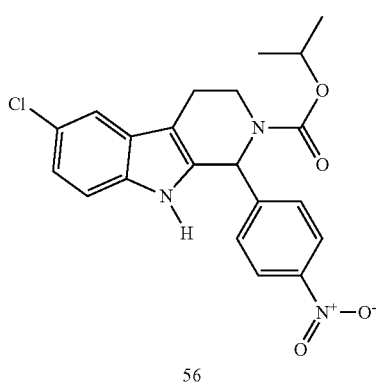
56
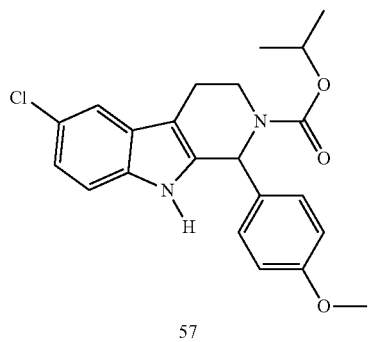
57
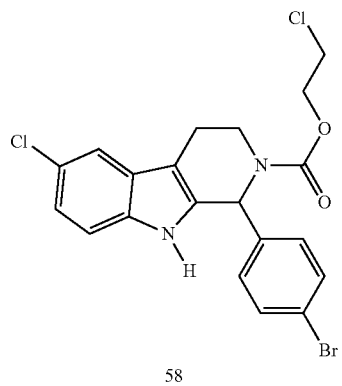
58
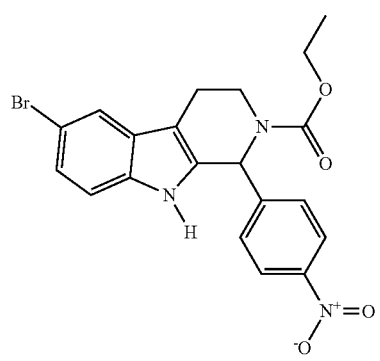
59

TABLE A-continued
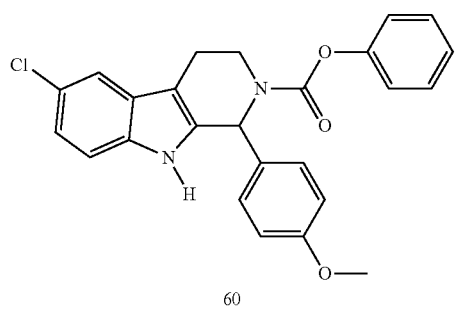
60
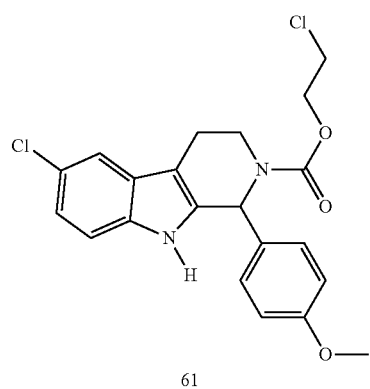
61
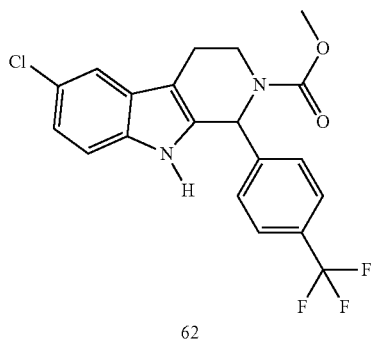
62
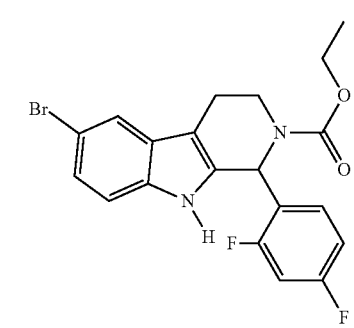
63
TABLE A-continued
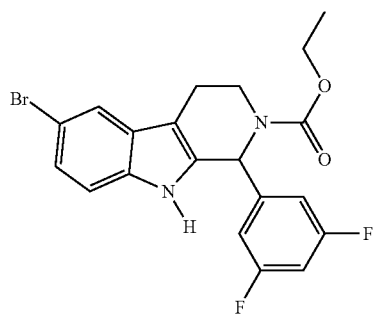
64
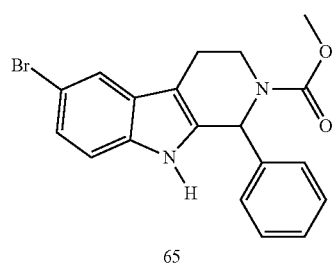
65
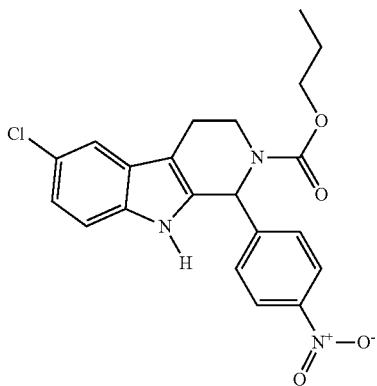
66
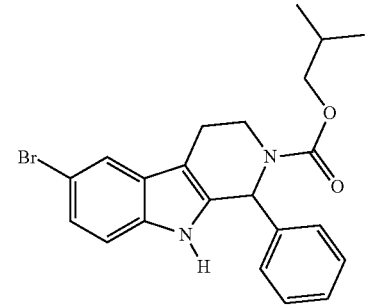
67

TABLE A-continued
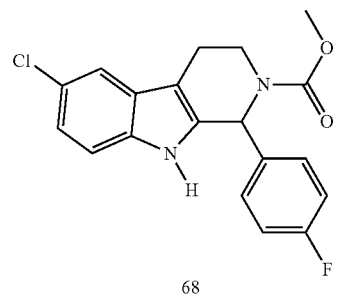
68
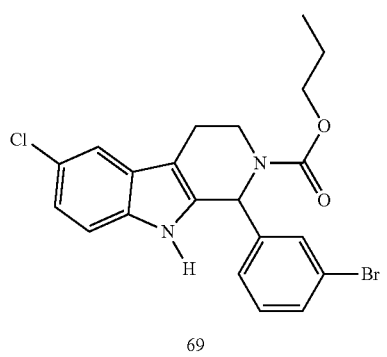
69
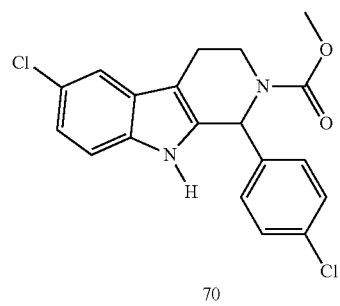
70
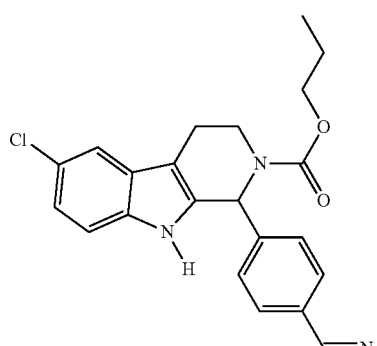
71
TABLE A-continued
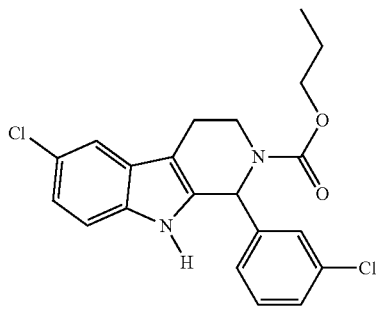
72
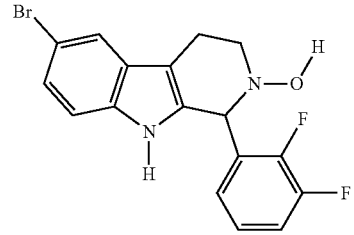
73
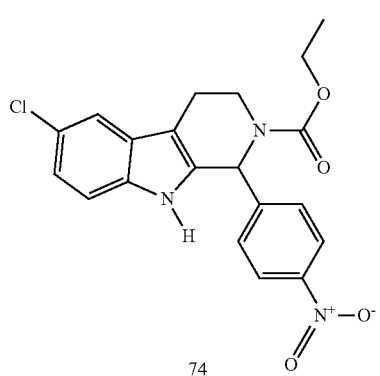
74
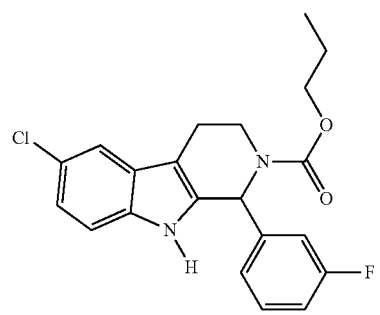
75

TABLE A-continued
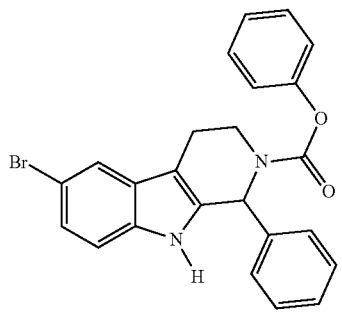
76
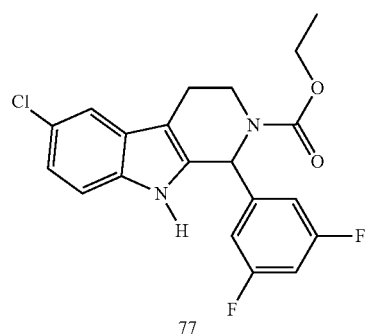
77
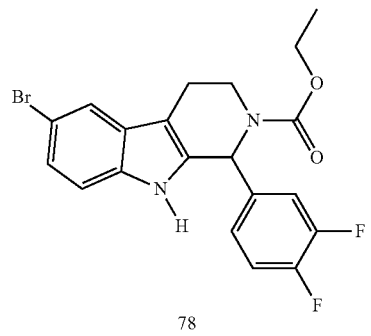
78
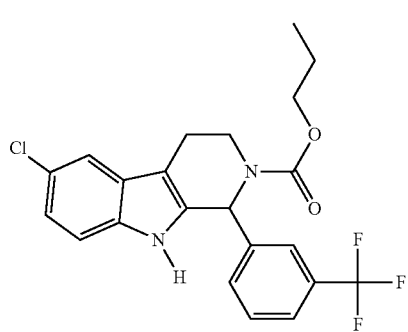
79
TABLE A-continued
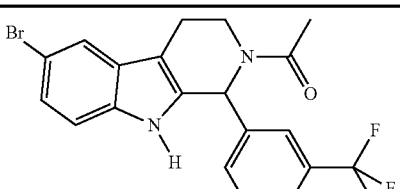
80
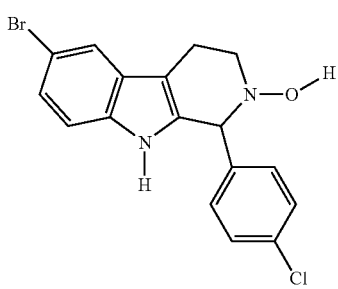
81
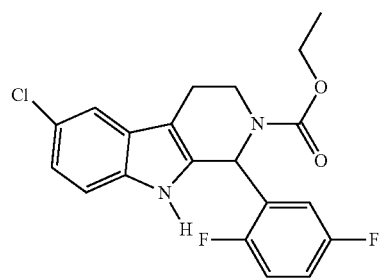
82
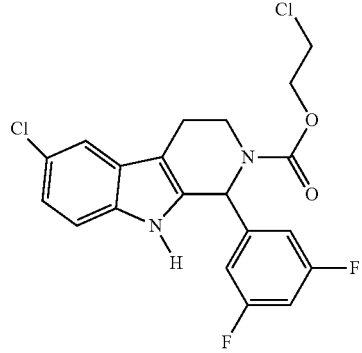
83
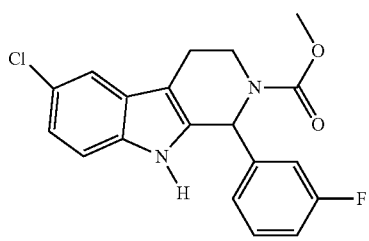
84

TABLE A-continued
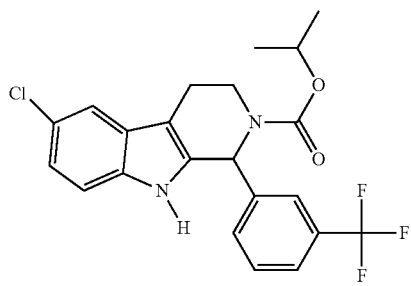
85
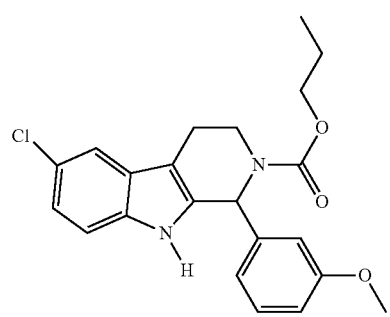
86
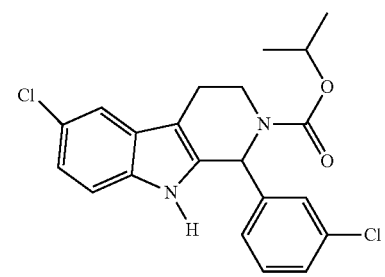
87
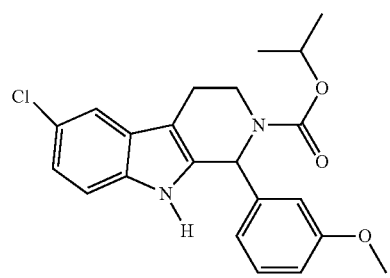
88
TABLE A-continued
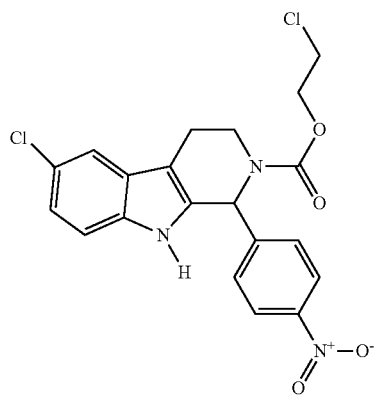
89
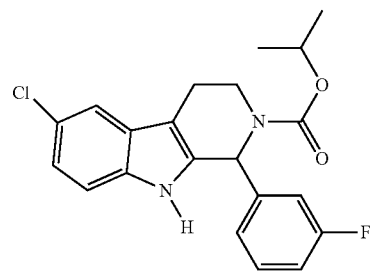
90
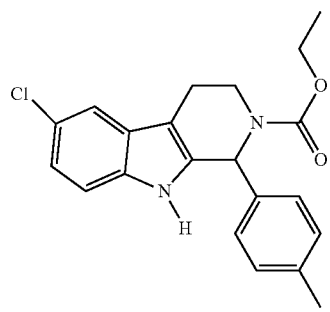
91
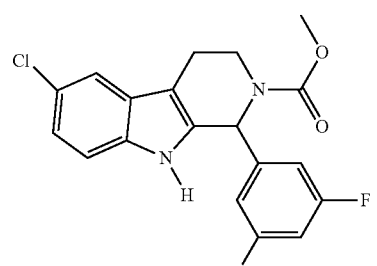
92

TABLE A-continued
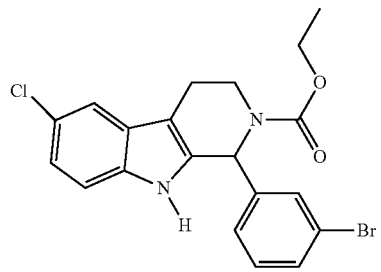
93
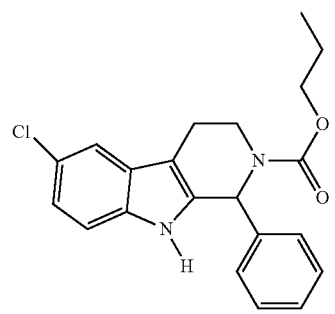
94
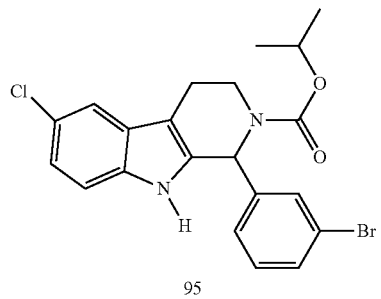
95
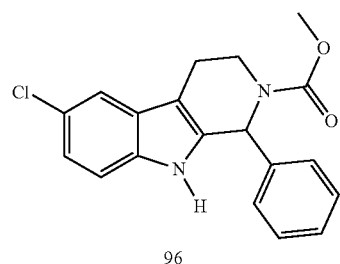
96
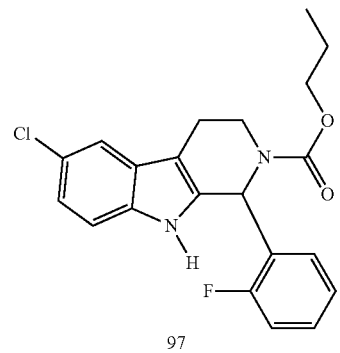
97
TABLE A-continued
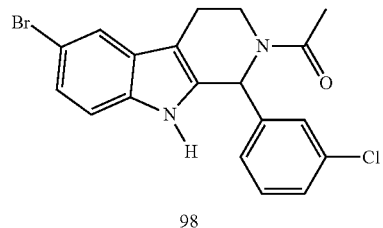
98
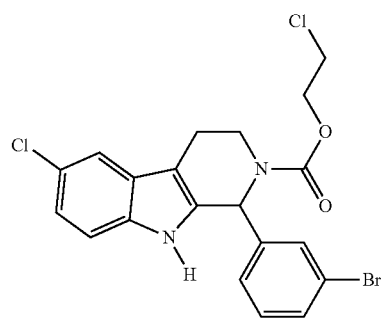
99
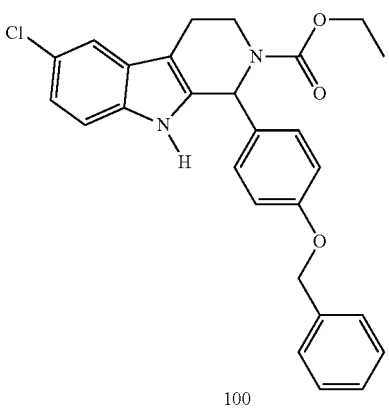
100
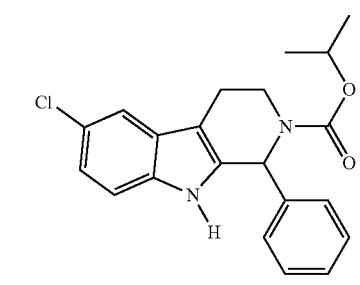
101
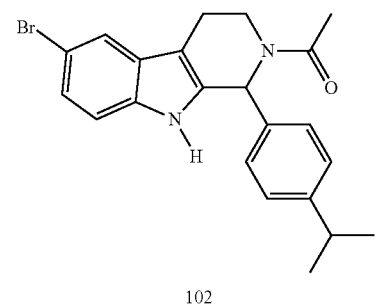
102

TABLE A-continued
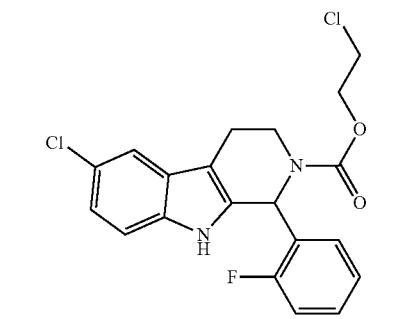
103
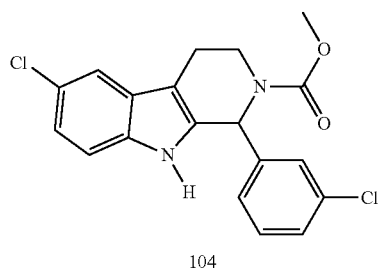
104
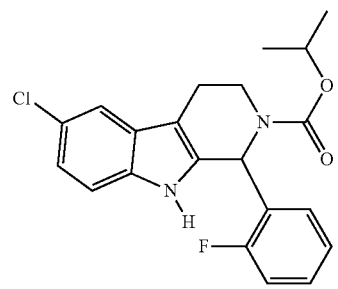
105
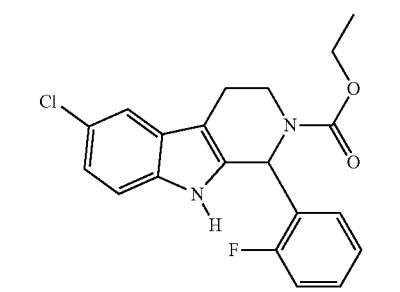
106
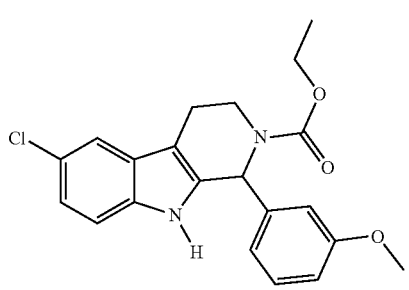
107
TABLE A-continued
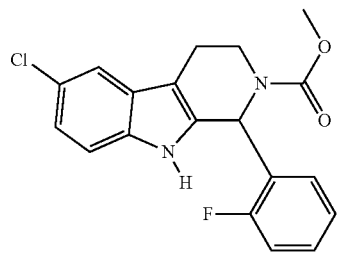
108
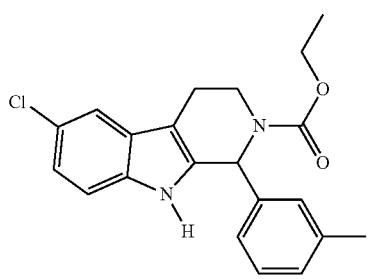
109
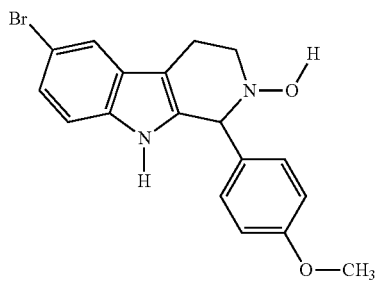
110
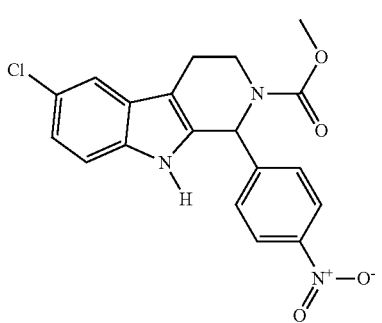
111
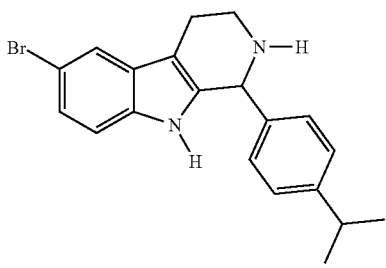
112

TABLE A-continued
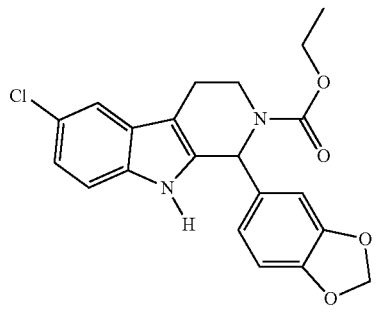
113
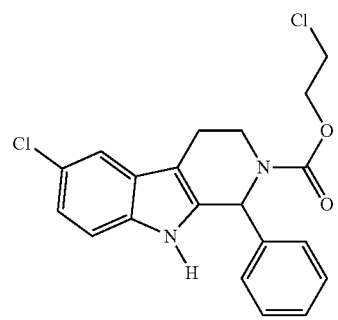
114
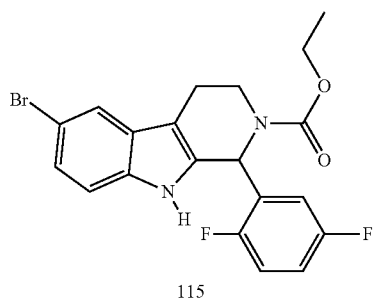
115
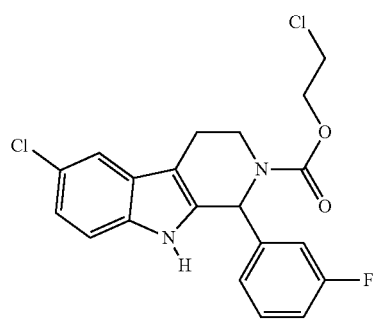
116
TABLE A-continued
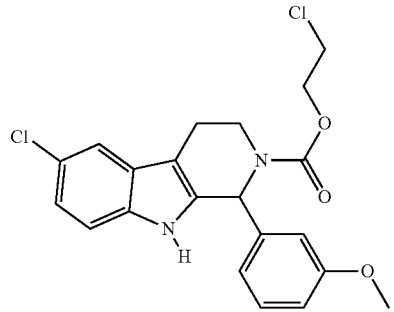
117
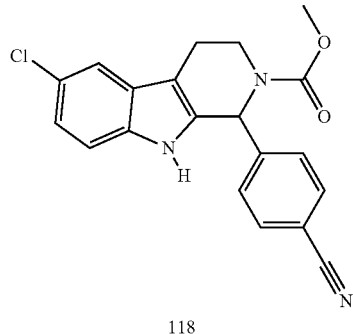
118
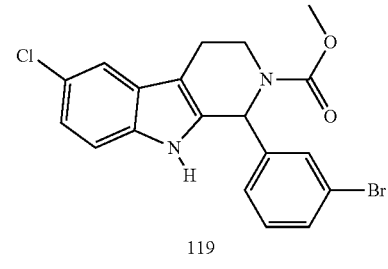
119
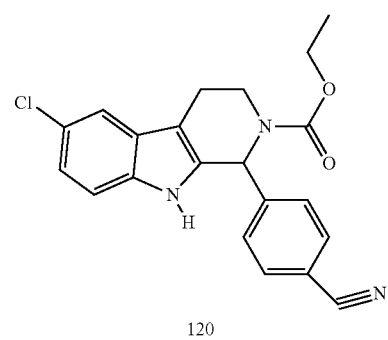
120
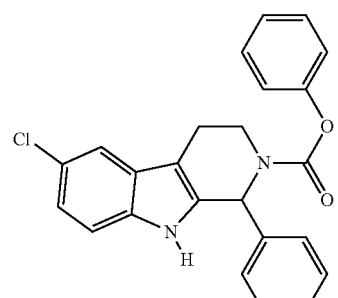
121

TABLE A-continued
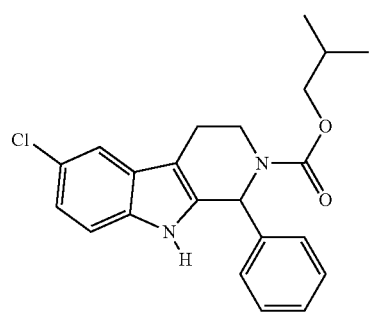
122
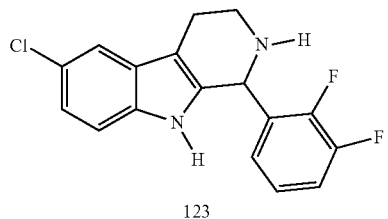
123
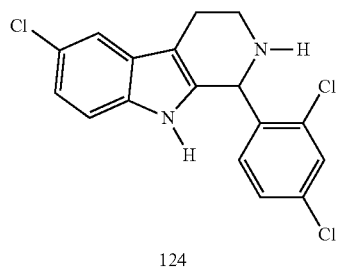
124
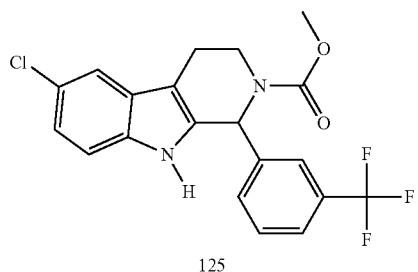
125
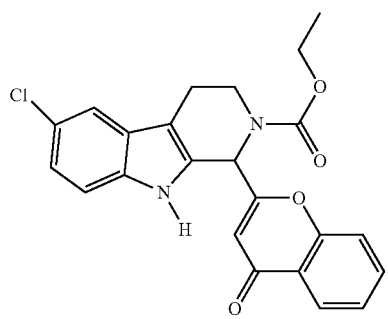
126
TABLE A-continued
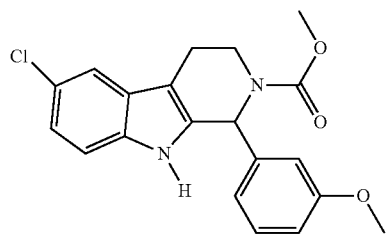
127
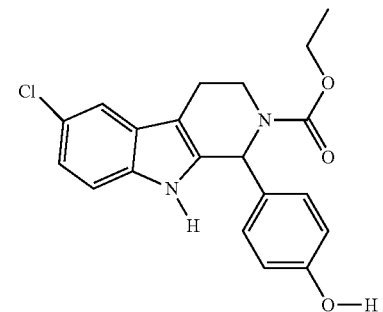
128
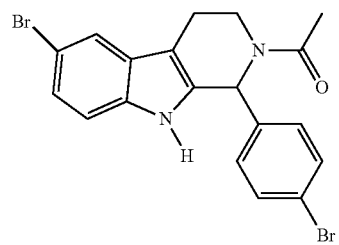
129
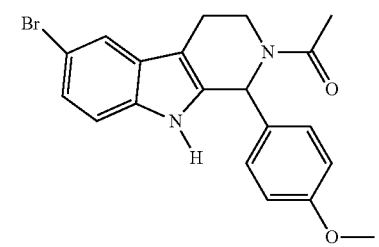
130
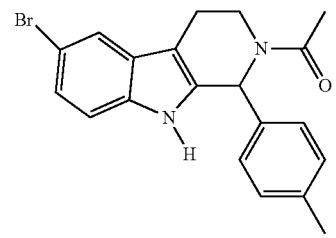
131

TABLE A-continued
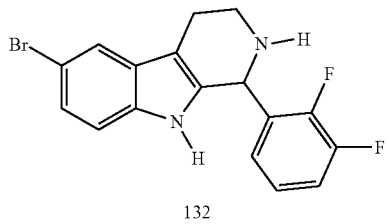
132
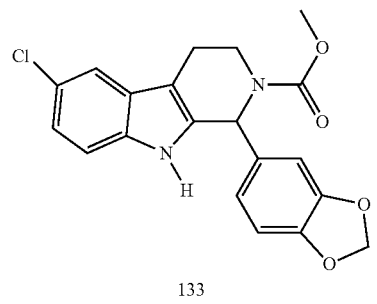
133
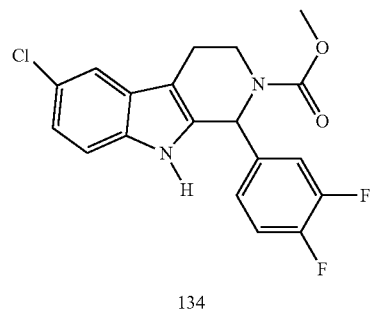
134
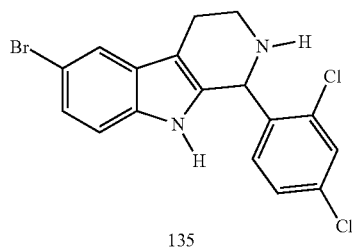
135
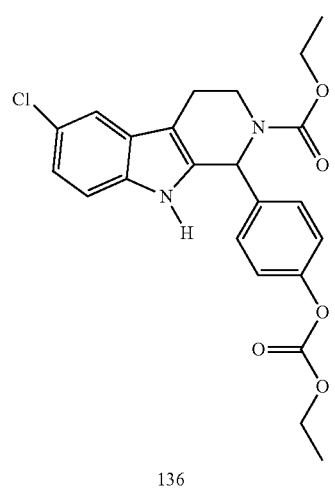
136
TABLE A-continued
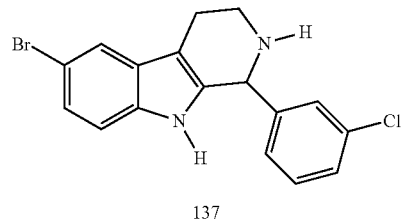
137
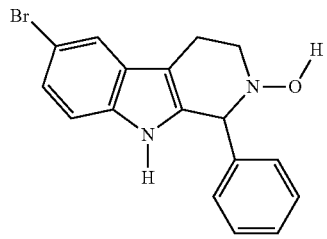
138
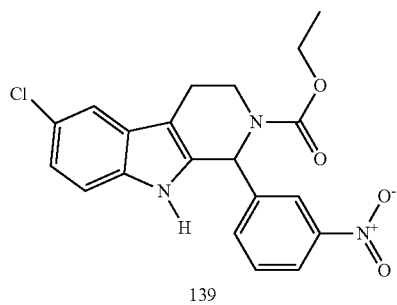
139
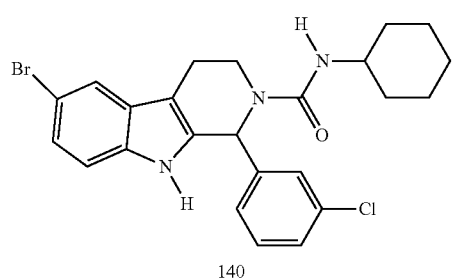
140
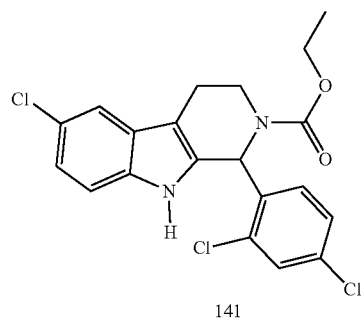
141

TABLE A-continued
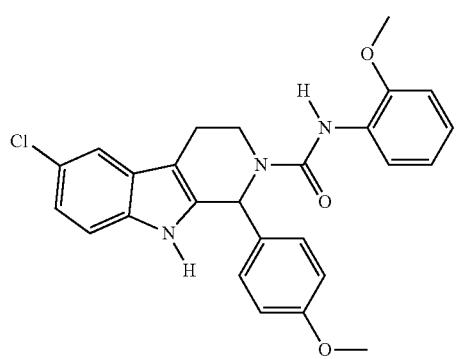
142
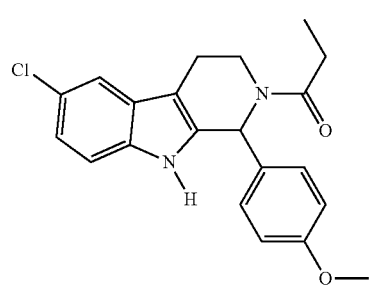
143
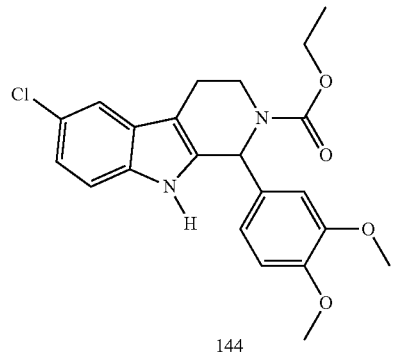
144
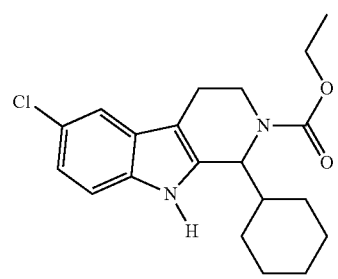
145
TABLE A-continued
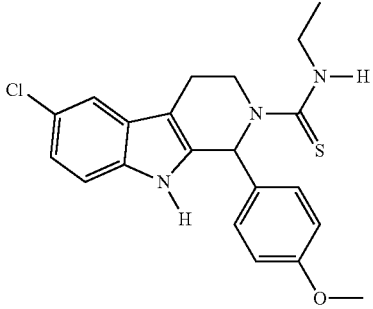
146
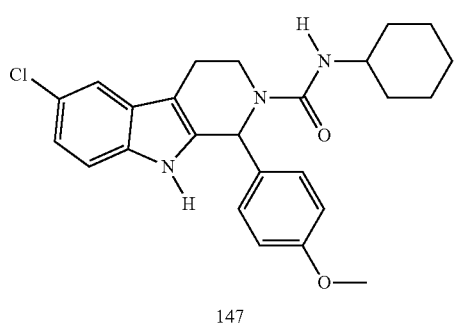
147
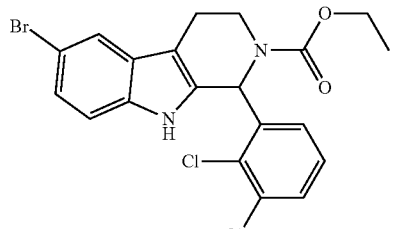
148
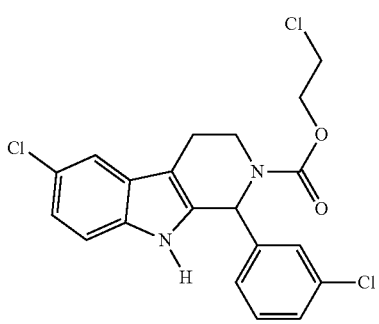
149
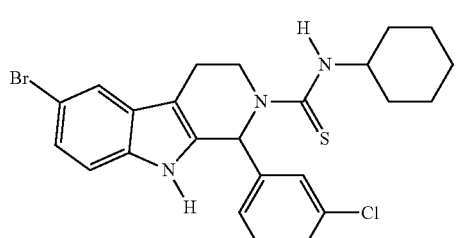
150

TABLE A-continued
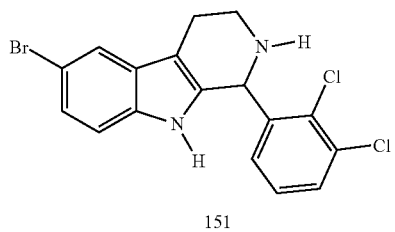
151
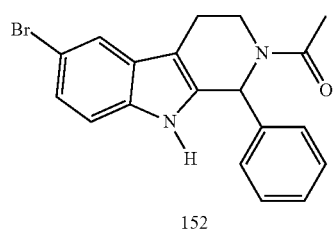
152
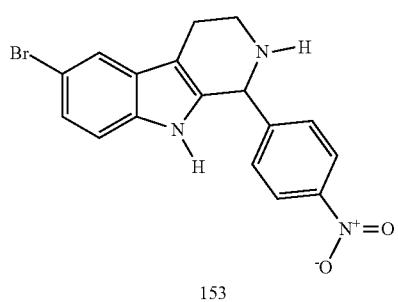
153
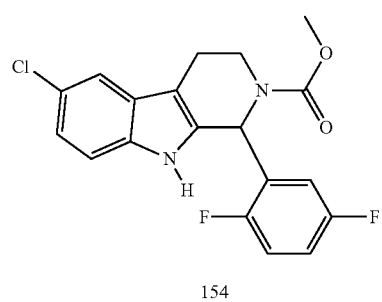
154
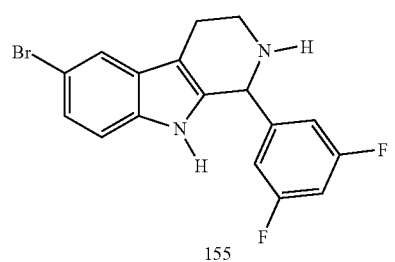
155
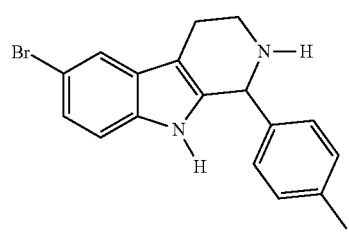
156
TABLE A-continued
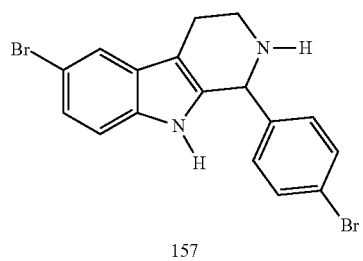
157
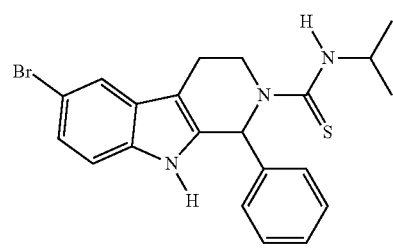
158
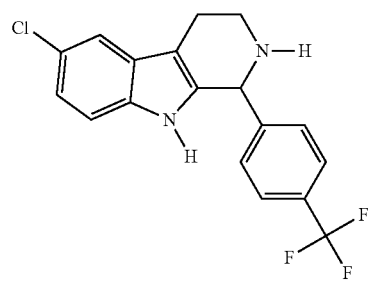
159
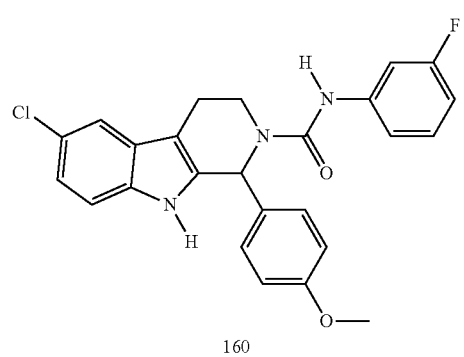
160
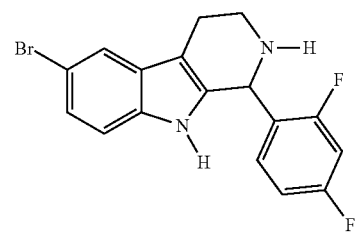
161

TABLE A-continued
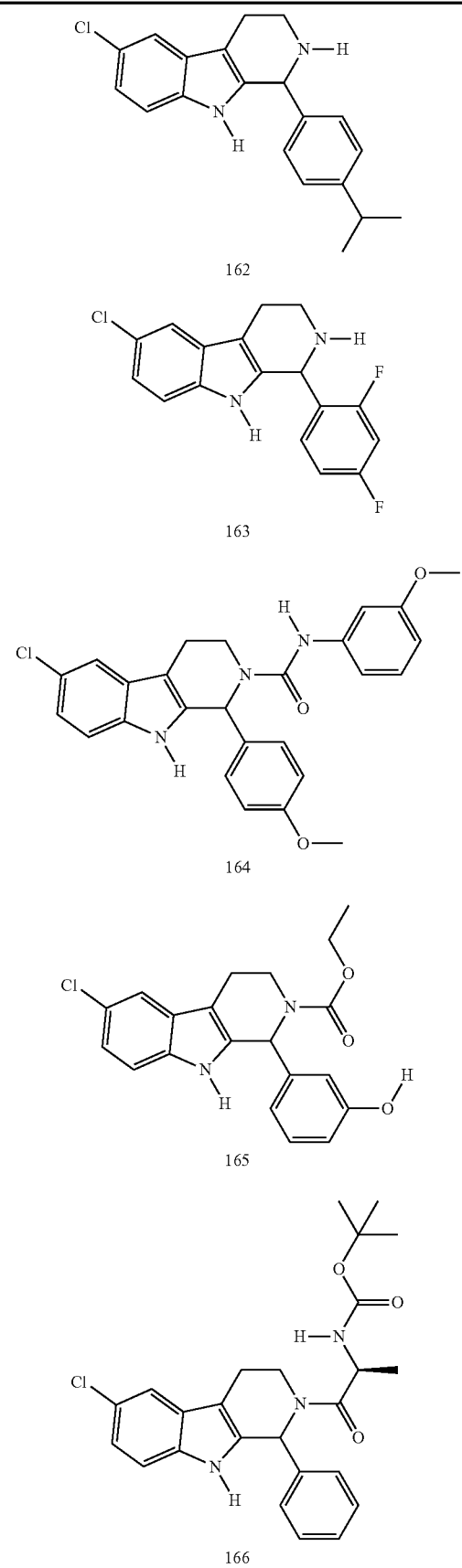
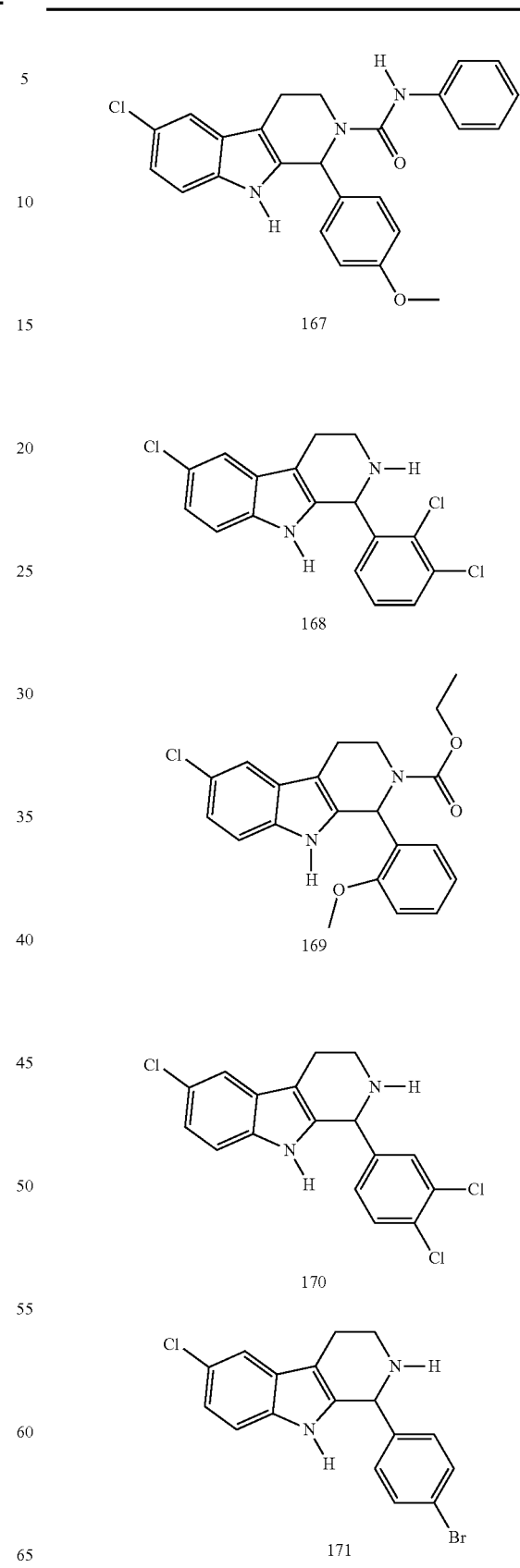

TABLE A-continued
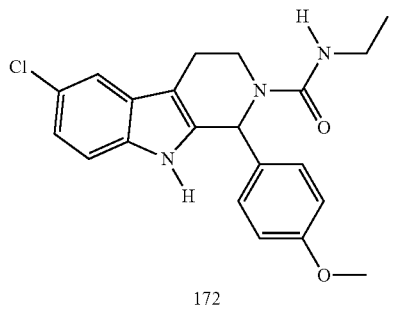
172
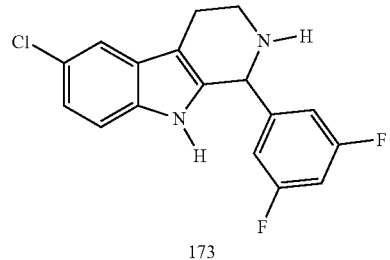
173
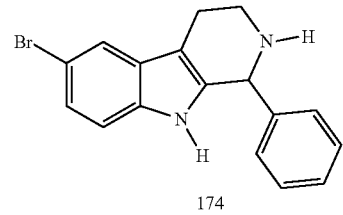
174
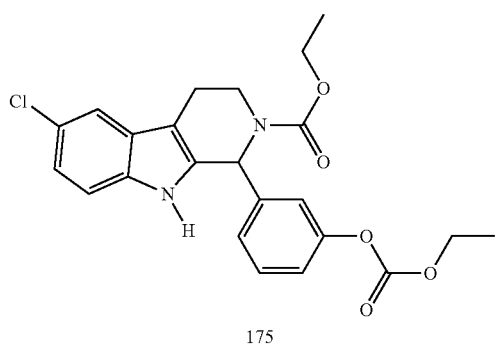
175
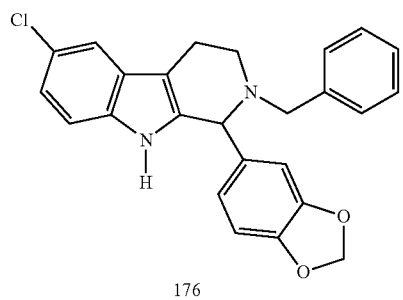
176
TABLE A-continued
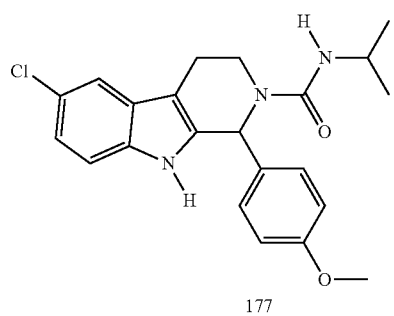
177
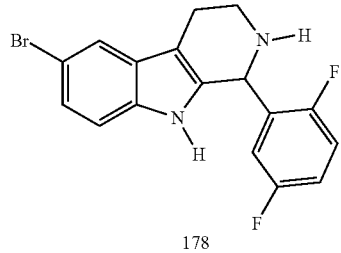
178
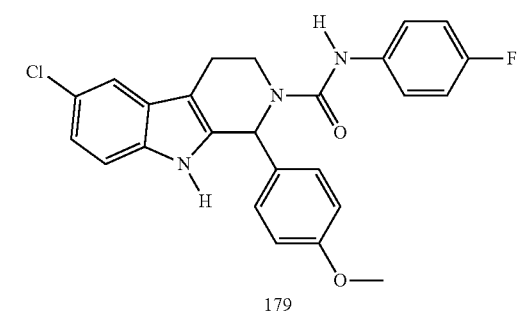
179
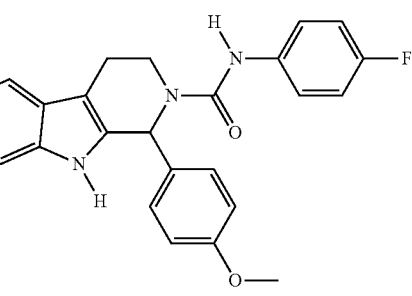
180
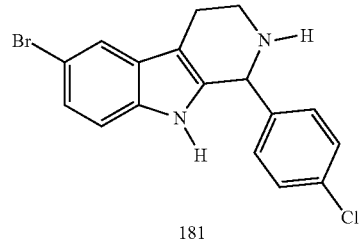
181

TABLE A-continued
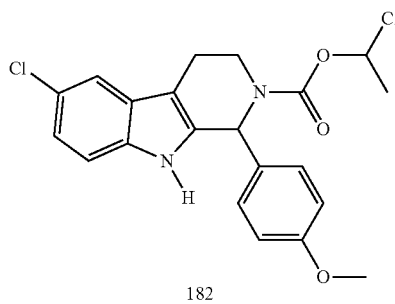
182
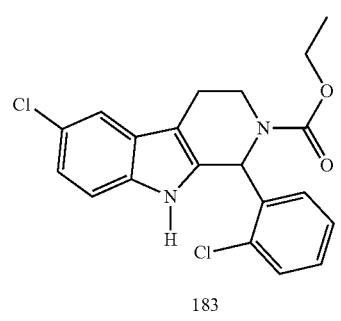
183
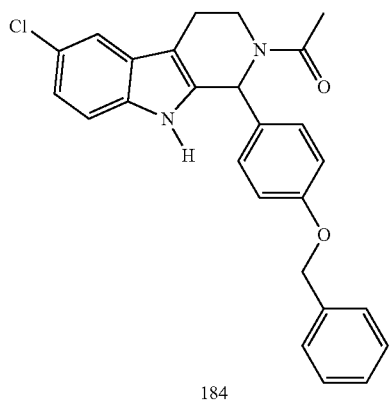
184
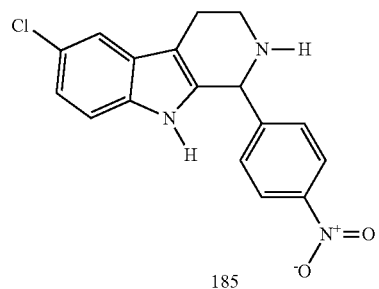
185
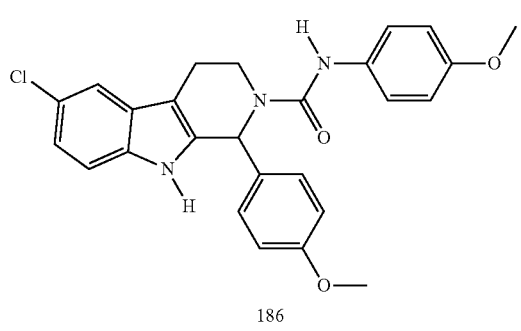
186
TABLE A-continued
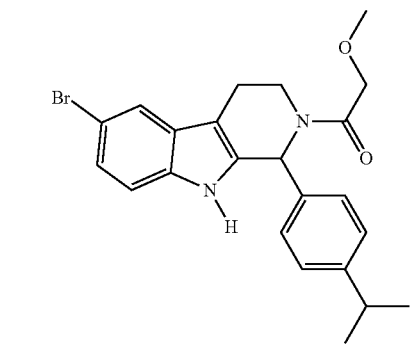
187
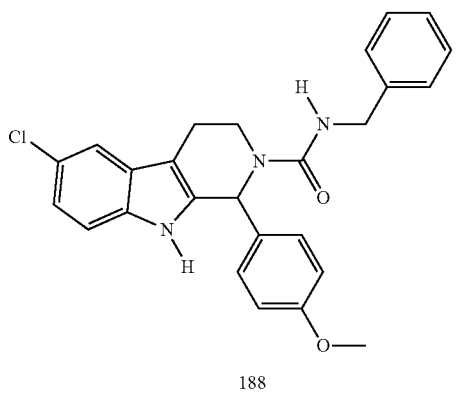
188
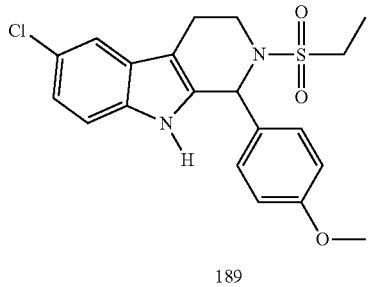
189
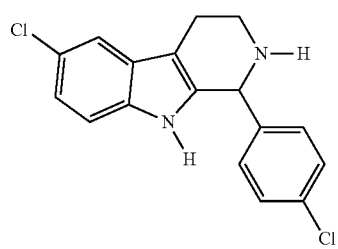
190

TABLE A-continued

191

192

193

194

195

196

197

198

199

TABLE A-continued
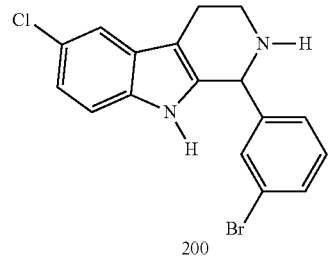
200
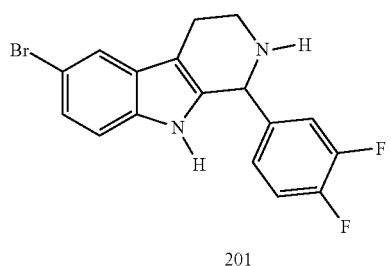
201
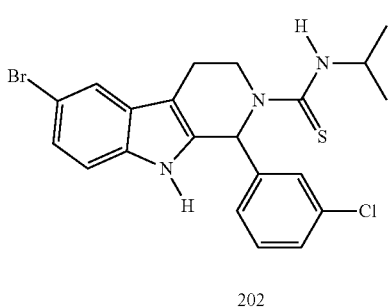
202
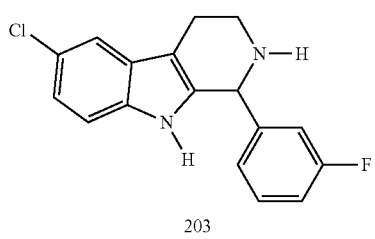
203
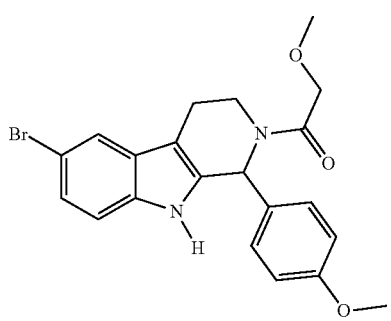
204
TABLE A-continued
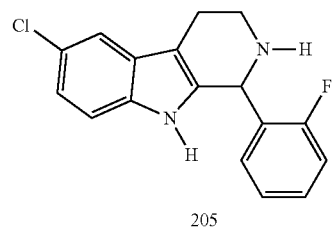
205
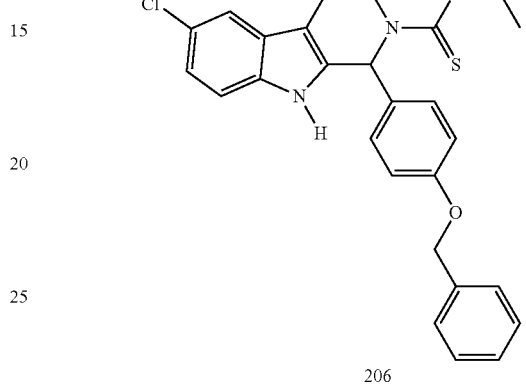
206
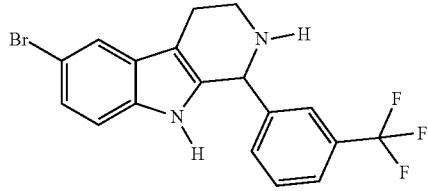
207
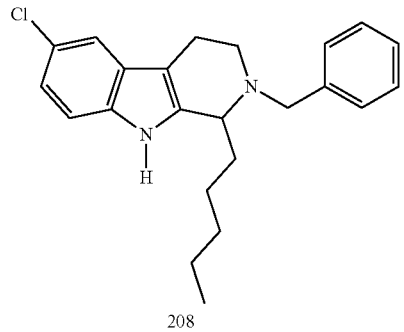
208
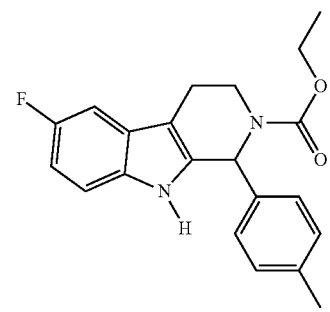
209

TABLE A-continued
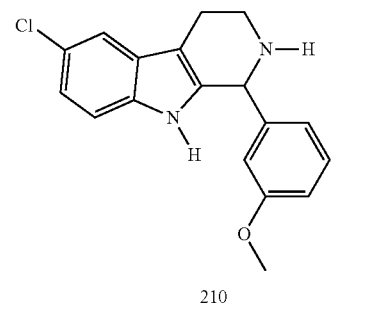
210
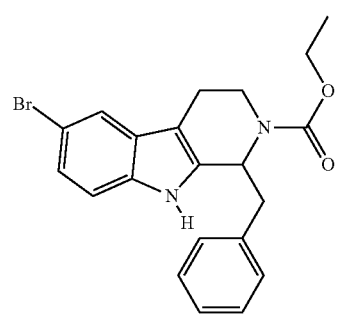
211
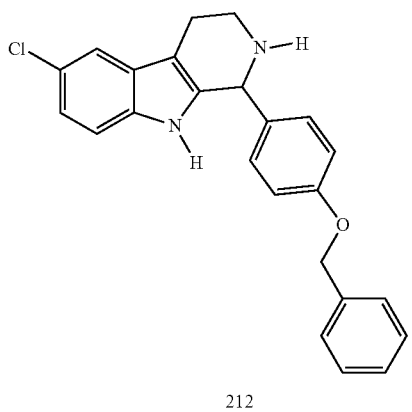
212
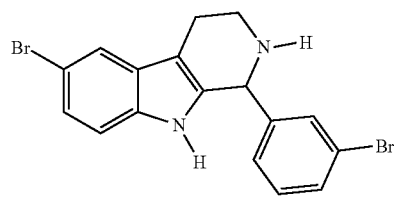
213
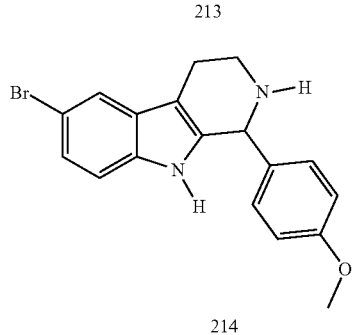
214
TABLE A-continued
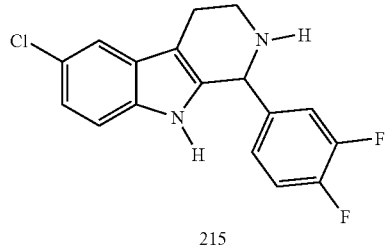
215
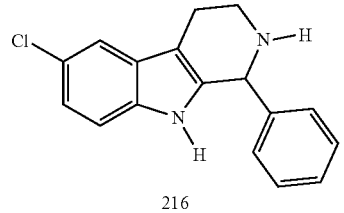
216
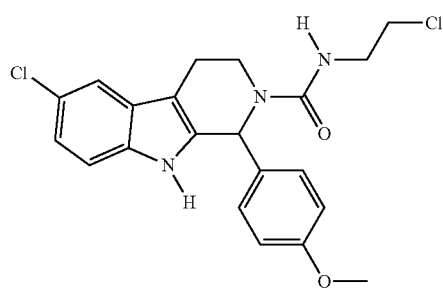
217
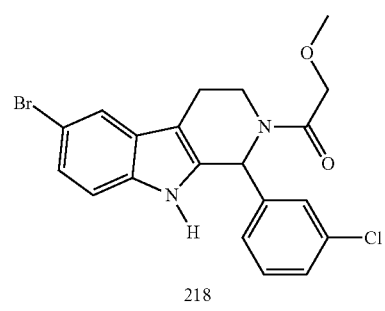
218
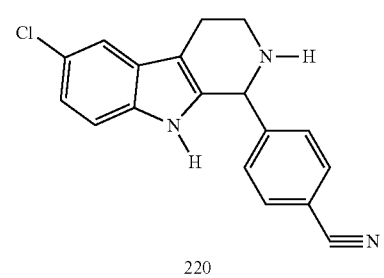
220

TABLE A-continued
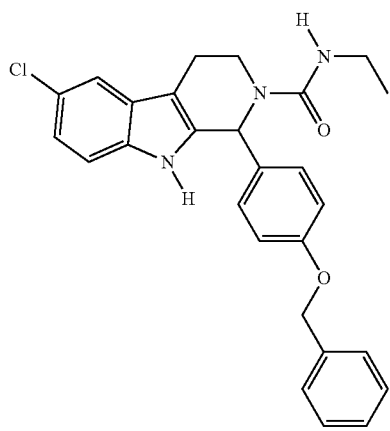
221
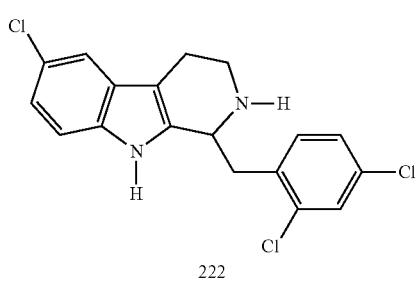
222
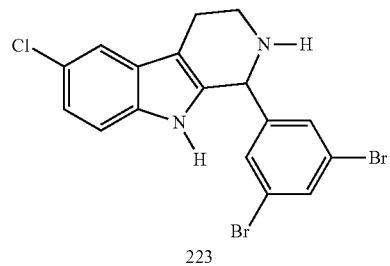
223
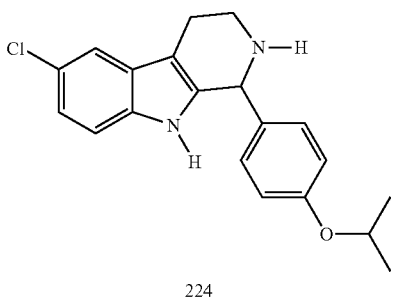
224
TABLE A-continued
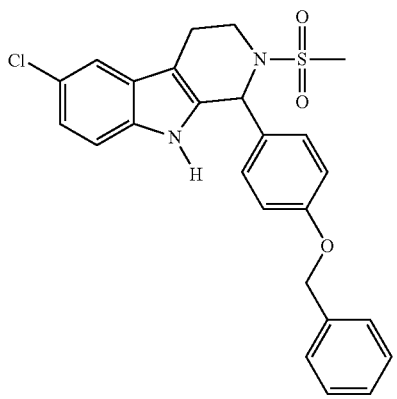
225
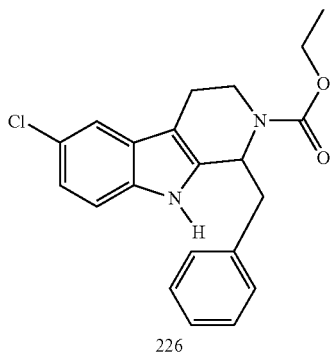
226
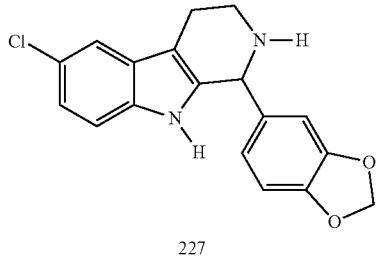
227
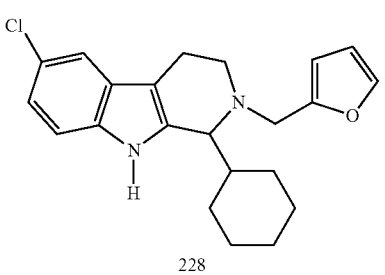
228

TABLE A-continued
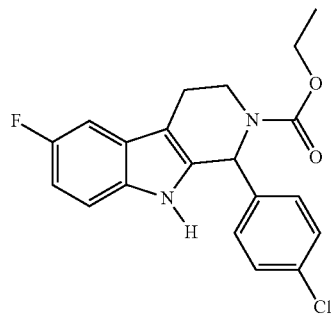
229
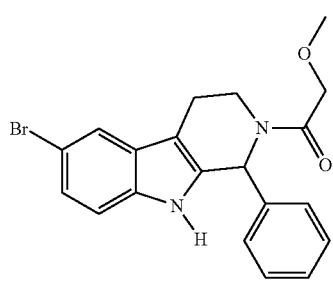
230
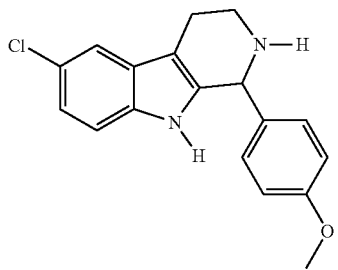
231
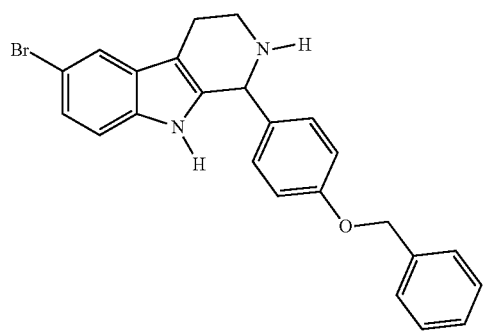
232
TABLE A-continued
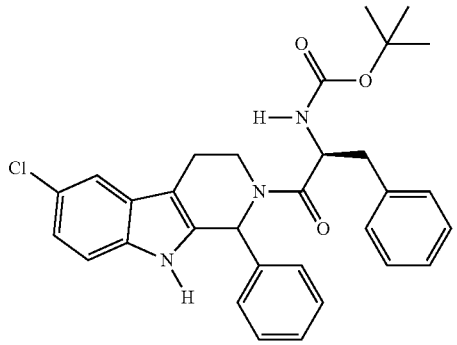
233
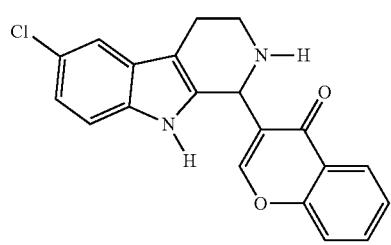
234
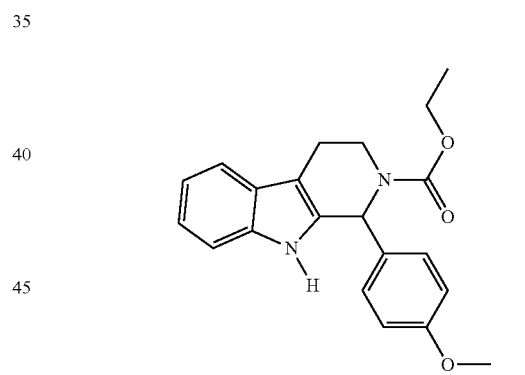
235
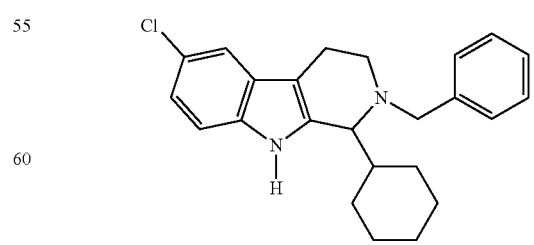
236

TABLE A-continued
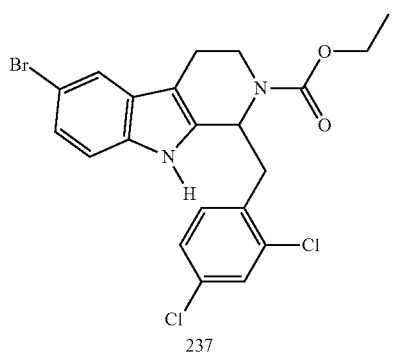
237
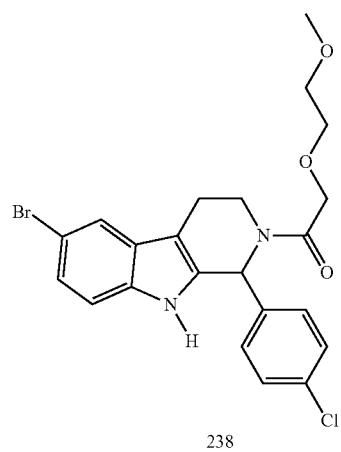
238
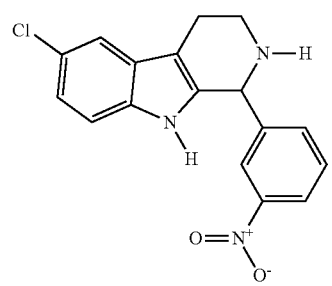
239
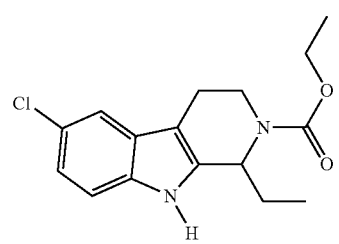
240
TABLE A-continued
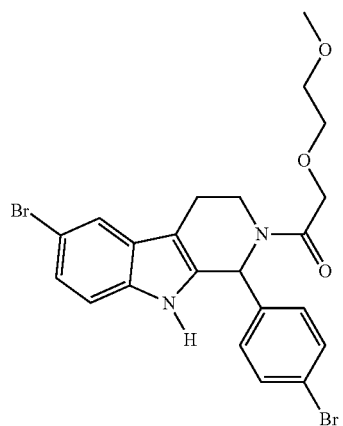
241
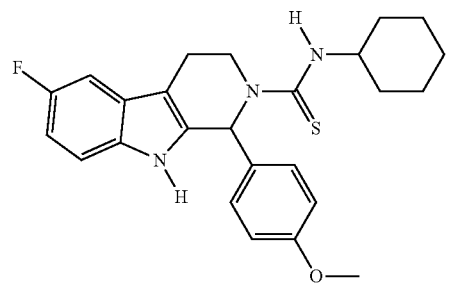
242
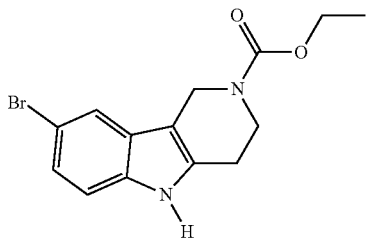
243
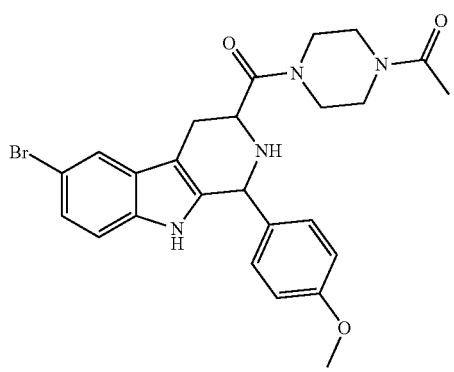
244

TABLE A-continued
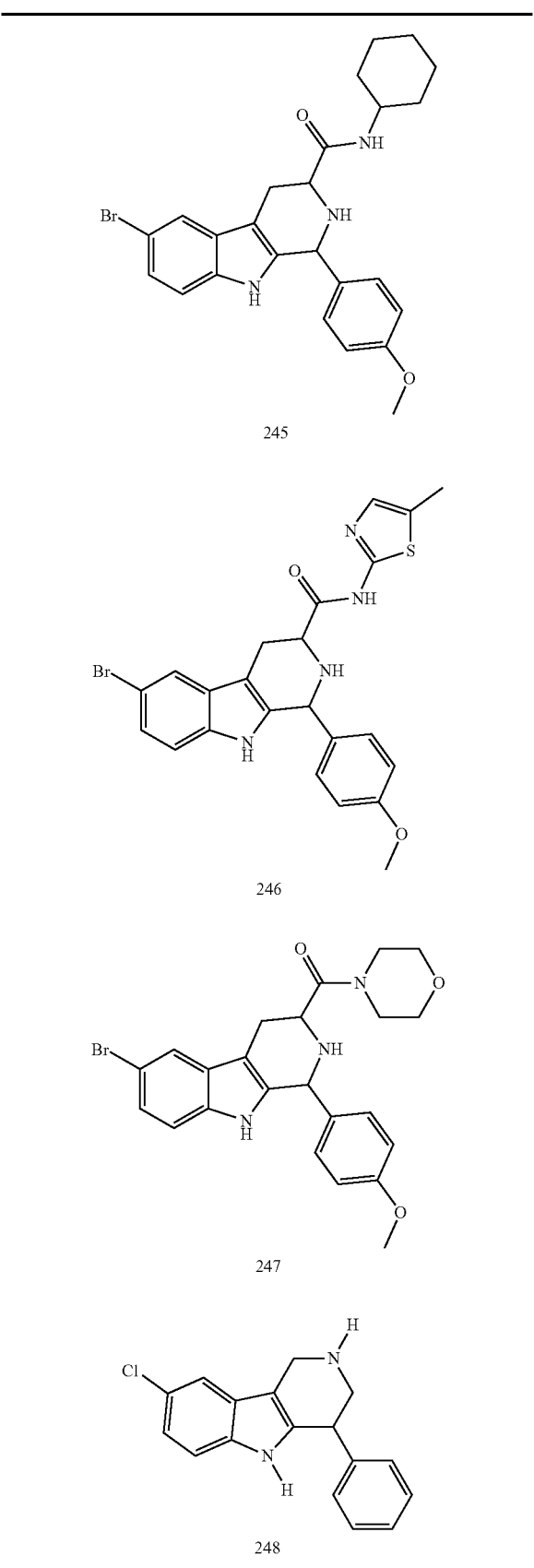
245
246
247
248
TABLE A-continued
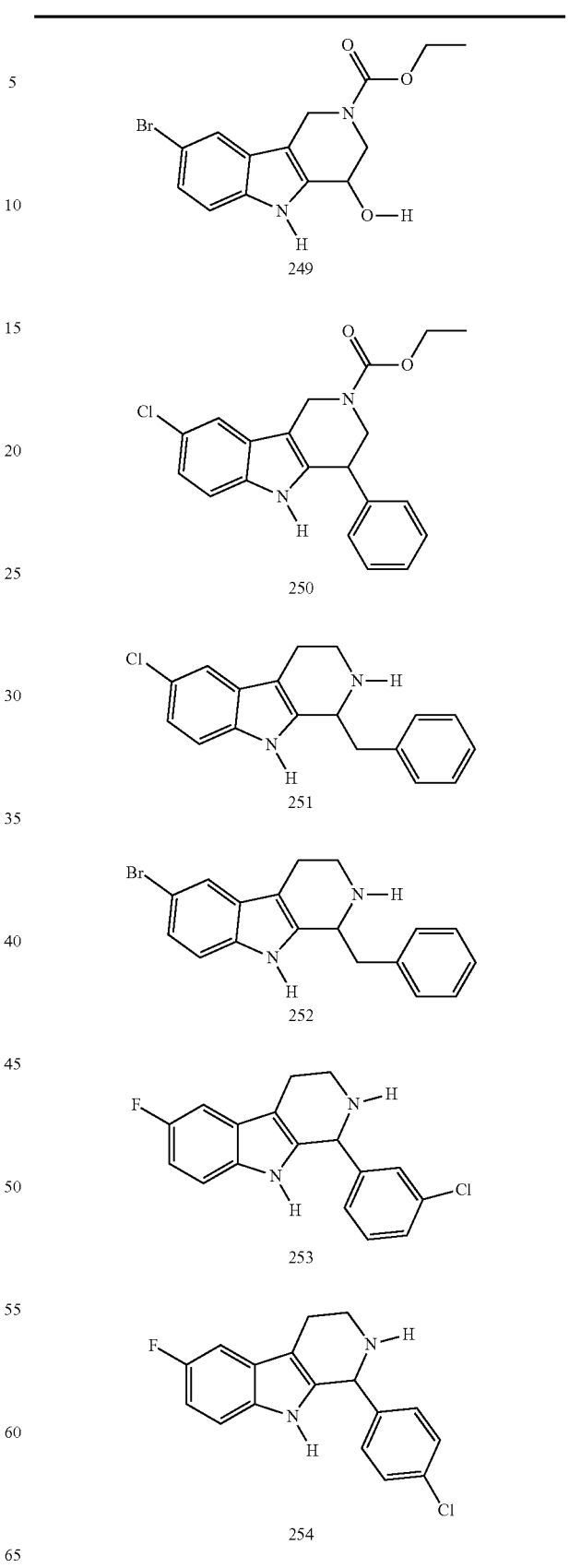
249
250
251
252
253
254

TABLE A-continued
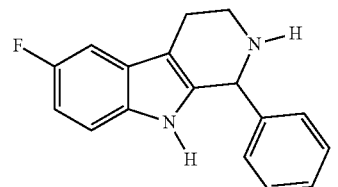
255
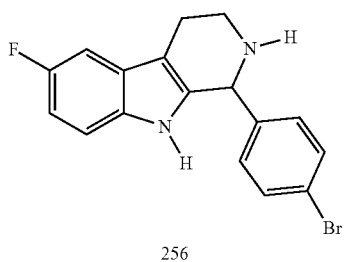
256
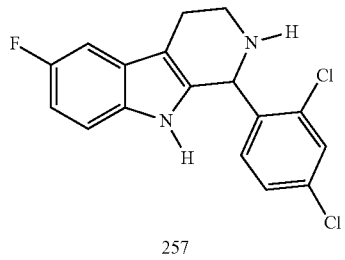
257
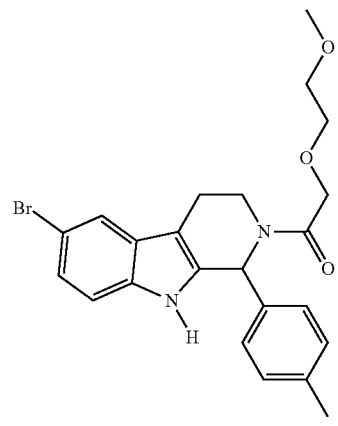
258
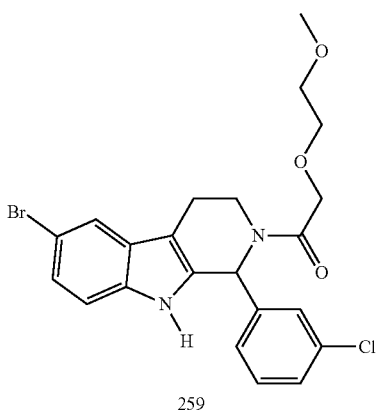
259
TABLE A-continued
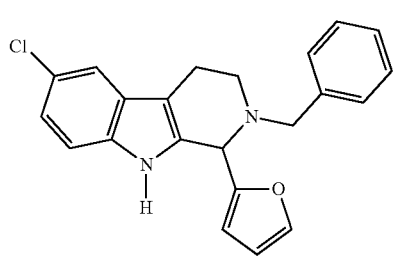
260
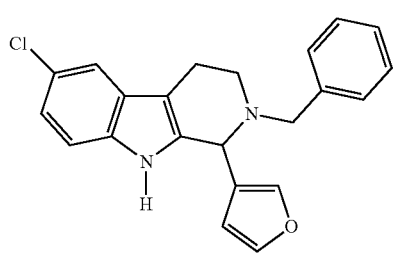
261
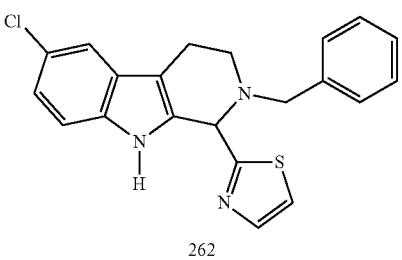
262
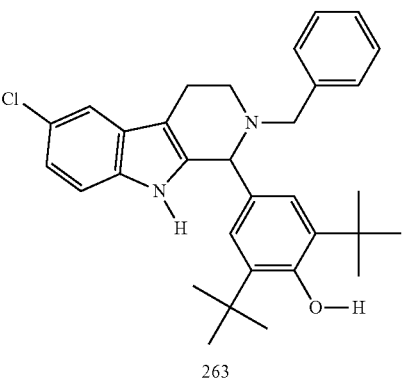
263
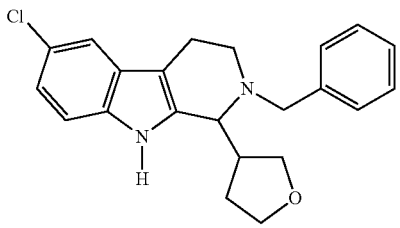
264

TABLE A-continued
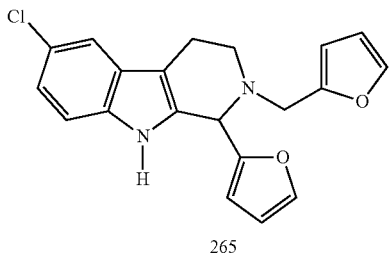
265
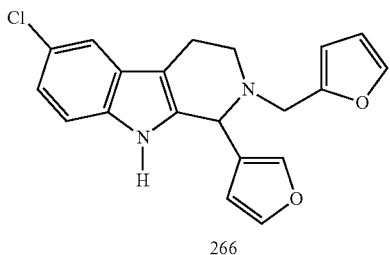
266
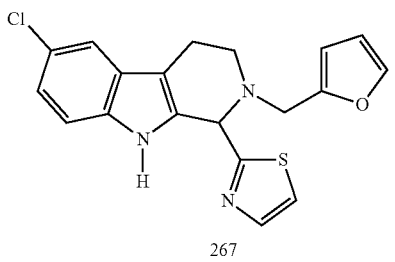
267
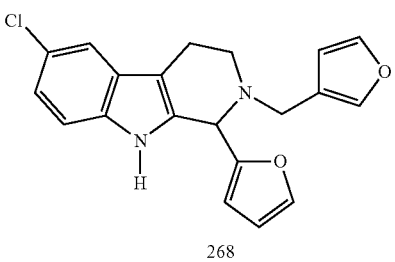
268
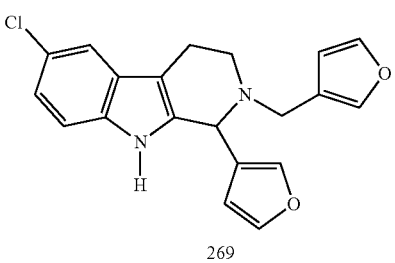
269
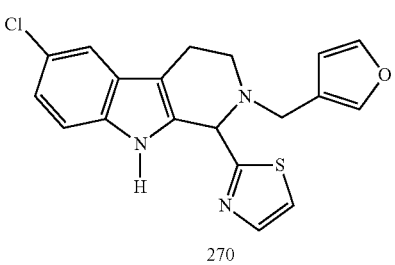
270
TABLE A-continued
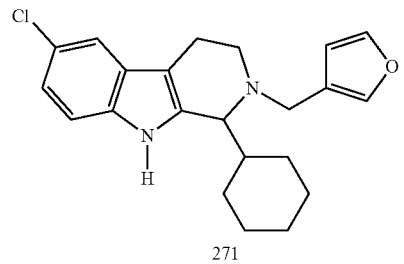
271
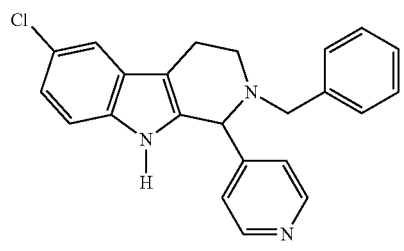
272
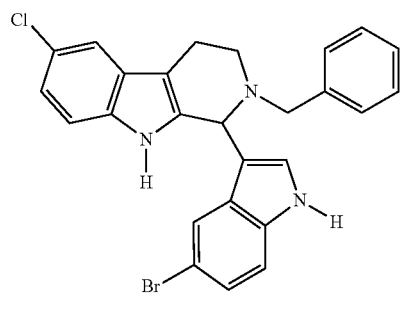
273
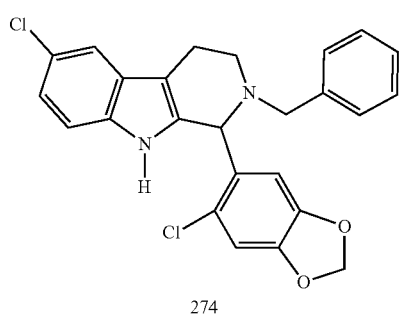
274
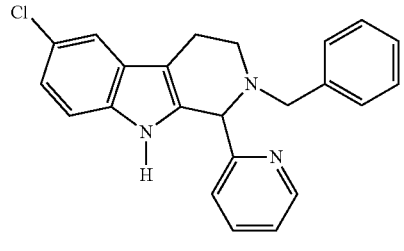
275

TABLE A-continued
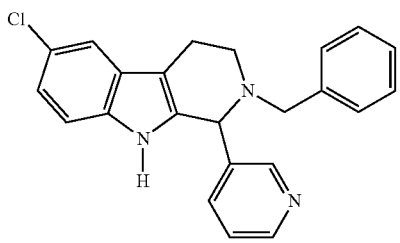
276
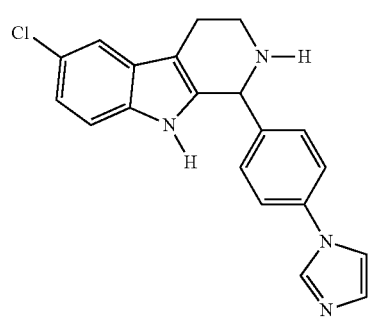
277
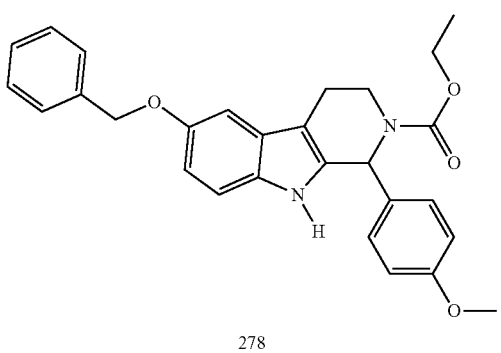
278
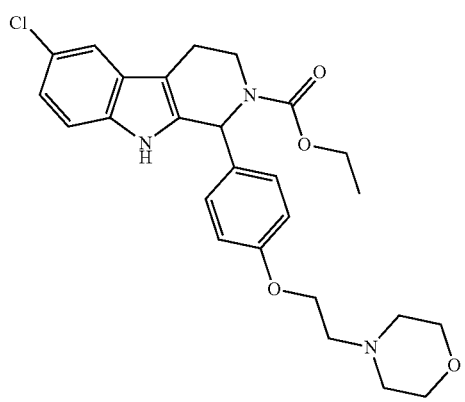
279
TABLE A-continued
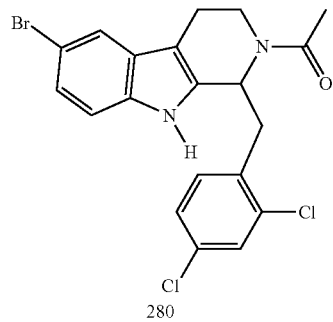
280
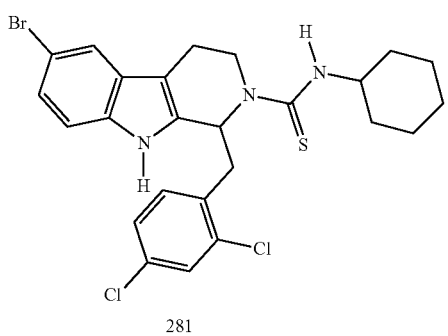
281
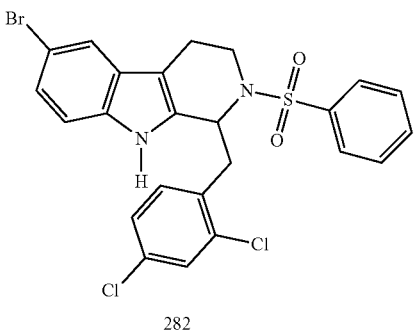
282
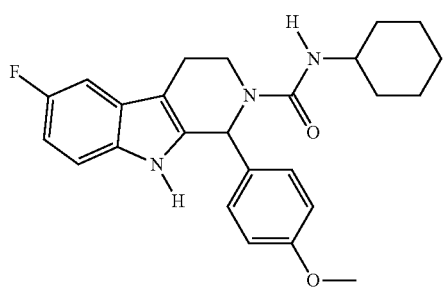
283
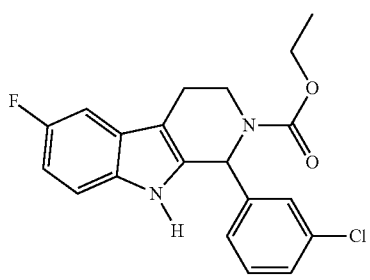
284

TABLE A-continued
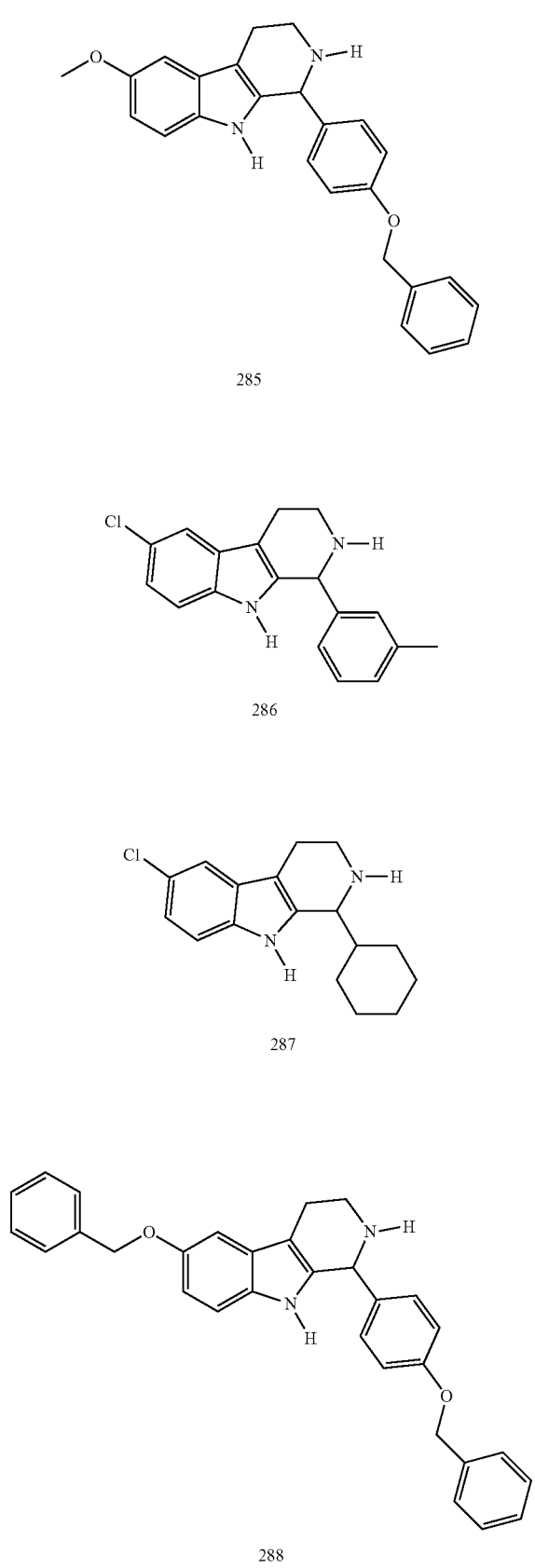
285
286
287
288
TABLE A-continued
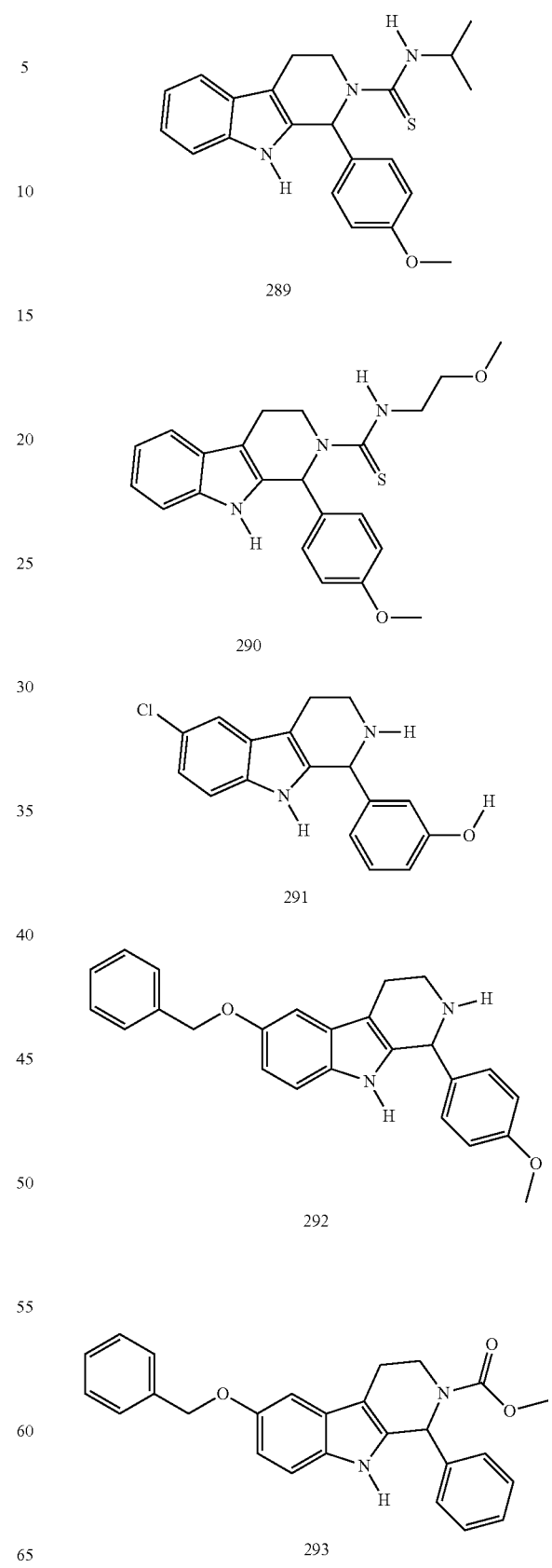
289
290
291
292
293

TABLE A-continued
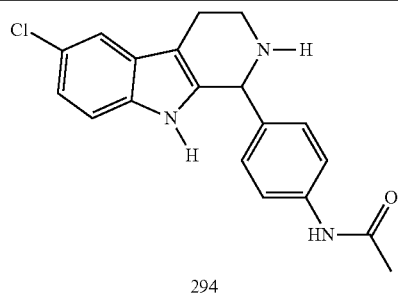
294
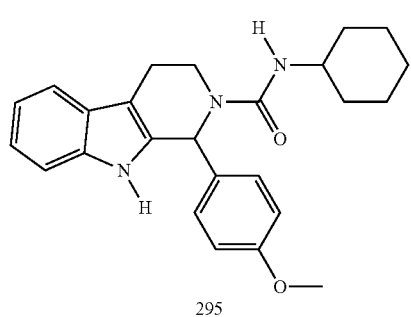
295
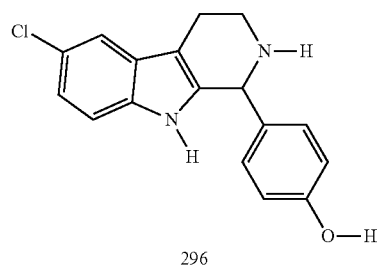
296
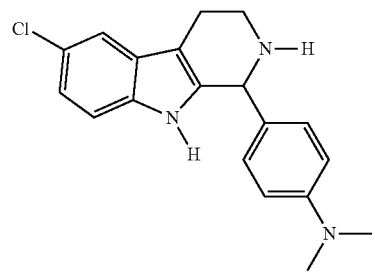
297
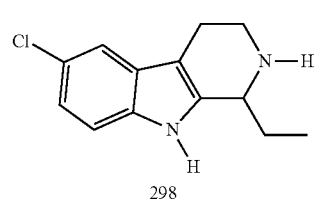
298
TABLE A-continued
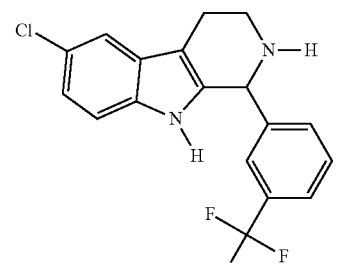
299
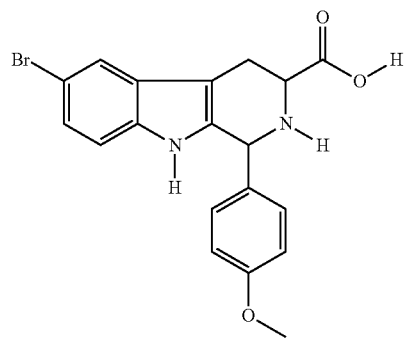
300
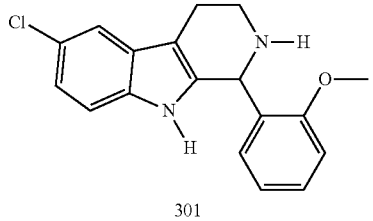
301
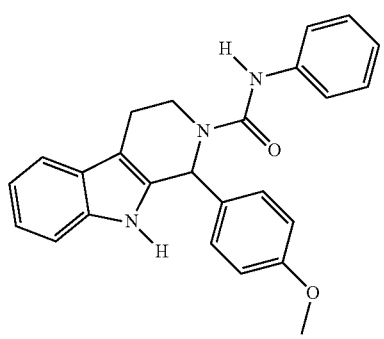
302
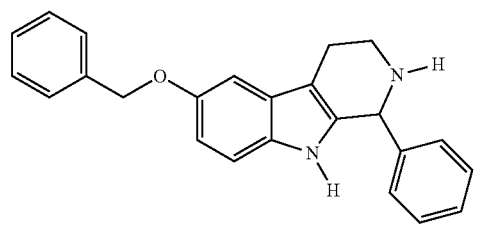
303

TABLE A-continued
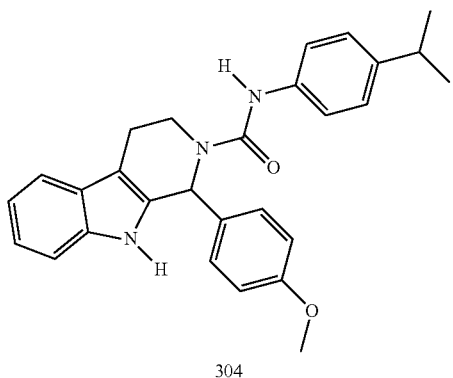
304
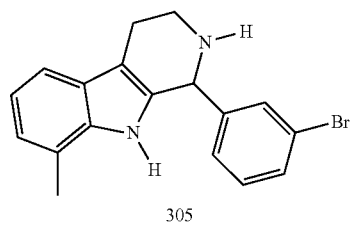
305
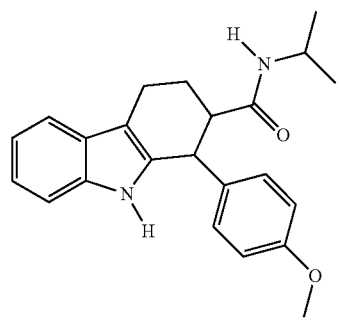
306
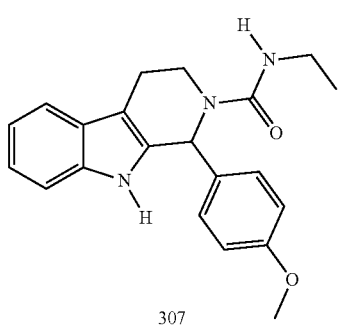
307
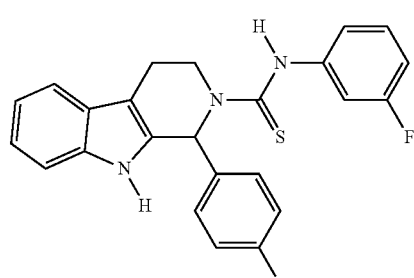
308
TABLE A-continued
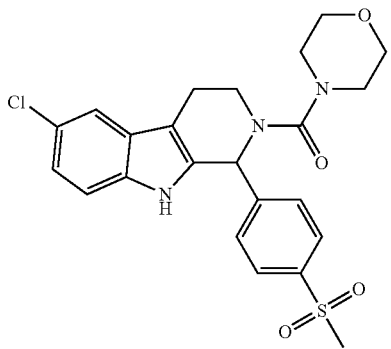
309
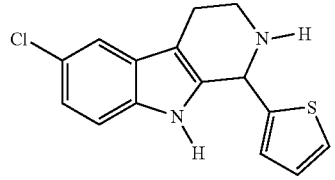
310
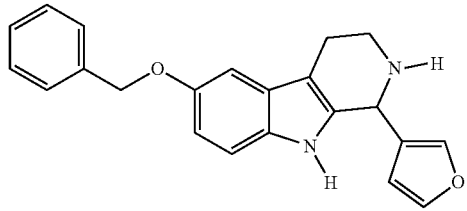
311
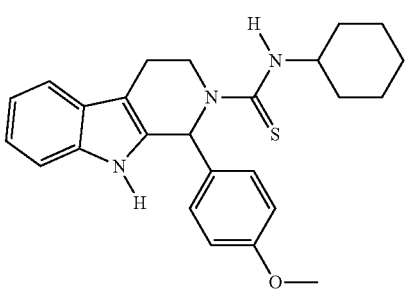
312
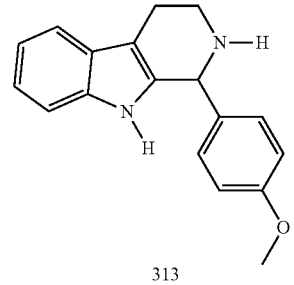
313

TABLE A-continued
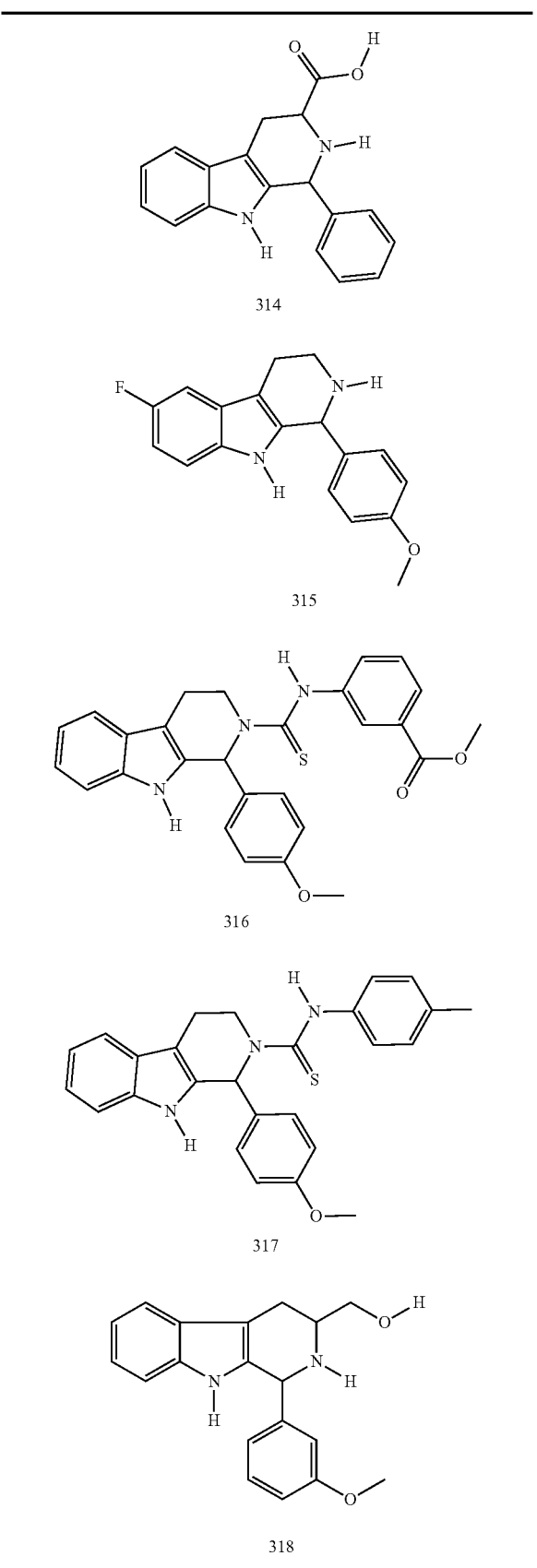
314, 315, 316, 317, 318
TABLE A-continued
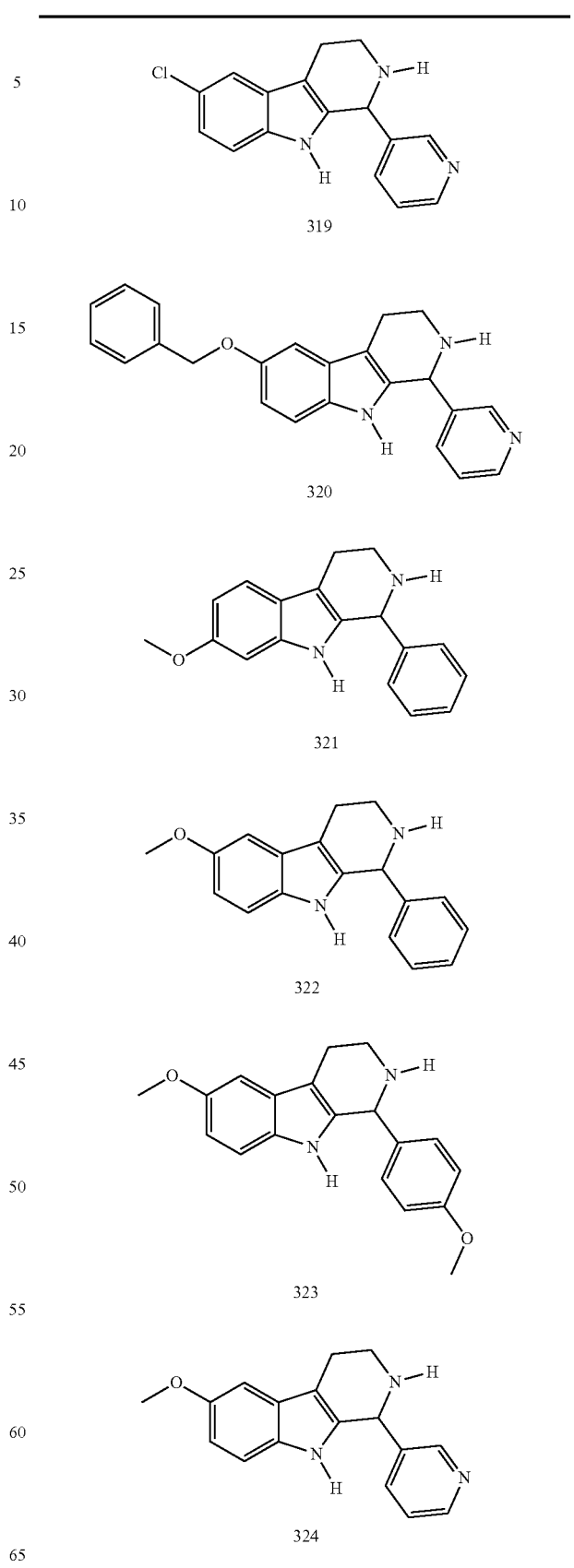
319, 320, 321, 322, 323, 324

TABLE A-continued
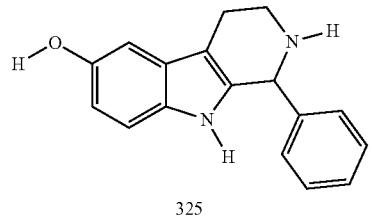
325
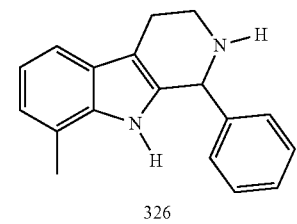
326
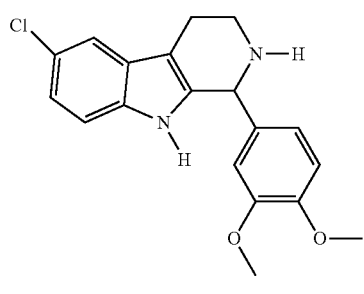
327
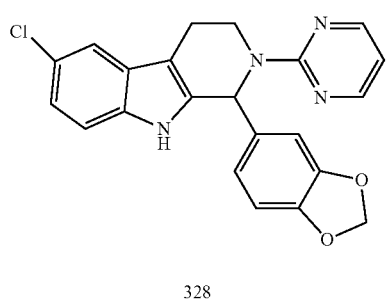
328
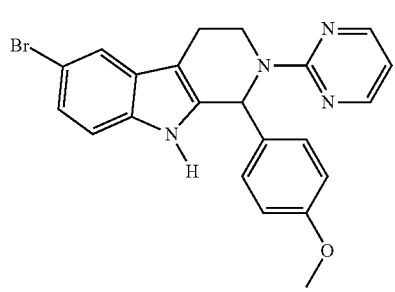
329
TABLE A-continued
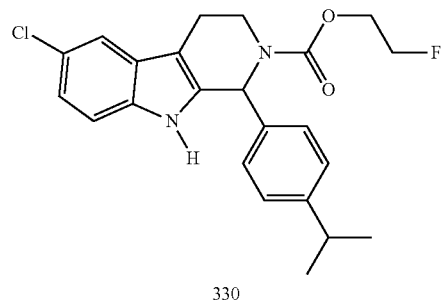
330
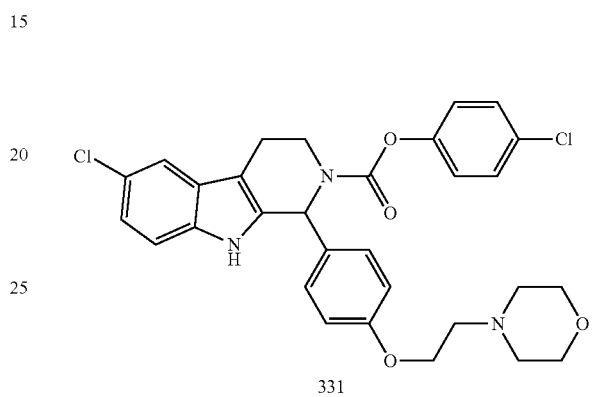
331
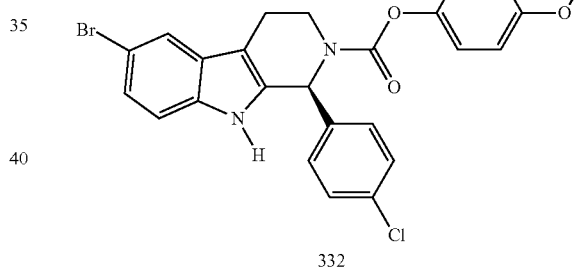
332
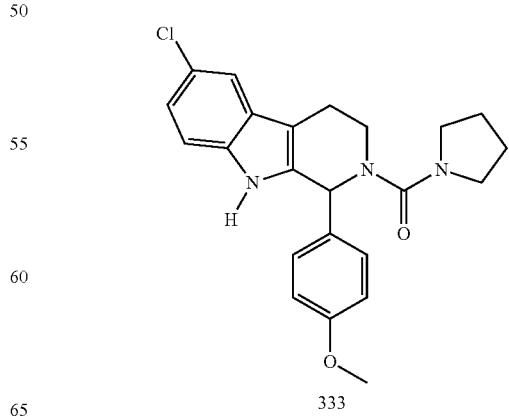
333

TABLE A-continued
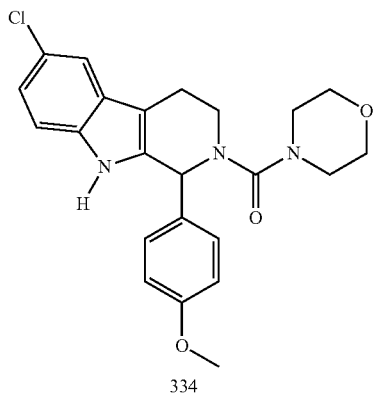
334
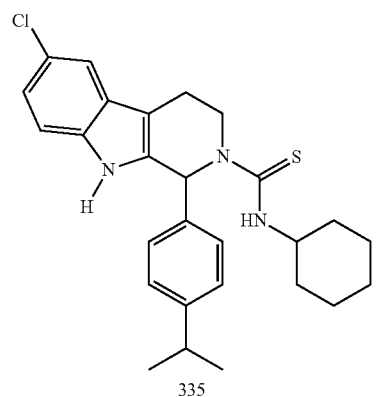
335
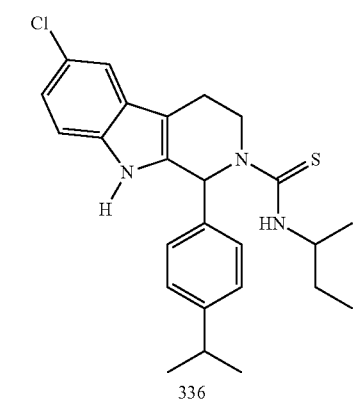
336
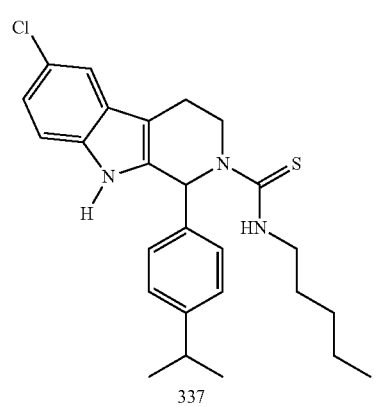
337
TABLE A-continued
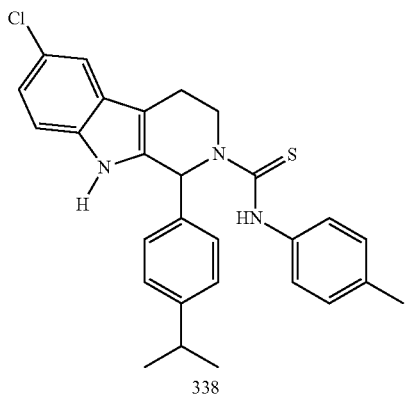
338
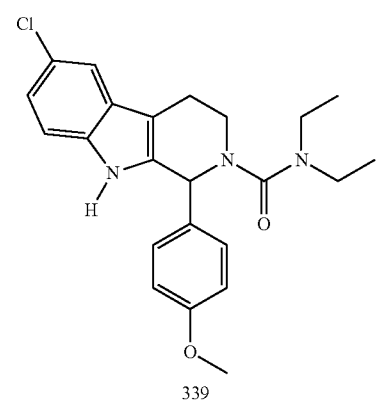
339
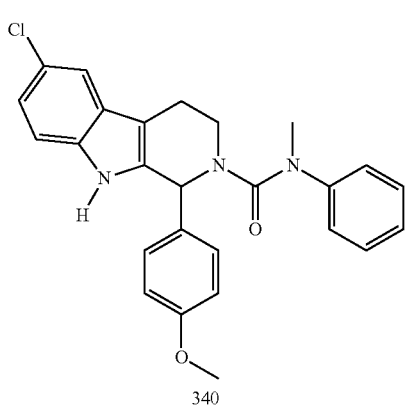
340
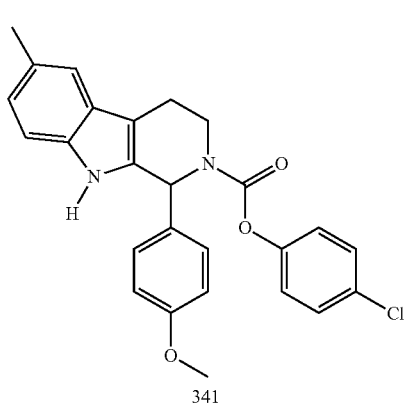
341

TABLE A-continued
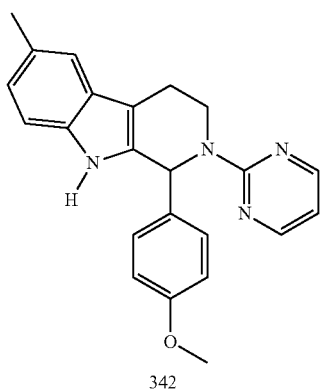
342
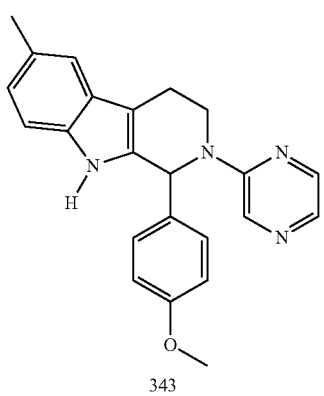
343
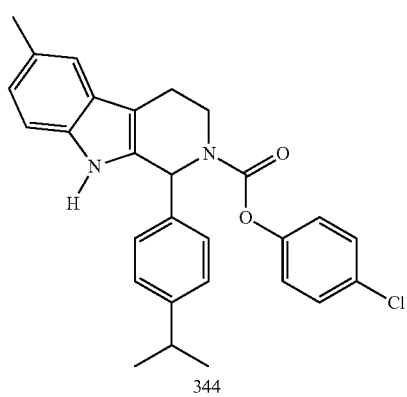
344
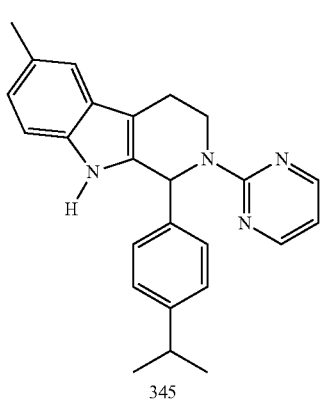
345
TABLE A-continued
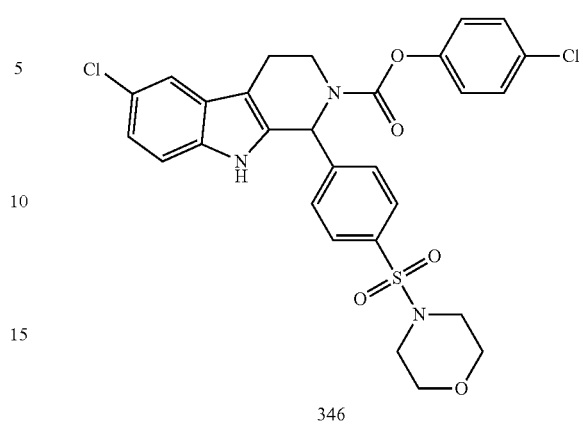
346
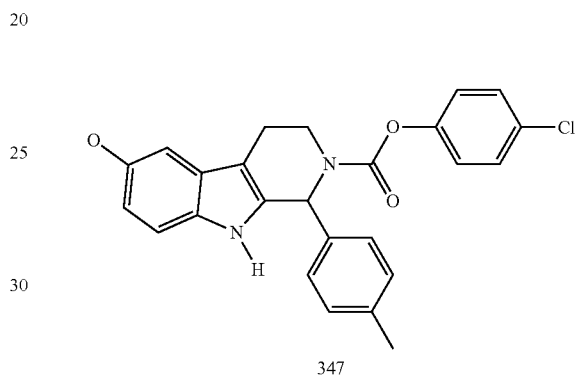
347
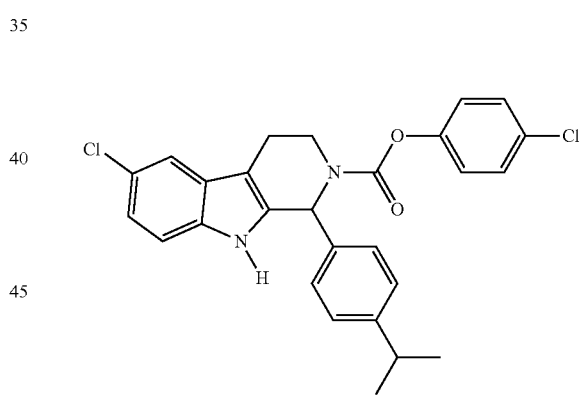
348
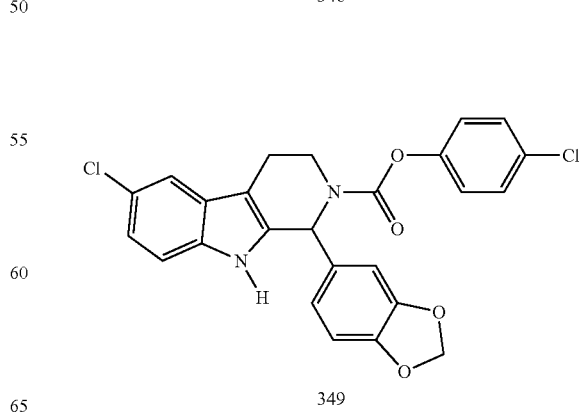
349

TABLE A-continued
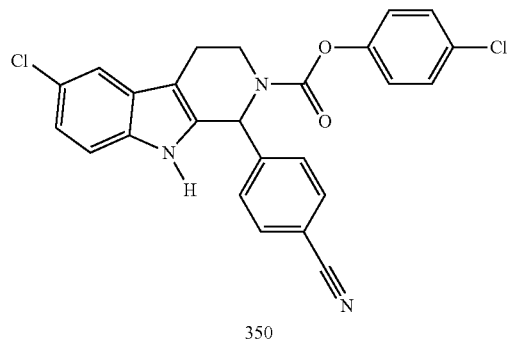
350
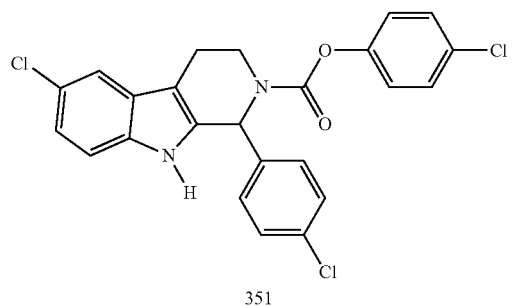
351
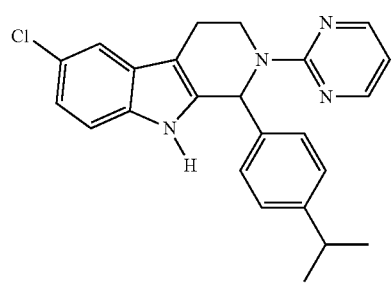
352
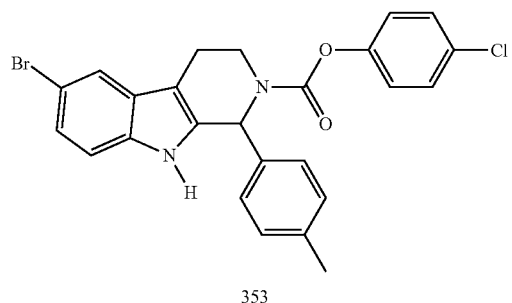
353
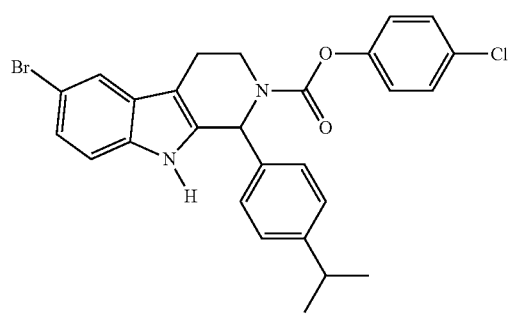
354
TABLE A-continued
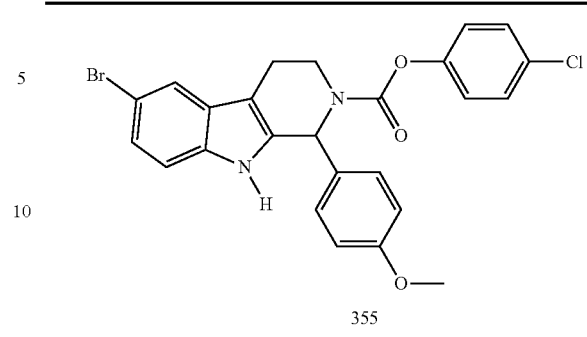
355
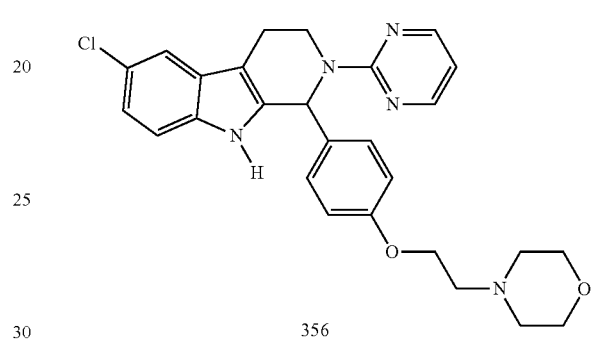
356
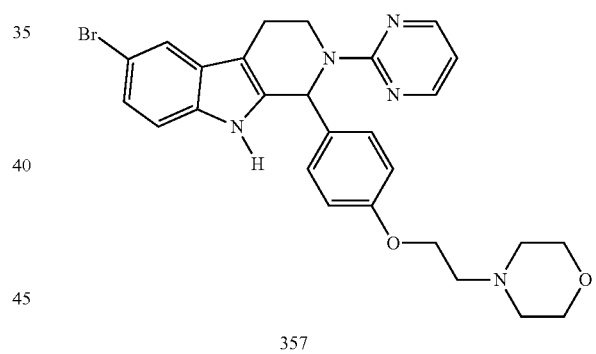
357
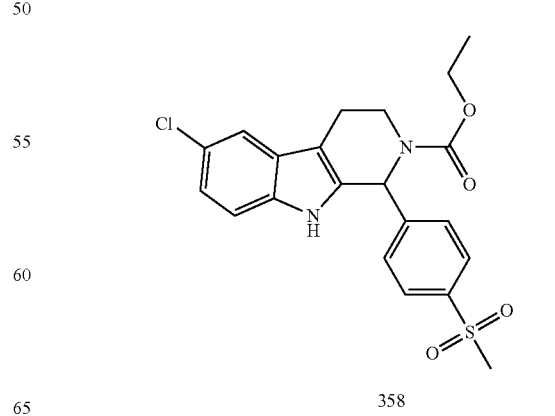
358

TABLE A-continued
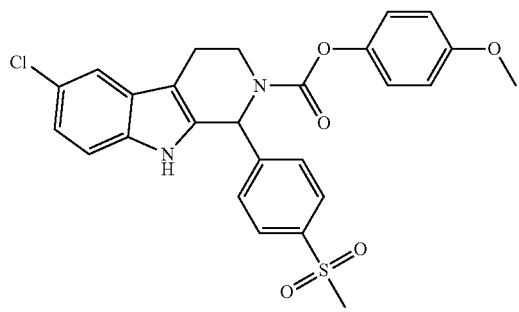
359
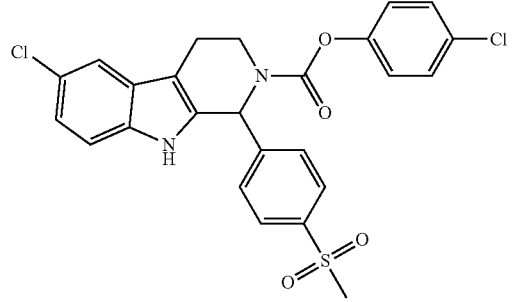
360
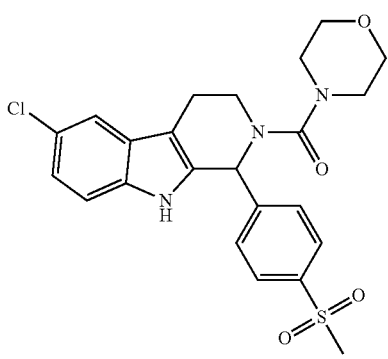
361
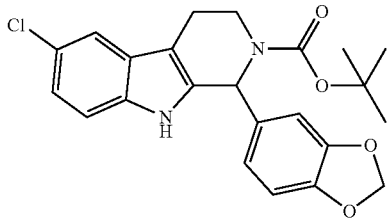
362
TABLE A-continued
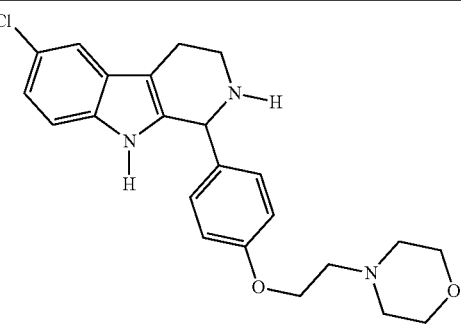
363
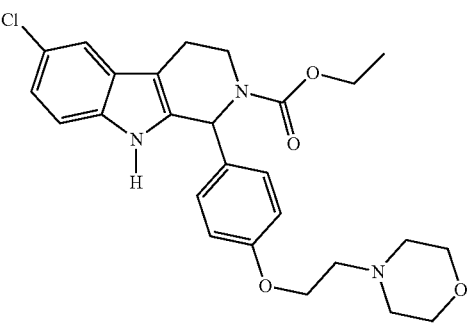
364
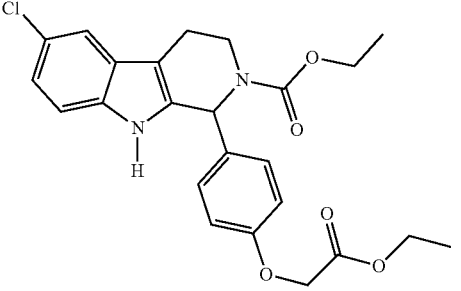
365
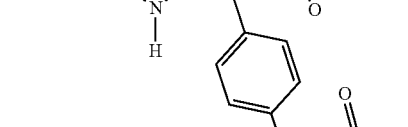
366

TABLE A-continued
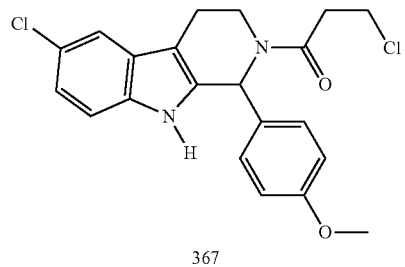
367
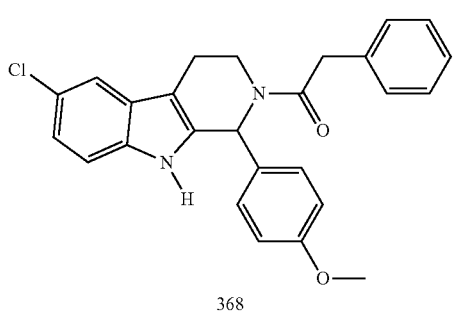
368
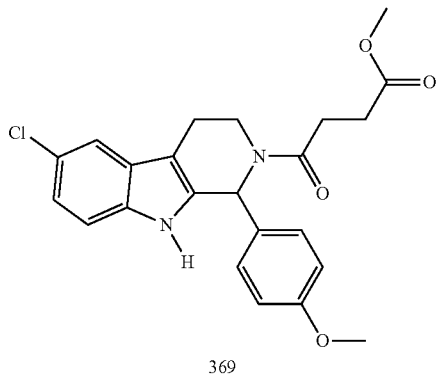
369
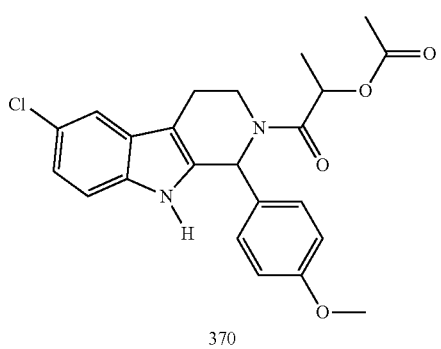
370
TABLE A-continued
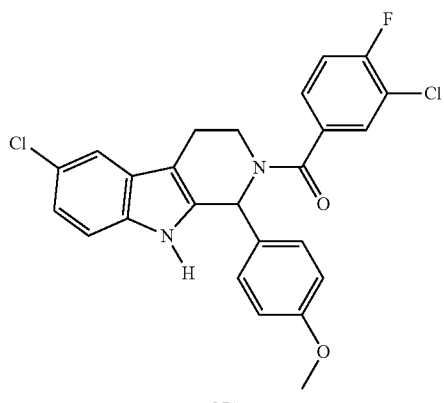
371
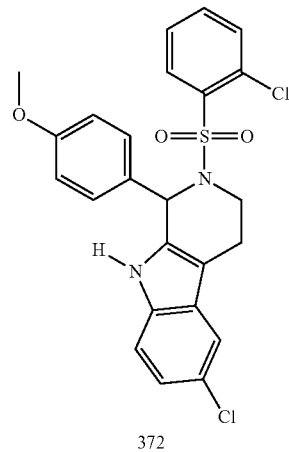
372
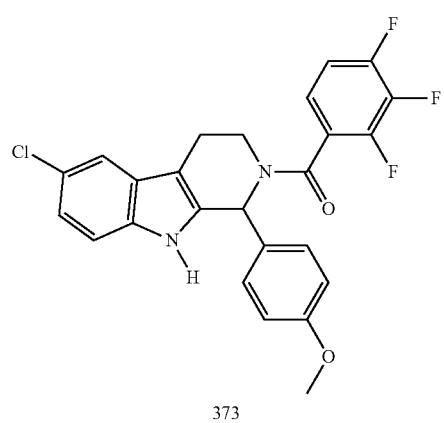
373
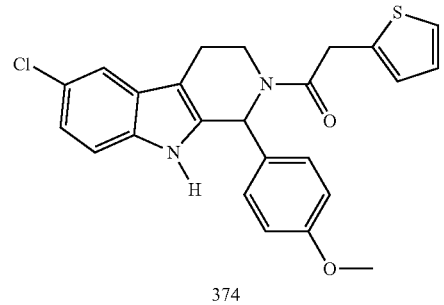
374

TABLE A-continued

375

376

377

378

379

380

TABLE A-continued

381

382

383

384

385

TABLE A-continued
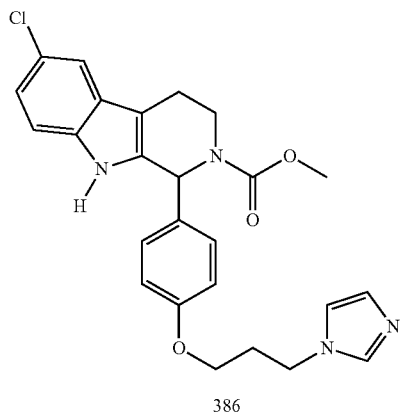
386
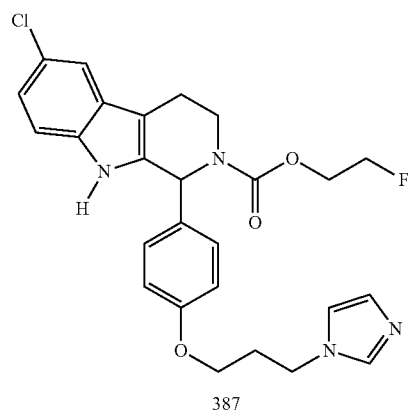
387
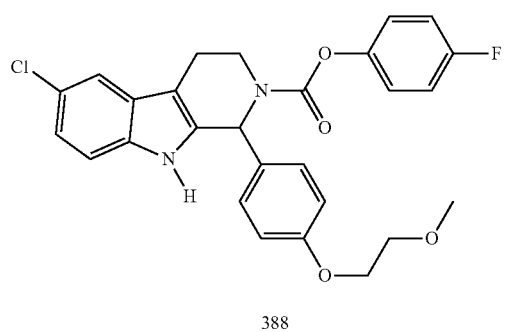
388
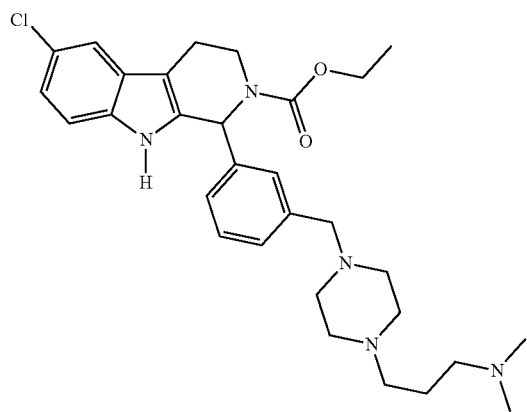
389
TABLE A-continued
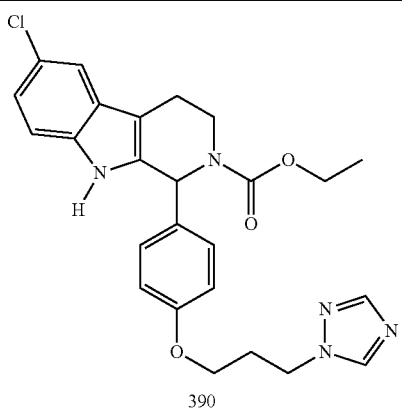
390
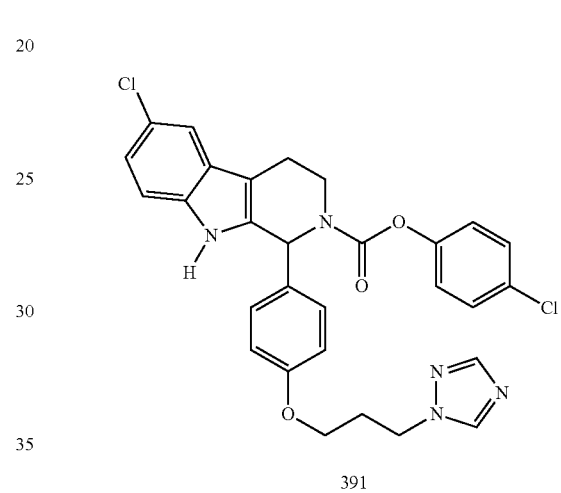
391
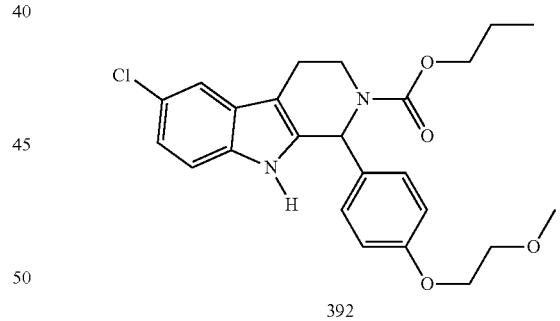
392
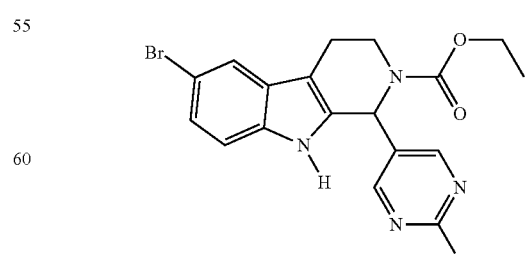
393

TABLE A-continued
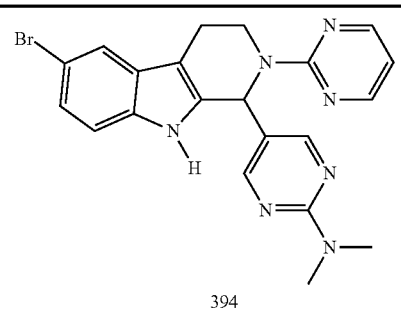
394
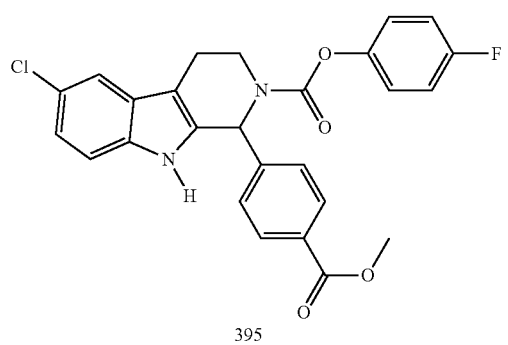
395
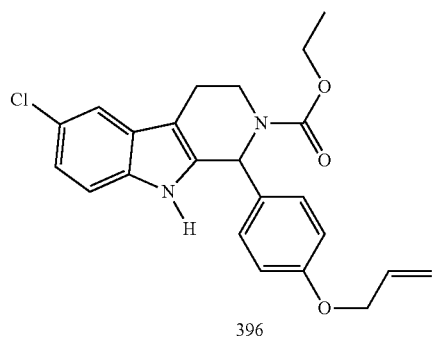
396
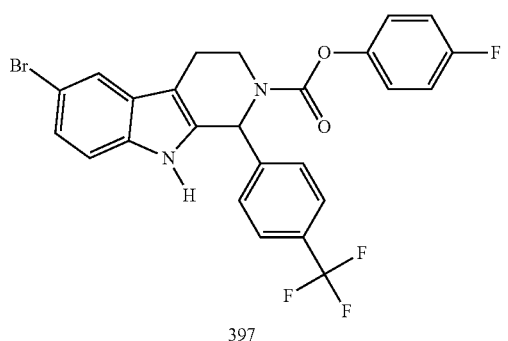
397
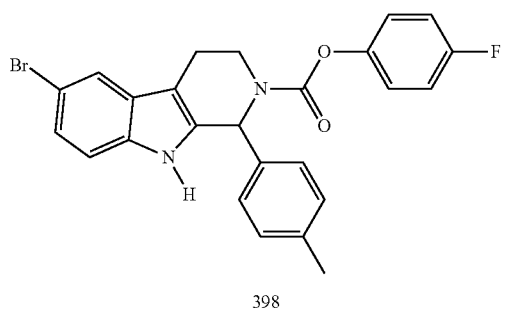
398
TABLE A-continued
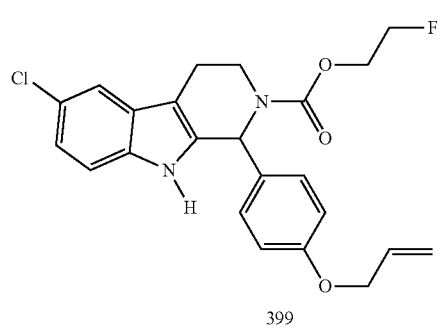
399
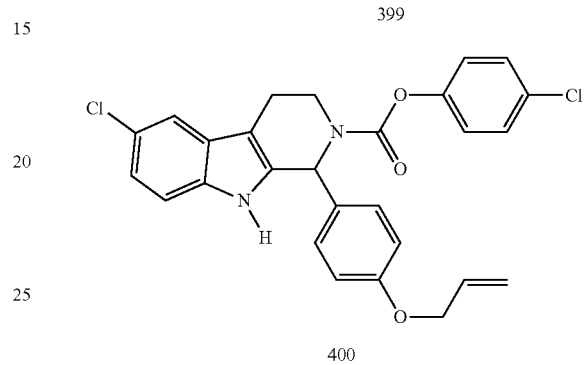
400
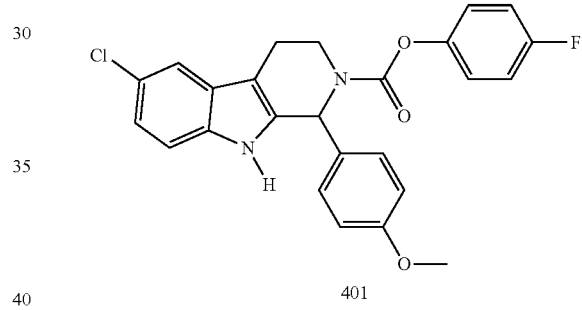
401
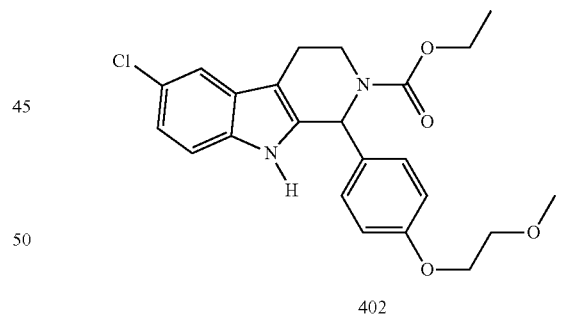
402
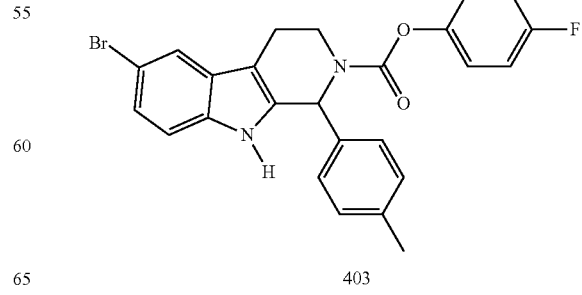
403

TABLE A-continued
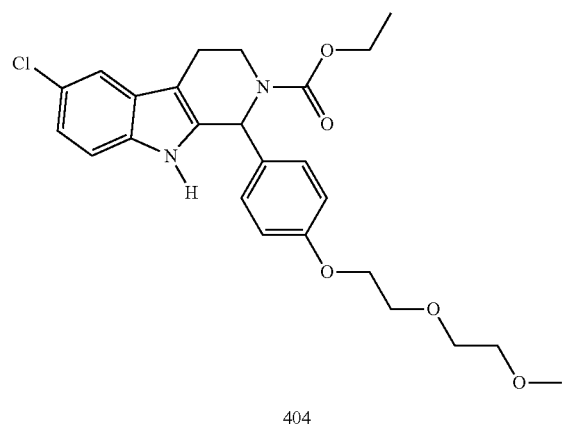
404
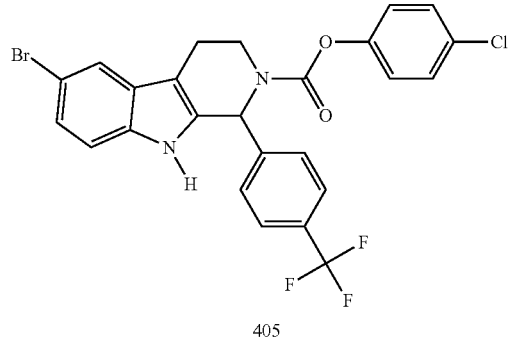
405
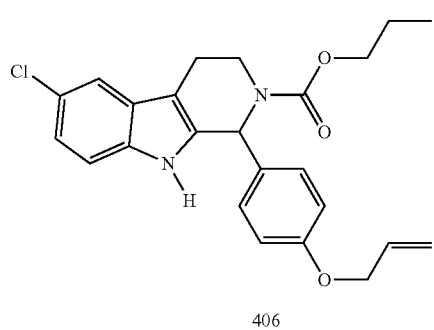
406
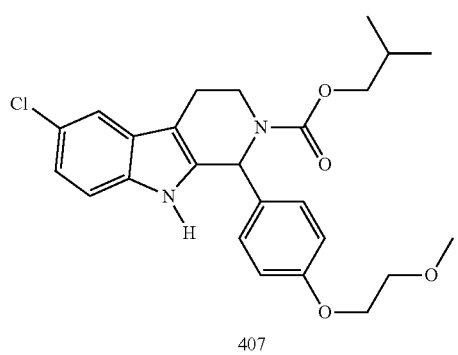
407
TABLE A-continued
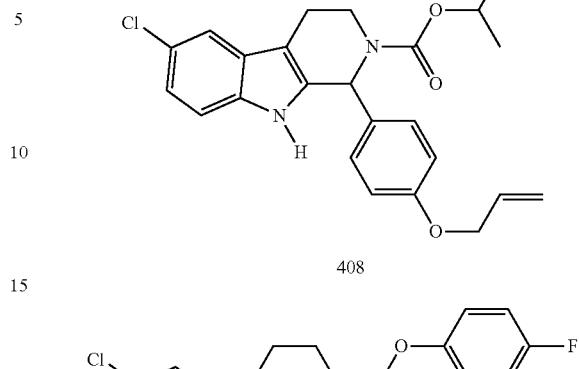
408
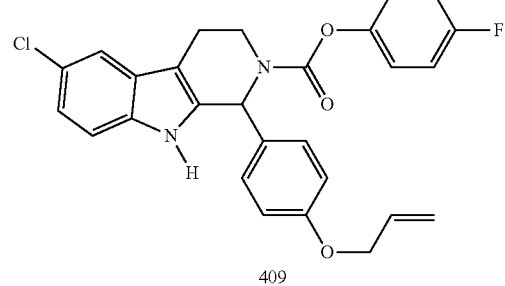
409
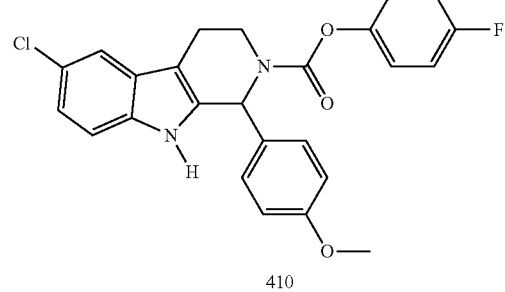
410
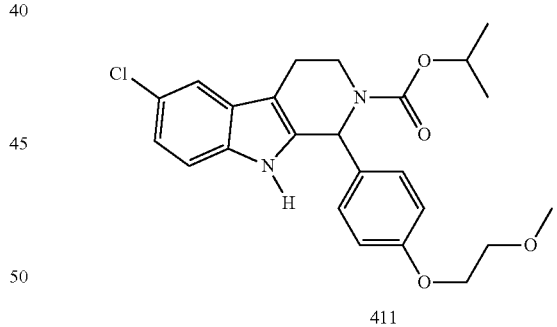
411
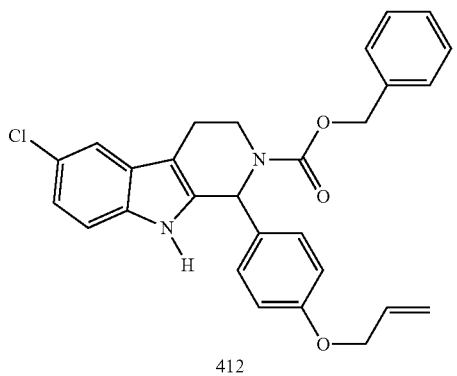
412

TABLE A-continued
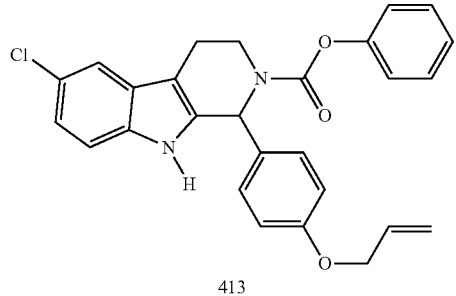
413
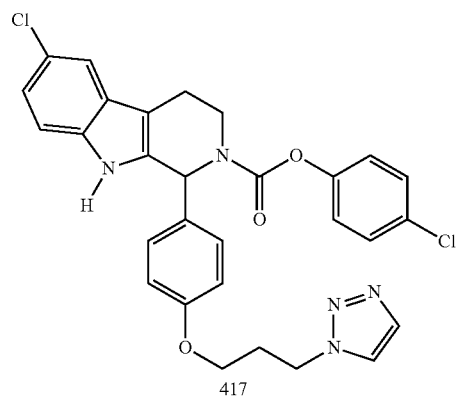
417
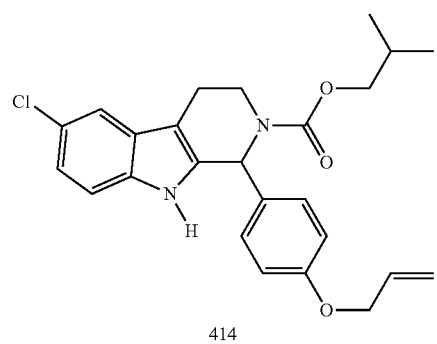
414
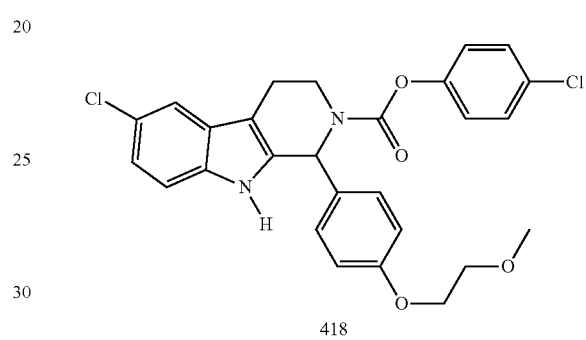
418
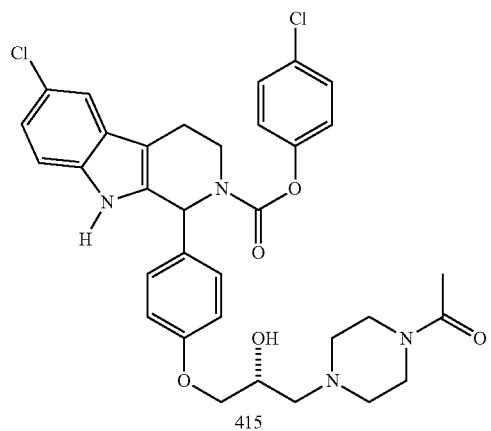
415
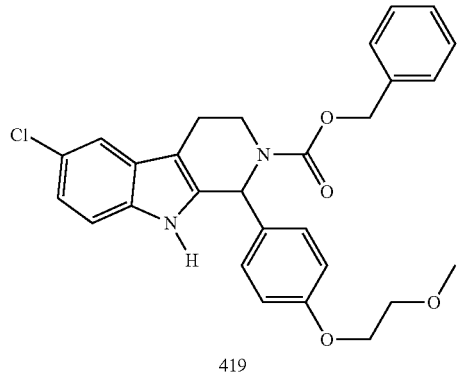
419
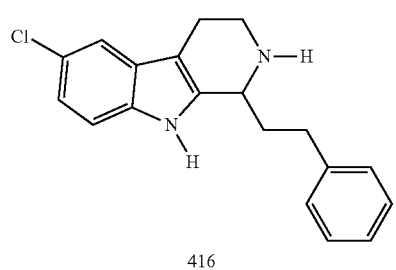
416
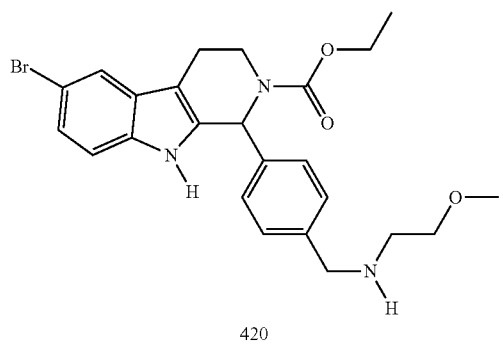
420

TABLE A-continued
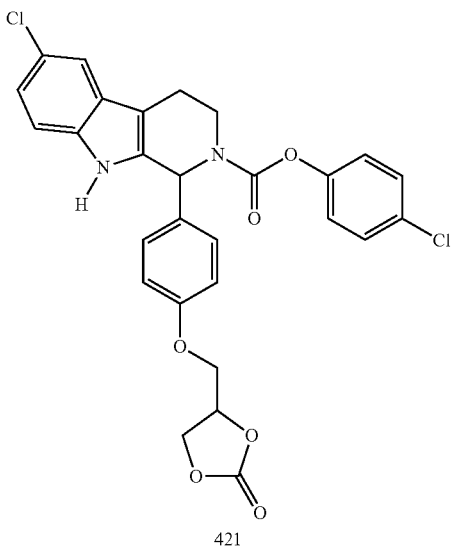
421
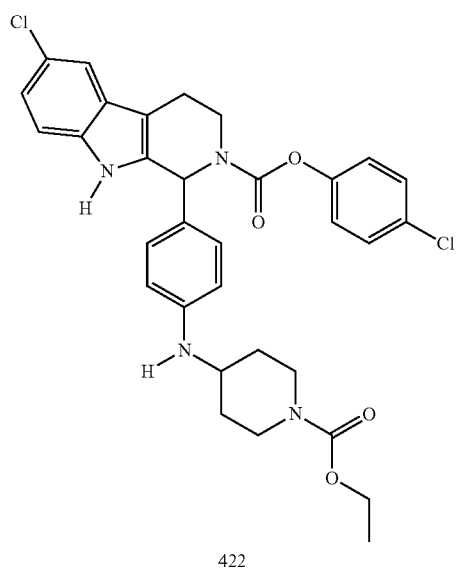
422
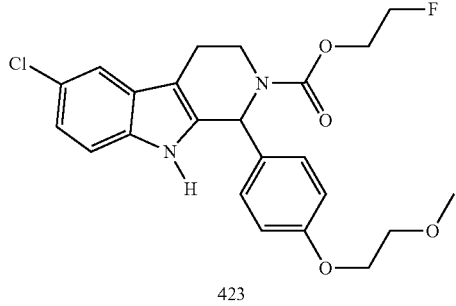
423
TABLE A-continued
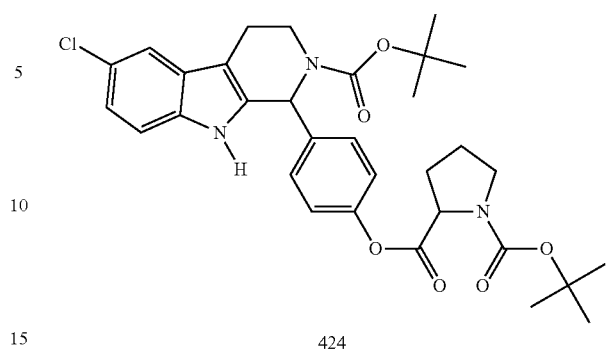
424
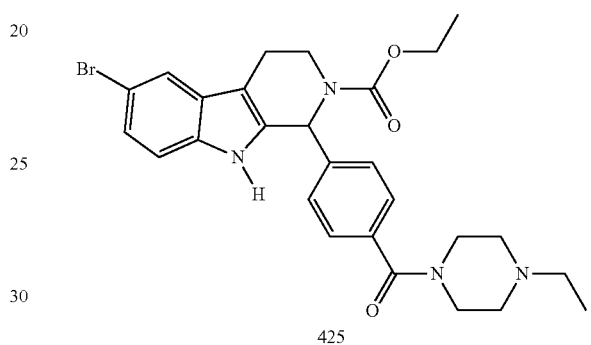
425
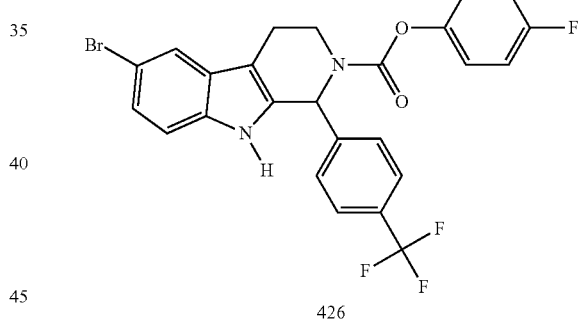
426
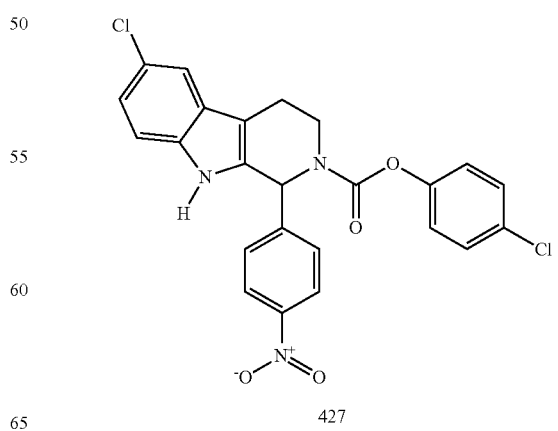
427

TABLE A-continued
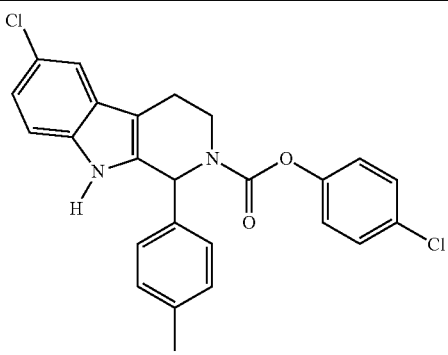
428
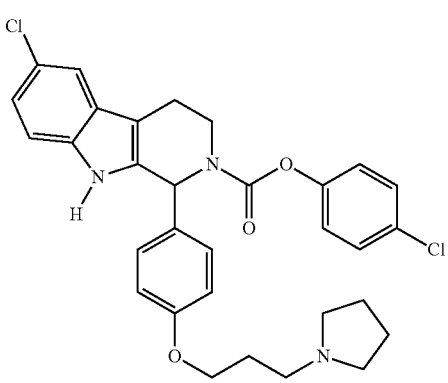
429
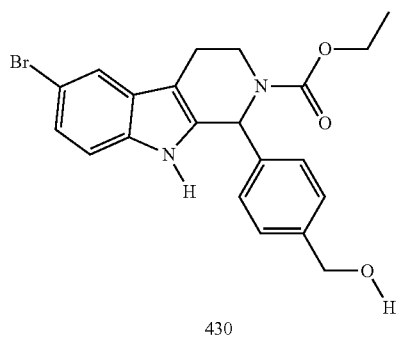
430
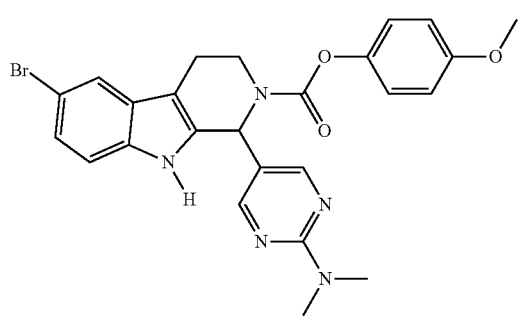
431
TABLE A-continued
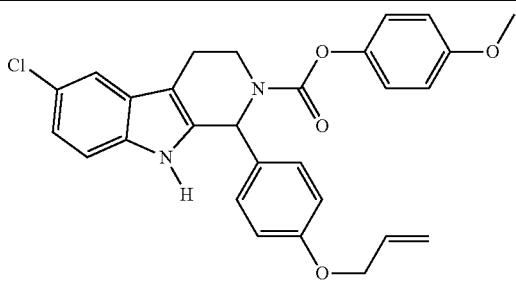
432
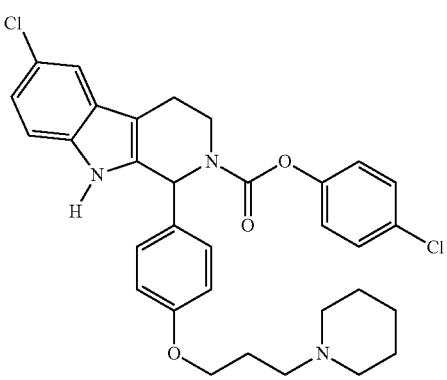
433
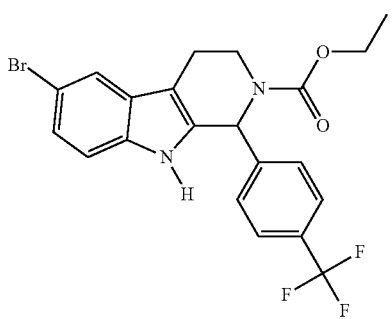
434
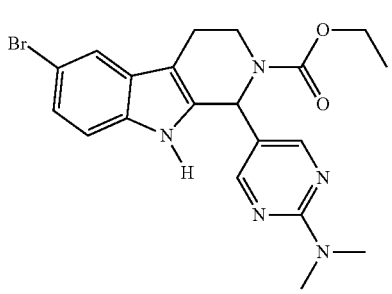
435

TABLE A-continued
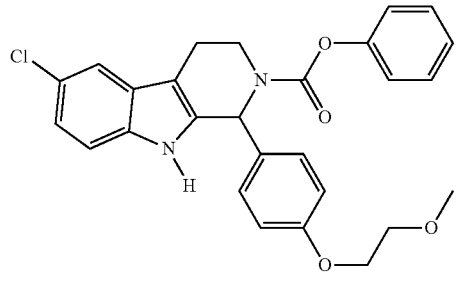
436
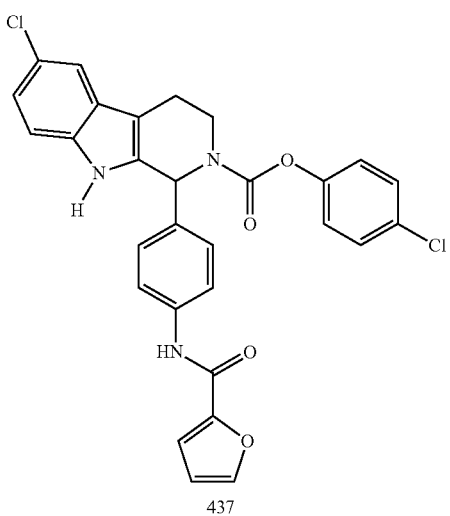
437
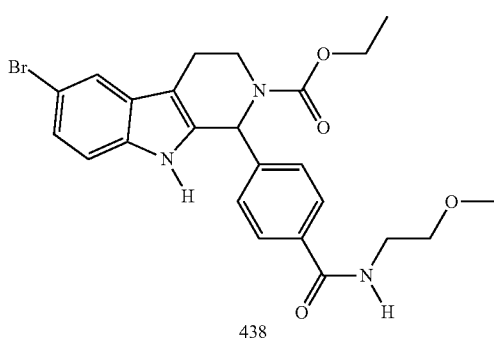
438
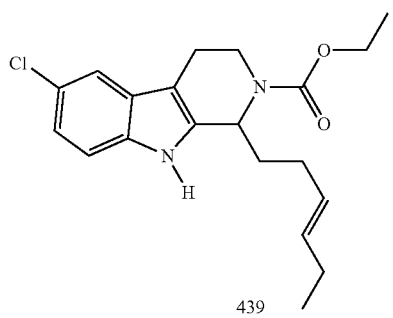
439
TABLE A-continued
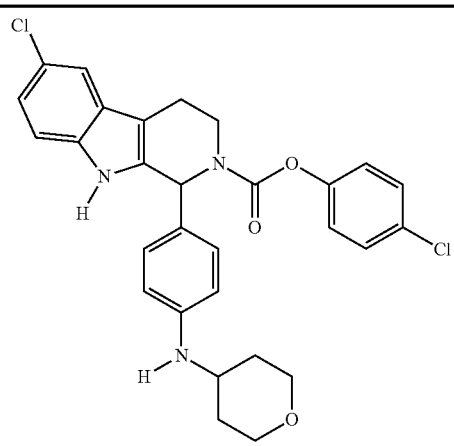
440
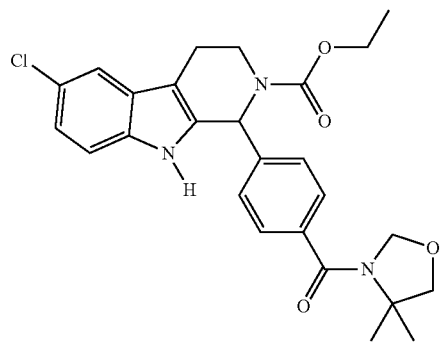
441
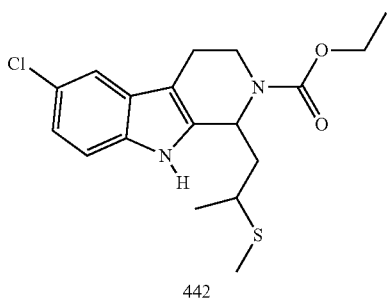
442
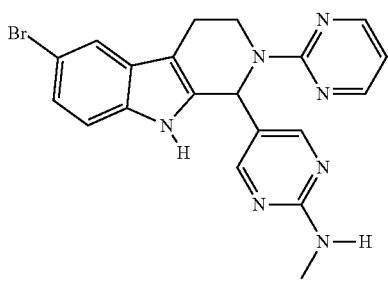
443

TABLE A-continued
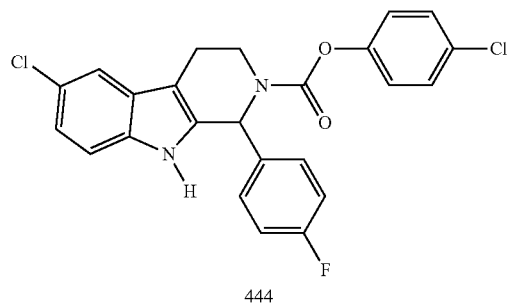
444
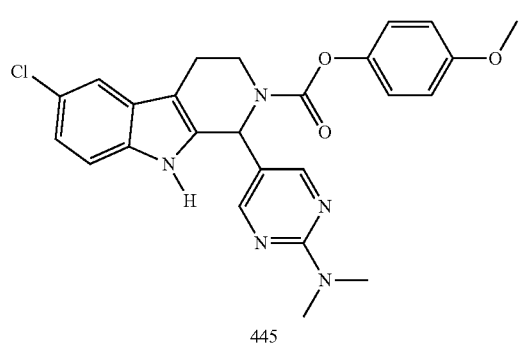
445
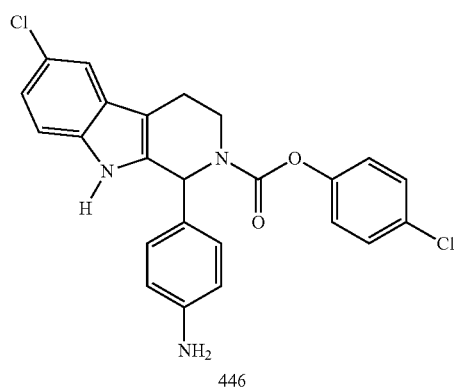
446
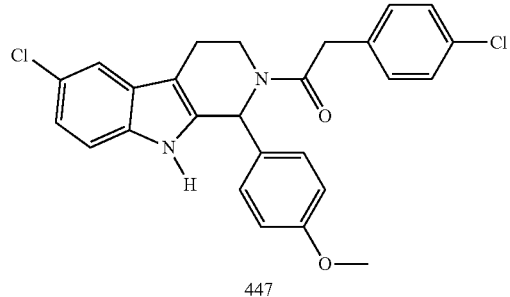
447
TABLE A-continued
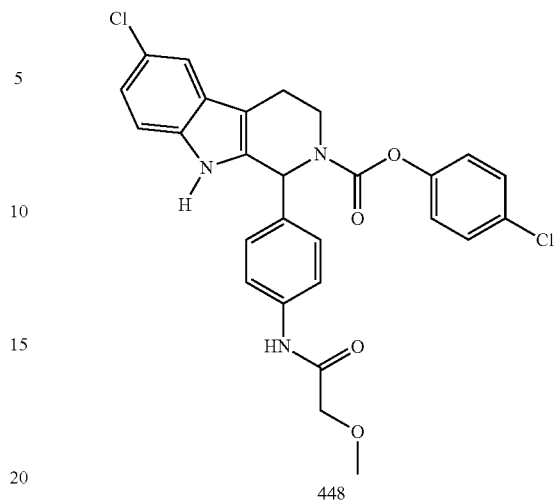
448
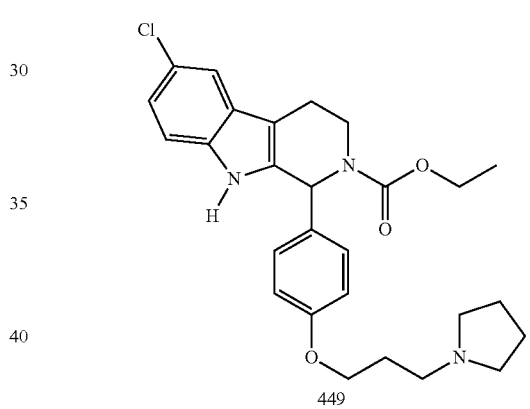
449
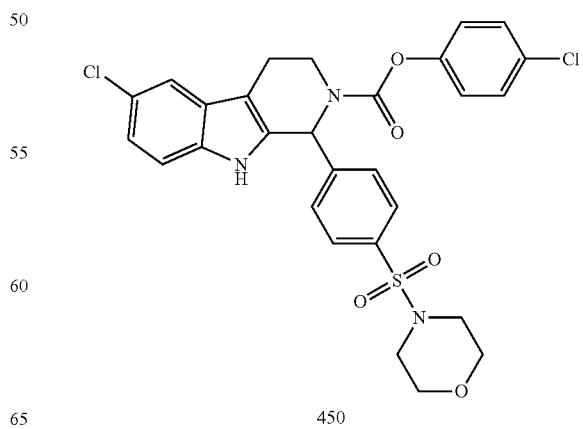
450

TABLE A-continued
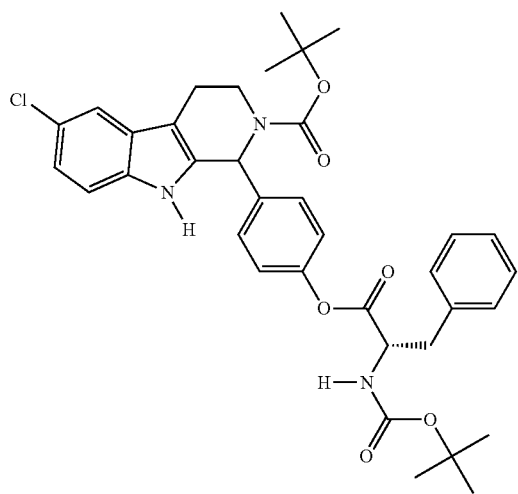
451
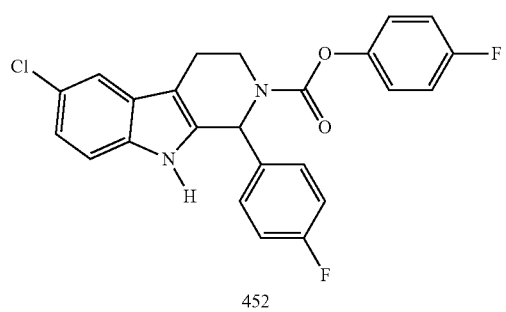
452
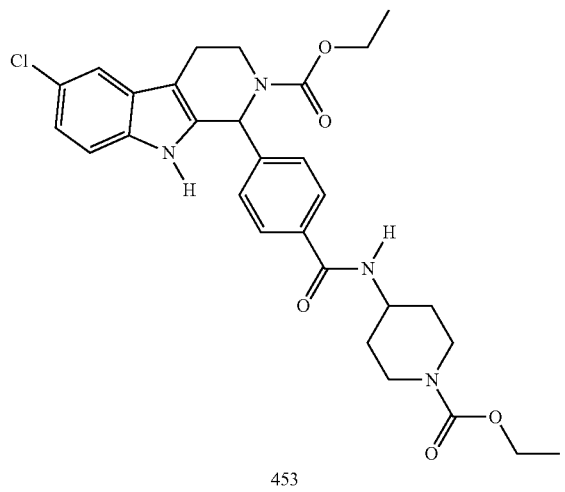
453
TABLE A-continued
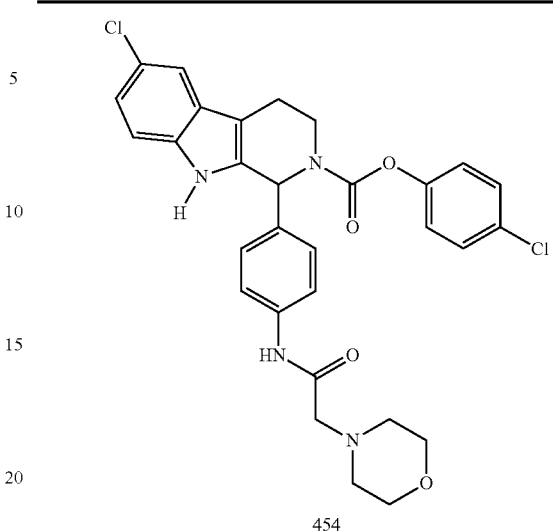
454
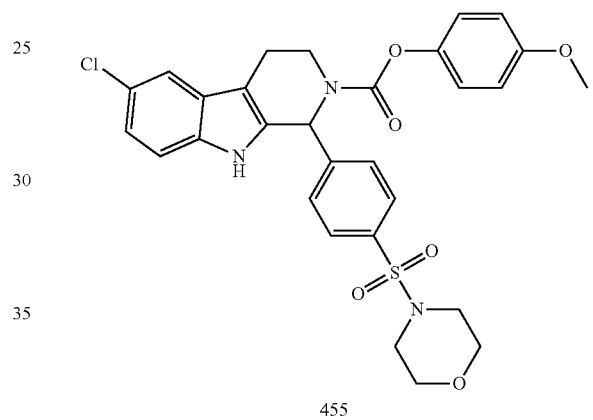
455
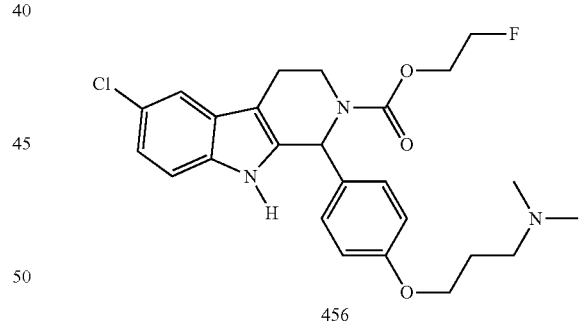
456
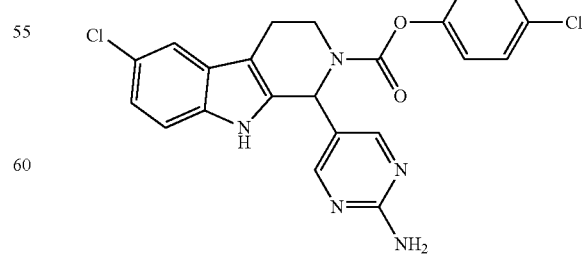
457

TABLE A-continued
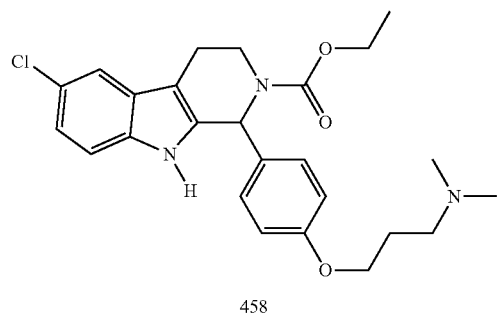
458
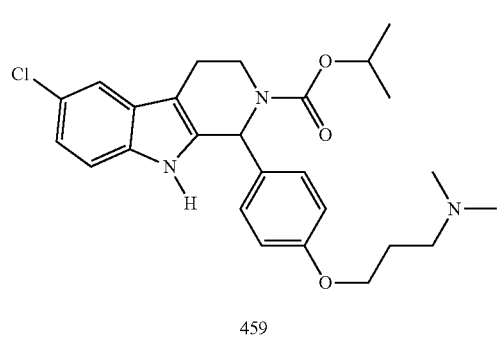
459
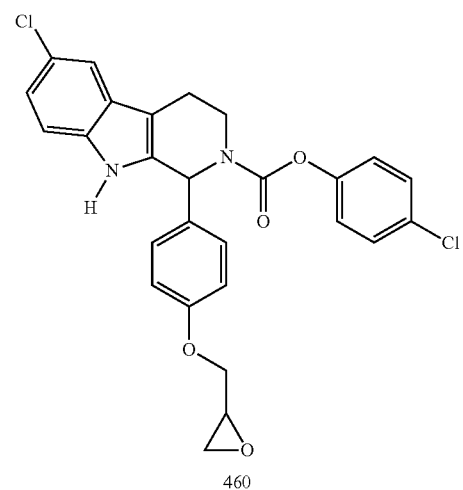
460
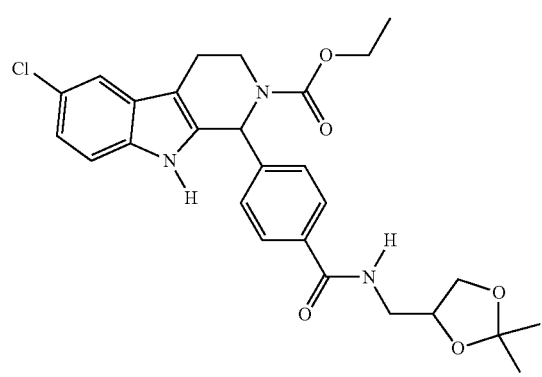
461
TABLE A-continued
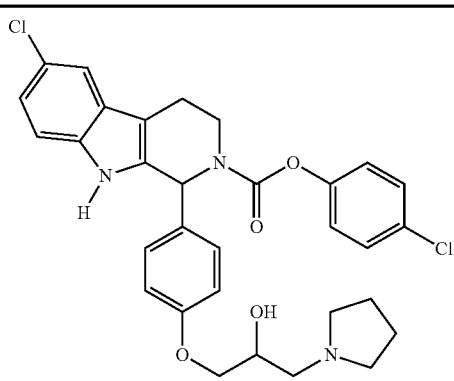
462
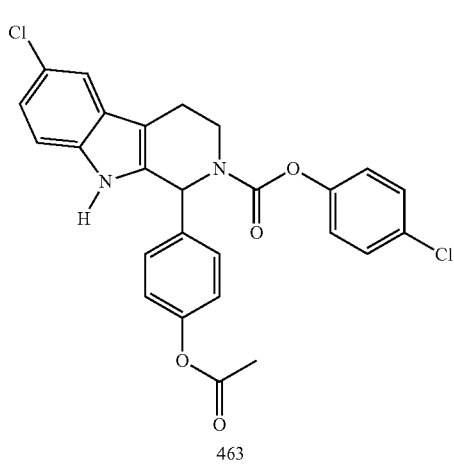
463
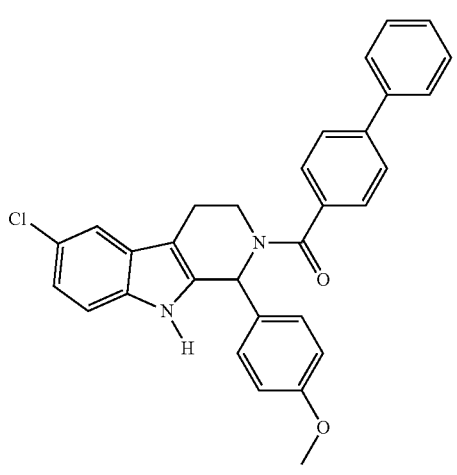
464

TABLE A-continued
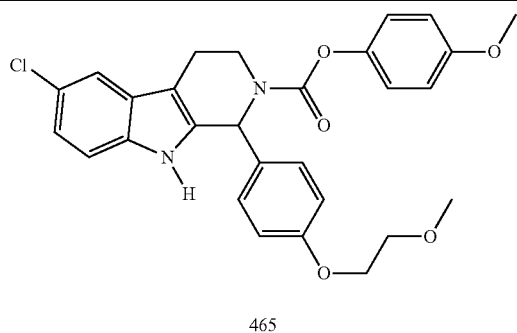
465
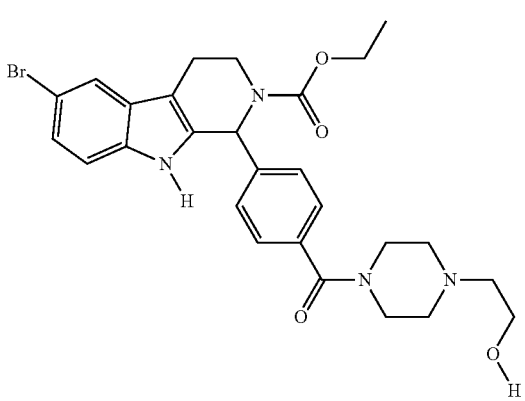
466
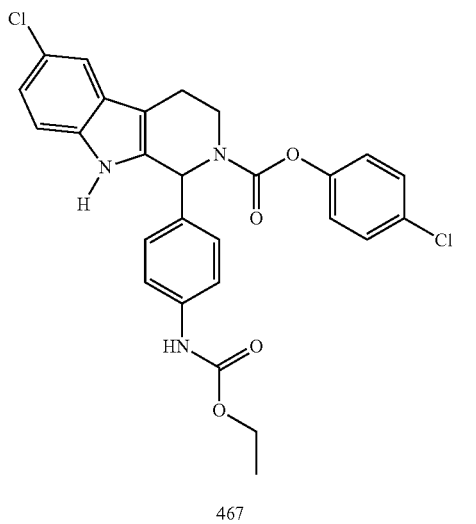
467
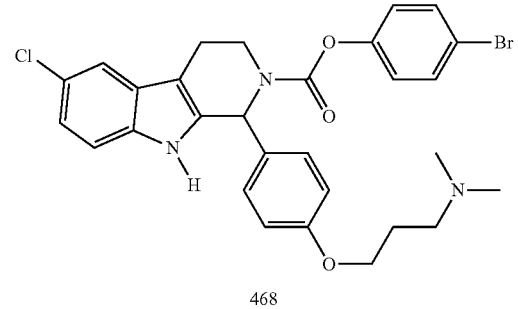
468
TABLE A-continued
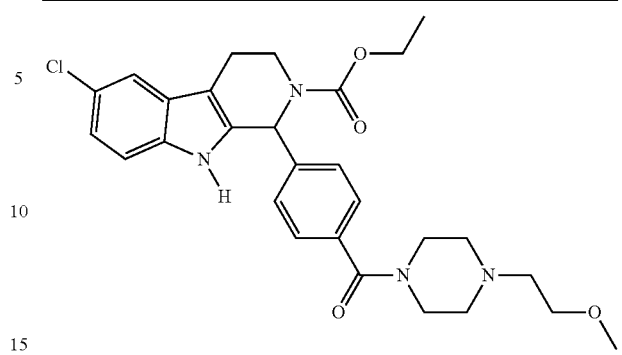
469
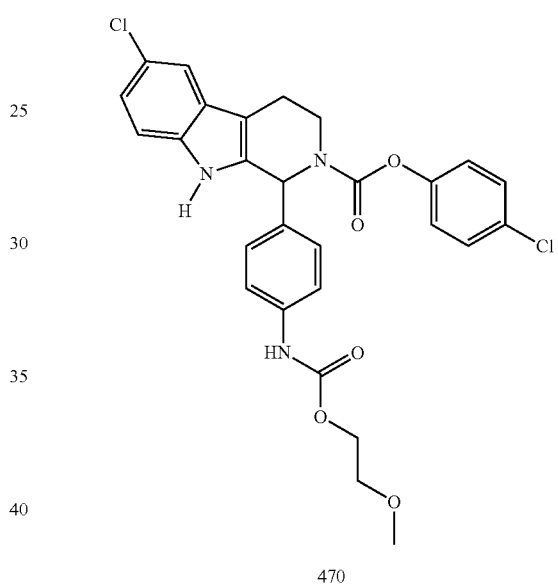
470
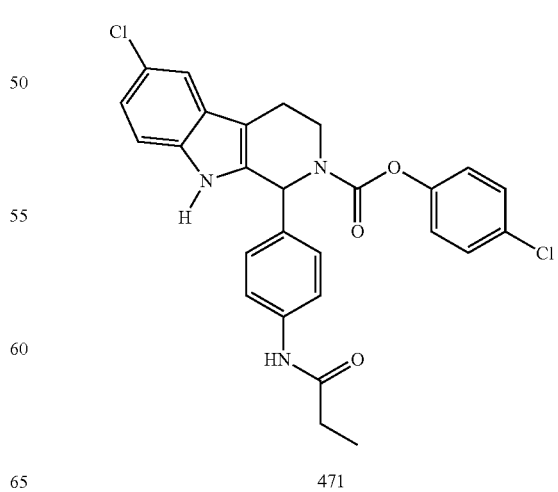
471

TABLE A-continued
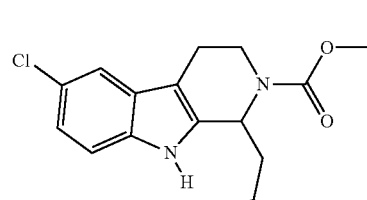
472
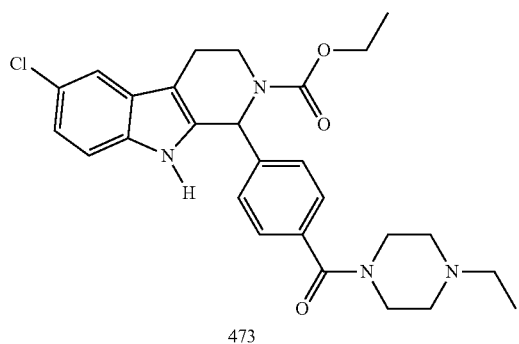
473
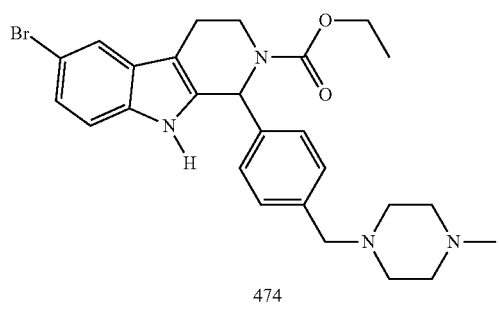
474
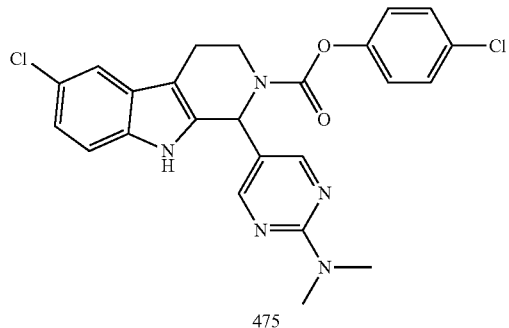
475
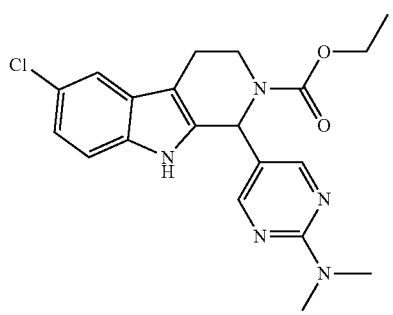
476
TABLE A-continued
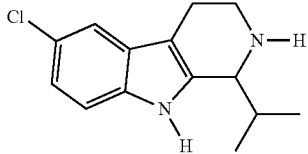
477
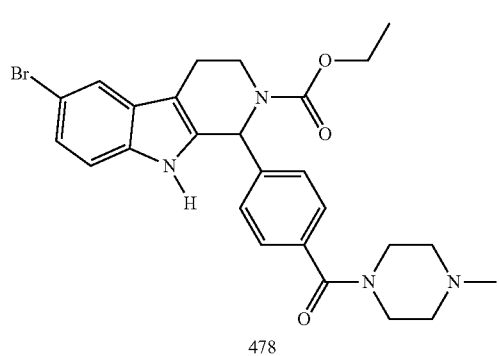
478
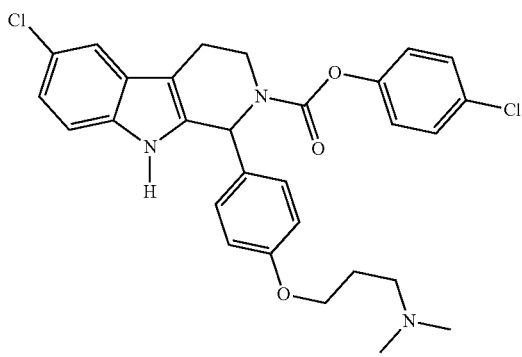
479
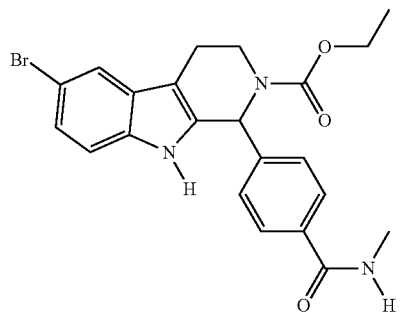
480

TABLE A-continued
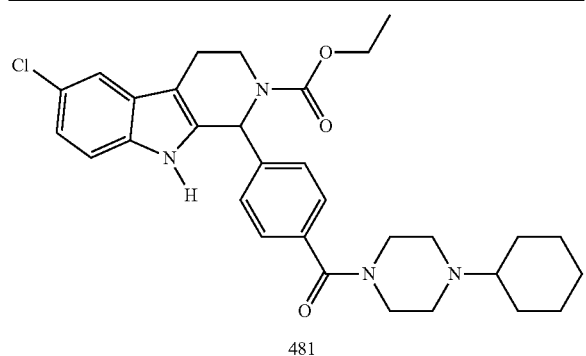
481
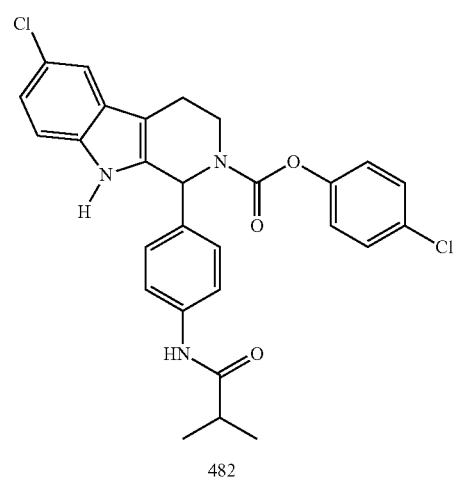
482
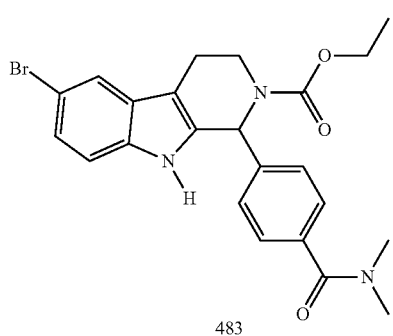
483
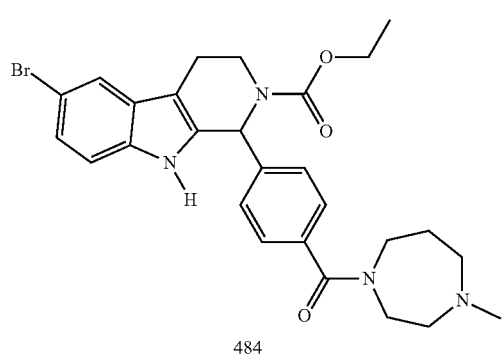
484
TABLE A-continued
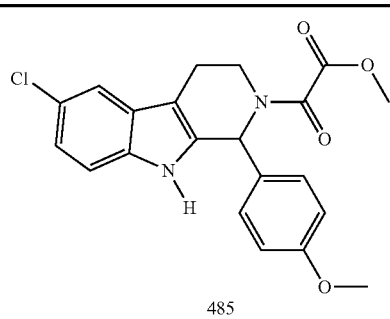
485
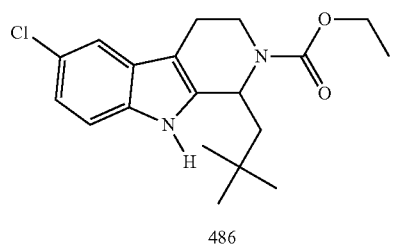
486
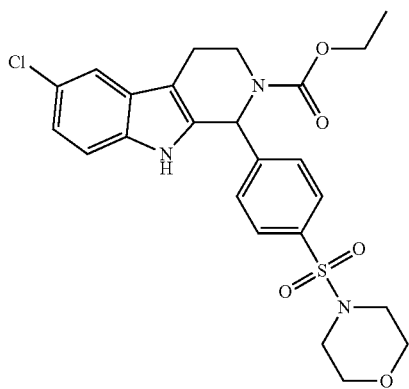
487
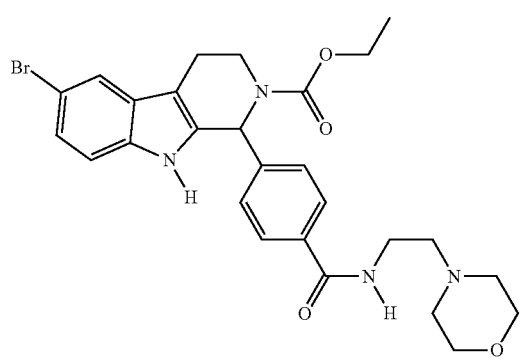
488

TABLE A-continued
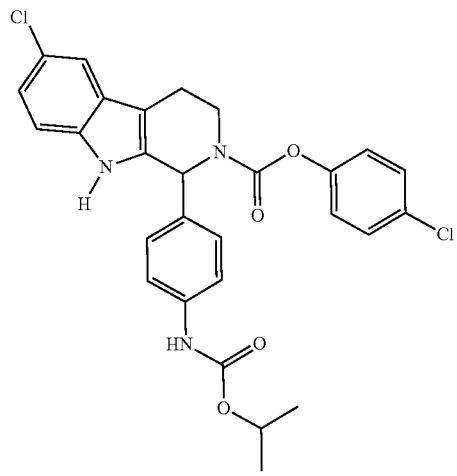
489
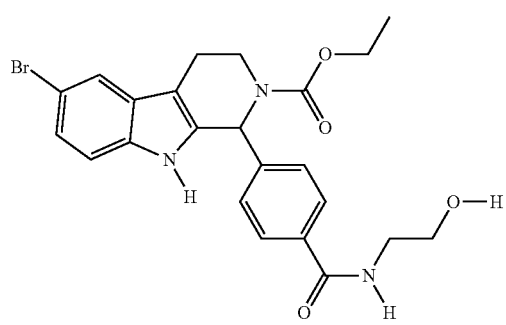
490
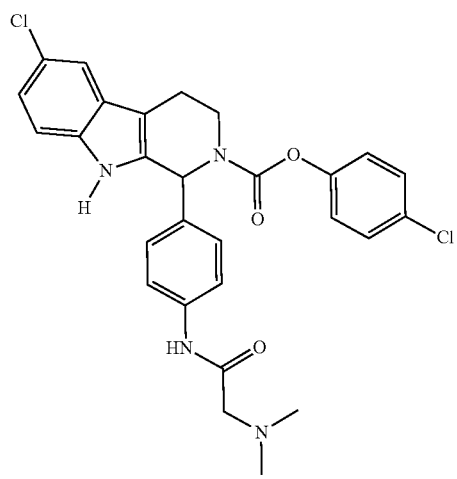
491
TABLE A-continued
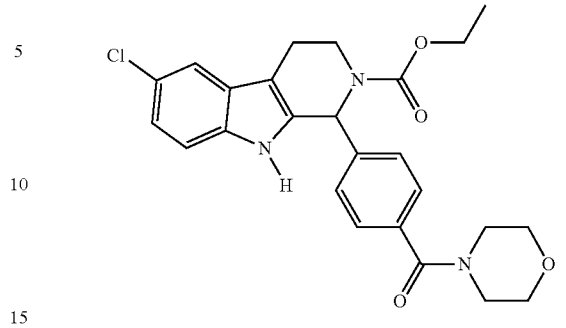
492
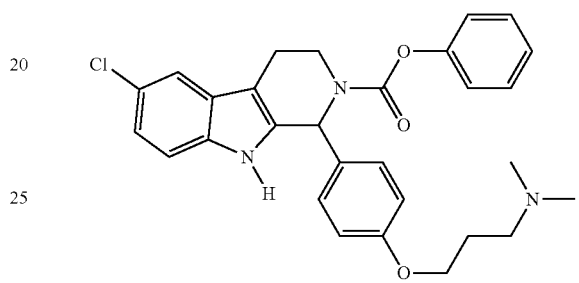
493
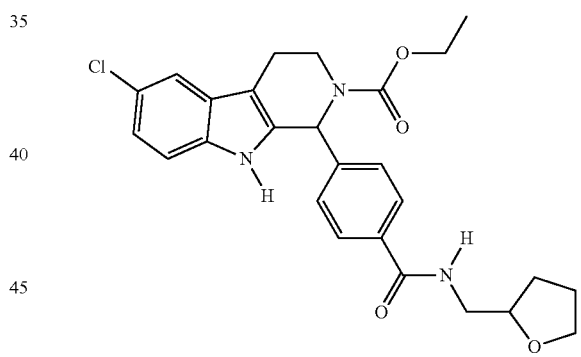
494
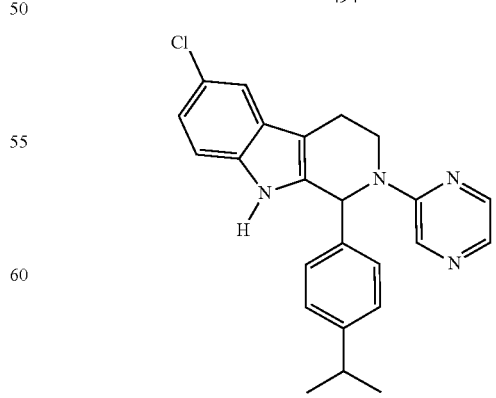
495

TABLE A-continued
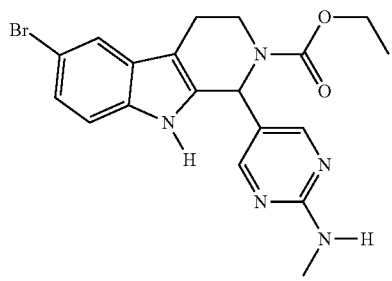
496
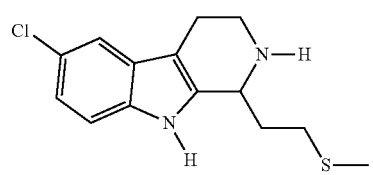
497
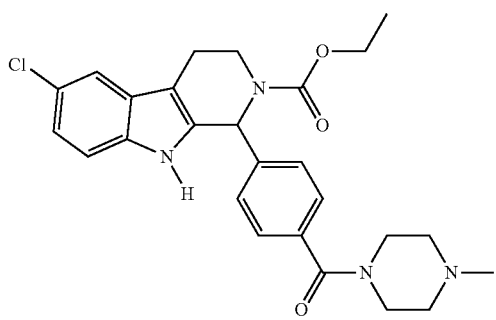
498
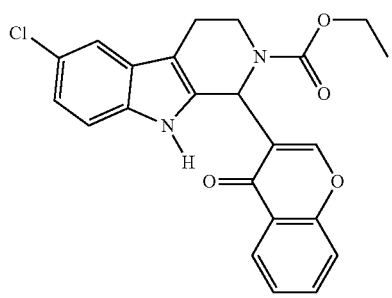
499
TABLE A-continued
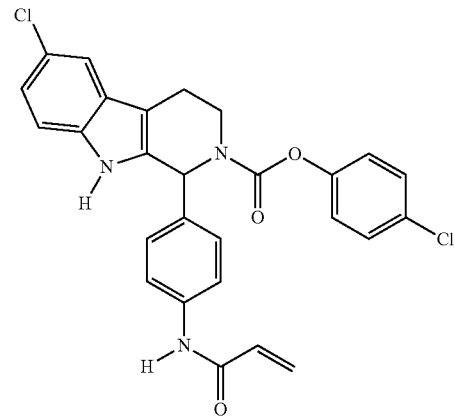
500
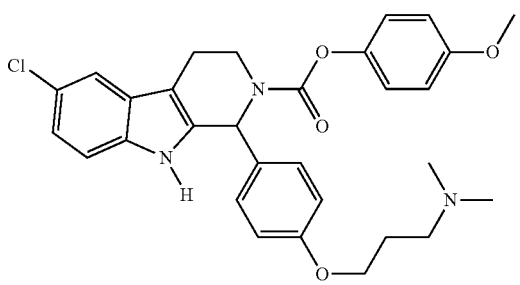
501
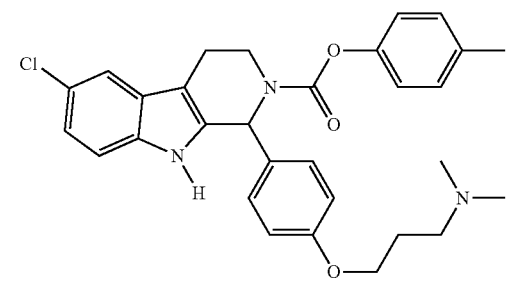
502
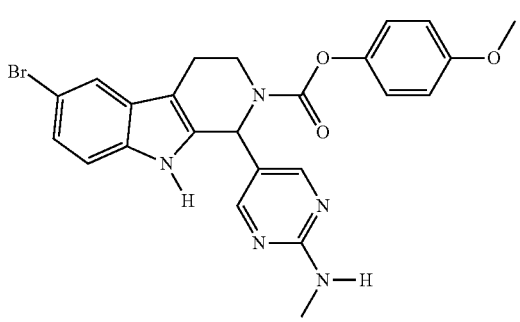
503

TABLE A-continued
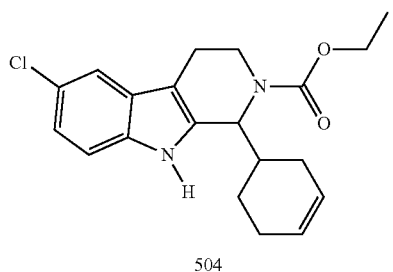
504
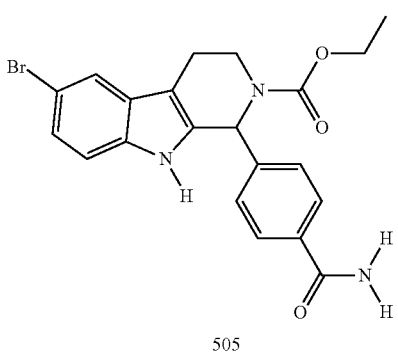
505
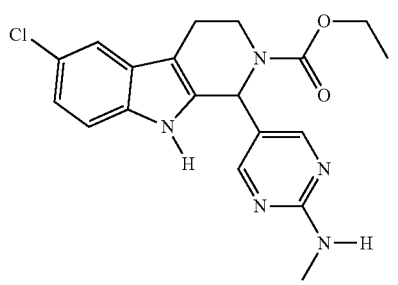
506
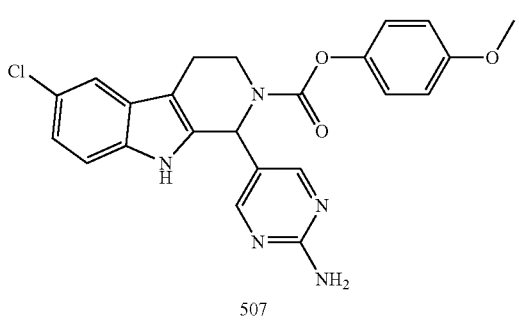
507
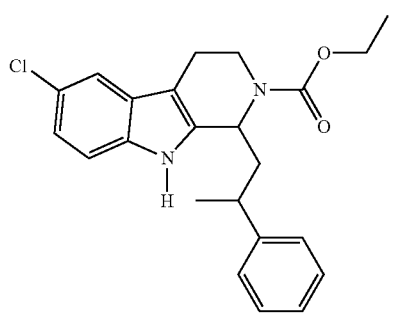
508
TABLE A-continued
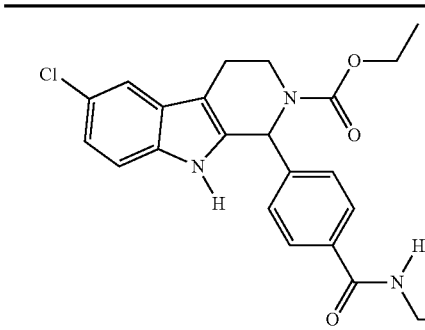
509
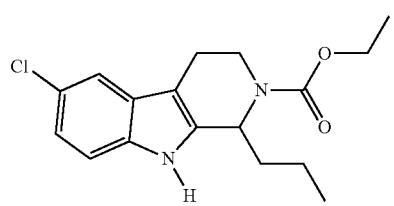
510
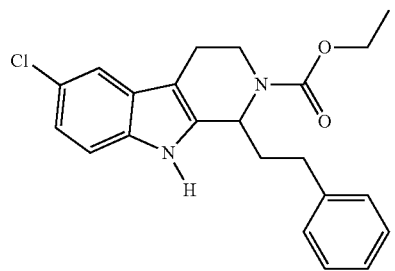
511
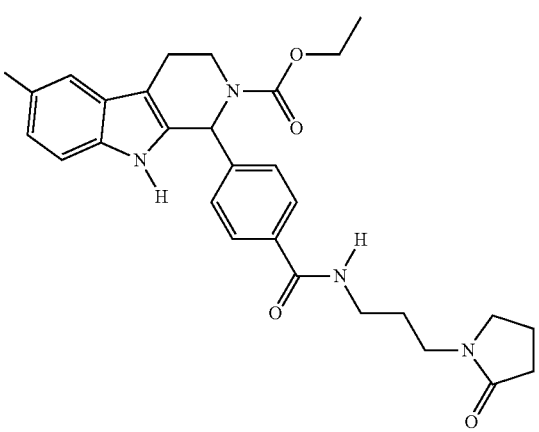
512

TABLE A-continued
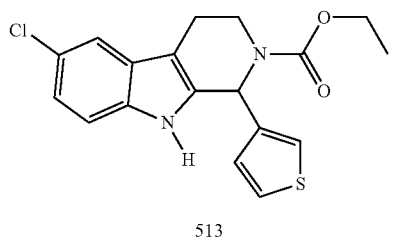
513
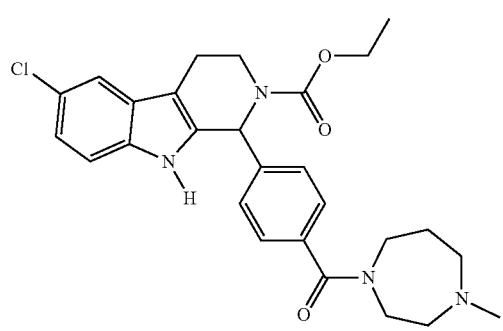
514
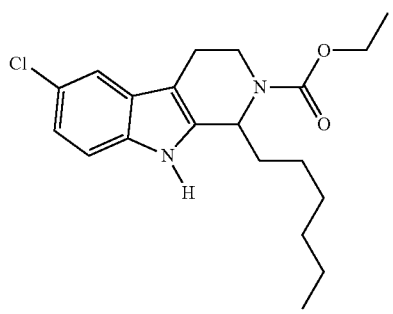
515
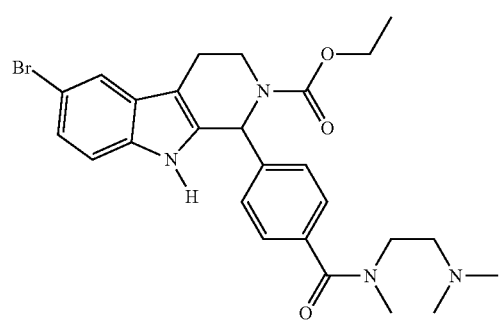
516
TABLE A-continued
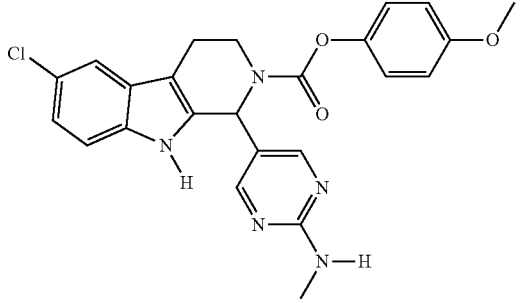
517
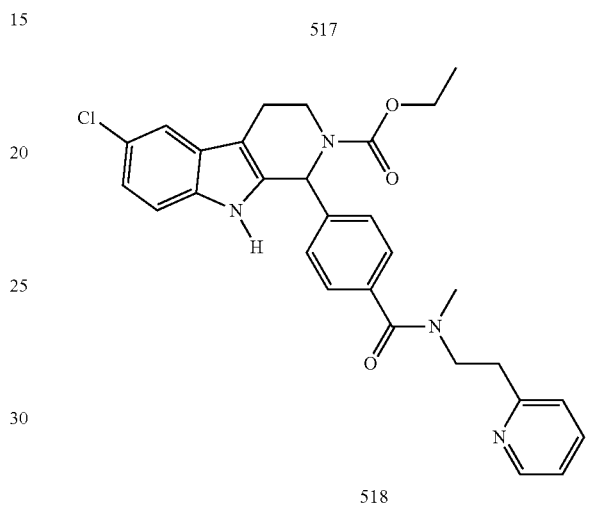
518
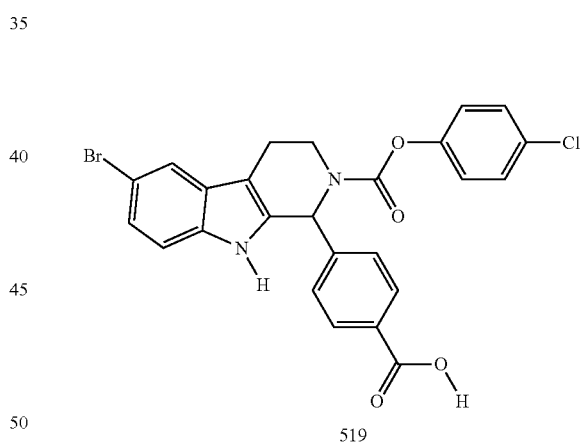
519
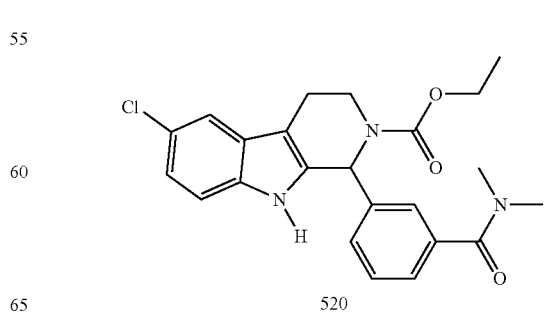
520

TABLE A-continued
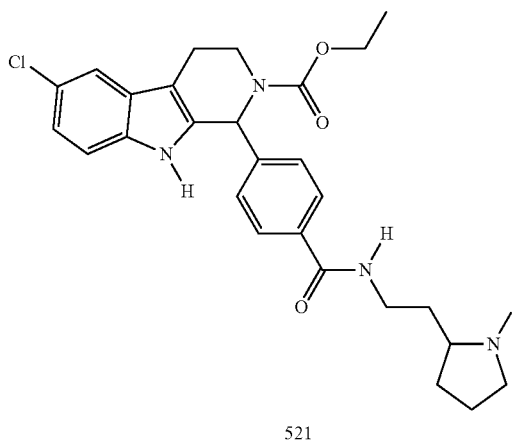
521
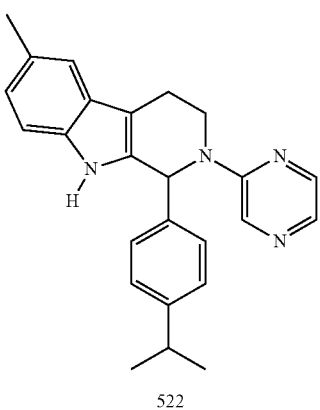
522
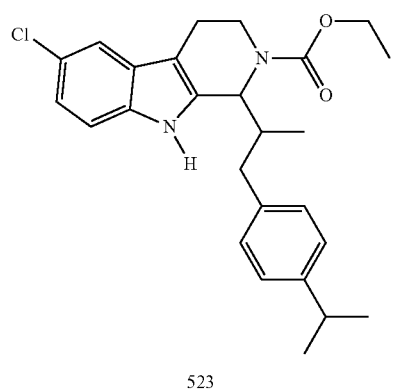
523
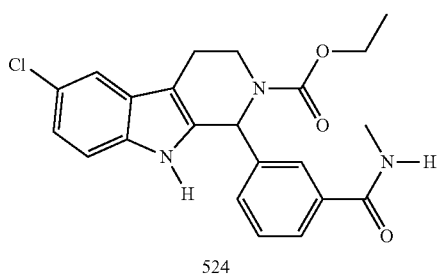
524
TABLE A-continued
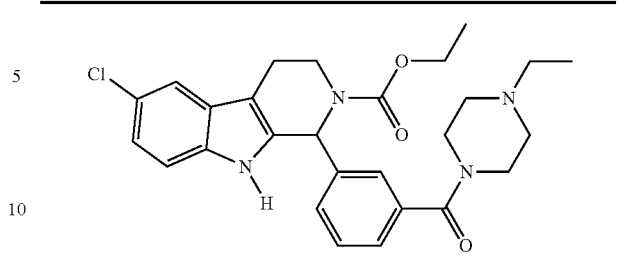
525
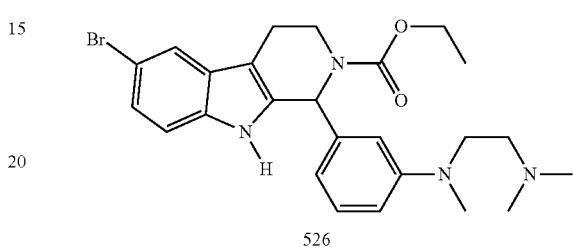
526
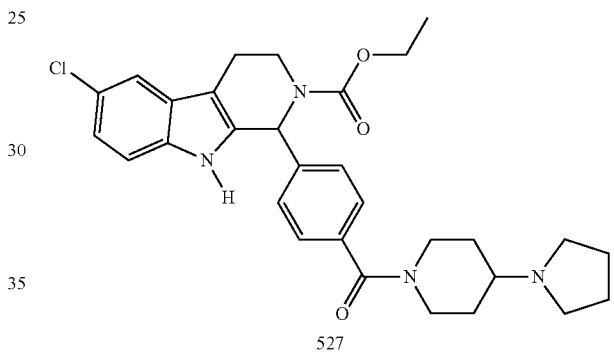
527
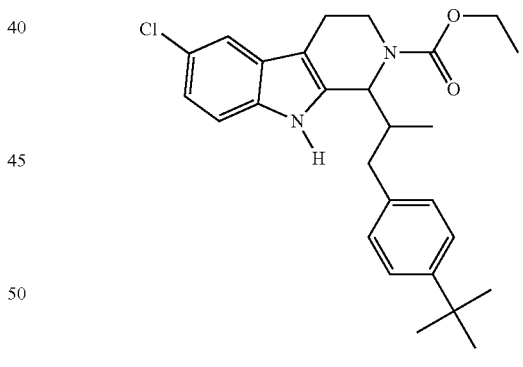
528
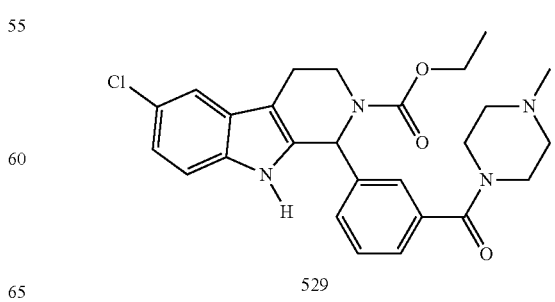
529

TABLE A-continued
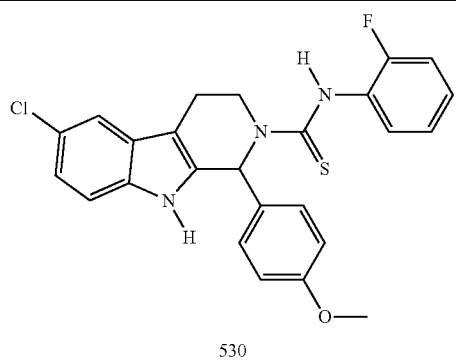
530
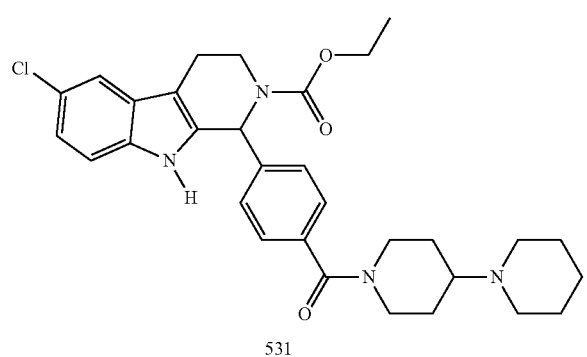
531
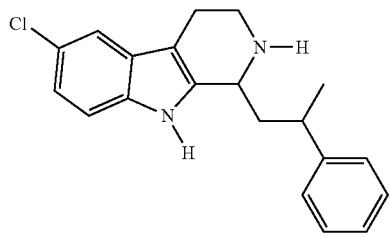
532
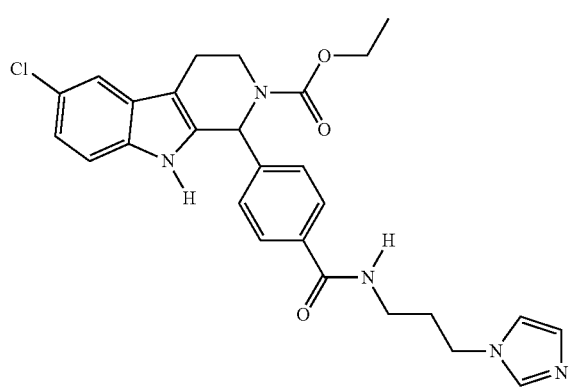
533
TABLE A-continued
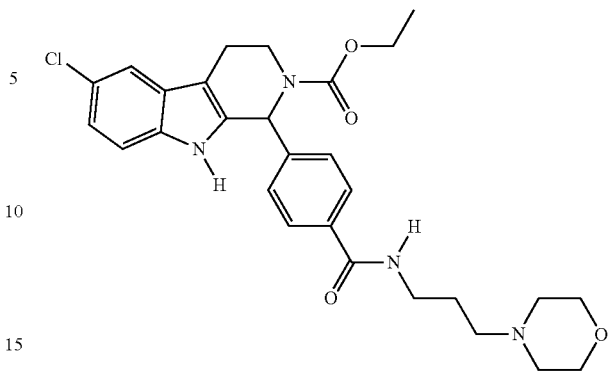
534
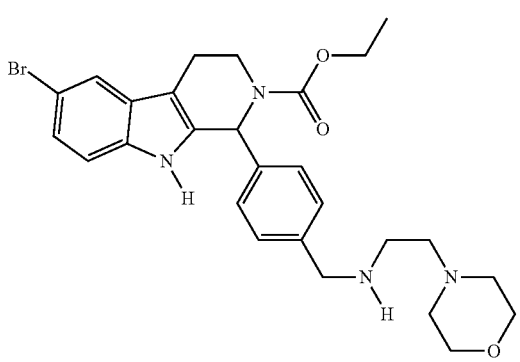
535
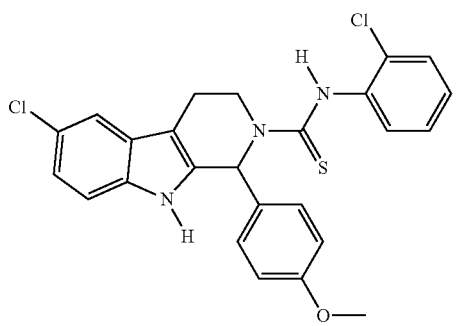
536
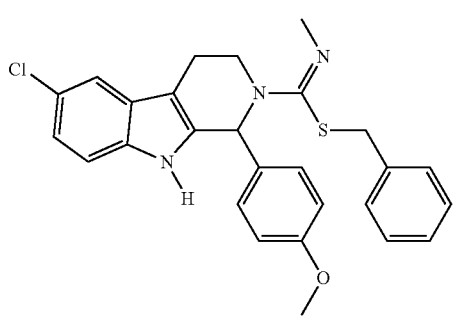
537

TABLE A-continued
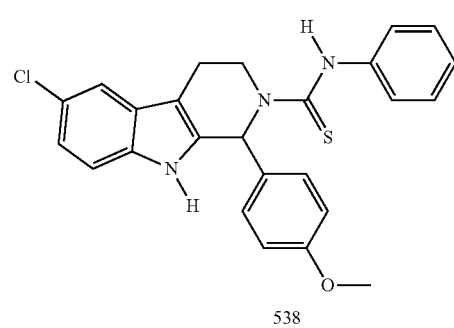
538
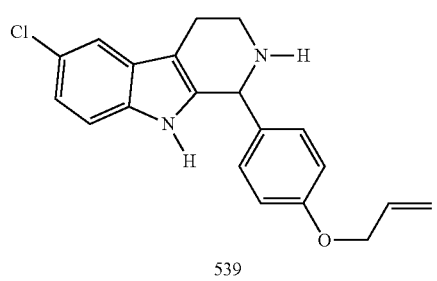
539
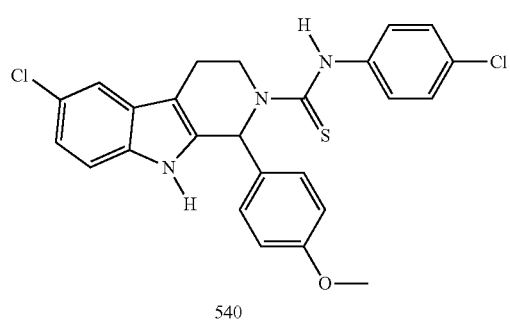
540
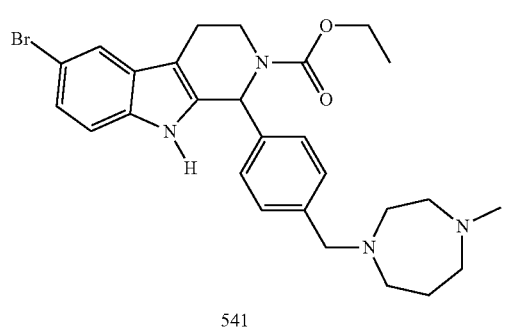
541
542
TABLE A-continued
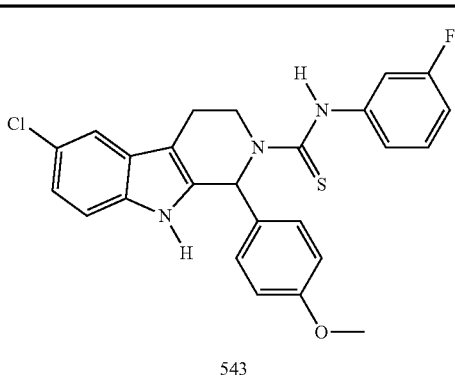
543
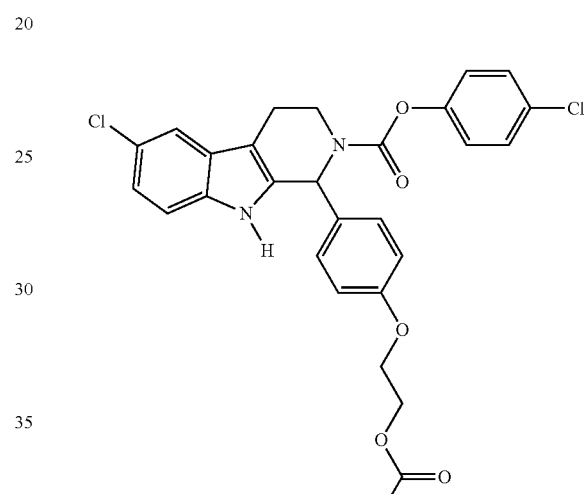
544
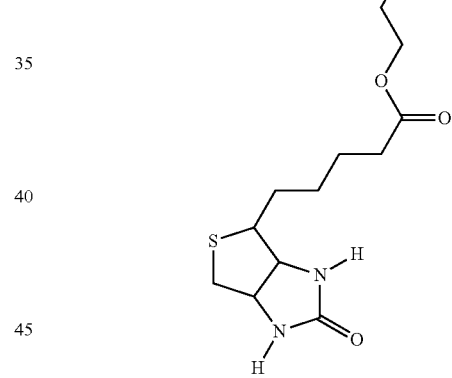
545

TABLE A-continued
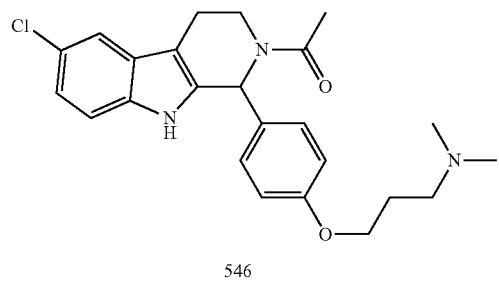
546
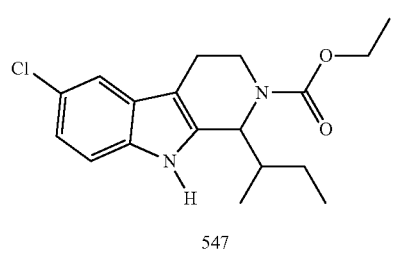
547
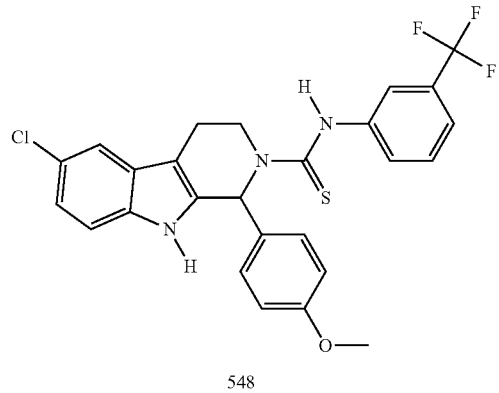
548
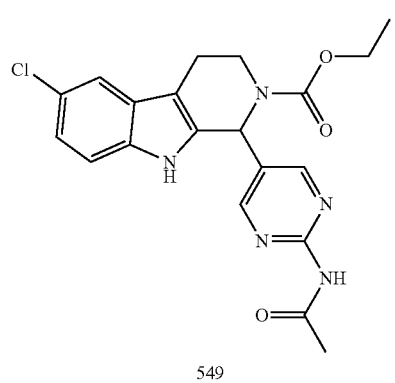
549
TABLE A-continued
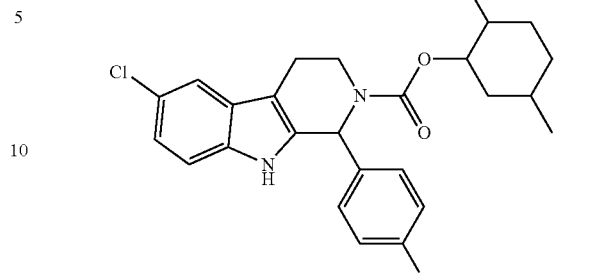
550
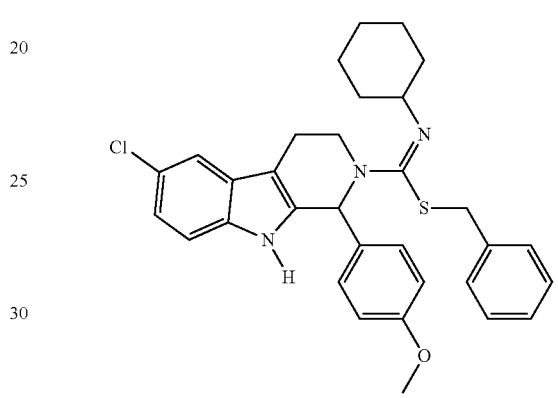
551
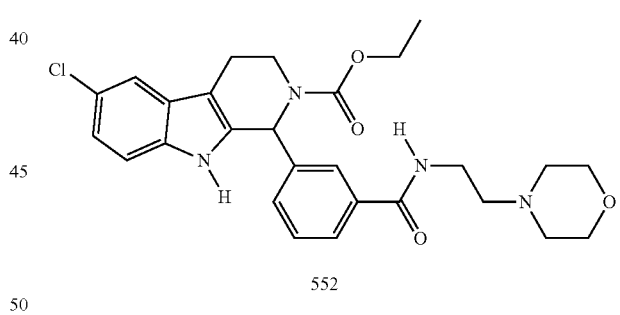
552
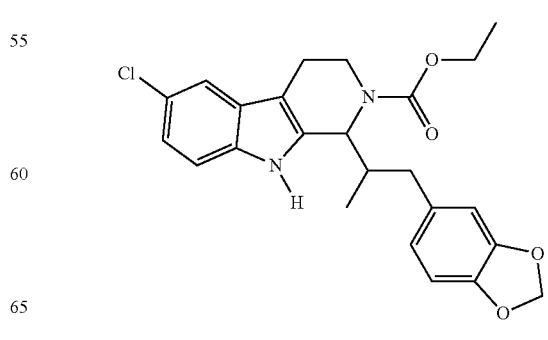
553

TABLE A-continued
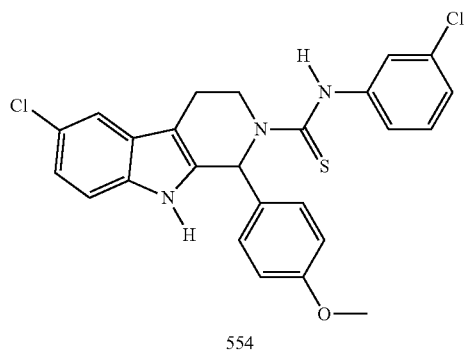
554
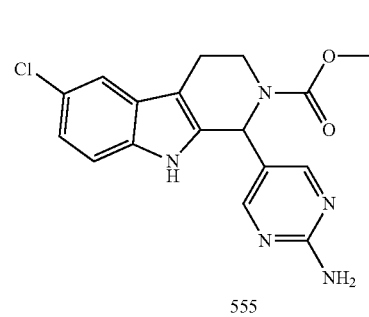
555
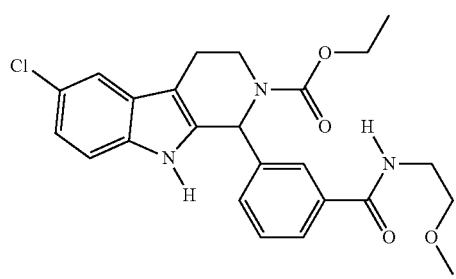
556
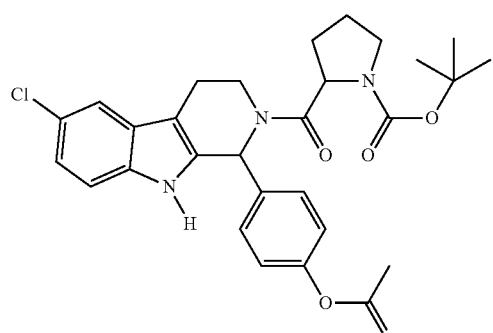
557
TABLE A-continued
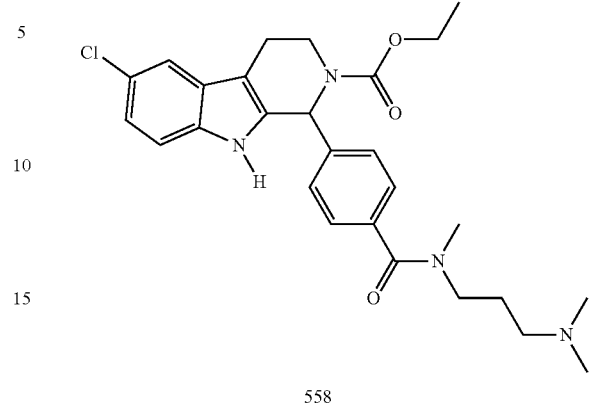
558
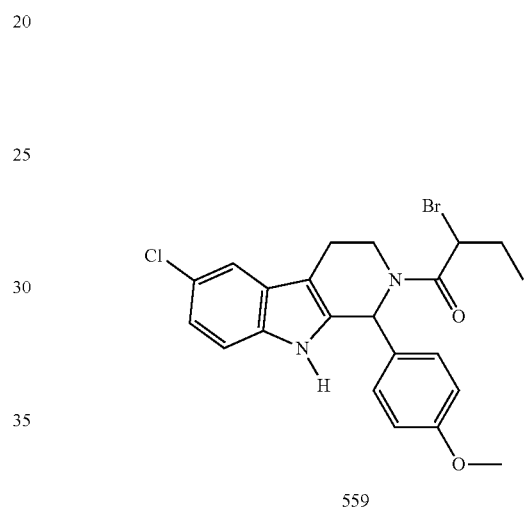
559
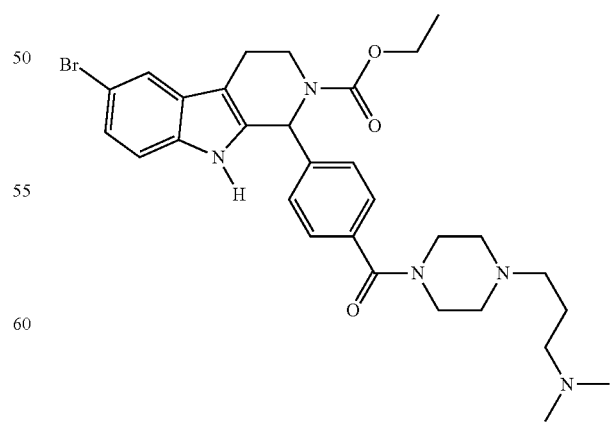
560

TABLE A-continued
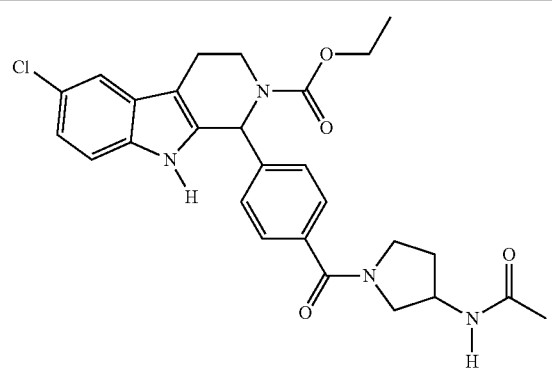
561
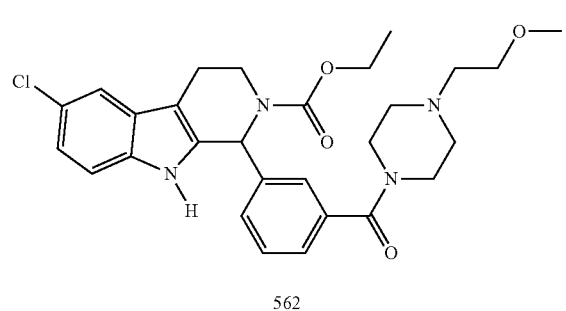
562
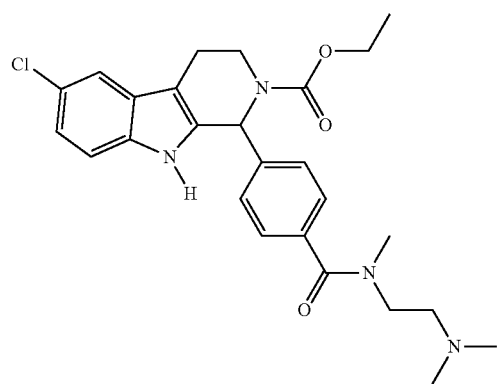
563
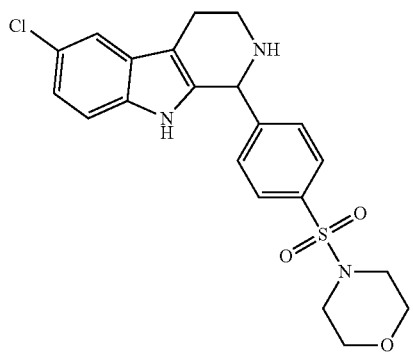
564
TABLE A-continued
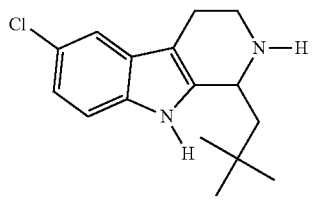
565
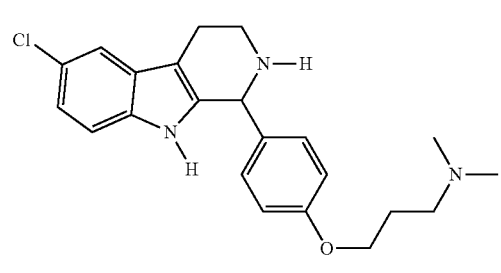
566
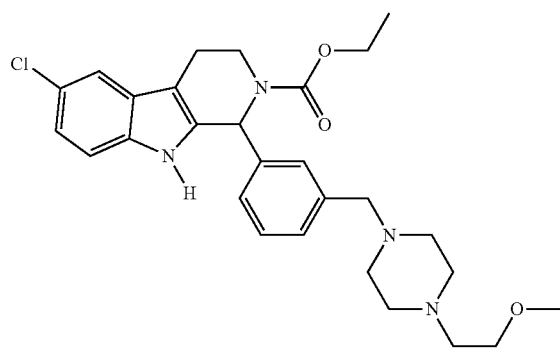
567
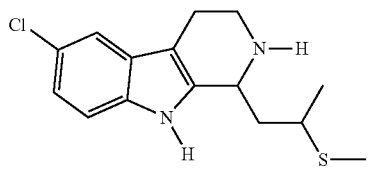
568
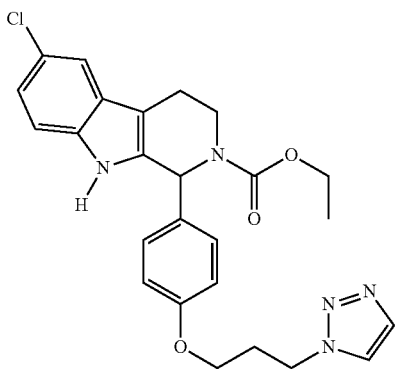
569

TABLE A-continued
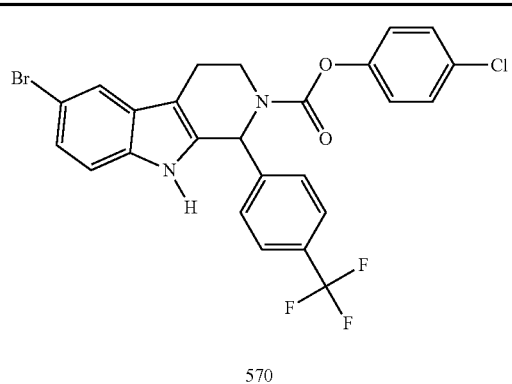
570
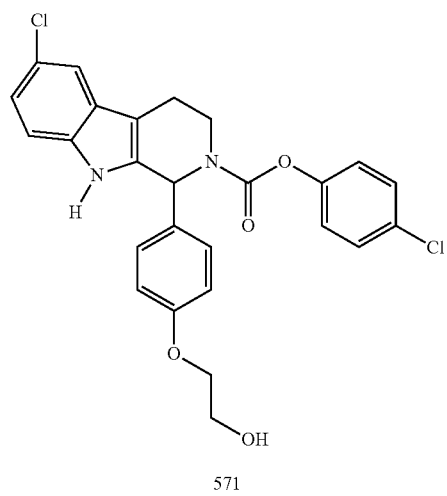
571
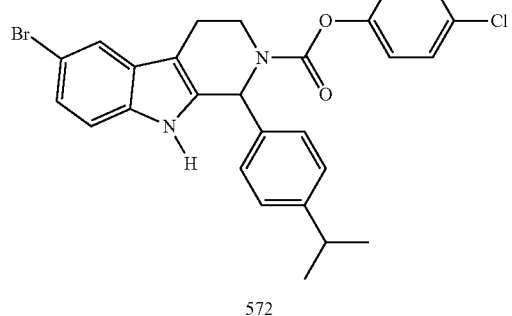
572
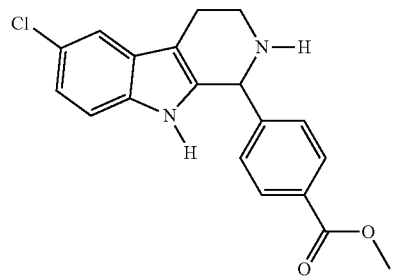
573
TABLE A-continued
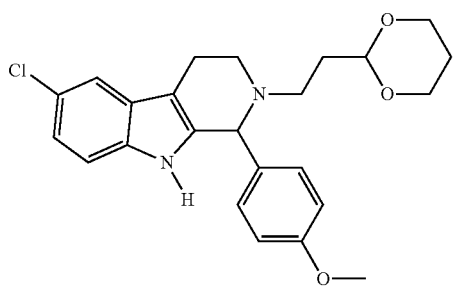
574
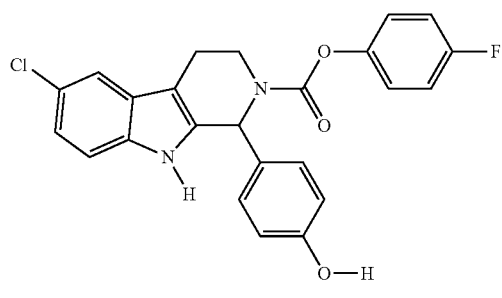
575
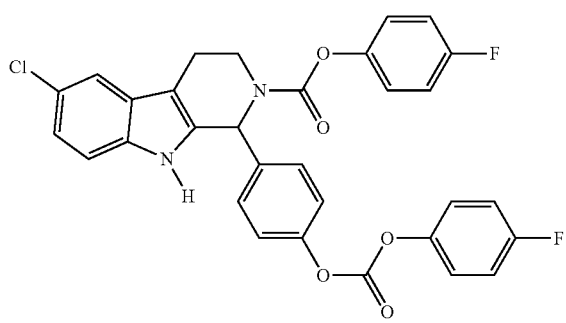
576
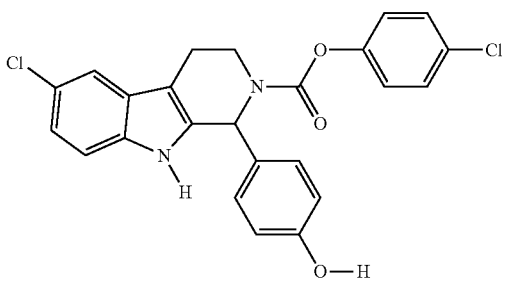
577

TABLE A-continued
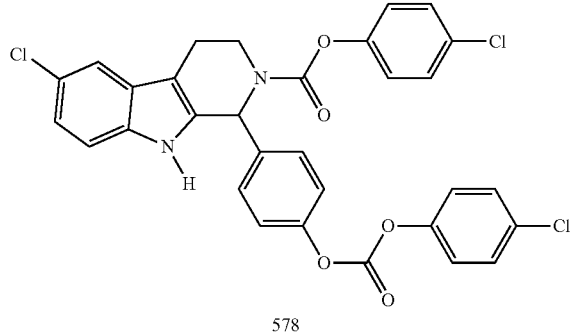
578
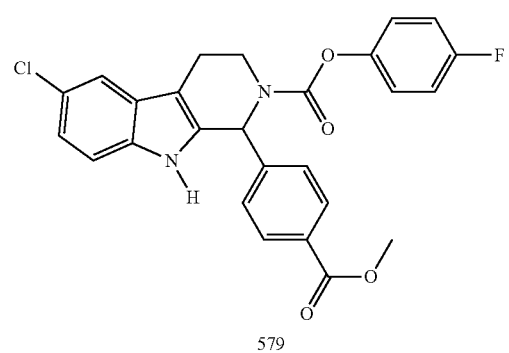
579
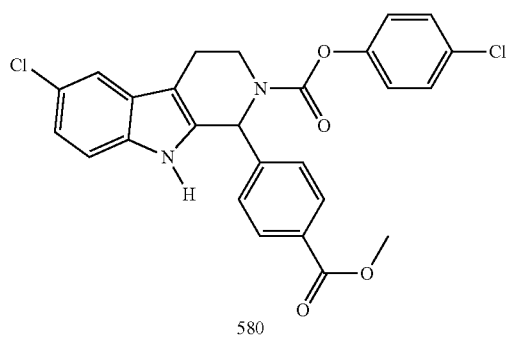
580
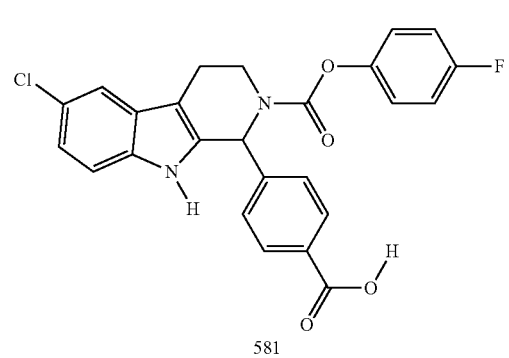
581
TABLE A-continued
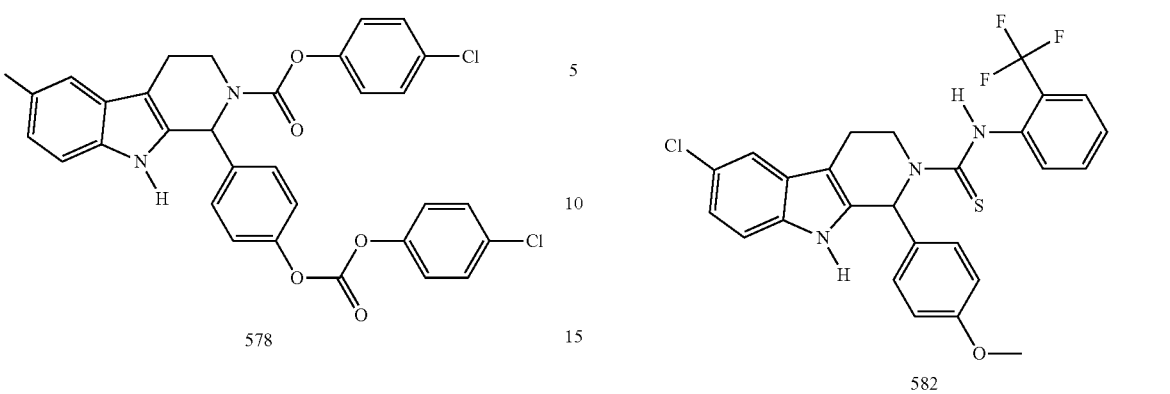
582
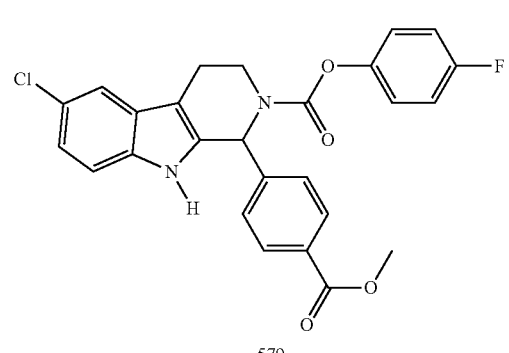
583
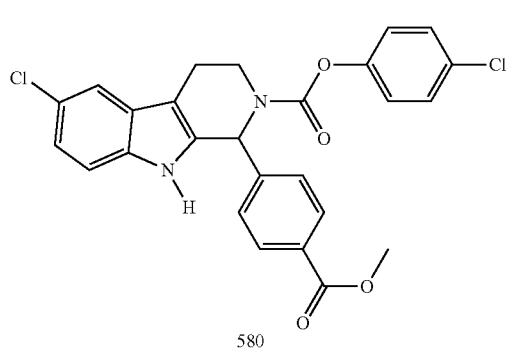
584
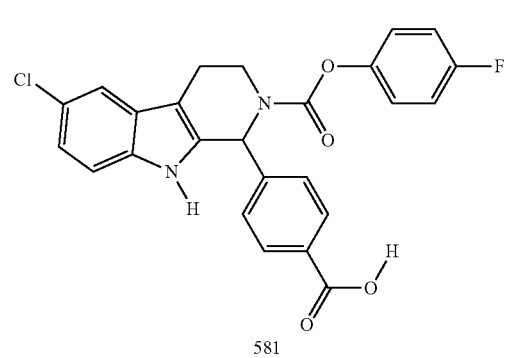
585

TABLE A-continued
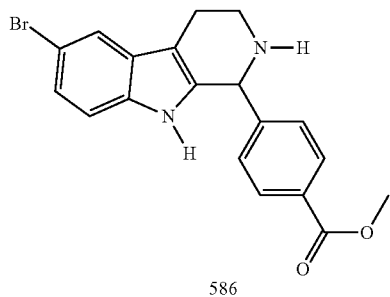
586
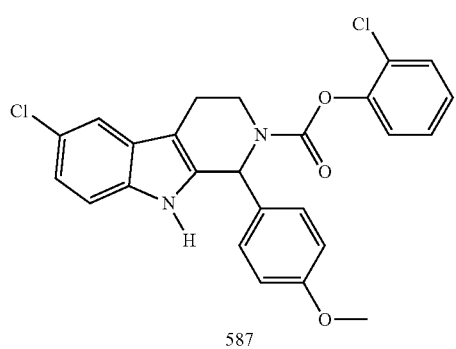
587
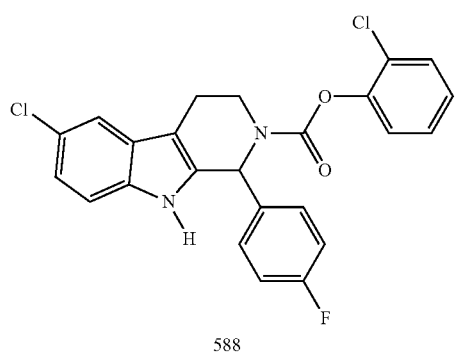
588
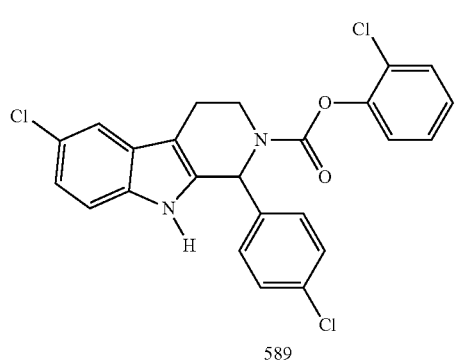
589
TABLE A-continued
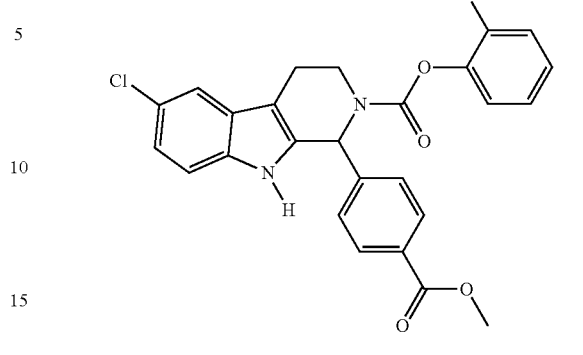
590
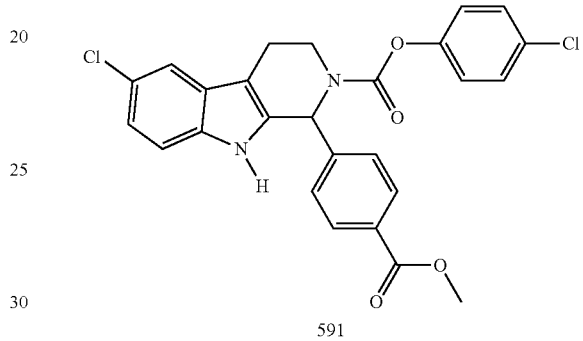
591
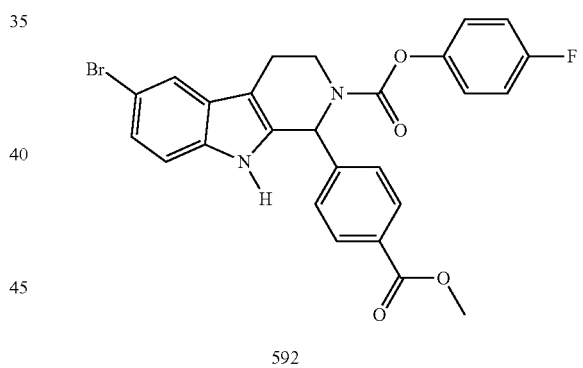
592
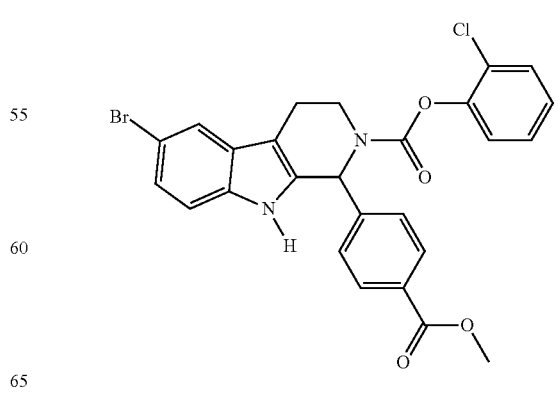
593

TABLE A-continued
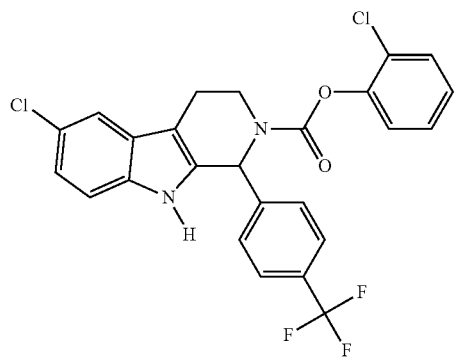
594
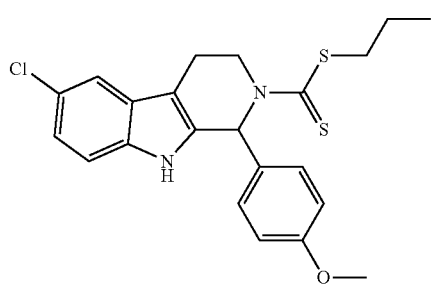
595
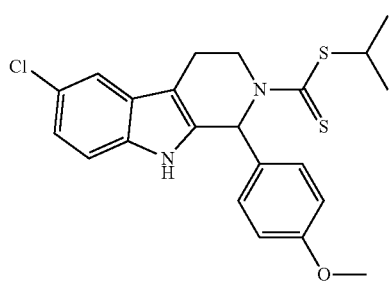
596
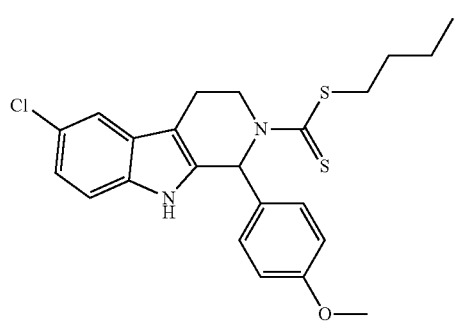
597
TABLE A-continued
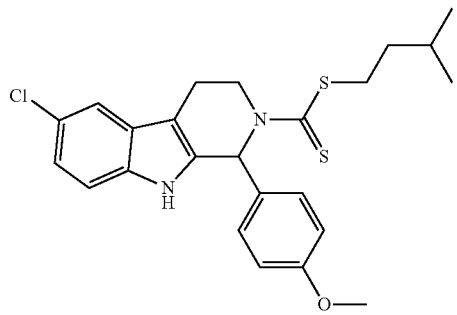
598
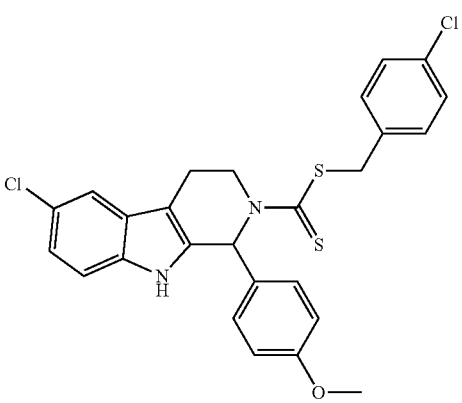
599
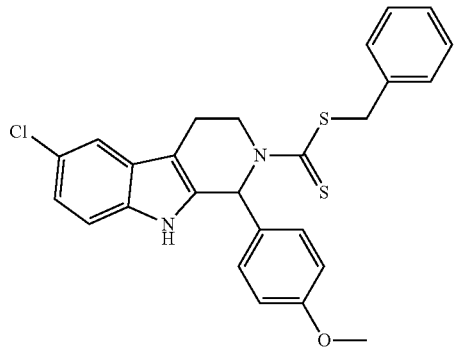
600

TABLE A-continued
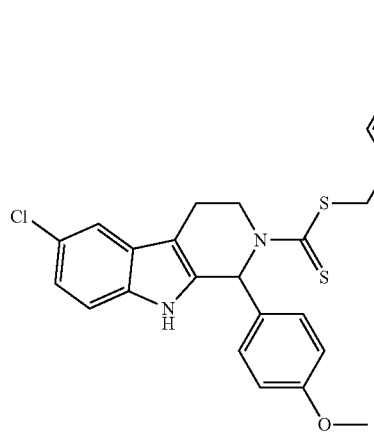
601
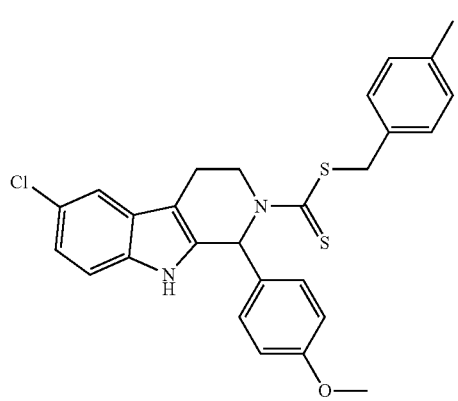
602
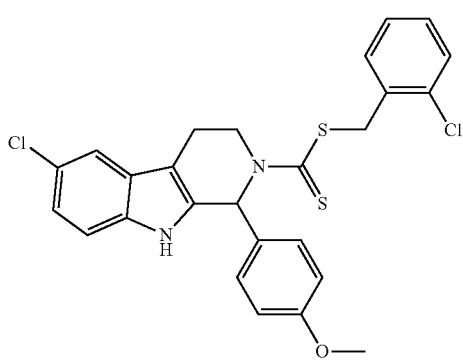
603
TABLE A-continued
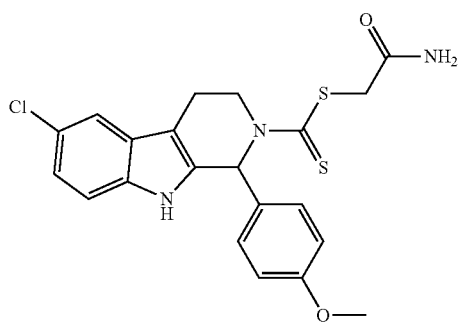
604
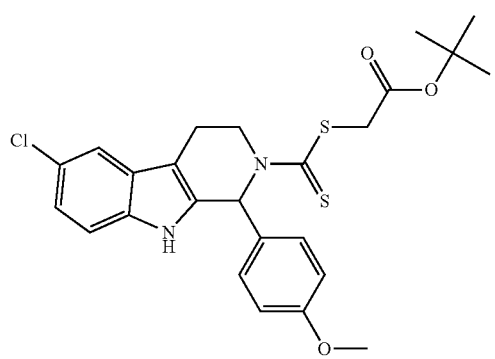
605
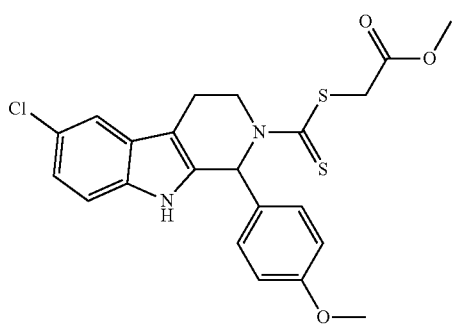
606
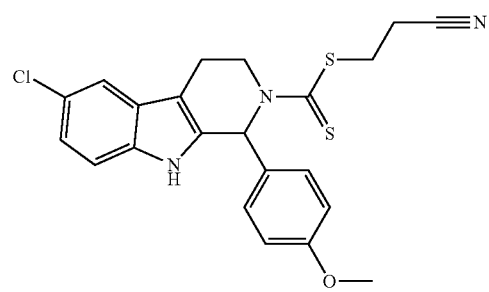
607

TABLE A-continued
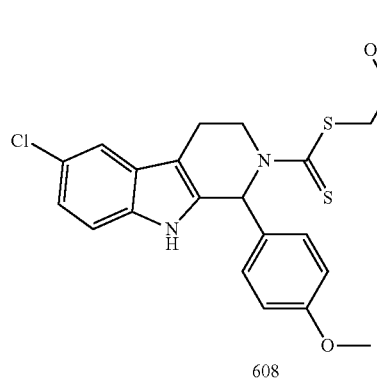
608
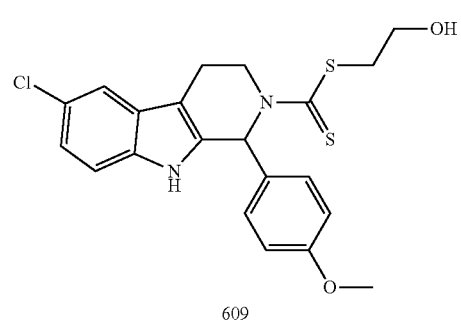
609
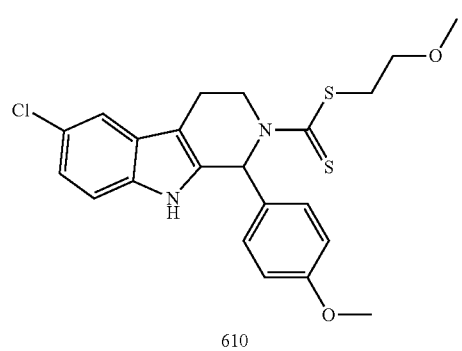
610
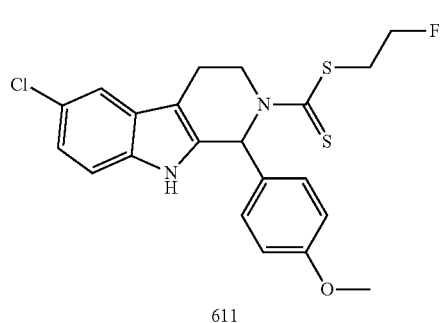
611
TABLE A-continued
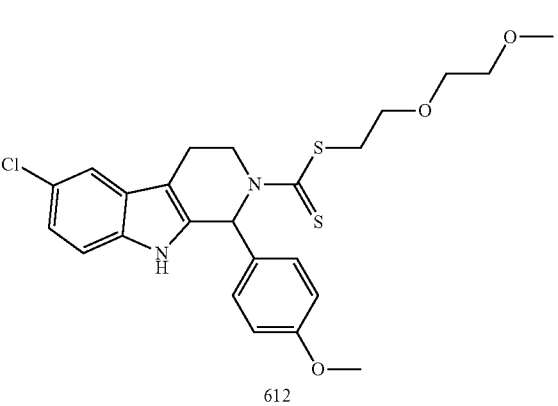
612
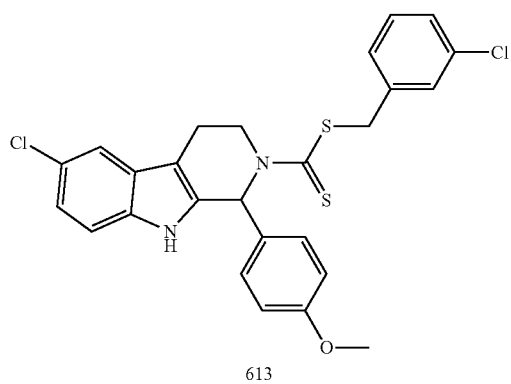
613
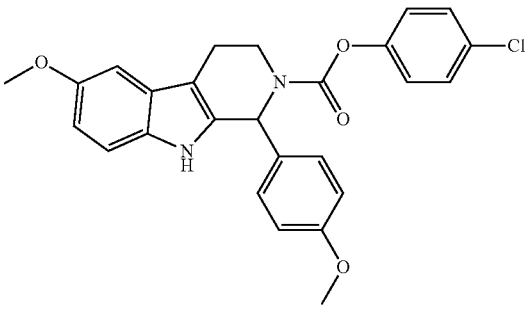
614
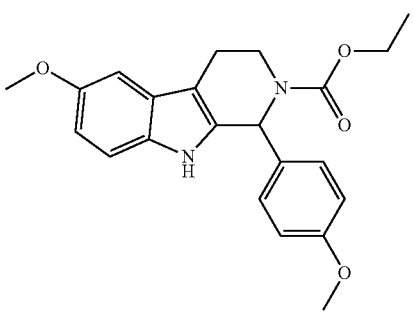
615

TABLE A-continued
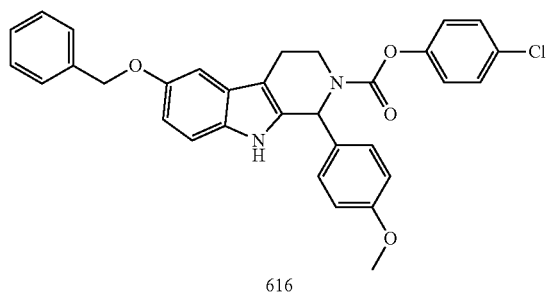
616
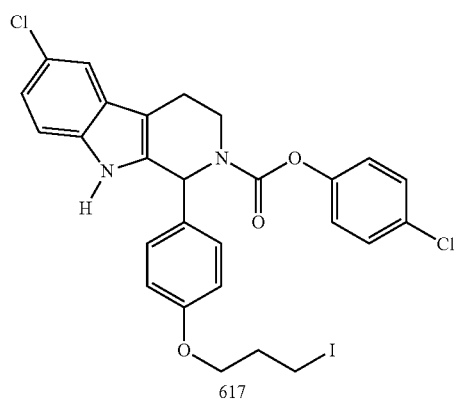
617
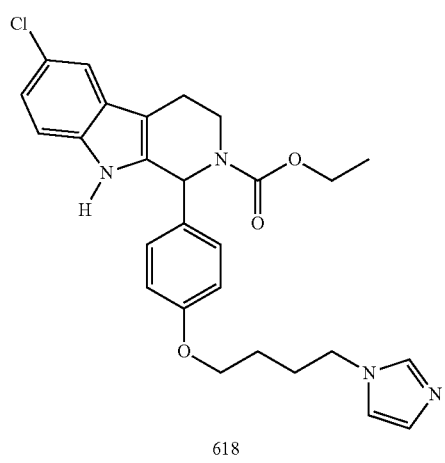
618
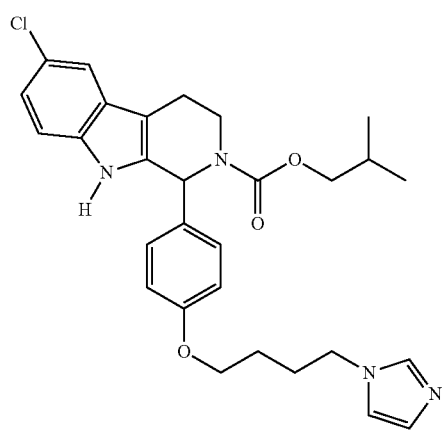
619
TABLE A-continued
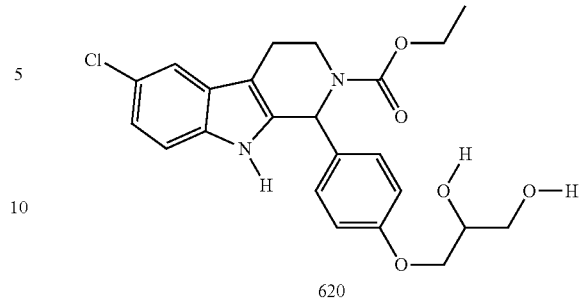
620
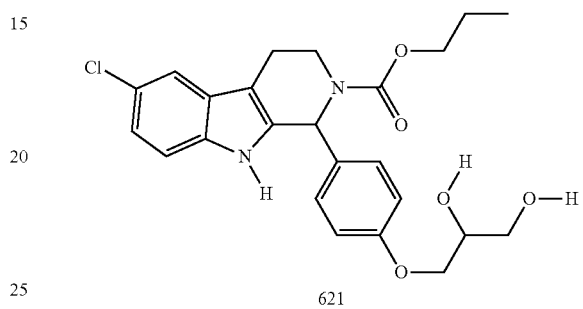
621
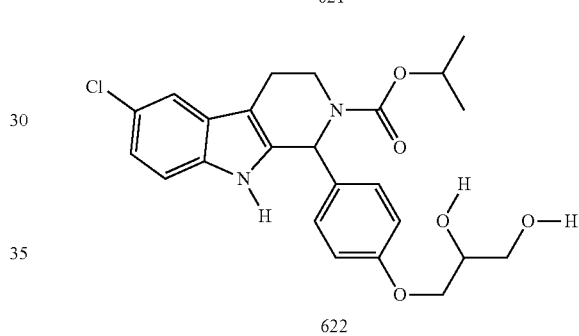
622
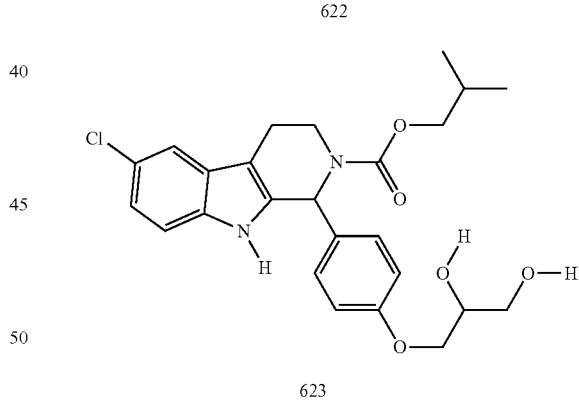
623
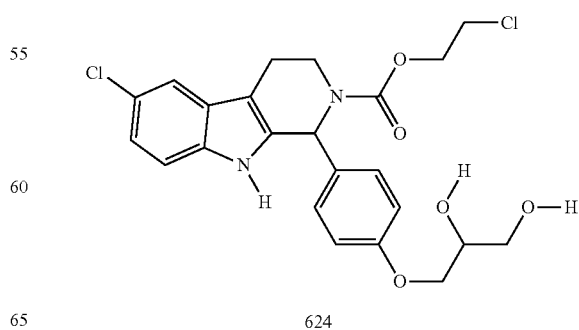
624

TABLE A-continued
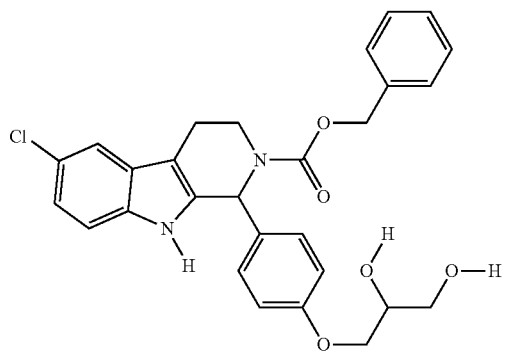
625
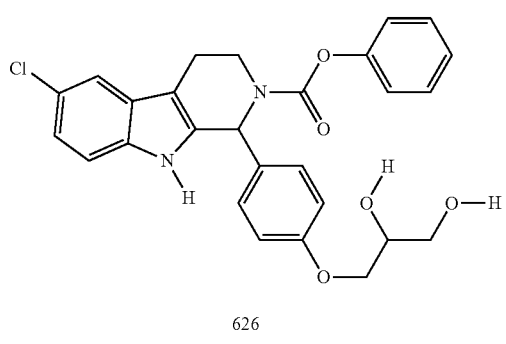
626
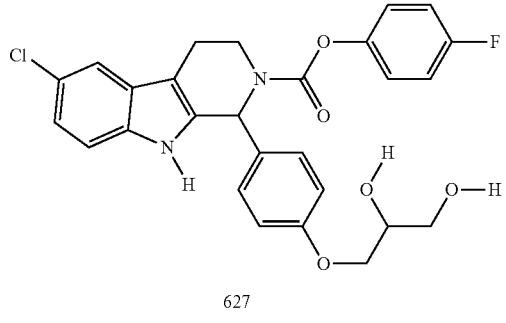
627
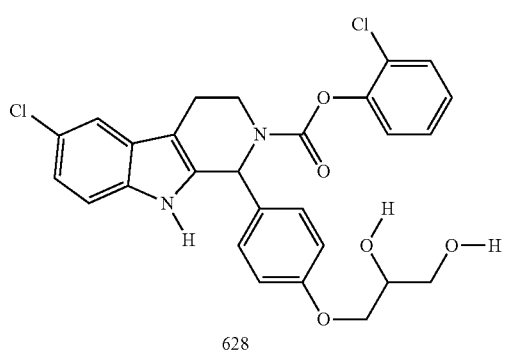
628
TABLE A-continued
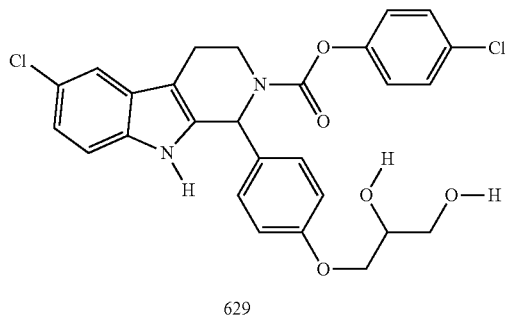
629
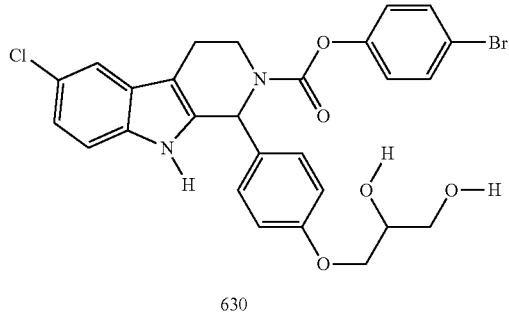
630
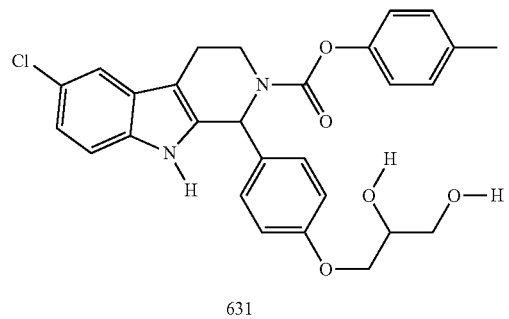
631
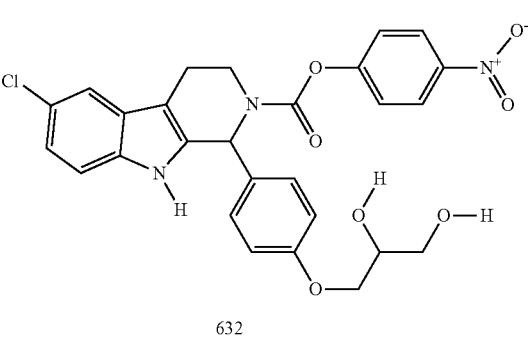
632
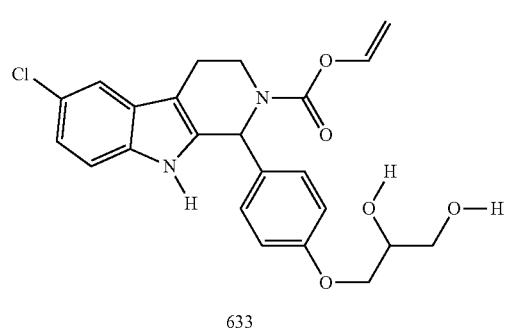
633

TABLE A-continued
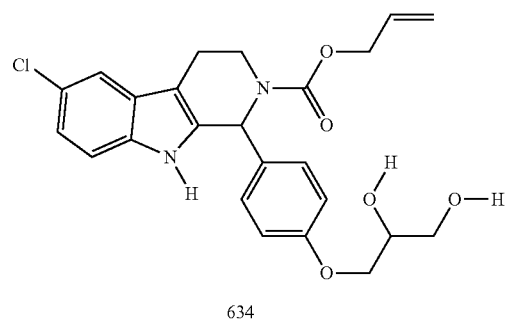
634
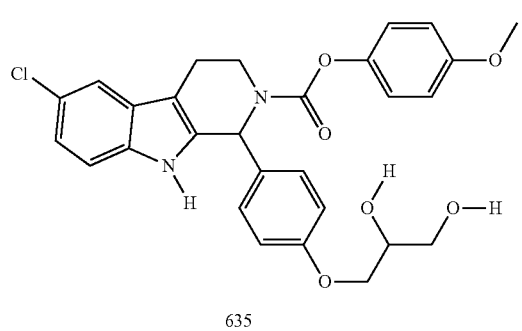
635
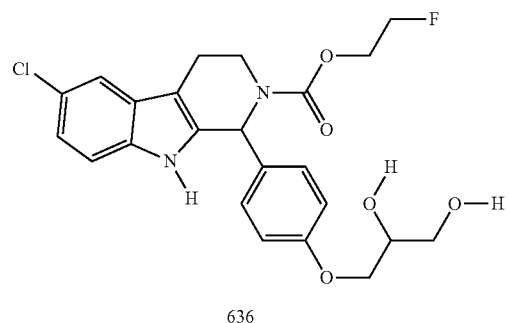
636
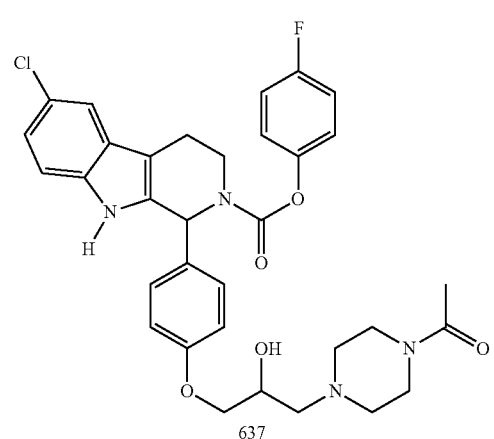
637
TABLE A-continued
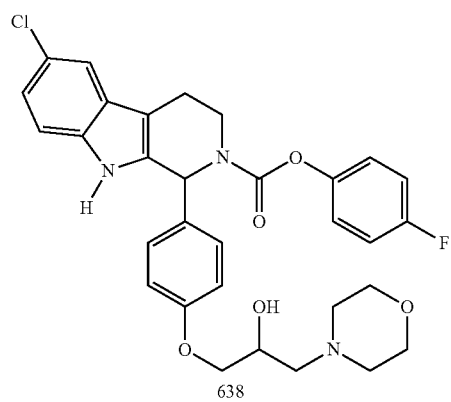
638
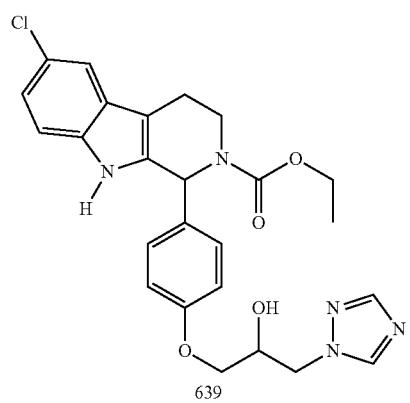
639
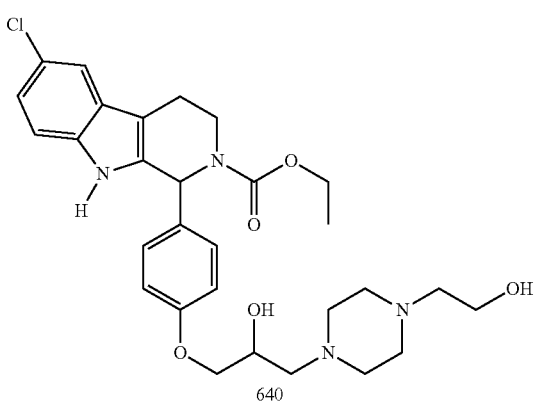
640
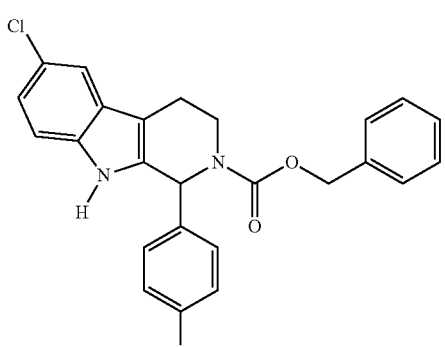
641

TABLE A-continued
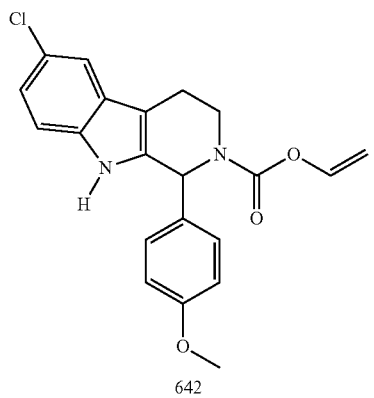
642
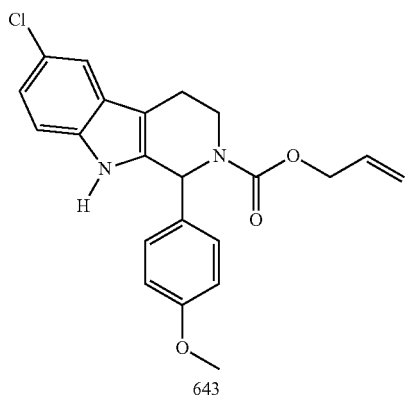
643
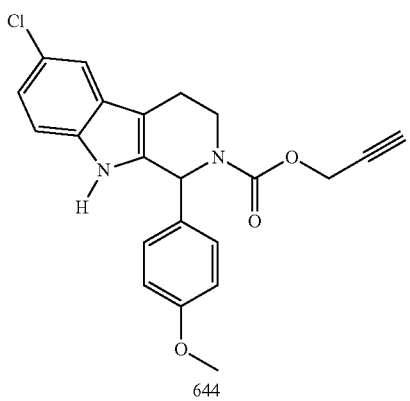
644
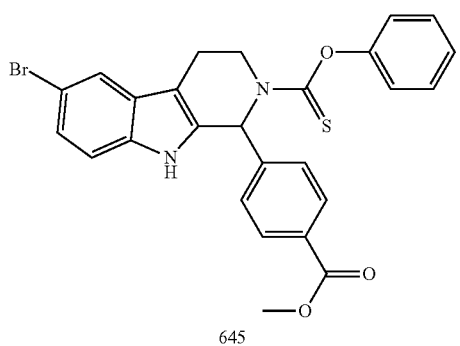
645
TABLE A-continued
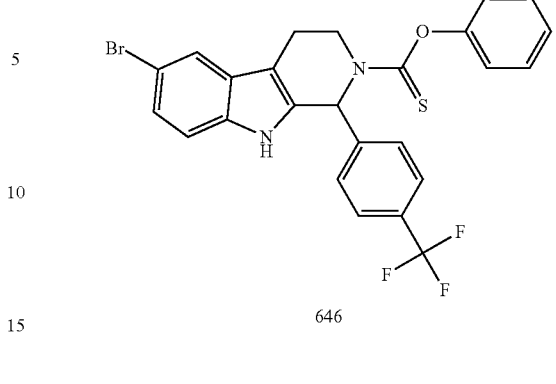
646
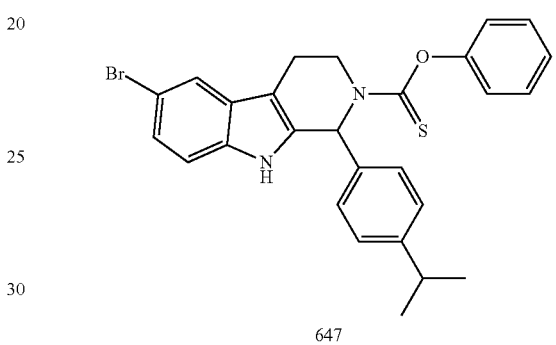
647
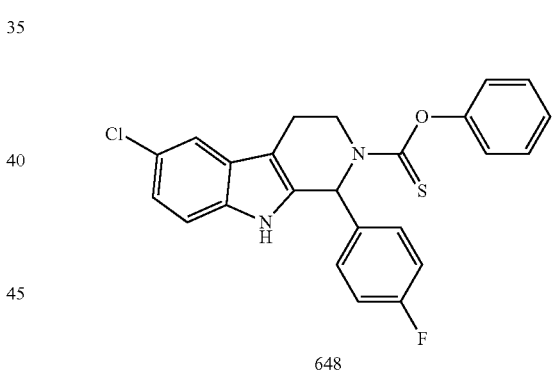
648
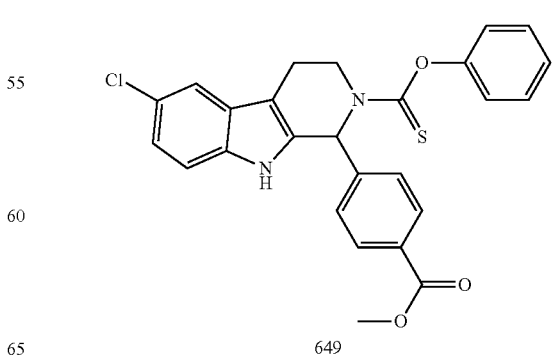
649

TABLE A-continued
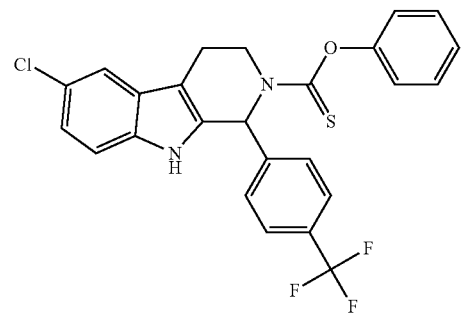
650
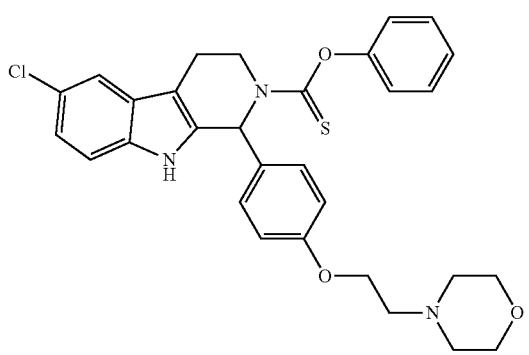
651
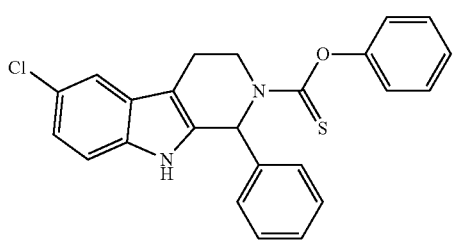
652
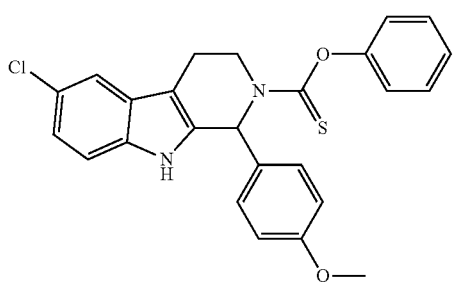
653
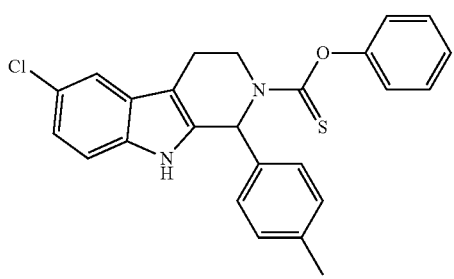
654
TABLE A-continued
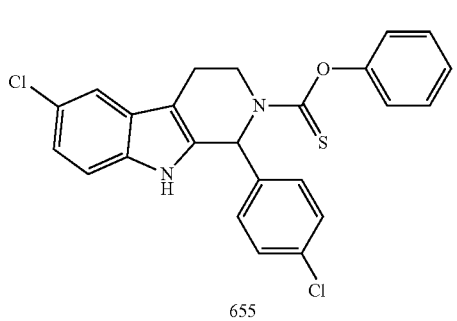
655
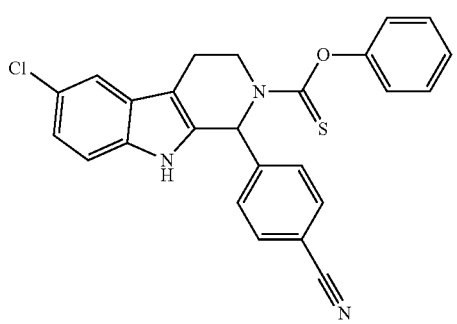
656
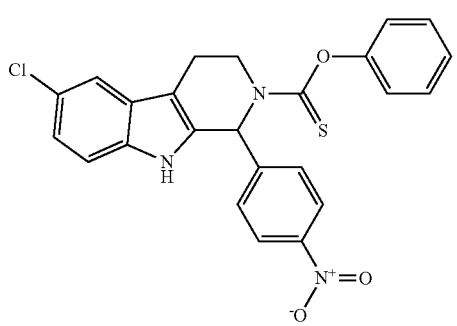
657
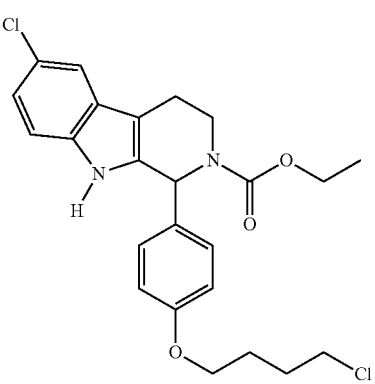
658

TABLE A-continued
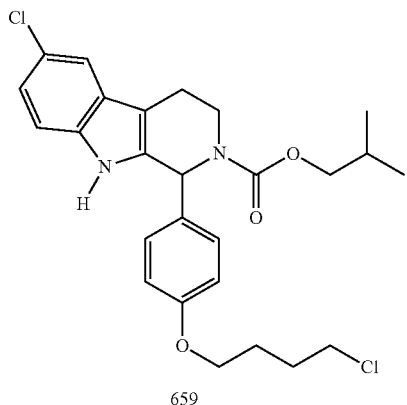
659
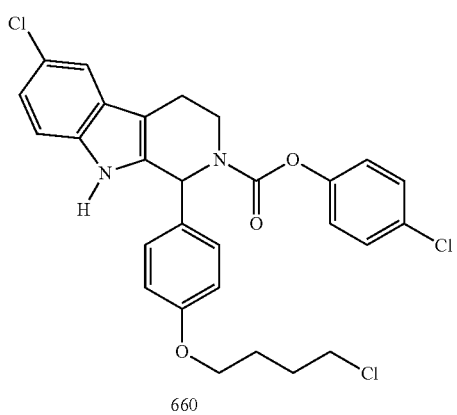
660
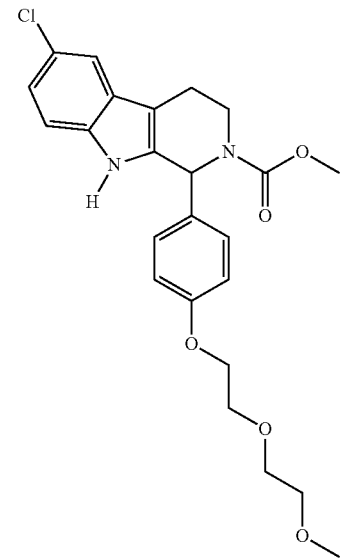
661
TABLE A-continued
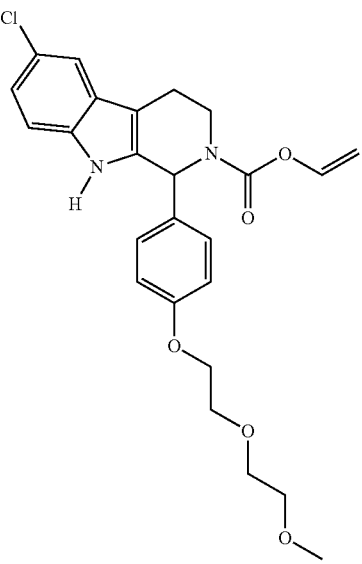
662
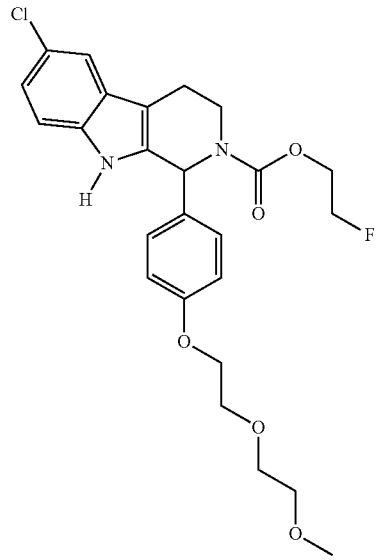
663

TABLE A-continued
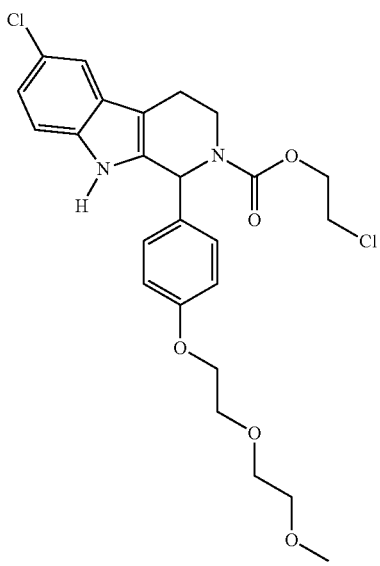
664
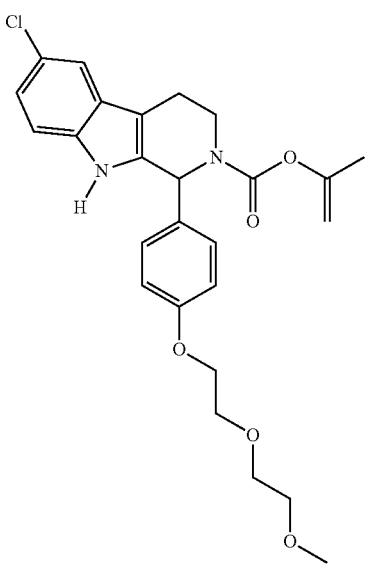
666
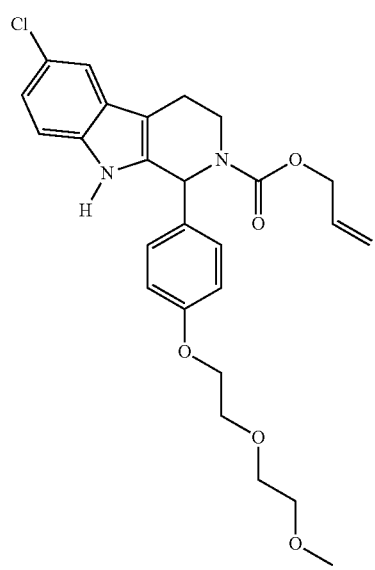
665
667

TABLE A-continued
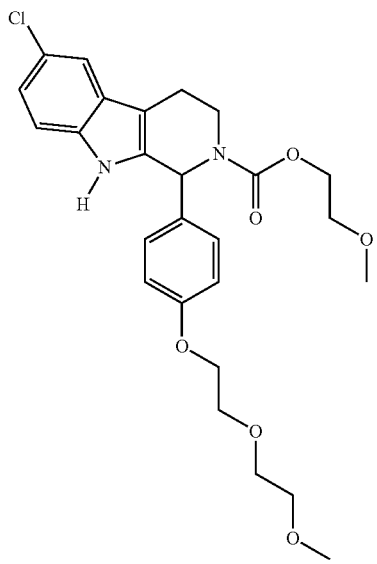
668
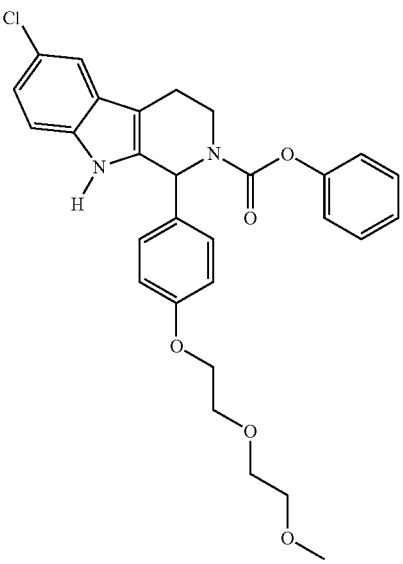
670
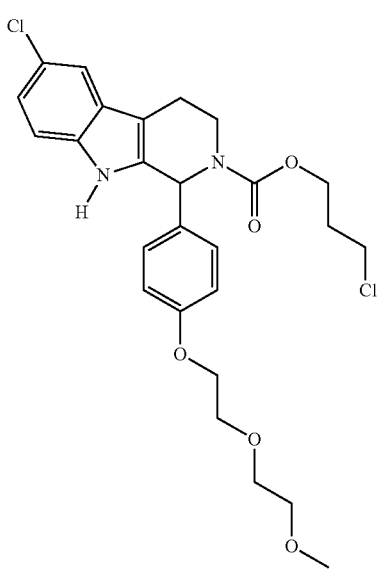
669
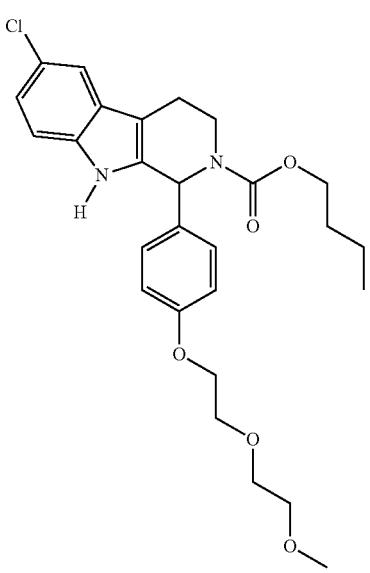
671

TABLE A-continued
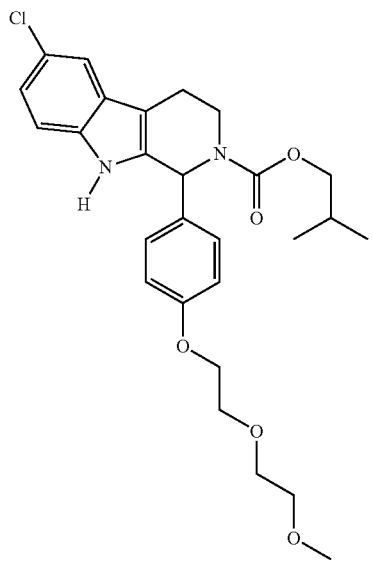
672
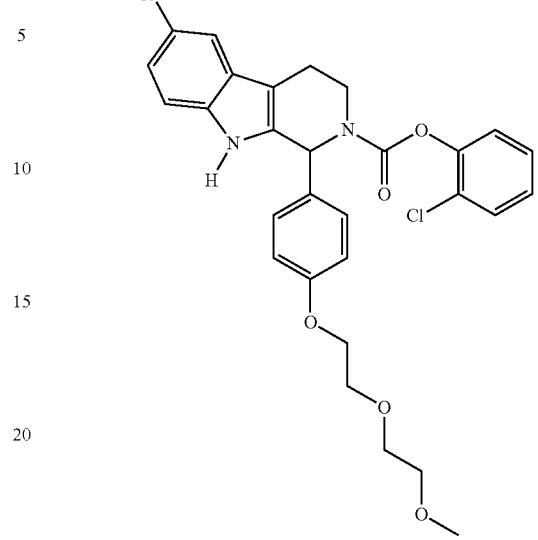
674
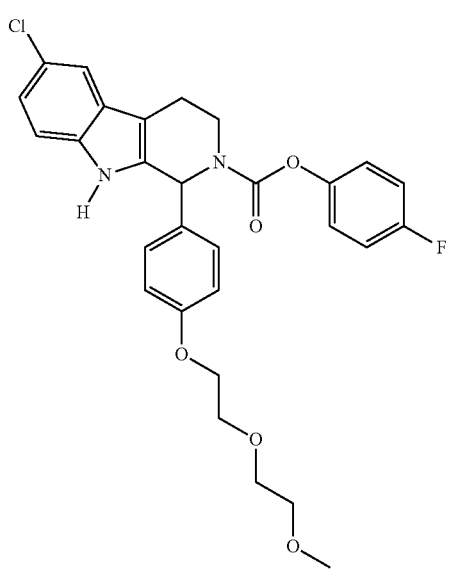
673
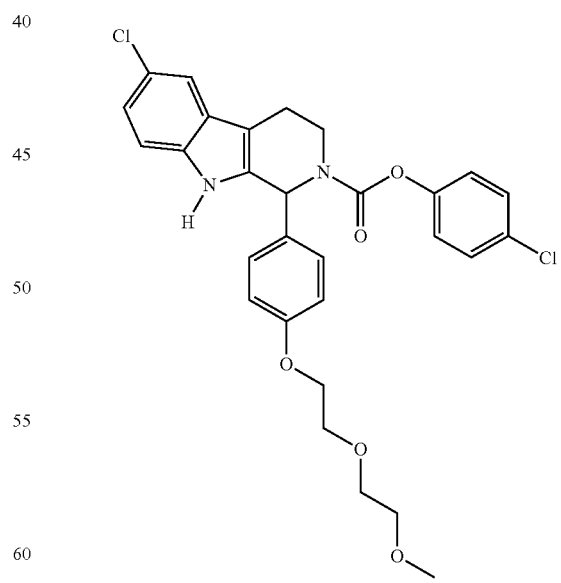
675

TABLE A-continued
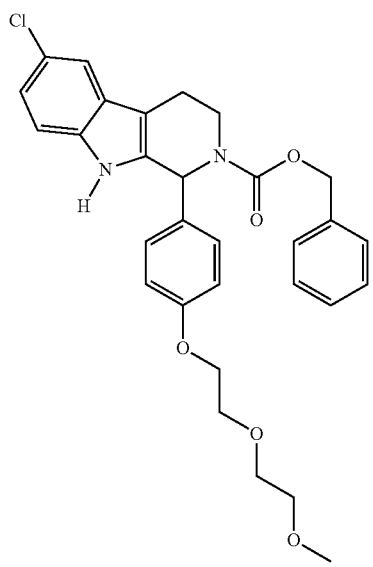
676
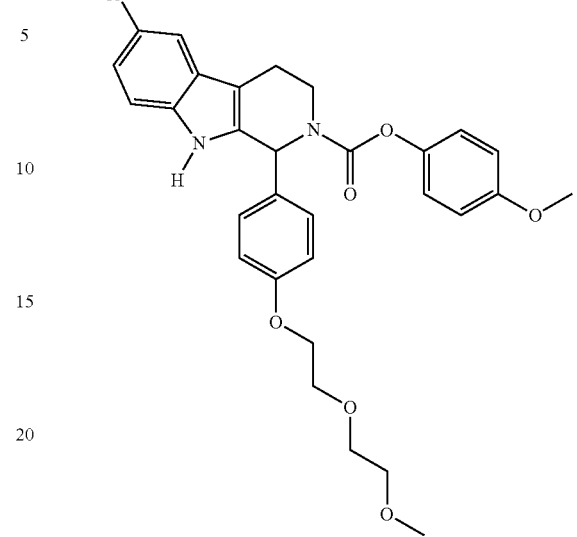
678
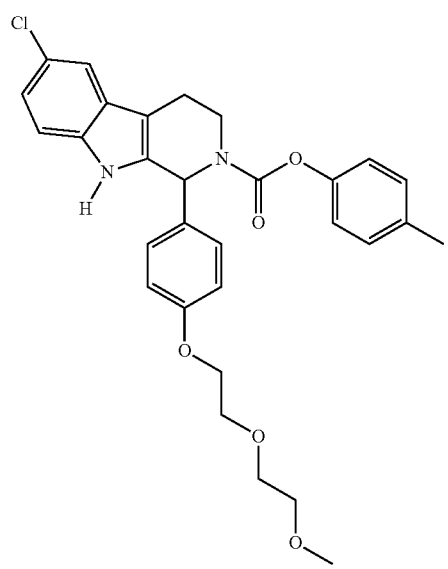
677
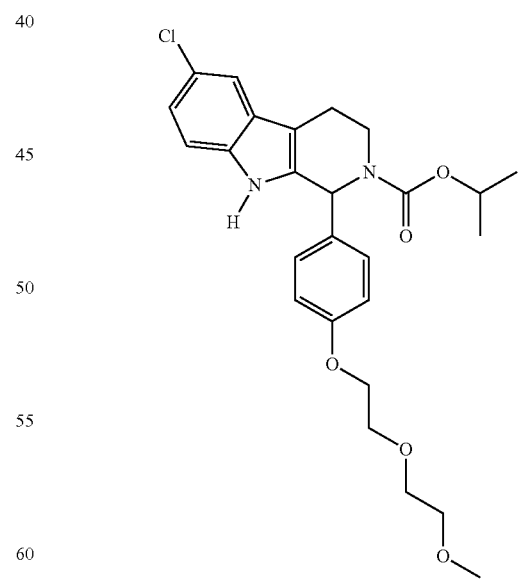
679

TABLE A-continued
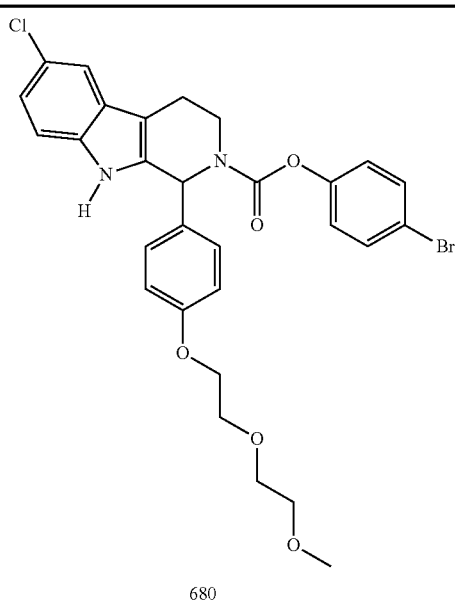
680
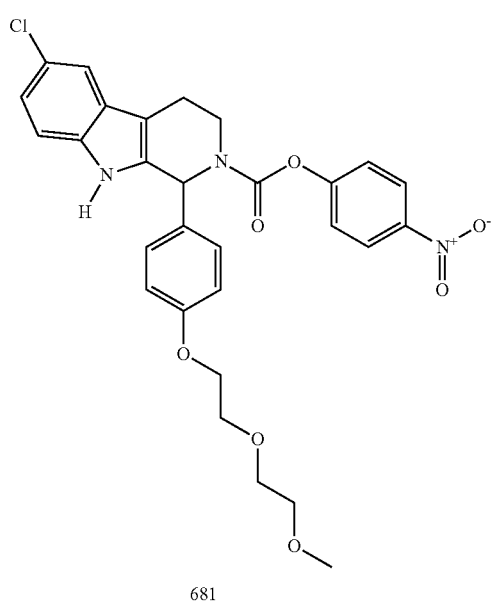
681
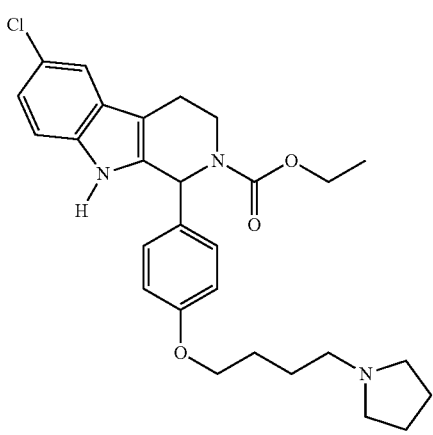
682
TABLE A-continued
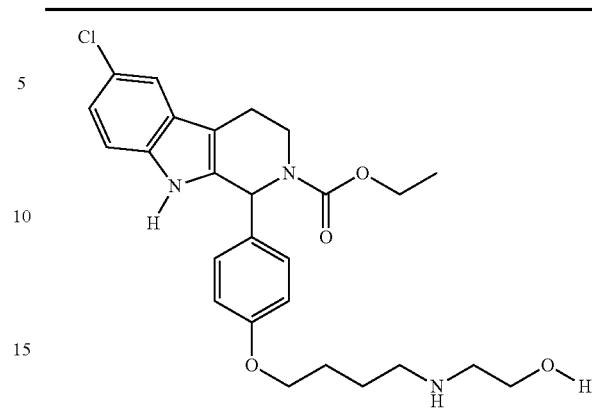
683
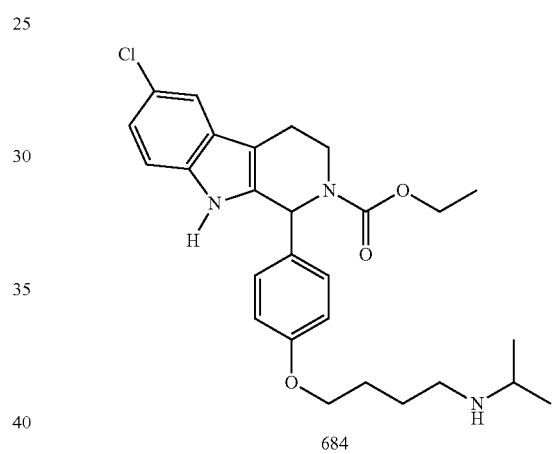
684
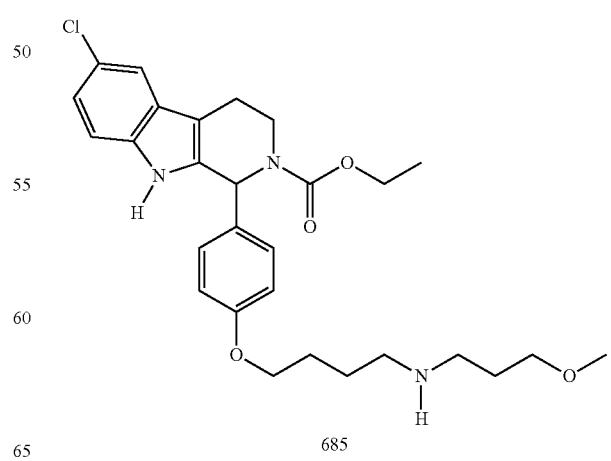
685

TABLE A-continued
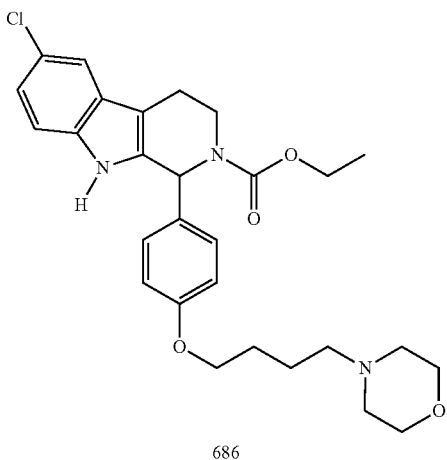
686
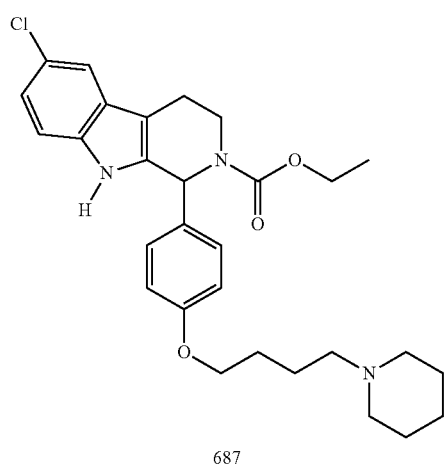
687
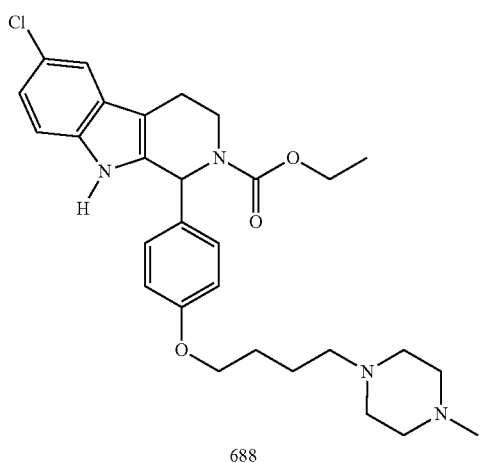
688
TABLE A-continued
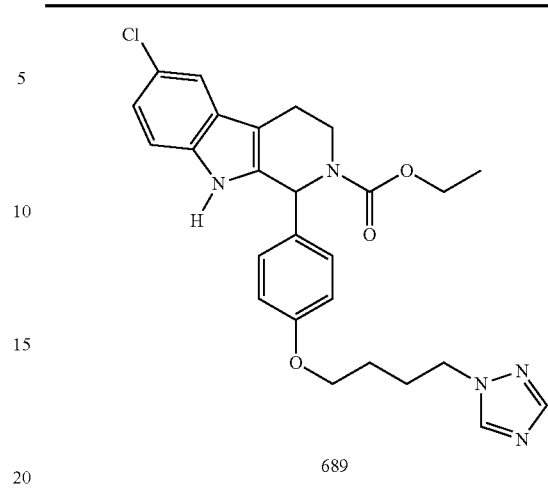
689
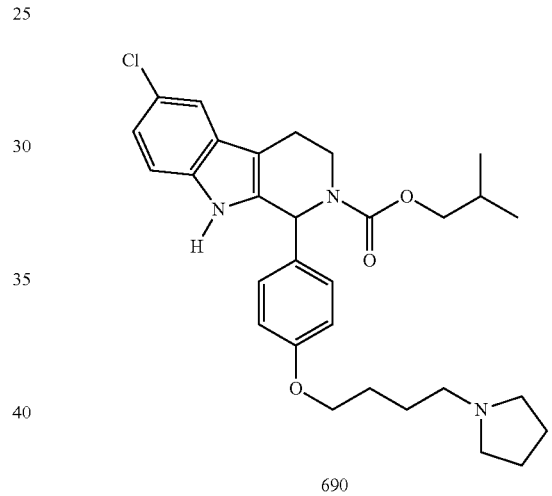
690
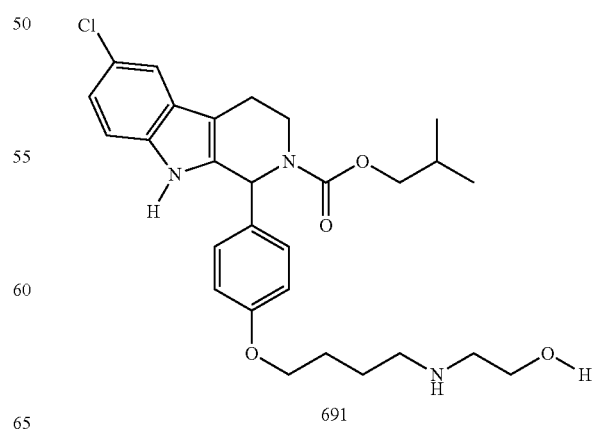
691

TABLE A-continued
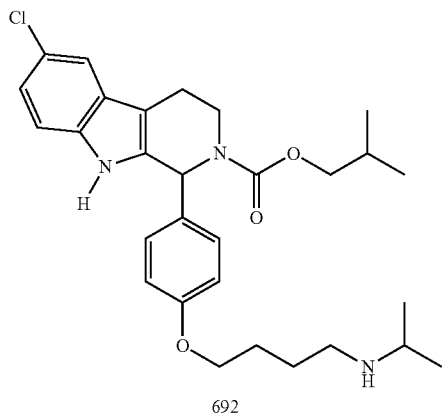
692
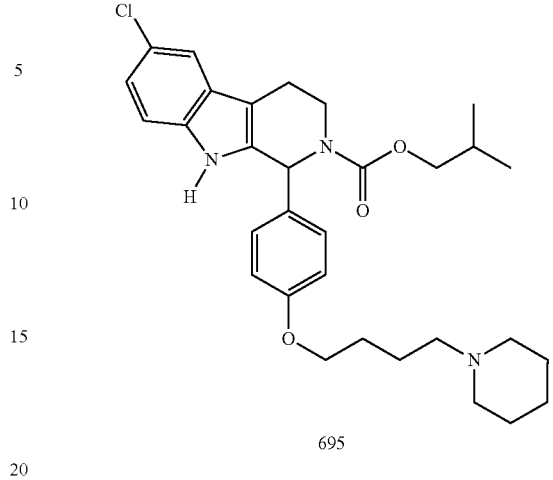
695
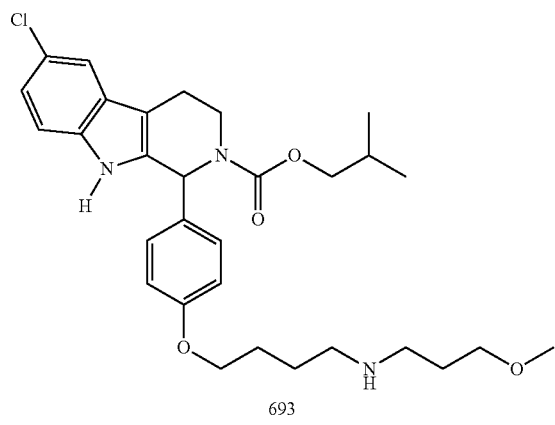
693
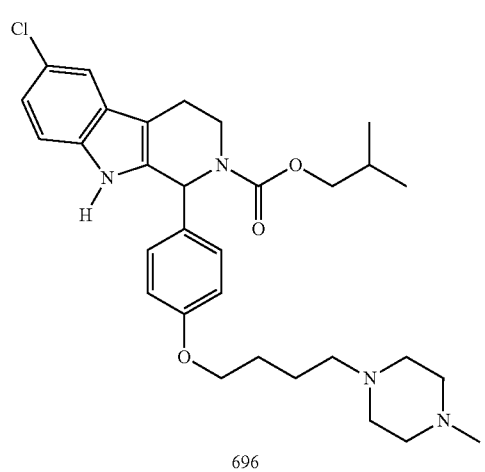
696
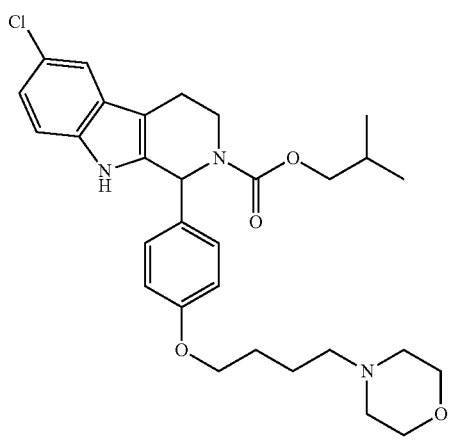
694
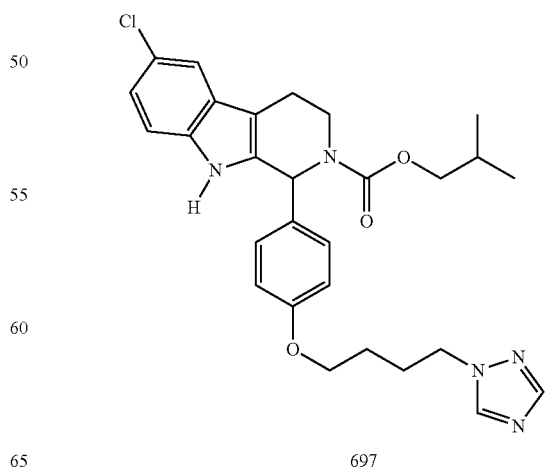
697

TABLE A-continued
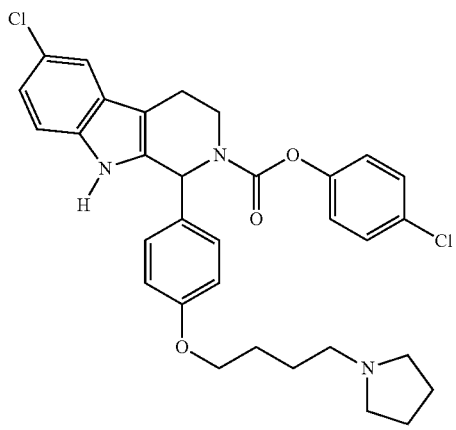
698
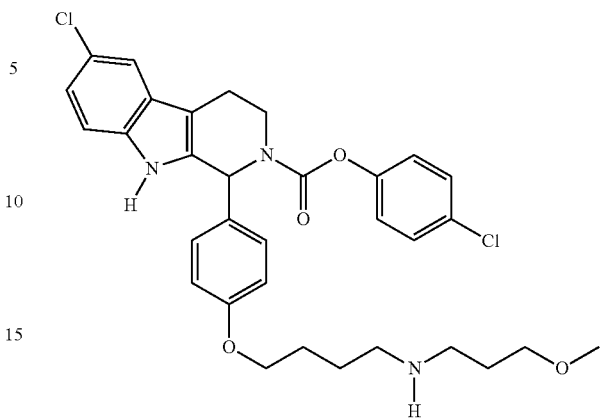
701
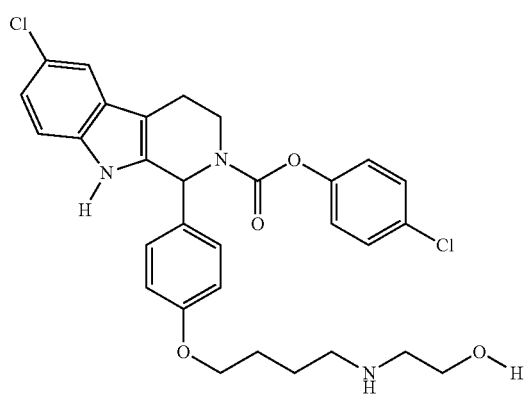
699
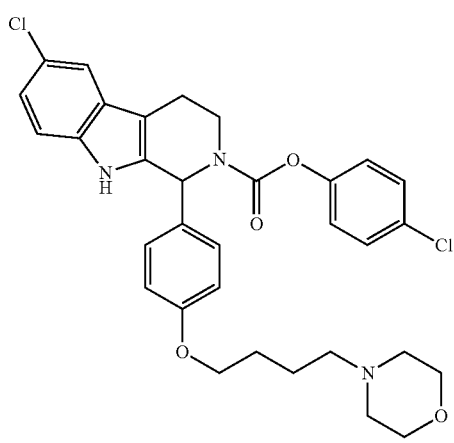
702
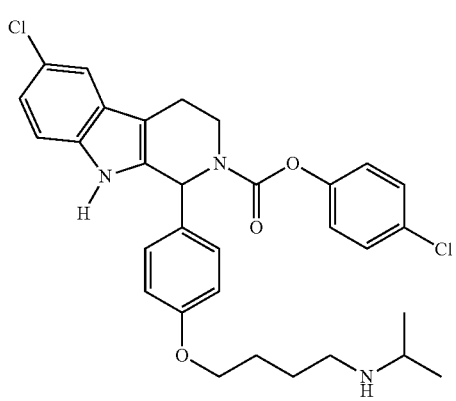
700
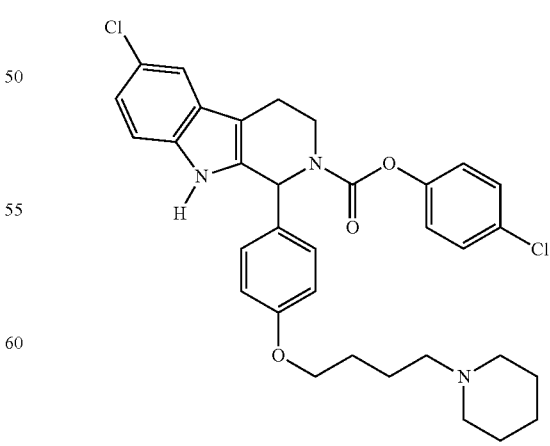
703

TABLE A-continued
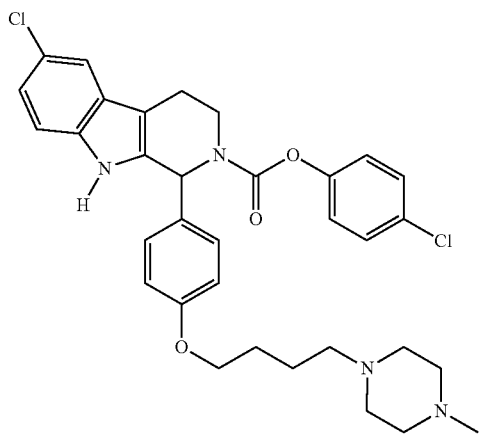
704
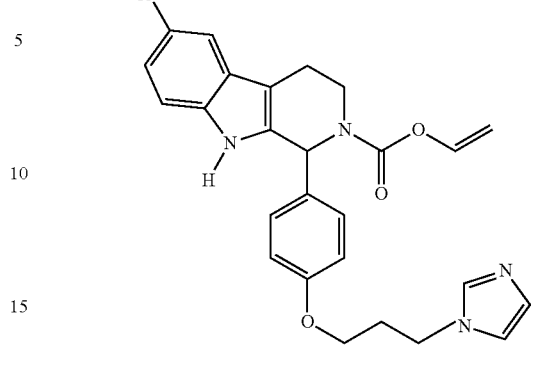
707
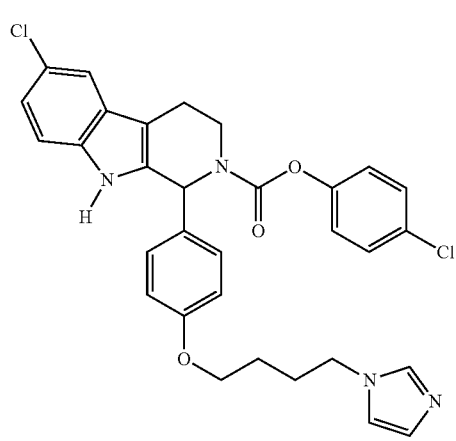
705
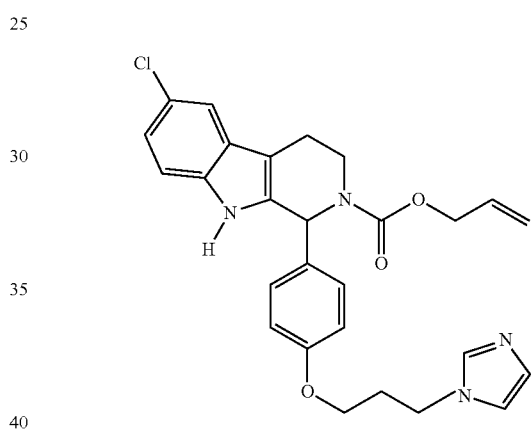
708
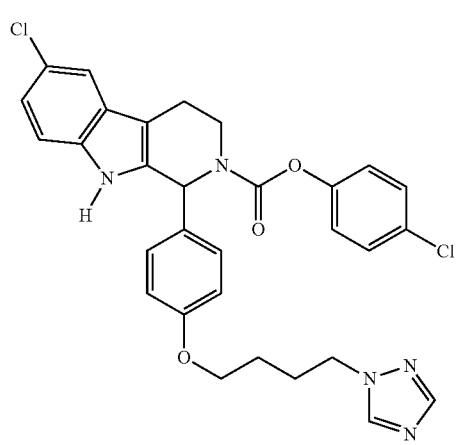
706
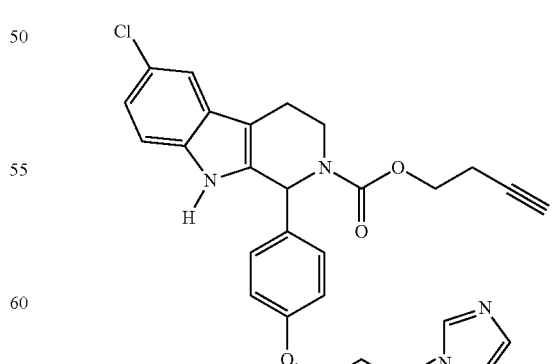
709

TABLE A-continued
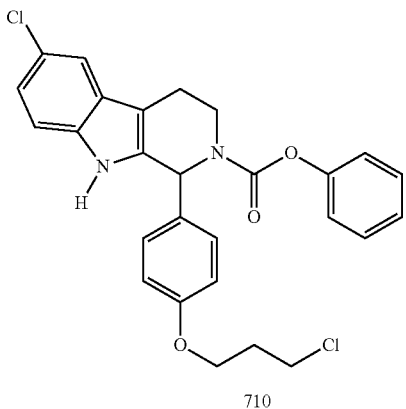
710
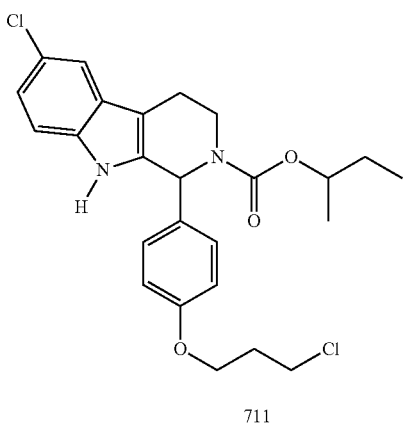
711
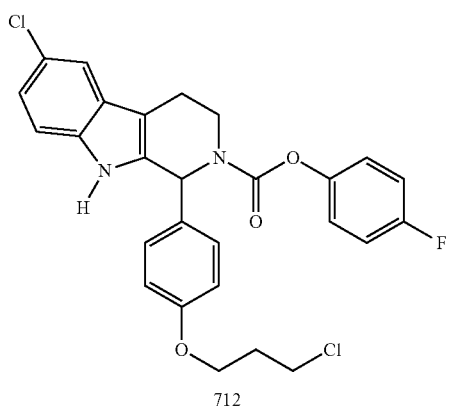
712
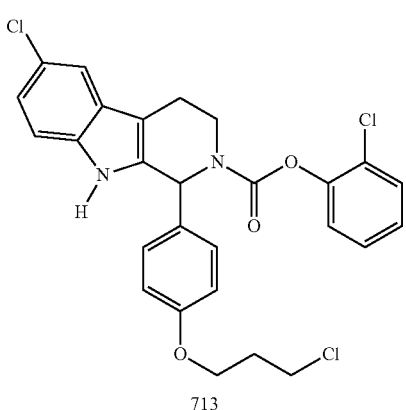
713
TABLE A-continued
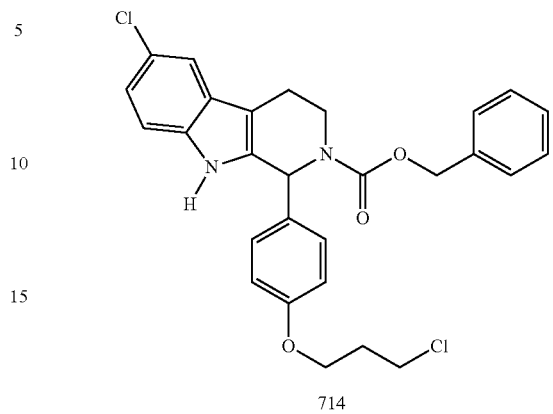
714
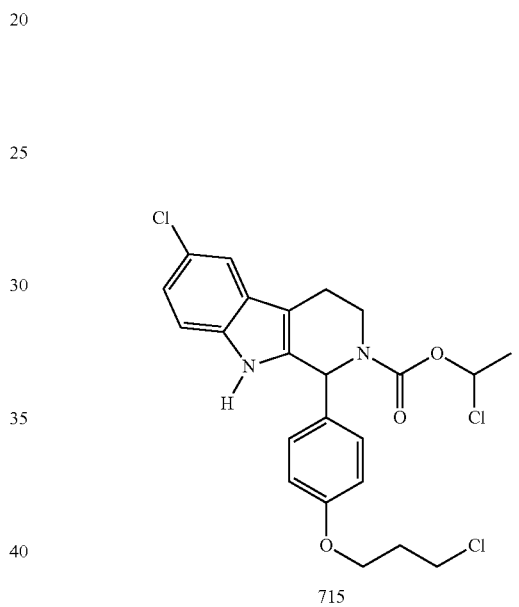
715
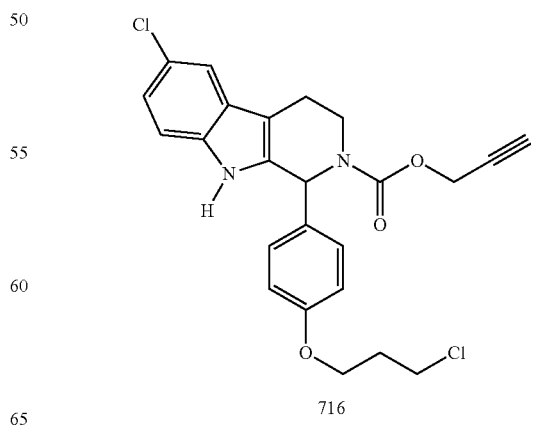
716

TABLE A-continued
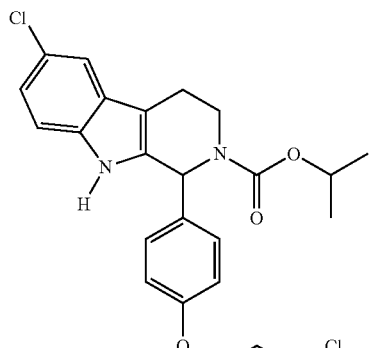
717
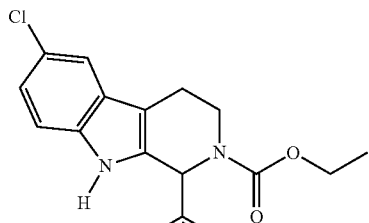
720
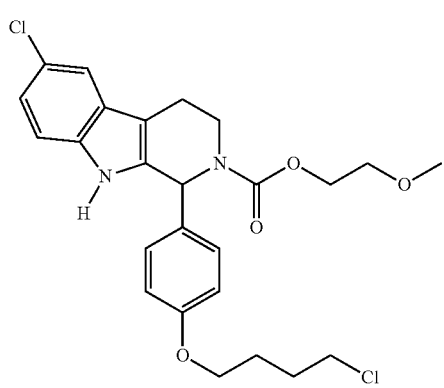
718
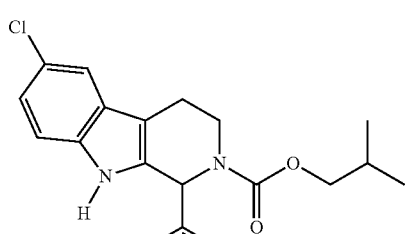
721
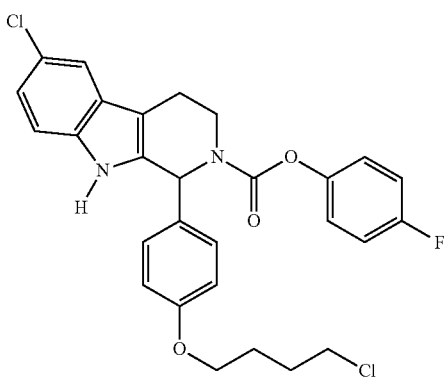
719
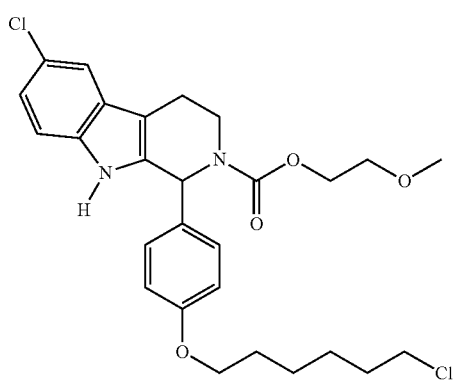
722

TABLE A-continued
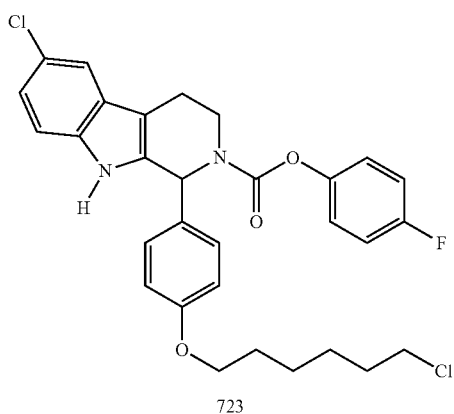
723
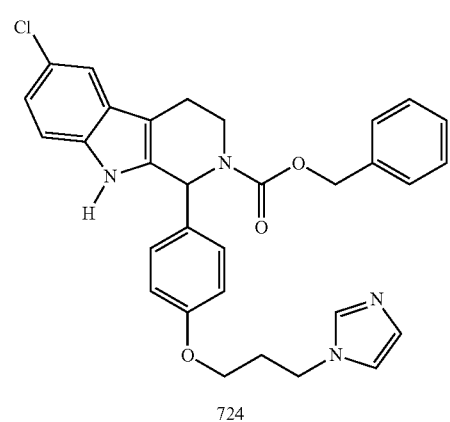
724
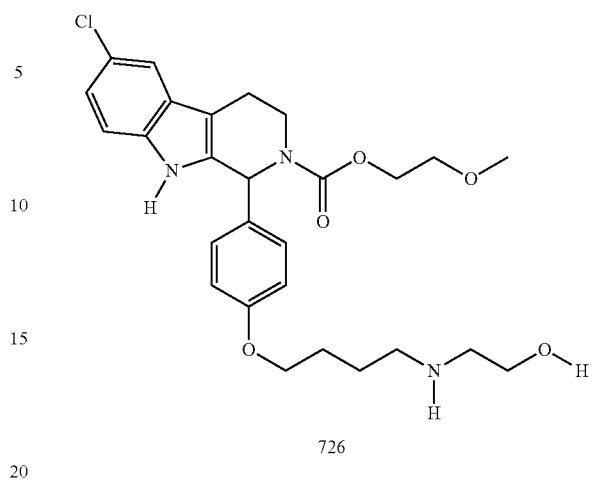
726
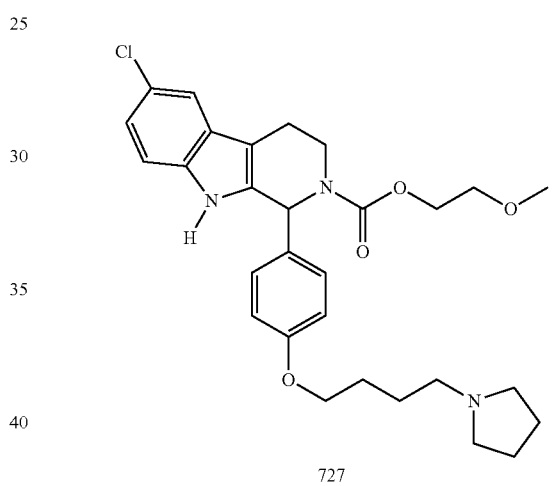
727
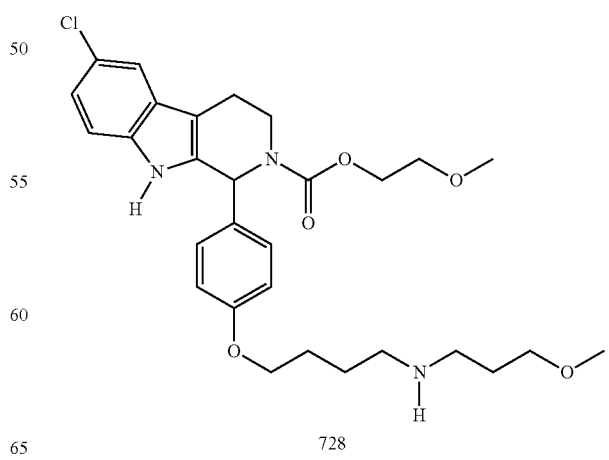
728

TABLE A-continued
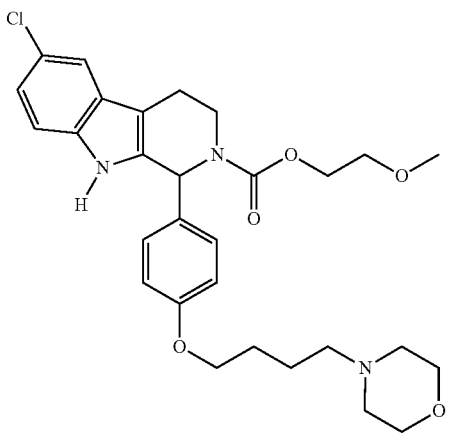
729
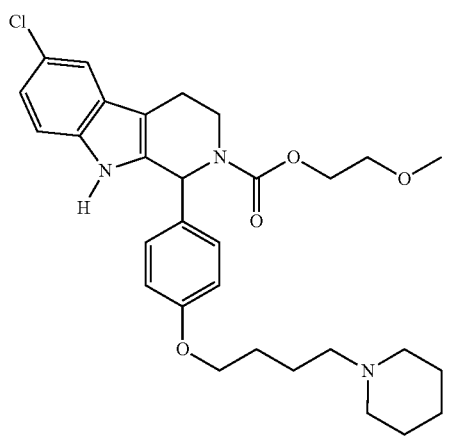
730
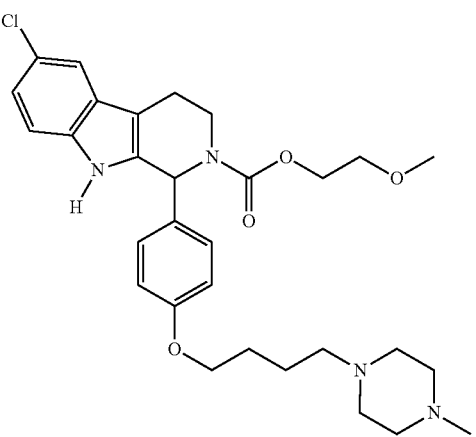
731
TABLE A-continued
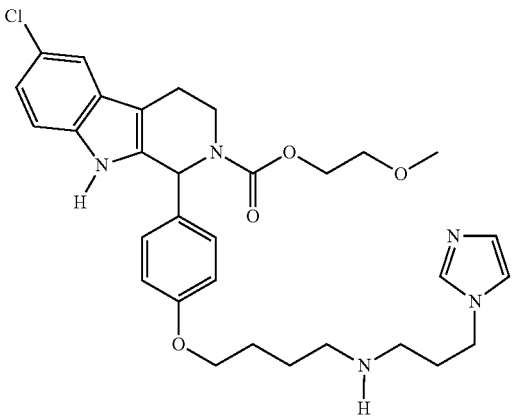
732
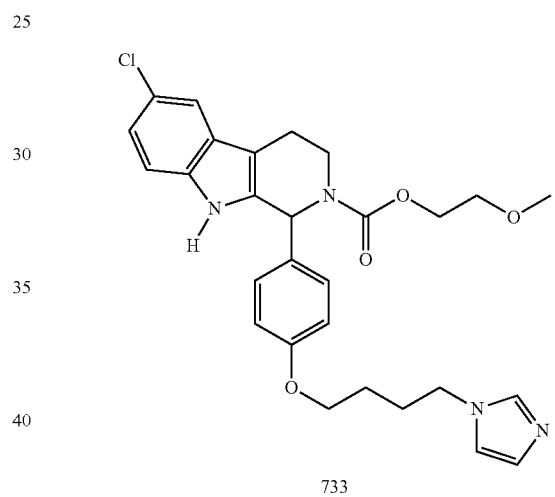
733
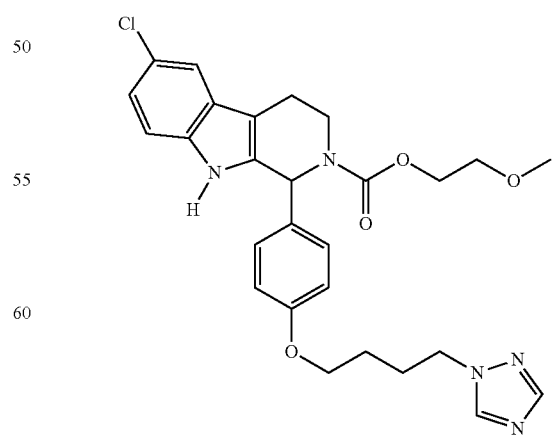
734

TABLE A-continued
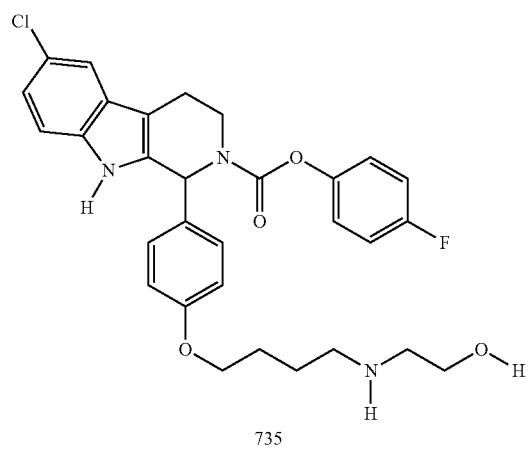
735
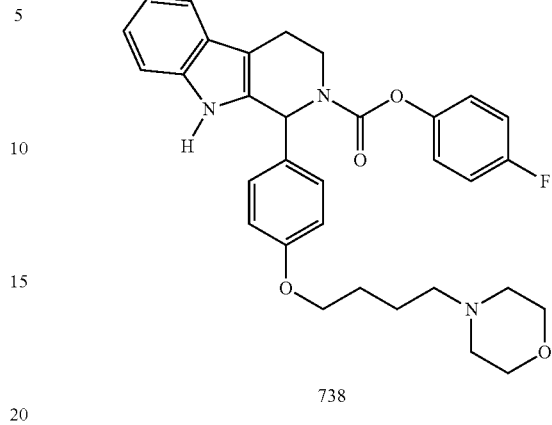
738
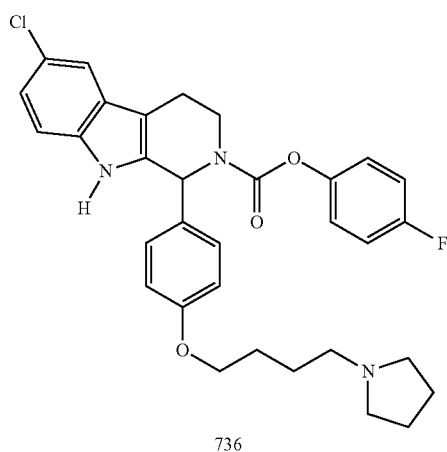
736
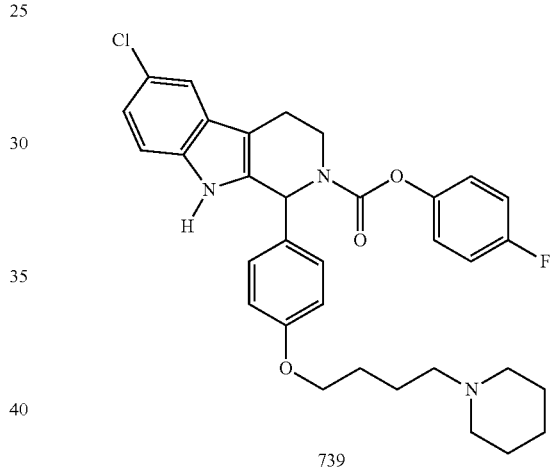
739
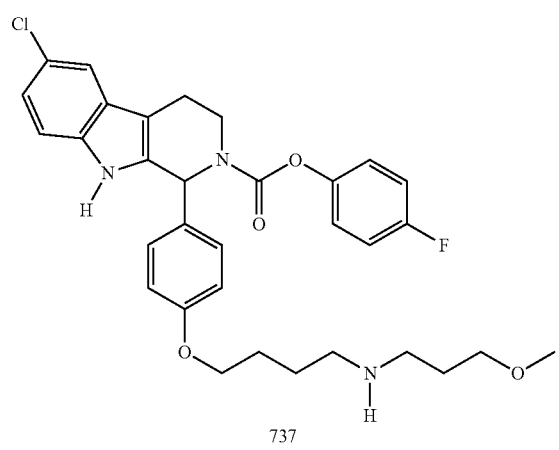
737
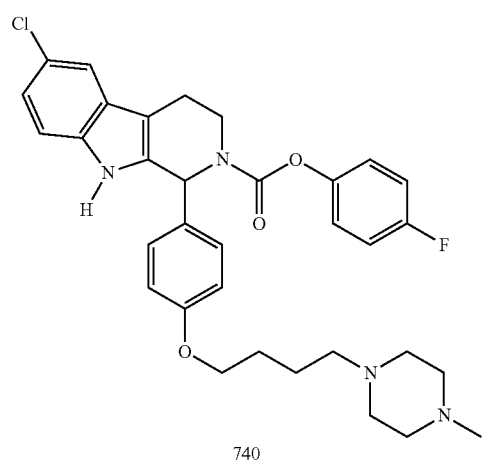
740

TABLE A-continued
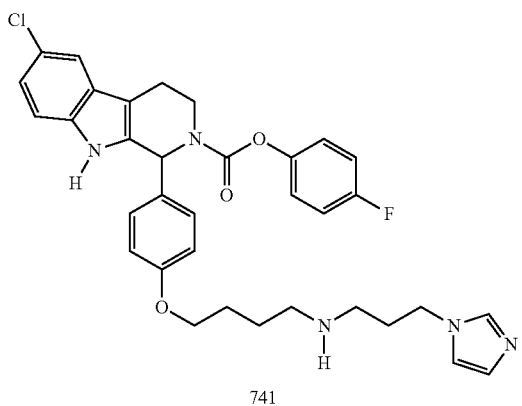
741
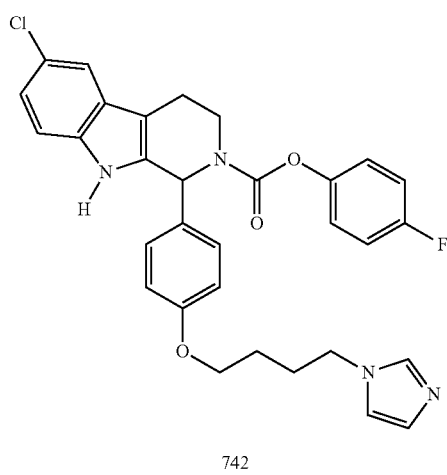
742
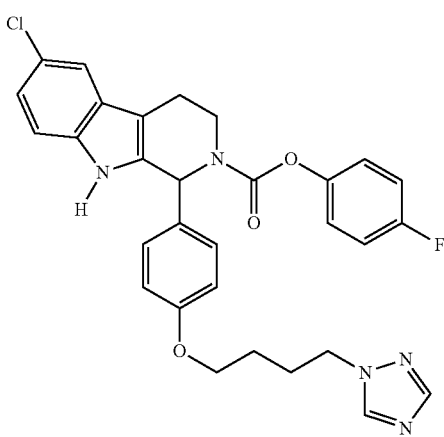
743
TABLE A-continued
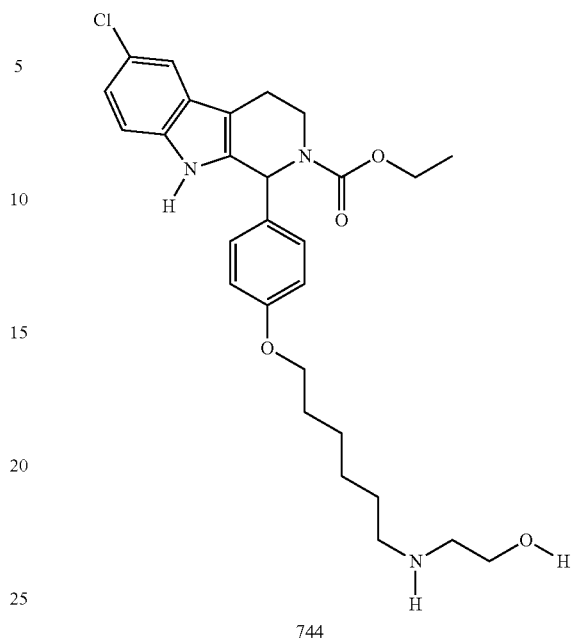
744
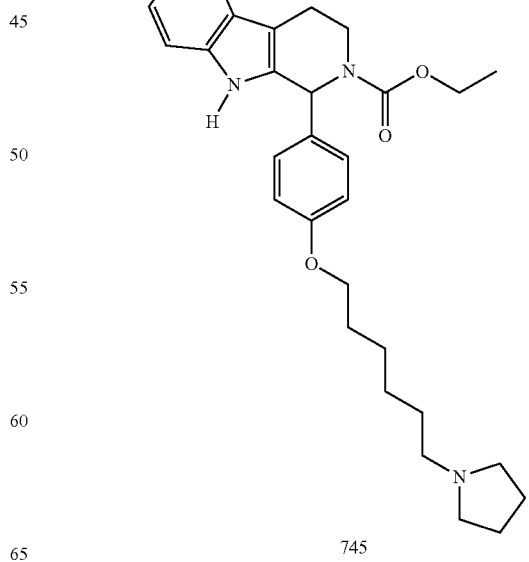
745

TABLE A-continued
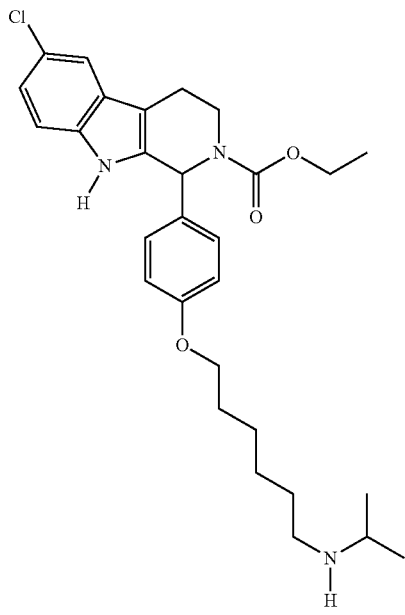
746
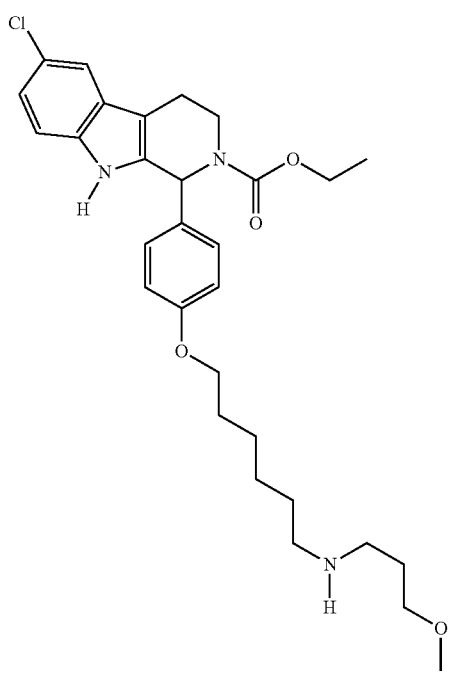
747
TABLE A-continued
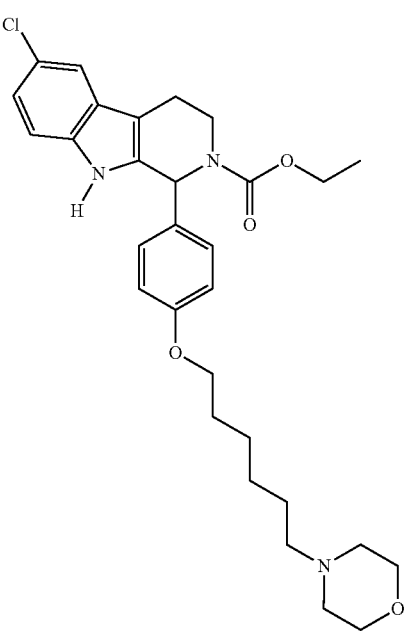
748
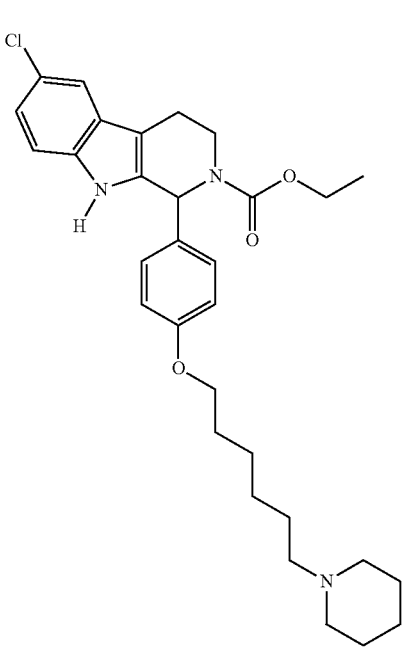
749

TABLE A-continued
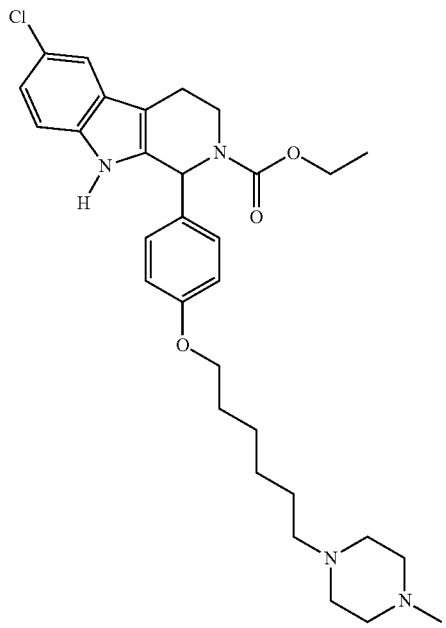
750
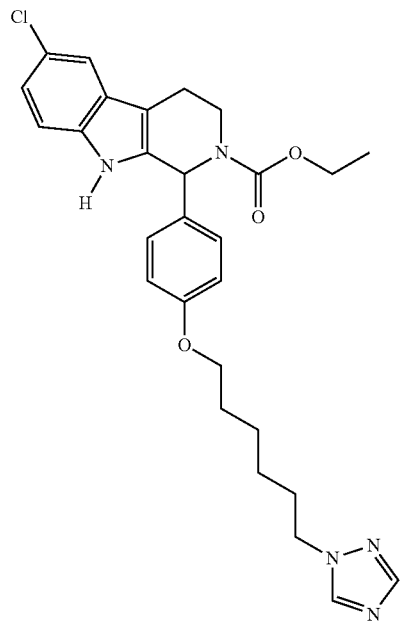
752
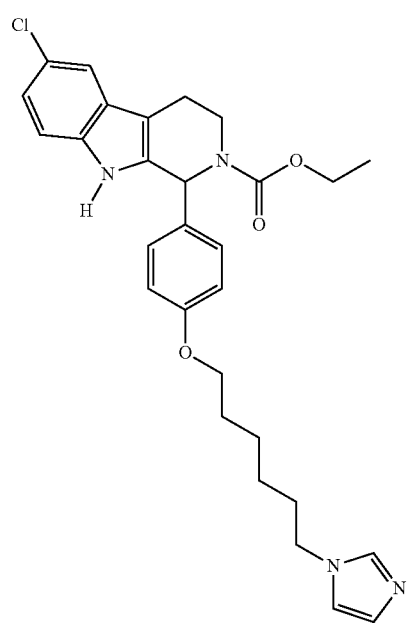
751
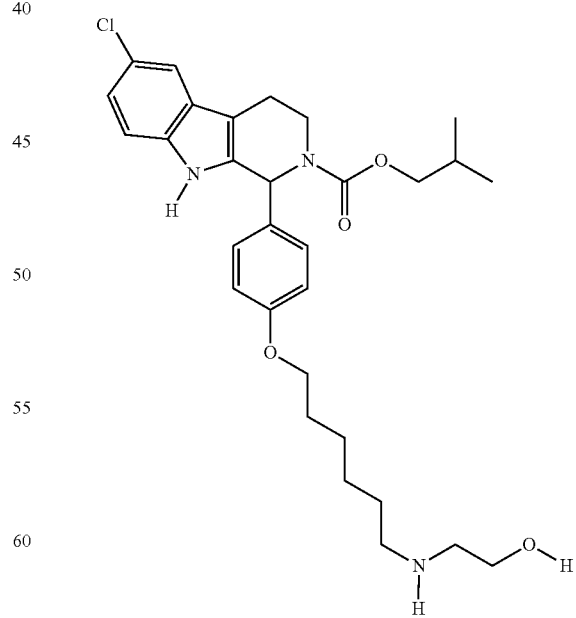
753

TABLE A-continued
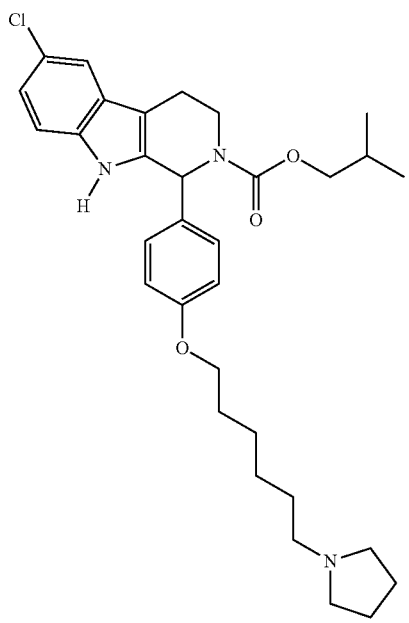
754
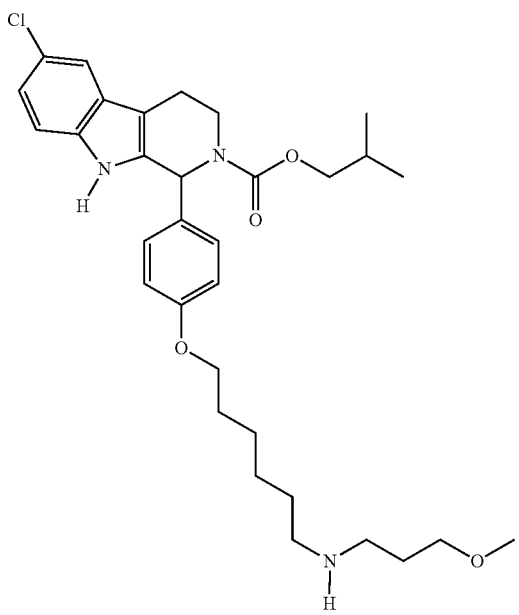
756
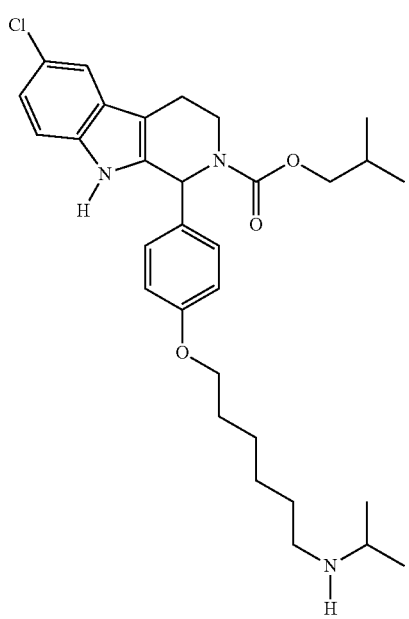
755
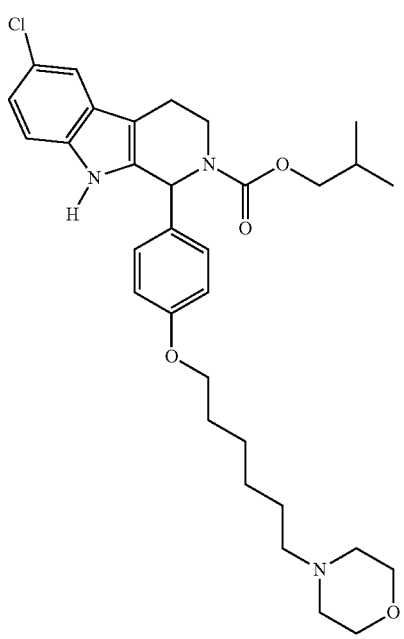
757

TABLE A-continued
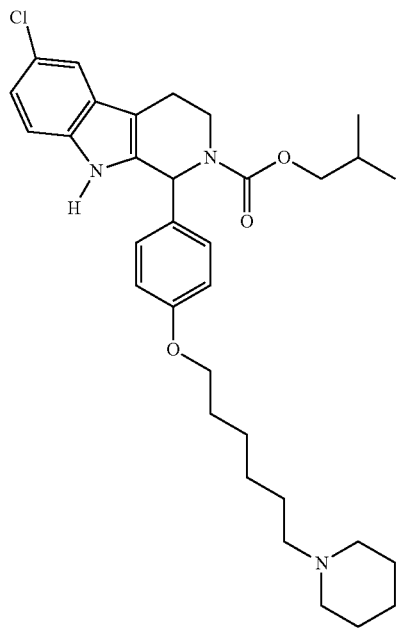
758
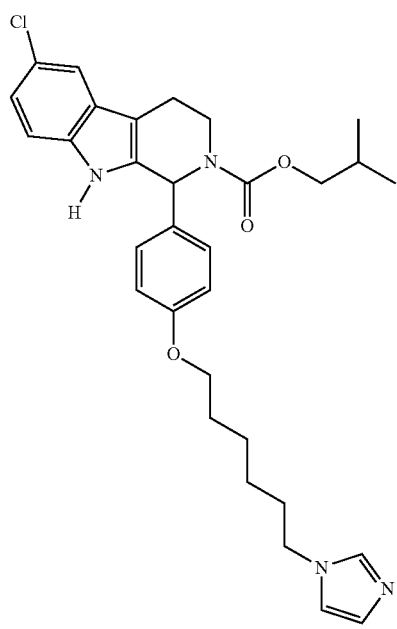
760
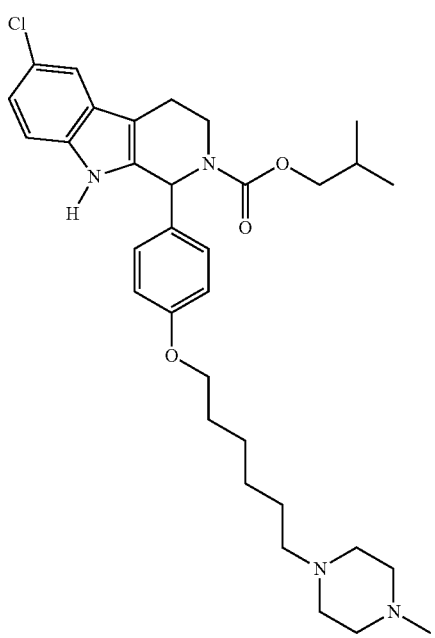
759
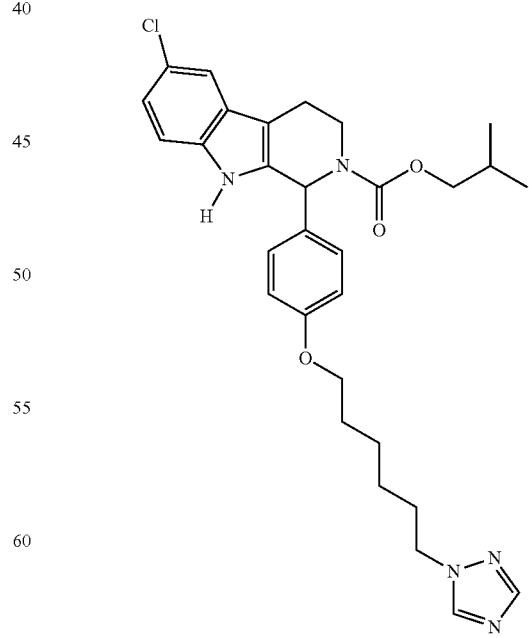
761

TABLE A-continued
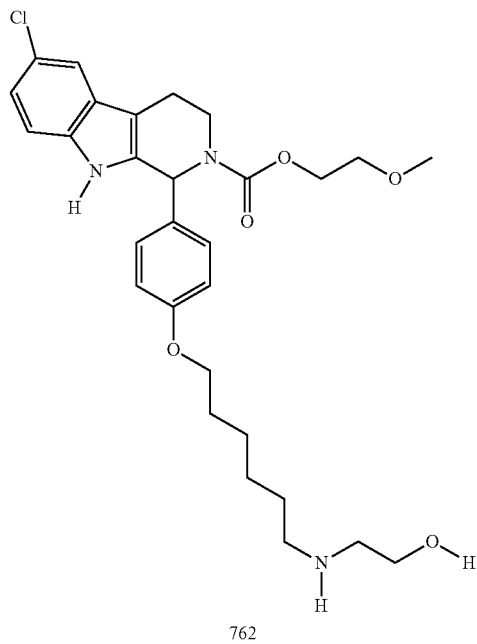
762
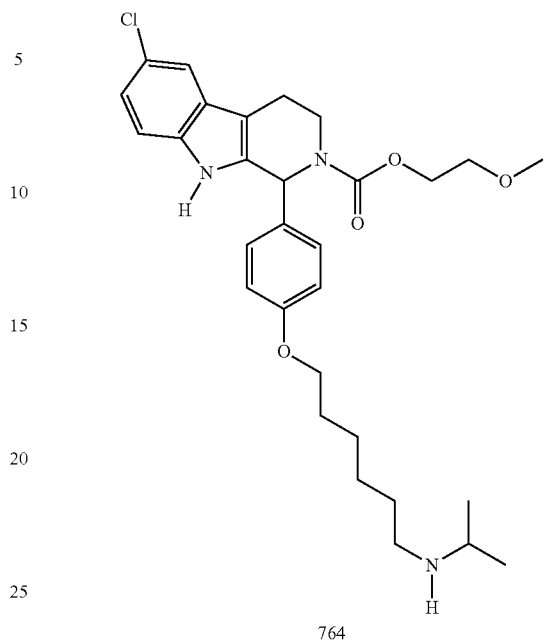
764
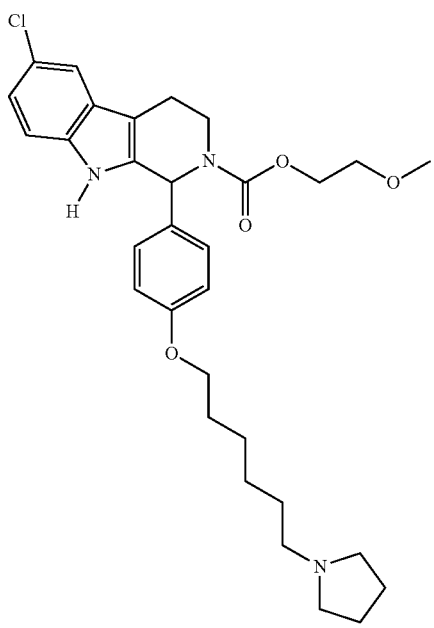
763
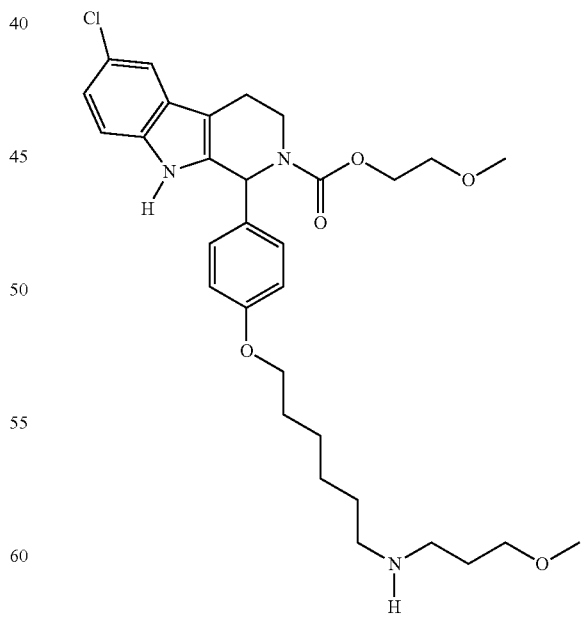
765

TABLE A-continued
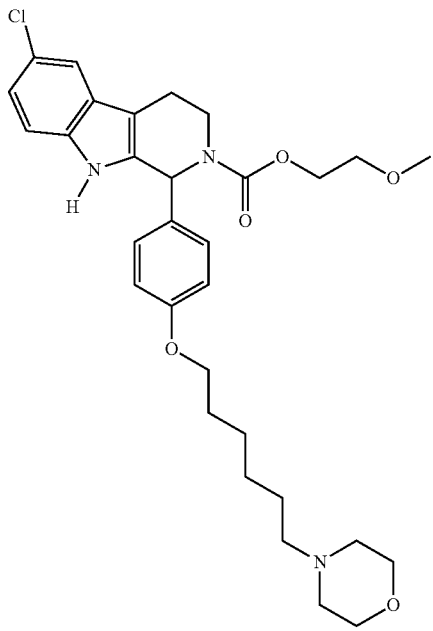
766
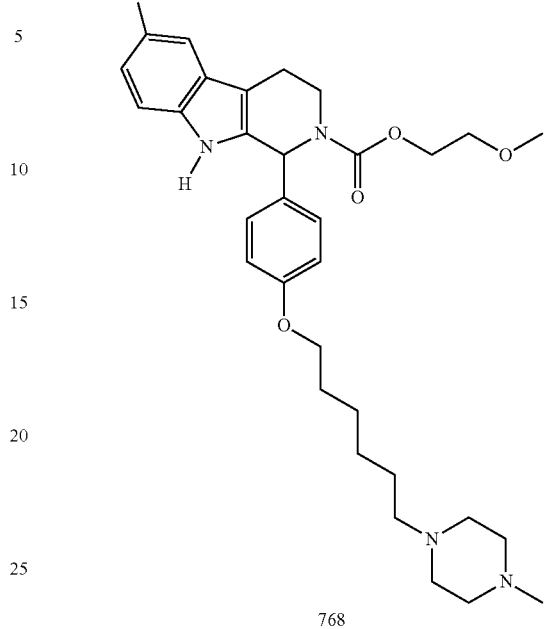
768
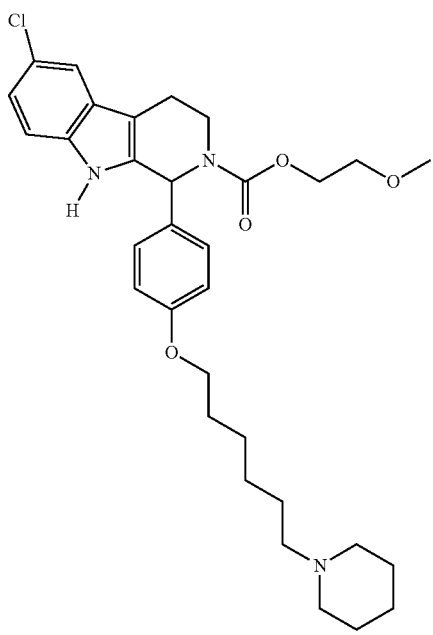
767
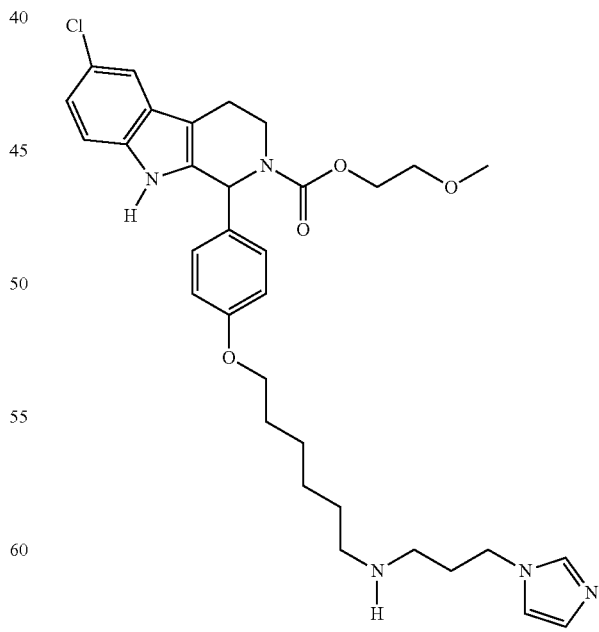
769

TABLE A-continued
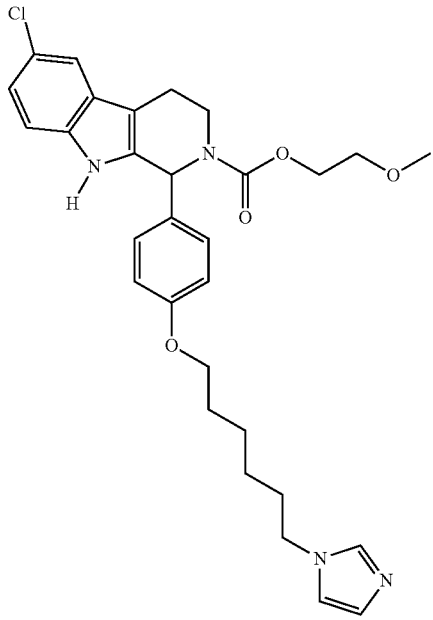
770
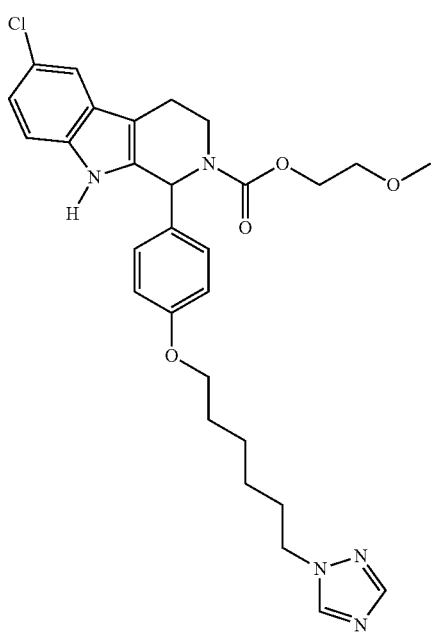
771
TABLE A-continued
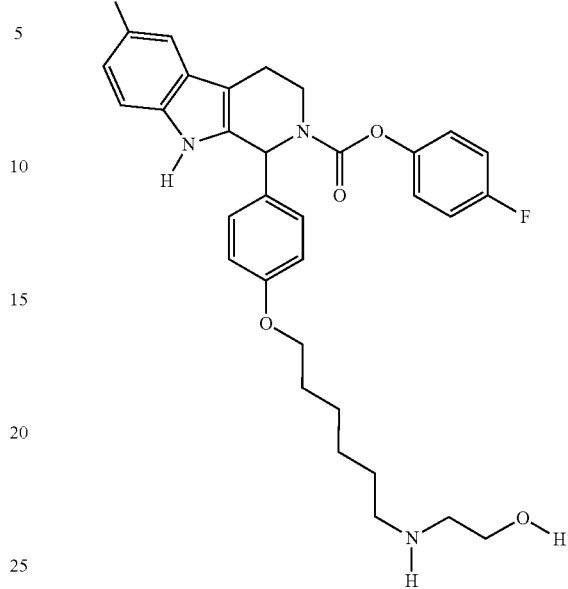
772
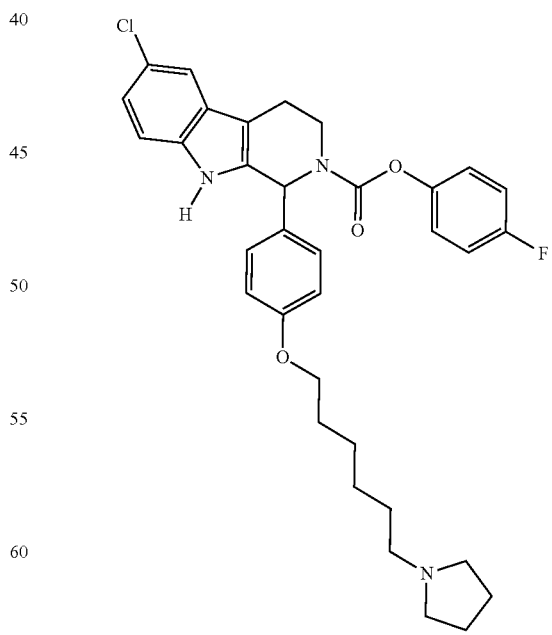
773

TABLE A-continued
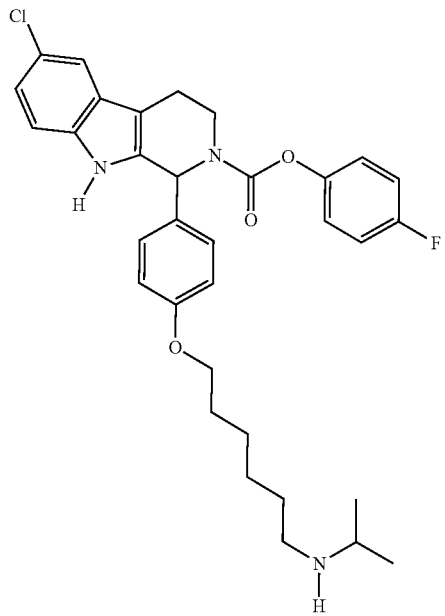
774
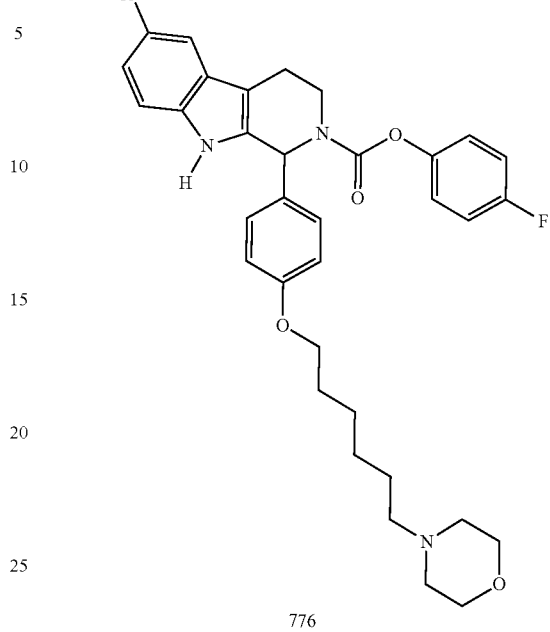
776
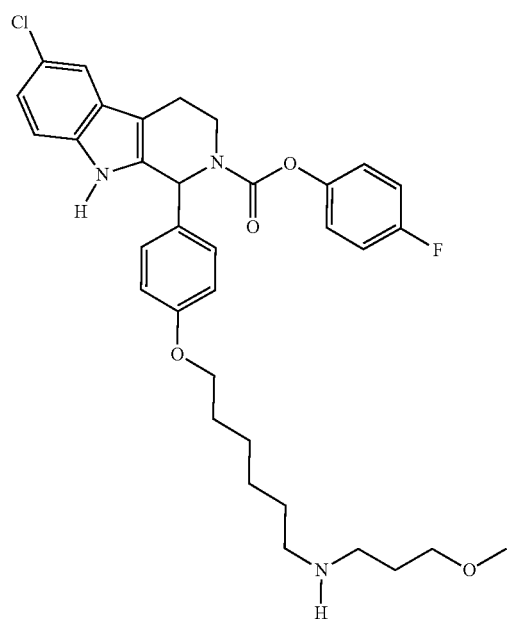
775
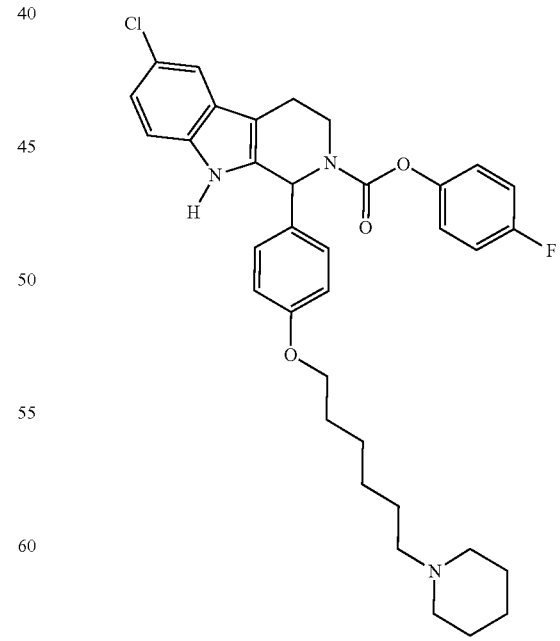
777

TABLE A-continued
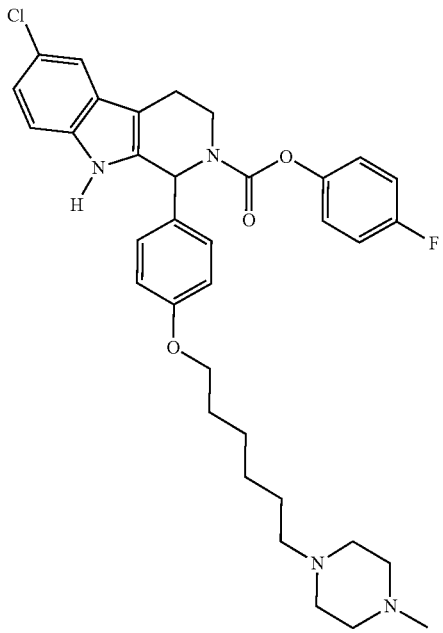
778
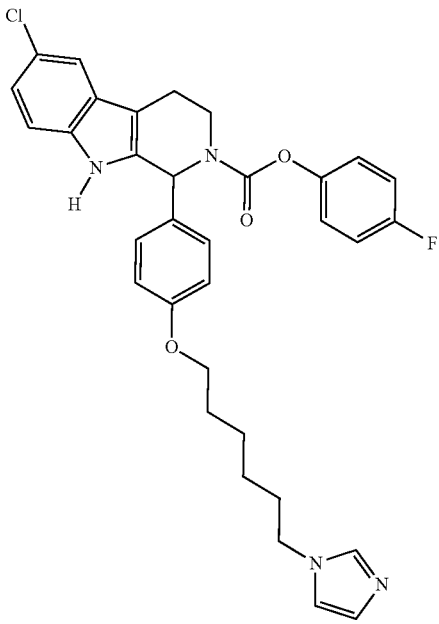
780
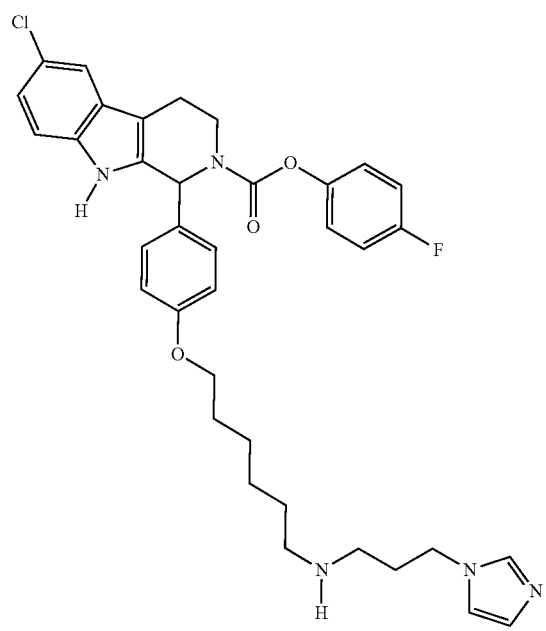
779
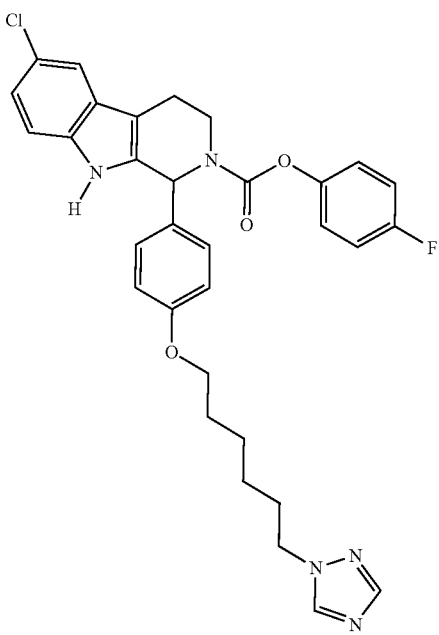
781

TABLE A-continued
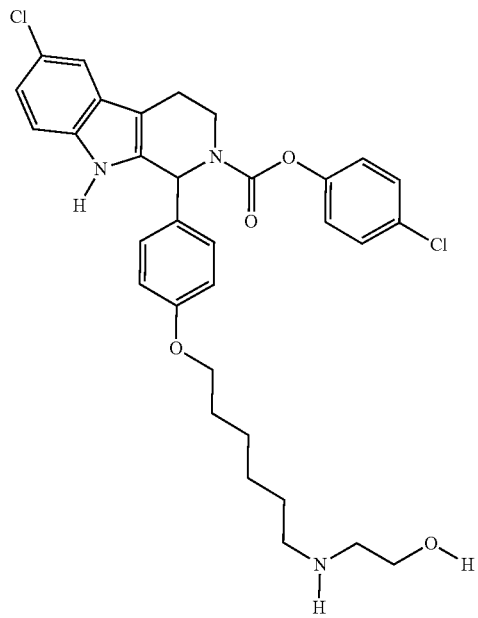
782
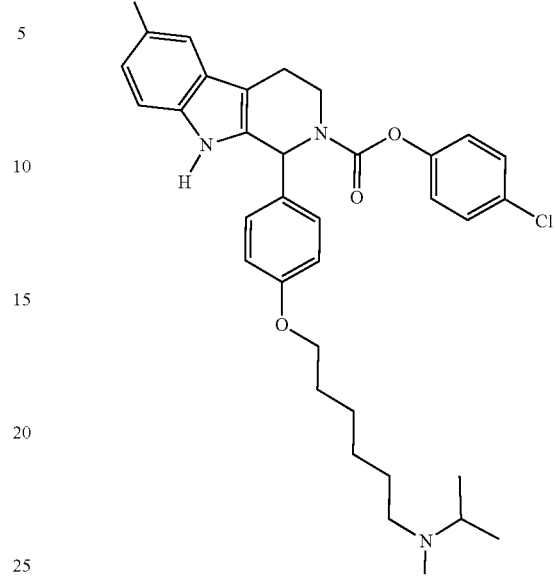
784
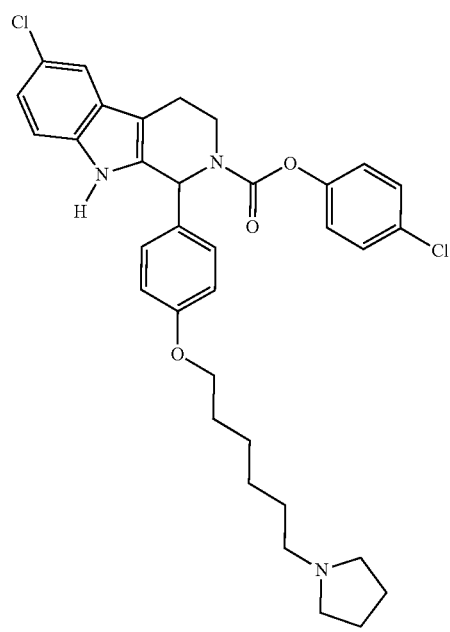
783
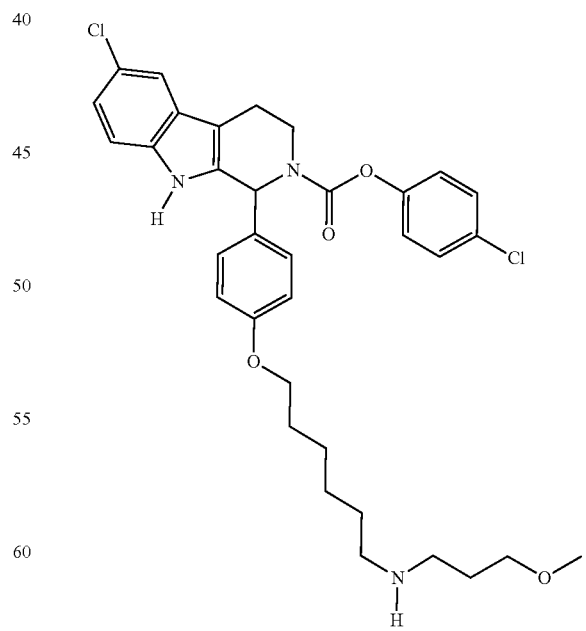
785

TABLE A-continued
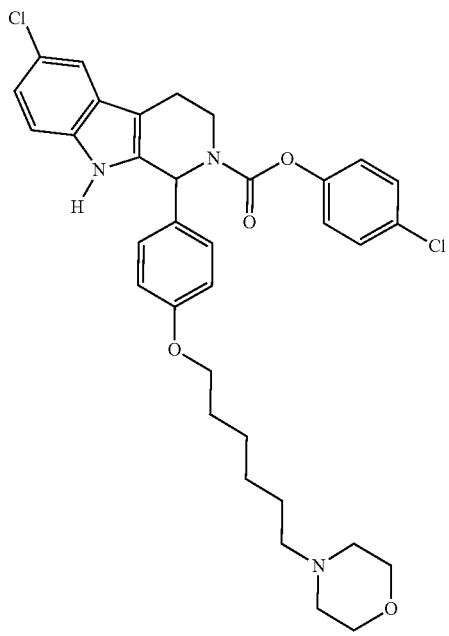
786
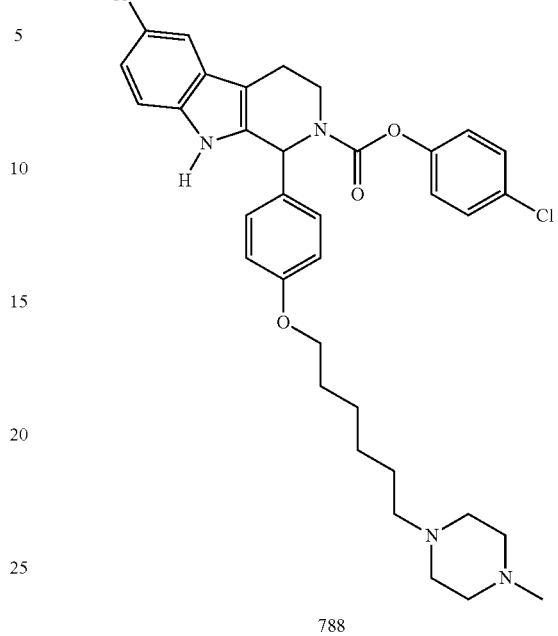
788
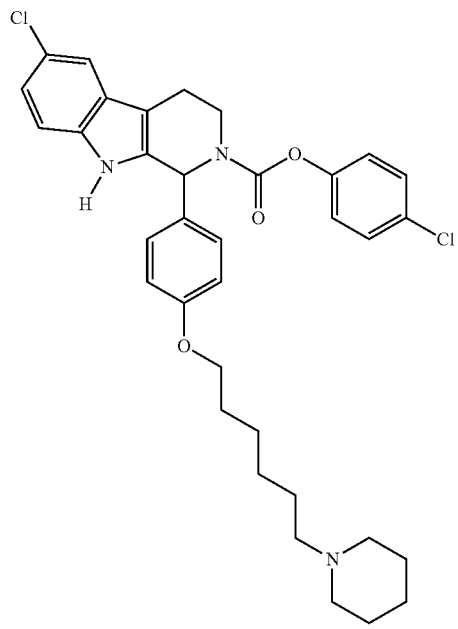
787
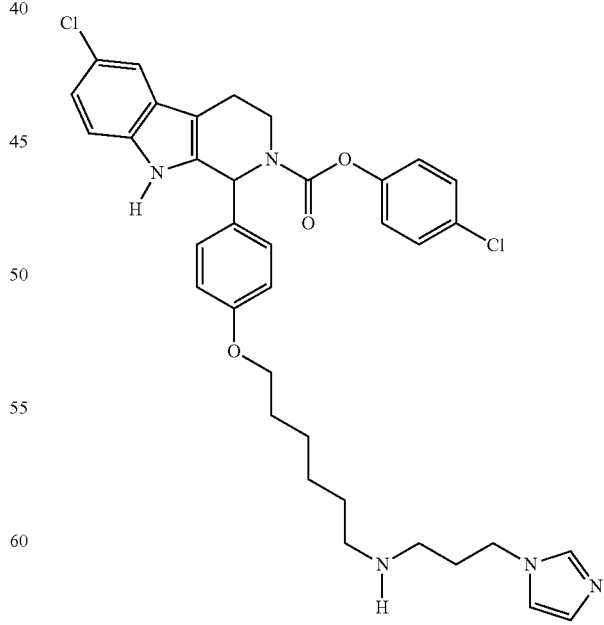
789

TABLE A-continued
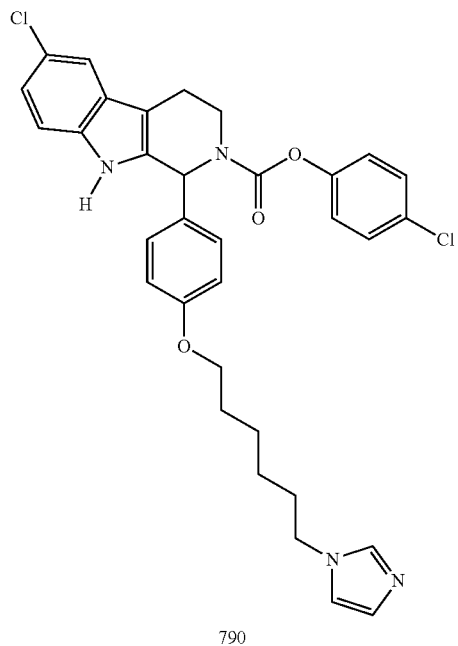
790
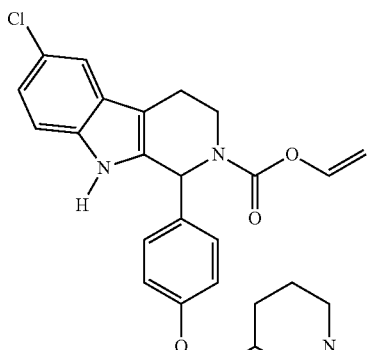
792
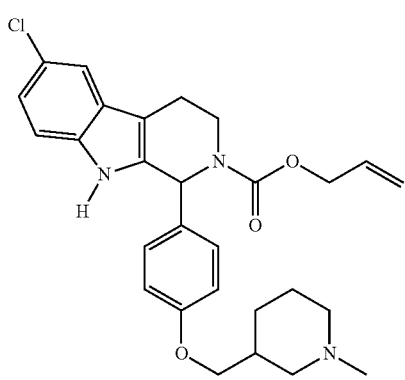
793
791
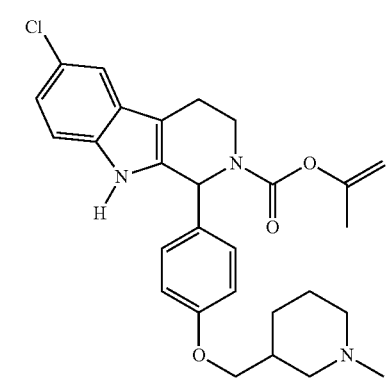
794

TABLE A-continued
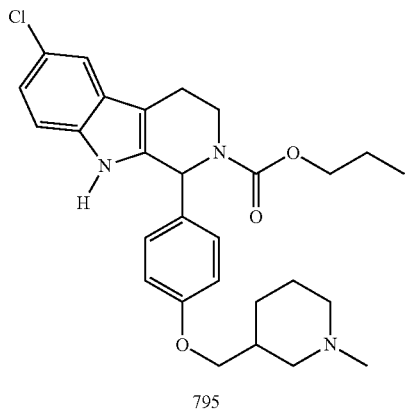
795
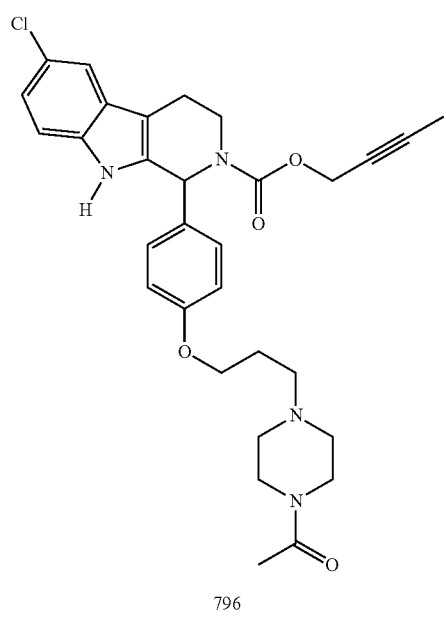
796
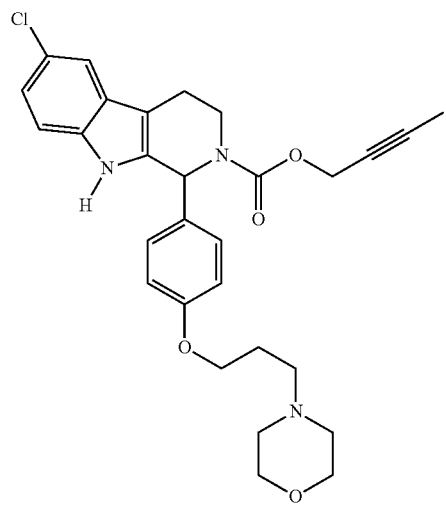
797
TABLE A-continued
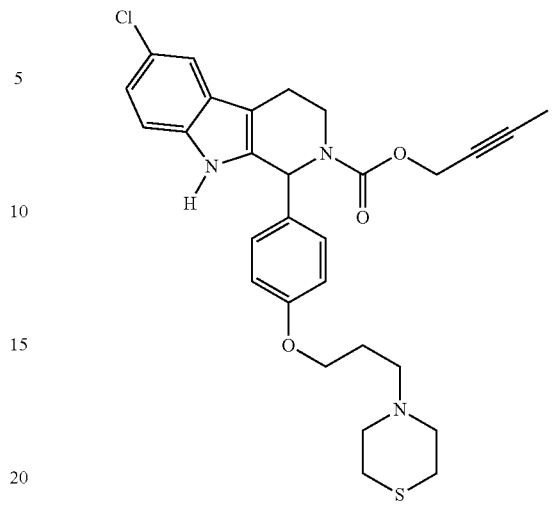
798
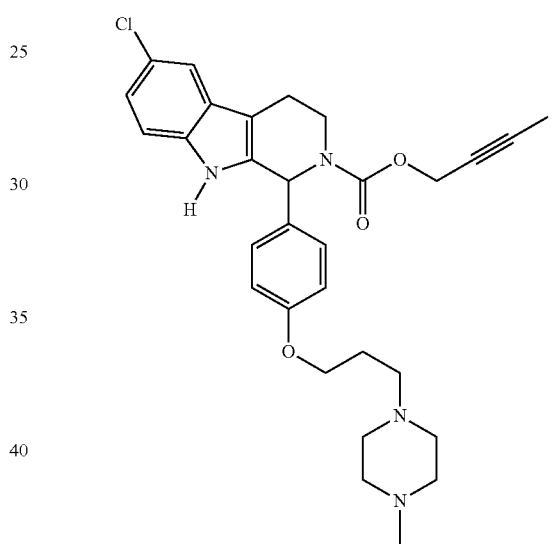
799
800

TABLE A-continued
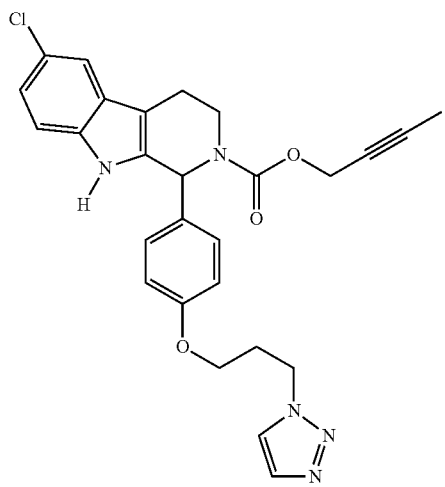
801
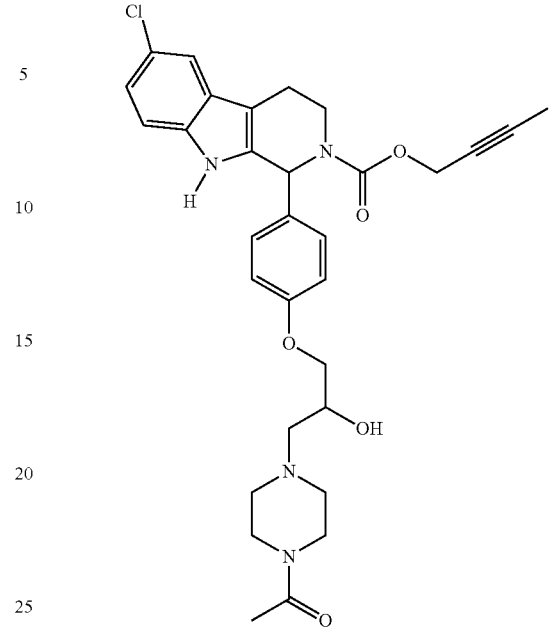
803
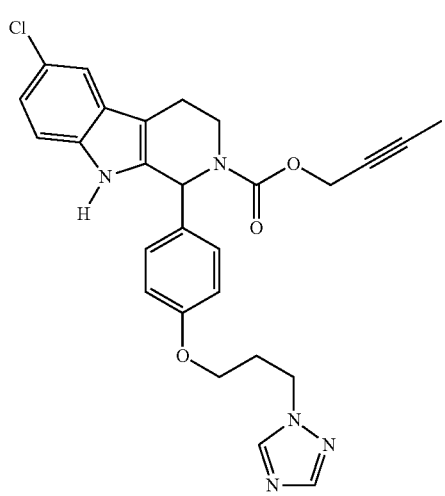
802
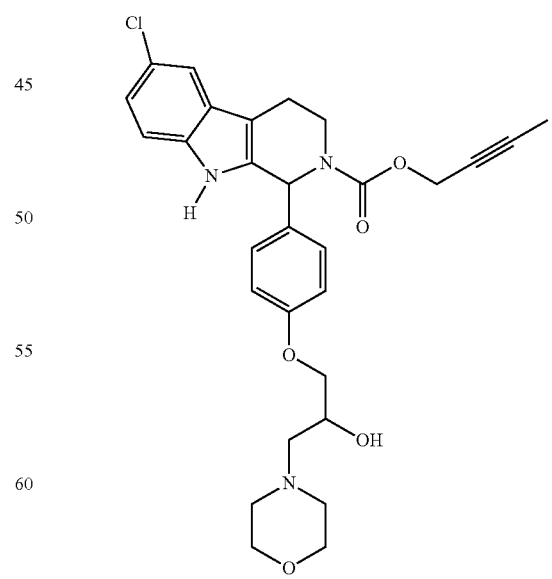
804

TABLE A-continued
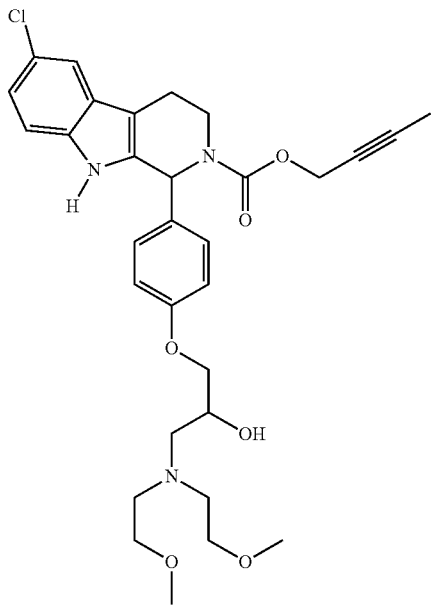
805
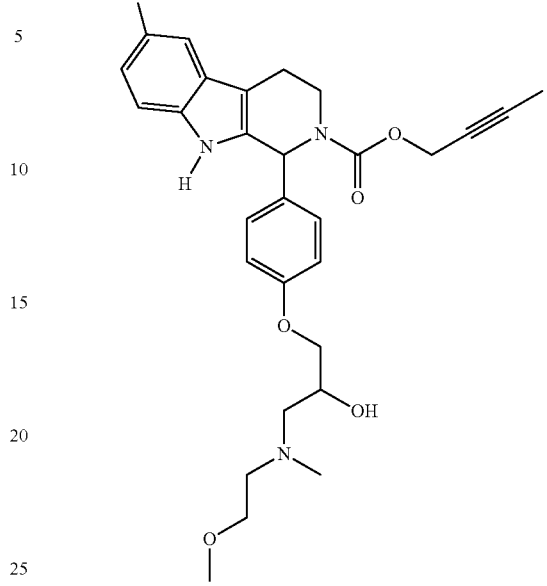
807
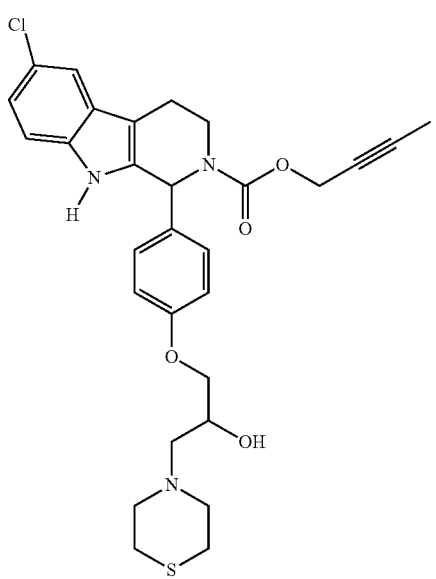
806
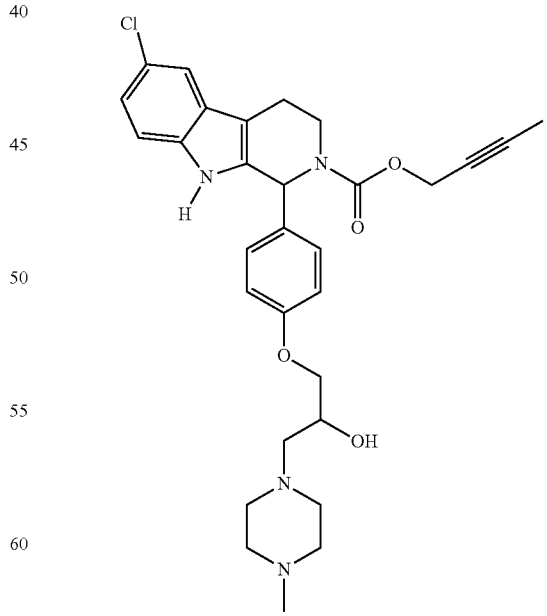
808

TABLE A-continued
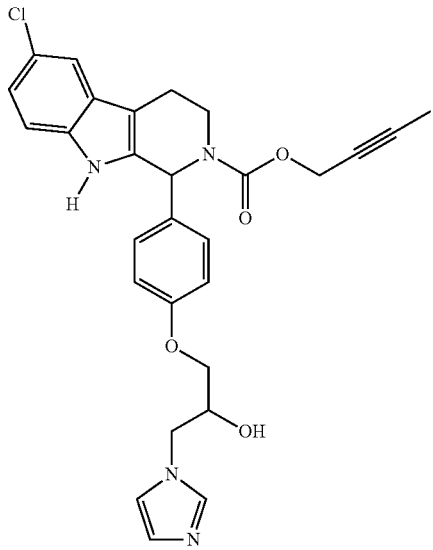
809
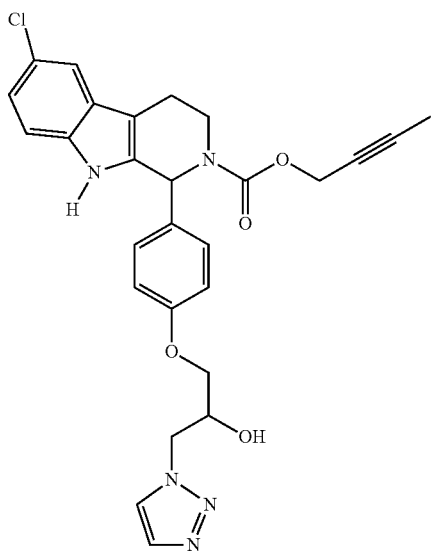
810
TABLE A-continued
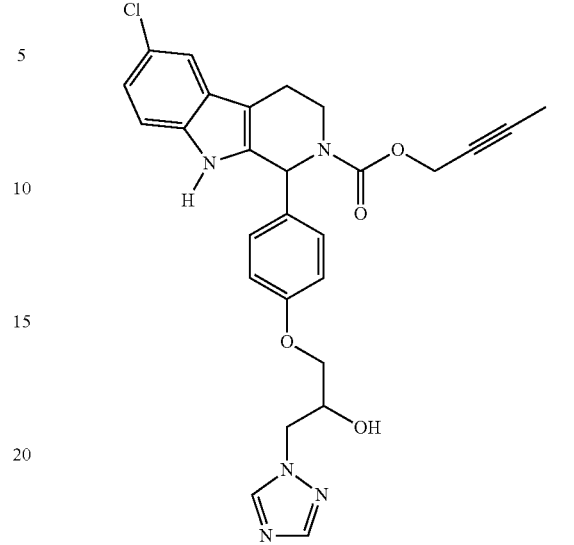
811
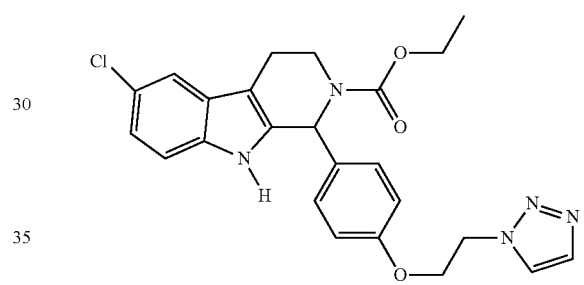
812
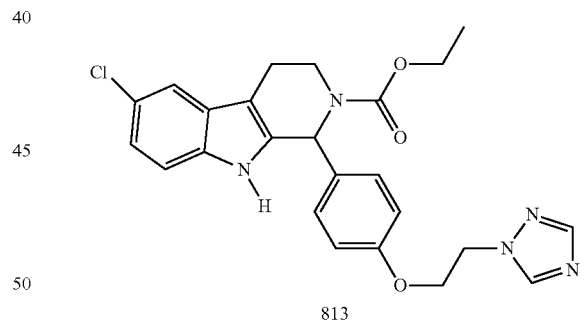
813
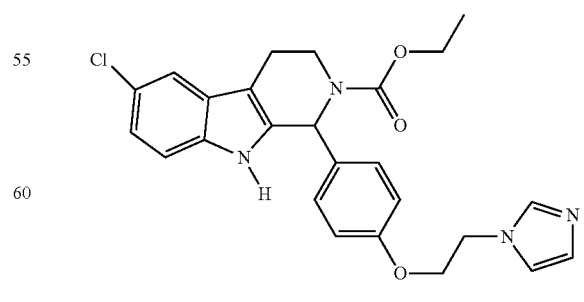
814

TABLE A-continued
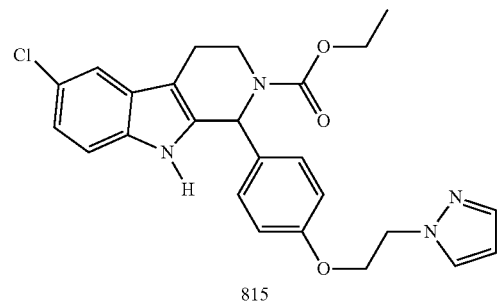
815
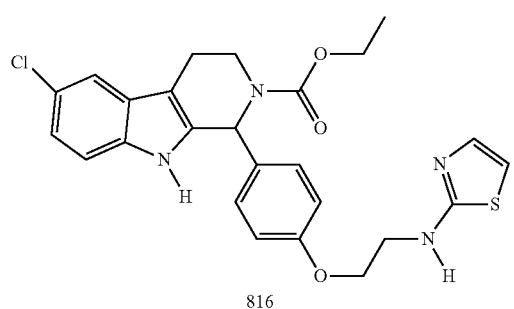
816
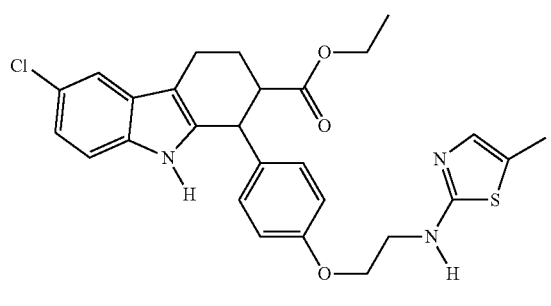
817
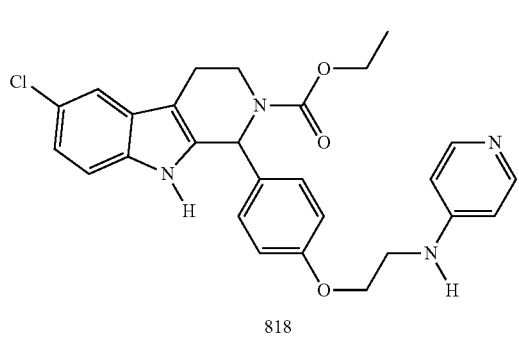
818
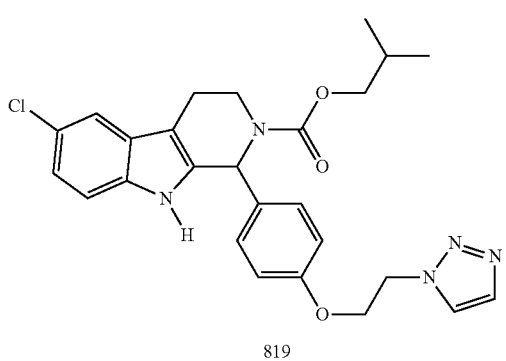
819
TABLE A-continued
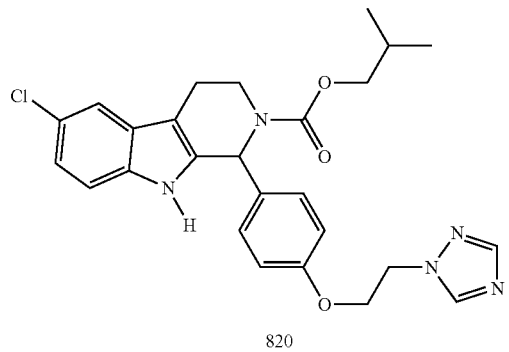
820
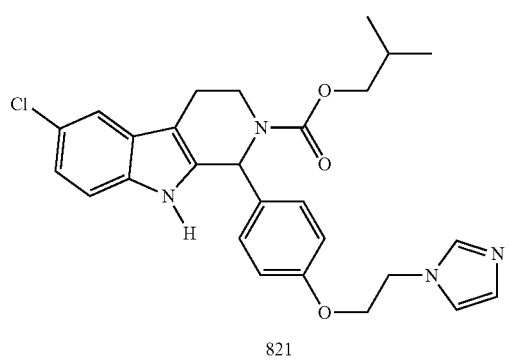
821
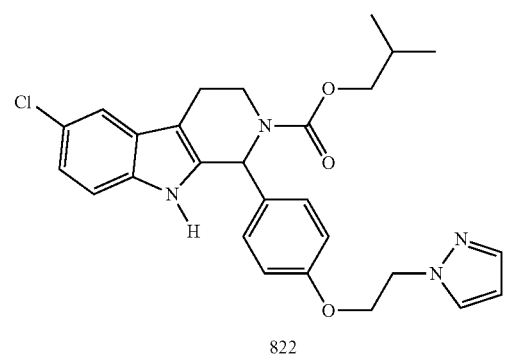
822
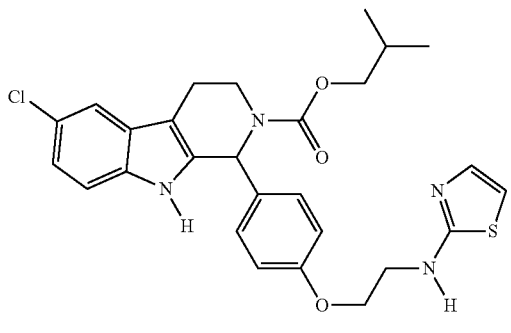
823

TABLE A-continued
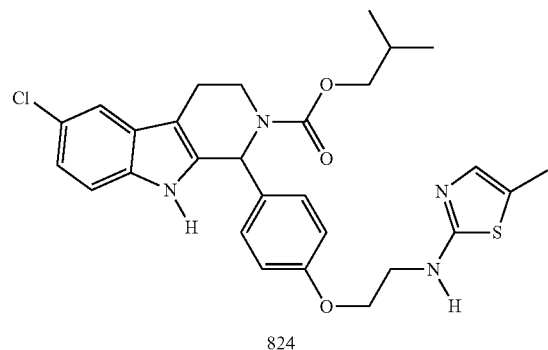
824
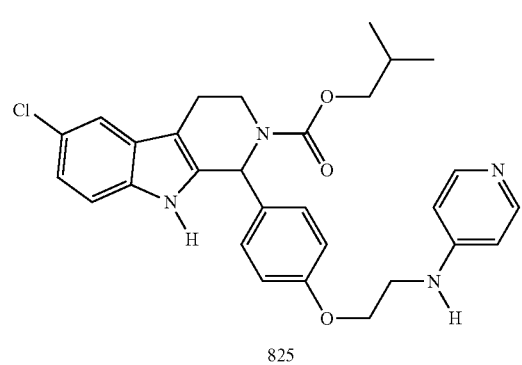
825
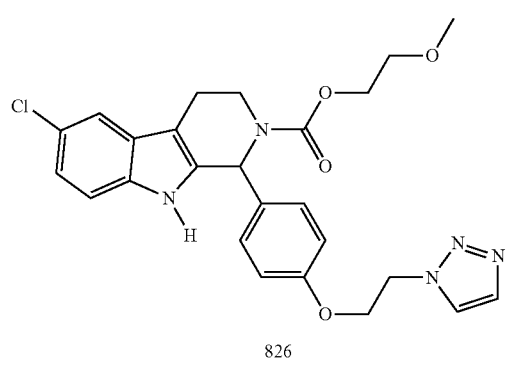
826
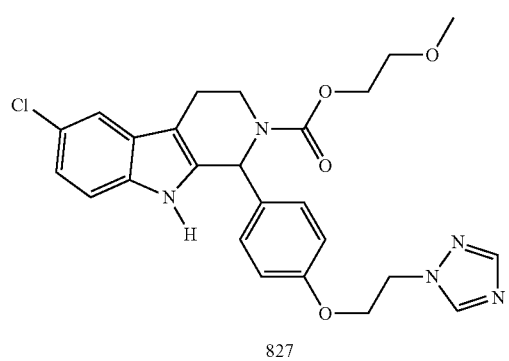
827
TABLE A-continued
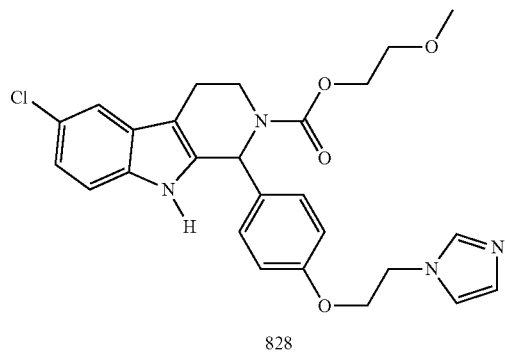
828
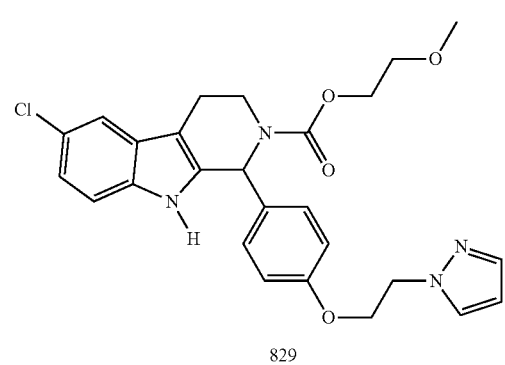
829
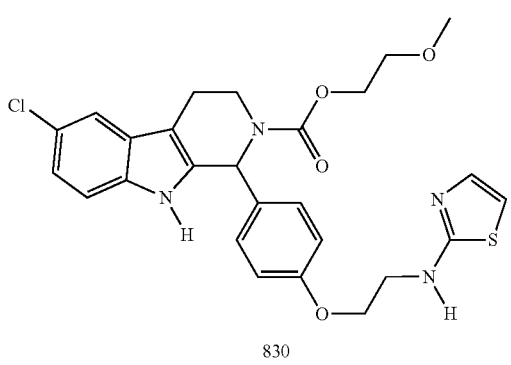
830
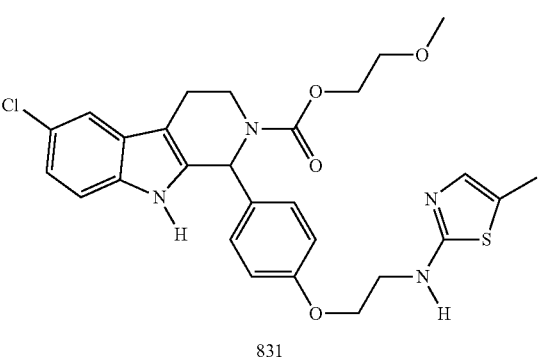
831

TABLE A-continued
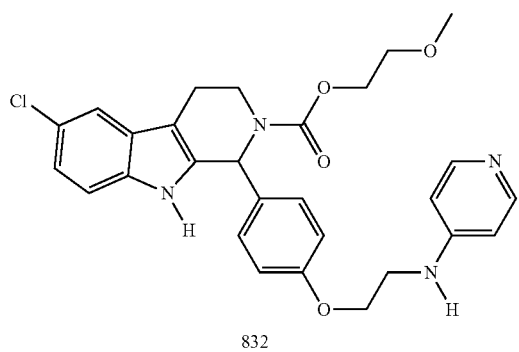
832
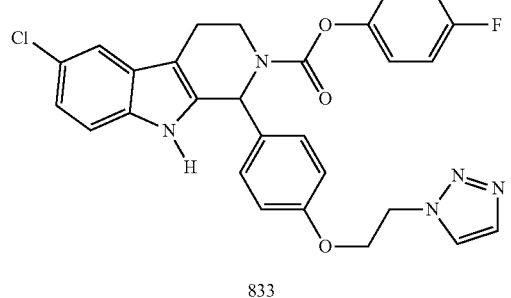
833
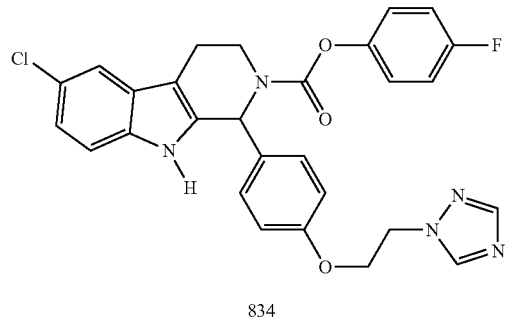
834
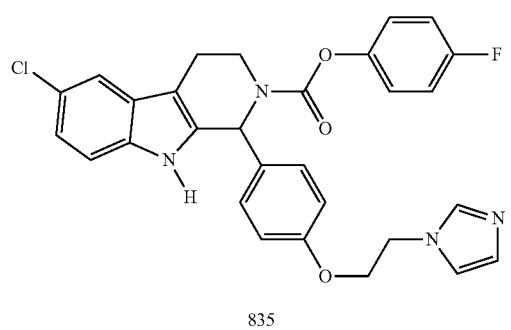
835
TABLE A-continued
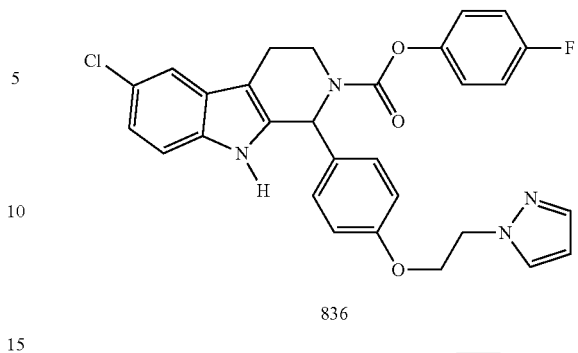
836
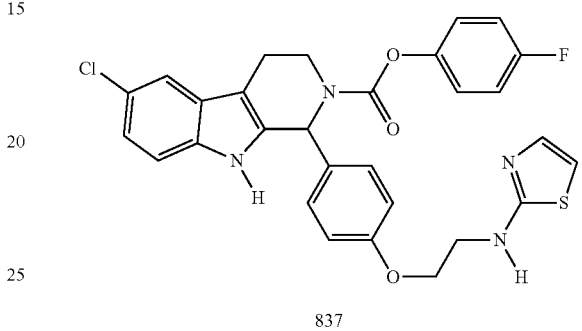
837
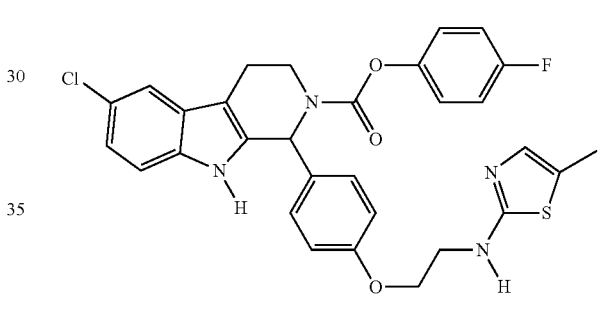
838
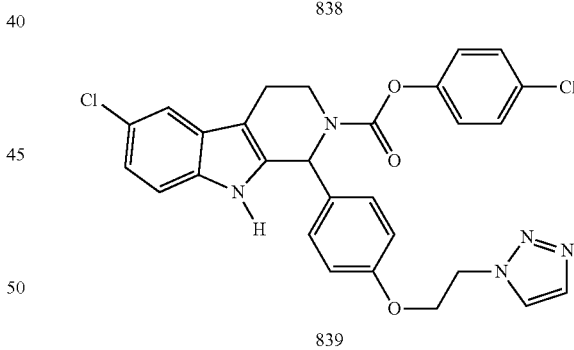
839
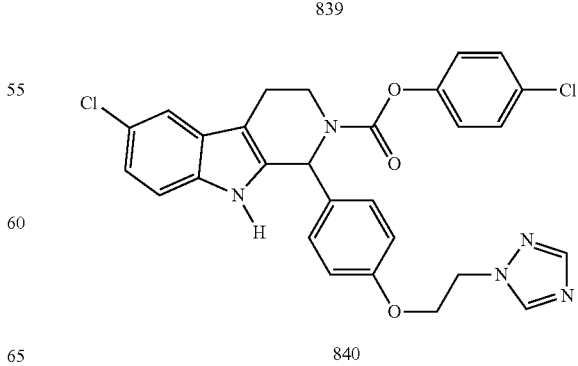
840

TABLE A-continued
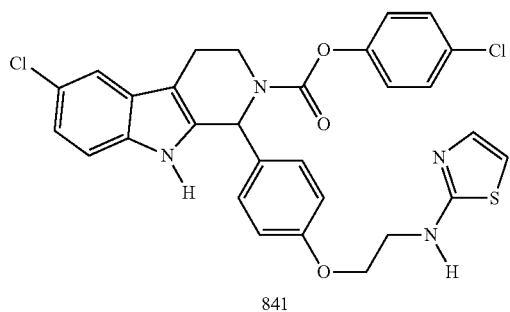
841
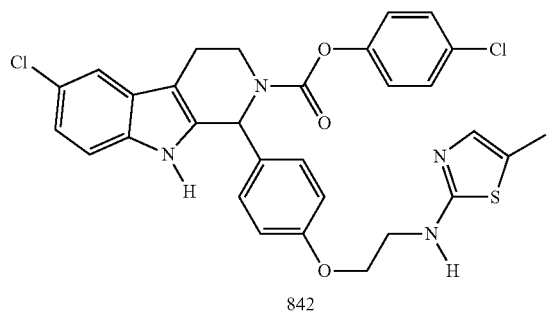
842
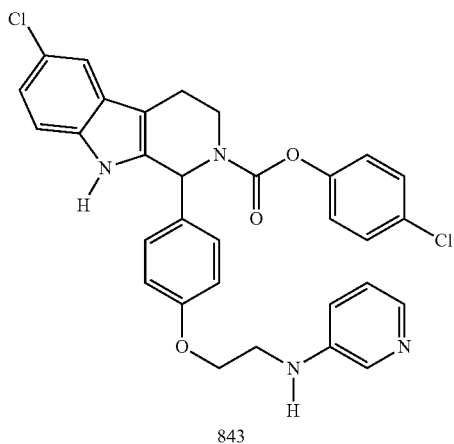
843
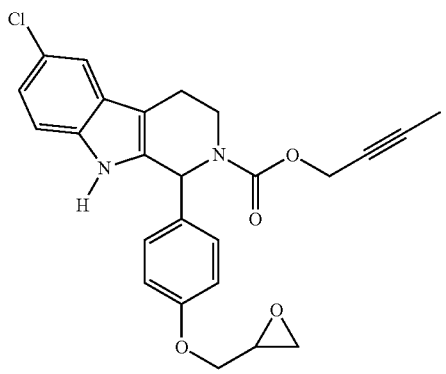
844
TABLE A-continued
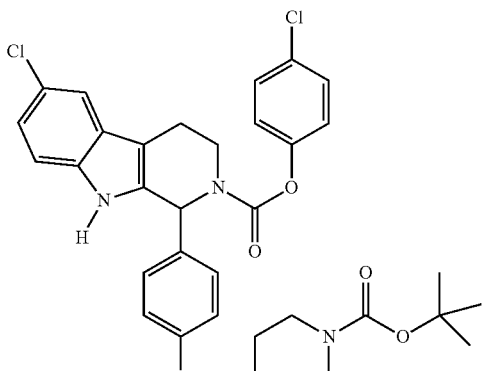
845
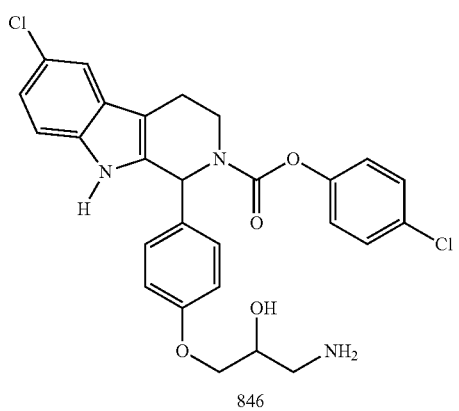
846
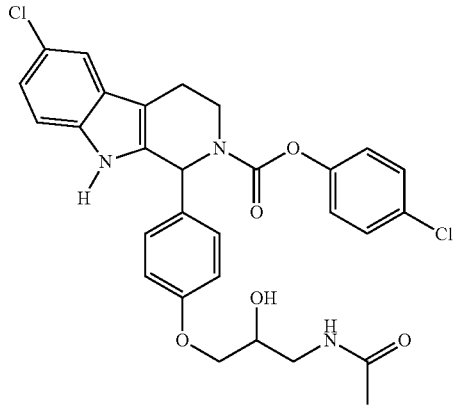
847

TABLE A-continued
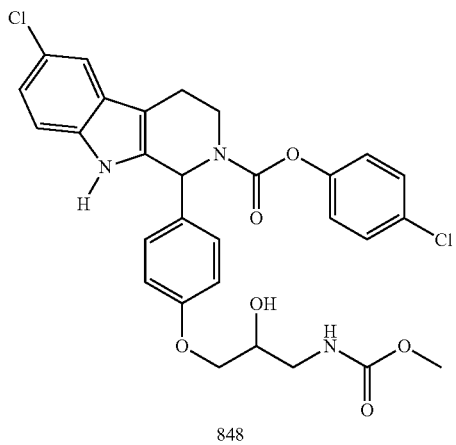
848
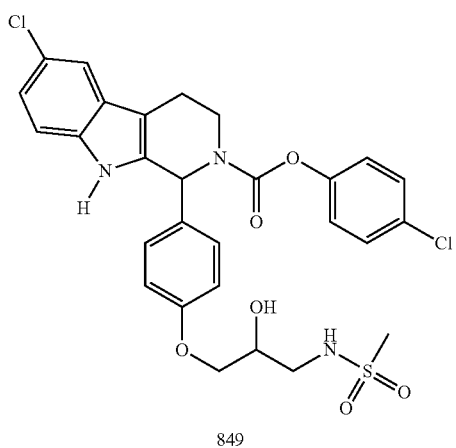
849
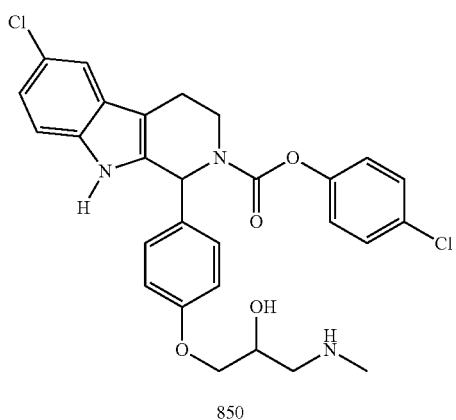
850
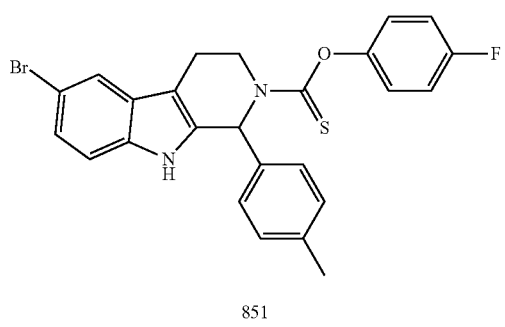
851
TABLE A-continued
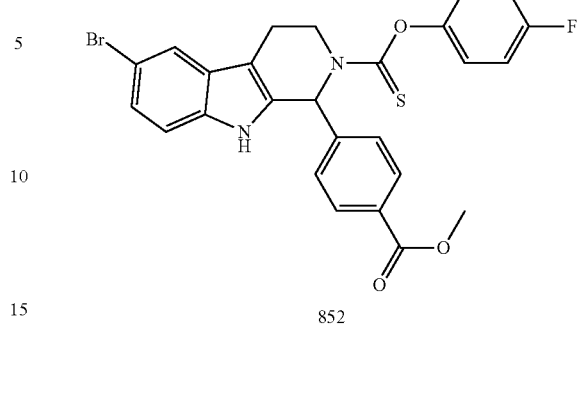
852
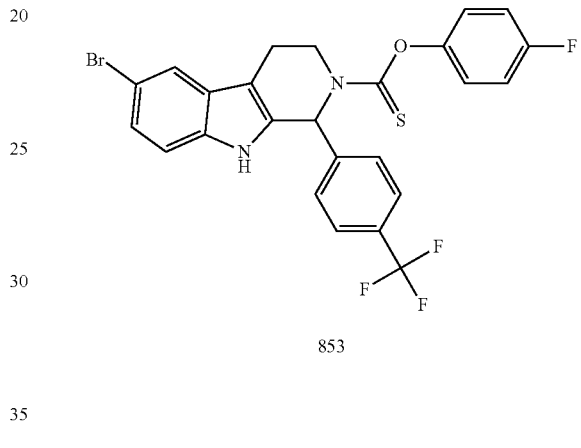
853
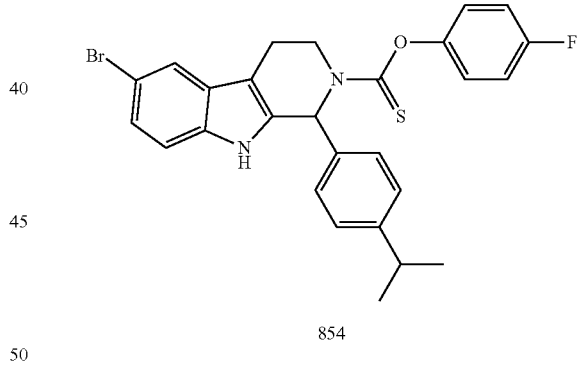
854
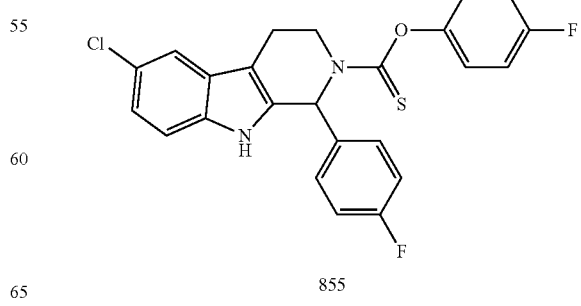
855

TABLE A-continued
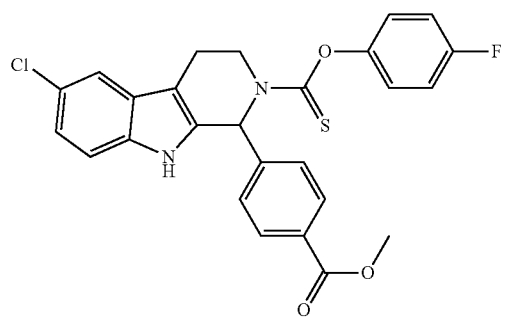
856
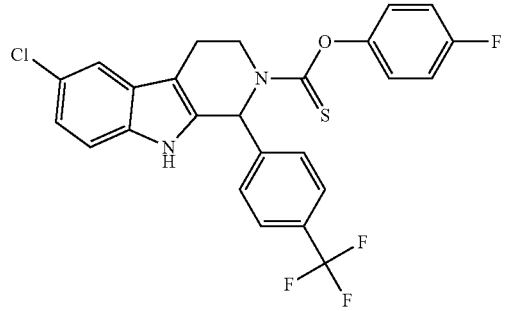
857
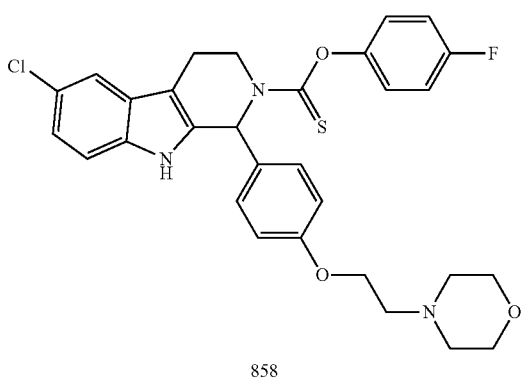
858
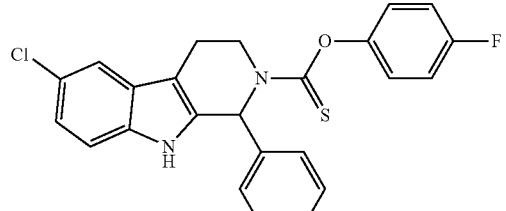
859
TABLE A-continued
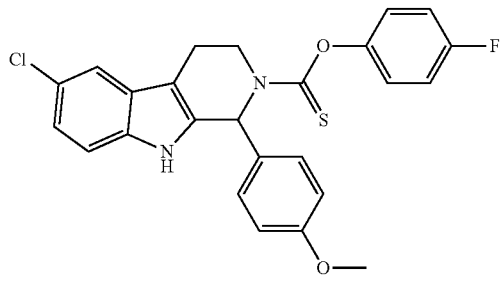
860
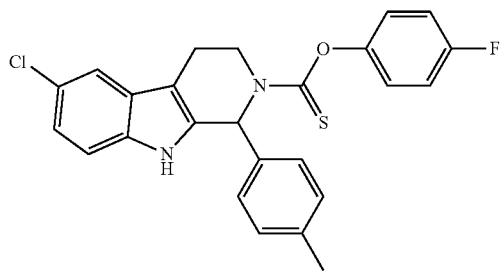
861
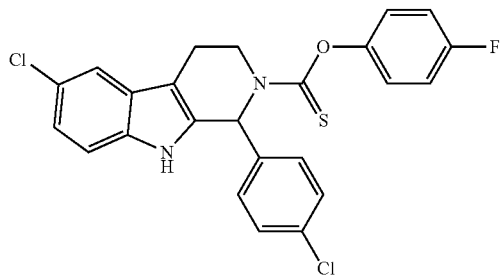
862
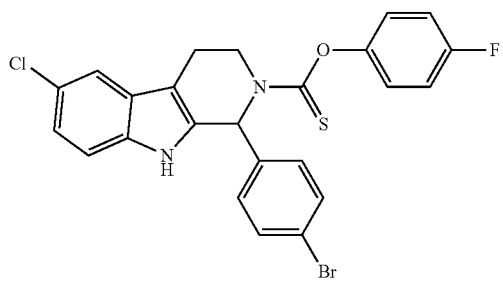
863
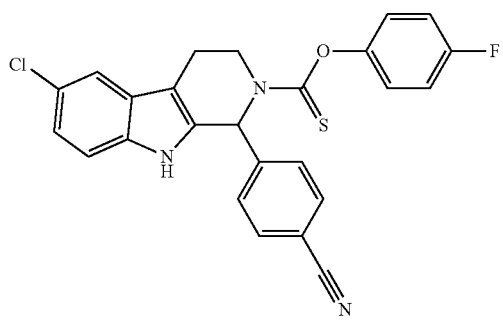
864

TABLE A-continued
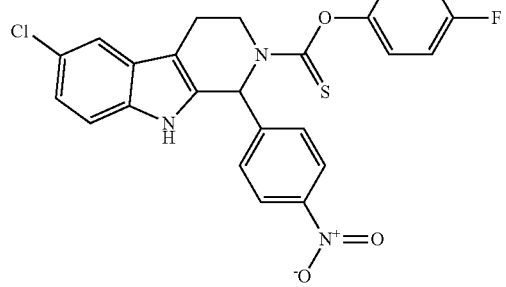
865
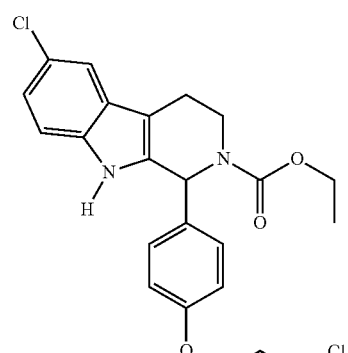
866
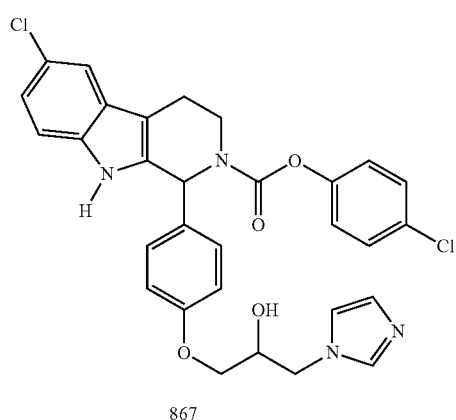
867
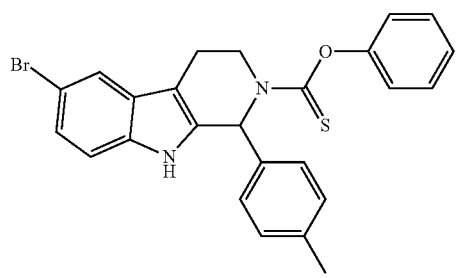
868
TABLE A-continued
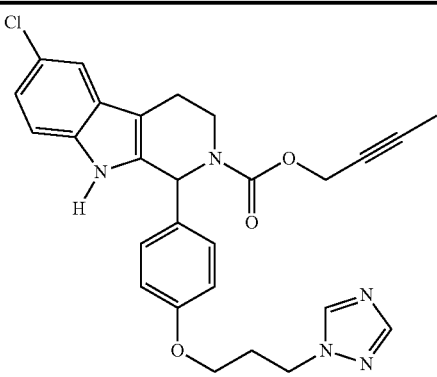
869
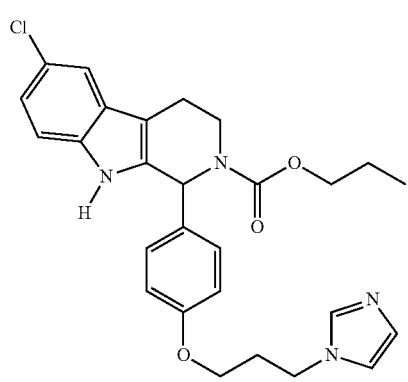
870
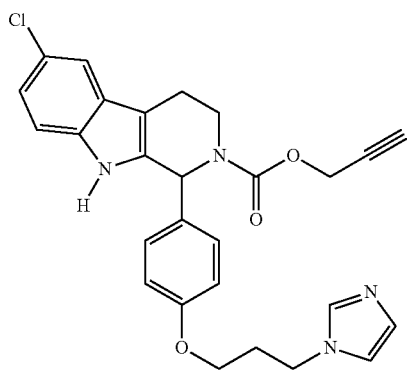
871

TABLE A-continued
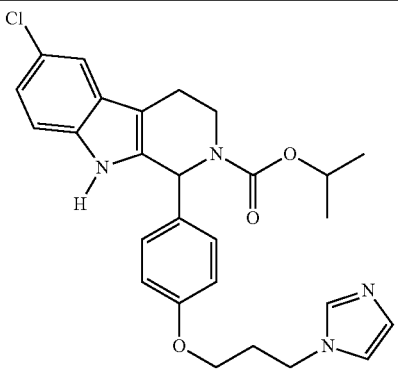
872
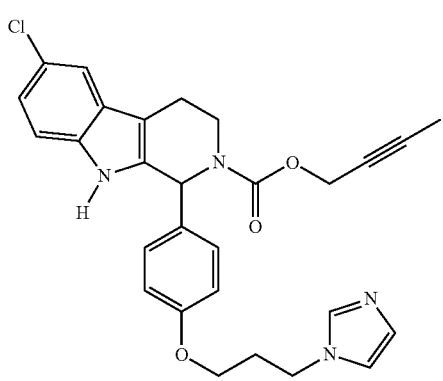
873
874
TABLE A-continued
875
876
877

TABLE A-continued
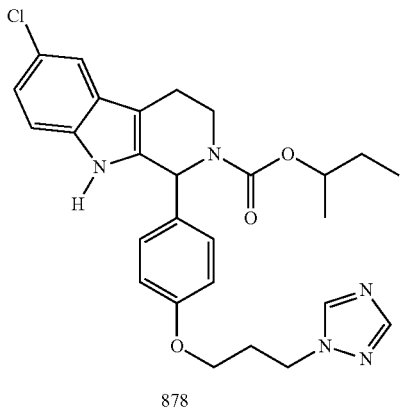
878
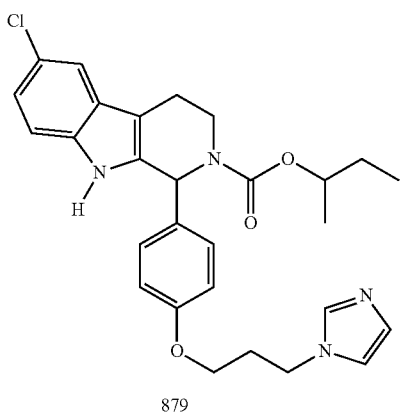
879
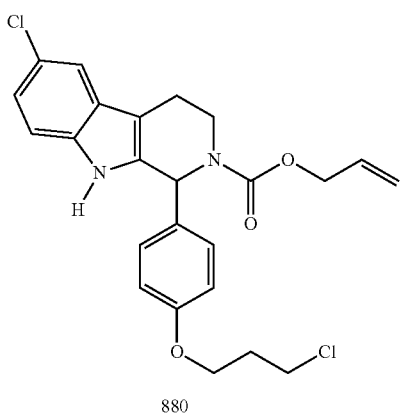
880
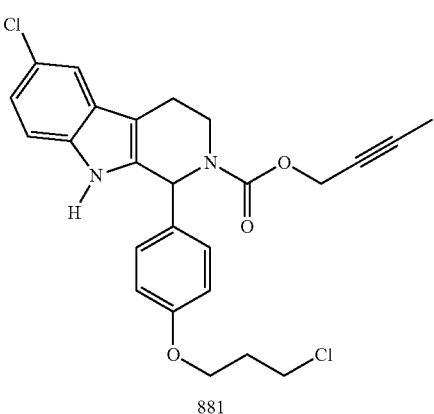
881
TABLE A-continued
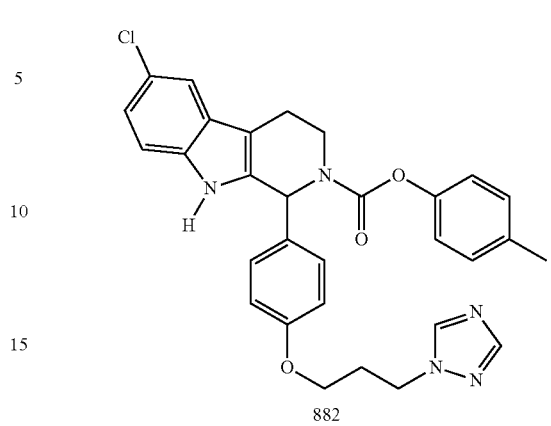
882
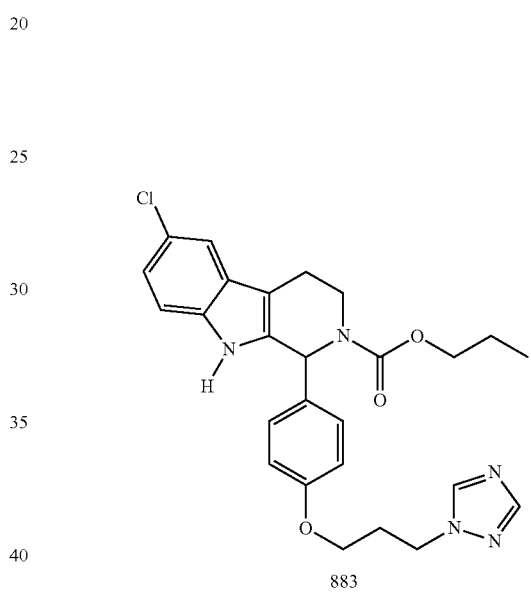
883
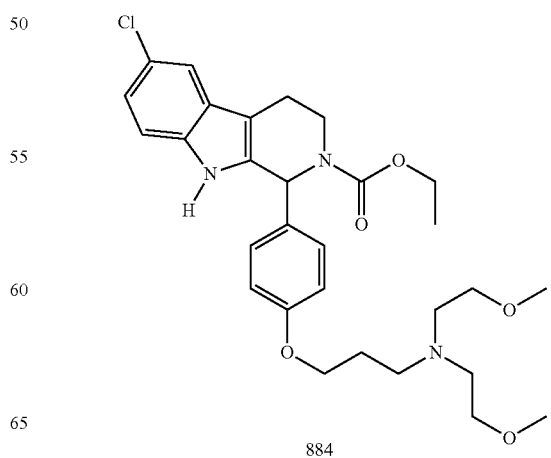
884

TABLE A-continued
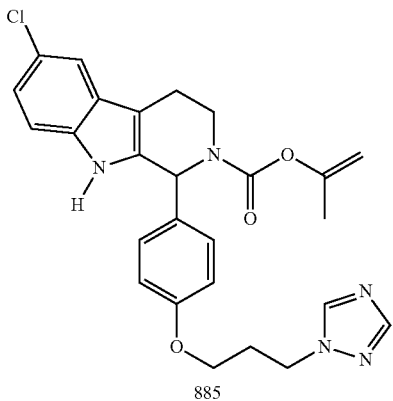
885
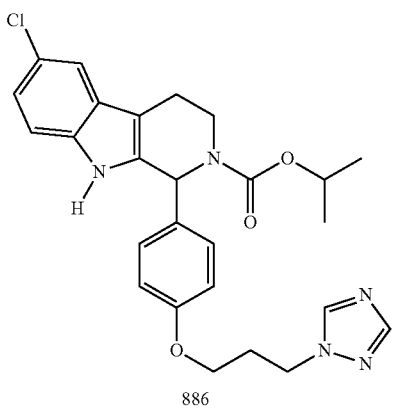
886
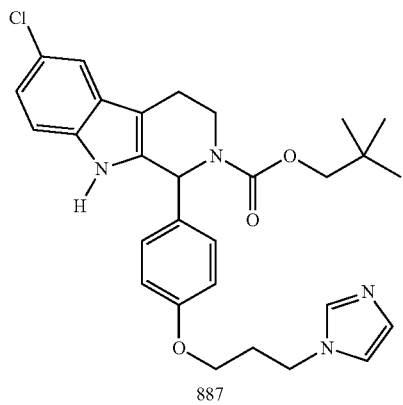
887
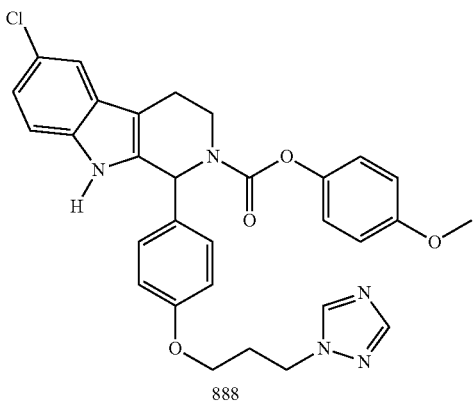
888
TABLE A-continued
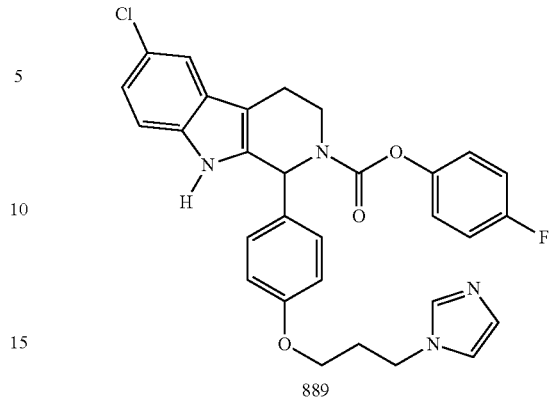
889
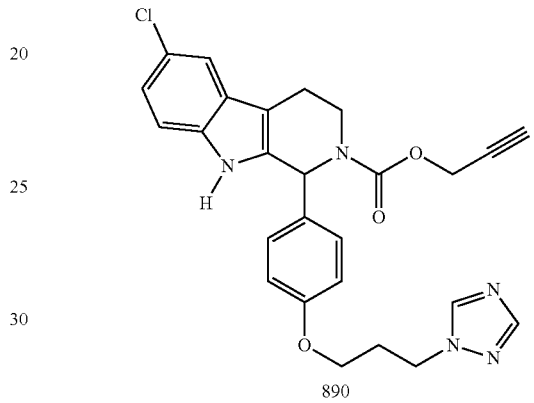
890
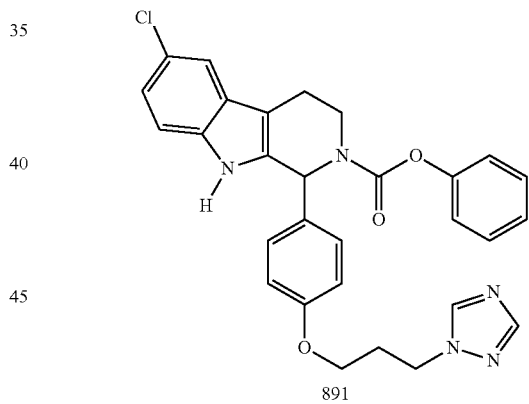
891
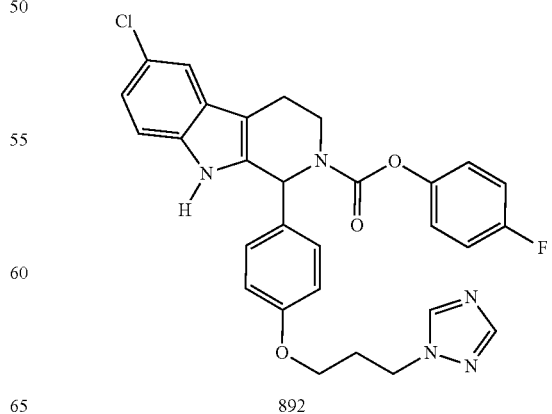
892

TABLE A-continued
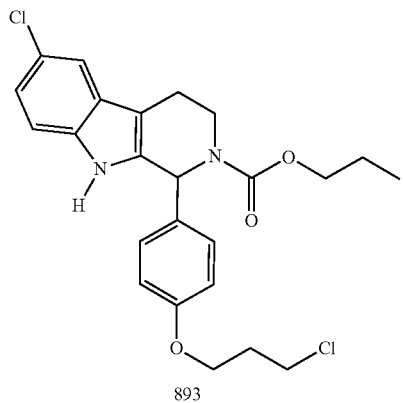
893
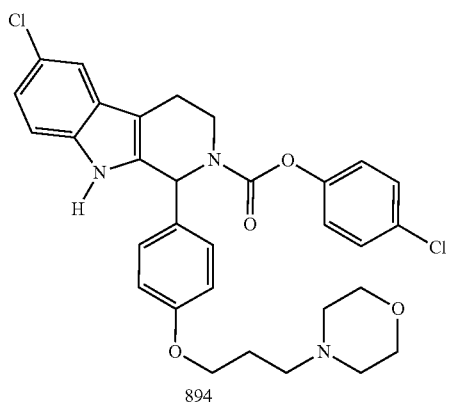
894
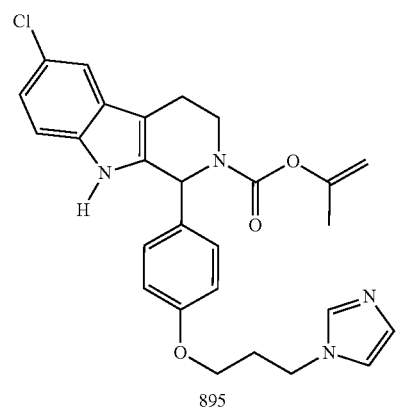
895
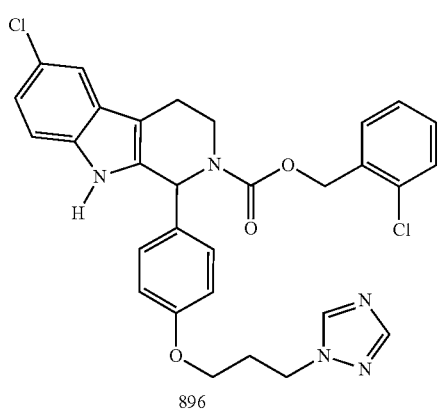
896
TABLE A-continued
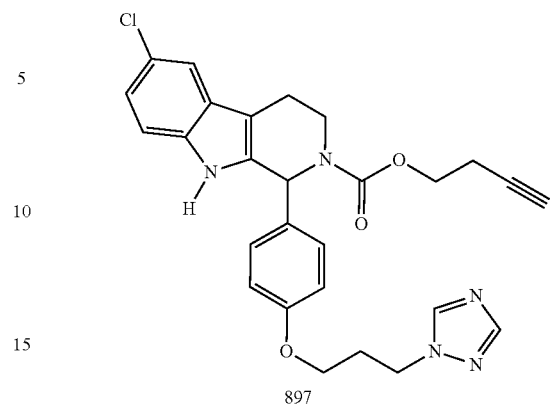
897
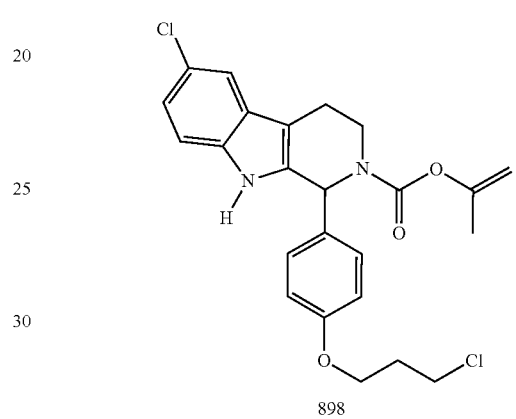
898
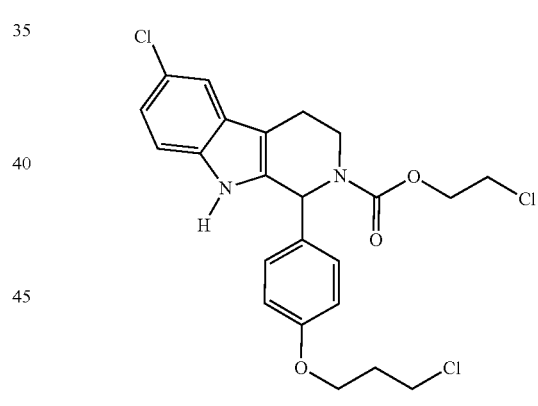
899
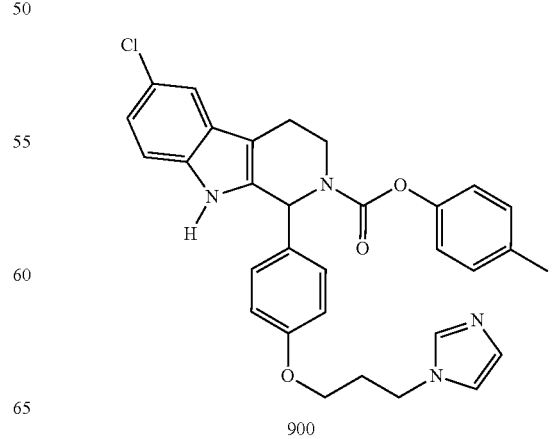
900

TABLE A-continued
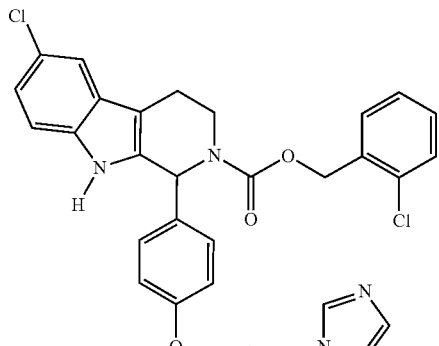
901
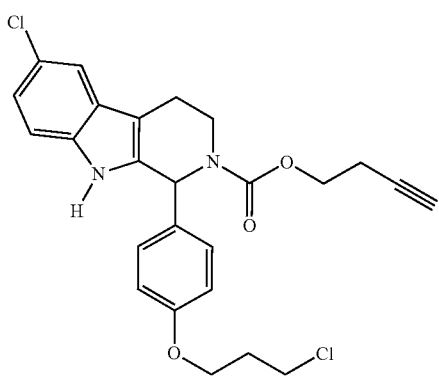
902
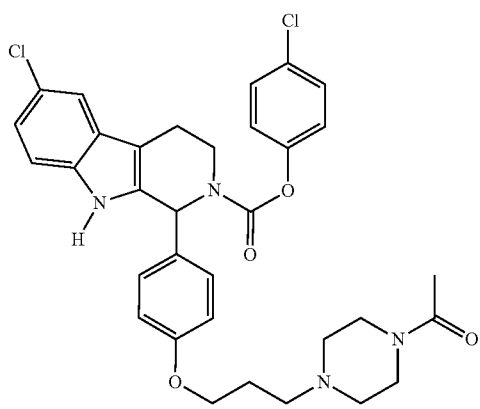
903
TABLE A-continued
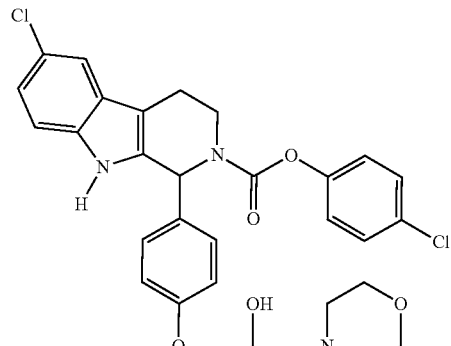
904
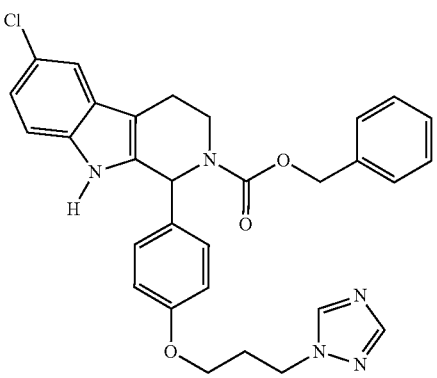
905
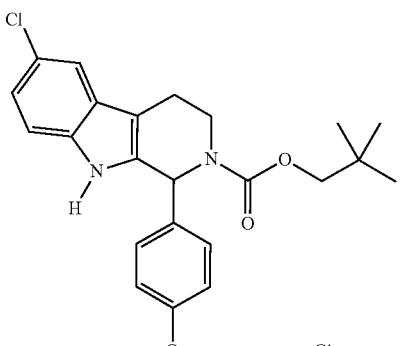
906
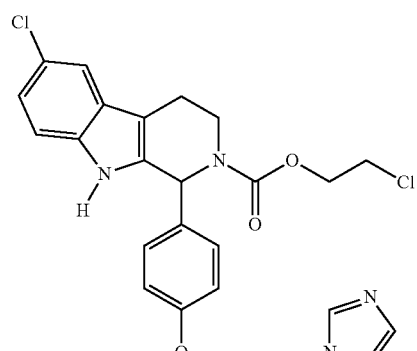
907

TABLE A-continued
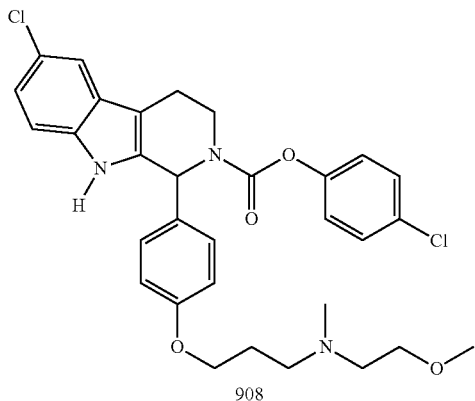
908
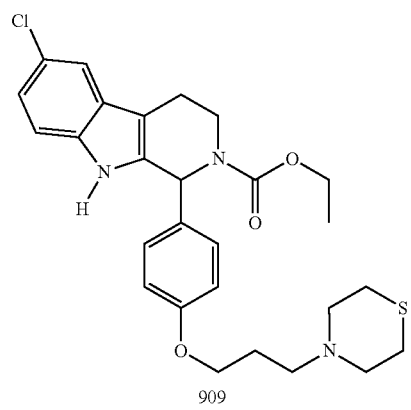
909
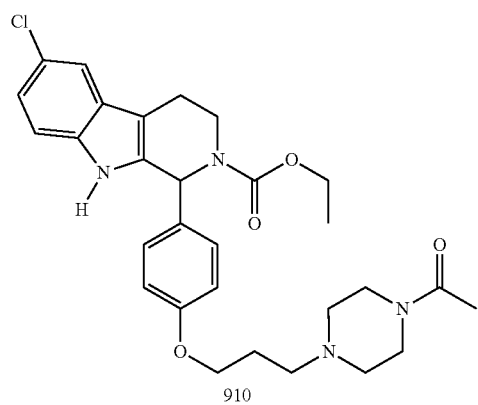
910
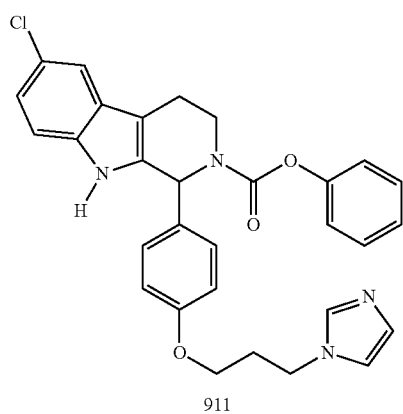
911
TABLE A-continued
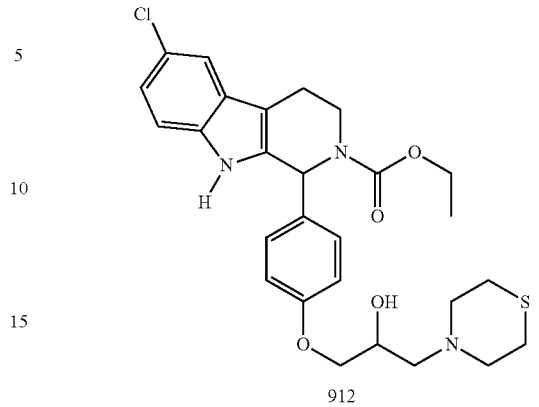
912
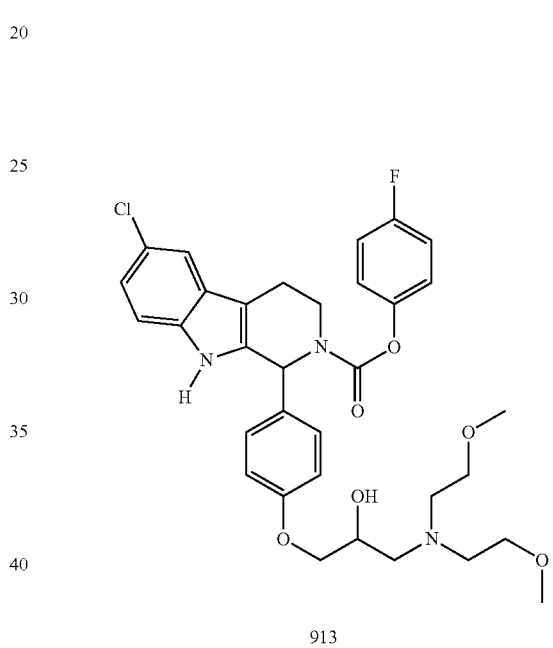
913
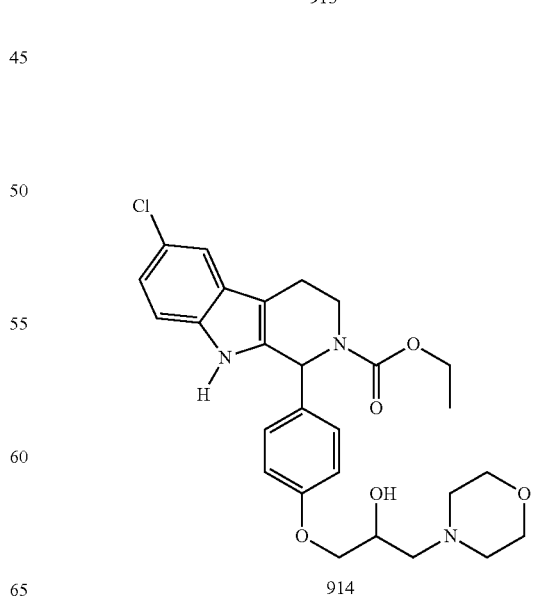
914

TABLE A-continued
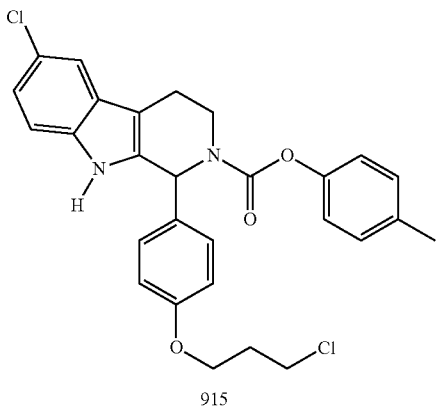
915
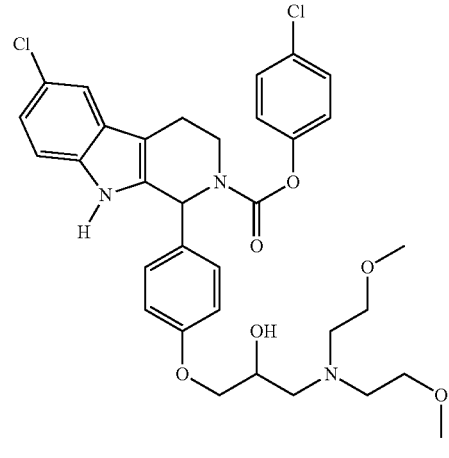
918
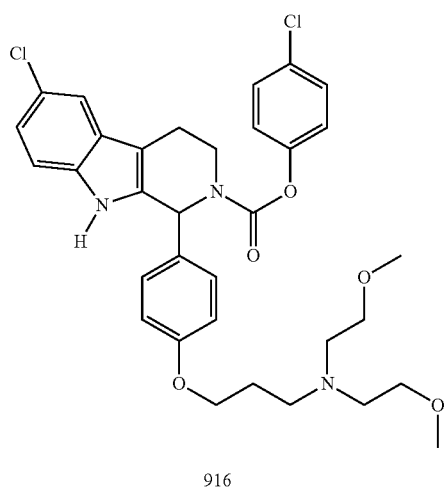
916
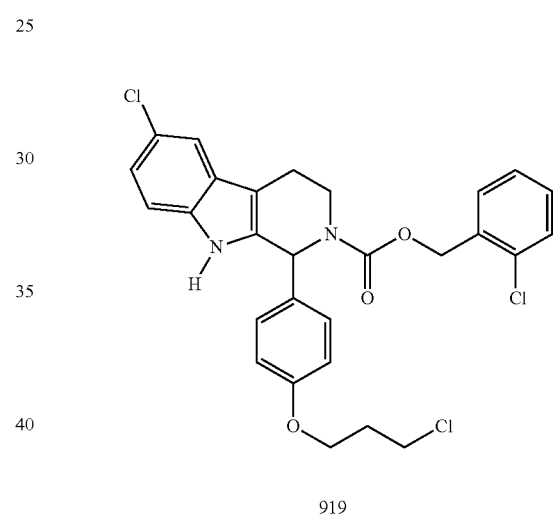
919
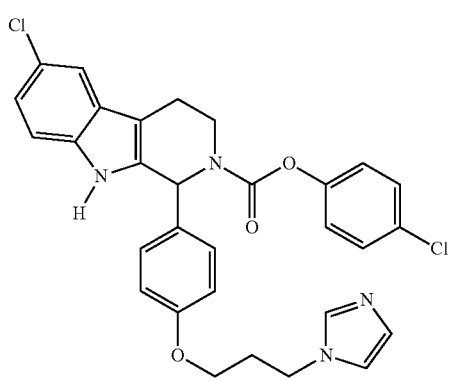
917
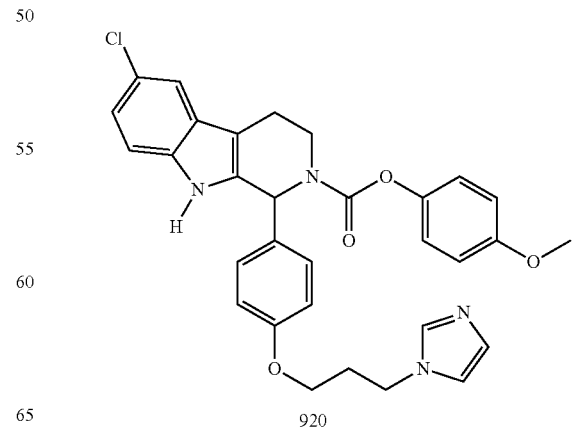
920

TABLE A-continued
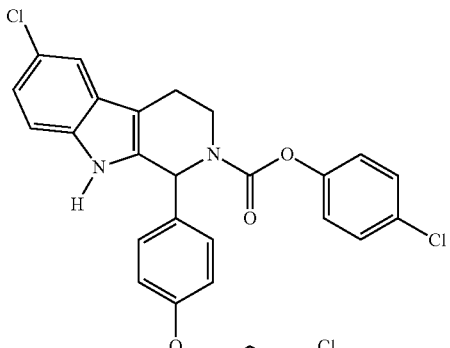
921
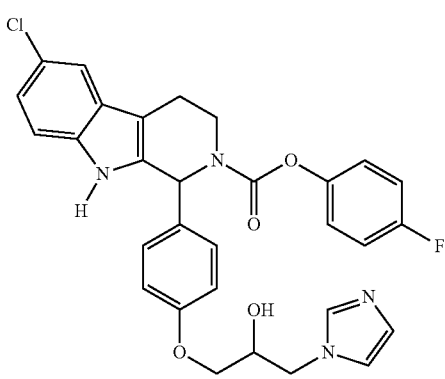
922
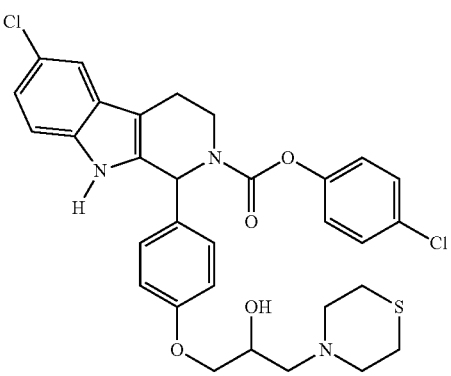
923
TABLE A-continued
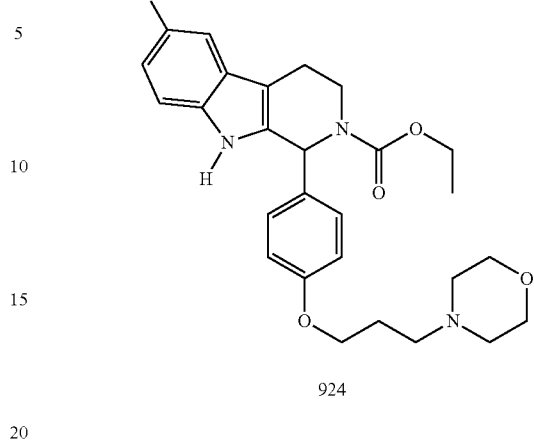
924
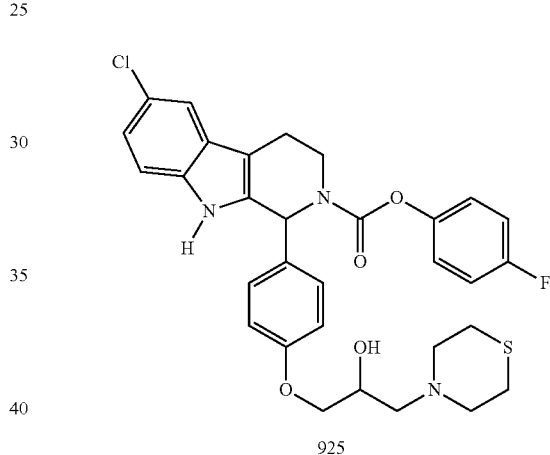
925
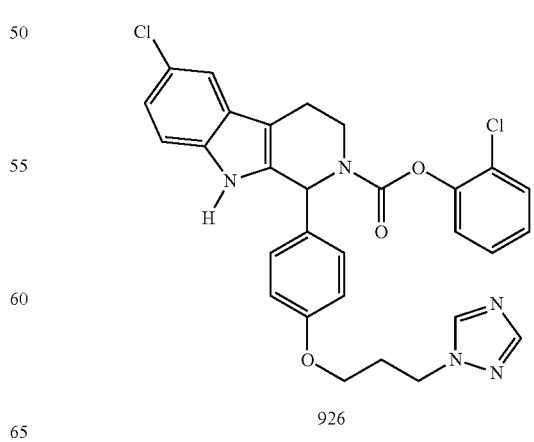
926

TABLE A-continued
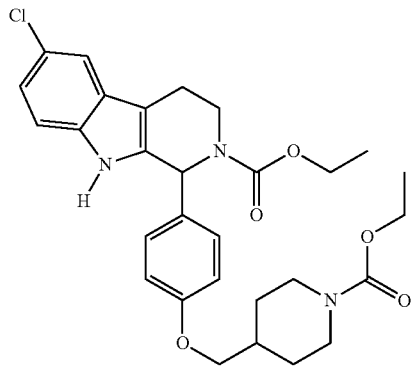
927
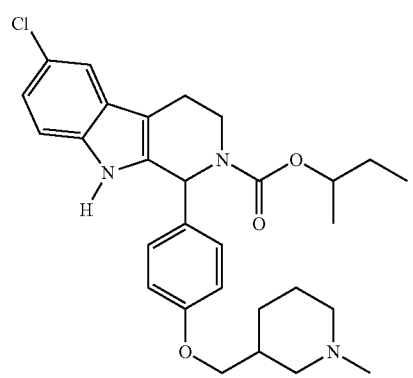
928
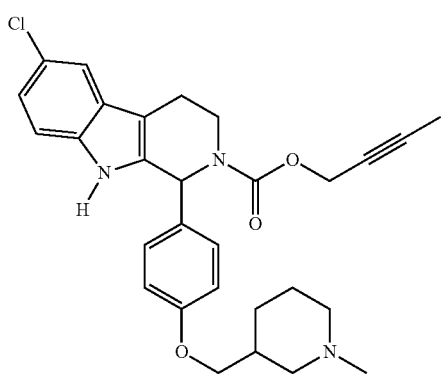
929
TABLE A-continued
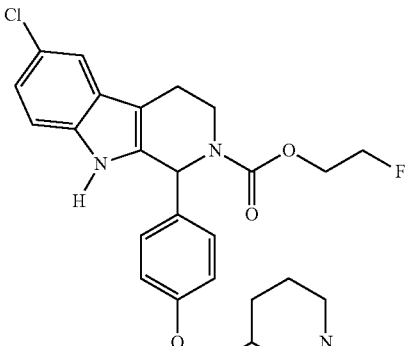
930
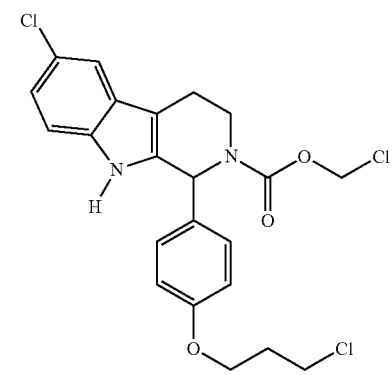
931
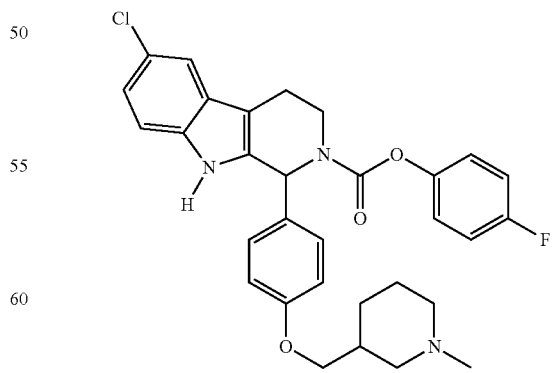
932

TABLE A-continued
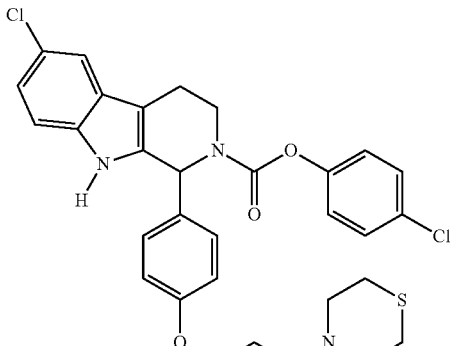
933
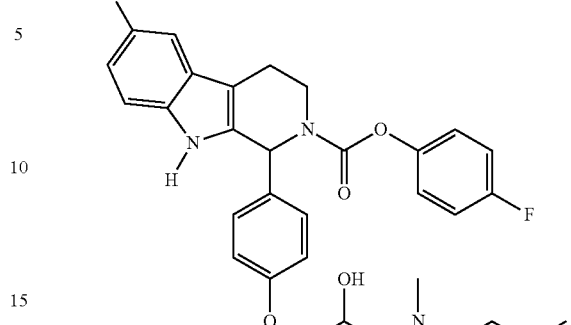
936
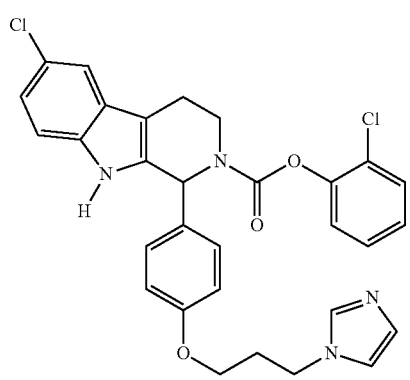
934
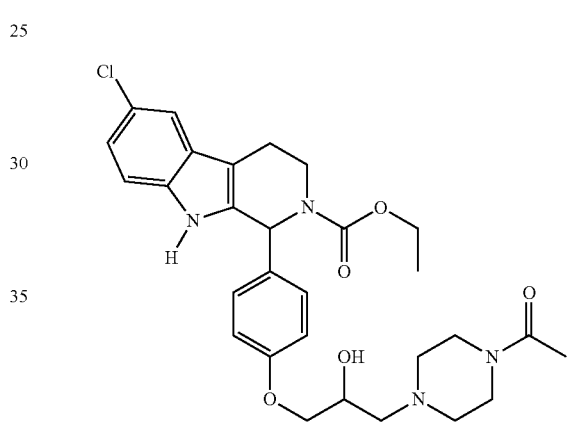
937
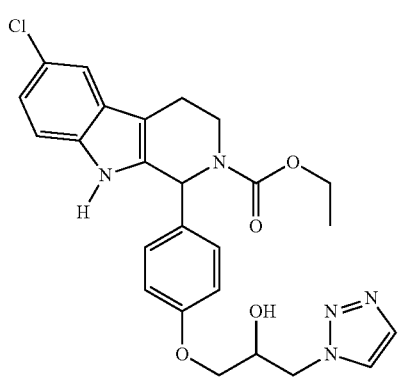
935
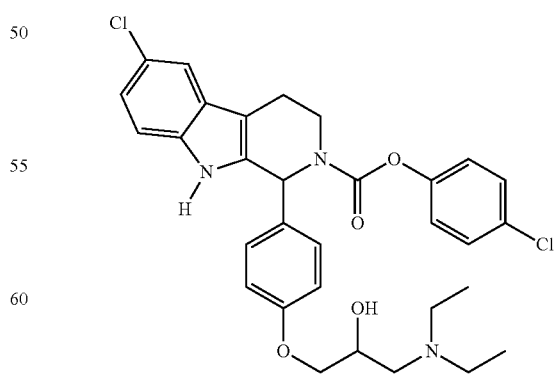
938

TABLE A-continued
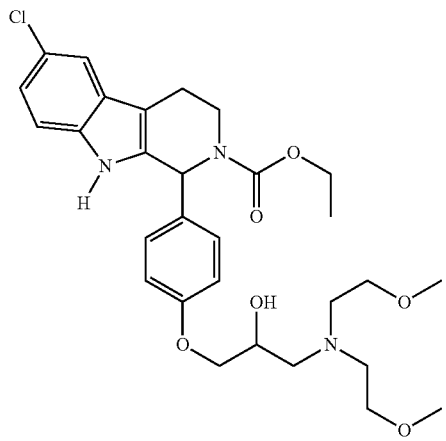
939
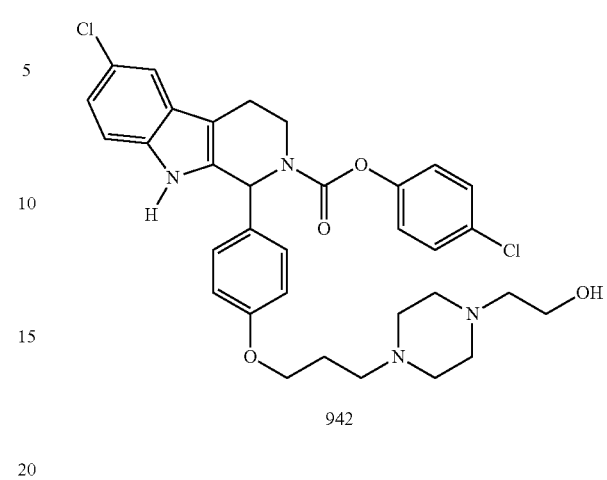
942
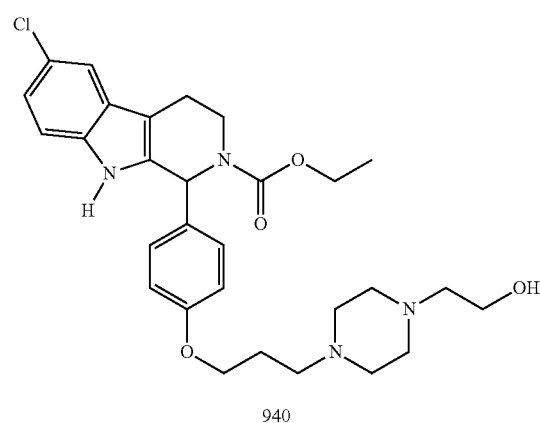
940
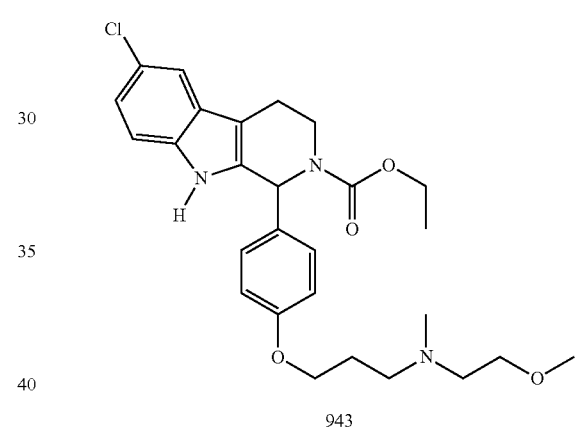
943
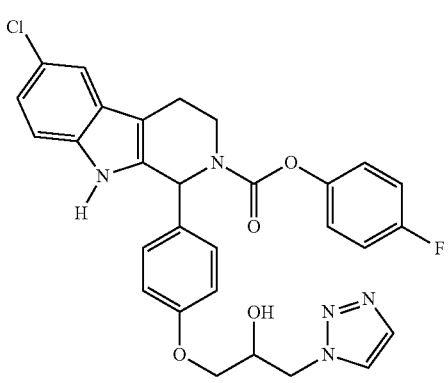
941
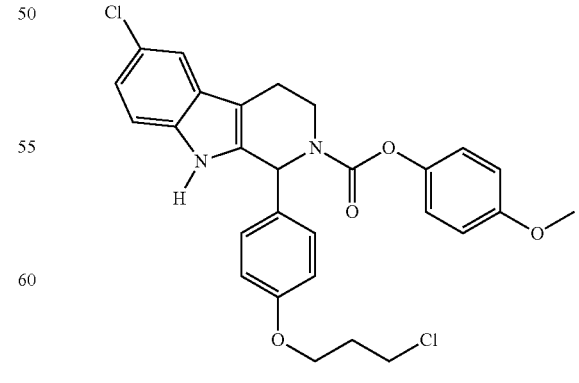
944

TABLE A-continued
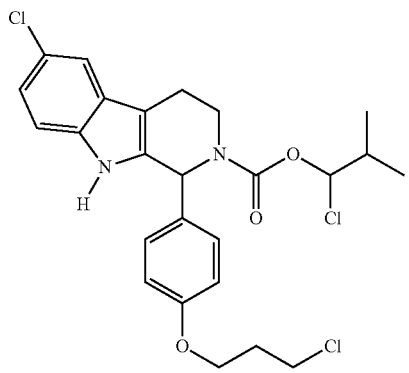
945
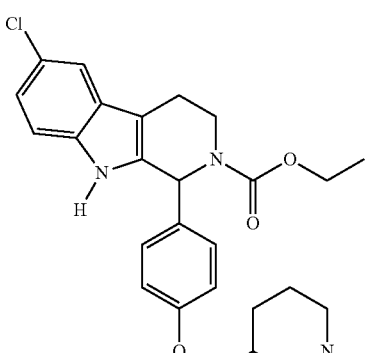
948
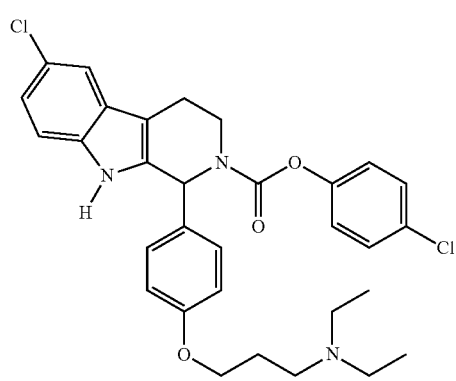
946
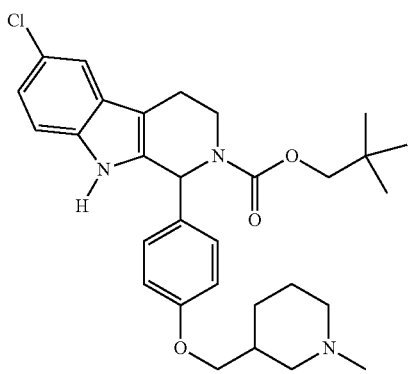
949
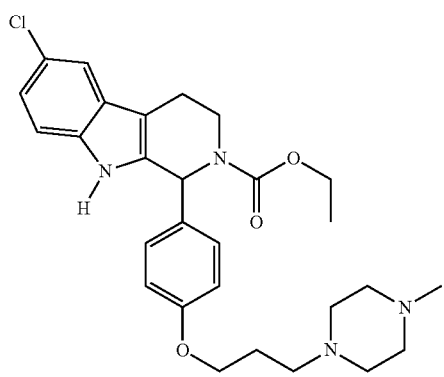
947
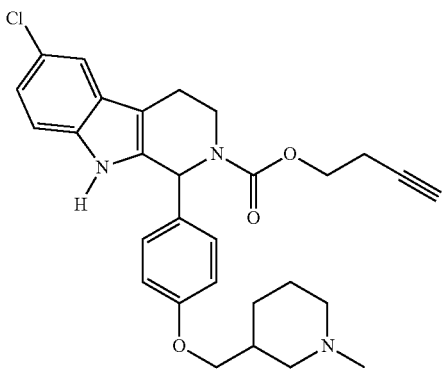
950

TABLE A-continued
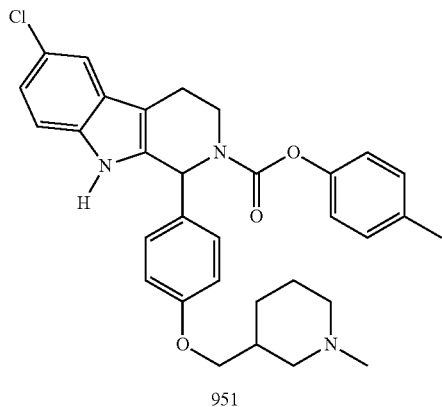
951
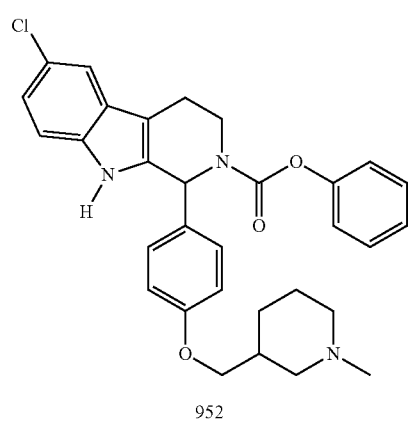
952
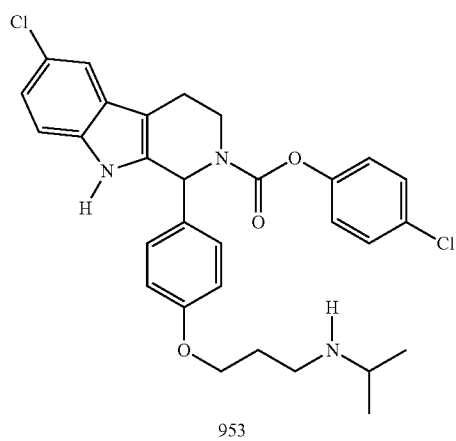
953
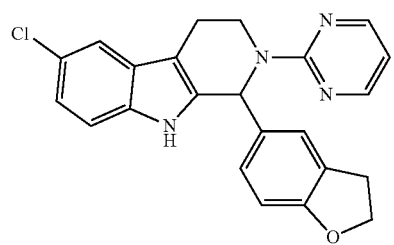
954
TABLE A-continued
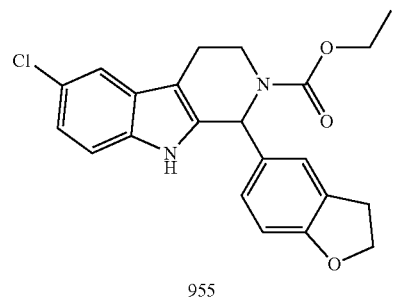
955
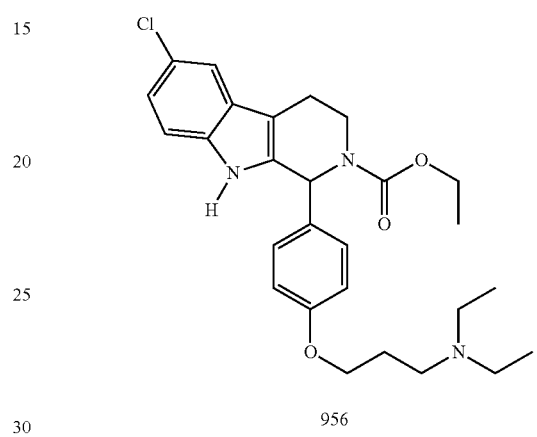
956
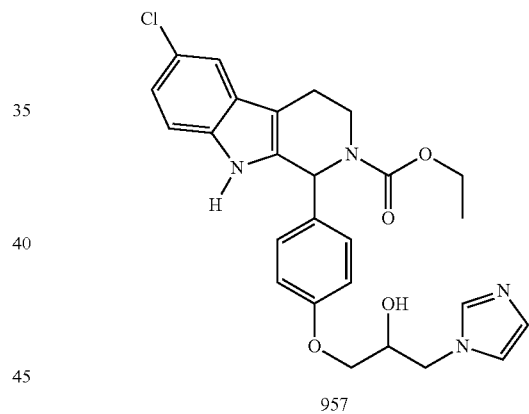
957
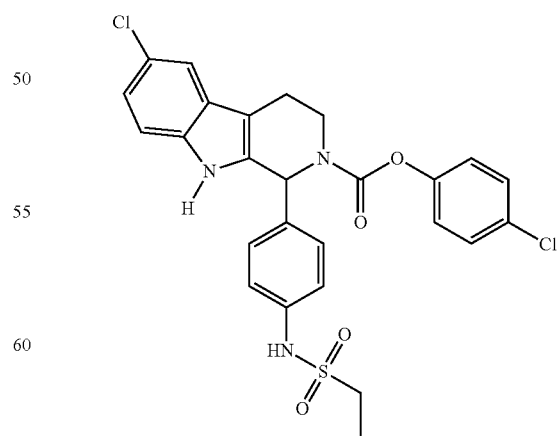
958

TABLE A-continued
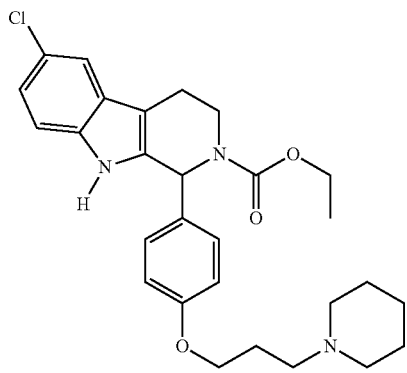
959
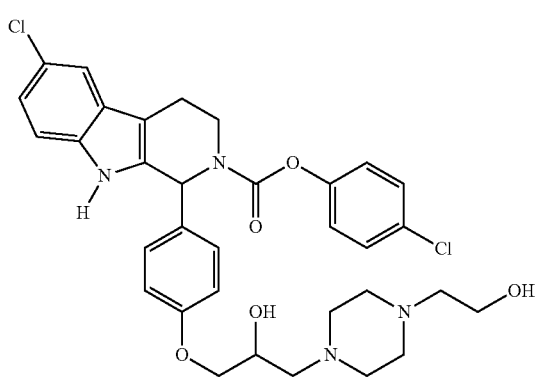
960
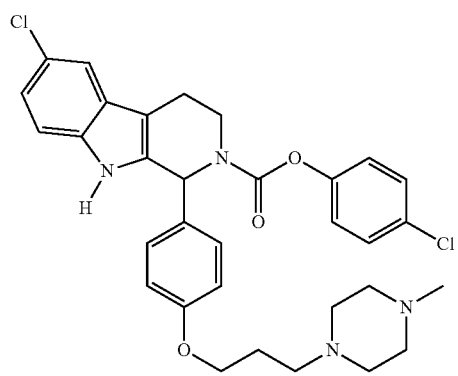
961
TABLE A-continued
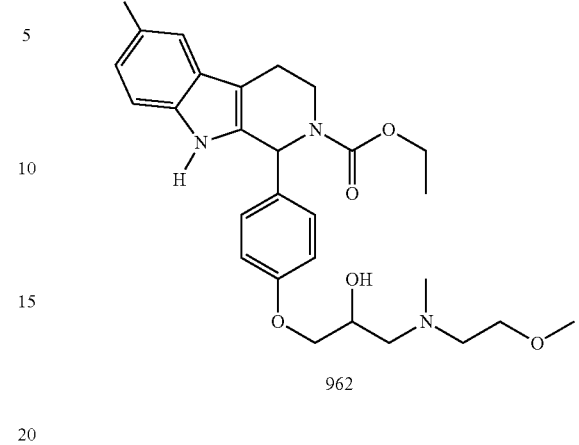
962
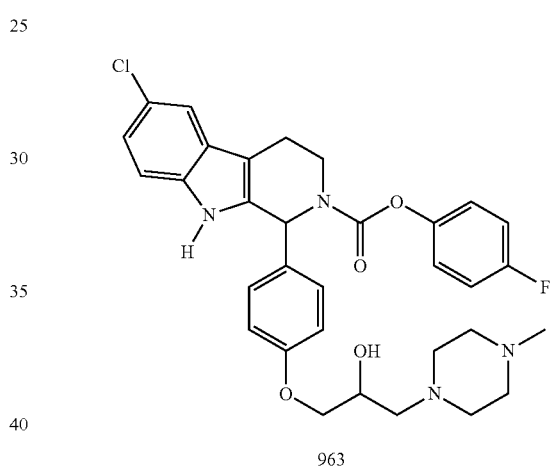
963
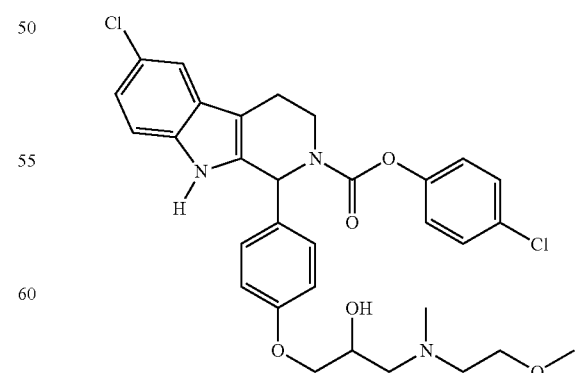
964

TABLE A-continued
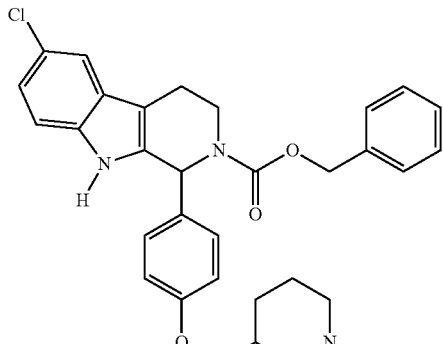
965
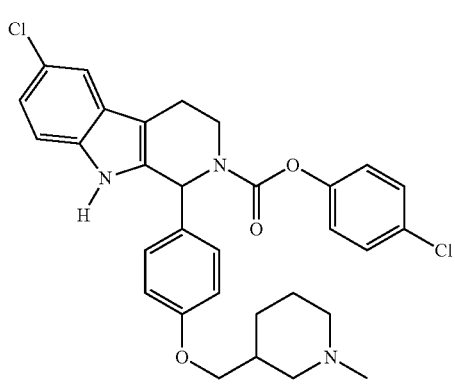
966
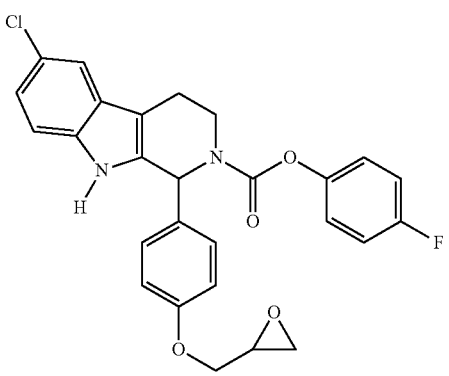
967
TABLE A-continued
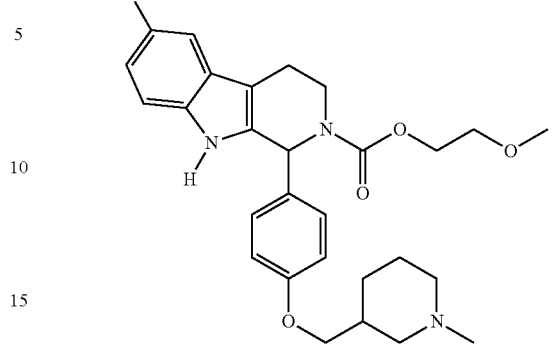
968
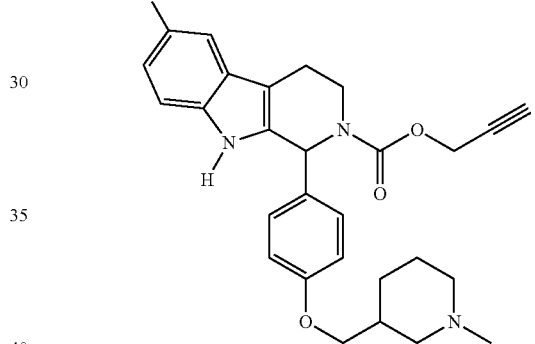
969
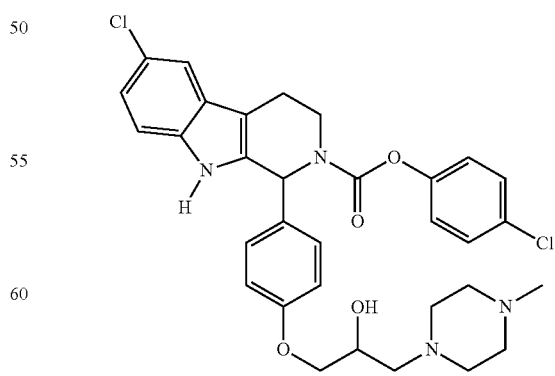
970

TABLE A-continued
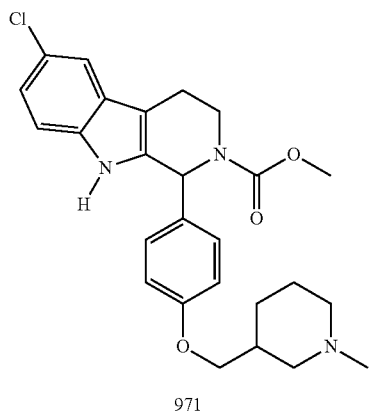
971
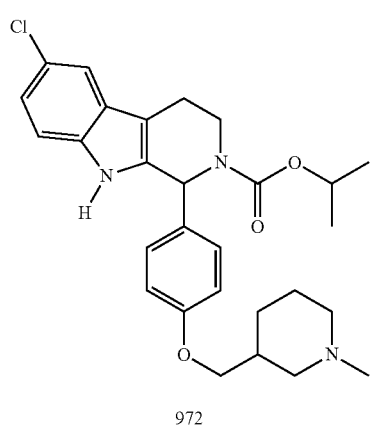
972
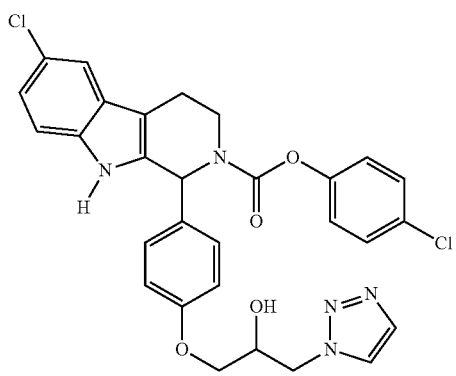
973
TABLE A-continued
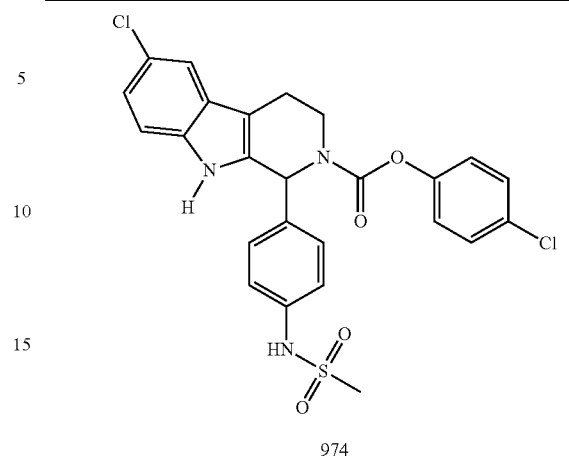
974
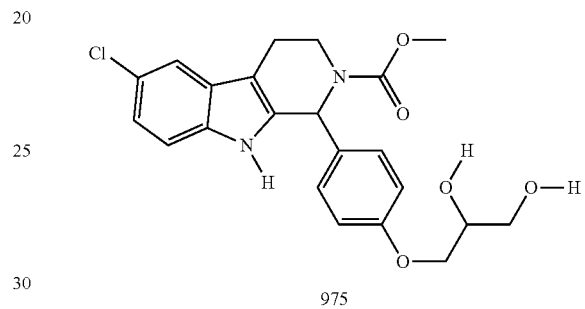
975
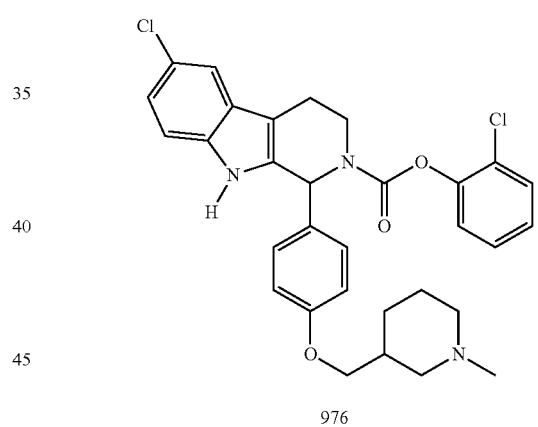
976
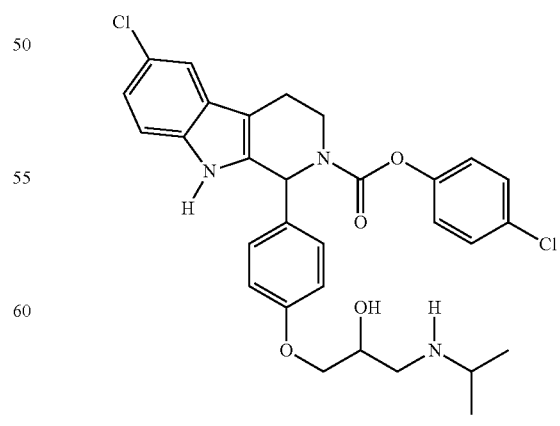
977

TABLE A-continued
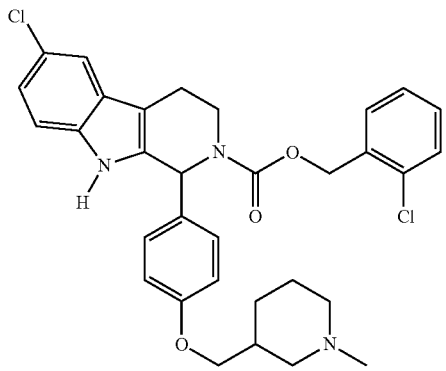
978
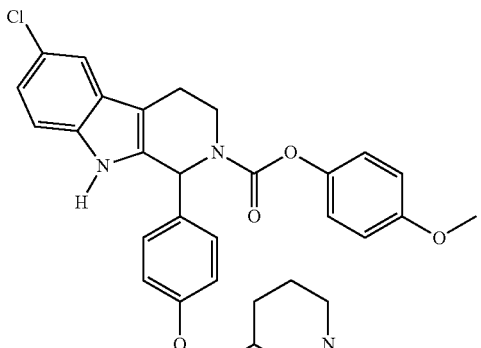
981
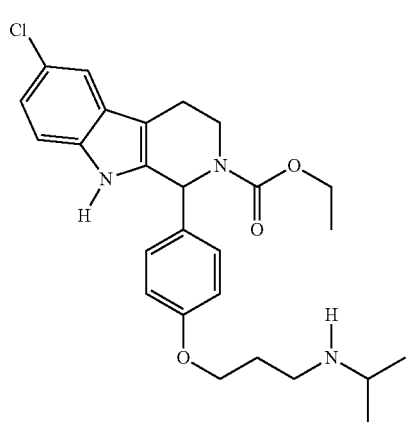
979
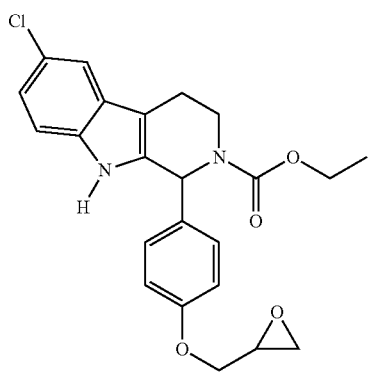
982
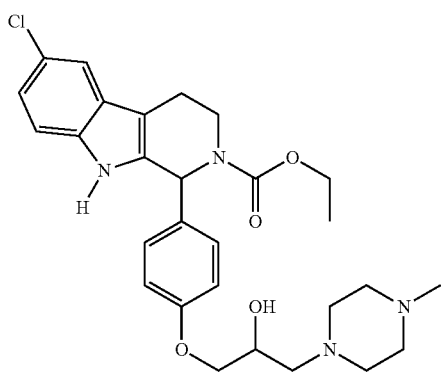
980
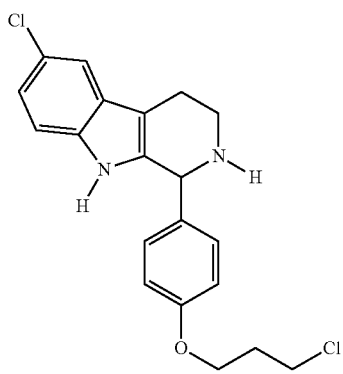
983

TABLE A-continued
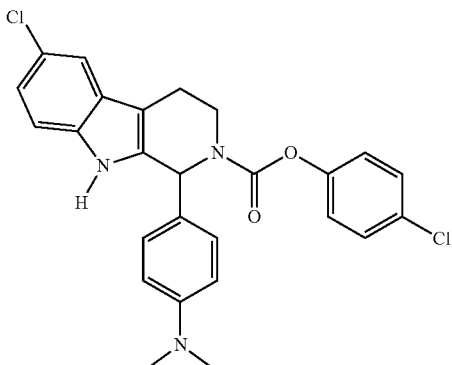
984
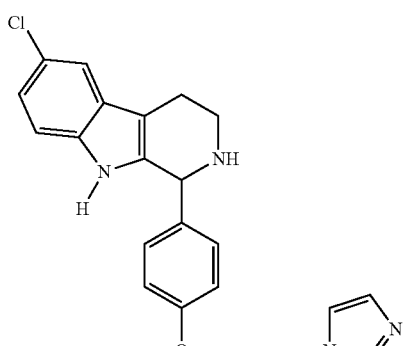
985
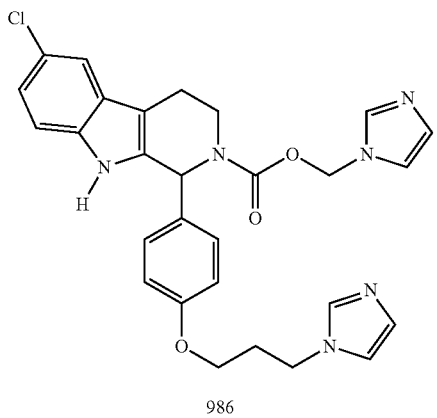
986
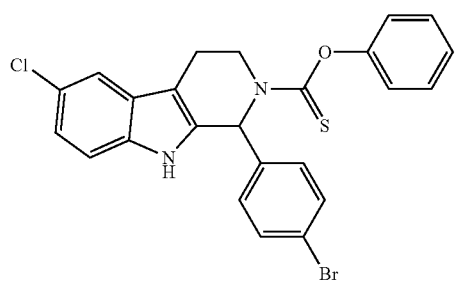
987
TABLE A-continued
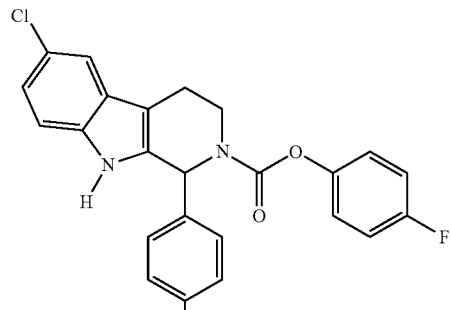
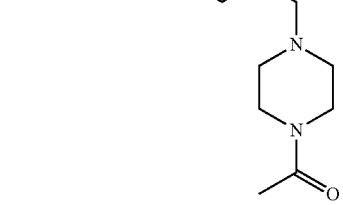
988
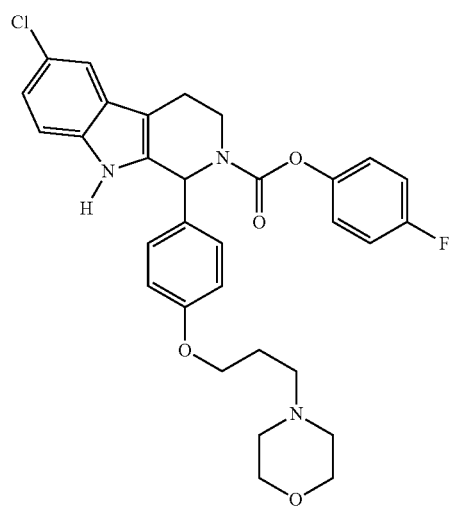
989

TABLE A-continued
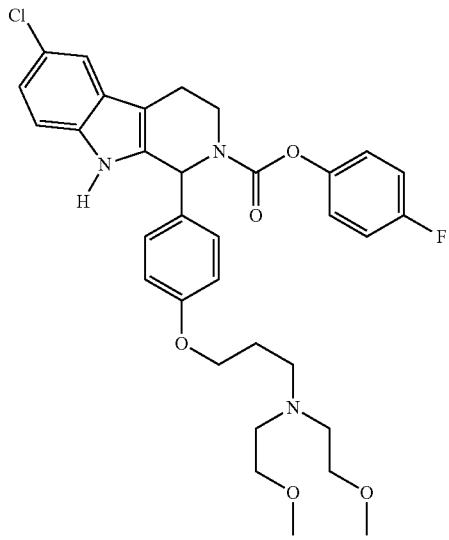
990
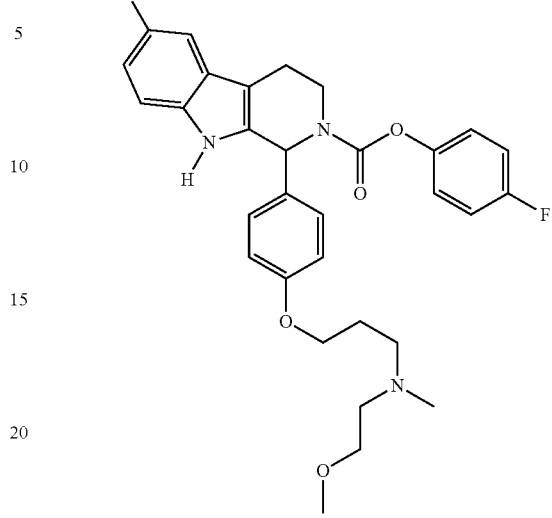
992
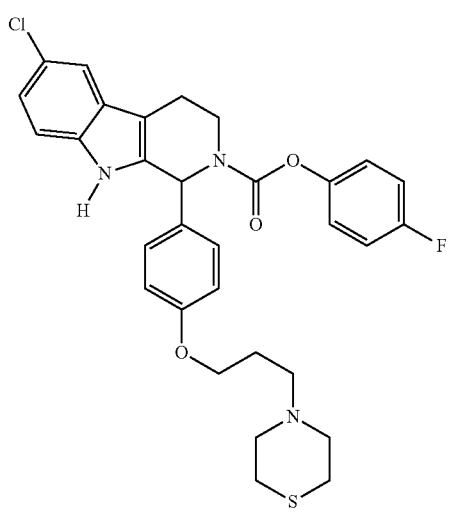
991
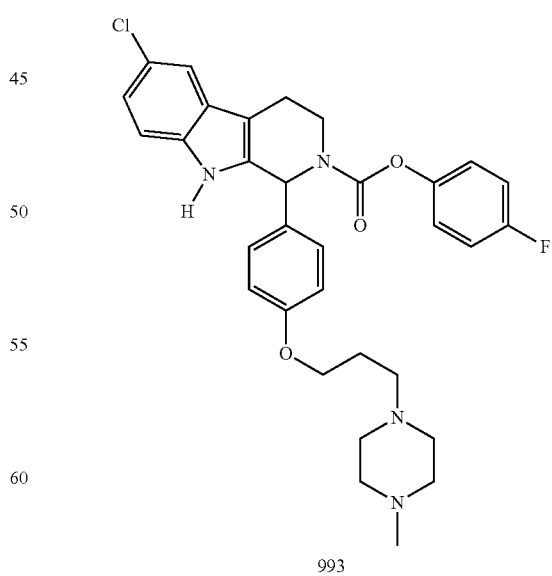
993

TABLE A-continued

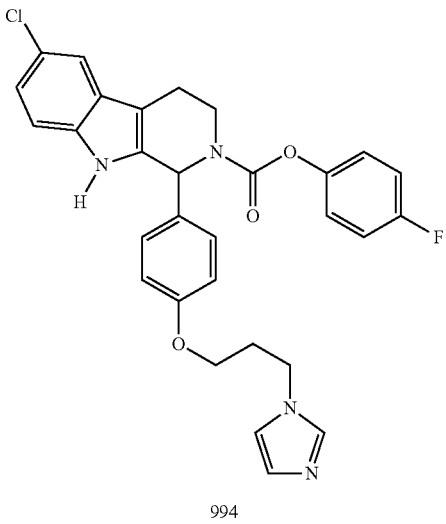

994

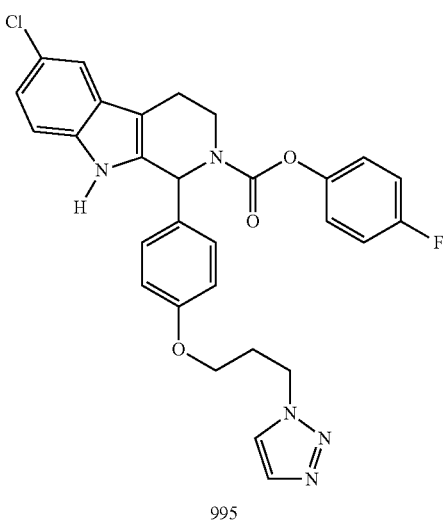

995

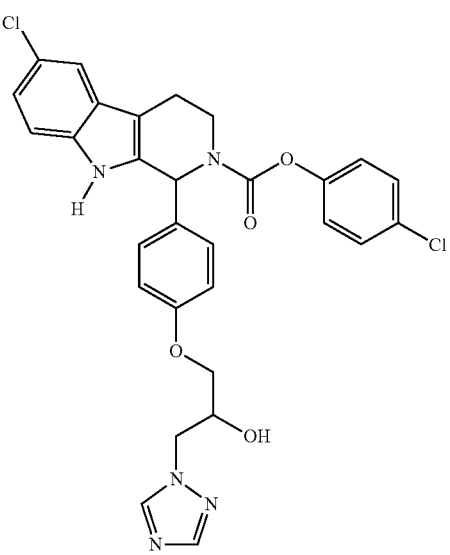

996

In certain embodiments, preferred compounds for inhibition of VEGF translation include those with an $EC_{50}$ in the VEGF ELISA assay described in Example 5 of less than about 2 uM, more preferably between about 2 uM and about 0.04 uM (2000 nM to 40 nM); more preferably from about 0.04 uM to about 0.008 uM to (40 nM to 8 nM); and more preferably less than about 0.008 uM (<8 nM). Preferred compounds are Compound Nos: 2, 4, 5, 7, 8, 10, 11, 12, 17, 23, 25, 81, 102, 112, 140, 328, 329, 330, 331, 332, 355, 816, 817, 818, 823, 824, 825, 830, 831, 832, 837, 838, 841, 842, 843, and regioisomers thereof. In one embodiment, the compounds of the invention form a racemic mixture, and in another embodiment, the compounds of the invention are the (R), (S), (R,R), (S,S), (R,S), (S,R) isomer, in an enantiomerically pure composition. In a further embodiment, the compounds of the invention are the (S) isomers, in an enantiomerically pure composition.

In an embodiment, the above compounds provide examples of VEGF translation-inhibiting compounds. In an embodiment, such compounds may be used in the methods of the invention. In addition, based upon the instant disclosure, the skilled artisan will recognize other compounds intended to be included within the scope of the presently claimed invention.

The present invention includes and provides a method of inhibiting translation of VEGF in a subject comprising administering an effective amount of one or more VEGF translation-inhibiting compounds to a subject in need thereof, wherein translation of VEGF is inhibited. The present invention includes and provides a method of inhibiting translation of VEGF in a subject comprising administering an effective amount of a VEGF translation-inhibiting compound to a subject in need thereof, wherein translation of VEGF is inhibited. In a further embodiment, the present invention includes and provides a method of inhibiting translation of VEGF in a human with an elevated VEGF level comprising administering an effective amount of a VEGF translation-inhibiting compound to the human, wherein translation of VEGF is inhibited.

In an embodiment of the present invention, a "subject" may include any animal. In an embodiment, a subject may include any mammal, such as by way of non-limiting example a human. A "subject" may also include pets (e.g., dogs, cats, horses), as well as livestock, such as for example cows, pigs, and sheep. In a preferred embodiment, a subject is a human.

As used herein, a "subject in need thereof" is any subject who may benefit from administration of a VEGF translation-inhibiting compound. In another embodiment, a subject in need thereof may benefit from a decrease in VEGF level. Exemplary, non-limiting subjects who may benefit from the methods of the invention include those who have or who are at risk of having elevated VEGF levels, cancer, angiogenesis, chronic inflammatory diseases, and combinations thereof.

In a preferred embodiment, the subject in need of VEGF translation inhibition has an elevated VEGF level. In two embodiments, an elevated VEGF level refers to an elevated plasma VEGF level or an elevated serum VEGF level. In another embodiment, an elevated VEGF level refers to an elevated local VEGF level, such as by way of non-limiting example an elevated tumor VEGF level. In another embodiment, an elevated VEGF level refers to an elevated VEGF level in any tissue sample, including for example without limitation, whole blood, cyst or tumor biopsy, or excised tumor. In a further embodiment, an elevated VEGF level refers to an elevated VEGF level in any bodily fluid, including without limitation, sweat, saliva, semen, vaginal secretion, tears, or mucous. In a further embodiment, an elevated VEGF level refers to any combination of such elevated VEGF levels.

In another embodiment, an elevated VEGF level is a VEGF level in a subject that is higher than normal for that subject when healthy. In another aspect, an elevated VEGF level is a VEGF protein level in a subject that is higher than normal for a healthy population of the same species as the subject. In a further embodiment, an elevated VEGF level is a VEGF level in a tissue of a subject that is locally higher than normal in that tissue when the subject is healthy. In another embodiment, an elevated VEGF level is a VEGF level in a tissue of a subject that is locally higher than normal for a healthy population of the same species as the subject. In an embodiment, an elevated VEGF level may be about 10%, about 25%, about 50%, about 75%, about 100%, about 200% about 300%, about 500%, about 1000%, or more than about 1000% higher than normal for the subject when healthy or for a healthy population.

In further embodiments, an elevated VEGF level is a serum VEGF level that is greater than about 300 pg/mL, greater than about 350 pg/mL, greater than about 400 pg/mL, greater than about 450 pg/mL, greater than about 500 pg/mL, greater than about 550 pg/mL, greater than about 600 pg/mL, greater than about 650 pg/mL, greater than about 700 pg/mL, greater than about 750 pg/mL, greater than about 800 pg/mL, greater than about 900 pg/mL, greater than about 1000 pg/mL, greater than about 1250 pg/mL, or greater than about 1500 pg/mL, measured by ELISA assay.

In another aspect, a subject in need has cancer or angiogenesis or both cancer and angiogenesis. In yet another aspect, a subject in need has been diagnosed with cancer. In another embodiment, a subject has an elevated VEGF level and has cancer. In another embodiment, a subject in need has an elevated VEGF level and has been diagnosed with cancer.

As used herein, diagnosis of a subject with any disease or condition refers to an assessment of disease or condition, such as for example by medical or laboratory personnel or a combination of such personnel.

In another embodiment, a subject in need includes a subject with a solid tumor cancer. Solid tumor cancers include by way of non-limiting example solid tumor carcinomas and solid tumor sarcomas. Solid tumor carcinomas include, but are not limited to, pediatric solid tumors, such as Wilms tumor and neuroblastoma, and carcinomas of the epidermis, such as malignant melanomas, as well as lung cancers, cervical cancers, colon cancers and renal cancers. Solid tumor sarcomas include, but are not limited to, fibrosarcomas. The methods of treating cancer can further include the administration of one or more additional agents useful for treating cancer. In an embodiment, a subject with a solid tumor cancer has an elevated VEGF level.

In a further embodiment of the present invention, methods are provided wherein a subject in need has been diagnosed with diabetic retinopathy, rheumatoid arthritis, psoriasis, atherosclerosis, chronic inflammation, a chronic inflammation-related disease or disorder, obesity, or exudative macular degeneration. In another embodiment, a subject in need has an elevated VEGF level and has been diagnosed with diabetic retinopathy, rheumatoid arthritis, psoriasis, atherosclerosis, chronic inflammation, a chronic inflammation-related disease or disorder, obesity, or exudative macular degeneration.

In another embodiment, a subject in need has been diagnosed with a disease or condition associated with aberrant angiogenesis. In an embodiment, a subject diagnosed with a disease or condition associated with aberrant angiogenesis has an elevated VEGF level.

In an embodiment, aberrant angiogenesis refers to any angiogenesis that is inappropriate to the healthy state of a subject. In another embodiment, aberrant angiogenesis refers to any angiogenesis that contributes to the disease state of a subject. In an embodiment, aberrant angiogenesis refers to angiogenesis associated with tumorigenesis. In further embodiments, non-limiting examples of diseases or conditions associated with aberrant angiogenesis include diabetic retinopathy, rheumatoid arthritis, psoriasis, atherosclerosis, chronic inflammation, a chronic inflammation-related disease or disorder, obesity, or exudative macular degeneration, cancer, including a solid tumor cancer, Wilms tumor, neuroblastoma, malignant melanoma, cervical cancer, lung cancer or colon cancer. Additional diseases and conditions associated with aberrant angiogenesis are apparent to those of skill in the art.

The terms VEGF translation inhibiting amount, anti-angiogenic amount, and effective amount, as used herein, refer to an amount of a pharmaceutical agent to treat, ameliorate, or prevent the identified disease or condition, or to exhibit a detectable therapeutic or inhibitory effect. For example, in an embodiment, an effective amount of a VEGF translation-inhibiting compound is an amount sufficient to produce a detectable inhibition of VEGF translation.

The precise effective amount for a subject will depend upon the subject's body weight, size, and health; the nature and extent of the condition; and the therapeutic or combination of therapeutics selected for administration. Therapeutically effective amounts for a given subject can be determined by routine experimentation that is within the skill and judgment of the clinician.

In an embodiment of the present invention, VEGF translation-inhibiting compounds may be administered to a subject via any drug delivery route known in the art. Specific exemplary administration routes include oral, ocular, rectal, buccal, topical, nasal, ophthalmic, subcutaneous, intramuscular, intravenous (bolus and infusion), intracerebral, transdermal, and pulmonary. In one embodiment, a VEGF translation-inhibiting compound is administered orally. In another embodiment, a VEGF translation-inhibiting compound is administered intravenously. In another embodiment, the VEGF translation-inhibiting compound is administered at the site of a tumor. Administration at the site of a tumor may include without limitation administering to one or more sites at the periphery of a tumor, to the entire periphery of a tumor, or injection directly into a tumor.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The data obtained from cell culture assays and animal studies may be used in formulating a range of dosage for human use. The dosage contained in such compositions is preferably within a range of circulating concentrations that include an $ED_{50}$ with little or no toxicity. The dosage may vary within this range depending upon the dosage form employed, sensitivity of the patient, and the route of administration.

More specifically, the concentration-biological effect relationships observed with regard to the compound(s) of the present invention indicate an initial target plasma concentration ranging from approximately 0.1 µg/mL to approximately 100 µg/mL, preferably from approximately 5 µg/mL to approximately 50 µg/mL, more preferably from approximately 5 µg/mL to approximately 10 µg/mL. To achieve such plasma concentrations, the compounds of the invention may be administered at doses that vary from 0.1 µg to 100,000 mg, depending upon the route of administration. Guidance as to particular dosages and methods of delivery is provided in the literature and is generally available to practitioners in the art. In general the dose will be in the range of about 1 mg/day to about 10 g/day, or about 0.1 g to about 3 g/day, or about 0.3 g to about 3 g/day, or about 0.5 g to about 2 g/day, in single, divided, or continuous doses for a patient weighing between about 40 to about 100 kg (which dose may be adjusted for patients above or below this weight range, particularly children under 40 kg).

The exact dosage will be determined by the practitioner, in light of factors related to the subject that requires treatment. Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

In an embodiment, more than one compound of the invention may be administered to a subject in order to inhibit VEGF translation. In another embodiment, a second active ingredient, such as for example an ingredient useful in the treatment of cancer, diabetic retinopathy, or exudative macular degeneration, may be formulated together or separately, and may be administered concurrently with, or sequentially to one or more VEGF translation-inhibiting compounds. In an embodiment, the administration of more than one compound to a subject may have a synergistic effect.

In various embodiments, administration of an effective amount of a VEGF translation-inhibiting compound produces inhibition of translation. In an embodiment, inhibition is measured as percentage reduction in VEGF translation following administration of a translation-inhibiting compound. e.g., expressed as ((original VEGF level minus VEGF level after administration)/original VEGF translation)×100. In an embodiment, VEGF translation is inhibited by at least about 10%, by at least about 17%, by at least about 25%), by at least about 33%, by at least about 50%, by at least about 75%, by at least about 80%, by at least about 85%, by at least about 90%, by at least about 95%, by at least about 98%, or by at least about 99%. In another embodiment, translation of VEGF is completely (100%) inhibited.

In other embodiments, translation of VEGF is inhibited between about 10% and about 100%, between about 25% and about 99%, between about 33% and about 99%, between about 50% and about 99%, between about 75% and about 99%, or between about 92% and about 99%.

In a preferred embodiment, inhibition of VEGF translation is measured by measuring a reduction in VEGF protein level. In another preferred embodiment, inhibition of VEGF translation is measured by measuring a reduction in VEGF protein level using R&D Systems ELISA assay according to manufacturer's instructions.

In an embodiment, inhibition of VEGF translation is measured by comparing VEGF protein level before and after administration of a VEGF translation-inhibiting compound. In an embodiment, VEGF protein level is measured at any time before administration of a translation-inhibiting compound. In another embodiment, VEGF protein level before administration is measured by measuring protein level at about 15 minutes, about 30 minutes, about 1 hour, about 3 hours, about 5 hours, about 10 hours, about 24 hours, about 2 days, about 5 days, about 7 days, about 10 days, about 20 days, about 30 days, about 60 days, about 100 days, or more than one year prior to administration of a VEGF translation-inhibiting compound. In another embodiment, VEGF protein level is measured at about 15 minutes, about 30 minutes, about 1 hour, about 3 hours, about 5 hours, about 10 hours, about 24 hours, about 2 days, about 5 days, about 7 days, about 10 days, about 20 days, about 30 days, about 60 days, about 100 days, more than one year, or more than five years after administration of a VEGF translation-inhibiting compound.

In another embodiment, VEGF protein level measured at any time before administration of a translation-inhibiting compound is compared with VEGF protein level measured at about 15 minutes, about 30 minutes, about 1 hour, about 3 hours, about 5 hours, about 10 hours, about 24 hours, about 2 days, about 5 days, about 7 days, about 10 days, about 20 days, about 30 days, about 60 days, about 100 days, more than one year, or more than five years after administration of a VEGF translation-inhibiting compound. In a further embodiment, VEGF protein level measured at about 1 hour, about 3 hours, about 5 hours, about 10 hours, about 24 hours, about 2 days, about 5 days, about 7 days, about 10 days, about 20 days, about 30 days before administration of a VEGF translation-inhibiting compound is compared with VEGF level measured at about 1 hour, about 3 hours, about 5 hours, about 10 hours, about 24 hours, about 2 days, about 5 days, about 7 days, about 10 days, about 20 days, about 30 days, about 60 days, about 100 days, or more than one year after administration of a VEGF translation-inhibiting compound.

In an embodiment, reduction in VEGF protein level may be expressed as a percentage change compared to VEGF level prior to administration of a translation-inhibiting compound, for example as ((VEGF protein level before administering a VEGF translation-inhibiting compound minus VEGF protein level after administration)/VEGF protein level before administration)×100.

In an embodiment, VEGF protein level may be reduced by about 10%, about 20%, about 30%, about 40%, about 50%, about 60%, about 70%, about 75%, about 80%, about 85%, about 90%, about 92%, about 95%, about 97%, about 98%, about 99%, or about 100% as compared with VEGF protein level prior to administration of a VEGF translation-inhibiting compound.

In an embodiment, inhibition of VEGF translation is measured by a reduction in serum VEGF level. In another embodiment, inhibition of VEGF translation is measured by a reduction in plasma VEGF level. In a further embodiment, inhibition of VEGF translation is measured by a reduction in local VEGF level, including for example a reduction in VEGF level in a tumor, tissue sample, or bodily fluid.

In an embodiment, reduction of VEGF protein level can be measured by ELISA assay or by quantitative immunofluorescence. In another embodiment, reduction of VEGF protein level can be measured as in Example 4. In a preferred embodiment, VEGF protein levels are measured according to manufacturer's instructions, using R&D Systems ELISA assay for determining VEGF level.

In an embodiment of the invention, a method of inhibiting VEGF translation further comprises measuring the inhibition of translation.

In another embodiment, a method of inhibiting VEGF translation further comprises treating sepsis.

In another embodiment, a method of inhibiting VEGF translation further comprises treating angiogenesis in a subject. In another embodiment, a method of inhibiting VEGF translation further comprises treating a disease or condition associated with aberrant angiogenesis.

In other embodiments, a method of inhibiting VEGF translation further comprises treating diabetic retinopathy, rheumatoid arthritis, psoriasis, atherosclerosis, chronic inflammation, a chronic inflammation-related disease or disorder, obesity, or exudative macular degeneration.

In another embodiment, a method of inhibiting VEGF translation further comprises treating cancer. In an embodiment, a method of inhibiting VEGF translation further comprises treating a solid tumor cancer. In another embodiment, a method of inhibiting VEGF translation comprises treating Wilms tumor, neuroblastoma, malignant melanoma, cervical cancer, lung cancer or colon cancer.

In a further embodiment, a method of inhibiting VEGF translation further comprises slowing tumorigenesis at a pre-vascular stage. A pre-vascular stage of tumorigenesis is known as "carcinoma in situ", and tumors at this stage are characterized by their reliance on nearby blood vessels for oxygen and diffusion nutrients, due to a lack of vascular infrastructure in the tumor itself at this stage.

In another embodiment, a method of inhibiting VEGF translation further comprises reducing perivascularly sequestered or intratumoral VEGF. In this aspect, reduced perivascularly sequestered VEGF is an in situ comparison of perivascular VEGF in tumors treated with a VEGF translation-inhibiting compound and tumors not treated with a VEGF translation-inhibiting compound. In another embodiments reduced perivascularly sequestered VEGF is compared with levels of perivascular VEGF in tumors treated with antibodies to VEGF.

Another embodiment of the present invention relates to a method of decreasing VEGF level in a subject in need thereof comprising inhibiting translation of VEGF in the subject by administration of a VEGF translation-inhibiting compound; and measuring a decrease in VEGF level in the subject. A further embodiment of the present invention relates to a method of decreasing VEGF level in a human with an elevated VEGF level comprising inhibiting translation of VEGF in the human by administration of a VEGF translation-inhibiting compound; and measuring a decrease in VEGF level in the human.

Another embodiment of the present invention relates to a method of identifying a compound as a VEGF translation-inhibiting compound, the method comprising contacting a test compound with one or more cells having an elevated VEGF level; measuring a decrease in VEGF translation; and identifying the test compound as a VEGF translation-inhibiting compound by a decrease in VEGF translation.

In an embodiment, a test compound is any compound being tested for VEGF translation-inhibition activity. In one embodiment, the test compound has not previously been identified as a VEGF translation-inhibiting compound. In another embodiment, the test compound has not previously been used to treat angiogenesis or cancer. In a further embodiment, the test compound is a compound of Formula I.

In an embodiment of the present invention, contacting a test compound with one or more cells having an elevated VEGF level refers to placing the compound and cells in the same container or solution. In another embodiment, contacting refers to permitting the compound and the cells to touch one another. In an embodiment, contacting is performed in vitro. In another embodiment, contacting is performed in cell culture. In a further embodiment, contacting is performed in vivo.

The following Examples describe aspects and embodiments of the present invention and are provides for illustrative purposes only. These Examples are not meant to limit the scope of the invention in any way.

EXAMPLES

Example 1

Amplification of VEGF 3'- and 5'-UTRs

VEGF-A 5'- & 3'-UTRs are amplified from a HeLa cell cDNA library and cloned into a GEMS (Gene Expression Modulation by Small Molecules) reporter construct by cloning into the polylinker of pcDNA3.1 (Invitrogen, Carlsbad, Calif.).

The VEGF 5'-UTR is quite long and because of its high GC-content, is highly structured. The 5'-UTR of VEGF contains an IRES element that bypasses the stress-induced (e.g. hypoxia) shutdown of translation initiation. Additionally, the 3'UTR contains multiple AREs (AU-rich elements) that, without being limited by any theory, are believed to be involved in mRNA stability in both stress and developmentally regulated VEGF expression. These features of the VEGF mRNA make VEGF a desirable GEMS target.

Example 2

Screening of VEGF-Inhibiting Compounds

High-throughput screening (HTS) assays are conducted using compounds of Formula I. Each compound is screened for inhibition of reporter activity at a single concentration (7.5 µM). Compounds are dissolved in DMSO to a final DMSO concentration of 0.5%. 293T cells stably expressing luciferase reporter construct from Example 1 are seeded at 10,000 cells/well in a 384-well plate and incubated with compound at 7.5 uM overnight for about 16 hrs. Luciferase activity is monitored by adding 20 uL of Luclite® (Perkin Elmer, Wellesley, Mass.) and measuring fluorescence in a ViewLux. Percent inhibition is calculated by the following formula [((1-treated sample)/untreated control)*100].

Compounds exhibiting more than 62% inhibition of reporter activity are selected for cherry-picking and reconfirmation assays. This results in about 1100 hits. Approximately 60% of all HTS hits are confirmed in subsequent HTS reporter assays. These compounds are repurchased for further analysis, including UTR-specificity assays, endogenous protein assays (e.g. ELISAs), and selectivity assays.

Example 3

Compounds that inhibit luciferase activity in HTS are assayed in a dose-dependent manner in the firefly luciferase reporter system as described above.

The activity of hits against stable cell lines that contain the VEGF 5' and 3' untranslated regions is compared to activity against constructs containing other post-transcriptionally controlled UTRs (IRES, HIF1a and DPPIV) or a synthetic, non-post-transcriptionally regulated UTR. As shown in FIG. 1, a compound of Formula I specifically inhibits reporter gene expression in a VEGF UTR-dependent manner when compared to the other UTR-containing constructs in a low nanomolar range.

In cell based reporter assays, UTR specificity does not require a physical association between the compound and the 5'- and 3'-UTR RNAs. Compounds can modulate gene expression in a UTR-dependent manner by interacting with proteins or complexes of proteins that are involved in post-transcriptional control of gene expression. For example, in the case of VEGF, compounds could interfere with one or more of the required cofactors for cap-independent translation which would result in the UTR-dependent inhibition of both the luciferase reporter and, likely, endogenous VEGF.

Example 4

Inhibition of VEGF Variants

Figure 2:
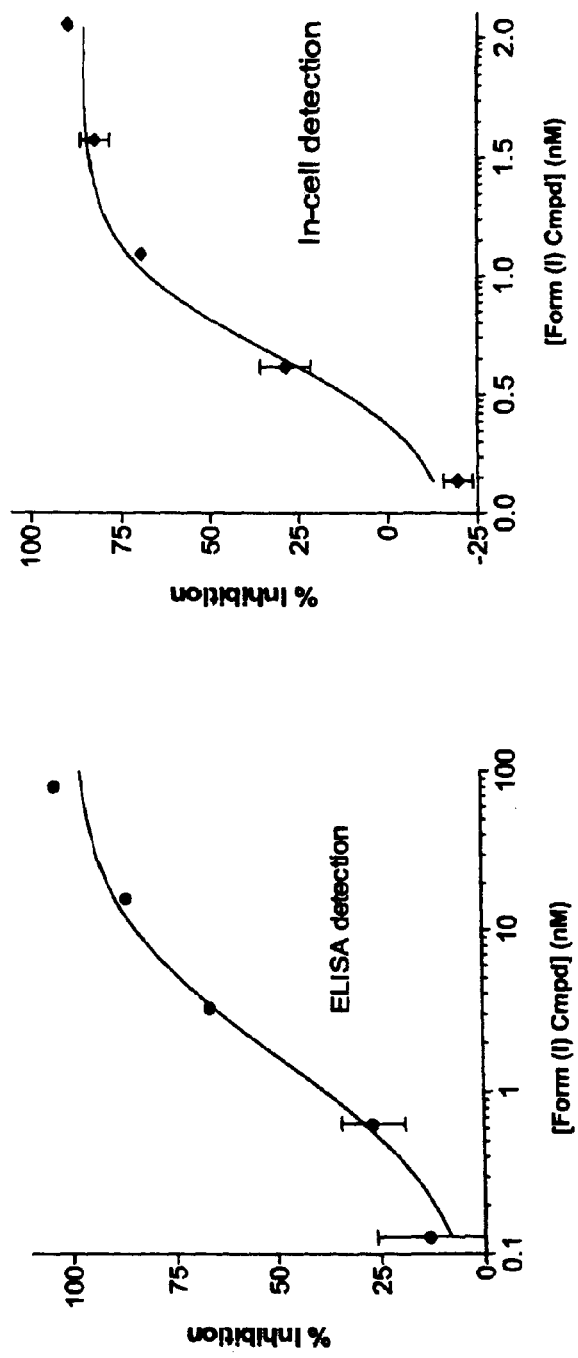
FIG. 2 illustrates attenuated expression of four subunits of the endogenous VEGF gene (VEGF121 and 165, soluble, and VEGF189 and 206, cell associated) by a compound of Formula I, with protein levels monitored via ELISA assay (R&D Systems) in HeLa cells (left panel) and via quantitative immunoflouresence (In-Cell Western) in HT1080 cells (right panel).

VEGF is alternatively spliced to produce four variants (VEGF121, 165, 189 and 206). The two smaller forms of VEGF (VEGF121 and 165) are secreted and soluble while the larger forms (VEGF189 & 206) are both cell associated and remain bound to the extracellular matrix. To determine if the compound of Formula I attenuates expression of the major forms of the endogenous VEGF gene, protein levels are monitored via ELISA assay (R&D Systems) in HeLa cells (FIG. 2, left panel) and quantitative immunoflouresence (In-Cell Western) in HT1080 cells (FIG. 2, right panel).

The ELISA (R&D Systems, Catalog No. DY293B) monitors the soluble isoforms of VEGF in the conditioned media and the In-Cell Western monitors the larger, cell-associated forms of VEGF. The Western is performed with three independent antibodies against VEGF, including ELISA capture antibody (R&D Systems, Catalog No. DY293B), C-1 (Santa Cruz Biotechnology, Catalog No. sc-7269), and G143-850 (BD PharMingen, Catalog No. 554539).

The results suggest that the compound of Formula I inhibits all four alternatively spliced isoforms of VEGF. In addition, the compound of Formula I inhibits VEGF in a wide variety of cell lines and tumor types, exhibiting $EC_{50}$s in the 5-10 nM range.

Example 5

Epitope-Tagged VEGF Expression Constructs

To show that the VEGF 5'-UTR plays a role in the activity and specificity of the compound of Formula I, epitope-tagged VEGF expression constructs are constructed in which the VEGF coding sequence contains a C-terminal VS epitope tag and is preceded by the VEGF or control (or non-specific) 5'-UTR. Cell lines exhibiting stable expression of epitope-tagged exogenous VEGF are generated to permit greater sensitivity in monitoring differences in VEGF expression and to provide sufficient VEGF expression for pulse-labeling immunoprecipitation studies.

The expression levels of secreted and intracellular exogenous epitope-tagged VEGF is monitored in HT1080 VEGF-V5+/−5'-UTR stable clones following an overnight treatment of the compound of Formula I dose response curve (starting concentration of 100 nM with serial three-fold dilutions) with a polyclonal anti-V5 antibody. Actin levels are also monitored as a control. Supernatant and lysate VEGF protein levels remain unchanged with varying compound concentration in the absence of 5' UTR. Supernatant and lysate VEGF protein levels are reduced with increasing compound concentration in the presence of a 5' UTR. Actin levels remain unchanged in the presence of 5'UTR and varying amounts of compound. These results suggest the involvement of the VEGF 5'-UTR in inhibition of both secreted and intracellular VEGF.

Example 6

Determination of Inhibition of VEGF Translation

Figure 3:
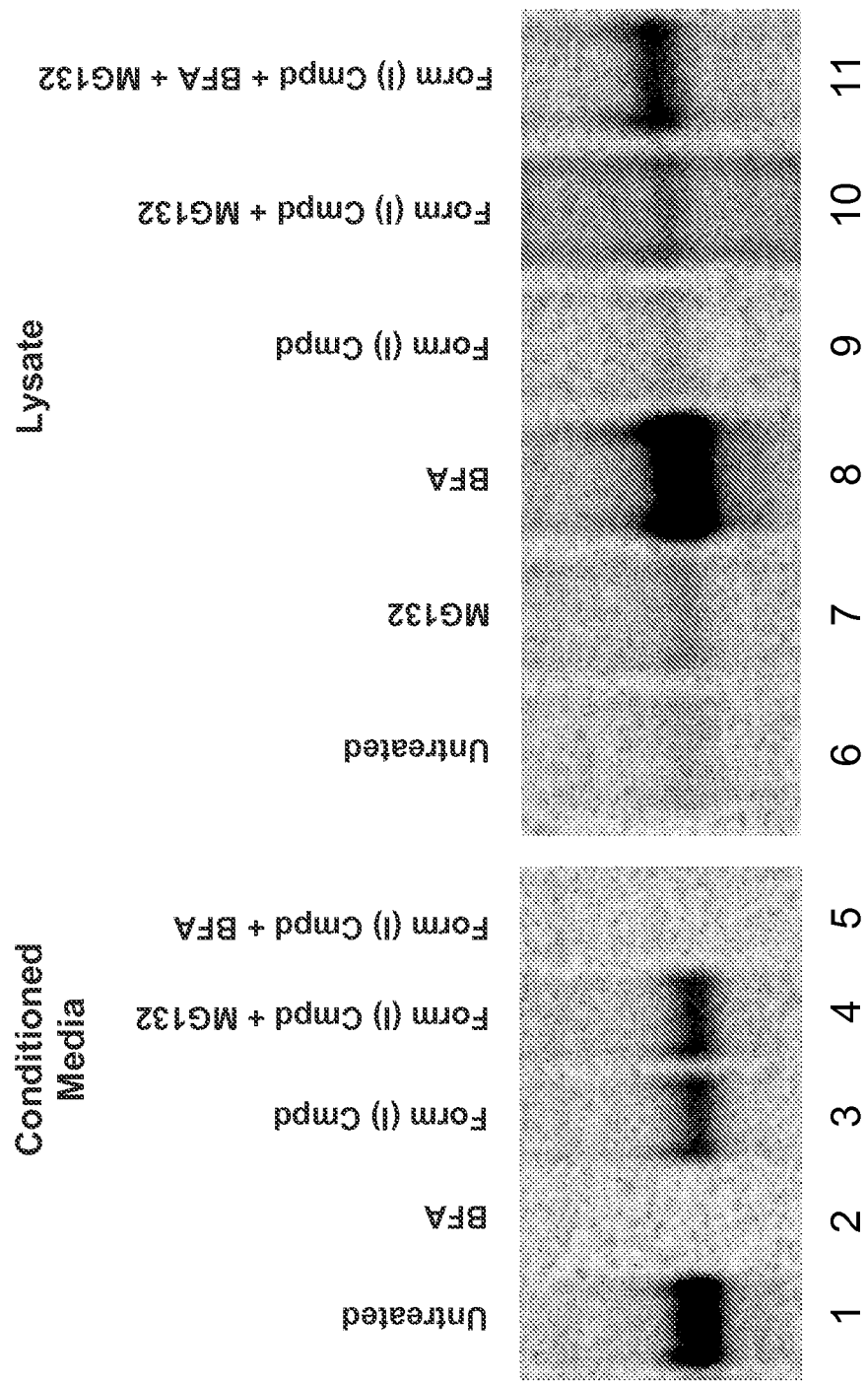
FIG. 3 illustrates immunoprecipation studies of pulse-labeled VEGF to identify inhibition of VEGF translation or steps following translation (e.g. secretion or protein degradation).

To determine if compounds of Formula I inhibit VEGF translation or steps following protein synthesis (e.g. secretion or protein degradation), immunoprecipitation studies of pulse-labeled VEGF are performed. HT1080 clones stably expressing epitope-tagged VEGF with the 5'-UTR are pretreated overnight with 100 nM of a compound of Formula I, followed by a four hour "pulse" of $^{35}$S-Met along with various secretion and proteasome blocking agents. As shown in FIG. 3, the compound of Formula I (100 nM) significantly inhibits VEGF expression (lane 1 compared to lane 3).

To determine if the reduction of VEGF in conditioned media upon treatment by the compound of Formula I is a result of a block in the VEGF secretory pathway, the effect of the compound of Formula I is compared to a known secretion blocking agent, Brefeldin A (BFA). (Sigma, Catalog No. B6542). HT1080 clones stably expressing epitope-tagged VEGF with the 5'-UTR are pretreated overnight with 100 nM of a compound of Formula I, followed by a four hour "pulse" of $^{35}$S-Met along with BFA at a final concentration of 1.6 uM.

While BFA resulted in a block in secretion and a dramatic accumulation of intracellular VEGF (FIG. 3, lanes 2 and 1 compared to lanes 8 and 6), the compound of Formula I does not prevent detection of VEGF in the conditioned media or result in an increase in intracellular VEGF levels (FIG. 3, lanes 3 and 1 compared to lanes 9 and 6). Therefore, the compound of Formula I does not inhibit secretion of VEGF.

To determine if the compound of Formula I accelerates ER-associated proteasomal degradation of VEGF, the effect of the compound of Formula I is compared to a known 20S proteasome inhibitor, MG132 (Calbiochem, Catalog No. 474790). HT1080 clones stably expressing epitope-tagged VEGF with the 5'-UTR are pretreated overnight with 100 nM of a compound of Formula I, followed by a four hour "pulse" of $^{35}$S-Met along with MG132 at a final concentration of 2 uM.

Co-incubation of the compound of Formula I with MG132 did not significantly increase the levels of VEGF in either the conditioned media or the lysate (FIG. 3, lane 4 compared to lane 3 and lane 10 compared to lane 9). This strongly suggests that proteasomal degradation of VEGF does not play a role in the inhibition of VEGF by the compound of Formula I.

To determine if the compound of Formula I blocks the synthesis of VEGF, the amount of intracellular VEGF in the presence of the compound of Formula I and MG132 is compared when secretion of VEGF is completely blocked. HT1080 clones stably expressing epitope-tagged VEGF with the 5'-UTR are pretreated overnight with 100 nM of the compound of Formula I, followed by a four hour "pulse" of $^{35}$S-Met along with BFA at a final concentration of 1.6 uM and MG132 at a final concentration of 2 uM.

The compound of Formula I inhibits intracellular VEGF expression when both secretion and proteasome degradation is blocked (FIG. 3, lane 11 compared to lane 8), indicating that inhibition of VEGF production by the compound of Formula I at the level of translation.

All publications and patent applications identified above are herein incorporated by reference.

Although certain embodiments have been described in detail above, those having ordinary skill in the art will clearly understand that many modifications are possible in the embodiments without departing from the teachings thereof. All such modifications are intended to be encompassed within the claims of the invention.

We claim:

1. A method for treating a disease associated with elevated levels of VEGF in a subject in need thereof comprising administering a therapeutically effective amount of a compound of Formula (IV):

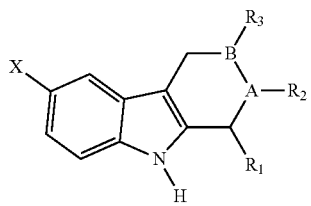

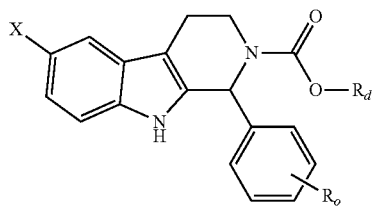

or a pharmaceutically acceptable salt, racemate or stereoisomer thereof, wherein, X is hydrogen; $C_1$ to $C_6$ alkyl optionally substituted with one or more halogens; hydroxyl; halogen; or $C_1$ to $C_5$ alkoxy optionally substituted with phenyl;

$R_o$ is halogen; cyano; nitro; sulfonyl substituted with $C_1$ to $C_6$ alkyl or morpholinyl; amino optionally substituted with $C_1$ to $C_6$ alkyl, —C(O)—$R_b$, —C(O)O—$R_b$, alkylsulfonyl, piperidinyl, morpholinyl or tetrahydropyranyl, wherein piperidinyl, morpholinyl or tetrahydropyranyl are optionally further substituted with —C(O)O—$R_n$; $C_1$ to $C_6$ alkyl optionally substituted with one or more substituents independently selected from hydroxl, halogen or amino; —C(O)—$R_n$; —O$R_a$;

$R_a$ is hydrogen; $C_2$ to $C_8$ alkenyl; —C(O)O—$R_b$; —C(O)—NH—$R_b$; $C_1$ to $C_8$ alkyl optionally substituted with one or more substituents independently selected from hydroxyl, halogen, $C_1$ to $C_4$ alkoxy, $C_1$ to $C_4$ alkoxy-$C_1$ to $C_4$ alkoxy, amino, alkylamino, dialkylamino, acetamide, —C(O)—$R_b$, —C(O)O—$R_b$, aryl, morpholinyl, thiomorpholinyl, pyrrolidinyl, piperidinyl, piperazinyl, 1,3-dioxolan-2-one, oxiranyl, tetrahydrofuranyl, tetrahydropyranyl, 1,2,3-triazole, 1,2,4-triazole, furan, imidazole, isoxazole, isothiazole, oxazole, pyrazole, thiazole, thiophene or tetrazole;
wherein amino is optionally substituted with $C_1$ to $C_4$ alkoxycarbonyl, imidazole, isothiazole, pyrazole, pyridine, pyrazine, pyrimidine, pyrrole or thiazole, wherein pyridine and thiazole are each optionally substituted with $C_1$ to $C_4$ alkyl;
wherein alkylamino and dialkylamino are each optionally substituted on alkyl with hydroxyl, $C_1$ to $C_4$ alkoxy, imidazole, pyrazole, pyrrole or tetrazole; and
wherein morpholinyl, thiomorpholinyl, pyrrolidinyl, piperidinyl, piperazinyl and oxiranyl are each optionally substituted with —C(O)—$R_n$, —C(O)O—$R_n$ or $C_1$ to $C_4$ alkyl, wherein $C_1$ to $C_4$ alkyl is optionally substituted with hydroxyl;

$R_b$ is hydroxyl; amino; alkylamino, optionally substituted on alkyl with hydroxyl, amino, alkylamino or $C_1$ to $C_4$ alkoxy; $C_1$ to $C_4$ alkoxy; $C_2$ to $C_8$ alkenyl; $C_2$ to $C_8$ alkynyl; aryl optionally substituted with one or more substituents independently selected from halogen and $C_1$ to $C_4$ alkoxy; furan; or $C_1$ to $C_8$ alkyl optionally substituted with one or more substituents independently selected from $C_1$ to $C_4$ alkoxy, aryl, amino, morpholinyl, piperidinyl or piperazinyl, wherein the amino, morpholinyl, piperidinyl and piperazinyl groups are optionally substituted with at least one independently selected $C_1$ to $C_8$ alkyl, oxo or —C(O)O—$R_n$ substituent;

$R_d$ is phenyl optionally substituted by one or more substituents independently selected from halogen, nitro, $C_1$ to $C_6$ alkyl, —C(O)O—$R_e$, and —O$R_e$;

$R_e$ is hydrogen; $C_1$ to $C_6$ alkyl optionally substituted with one or more substituents independently selected from halogen and alkoxy; or phenyl, wherein phenyl is optionally substituted with one or more substituents independently selected from halogen and alkoxy; and $R_n$ is hydroxyl, $C_1$ to $C_4$ alkoxy, amino or $C_1$ to $C_6$ alkyl;

wherein the compound reduces VEGF levels as measured by an ELISA assay or a quantitative immunofluorescence assay, or reduces VEGF levels in HT1080 clones stably expressing epitope-tagged VEGF with a 5'-UTR; and wherein the disease is solid tumor cancer, diabetic retinopathy, rheumatoid arthritis, psoriasis, atherosclerosis, chronic inflammation, a chronic inflammation-related disease or disorder, obesity, or exudative macular degeneration.

2. The method of claim 1, wherein

X is $C_1$ to $C_6$ alkyl optionally substituted with one or more halogen; halogen; or $C_1$ to $C_5$ alkoxy optionally substituted with phenyl;

$R_o$ is halogen; cyano; nitro; sulfonyl substituted with $C_1$ to $C_6$ alkyl or morpholinyl; amino optionally substituted with $C_1$ to $C_6$ alkyl, —C(O)—$R_b$, —C(O)O—$R_b$, alkylsulfonyl, piperidinyl and tetrahydropyranyl, wherein piperidinyl is optionally further substituted with —C(O)O—$R_n$; $C_1$ to $C_6$ alkyl optionally substituted with one or more halogen substituents; —C(O)—$R_n$; —O$R_a$;

$R_a$ is hydrogen; $C_2$ to $C_8$ alkenyl; —C(O)O—$R_b$ $C_1$ to $C_8$ alkyl optionally substituted with one or more substituents independently selected from hydroxyl, halogen, $C_1$ to $C_4$ alkoxy, $C_1$ to $C_4$ alkoxy-$C_1$ to $C_4$ alkoxy, amino, alkylamino, dialkylamino, acetamide, —C(O)—$R_b$, —C(O)O—$R_b$, aryl, morpholinyl, thiomorpholinyl, pyrrolidinyl, piperidinyl, piperazinyl, 1,3-dioxolan-2-one, oxiranyl, 1,2,3-triazole, 1,2,4-triazole, imidazole or pyrazole;
wherein amino is optionally substituted with $C_1$ to $C_4$ alkoxycarbonyl, pyridine or thiazole, wherein pyridine and thiazole are each optionally substituted with $C_1$ to $C_4$ alkyl;
wherein alkylamino and dialkylamino are each optionally substituted on alkyl with hydroxyl, $C_1$ to $C_4$ alkoxy or imidazole; and wherein morpholinyl, thiomorpholinyl, pyrrolidinyl, piperidinyl, piperazinyl and oxiranyl are each optionally substituted with —C(O)—$R_n$, —C(O)O—$R_n$ or $C_1$ to $C_4$ alkyl, wherein $C_1$ to $C_4$ alkyl is optionally substituted with hydroxyl;

$R_b$ is hydroxyl; $C_1$ to $C_4$ alkoxy; $C_2$ to $C_8$ alkenyl; phenyl optionally substituted with one or more halogen substituents; furan; or $C_1$ to $C_8$ alkyl optionally substituted with one or more substituents independently selected from $C_1$ to $C_4$ alkoxy, phenyl, amino or morpholinyl, wherein the amino is optionally substituted with at least one independently selected $C_1$ to $C_8$ alkyl substituent; and, $R_d$ is phenyl optionally substituted by one or more substituents independently selected from halogen, nitro, $C_1$ to $C_6$ alkyl and —$OR_e$; and, wherein all other variables are as previously defined.

3. The method of claim 1, wherein

X is $C_1$ to $C_6$ alkyl; halogen; or $C_1$ to $C_5$ alkoxy optionally substituted with phenyl;

$R_o$ is halogen; cyano; nitro; sulfonyl substituted with $C_1$ to $C_6$ alkyl or morpholinyl; amino optionally substituted with —C(O)—$R_b$, —C(O)—$R_b$, alkylsulfonyl, piperidinyl and tetrahydropyranyl, wherein piperidinyl is optionally further substituted with —C(O)O—$R_n$; $C_1$ to $C_6$ alkyl optionally substituted with one or more halogen substituents; —C(O)—$R_n$; —$OR_a$;

$R_a$ is hydrogen; $C_2$ to $C_8$ alkenyl; —C(O)O—$R_b$; $C_1$ to $C_8$ alkyl optionally substituted with one or more substituents independently selected from hydroxyl, halogen, $C_1$ to $C_4$ alkoxy, $C_1$ to $C_4$ alkoxy-$C_1$ to $C_4$ alkoxy, amino, alkylamino, dialkylamino, acetamide, —C(O)O—$R_b$, morpholinyl, thiomorpholinyl, pyrrolidinyl, piperidinyl, 1,3-dioxolan-2-one, oxiranyl, 1,2,3-triazole, 1,2,4-triazole, imidazole or pyrazole;

wherein amino is optionally substituted with $C_1$ to $C_4$ alkoxycarbonyl, pyridine or thiazole, wherein pyridine and thiazole are each optionally substituted with $C_1$ to $C_4$ alkyl;

wherein alkylamino and dialkylamino are each optionally substituted on alkyl with hydroxyl, $C_1$ to $C_4$ alkoxy or imidazole; and wherein morpholinyl, thiomorpholinyl, pyrrolidinyl, piperidinyl, piperazinyl and oxiranyl are each optionally substituted with —C(O)O—$R_n$, —C(O)O—$R_n$ or $C_1$ to $C_4$ alkyl, wherein $C_1$ to $C_4$ alkyl is optionally substituted with hydroxyl; and, $R_b$ is hydroxyl; $C_1$ to $C_4$ alkoxy; $C_2$ to $C_8$ alkenyl; phenyl optionally substituted with one or more halogen substituents; furan; or $C_1$ to $C_8$ alkyl optionally substituted with one or more substituents independently selected from $C_1$ to $C_4$ alkoxy or morpholinyl; and wherein all other variables are as previously defined.

4. The method of claim 1, wherein the compound is administered orally.

5. The method of claim 1, wherein the reduction of VEGF levels is measured in an assay using HT1080 clones stably expressing epitope-tagged VEGF with a 5'-UTR.

6. The method of claim 1, wherein the reduction of elevated VEGF levels is measured by an ELISA assay or a quantitative immunofluorescence assay.

7. The method of claim 1, wherein said stereoisomer of said compound has a chiral carbon at the point of attachment of the phenyl substituted with $R_o$ and said stereoisomer is an (S) isomer at said chiral carbon.

8. A method for treating a disease associated with elevated levels of VEGF in a subject in need thereof comprising administering a therapeutically effective amount of a compound selected from the group consisting of:

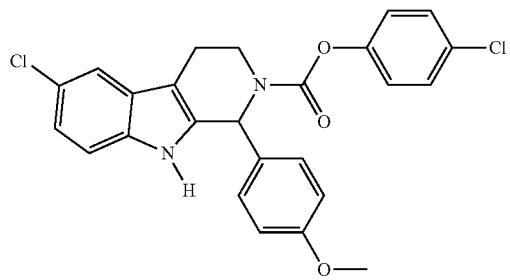

10

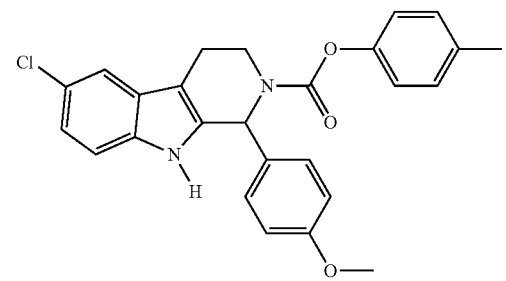

17

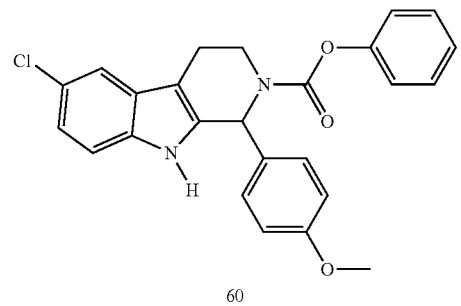

60

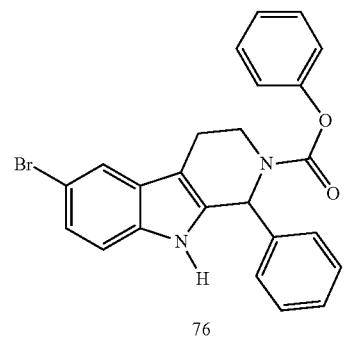

76

| 293 -continued | 294 -continued |
|---|---|
| 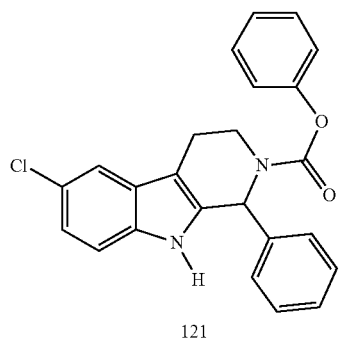 121 | 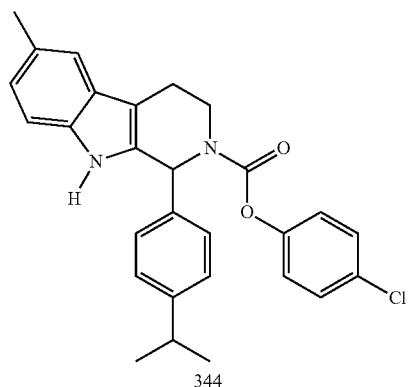 344 |
| 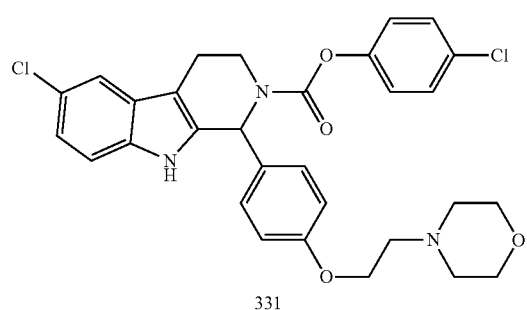 331 | 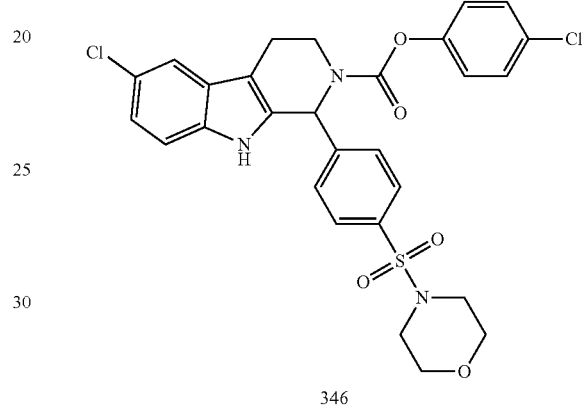 346 |
| 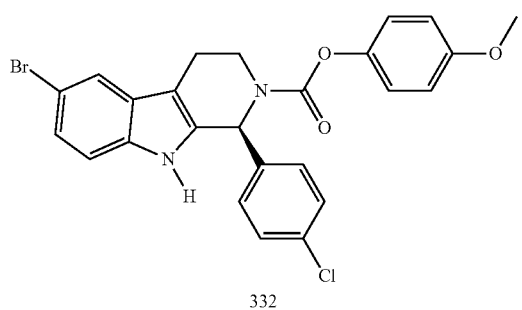 332 | 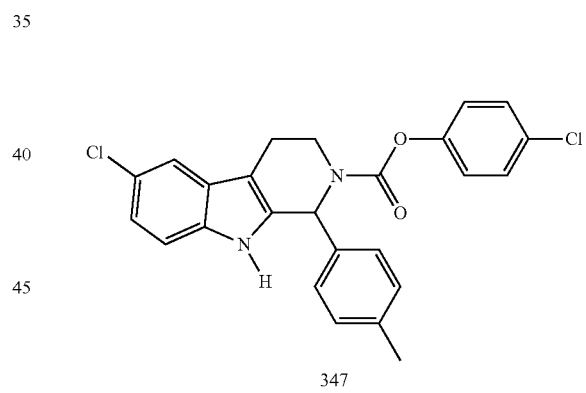 347 |
| 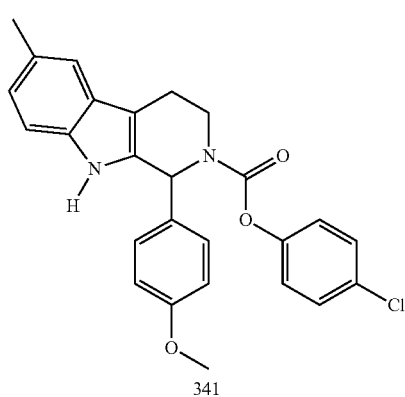 341 | 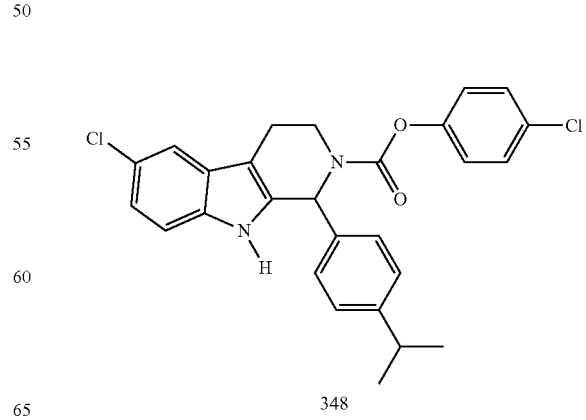 348 |

| 295 -continued | 296 -continued |
|---|---|
| 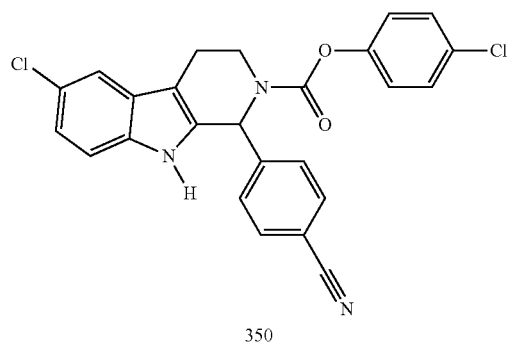<br>350 | 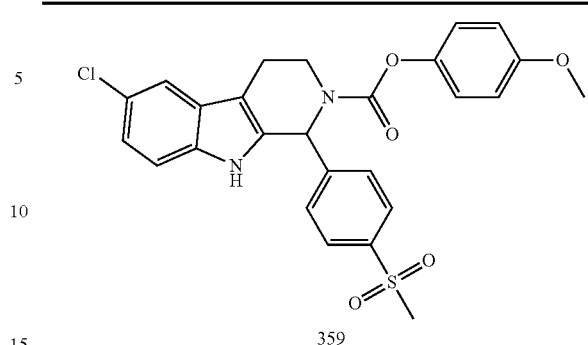<br>359 |
| 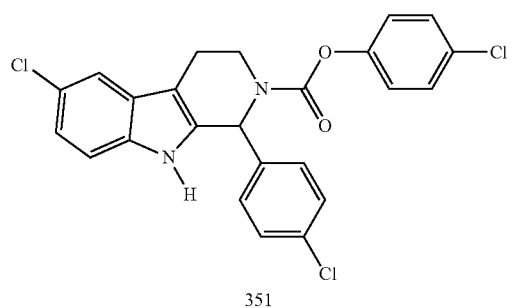<br>351 | 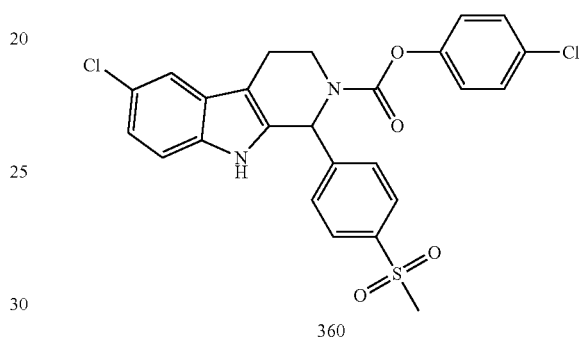<br>360 |
| 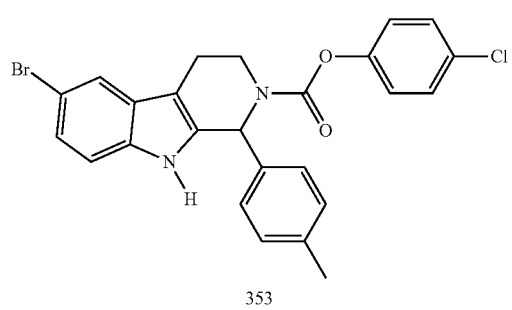<br>353 | 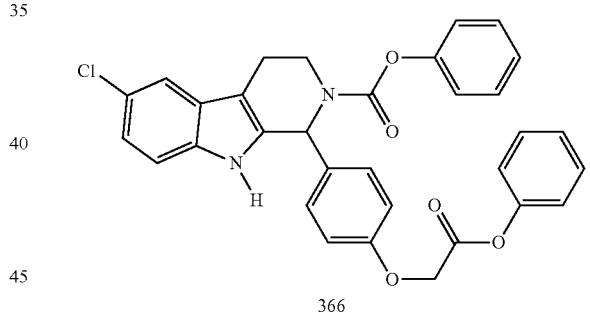<br>366 |
| 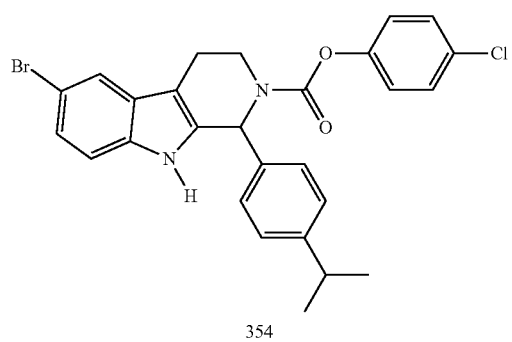<br>354 | |
| 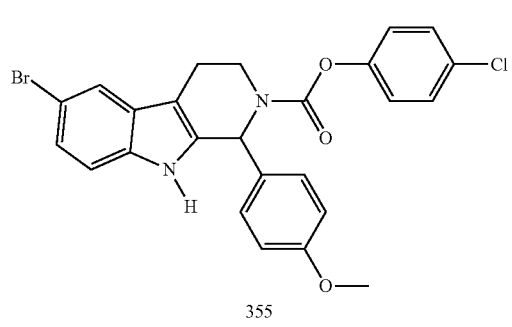<br>355 | 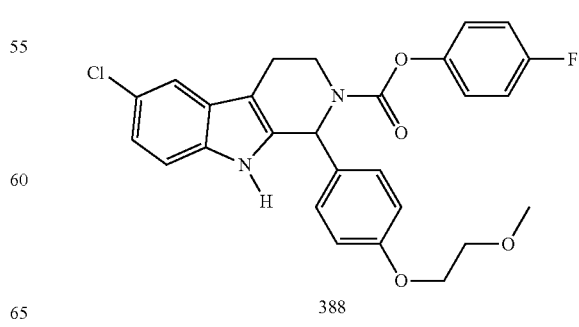<br>388 |

297
-continued
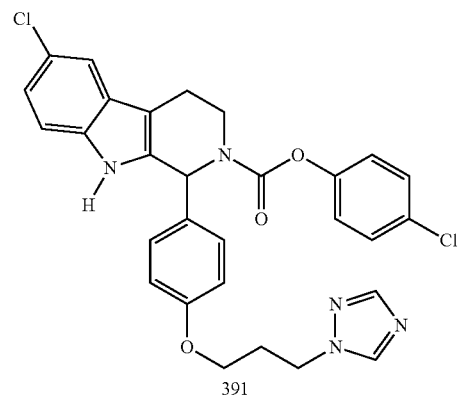
391
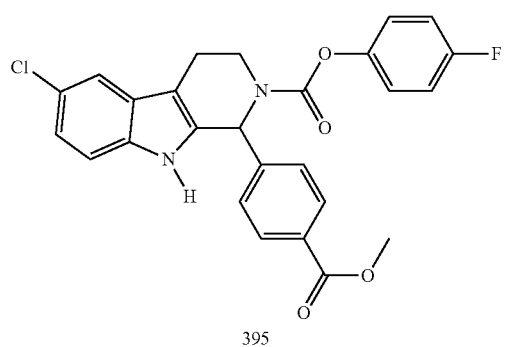
395
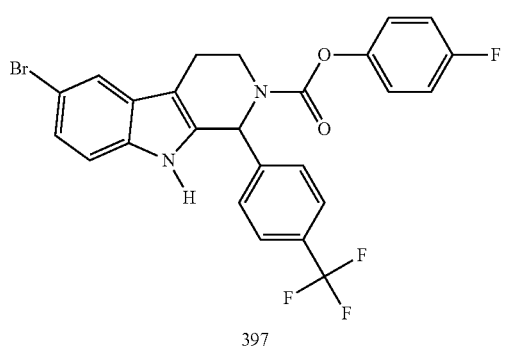
397
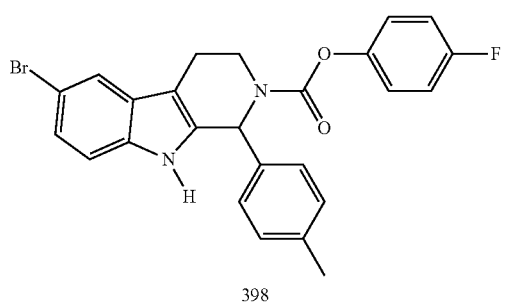
398
298
-continued
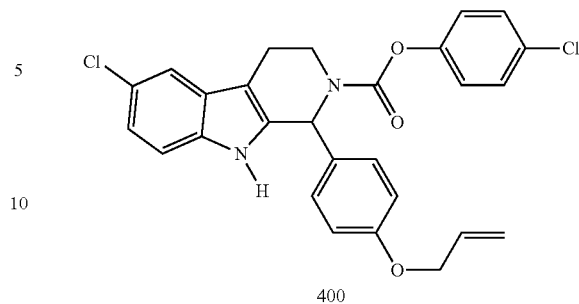
400
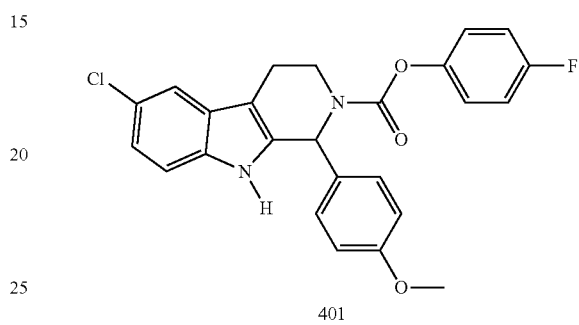
401
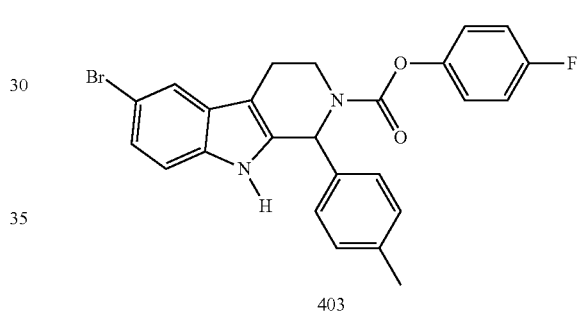
403
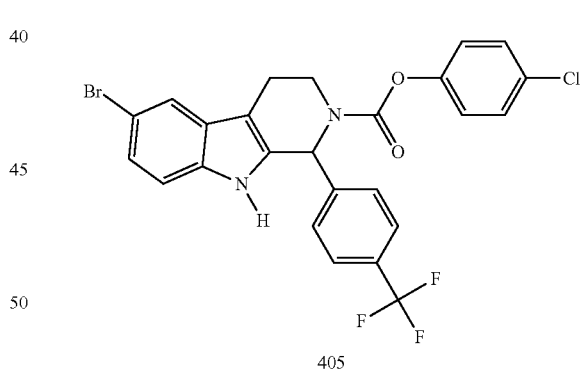
405
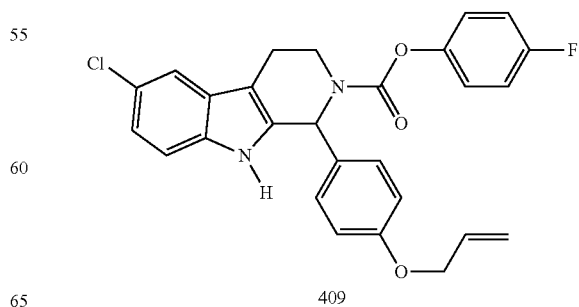
409

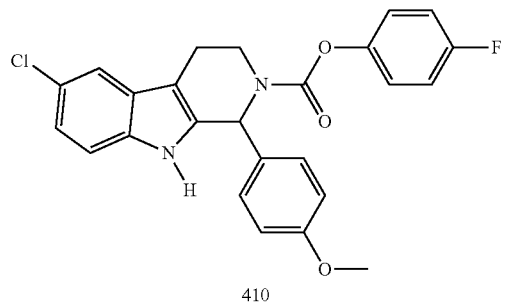
410
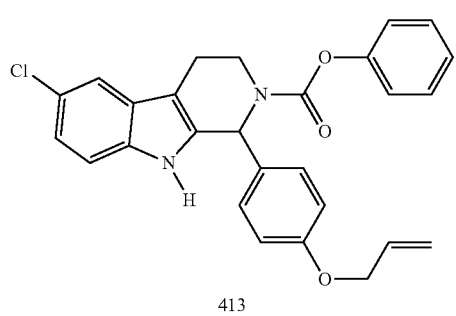
413
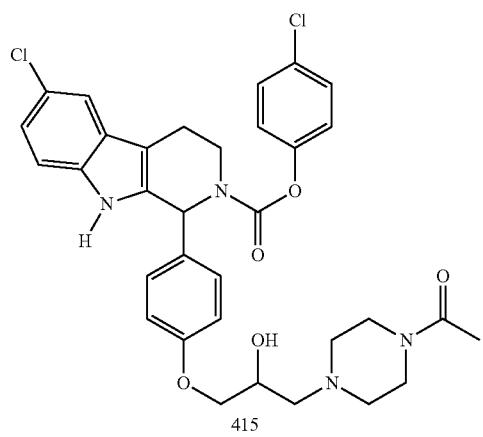
415
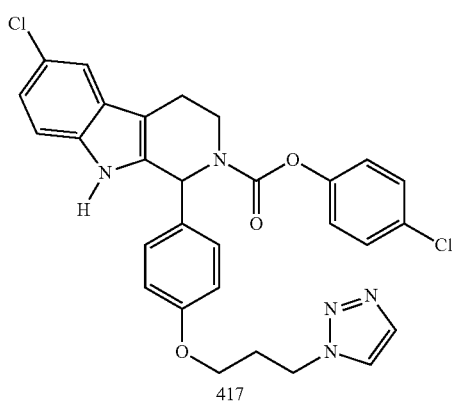
417
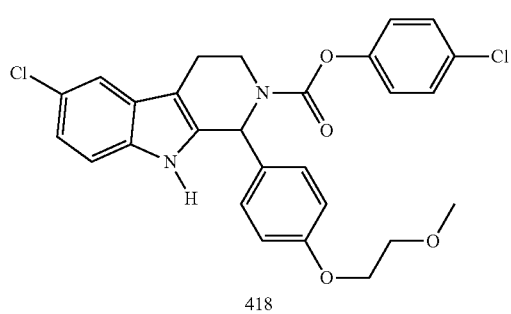
418
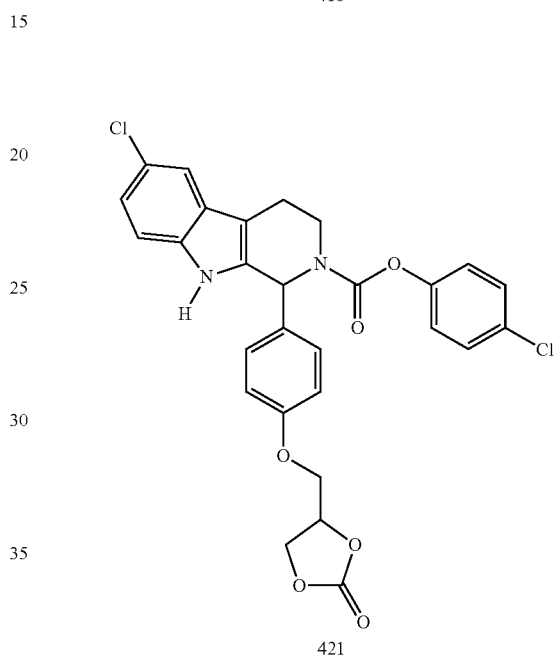
421
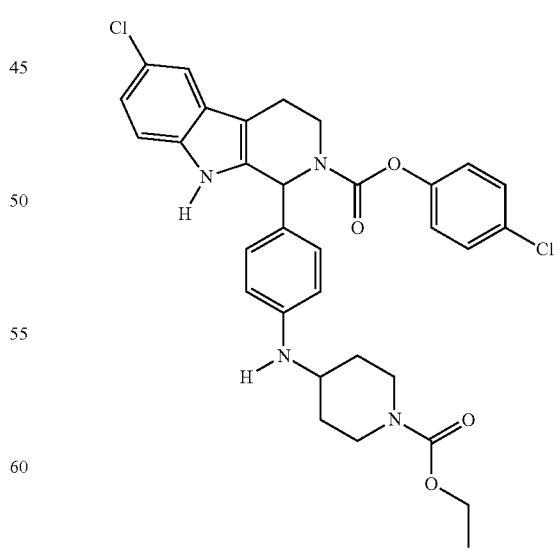
422

301
-continued
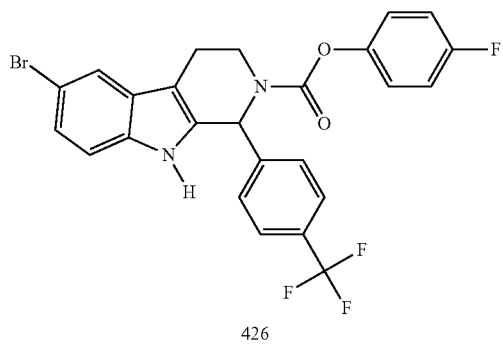
426
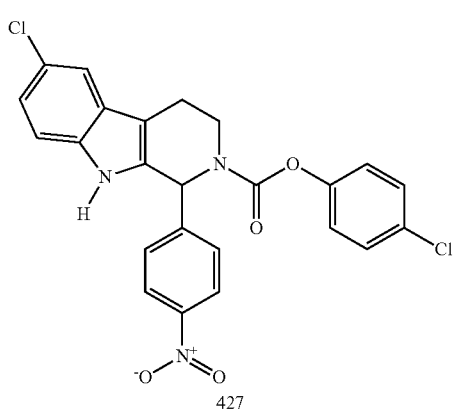
427
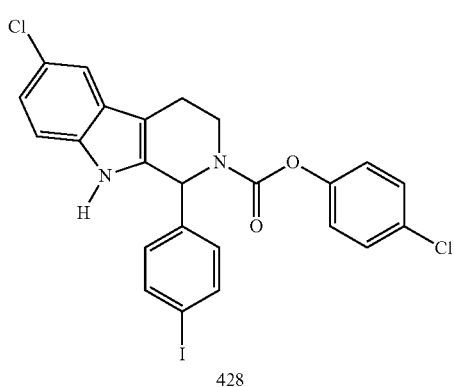
428
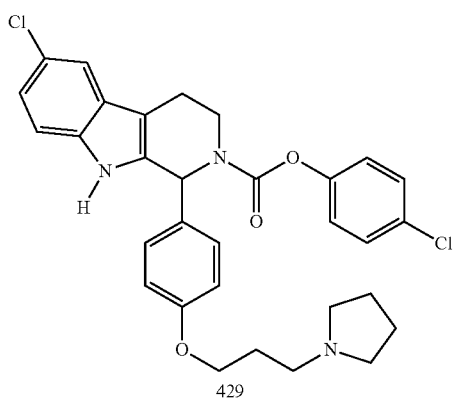
429
302
-continued
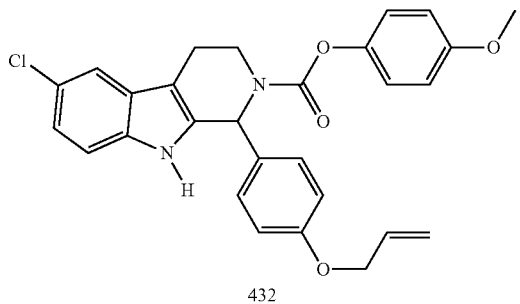
432
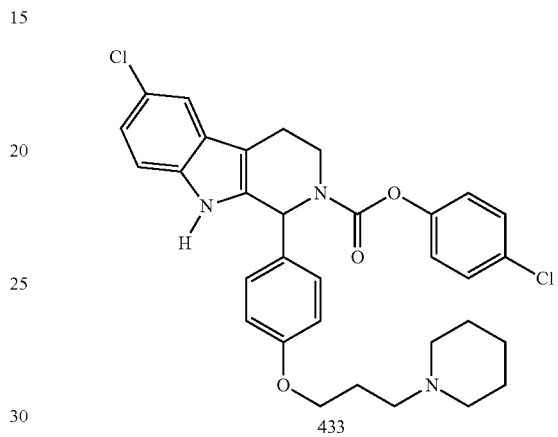
433
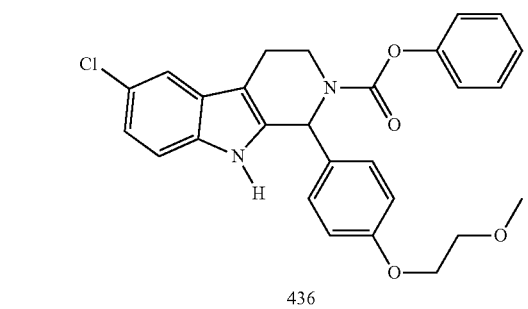
436
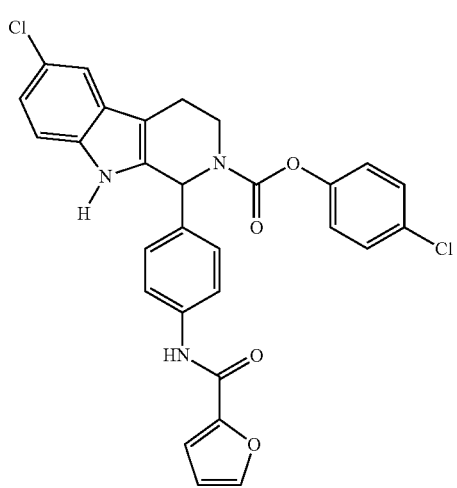
437

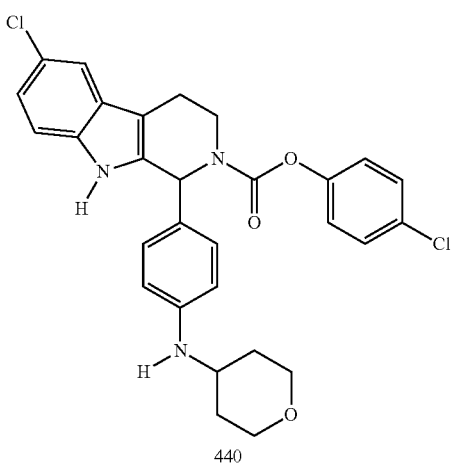
440
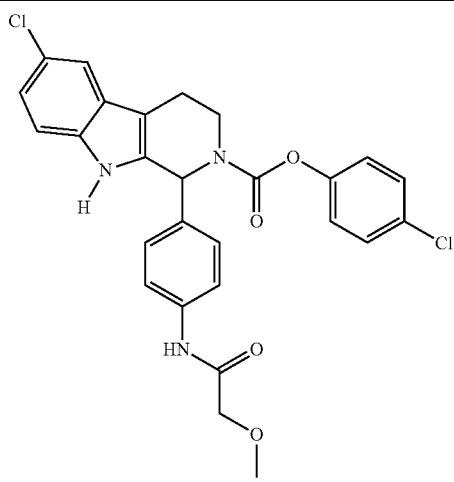
448
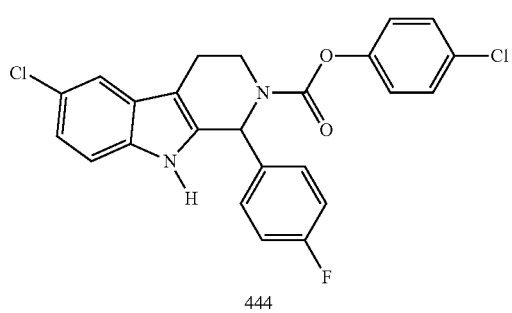
444
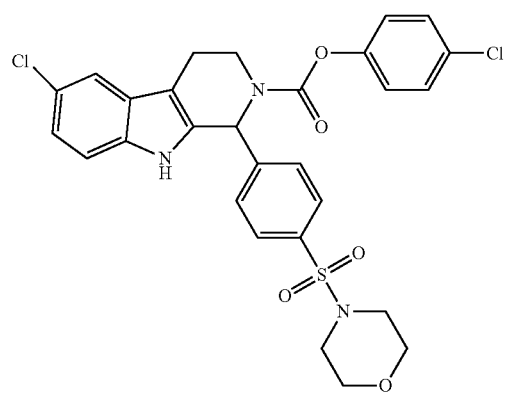
450
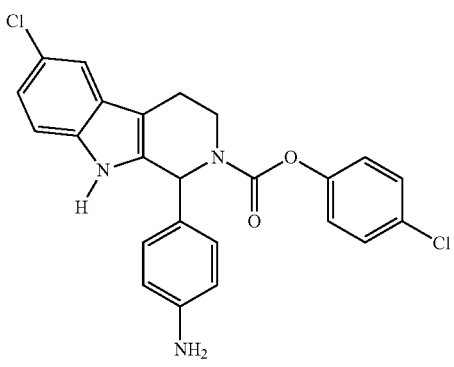
446
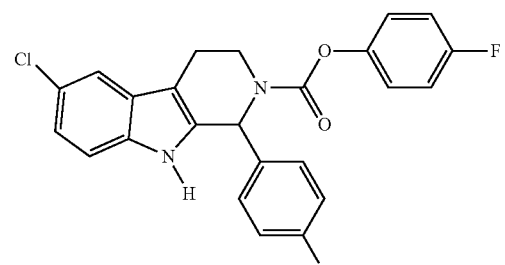
452

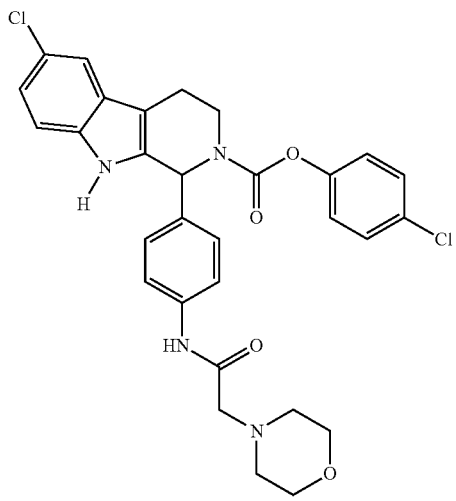
454
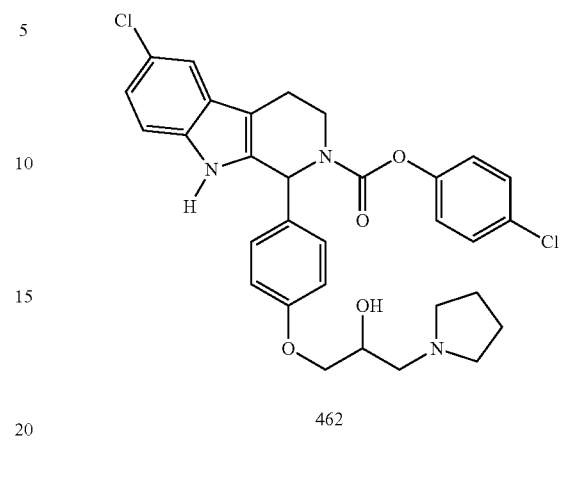
462
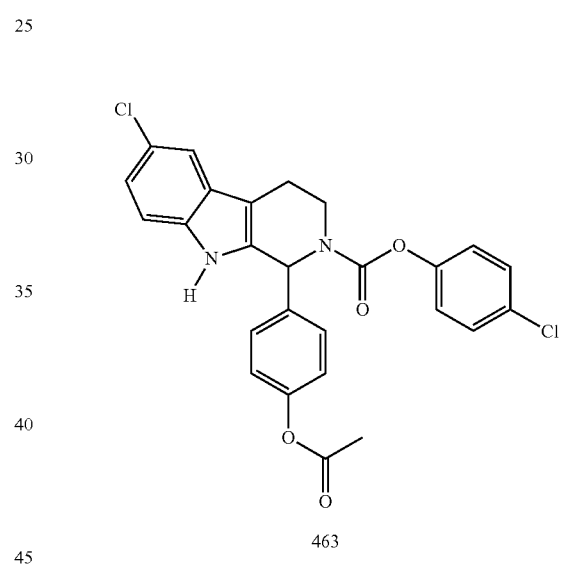
463
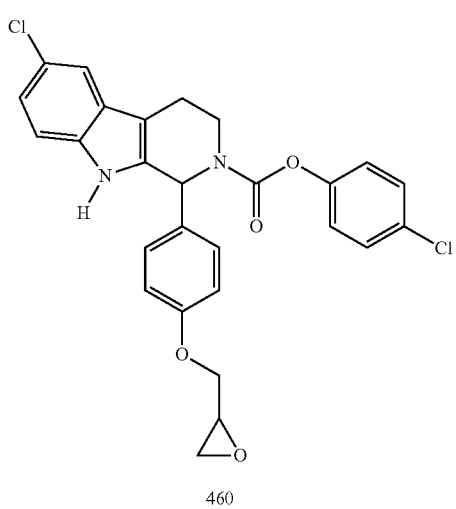
455
460
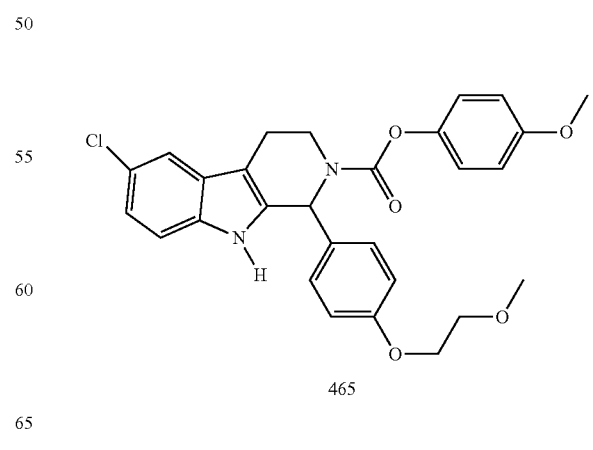
465

| 307 -continued | 308 -continued |
|---|---|
| 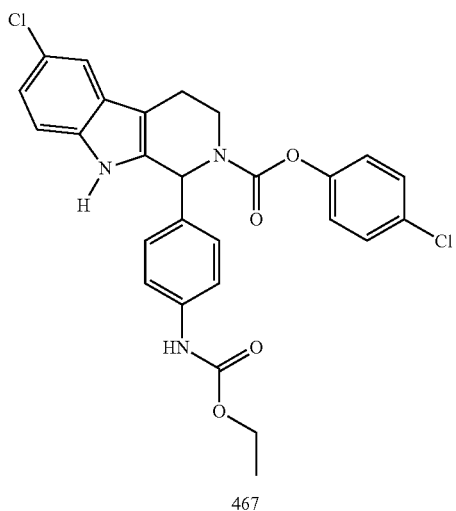<br>467 | 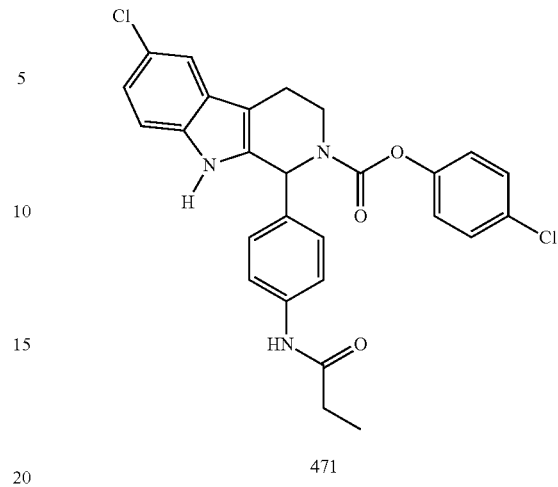<br>471 |
| 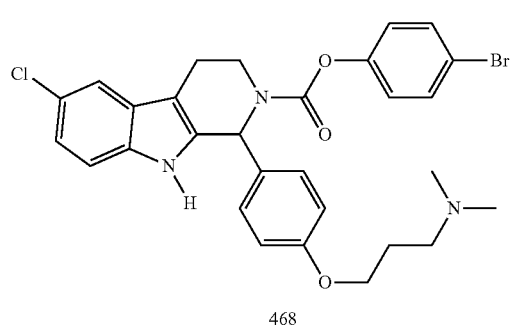<br>468 | 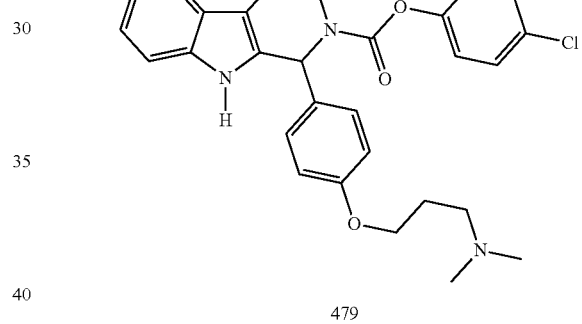<br>479 |
| 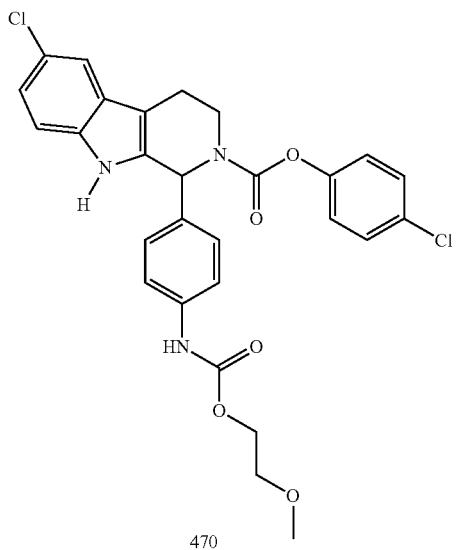<br>470 | 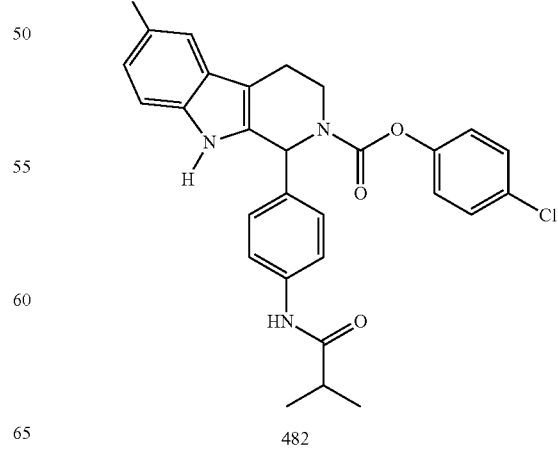<br>482 |

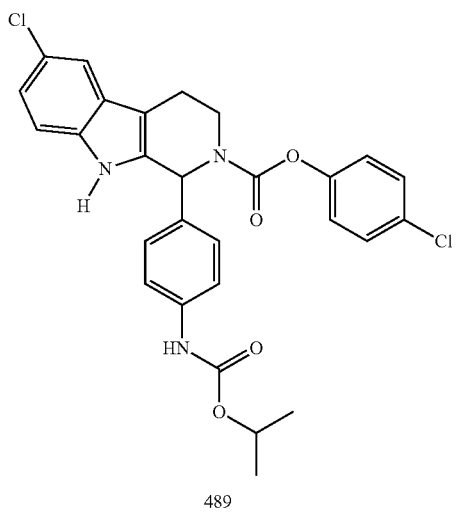
489
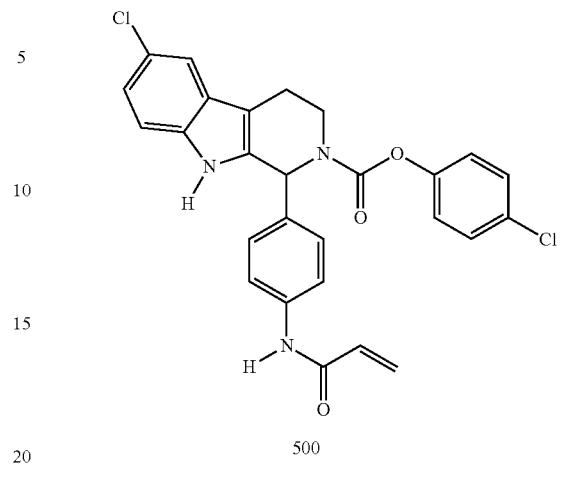
500
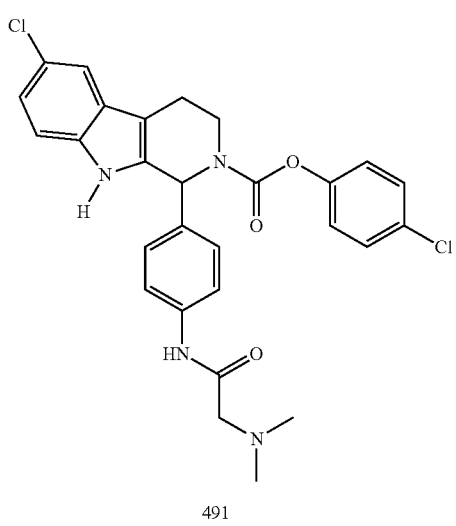
491
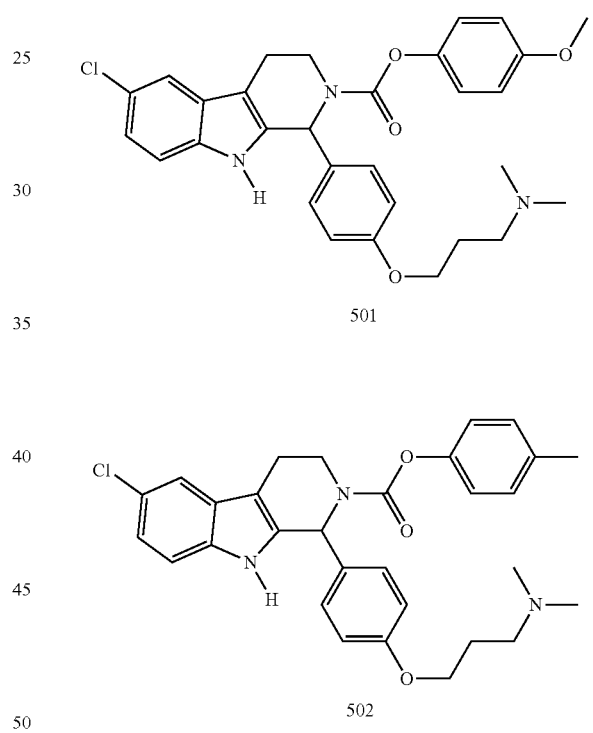
501
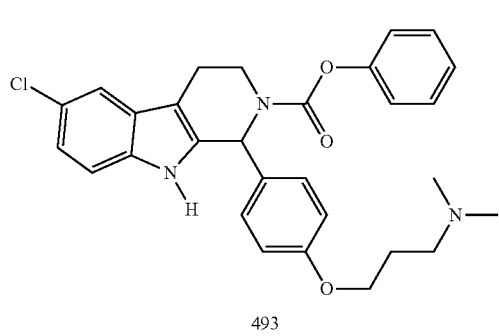
493
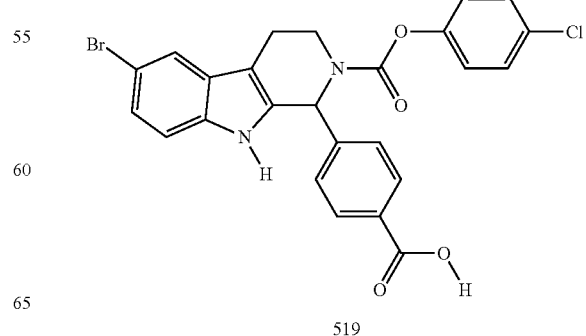
502

311
-continued
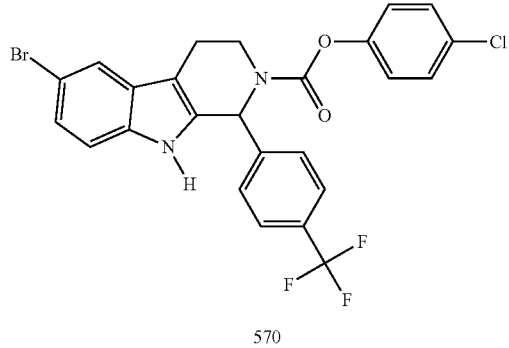
570
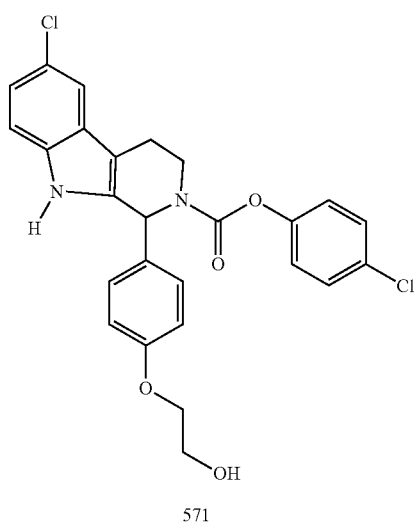
571
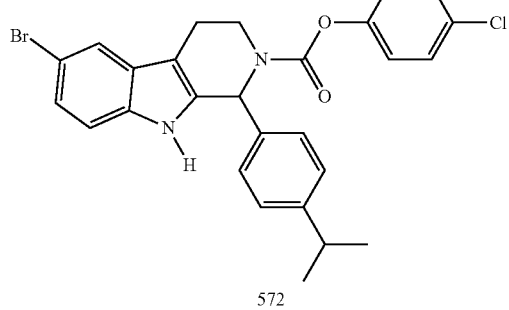
572
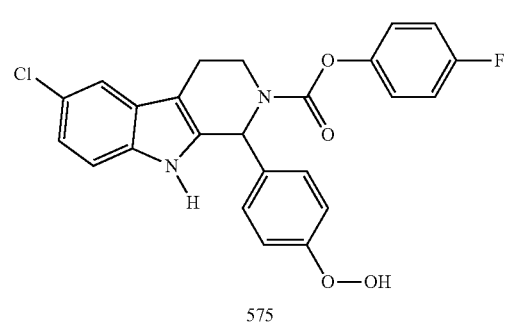
575
312
-continued
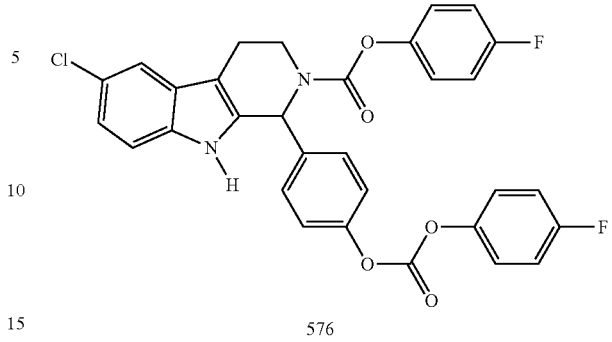
576
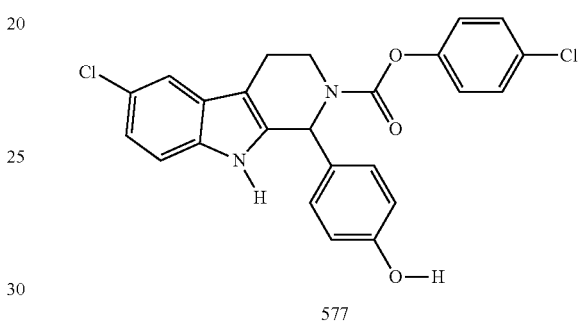
577
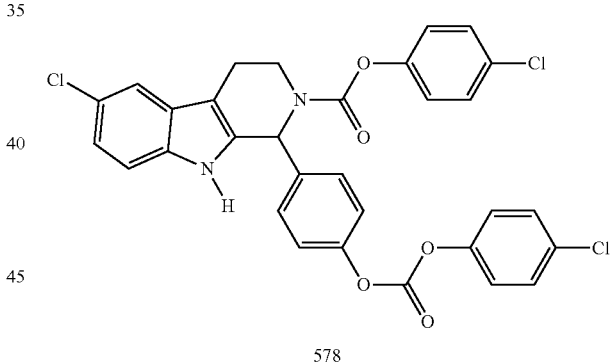
578
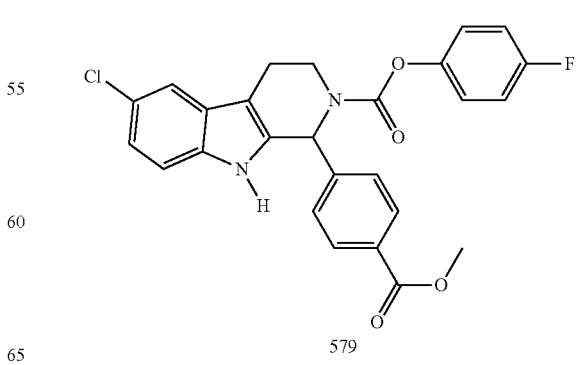
579

| 313 -continued | 314 -continued |
|---|---|
| 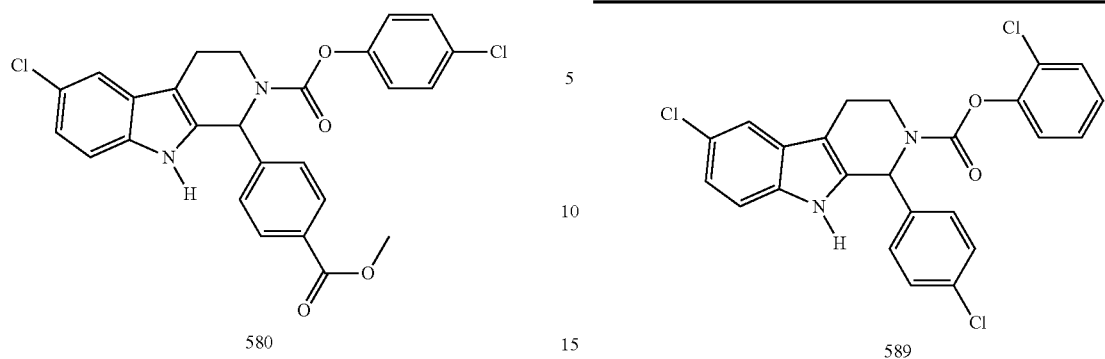 580 | 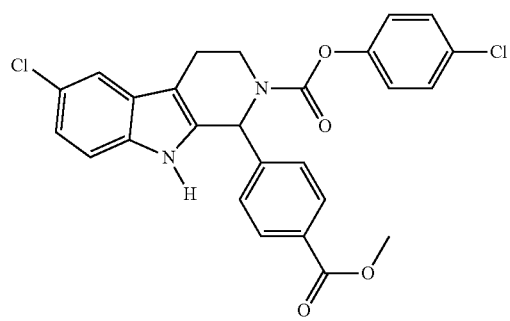 589 |
| 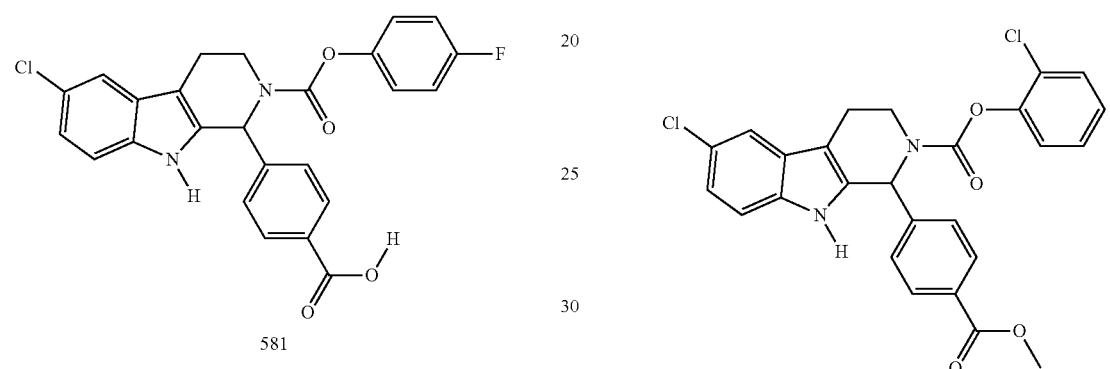 581 | 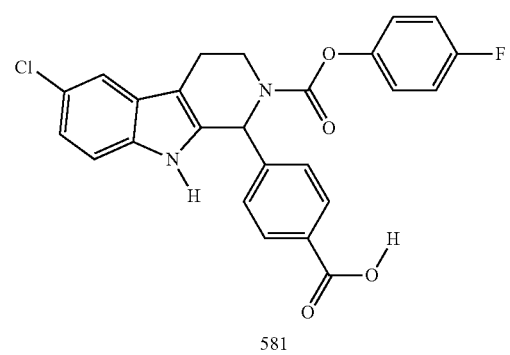 590 |
| 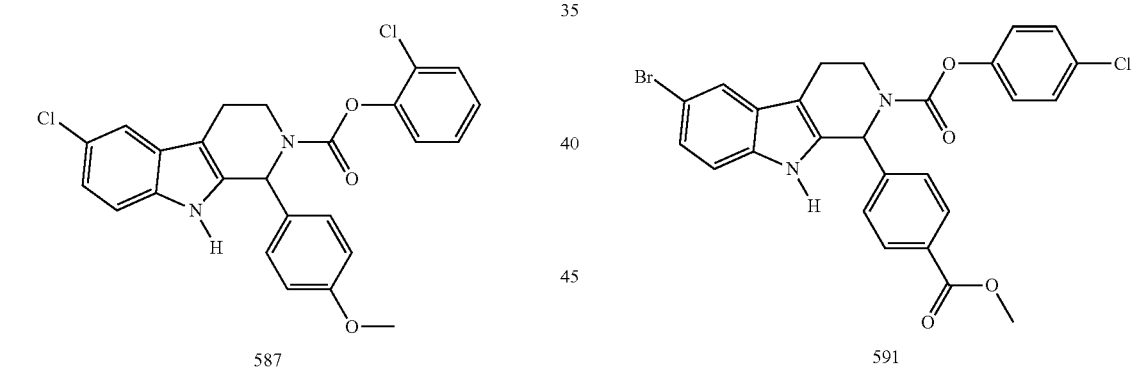 587 | 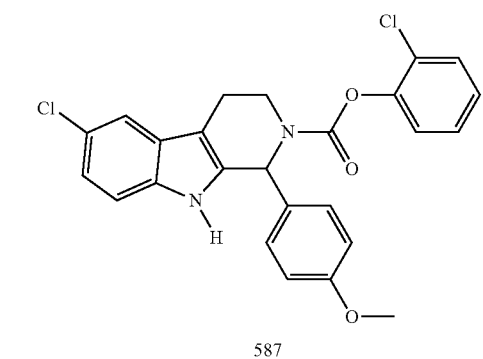 591 |
| 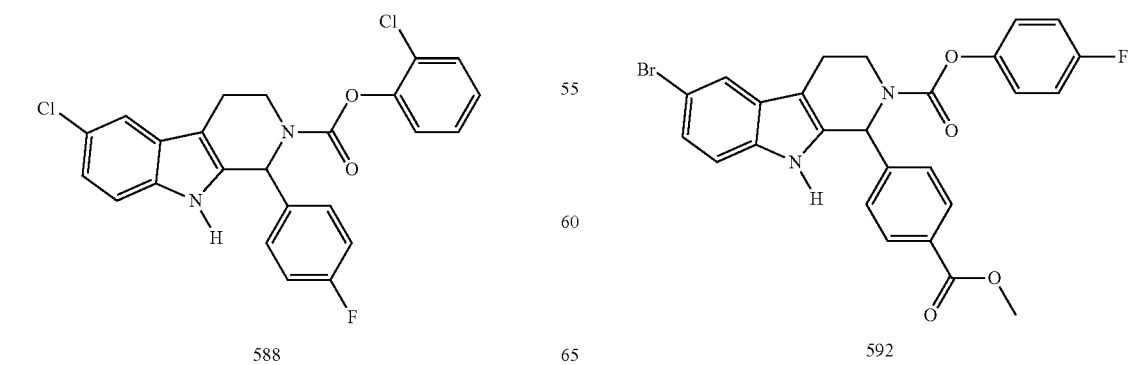 588 | 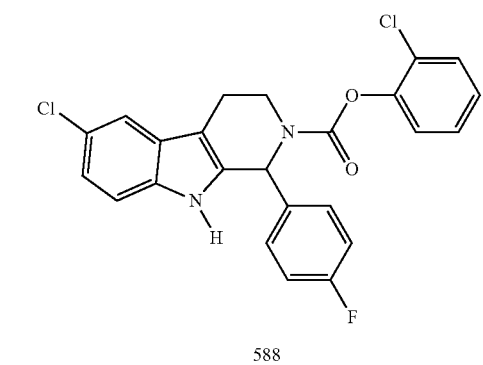 592 |

315
-continued
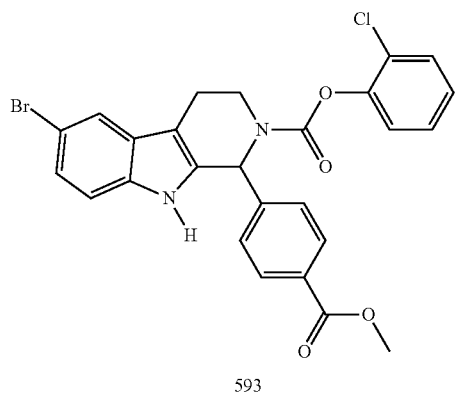
593
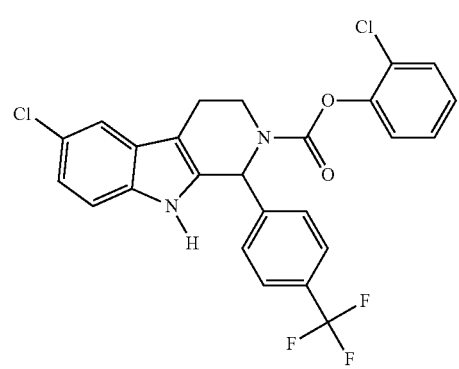
594
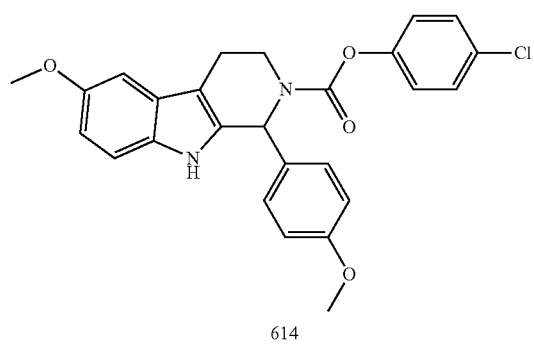
614
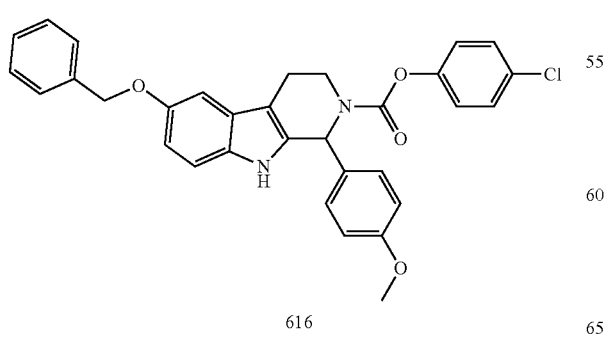
616
316
-continued
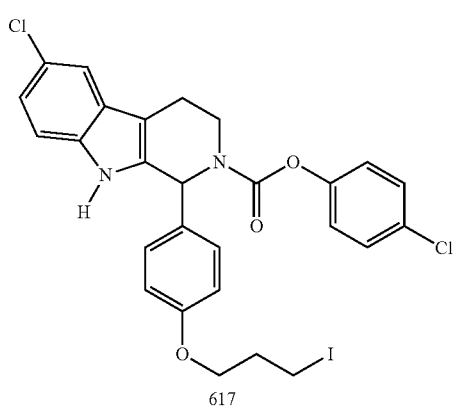
617
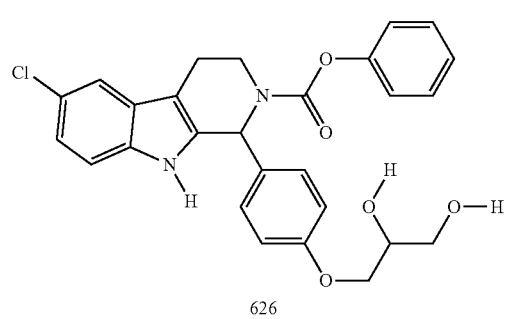
626
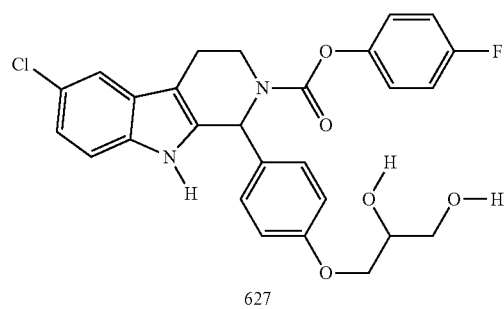
627
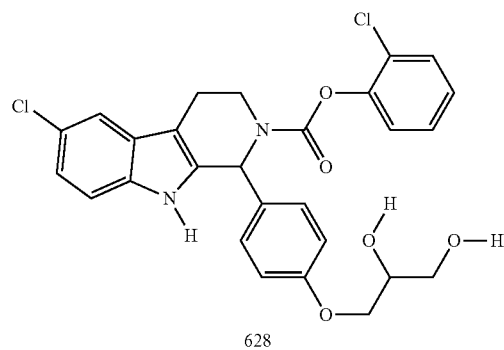
628

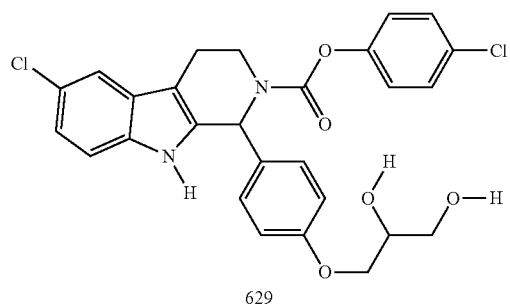
629
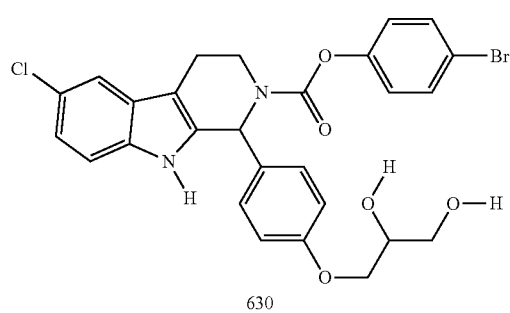
630
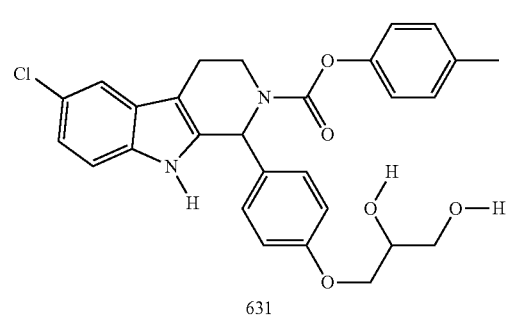
631
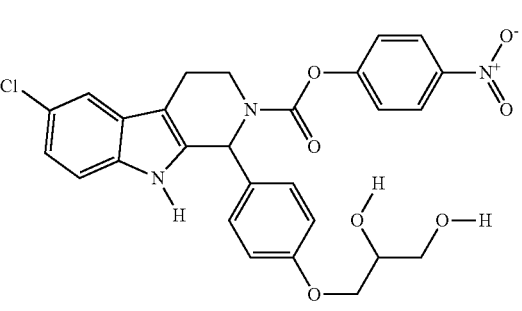
632
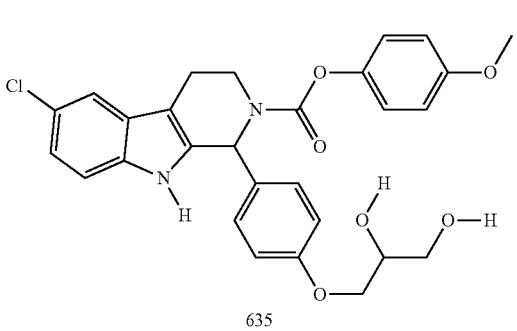
635
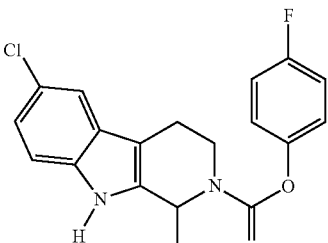
637
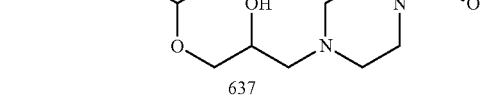
638
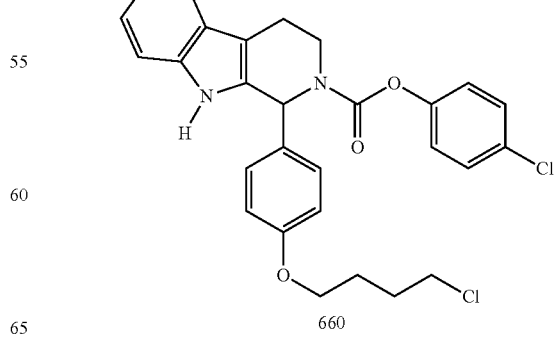
660

319
-continued
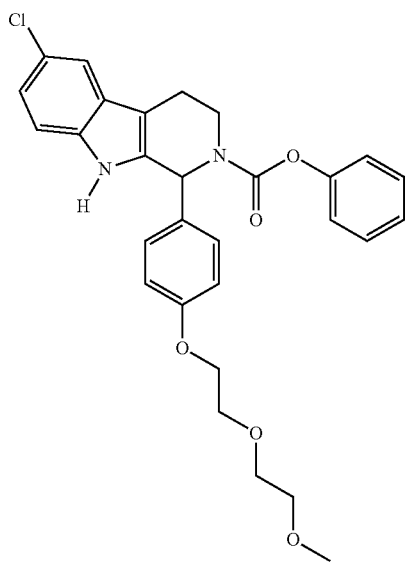
670
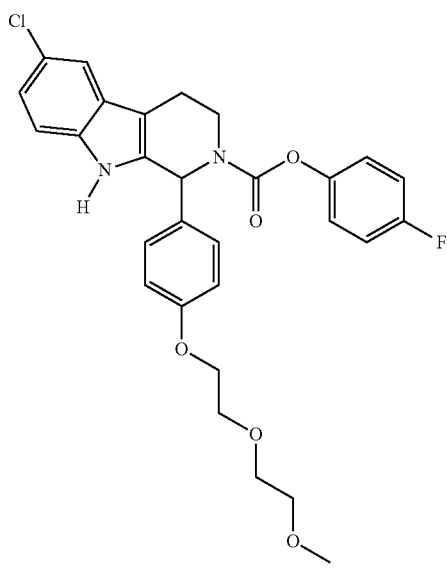
673
320
-continued
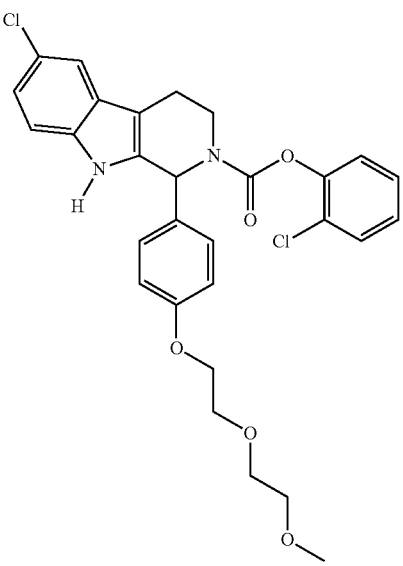
674
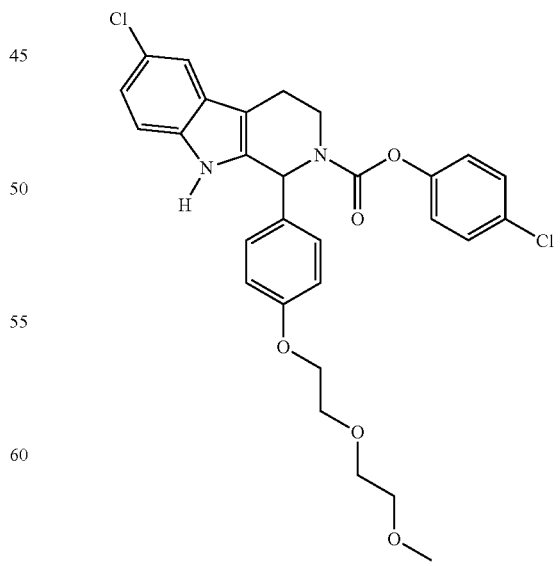
675

| 321 -continued | 322 -continued |
|---|---|
| 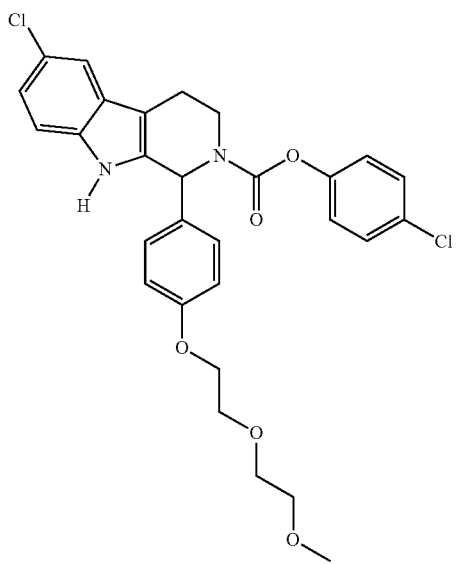 677 | 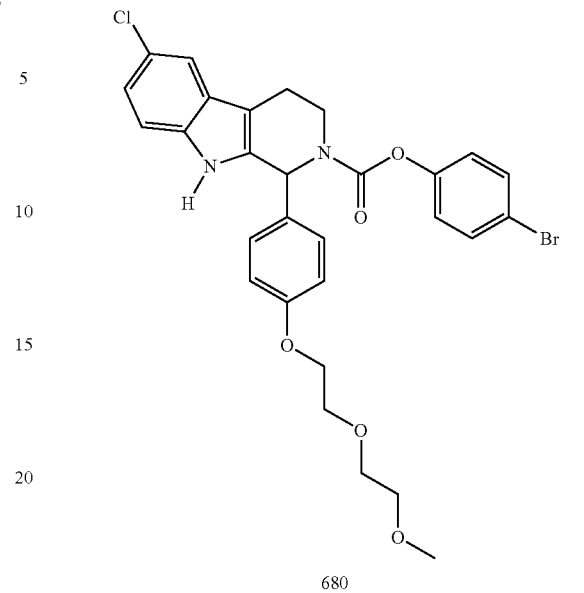 680 |
| | 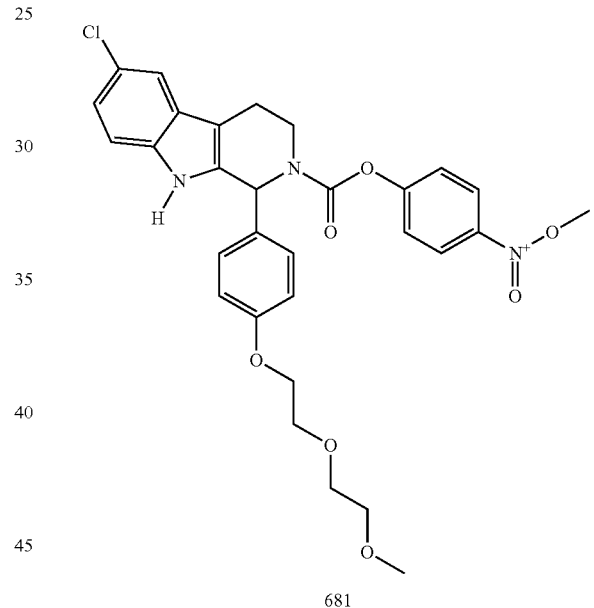 681 |
| 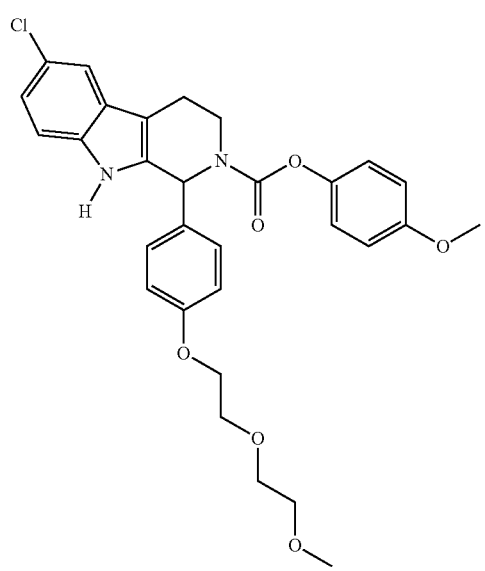 678 | 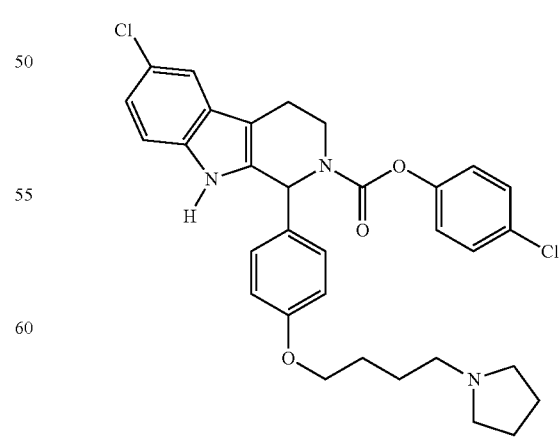 698 |

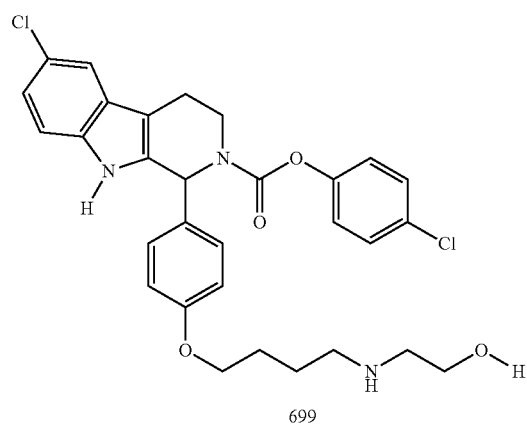
699
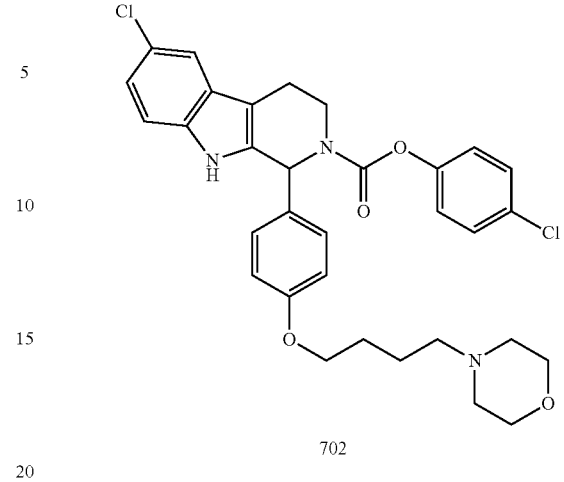
702
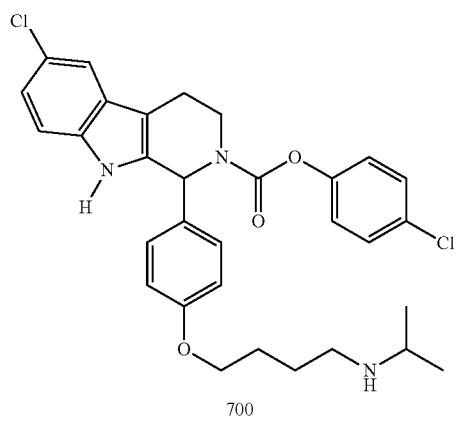
700
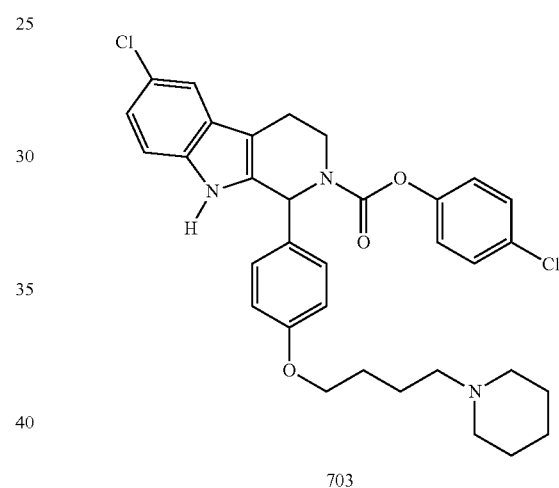
703
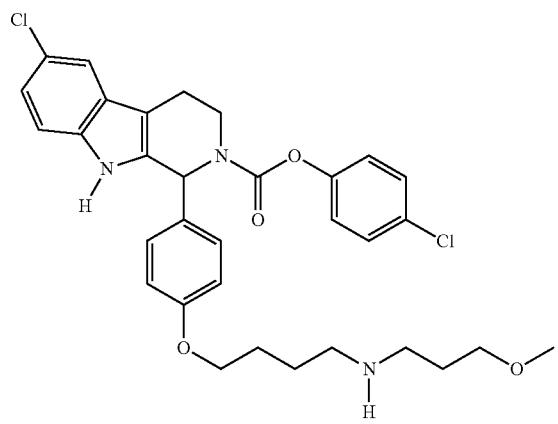
701
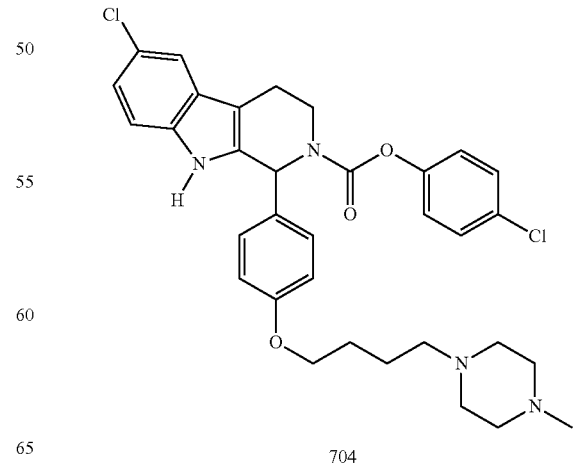
704

-continued
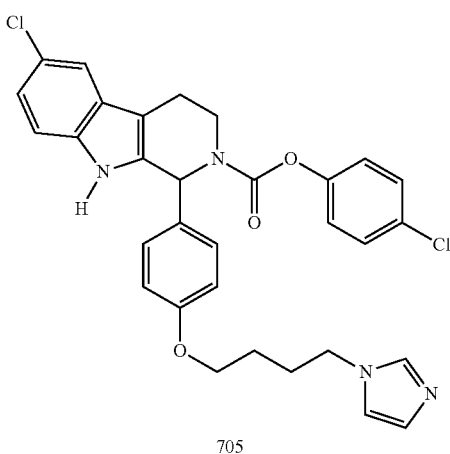
705
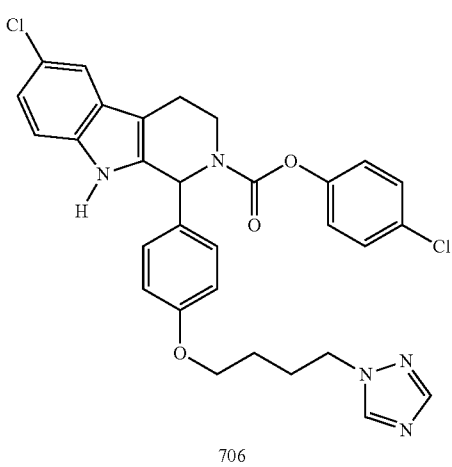
706
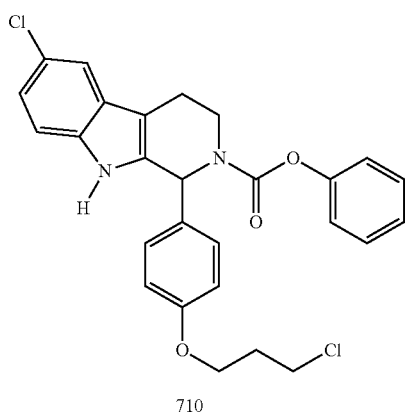
710
-continued
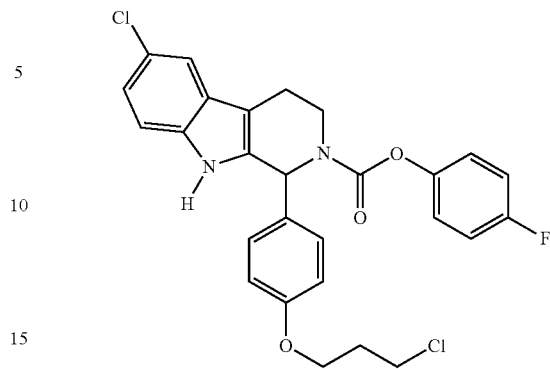
712
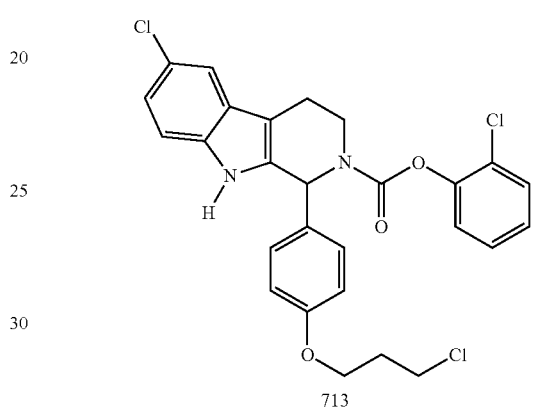
713
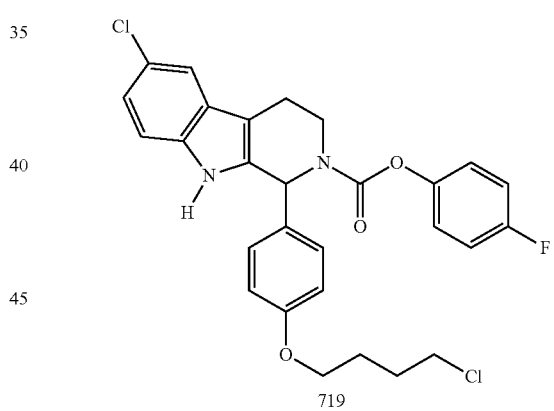
719
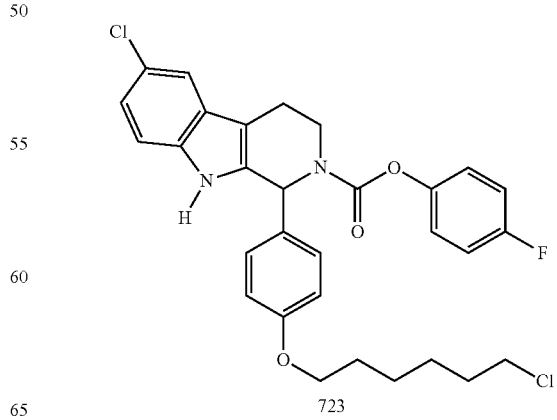
723

| 327 -continued | 328 -continued |
|---|---|
| 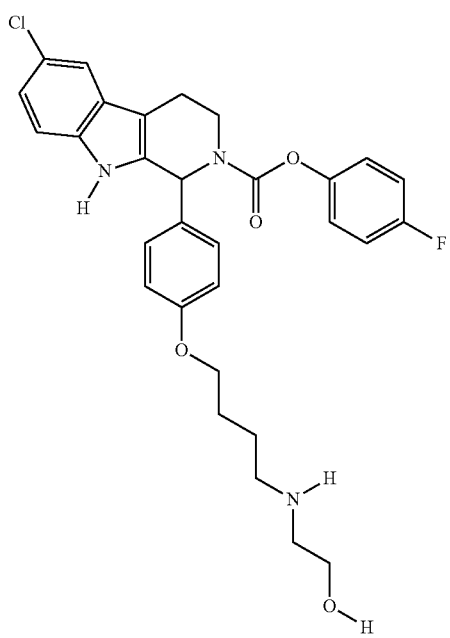 735 | 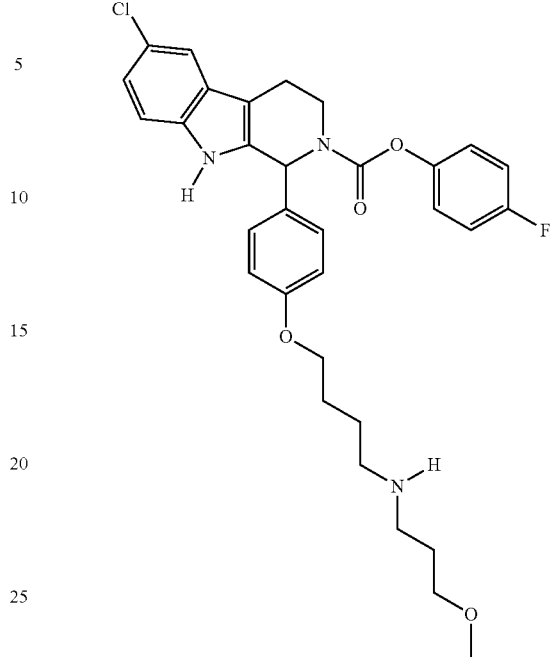 737 |
| 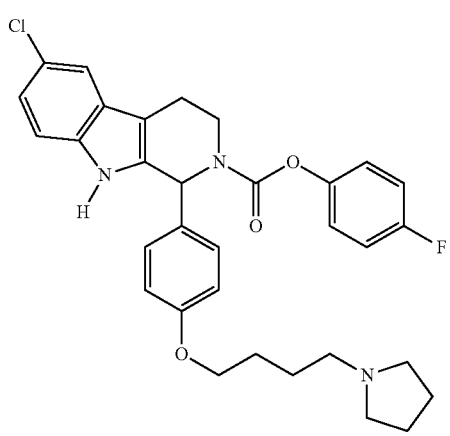 736 | 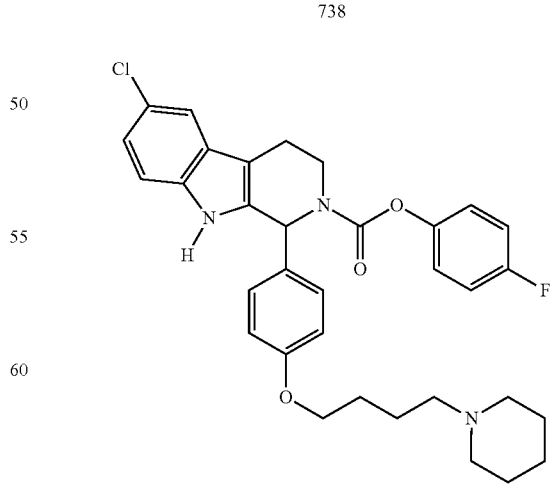 738, 739 |

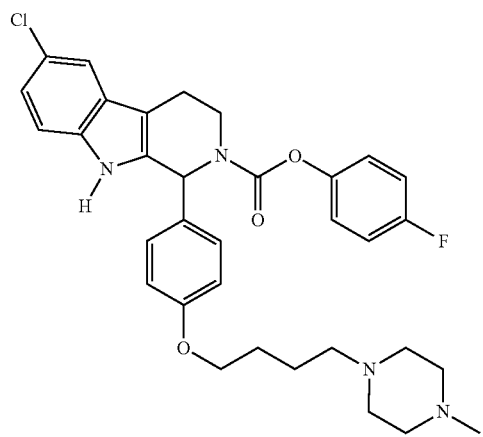
740
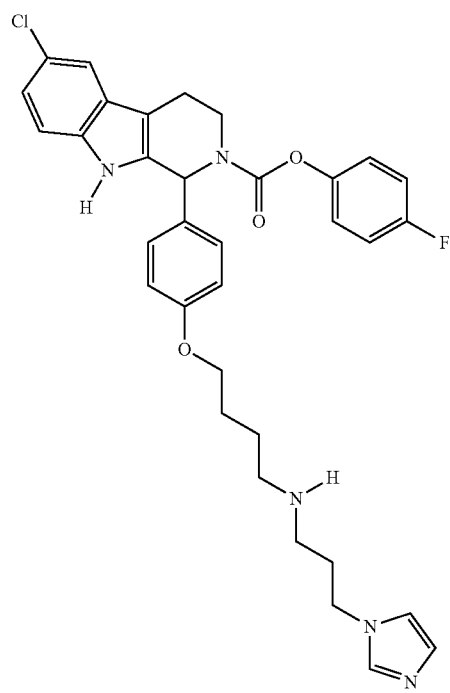
741
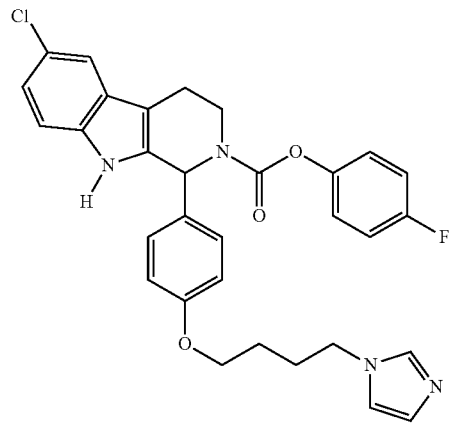
742
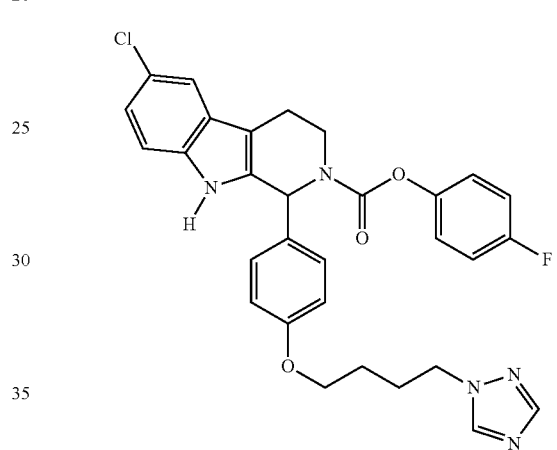
743
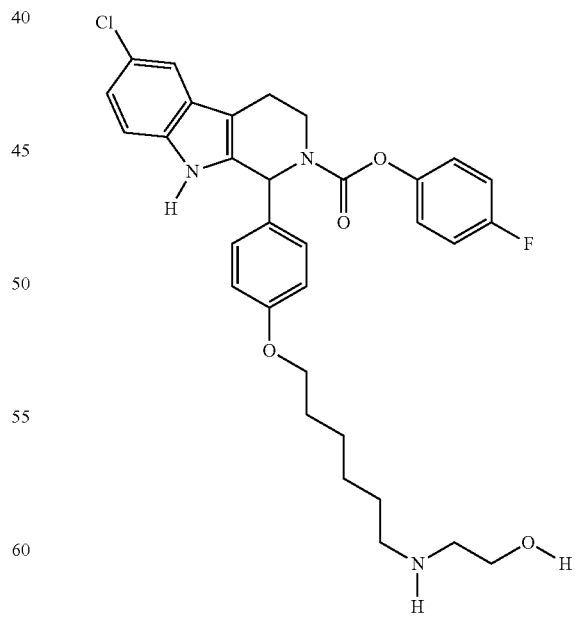
772

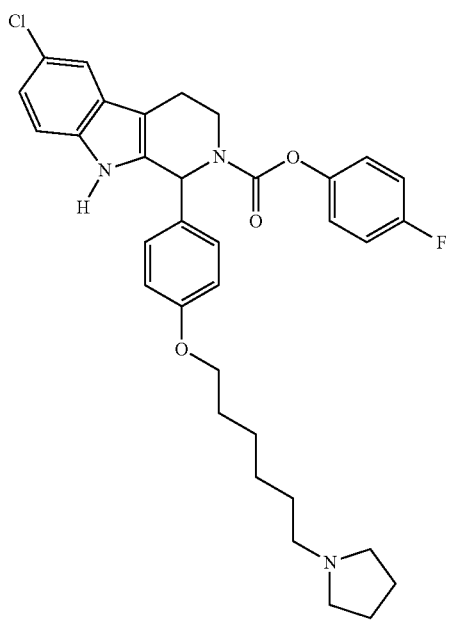

333
-continued
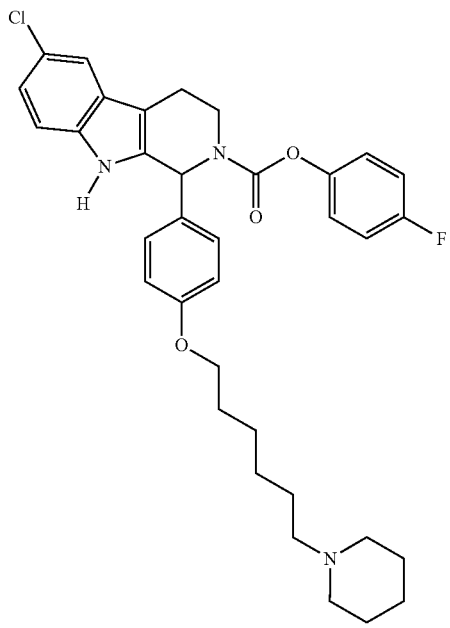
777
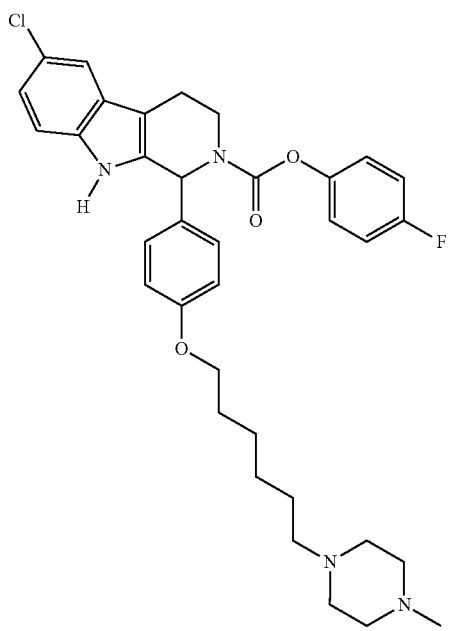
778
334
-continued
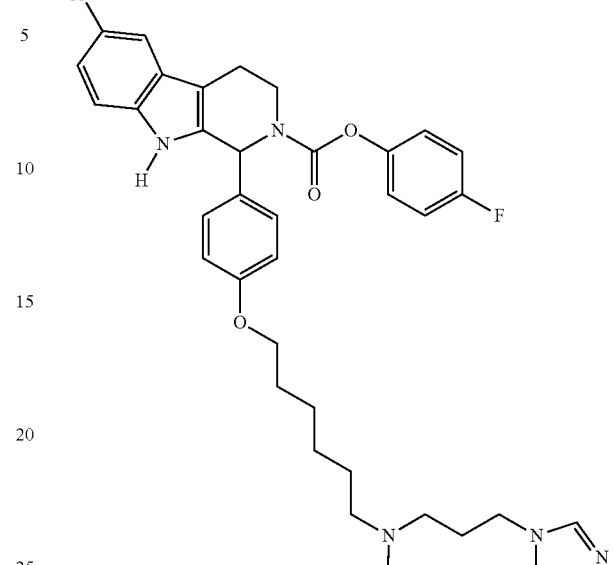
779
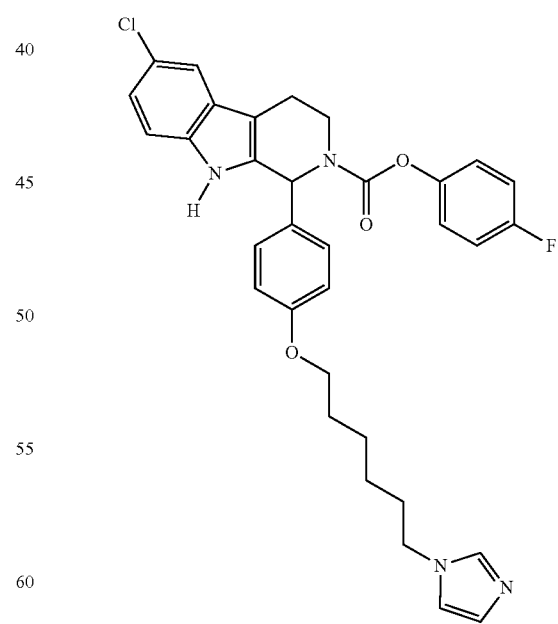
780

335
-continued
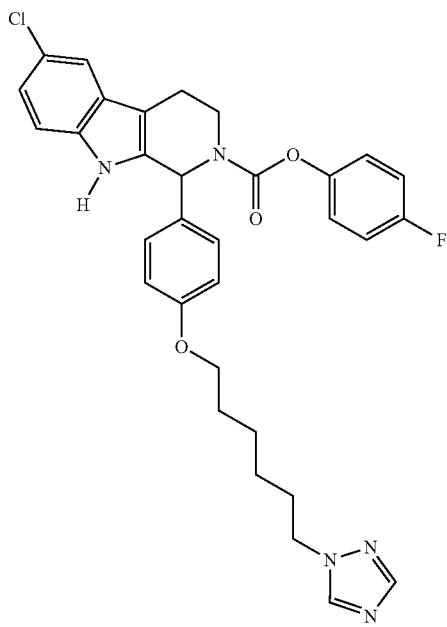
781
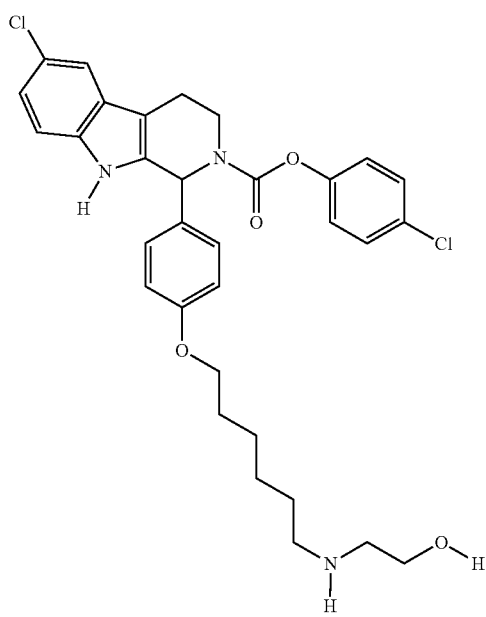
782
336
-continued
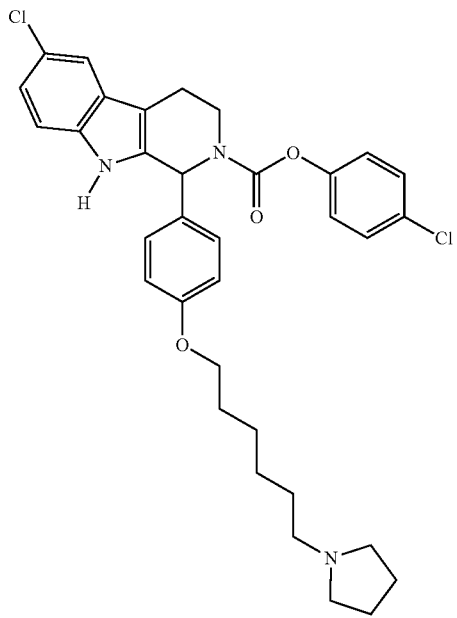
783
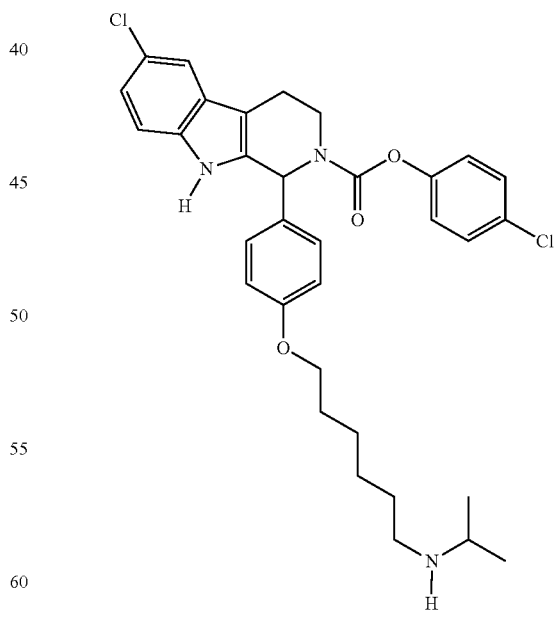
784

337
-continued
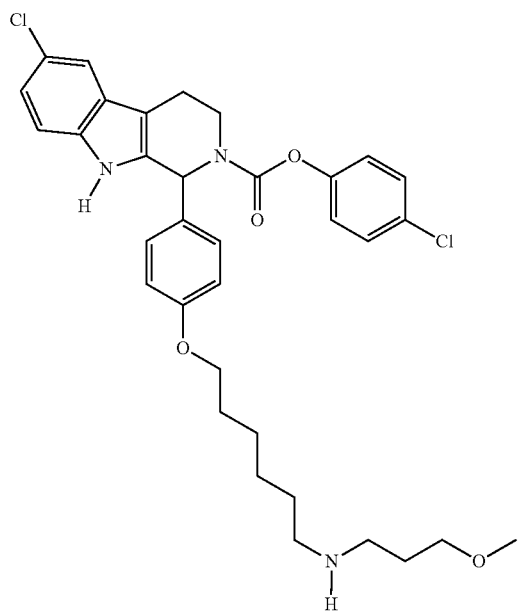
785
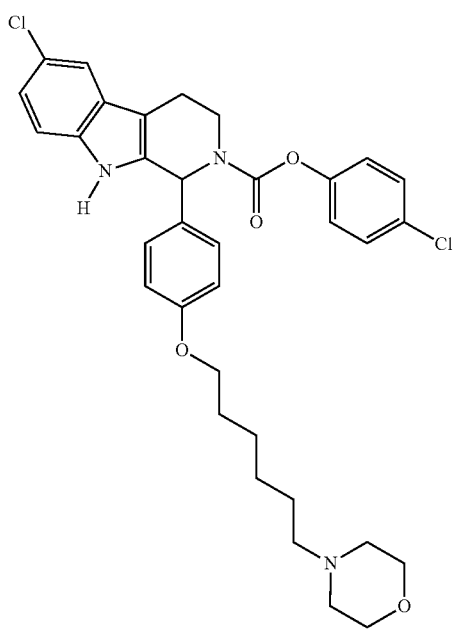
786
338
-continued
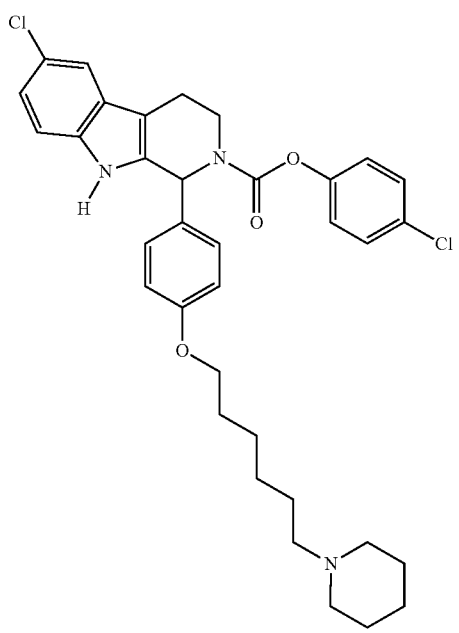
787
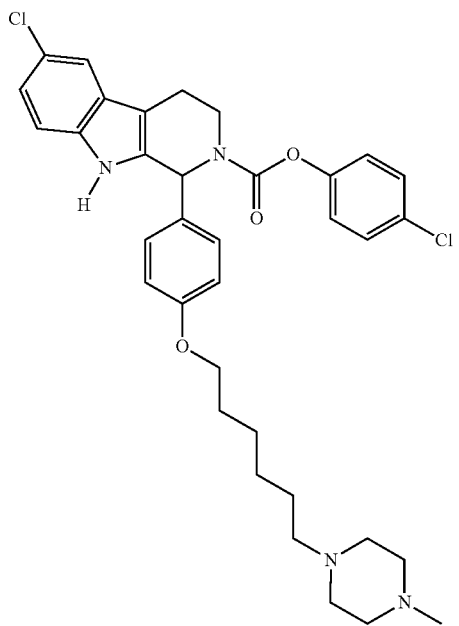
788

| 339 -continued | 340 -continued |
|---|---|
| 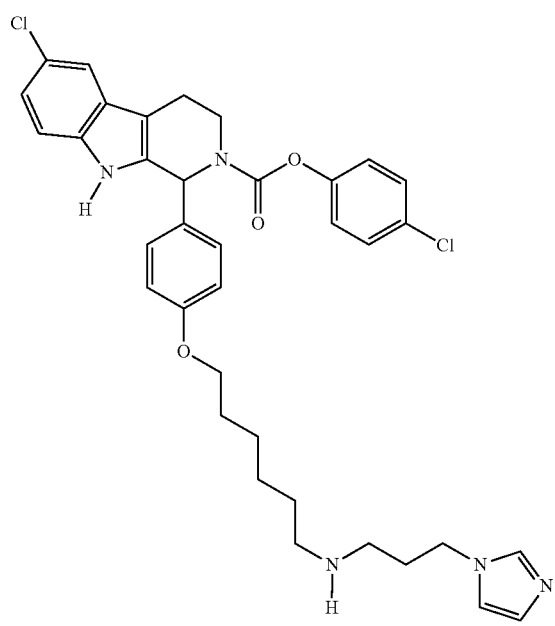 789 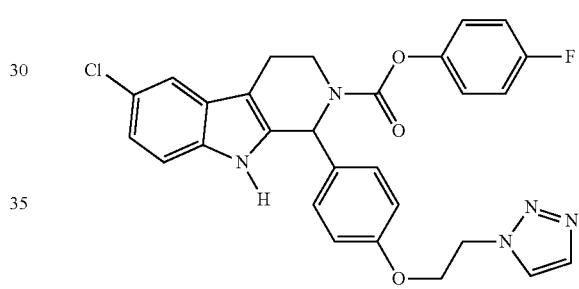 790 | 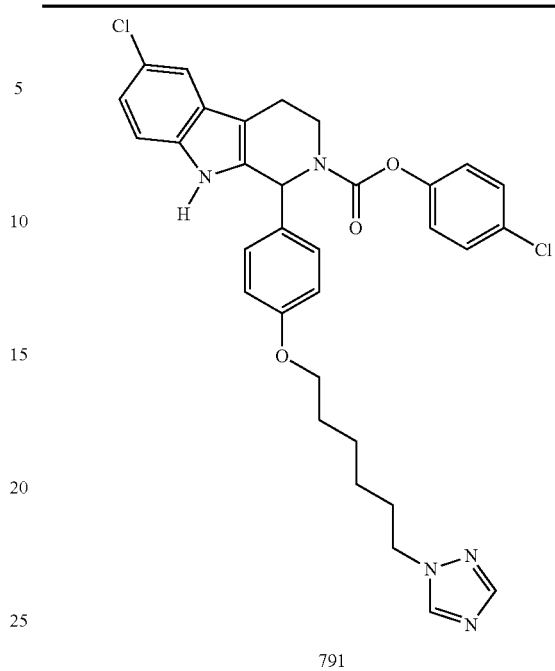 791 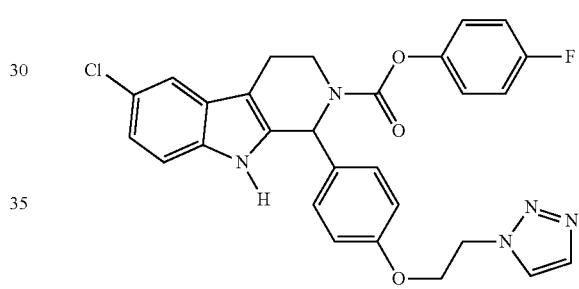 833 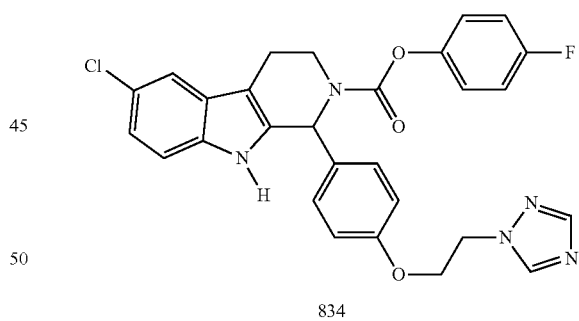 834 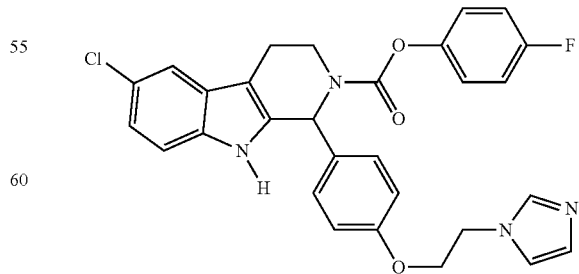 835 |

| 341 -continued | 342 -continued |
|---|---|
| 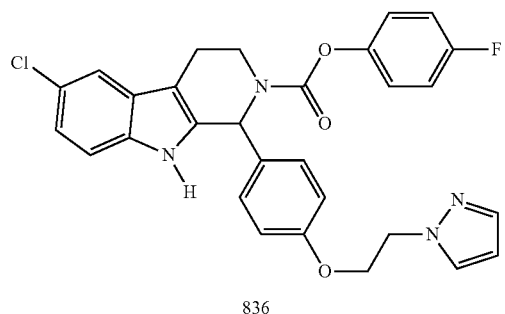<br>836 | 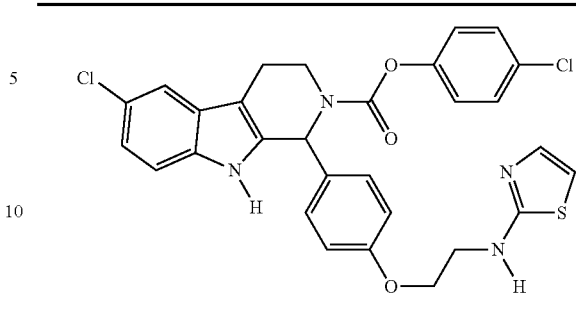<br>841 |
| 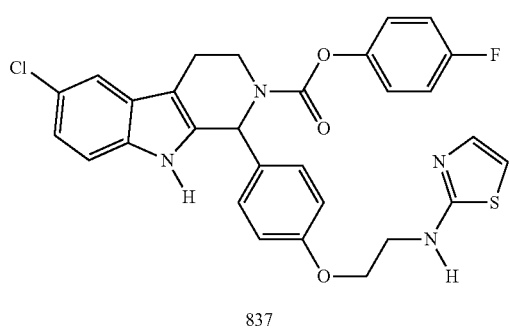<br>837 | 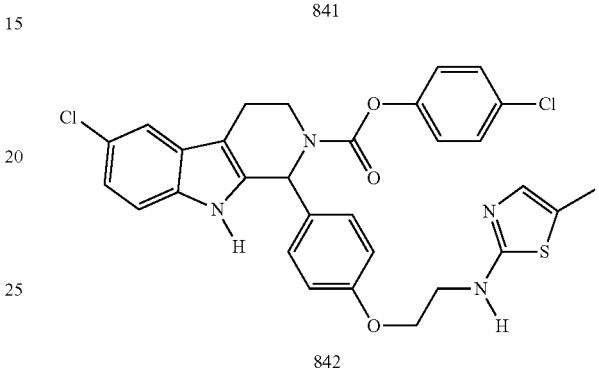<br>842 |
| 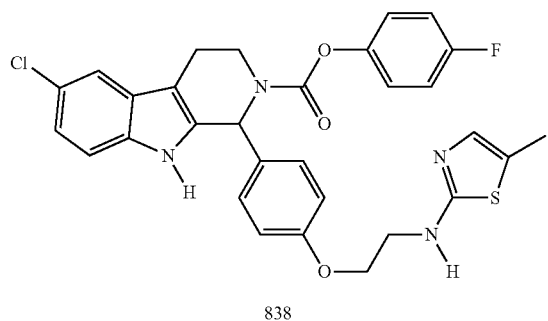<br>838 | 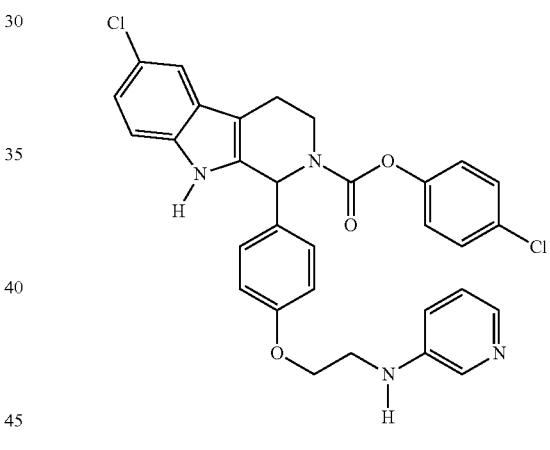<br>843 |
| 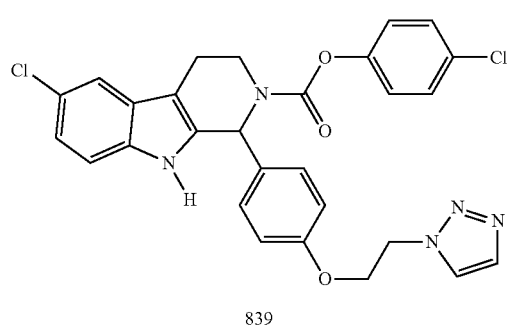<br>839 | |
| 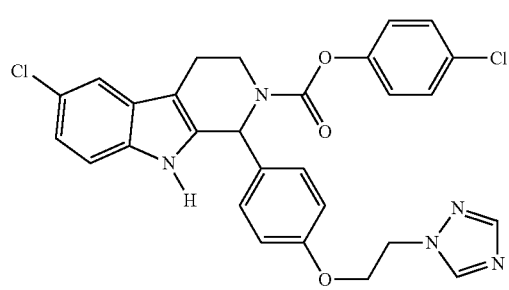<br>840 | 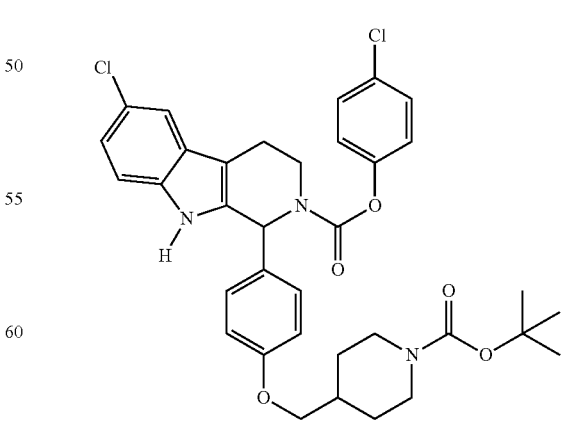<br>845 |

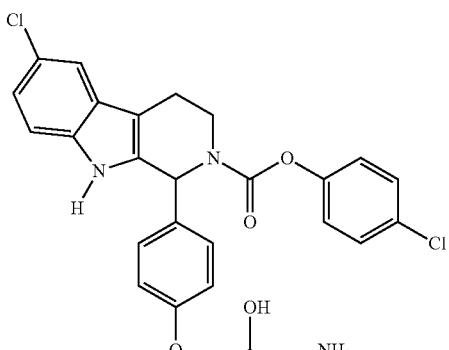
846
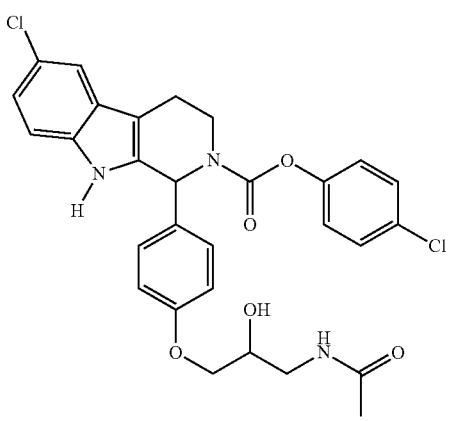
847
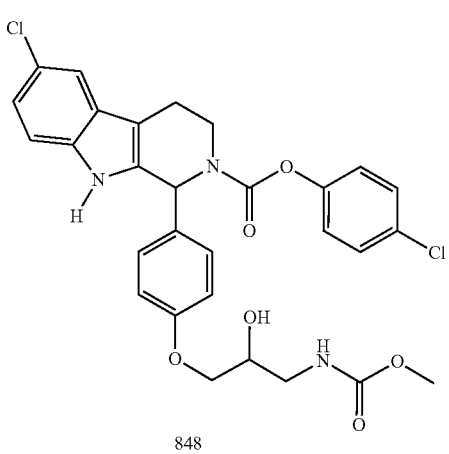
848
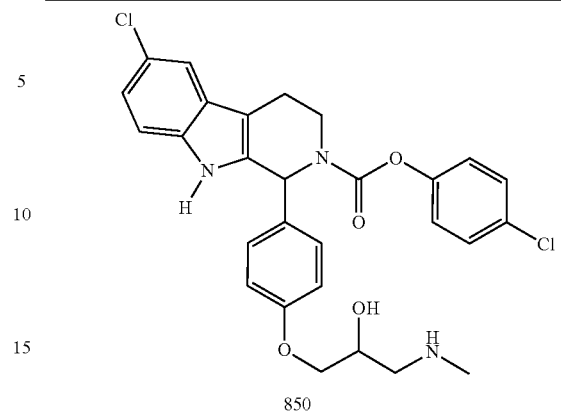
850
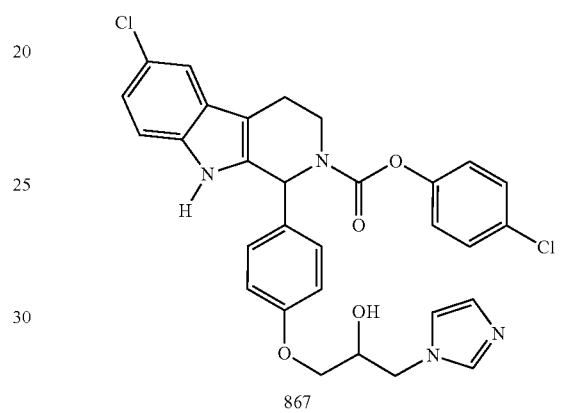
867
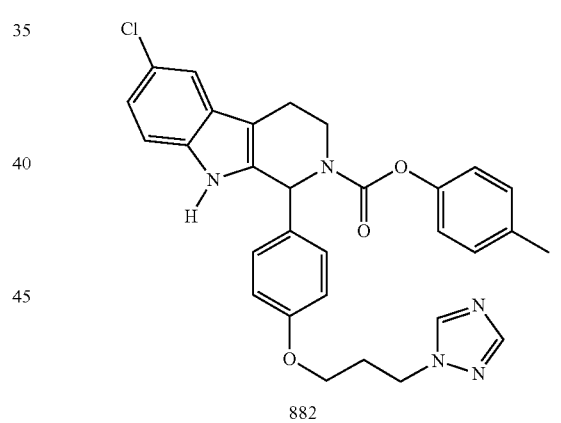
882
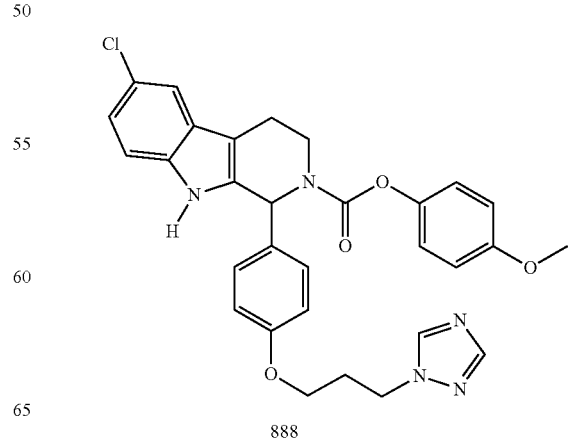
888

| 345 -continued | 346 -continued |
|---|---|
| 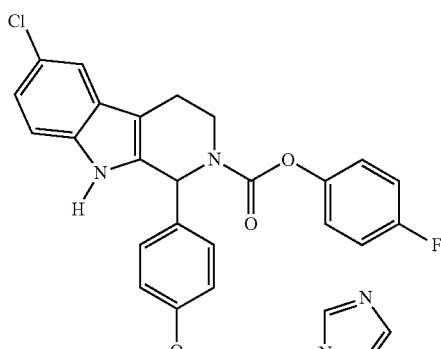 889 | 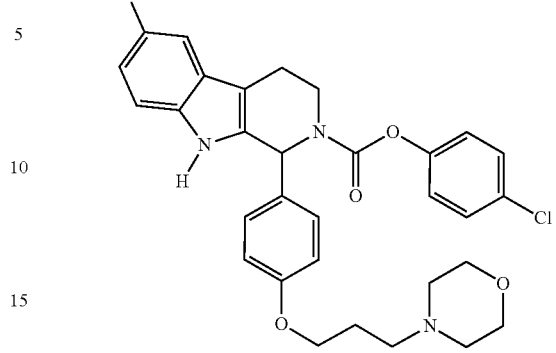 894 |
| 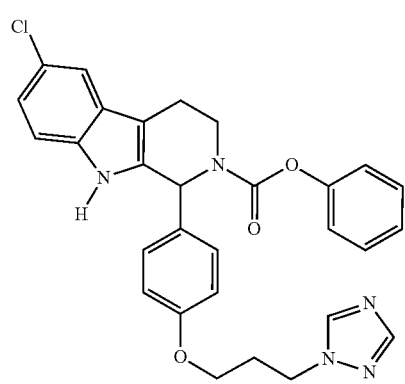 891 | 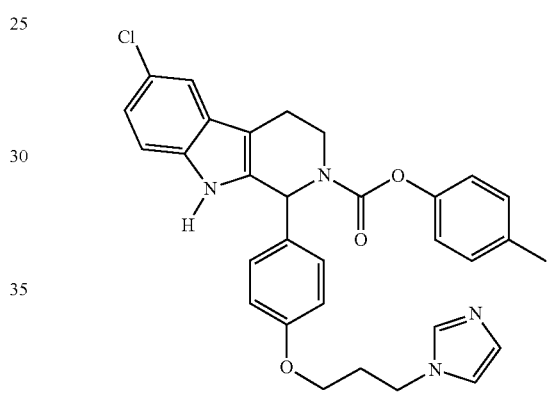 900 |
| 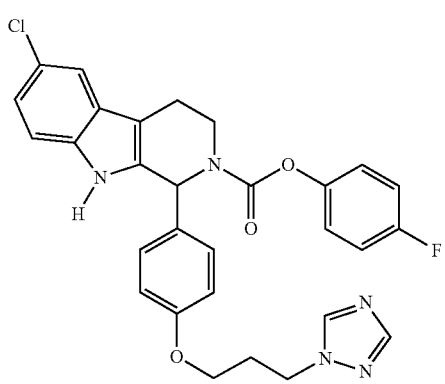 892 | 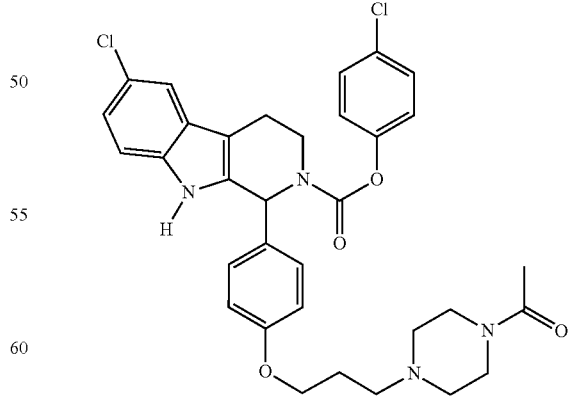 903 |

347
-continued
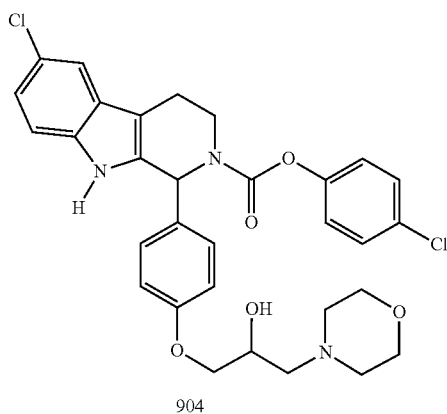
904
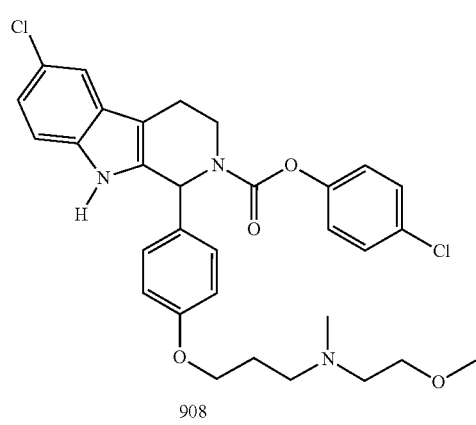
908
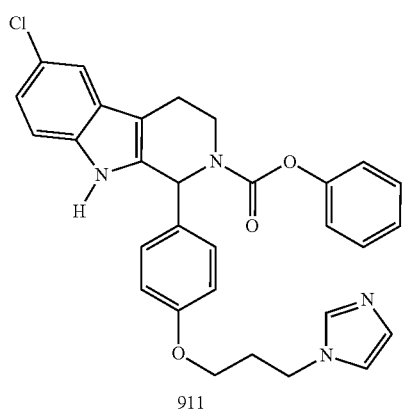
911
348
-continued
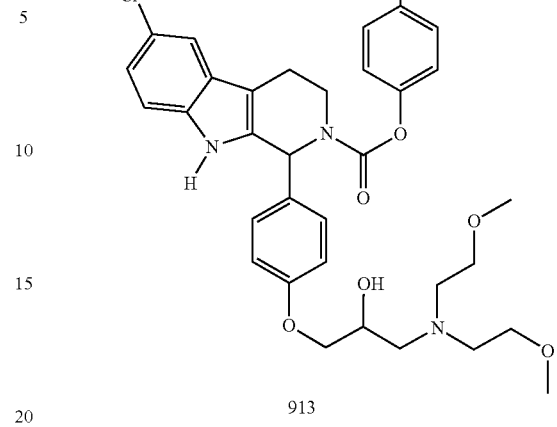
913
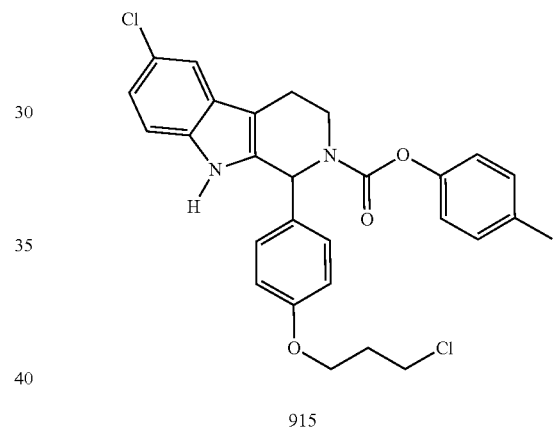
915
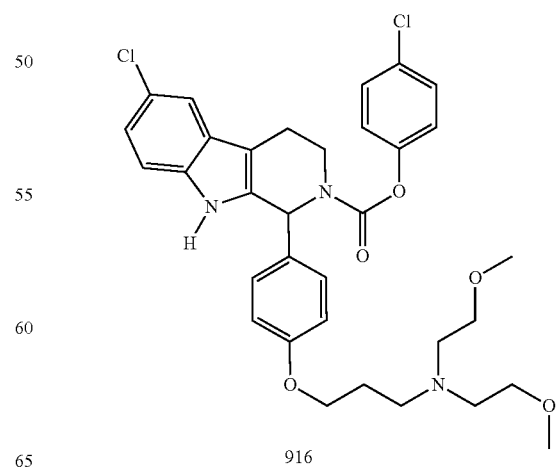
916

| 349 -continued | 350 -continued |
|---|---|
| 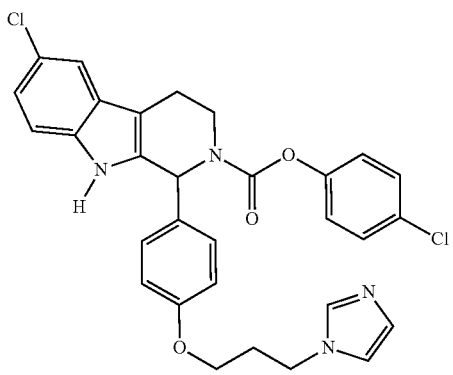<br>917 | 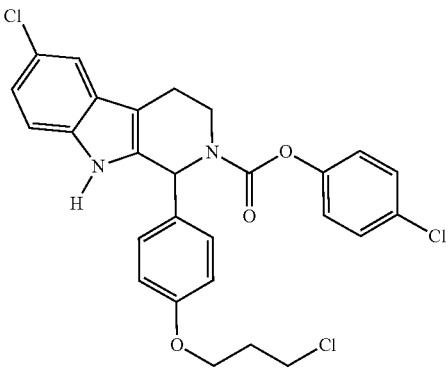<br>921 |
| 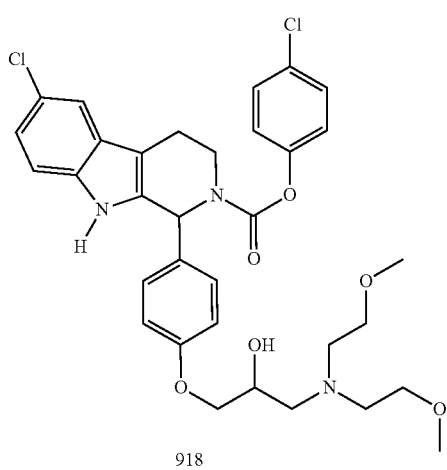<br>918 | 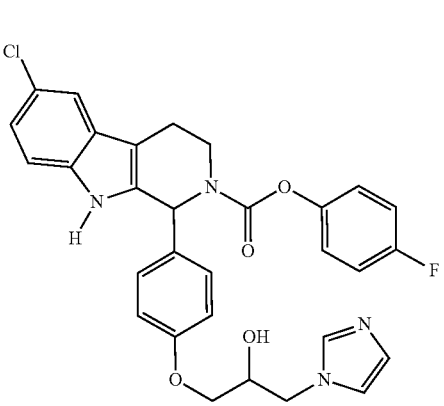<br>922 |
| 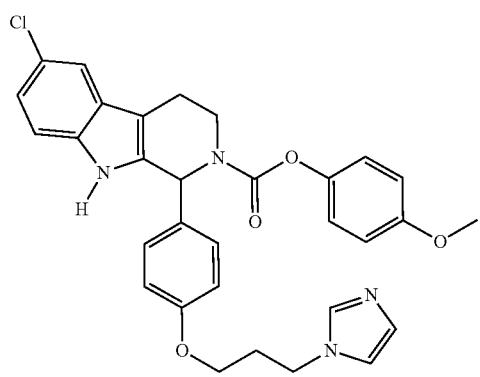<br>920 | 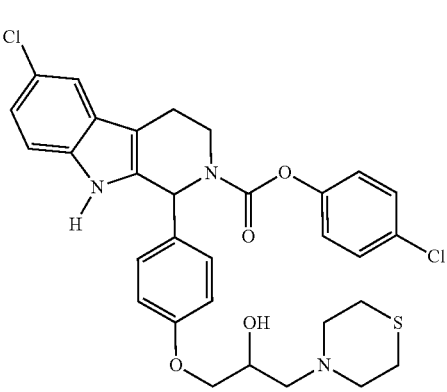<br>923 |

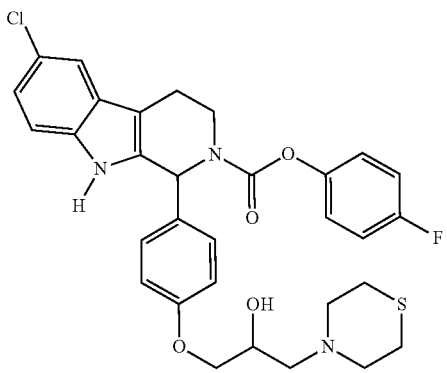
925
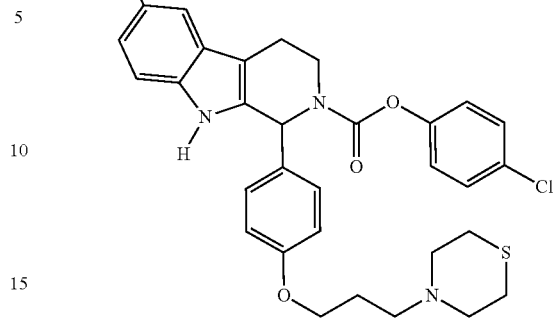
933
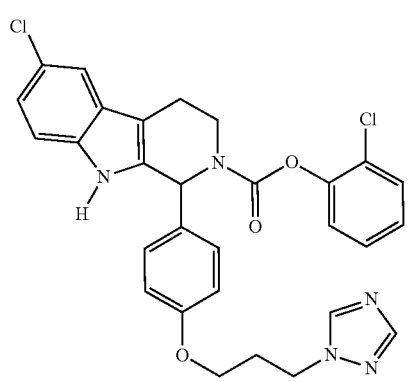
926
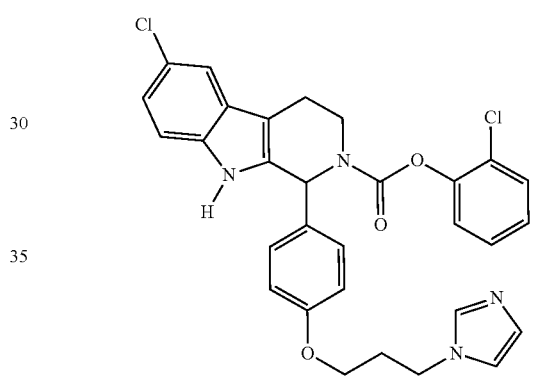
934
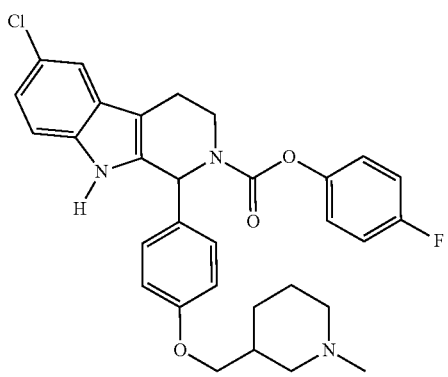
932
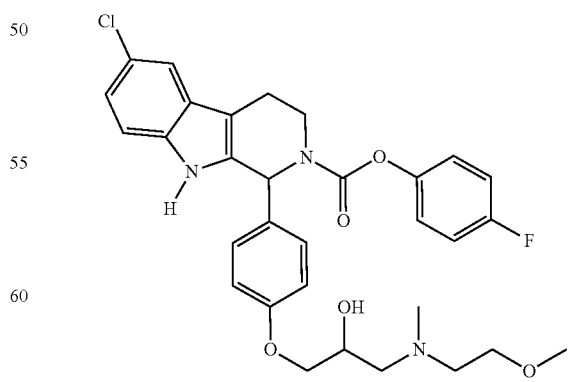
936

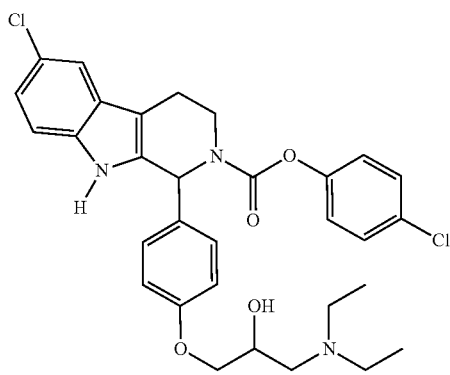
938
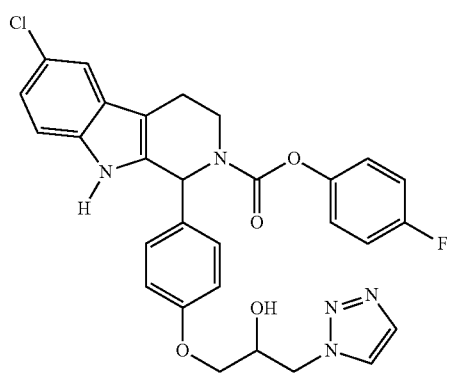
941
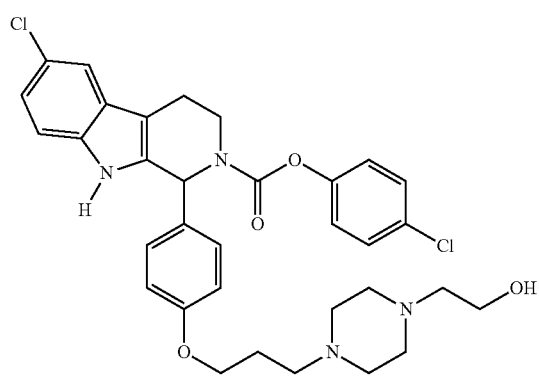
942
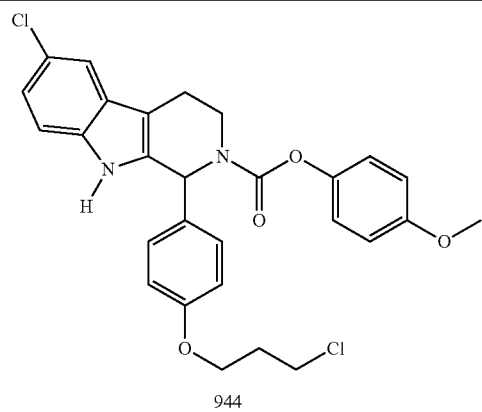
944
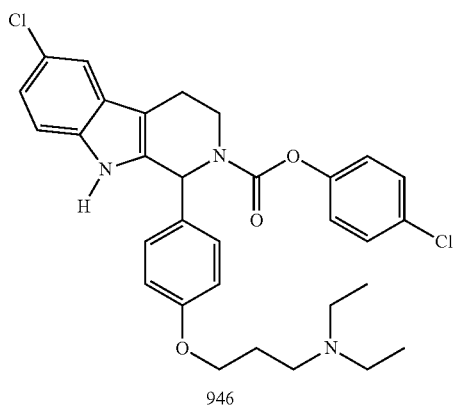
946
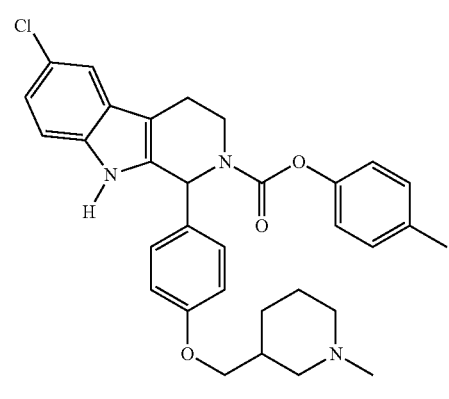
951
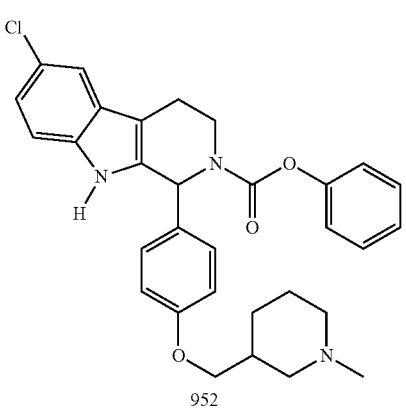
952

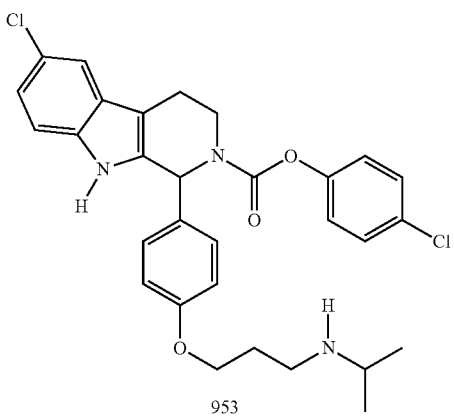
953
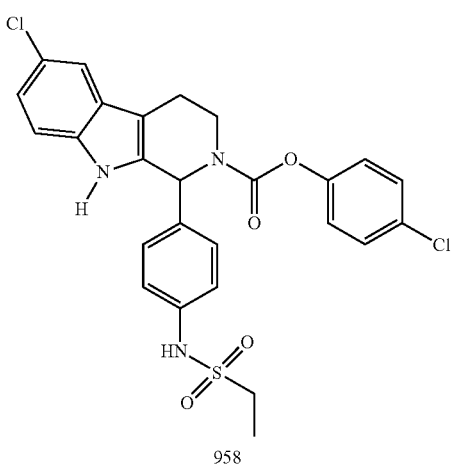
958
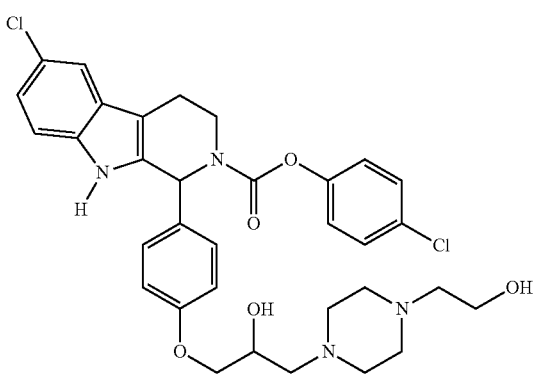
960
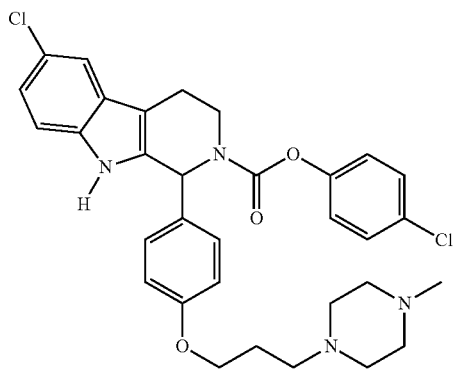
961
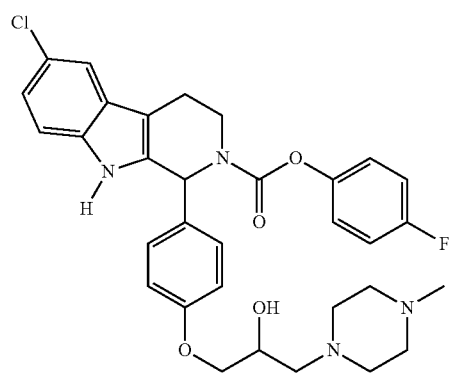
963
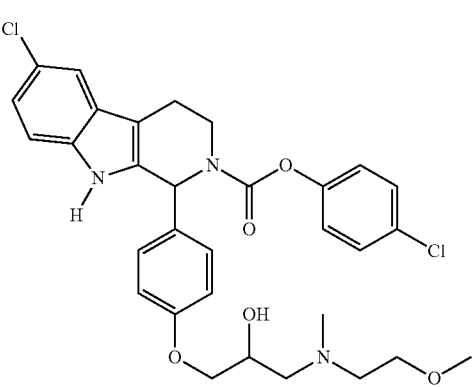
964
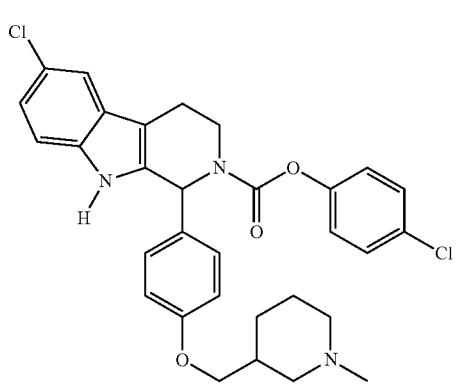
966

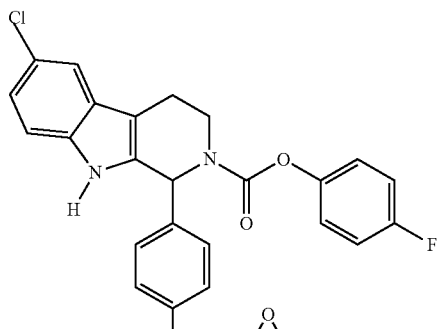
967
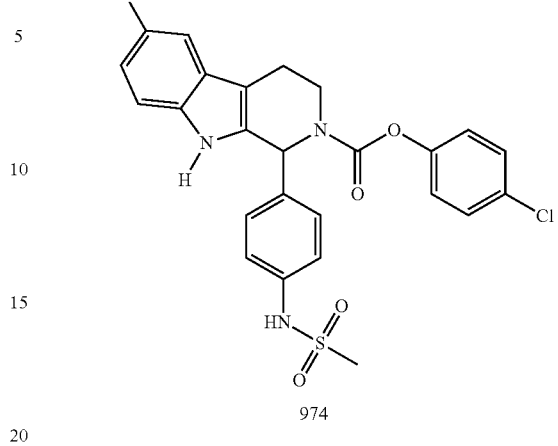
974
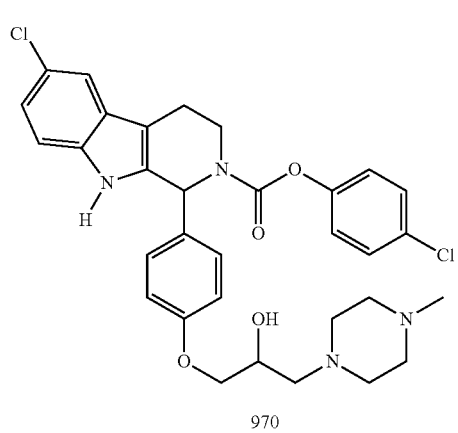
970
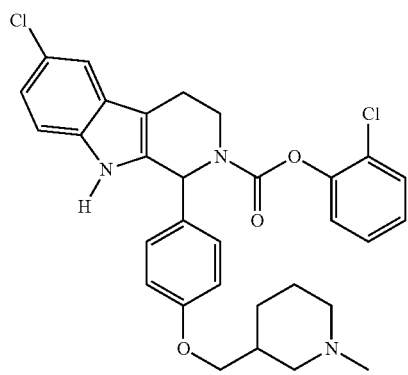
976
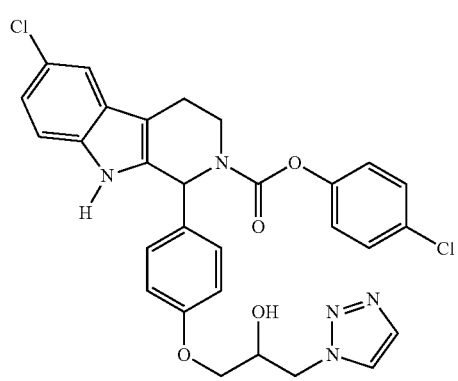
973
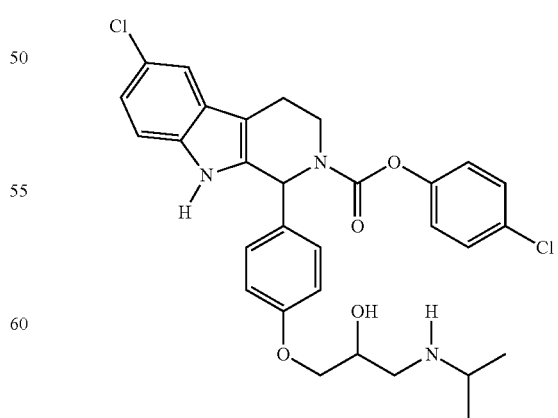
977

| 359 -continued | 360 -continued |
|---|---|
| 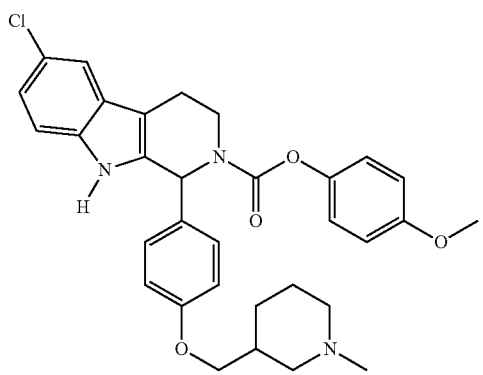 981 | 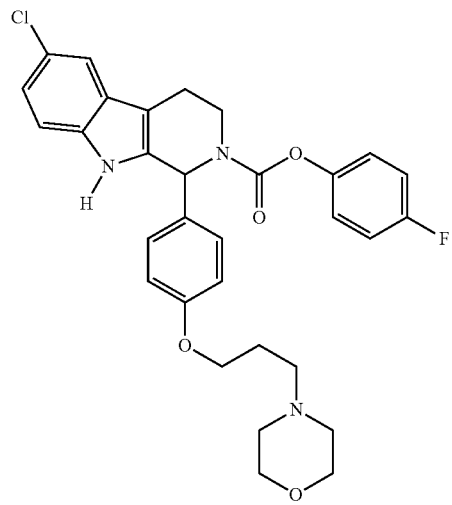 989 |
| 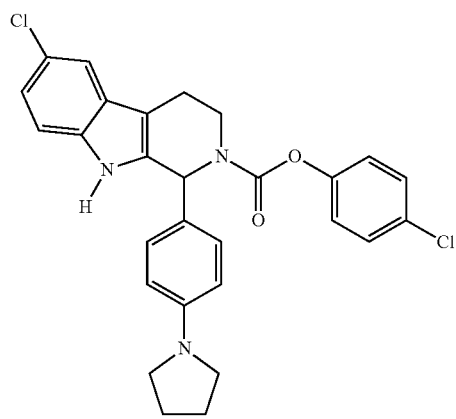 984 | 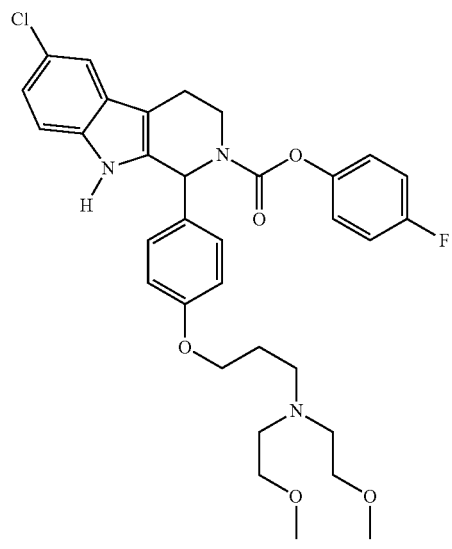 990 |
| 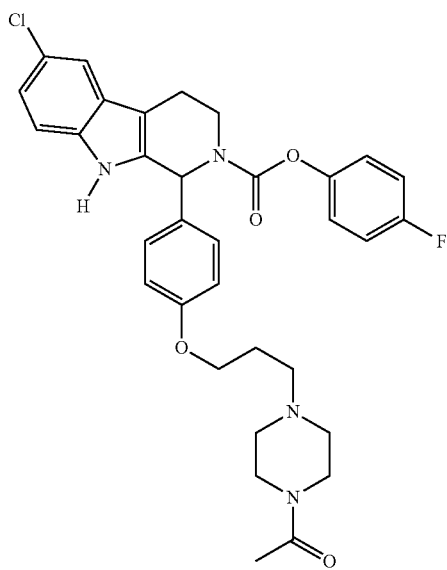 988 | 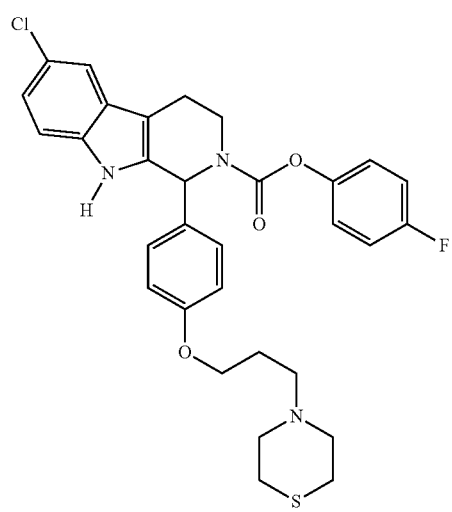 991 |

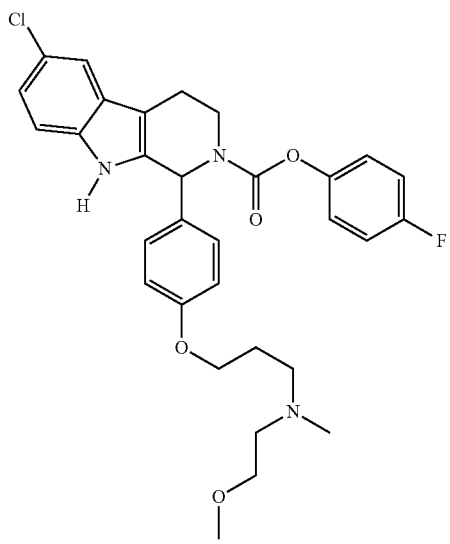
992
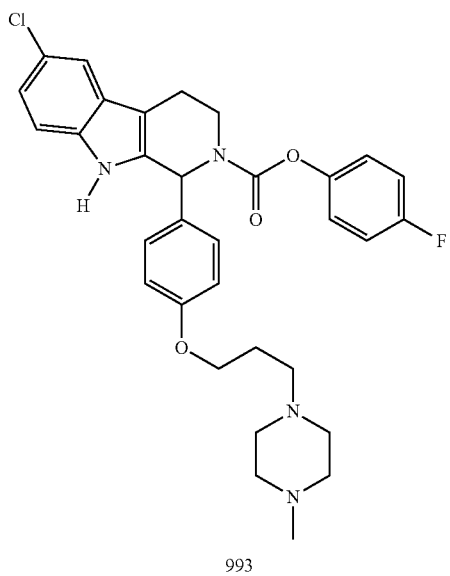
993
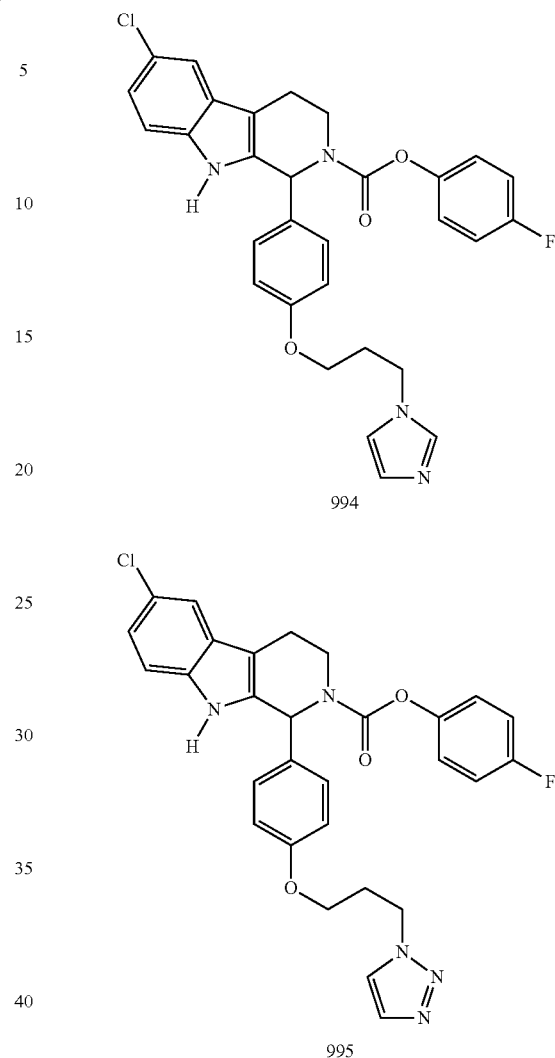
994
995
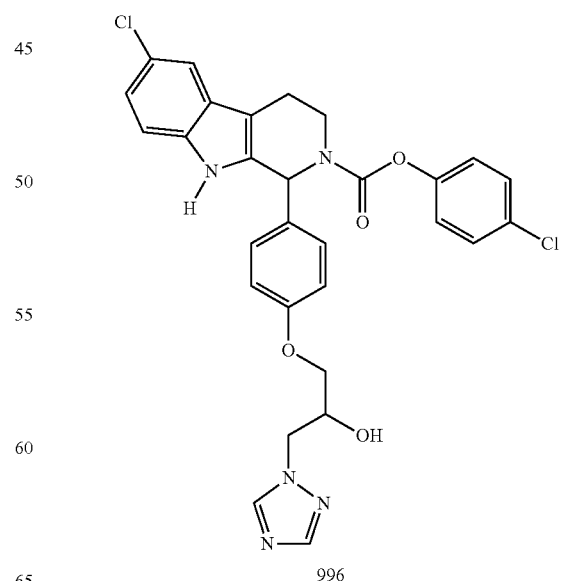
996 or a pharmaceutically acceptable salt, racemate or stereoisomer thereof, to the subject; and wherein the disease is solid tumor cancer, diabetic retinopathy, rheumatoid arthritis, psoriasis, atherosclerosis, chronic inflammation, a chronic inflammation-related disease or disorder, obesity, or exudative macular degeneration.

9. The method of claim 8, wherein said stereoisomer of said compound has a chiral carbon at the point of attachment of the phenyl ring directly attached to the tricyclic scaffol and said stereoisomer is an (S) isomer at said chiral carbon atom.

10. The method of claim 1, wherein the disease is solid tumor cancer.

11. The method of claim 10, wherein the solid tumor cancer is selected from the group consisting of Wilms tumor, neuroblastoma, malignant melanoma, cervical cancer, lung cancer and colon cancer.

12. The method of claim 1, wherein the disease is diabetic retinopathy.

13. The method of claim 1, wherein the disease is rheumatoid arthritis.

14. The method of claim 1, wherein the disease is psoriasis.

15. The method of claim 1, wherein the disease is atherosclerosis.

16. The method of claim 1, wherein the disease is chronic inflammation.

17. The method of claim 1, wherein the disease is a chronic inflammation-related disease or disorder.

18. The method of claim 1, wherein the disease is obesity.

19. The method of claim 1, wherein the disease is exudative macular degeneration.

20. The method of claim 10, wherein said compound is selected from the group consisting of:

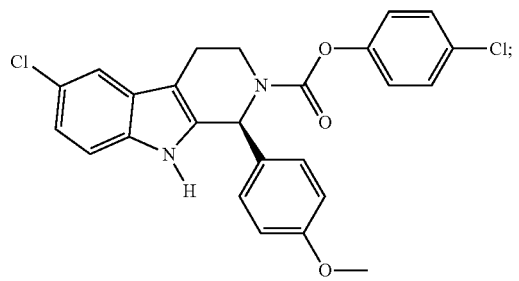

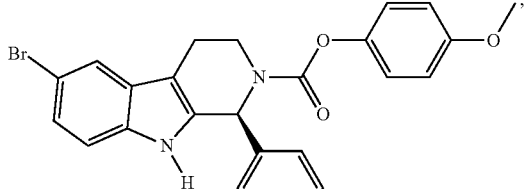

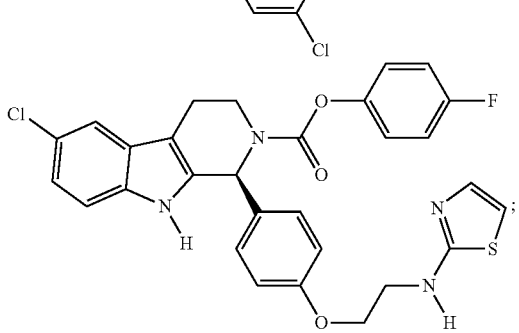

-continued

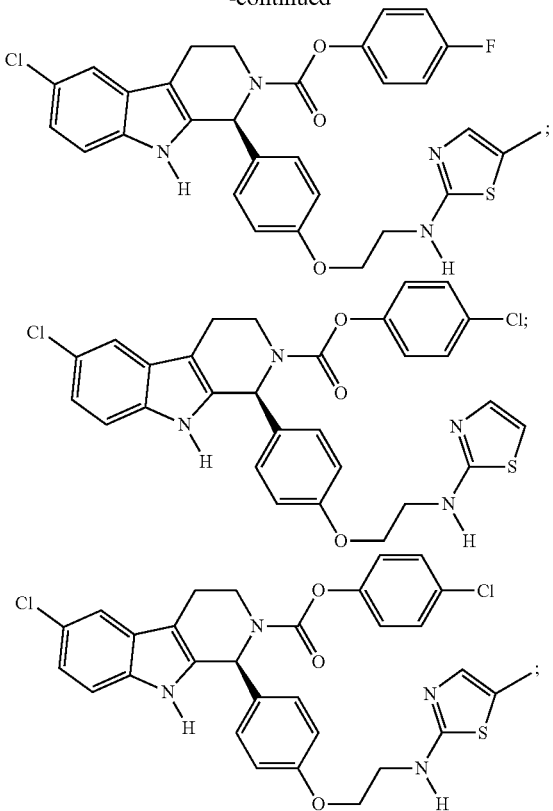

and

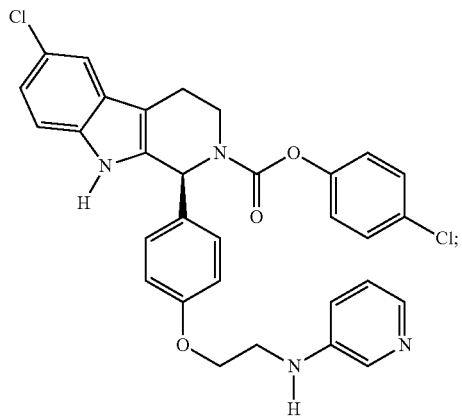

or a pharmaceutically acceptable salt thereof.

21. The method of claim 20, wherein said compound is:

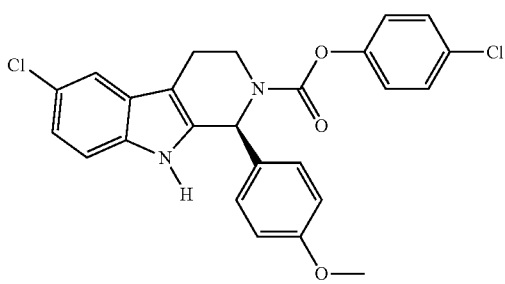

or a pharmaceutically acceptable salt thereof.

22. The method of claim 20, wherein said compound is:

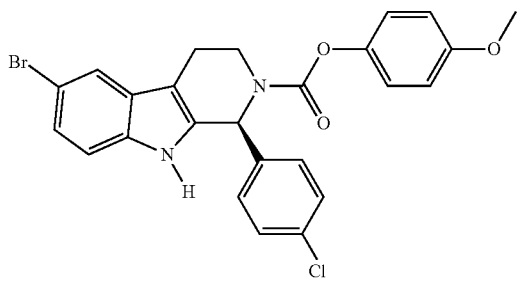

or a pharmaceutically acceptable salt thereof.

23. The method of claim 20, wherein said compound is:

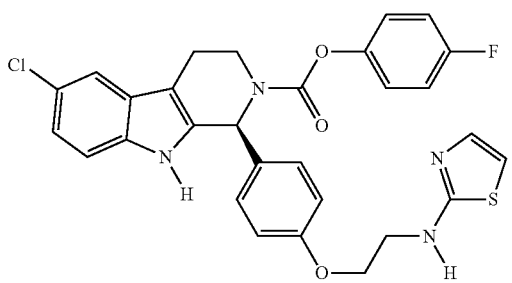

or a pharmaceutically acceptable salt thereof.

24. The method of claim 20, wherein said compound is:

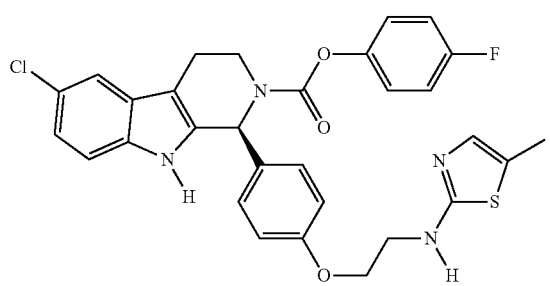

or a pharmaceutically acceptable salt thereof.

25. The method of claim 20, wherein said compound is:

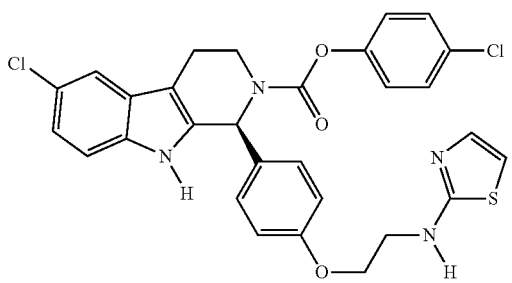

or a pharmaceutically acceptable salt thereof.

26. The method of claim 20, wherein said compound is:

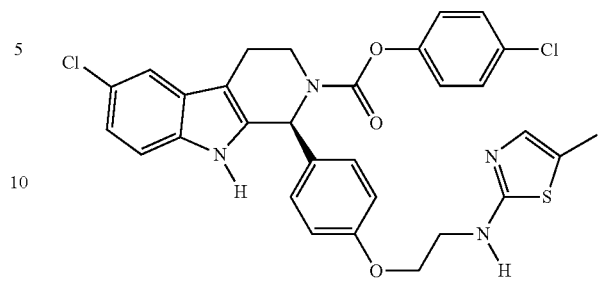

or a pharmaceutically acceptable salt thereof.

27. The method of claim 20, wherein said compound is:

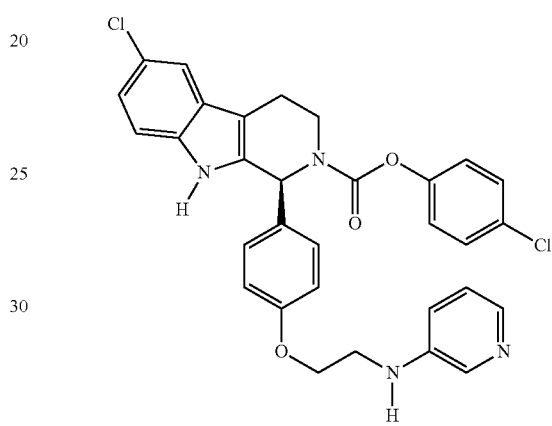

or a pharmaceutically acceptable salt thereof

28. The method of claim 8, wherein the disease is solid tumor cancer.

29. The method of claim 28, wherein the solid tumor cancer is selected from the group consisting of Wilms tumor, neuroblastoma, malignant melanoma, cervical cancer, lung cancer and colon cancer.

30. The method of claim 8, wherein the disease is diabetic retinopathy.

31. The method of claim 8, wherein the disease is rheumatoid arthritis.

32. The method of claim 8, wherein the disease is psoriasis.

33. The method of claim 8, wherein the disease is atherosclerosis.

34. The method of claim 8, wherein the disease is chronic inflammation.

35. The method of claim 8, wherein the disease is a chronic inflammation-related disease or disorder.

36. The method of claim 8, wherein the disease is obesity.

37. The method of claim 8, wherein the disease is exudative macular degeneration.

38. The method of claim 6, wherein the reduction of elevated VEGF levels in HeLa cells is measured by an ELISA assay.

39. The method of claim 6, wherein the reduction of elevated VEGF levels in HT1080 cells is measured by a quantitative immunofluoresence assay.

* * * * *